US012600733B2

(12) United States Patent
Abraham et al.

(10) Patent No.: US 12,600,733 B2
(45) Date of Patent: Apr. 14, 2026

(54) KRAS INHIBITORS

(71) Applicant: ELI LILLY AND COMPANY, Indianapolis, IN (US)

(72) Inventors: Adedoyin David Abraham, Thornton, CO (US); Sean Aronow, Boulder, CO (US); Desta Bume, Erie, CO (US); Xiaohong Chen, Carmel, IN (US); Sonia Maria Gutierrez Sanfeliciano, Carmel, IN (US); Timothy Scott Kercher, Longmont, CO (US); Wenceslao Lumeras Amador, Madrid (ES); Ramkumar Rajamani, Acton, MA (US); Isabel Rojo Garcia, Madrid (ES); William Rush Scaggs, Broomfield, CO (US); Shane Walls, Broomfield, CO (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 19/344,841

(22) Filed: Sep. 30, 2025

(65) Prior Publication Data

US 2026/0092075 A1 Apr. 2, 2026

(30) Foreign Application Priority Data

Oct. 1, 2024 (EP) .................................... 24383052
Apr. 16, 2025 (EP) .................................... 25382392
Aug. 28, 2025 (EP) .................................... 25382911

(51) Int. Cl.

| | |
|---|---|
| ***C07D 519/00*** | (2006.01) |
| ***A61K 31/4741*** | (2006.01) |
| ***A61K 31/5025*** | (2006.01) |
| ***A61K 31/519*** | (2006.01) |
| ***A61K 31/5377*** | (2006.01) |
| ***A61K 31/5383*** | (2006.01) |
| ***A61K 45/06*** | (2006.01) |
| ***A61P 35/00*** | (2006.01) |
| ***C07B 59/00*** | (2006.01) |
| ***C07D 491/048*** | (2006.01) |

(52) U.S. Cl.

CPC ........ *C07D 519/00* (2013.01); *A61K 31/4741* (2013.01); *A61K 31/5025* (2013.01); *A61K 31/519* (2013.01); *A61K 31/5377* (2013.01); *A61K 31/5383* (2013.01); *A61K 45/06* (2013.01); *A61P 35/00* (2018.01); *C07B 59/002* (2013.01); *C07D 491/048* (2013.01)

(58) Field of Classification Search

CPC ... C07D 519/00; C07D 491/048; A61P 35/00; A61K 31/4741; A61K 31/5025; A61K 31/519; A61K 31/5377; A61K 31/5383; A61K 45/06; C07B 59/002

See application file for complete search history.

(56) References Cited

U.S. PATENT DOCUMENTS

2024/0043451 A1* 2/2024 Barda .................. C07D 519/00
2024/0343736 A1* 10/2024 Kercher ............ A61K 31/5377

FOREIGN PATENT DOCUMENTS

| | | | |
|---|---|---|---|
| CN | 120535536 | A | 8/2025 |
| WO | 2021/118877 | A1 | 6/2021 |
| WO | 2022/261154 | A1 | 12/2022 |
| WO | 2023/183585 | A1 | 9/2023 |
| WO | 2024/030633 | A1 | 2/2024 |
| WO | 2024/064335 | A1 | 3/2024 |
| WO | 2024/206747 | A1 | 10/2024 |
| WO | 2024/206766 | A1 | 10/2024 |
| WO | 2025/072457 | A1 | 4/2025 |
| WO | 2025/092798 | A1 | 5/2025 |

OTHER PUBLICATIONS

Patent Cooperation Treaty Written Opinion of the International Searching Authority pertaining to International Application No. PCT/US2025/048599; Feb. 3, 2026, 15 pages.

Patent Cooperation Treaty Written Opinion of the International Searching Authority pertaining to International Application No. PCT/US2025/048607; Jan. 23, 2026, 15 pages.

* cited by examiner

*Primary Examiner* — Timothy R Rozof
(74) *Attorney, Agent, or Firm* — Stefan Ochiana

(57) ABSTRACT

Provided herein are compounds of the formula:

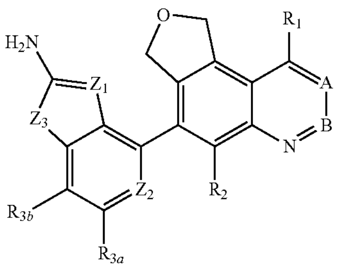

wherein A, B, $R_1$, $R_2$, $R_{3a}$, $R_{3b}$, $Z_1$, $Z_2$, and $Z_3$ are as described herein, pharmaceutically acceptable salts thereof, and methods of using these compounds and pharmaceutically acceptable salts thereof for treating patients with cancer.

30 Claims, No Drawings

KRAS INHIBITORS

CROSS-REFERENCE TO RELATED PATENT APPLICATIONS

The present application claims the benefit of priority to European Patent Application Nos. EP 24383052.8, filed Oct. 1, 2024, EP 25382392.6, filed on Apr. 16, 2025, and, EP 25382911.3, filed on Aug. 28, 2025, the contents of which are incorporated herein by reference in their entireties.

FIELD

The present disclosure is directed to KRAS inhibitors useful in the treatment of diseases or disorders associated with KRAS modulation.

BACKGROUND

The MAPK/ERK signaling pathway relays extracellular stimuli to the nucleus, thereby regulating diverse cellular responses including cell proliferation, differentiation, and apoptosis. KRAS protein is an initiator of the MAPK/ERK signaling pathway and functions as a switch responsible for inducing cell division. In its inactive state, KRAS binds guanosine diphosphate (GDP), effectively sending a negative signal to suppress cell division. In response to an extracellular signal, KRAS is allosterically activated allowing for nucleotide exchange of GDP for guanosine triphosphate (GTP). In its GTP-bound active state, KRAS recruits and activates proteins necessary for the propagation of growth factor induced signaling, as well as other cell signaling receptors. Examples of the proteins recruited by KRAS-GTP are c-Raf and PI3-kinase. KRAS, as a GTP-ase, converts the bound GTP back to GDP, thereby returning itself to an inactive state, and again propagating signals to suppress cell division. KRAS gain of function mutations exhibit an increased degree of GTP binding and a decreased ability to convert GTP into GDP. The result is an increased MAPK/ERK signal which promotes cancerous cell growth. Missense mutations of KRAS at codon 12 are the most common mutations and markedly diminish GTPase activity.

Oncogenic KRAS mutations have been identified in approximately 30% of human cancers and have been demonstrated to activate multiple downstream signaling pathways. Despite the prevalence of KRAS mutations, it has been a difficult therapeutic target. (Cox, A.D. *Drugging the Undruggable RAS: Mission Possible*? Nat. Rev. Drug Disc. 2014, 13, 828-851; Pylayeva-Gupta, y et al. *RAS Oncogenes: Weaving a Tumorigenic Web*. Nat. Rev. Cancer 2011, 11, 761-774).

Thus far, work has focused on KRAS G12C mutant inhibitors (e.g., WO2019/099524, WO2020/081282, WO2020/101736, WO2020/146613, and WO2021/118877 disclose KRAS G12C inhibitors), whereas WO2021/041671 discloses small molecules inhibitors of KRAS G12D and WO2017/011920 discloses small molecule inhibitors of KRAS G12C, G12D, and G12V.

There remains a need to provide alternative, small molecule KRAS inhibitors. In particular, there is a need to provide orally deliverable KRAS inhibitors that are useful for treating cancer. More particularly, there is a need to provide small molecule inhibitors that specifically inhibit KRAS GTP activity. There is also a need to provide small molecule KRAS inhibitors that exhibit greater efficacy at the same or reduced KRAS inhibitory activity. Further, there is a desire to provide KRAS inhibitors that exhibit better pharmacokinetic/pharmacodynamic properties. Even further, there is a desire to provide KRAS inhibitors that exhibit good oral bioavailability and target coverage (KRAS G12V inhibition). Additionally, there is a need to provide KRAS inhibitors that exhibit selective inhibition preference for KRAS G12V mutant over KRAS wild-type and preferably also exhibit selective inhibition preference for KRAS G12V mutant over HRAS or NRAS. Also, there is a need to provide more potent KRAS inhibitors that exhibit increased efficacy with reduced or minimized untoward or undesired effects. The present invention addresses one or more of these needs by providing novel KRAS inhibitors.

SUMMARY

Compounds of Formula I are provided herein

Formula I

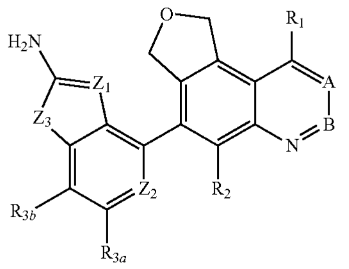

wherein:

A is —C(H)— or —N—;

B is —C($R_4$)— or —N—;

$R_1$ is a group of the formula

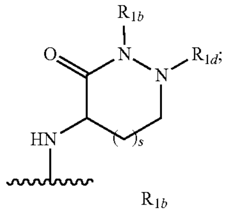

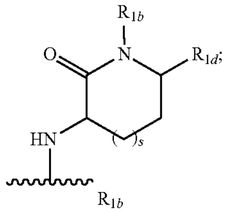

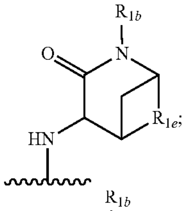

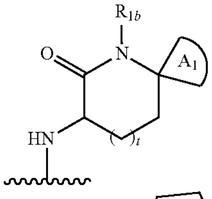

;

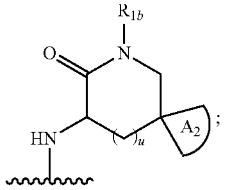

;

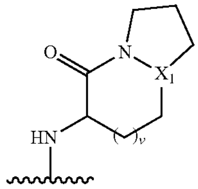

;

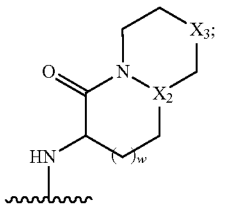

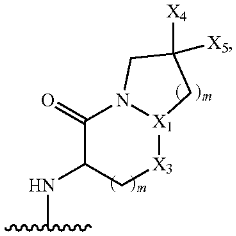

or

-continued

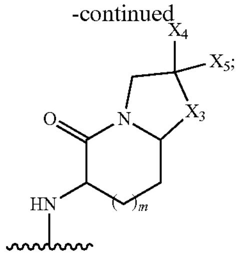

$R_{1b}$ is H or $C_{1-3}$ alkyl;

$R_{1d}$ is $C_{1-3}$ alkyl, $C_{1-3}$ haloalkyl, or $C_{3-4}$ cycloalkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

$X_4$ and $X_5$ are each independently $C_{1-3}$ alkyl, halogen, or H;

m, m', s, t, u, v, and w are each 0 or 1;

$R_2$ is halogen or $C_{1-3}$ alkyl;

$Z_1$ is —C(CN)— or —N—;

$Z_2$ is —$C(R_{3c})$— or —N—;

$Z_3$ is —O— or —S—;

$R_{3a}$, $R_{3b}$, and $R_{3c}$ are each independently H, halogen, or $C_{1-3}$ alkyl;

$R_4$ is H, $C_{1-3}$ alkyl, $C_{1-3}$ alkoxy optionally substituted with 1, 2, 3, or 4 substituents independently selected from hydroxyl and methyl, or $R_4$ is a group of the formula (i)

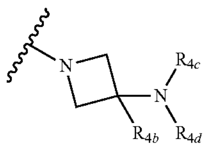

or

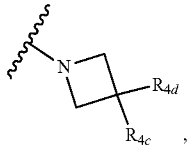

, wherein $R_{4b}$ is H or methyl; and $R_{4c}$ and $R_{4d}$ are each independently $C_{1-3}$ alkyl, hydroxyl, or $C_{1-3}$ haloalkyl; or $R_{4c}$ and $R_{4d}$ together with the nitrogen or carbon atom to which they are attached form a 4-, 5-, or 6-membered heterocycle;

or (ii)

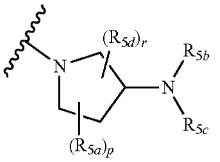

or

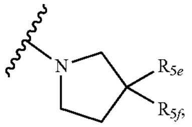

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5d}$ is $C_{1-3}$ alkyl;

$R_{5e}$ and $R_{5f}$ together with the carbon atom to which they are attached form a 4-, 5-, or 6-membered heterocycle;

$R_{5b}$ and $R_{5c}$ are each independently H, $C_{1-6}$ alkyl optionally substituted with one or more deuterium, $C_{3-5}$ cycloalkyl optionally substituted with halogen, hydroxyl, or $C_{1-3}$ haloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle or a 6-, 7-, or 8-membered spiro heterocycle optionally containing a further heteroatom selected from N, O, and S, and wherein the heterocycle and the spiro heterocycle is each optionally substituted with one or more halogen, deuterium, $C_{1-3}$ alkyl, or $C_{1-3}$ haloalkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p and r are each 0, 1, or 2;

(iii)

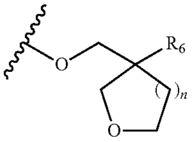

, wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, and $C_{1-3}$ dialkylamino; and n is 0 or 1; and (iv)

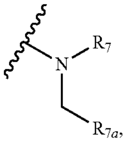

wherein $R_7$ is a $C_{1-3}$ alkyl; and $R_{7a}$ is a 4-, 5-, or 6-membered heterocycle optionally containing a further heteroatom selected from N, O, and S; or $R_7$ and $R_{7a}$ together with the atoms to which they are attached form a 4-, 5-, or 6-membered heterocyclic ring optionally containing a further heteroatom selected from N, O, and S;

or a pharmaceutically acceptable salt thereof.

Also provided herein are methods of using the compounds of Formula I, pharmaceutically acceptable salts thereof, and pharmaceutical compositions thereof, to treat cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. The methods include administering a therapeutically effective amount of a compound of Formula I, or a pharmaceutically acceptable salt thereof, to a patient in need thereof.

Further provided herein, are compounds of Formula I, and pharmaceutically acceptable salts thereof, for use in therapy. Additionally provided herein, are the compounds of Formula I, and pharmaceutically acceptable salts thereof, for use in the treatment of cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. Also additionally provided herein is the use of compounds of Formula I, or pharmaceutically acceptable salts thereof, in the manufacture of a medicament for treating cancer, in particular for the treatment of lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

DETAILED DESCRIPTION

Novel inhibitors of the KRAS gain of function mutation G12V are described herein. These new compounds could address the needs noted above for inhibitors of KRAS GTP activity in gain of function mutants in the treatment of cancers such as lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. Some of these new KRAS G12V mutant inhibitor compounds are selective to KRAS G12V mutants over wild-type KRAS, preferably they are also selective over hRAS and nRAS. Additionally, some of these new selective KRAS G12V mutant inhibitor compounds are also inhibitors of other mutant types such as KRAS G12C or G12D. Some of these new KRAS G12V mutant inhibitor compounds have good oral bioavailability and good target coverage (KRAS G12V mutant inhibition).

The present invention provides a compound of Formula I:

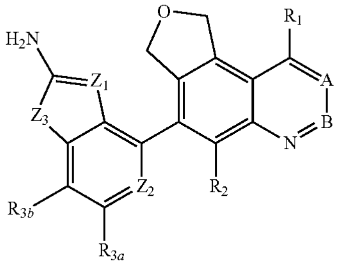

wherein A, B, $R_1$, $R_2$, $R_{3a}$, $R_{3b}$, $Z_1$, $Z_2$, and $Z_3$ are as defined above, or a pharmaceutically acceptable salt thereof. In some embodiments, the compound of Formula I is represented by Formula I':

Formula I'

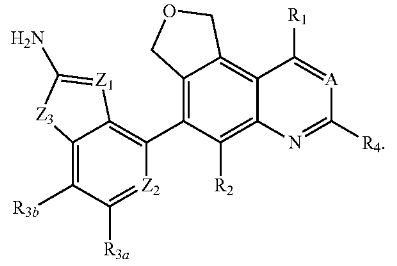

The present invention provides a compound of Formula I':

Formula I'

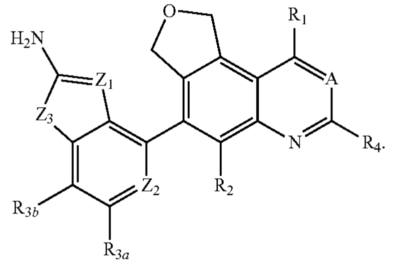

wherein $R_1$, $R_2$, $R_{3a}$, $R_{3b}$, $R_4$, $Z_1$, $Z_2$, and $Z_3$ are as defined above, or a pharmaceutically acceptable salt thereof.

As used herein, the term halogen means fluoro (F), chloro (Cl), bromo (Br), or iodo (I). As used herein, the term alkyl means saturated linear or branched-chain monovalent hydrocarbon radicals of one to a specified number of carbon atoms, e.g., "$C_{1-4}$ alkyl" or "$C_{1-3}$ alkyl." Examples of alkyls include, but are not limited to, methyl, ethyl, propyl, 1-propyl, isopropyl, butyl, and iso-butyl.

As used herein, the term "heterocyclyl" or "heterocycle" means mono, or polycyclic rings containing 3-24 atoms, preferably 3-10 atoms, which include carbon, and one, or more heteroatoms selected from N, O, S, P, and B, preferably 1, 2, 3, or 4 heteroatoms selected from N, O, and S, and wherein the rings are not aromatic. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

In an embodiment of a compound of Formula I, or a pharmaceutically acceptable salt thereof, $R_1$ is a group of formula

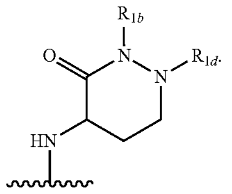

In an embodiment, $R_{1b}$ is methyl, or a pharmaceutically acceptable salt thereof. In an embodiment, $R_{1d}$ is methyl or ethyl, or a pharmaceutically acceptable salt thereof. In an embodiment, $R_{1d}$ is methyl, or a pharmaceutically acceptable salt thereof. In an embodiment, $R_{1d}$ is ethyl, or a pharmaceutically acceptable salt thereof. In an embodiment, $R_{1b}$ is methyl, and $R_{1d}$ is methyl or ethyl, or a pharmaceutically acceptable salt thereof. In an embodiment, $R_{1b}$ is methyl, and $R_{1d}$ is methyl, or a pharmaceutically acceptable salt thereof. In an embodiment, $R_{1b}$ is methyl, and $R_{1d}$ is ethyl, or a pharmaceutically acceptable salt thereof. In an embodiment, $R_{1b}$ is methyl, and $R_{1d}$ is $C_{3-4}$ cycloalkyl, or a pharmaceutically acceptable salt thereof. In an embodiment, $R_{1b}$ is methyl, and $R_{1d}$ is cyclopropyl, or a pharmaceutically acceptable salt thereof.

In an embodiment of a compound of Formula I, or a pharmaceutically acceptable salt thereof, $R_1$ is a group of formula

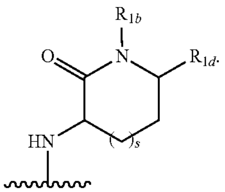

In an embodiment, $R_{1b}$ is methyl, or a pharmaceutically acceptable salt thereof. In an embodiment, $R_{1d}$ is methyl, ethyl, or difluoromethyl, or a pharmaceutically acceptable salt thereof. In an embodiment, $R_{1d}$ is methyl, or a pharmaceutically acceptable salt thereof. In an embodiment, $R_{1d}$ is ethyl, or a pharmaceutically acceptable salt thereof. In an embodiment, $R_{1b}$ is methyl, and $R_{1d}$ is methyl or ethyl, or a pharmaceutically acceptable salt thereof. In an embodiment, $R_{1b}$ is methyl, and $R_{1d}$ is methyl, or a pharmaceutically acceptable salt thereof. In an embodiment, $R_{1b}$ is methyl, and $R_{1d}$ is ethyl, or a pharmaceutically acceptable salt thereof. In an embodiment, $R_{1b}$ is methyl, and $R_{1d}$ is difluoromethyl, or a pharmaceutically acceptable salt thereof.

In an embodiment of a compound of Formula I, or a pharmaceutically acceptable salt thereof, A is —N—.

In an embodiment of a compound of Formula I, or a pharmaceutically acceptable salt thereof, A is —C(H)—.

In an embodiment of a compound of Formula I, or a pharmaceutically acceptable salt thereof, B is —N—.

In an embodiment of a compound of Formula I, or a pharmaceutically acceptable salt thereof, B is —C(H)—.

In an embodiment of a compound of Formula I, or a pharmaceutically acceptable salt thereof, B is —C($R_4$)—.

In an embodiment of a compound of Formula I, or a pharmaceutically acceptable salt thereof, $R_1$ is a group of formula

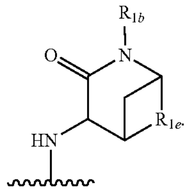

In an embodiment, $R_{1b}$ is methyl, or a pharmaceutically acceptable salt thereof. In an embodiment, $R_{1e}$ is methylene, or a pharmaceutically acceptable salt thereof. In an embodiment, $R_{1b}$ is methyl, and $R_{1e}$ is methylene, or a pharmaceutically acceptable salt thereof.

In an embodiment of a compound of Formula I, or a pharmaceutically acceptable salt thereof, $R_1$ is a group of formula

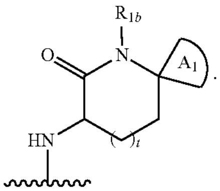

In an embodiment, $R_{1b}$ is methyl, or a pharmaceutically acceptable salt thereof. In an embodiment, $R_{1b}$ is H, or a pharmaceutically acceptable salt thereof. In an embodiment, Ring $A_1$ is $C_{3-4}$ cycloalkyl, or a pharmaceutically acceptable salt thereof. In an embodiment, Ring $A_1$ is cyclopropyl, or a pharmaceutically acceptable salt thereof. In an embodiment, Ring $A_1$ is cyclobutyl, or a pharmaceutically acceptable salt thereof. In an embodiment, t is 0 or 1. In an embodiment, t is 0. In an embodiment, t is 1. In an embodiment, Ring $A_1$ is a 3- or 4-membered heterocycle containing a heteroatom selected from N, O, and S, or a pharmaceutically acceptable salt thereof. In an embodiment, Ring $A_1$ is oxetanyl, or a pharmaceutically acceptable salt thereof. In an embodiment, $R_{1b}$ is methyl, and Ring $A_1$ is $C_{3-4}$ cycloalkyl, or a pharmaceutically acceptable salt thereof. In an embodiment, $R_{1b}$ is hydrogen, and Ring $A_1$ is $C_{3-4}$ cycloalkyl, or a pharmaceutically acceptable salt thereof. In an embodiment, $R_{1b}$ is methyl, and Ring $A_1$ is cyclopropyl, or a pharmaceutically acceptable salt thereof. In an embodiment, $R_{1b}$ is hydrogen, and Ring $A_1$ is cyclopropyl, or a pharmaceutically acceptable salt thereof. In an embodiment, $R_{1b}$ is methyl, and Ring $A_1$ is cyclobutyl, or a pharmaceutically acceptable salt thereof. In an embodiment, $R_{1b}$ is hydrogen, and Ring $A_1$ is cyclobutyl, or a pharmaceutically acceptable salt thereof. In an embodiment, $R_{1b}$ is methyl, and Ring $A_1$ is a 3- or 4-membered heterocycle containing a heteroatom selected from N, O, and S, or a pharmaceutically acceptable salt thereof. In an embodiment, $R_{1b}$ is methyl, and Ring $A_1$ is oxetanyl, or a pharmaceutically acceptable salt thereof.

In an embodiment of a compound of Formula I, or a pharmaceutically acceptable salt thereof, $R_1$ is a group of formula

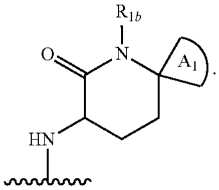

In an embodiment, $R_{1b}$ is methyl, or a pharmaceutically acceptable salt thereof. In an embodiment, Ring $A_1$ is $C_{3-4}$ cycloalkyl, or a pharmaceutically acceptable salt thereof. In an embodiment, Ring $A_1$ is cyclopropyl, or a pharmaceutically acceptable salt thereof. In an embodiment, Ring $A_1$ is cyclobutyl, or a pharmaceutically acceptable salt thereof. In an embodiment, Ring $A_1$ is a 3- or 4-membered heterocycle containing a heteroatom selected from N, O, and S, or a pharmaceutically acceptable salt thereof. In an embodiment, Ring $A_1$ is oxetanyl, or a pharmaceutically acceptable salt thereof. In an embodiment, $R_{1b}$ is methyl, and Ring $A_1$ is $C_{3-4}$ cycloalkyl, or a pharmaceutically acceptable salt thereof. In an embodiment, $R_{1b}$ is methyl, and Ring $A_1$ is cyclopropyl, or a pharmaceutically acceptable salt thereof. In an embodiment, $R_{1b}$ is methyl, and Ring $A_1$ is cyclobutyl, or a pharmaceutically acceptable salt thereof. In an embodiment, $R_{1b}$ is methyl, and Ring $A_1$ is a 3- or 4-membered heterocycle containing a heteroatom selected from N, O, and S, or a pharmaceutically acceptable salt thereof. In an embodiment, $R_{1b}$ is methyl, and Ring $A_1$ is oxetanyl, or a pharmaceutically acceptable salt thereof.

In an embodiment of a compound of Formula I, or a pharmaceutically acceptable salt thereof, $R_1$ is a group of formula

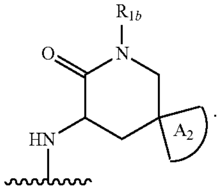

In an embodiment, $R_{1b}$ is methyl, or a pharmaceutically acceptable salt thereof. In an embodiment, Ring $A_2$ is $C_{3-4}$ cycloalkyl, or a pharmaceutically acceptable salt thereof. In an embodiment, Ring $A_2$ is cyclopropyl, or a pharmaceutically acceptable salt thereof. In an embodiment, Ring $A_2$ is cyclobutyl, or a pharmaceutically acceptable salt thereof. In an embodiment, Ring $A_2$ is a 3- or 4-membered heterocycle containing a heteroatom selected from N, O, and S, or a pharmaceutically acceptable salt thereof. In an embodiment, Ring $A_2$ is oxetanyl, or a pharmaceutically acceptable salt thereof. In an embodiment, $R_{1b}$ is methyl, and Ring $A_2$ is $C_{3-4}$ cycloalkyl, or a pharmaceutically acceptable salt thereof. In an embodiment, $R_{1b}$ is methyl, and Ring $A_2$ is cyclopropyl, or a pharmaceutically acceptable salt thereof. In an embodiment, $R_{1b}$ is methyl, and Ring $A_2$ is cyclobutyl, or a pharmaceutically acceptable salt thereof. In an embodiment, $R_{1b}$ is methyl, and Ring $A_2$ is a 3- or 4-membered heterocycle containing a heteroatom selected from N, O, and S, or a pharmaceutically acceptable salt thereof. In an embodiment, $R_{1b}$ is methyl, and Ring $A_2$ is oxetanyl, or a pharmaceutically acceptable salt thereof.

In an embodiment of a compound of Formula I, or a pharmaceutically acceptable salt thereof, $R_1$ is a group of formula

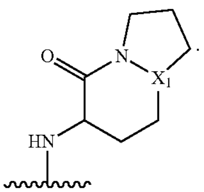

In an embodiment, $X_1$ is —CH—, or a pharmaceutically acceptable salt thereof. In an embodiment, $X_1$ is —N—, or a pharmaceutically acceptable salt thereof.

In an embodiment of a compound of Formula I, or a pharmaceutically acceptable salt thereof, $R_1$ is a group of formula

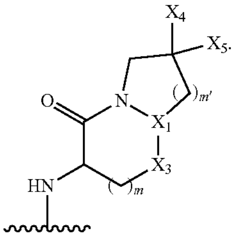

In an embodiment, $X_1$ is —CH—, or a pharmaceutically acceptable salt thereof. In an embodiment, $X_1$ is —N—, or a pharmaceutically acceptable salt thereof. In an embodiment, $X_3$ is —O—, or a pharmaceutically acceptable salt thereof. In an embodiment, $X_3$ is —$CH_2$—, or a pharmaceutically acceptable salt thereof. In an embodiment, $X_4$ and $X_5$ are each halogen, or a pharmaceutically acceptable salt thereof. In an embodiment, $X_4$ and $X_5$ are each fluoro, or a pharmaceutically acceptable salt thereof. In an embodiment, $X_4$ is hydrogen, and $X_5$ is halogen (preferably fluoro), or a pharmaceutically acceptable salt thereof. In an embodiment, $X_4$ and $X_5$ are each hydrogen, or a pharmaceutically acceptable salt thereof. In an embodiment, $X_4$ is $C_{1-3}$ alkyl, and $X_5$ is hydrogen, or a pharmaceutically acceptable salt thereof. In an embodiment, $X_4$ is $C_{1-3}$ alkyl, and $X_5$ is halogen (preferably fluoro), or a pharmaceutically acceptable salt thereof. In an embodiment, m and m' are each 1. In an embodiment, m is 1 and m' is 0.

In an embodiment of a compound of Formula I, or a pharmaceutically acceptable salt thereof, $R_1$ is a group of formula

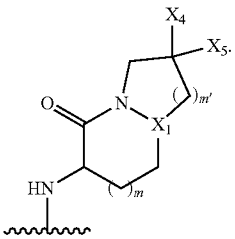

In an embodiment, $X_1$ is —CH—, or a pharmaceutically acceptable salt thereof. In an embodiment, $X_1$ is —N—, or a pharmaceutically acceptable salt thereof. In an embodiment, $X_4$ is halogen, and $X_5$ is halogen, or a pharmaceutically acceptable salt thereof. In an embodiment, $X_4$ is fluoro, and $X_5$ is fluoro, or a pharmaceutically acceptable salt thereof. In an embodiment, $X_4$ is hydrogen, and $X_5$ is halogen (preferably fluoro), or a pharmaceutically acceptable salt thereof. In an embodiment, $X_4$ is hydrogen, and $X_5$ is hydrogen, or a pharmaceutically acceptable salt thereof. In an embodiment, $X_4$ is $C_{1-3}$ alkyl, and $X_5$ is hydrogen, or a pharmaceutically acceptable salt thereof. In an embodiment, $X_4$ is $C_{1-3}$ alkyl, and $X_5$ is halogen (preferably fluoro), or a pharmaceutically acceptable salt thereof. In an embodiment, m and m' are each 1. In an embodiment, m is 1 and m' is 0.

In an embodiment of a compound of Formula I, or a pharmaceutically acceptable salt thereof, $R_1$ is a group of formula

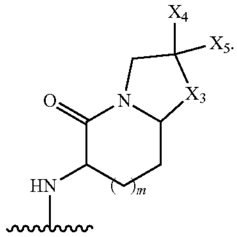

In an embodiment, $X_3$ is —CH—, or a pharmaceutically acceptable salt thereof. In an embodiment, $X_3$ is —O—, or a pharmaceutically acceptable salt thereof. In an embodiment, $X_4$ and $X_5$ are hydrogen, or a pharmaceutically acceptable salt thereof. In an embodiment, $X_4$ is $C_{1-2}$ alkyl, and $X_5$ is hydrogen, or a pharmaceutically acceptable salt thereof. In an embodiment, $X_4$ is methyl, and $X_5$ is hydrogen, or a pharmaceutically acceptable salt thereof. In an embodiment, m is 1.

In an embodiment of a compound of Formula I, or a pharmaceutically acceptable salt thereof, $R_1$ is a group of formula

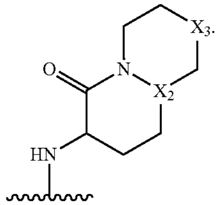

In an embodiment, $X_2$ is —CH—, or a pharmaceutically acceptable salt thereof. In an embodiment, $X_2$ is —N—, or a pharmaceutically acceptable salt thereof. In an embodiment, $X_3$ is —$CH_2$—, or a pharmaceutically acceptable salt thereof. In an embodiment, $X_3$ is —O—, or a pharmaceutically acceptable salt thereof. In an embodiment, $X_2$ is —CH—, and $X_3$ is —$CH_2$—, or a pharmaceutically acceptable salt thereof. In an embodiment, $X_2$ is —N—, and $X_3$ is —$CH_2$—, or a pharmaceutically acceptable salt thereof. In an embodiment, $X_2$ is —CH—, and $X_3$ is —O—, or a pharmaceutically acceptable salt thereof.

In an embodiment of a compound of Formula I, or a pharmaceutically acceptable salt thereof, $R_1$ is a group of the formula

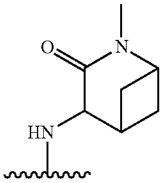 , 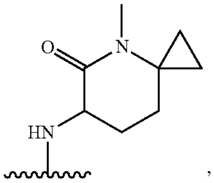 ,

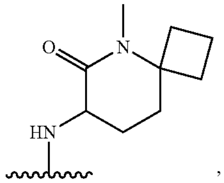 , 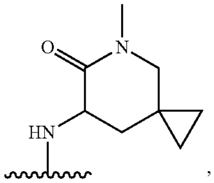 ,

-continued

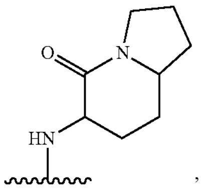 , 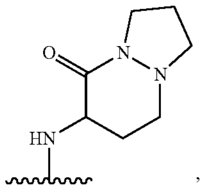 , or

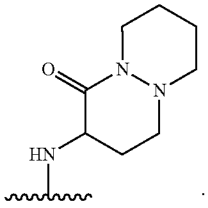 .

In an embodiment of a compound of Formula I, or a pharmaceutically acceptable salt thereof, $R_1$ is a group of the formula

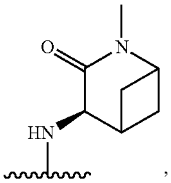 , 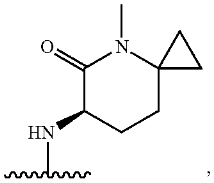 ,

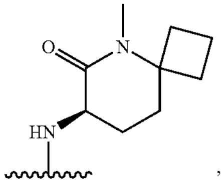 , 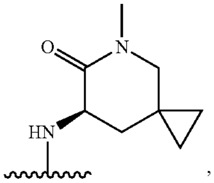 ,

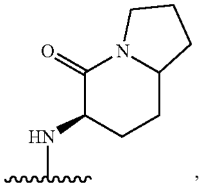 , 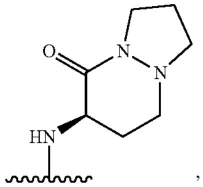 , or

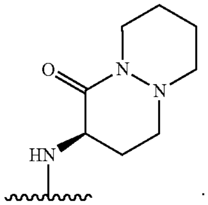 .

In an embodiment of a compound of Formula I, or a pharmaceutically acceptable salt thereof, $R_1$ is a group of the formula

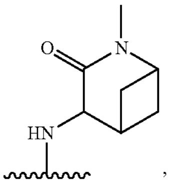 , 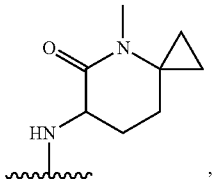 ,

-continued
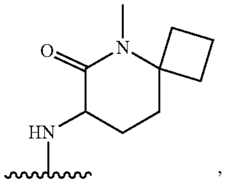,
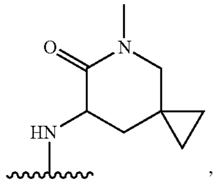,
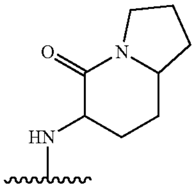,
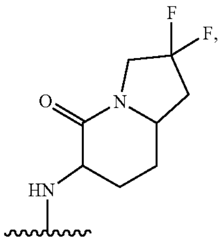
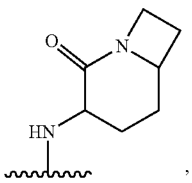,
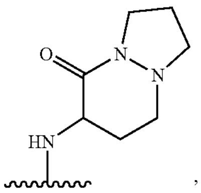,
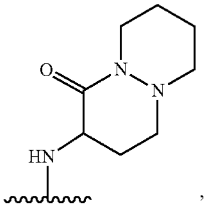,
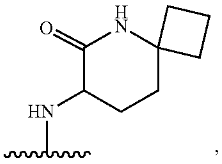,
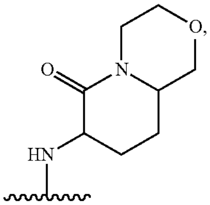 or
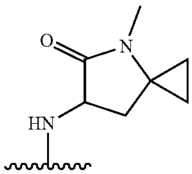.
In an embodiment of a compound of Formula I, or a pharmaceutically acceptable salt thereof, $R_1$ is a group of the formula
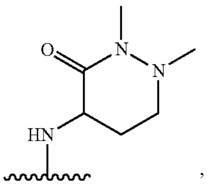,
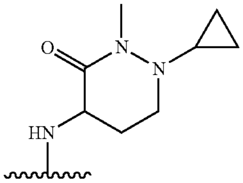,
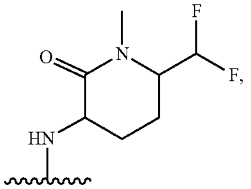
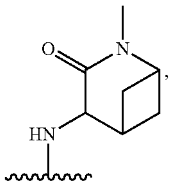
-continued
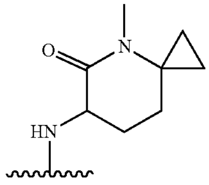,
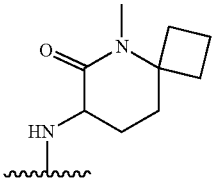,
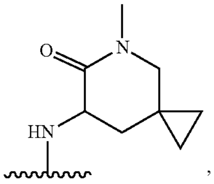,
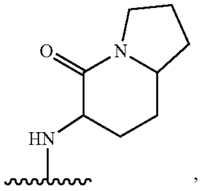,
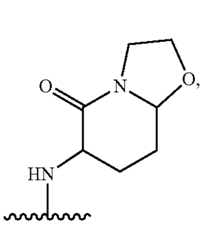
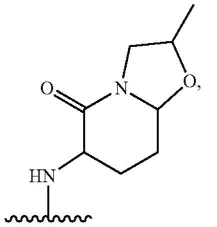,
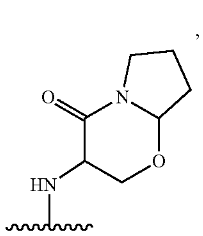
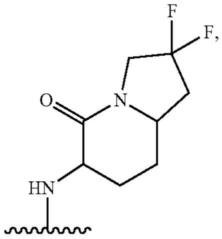
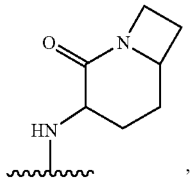,
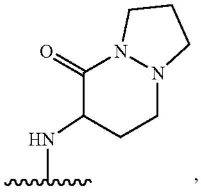,
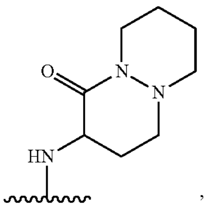,
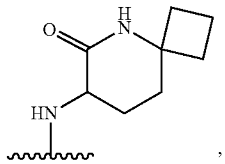,
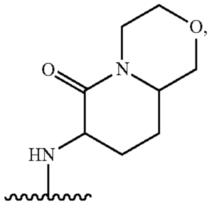 or
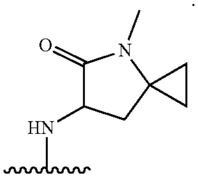.
In an embodiment of a compound of Formula I, or a pharmaceutically acceptable salt thereof, $R_1$ is a group of the formula

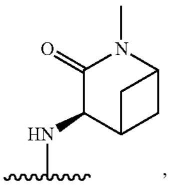
,
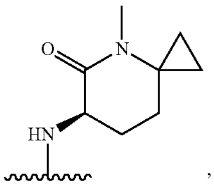
,
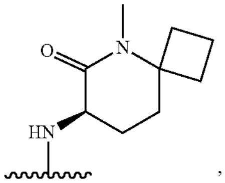
,
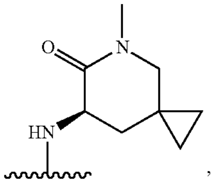
,
,
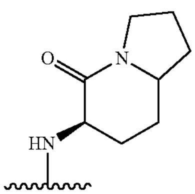
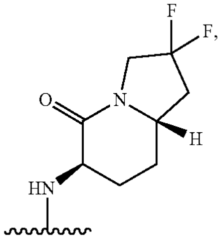
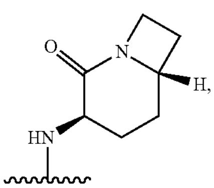
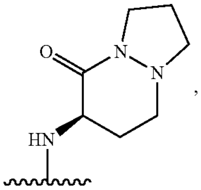
,
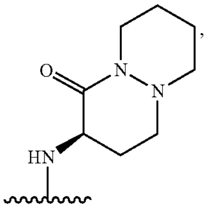
, or
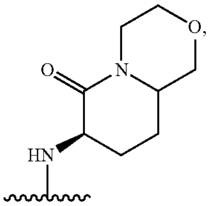

In an embodiment of a compound of Formula I, or a pharmaceutically acceptable salt thereof, $R_1$ is a group of the formula

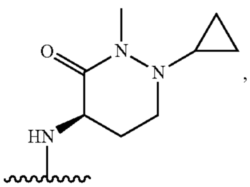
,
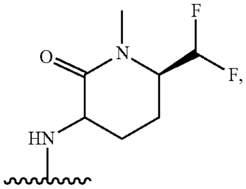
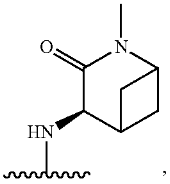
,
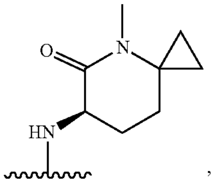
,
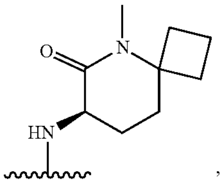
,
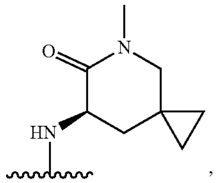
,

-continued

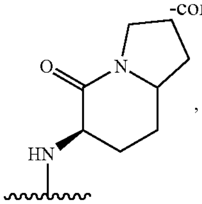
,
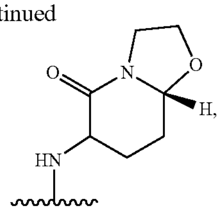
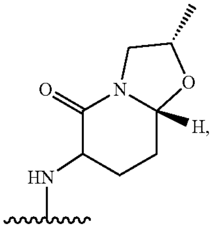
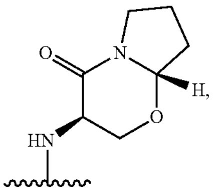
,
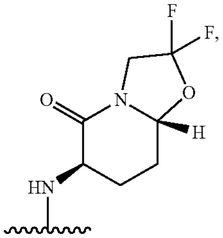
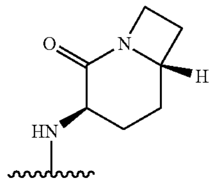
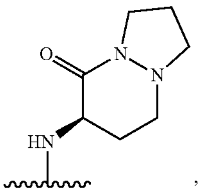
,
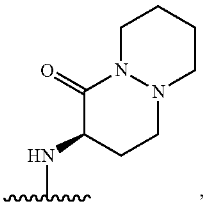
, or
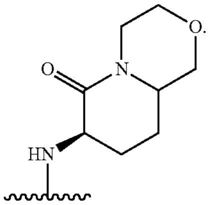

In an embodiment of a compound of Formula I, or a pharmaceutically acceptable salt thereof, $R_2$ is F, Cl, or methyl.

In an embodiment of a compound of Formula I or a pharmaceutically acceptable salt thereof, $R_2$ is F or Cl.

In an embodiment of a compound of Formula I, or a pharmaceutically acceptable salt thereof, $R_2$ is F.

In an embodiment of a compound of Formula I, or a pharmaceutically acceptable salt thereof, $R_2$ is Cl.

In an embodiment of a compound of Formula I, or a pharmaceutically acceptable salt thereof, $R_2$ is methyl.

In an embodiment of a compound of Formula I, or a pharmaceutically acceptable salt thereof, $Z_1$ is —C(CN)—, $Z_2$ is —C($R_{3c}$)—, and $Z_3$ is —S—. In an embodiment, $Z_1$ is —C(CN)—, $Z_2$ is —C($R_{3c}$)—, $Z_3$ is —S—, and $R_{3a}$ is H. In an embodiment, $Z_1$ is —C(CN)—, $Z_2$ is —C($R_{3c}$)—, $Z_3$ is —S—, $R_{3a}$ is H, $R_{3b}$ is halogen (preferably fluoro), and $R_{3c}$ is H. In an embodiment, $Z_1$ is —C(CN)—, $Z_2$ is —C($R_{3c}$)—, $Z_3$ is —S—, $R_{3a}$ is H, $R_{3b}$ is H, and $R_{3c}$ is halogen (preferably fluoro). In an embodiment, $Z_1$ is —C(CN)—, $Z_2$ is —C($R_{3c}$)—, $Z_3$ is —S—, $R_{3a}$ is H, $R_{3b}$ is halogen (preferably fluoro), and $R_{3c}$ is halogen (preferably fluoro).

In an embodiment of a compound of Formula I, or a pharmaceutically acceptable salt thereof, $Z_1$ is —C(CN)—, $Z_2$ is —N—, and $Z_3$ is —S—. In an embodiment, $Z_1$ is —C(CN)—, $Z_2$ is —N—, $Z_3$ is —S—, and $R_{3a}$ is H. In an embodiment, $Z_1$ is —C(CN)—, $Z_2$ is —N—, $Z_3$ is —S—, $R_{3a}$ is H, and $R_{3b}$ is halogen (preferably fluoro).

In an embodiment of a compound of Formula I, or a pharmaceutically acceptable salt thereof, $Z_1$ is —N—, $Z_2$ is —C($R_{3c}$)—, and $Z_3$ is —S—. In an embodiment, $Z_1$ is —N—, $Z_2$ is —C($R_{3c}$)—, $Z_3$ is —S—, and $R_{3a}$ is H. In an embodiment, $Z_1$ is —N—, $Z_2$ is —C($R_{3c}$)—, $Z_3$ is —S—, $R_{3a}$ is H, $R_{3b}$ is halogen (preferably fluoro), and $R_{3c}$ is H. In an embodiment, $Z_1$ is —N—, $Z_2$ is —C($R_{3c}$)—, $Z_3$ is —S—, $R_{3a}$ is H, $R_{3b}$ is H, and $R_{3c}$ is halogen (preferably fluoro). In an embodiment, $Z_1$ is —N—, $Z_2$ is —C($R_{3c}$)—, $Z_3$ is —S—, $R_{3a}$ is H, $R_{3b}$ is halogen (preferably fluoro), and $R_{3c}$ is halogen (preferably fluoro). In an embodiment, $Z_1$ is —N—, $Z_2$ is —C($R_{3c}$)—, $Z_3$ is —S—, $R_{3a}$ is H, $R_{3b}$ is H, and $R_{3c}$ is H.

In an embodiment of a compound of Formula I, or a pharmaceutically acceptable salt thereof, $Z_1$ is —N—, $Z_2$ is —N—, and $Z_3$ is —S—. In an embodiment, $Z_1$ is —N—, $Z_2$ is —N—, $Z_3$ is —S—, and $R_{3a}$ is H. In an embodiment, $Z_1$ is —N—, $Z_2$ is —N—, $Z_3$ is —S—, $R_{3a}$ is H, and $R_{3b}$ is halogen (preferably fluoro).

In an embodiment of a compound of Formula I, or a pharmaceutically acceptable salt thereof, $Z_1$ is —C(CN)—, $Z_2$ is —C($R_{3c}$)—, and $Z_3$ is —O—. In an embodiment, $Z_1$ is —C(CN)—, $Z_2$ is —C($R_{3c}$)—, $Z_3$ is —O—, and $R_{3a}$ is H. In an embodiment, $Z_1$ is —C(CN)—, $Z_2$ is —C($R_{3c}$)—, $Z_3$ is —O—, $R_{3a}$ is H, $R_{3b}$ is halogen (preferably fluoro), and $R_{3c}$ is H. In an embodiment, $Z_1$ is —C(CN)—, $Z_2$ is —C($R_{3c}$)—, $Z_3$ is —O—, $R_{3a}$ is H, $R_{3b}$ is H, and $R_{3c}$ is halogen (preferably fluoro). In an embodiment, $Z_1$ is —C(CN)—, $Z_2$ is —C($R_{3c}$)—, $Z_3$ is —O—, $R_{3a}$ is H, $R_{3b}$ is halogen (preferably fluoro), and $R_{3c}$ is halogen (preferably fluoro).

In an embodiment of a compound of Formula I, or a pharmaceutically acceptable salt thereof, $Z_1$ is —C(CN)—, $Z_2$ is —N—, and $Z_3$ is —O—. In an embodiment, $Z_1$ is —C(CN)—, $Z_2$ is —N—, $Z_3$ is —O—, and $R_{3a}$ is H. In an embodiment, $Z_1$ is —C(CN)—, $Z_2$ is —N—, $Z_3$ is —O—, $R_{3a}$ is H, and $R_{3b}$ is halogen (preferably fluoro).

In an embodiment of a compound of Formula I, or a pharmaceutically acceptable salt thereof, $Z_1$ is —N—, $Z_2$ is —C($R_{3c}$)—, and $Z_3$ is —O—. In an embodiment, $Z_1$ is —N—, $Z_2$ is —C($R_{3c}$)—, $Z_3$ is —O—, and $R_{3a}$ is H. In an embodiment, $Z_1$ is —N—, $Z_2$ is —C($R_{3c}$)—, $Z_3$ is —O—, $R_{3a}$ is H, $R_{3b}$ is halogen (preferably fluoro), and $R_{3c}$ is H. In an embodiment, $Z_1$ is —N—, $Z_2$ is —C($R_{3c}$)—, $Z_3$ is —O—, $R_{3a}$ is H, $R_{3b}$ is H, and $R_{3c}$ is halogen (preferably fluoro). In an embodiment, $Z_1$ is —N—, $Z_2$ is —C($R_{3c}$)—, $Z_3$ is —O—, $R_{3a}$ is H, $R_{3b}$ is halogen (preferably fluoro), and $R_{3c}$ is halogen (preferably fluoro). In an embodiment, $Z_1$ is —N—, $Z_2$ is —C($R_{3c}$)—, $Z_3$ is —O—, $R_{3a}$ is H, $R_{3b}$ is H, and $R_{3c}$ is H.

In an embodiment of a compound of Formula I, or a pharmaceutically acceptable salt thereof, $Z_1$ is —N—, $Z_2$ is —N—, and $Z_3$ is —O—. In an embodiment, $Z_1$ is —N—, $Z_2$ is —N—, $Z_3$ is —O—, and $R_{3a}$ is H. In an embodiment, $Z_1$ is —N—, $Z_2$ is —N—, $Z_3$ is —O—, $R_{3a}$ is H, and $R_{3b}$ is halogen (preferably fluoro).

In an embodiment of a compound of Formula I, or a pharmaceutically acceptable salt thereof, $R_4$ is H, $C_{1-3}$ alkyl, or $C_{1-3}$ alkoxy optionally substituted with 1, 2, 3, or 4 substituents independently selected from hydroxyl and methyl. In an embodiment of a compound of Formula I, or a pharmaceutically acceptable salt thereof, $R_4$ is H, $C_{1-3}$ alkyl, or $C_{1-3}$ alkoxy optionally substituted with 1, 2, or 3 substituents independently selected from hydroxyl and methyl. In an embodiment of a compound of Formula I, or a pharmaceutically acceptable salt thereof, $R_4$ is H, $C_{1-3}$ alkyl, or $C_{1-3}$ alkoxy optionally substituted with 3 substituents independently selected from hydroxyl and methyl. In an embodiment of a compound of Formula I, or a pharmaceutically acceptable salt thereof, $R_4$ is H, $C_{1-3}$ alkyl, or $C_{1-3}$ alkoxy optionally substituted with 2 substituents independently selected from hydroxyl and methyl. In an embodiment, $R_4$ is H. In an embodiment, $R_4$ is methyl. In an embodiment, $R_4$ is methoxy. In an embodiment, $R_4$ is

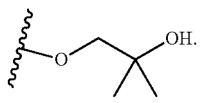 [SMILES: *OCC(C)(C)O]

In an embodiment of a compound of Formula I or a pharmaceutically acceptable salt thereof, $R_4$ is a group of the formula

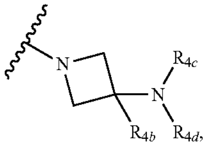

wherein $R_{4b}$ is H or methyl; and $R_{4c}$ and $R_{4d}$ are each independently $C_{1-3}$ alkyl. In an embodiment, $R_{4b}$ is H. In an embodiment, $R_{4b}$ is methyl.

In an embodiment of a compound of Formula I, or a pharmaceutically acceptable salt thereof, $R_4$ is a group of the formula

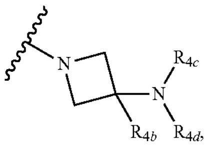

wherein $R_{4b}$ is H or methyl; and $R_{4c}$ and $R_{4d}$ are each independently $C_{1-3}$ alkyl. In an embodiment, $R_{4b}$ is H. In an embodiment, $R_{4b}$ is methyl. In an embodiment, $R_{4b}$ is H, and $R_{4c}$ and $R_{4d}$ together with the nitrogen atom to which they are attached form 4-, 5-, or 6-membered heterocycle. In an embodiment of a compound of Formula I, or a pharmaceutically acceptable salt thereof, $R_{4b}$ is H, and $R_{4c}$ and $R_{4d}$ together with the nitrogen atom to which they are attached form a 4-membered heterocycle (e.g., azetidinyl).

In an embodiment of a compound of Formula I, or a pharmaceutically acceptable salt thereof, $R_4$ is a group of the formula

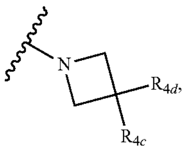

wherein $R_{4c}$ and $R_{4d}$ together with the carbon atom to which they are attached form a 4-, 5-, or 6-membered heterocycle.

In an embodiment of a compound of Formula I, or a pharmaceutically acceptable salt thereof, $R_{4c}$ and $R_{4d}$ together with the carbon atom to which they are attached form a 4-membered heterocycle (e.g., oxetanyl). In an embodiment of a compound of Formula I, or a pharmaceutically acceptable salt thereof, $R_{4c}$ and $R_{4d}$ together with the carbon atom to which they are attached form a 5-membered heterocycle. In an embodiment of a compound of Formula I, or a pharmaceutically acceptable salt thereof, $R_{4c}$ and $R_{4d}$ together with the carbon atom to which they are attached form a 6-membered heterocycle (e.g., tetrahydro-2H-pyran-4-yl, 1,4-dioxanyl).

In an embodiment of a compound of Formula I, or a pharmaceutically acceptable salt thereof, $R_4$ is a group of the formula

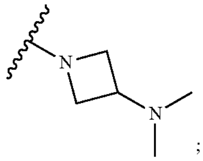 [SMILES: *N1CC(N(C)C)C1] ; 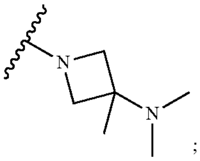 ; or

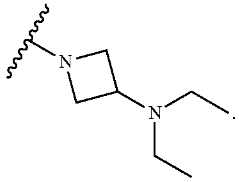 .

In an embodiment of a compound of Formula I, or a pharmaceutically acceptable salt thereof, $R_4$ is a group of the formula

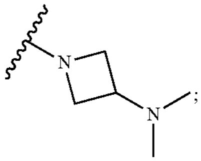 ;

In an embodiment of a compound of Formula I, or a pharmaceutically acceptable salt thereof, $R_4$ is a group of the formula

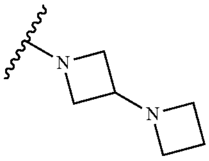 ; 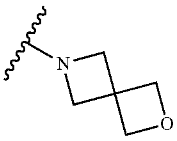 ;

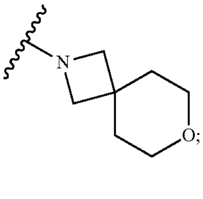 ; or 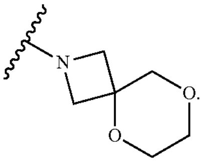 .

In an embodiment of a compound of Formula I, or a pharmaceutically acceptable salt thereof, $R_4$ is a group of the formula

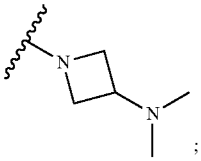 ; 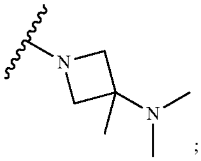 ;

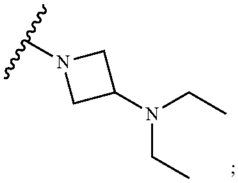 ; 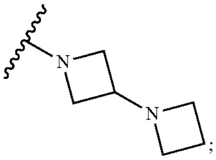 ;

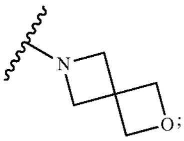 ; 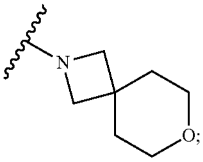 ; or

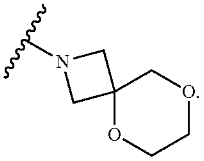 .

In an embodiment of a compound of Formula I, or a pharmaceutically acceptable salt thereof, $R_4$ is a group of the formula

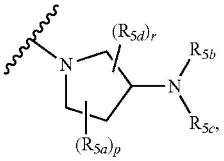 , wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5d}$ is $C_{1-3}$ alkyl, $R_{5b}$ and $R_{5c}$ are each independently H, $C_{1-5}$ alkyl optionally substituted with one or more deuterium (preferably trideuteromethyl), $C_{4-5}$ cycloalkyl optionally substituted with halogen (preferably F) or a $C_{1-3}$ haloalkyl (preferably fluoromethyl), or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle or a 6- or 7-membered spiro heterocycle, wherein each heterocycle or spiro heterocycle optionally contains a further heteroatom selected from N, O, and S, and wherein the heterocycle and the spiro heterocycle is each optionally substituted with one or more halogen (preferably F), deuterium, $C_{1-3}$ alkyl, or $C_{1-3}$ haloalkyl; or $R_{5a}$ and $R_{5b}$ together with the atoms to which they are attached form a 4-, 5-, or 6-membered heterocyclic fused ring optionally containing a further heteroatom selected from N, O, and S, $R_{5d}$ and $R_{5c}$ are each independently methyl; and p and r are each 0 or 1. In one embodiment, $R_{5b}$ and $R_{5c}$ are each independently H, $C_{1-5}$ alkyl optionally substituted with 1, 2, or 3 deuterium (e.g., trideuteromethyl), $C_{4-5}$ cycloalkyl optionally substituted with halogen (preferably F) or a $C_{1-3}$ haloalkyl (preferably fluoromethyl), or 3-, 4-, or 5-membered heterocycle containing a heteroatom selected from N, O, and S; In one embodiment, $R_{5b}$ and $R_{5c}$ together with the nitrogen atom to which they are attached form an optionally substituted 4-, 5-, or 6-membered heterocycle or a 6- or 7-membered spiro heterocycle, wherein each heterocycle or spiro heterocycle optionally contains a further heteroatom selected from N, O, and S, and wherein the heterocycle and the spiro heterocycle is each optionally substituted with 1, 2, 3, 4, 5, 6, 7, 8, 9, or 10 substituents selected from halogen (preferably F), deuterium, $C_{1-3}$ alkyl, or $C_{1-3}$ haloalkyl.

In an embodiment of a compound of Formula I, or a pharmaceutically acceptable salt thereof, $R_4$ is a group of the formula

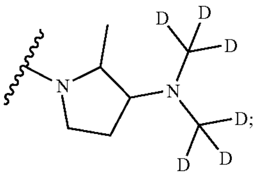

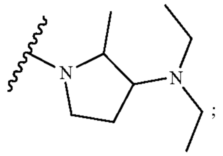

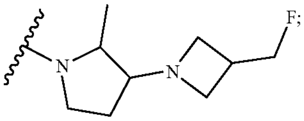

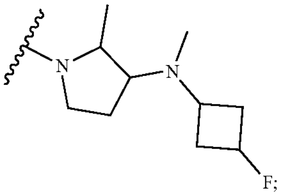

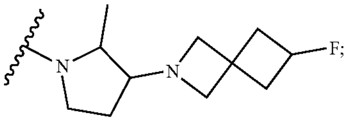

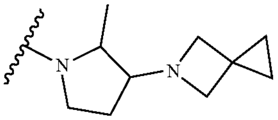

; or

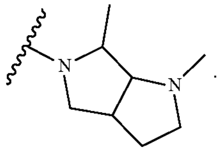

In an embodiment of a compound of Formula I, or a pharmaceutically acceptable salt thereof, $R_4$ is a group of the formula

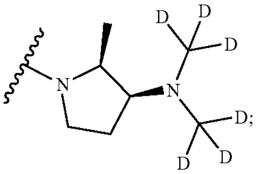

-continued

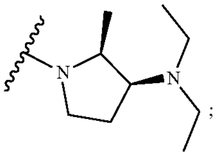

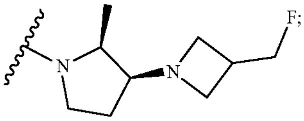

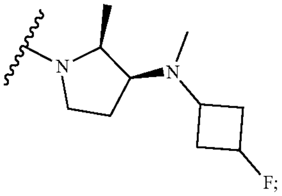

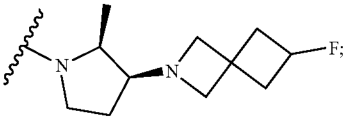

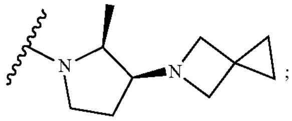

; or

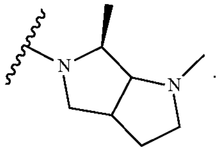

In an embodiment of a compound of Formula I, or a pharmaceutically acceptable salt thereof, $R_4$ is a group of the formula

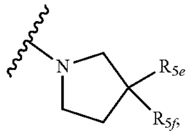

wherein $R_{5e}$ and $R_{5f}$ together with the carbon atom to which they are attached form a 4- or 5-membered heterocycle.

In an embodiment of a compound of Formula I, or a pharmaceutically acceptable salt thereof, $R_4$ is a group of the formula

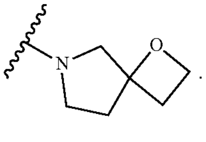 [SMILES: *N1CCC2(CCO2)C1]

In an embodiment of a compound of Formula I or a pharmaceutically acceptable salt thereof, $R_4$ is a group of the formula

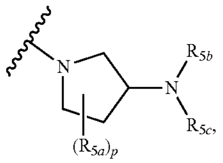

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p is 0 or 1.

In an embodiment of a compound of Formula I or a pharmaceutically acceptable salt thereof, $R_4$ is a group of the formula

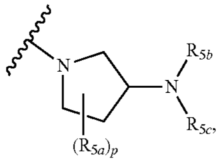

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; and p is 0 or 1. In an embodiment, $R_{5b}$ is H, $C_{1-6}$ alkyl, $C_{3-5}$ cycloalkyl, or 3-, 4-, or 5-membered heterocycle, and $R_{5c}$ is H or $C_{1-6}$ alkyl.

In an embodiment, $R_4$ is group of the formula:

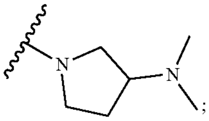 ; 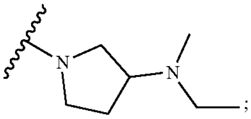 ;

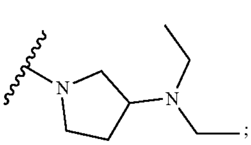 ; 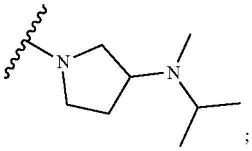 ;

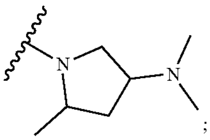 ; 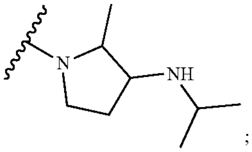 ;

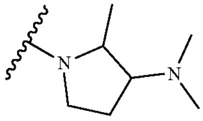 ; 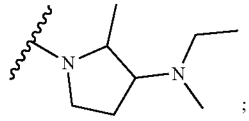 ;

-continued

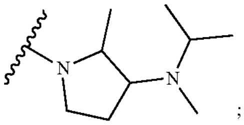 ; 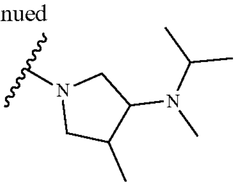 ;

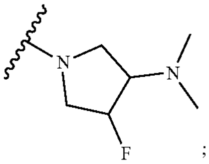 ; 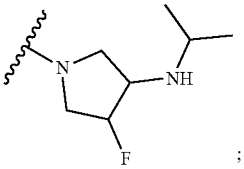 ;

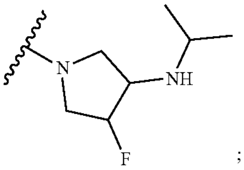 ; 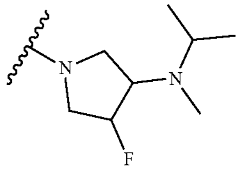 ;

; 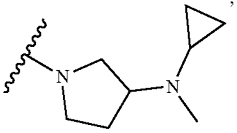 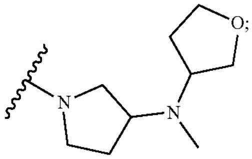 ;

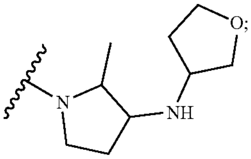 ; 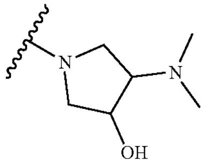 ;

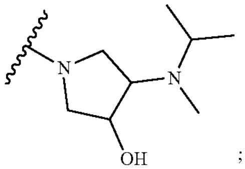 ; 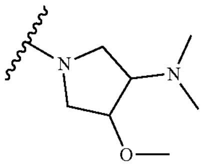 ; or

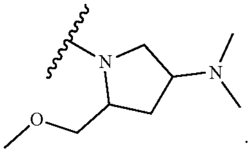 .

In an embodiment of a compound of Formula I or a pharmaceutically acceptable salt thereof, $R_4$ is a group of the formula

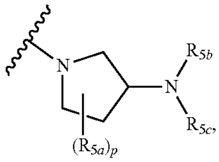

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; and p is 0 or 1. In an embodiment, $R_4$ is group of the formula:

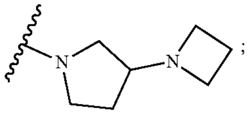

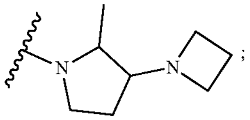

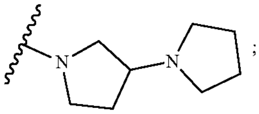

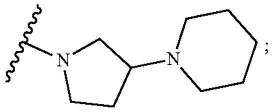

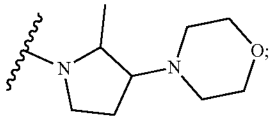

or

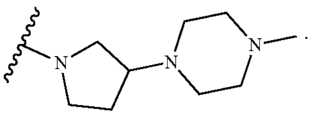

In an embodiment of a compound of Formula I, or a pharmaceutically acceptable salt thereof, $R_4$ is a group of the formula

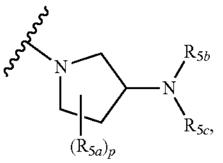

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; and p is 0 or 1. In an embodiment, $R_4$ is group of the formula:

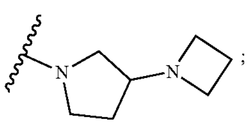

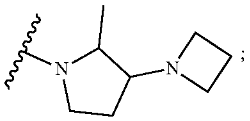

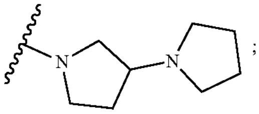

-continued

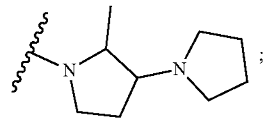

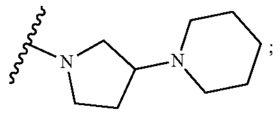

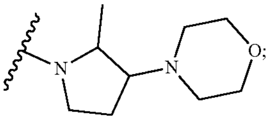

or

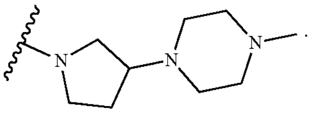

In an embodiment of a compound of Formula I or a pharmaceutically acceptable salt thereof, $R_4$ is a group of the formula

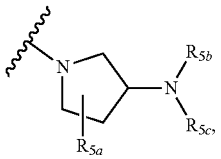

wherein $R_{5a}$ and $R_{5b}$ together with the atoms to which they are attached form a 4-, 5-, or 6-membered heterocyclic fused ring optionally containing a further heteroatom selected from N, O, and S; $R_{5c}$ is $C_{1-3}$ alkyl; and the 4-, 5-, or 6-membered fused ring is optionally further substituted with a $C_{1-3}$ alkyl. In an embodiment, $R_{5a}$ and $R_{5b}$ together with the atoms to which they are attached form a 4-membered heterocyclic fused ring, and $R_{5c}$ is $C_{1-3}$ alkyl. In an embodiment, $R_{5a}$ and $R_{5b}$ together with the atoms to which they are attached form a 5-membered heterocyclic fused ring, and $R_{5c}$ is $C_{1-3}$ alkyl. In an embodiment, $R_{5a}$ and $R_{5b}$ together with the atoms to which they are attached form a 6-membered heterocyclic fused ring, and $R_{5c}$ is $C_{1-3}$ alkyl. In an embodiment, $R_4$ is group of the formula:

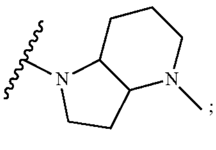

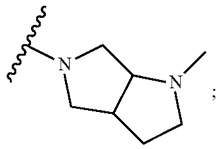

or

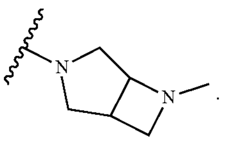

In an embodiment of a compound of Formula I or a pharmaceutically acceptable salt thereof, $R_4$ is a group of the formula

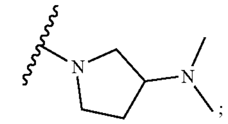
;
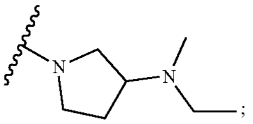
;
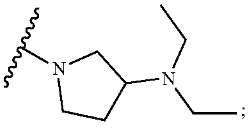
;
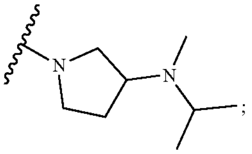
;
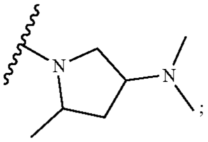
;
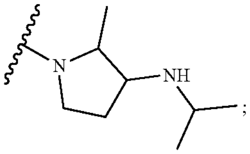
;
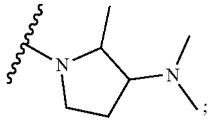
;
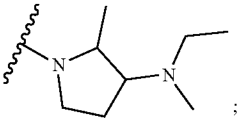
;
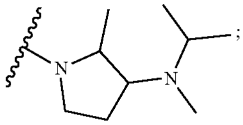
;
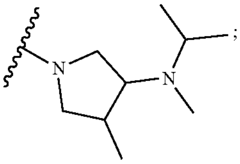
;
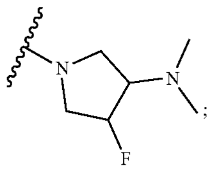
;
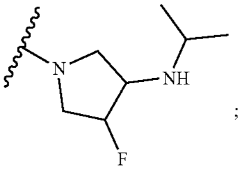
;
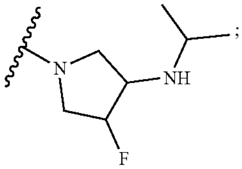
;
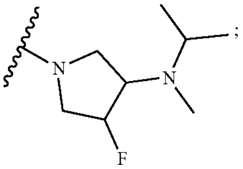
;
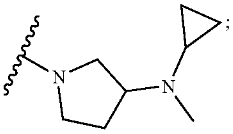
;
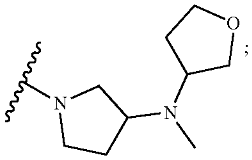
;
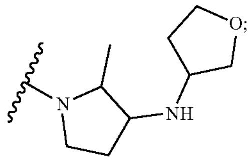
;
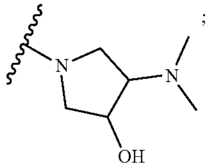
;
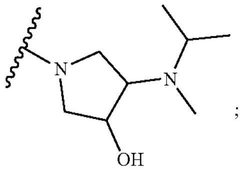
;
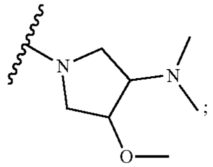
;
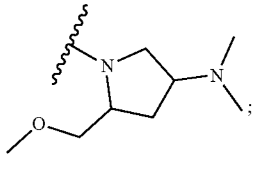
;
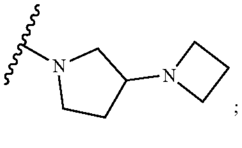
;
-continued
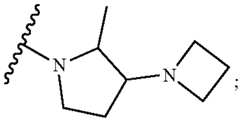
;
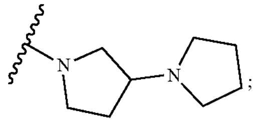
;
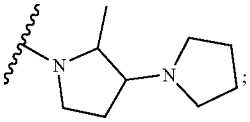
;
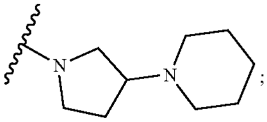
;
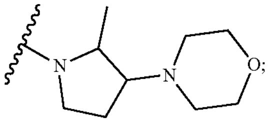
;
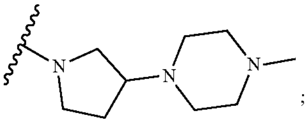
;
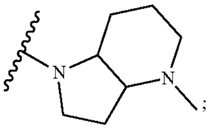
;
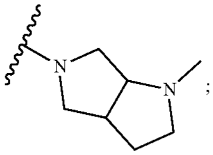
; or
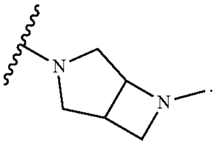
.
In an embodiment of a compound of Formula I, or a pharmaceutically acceptable salt thereof, $R_4$ is a group of the formula
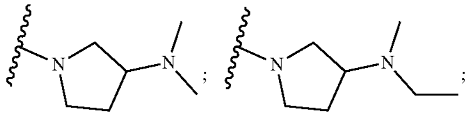
; ;
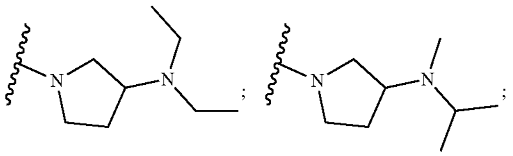
; ;
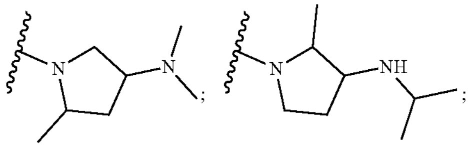
; ;
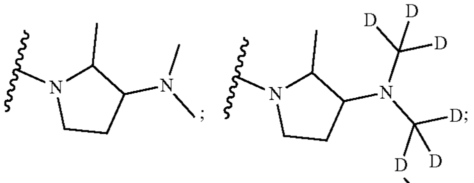
; ;
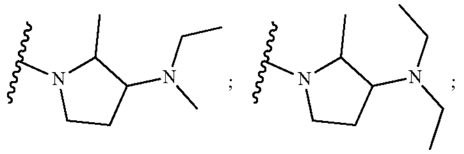
; ;
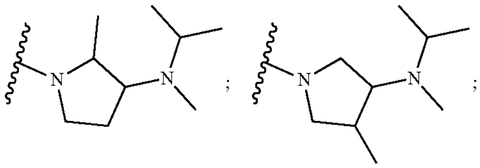
; ;

-continued

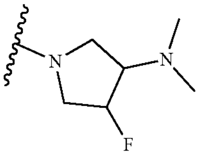 ;
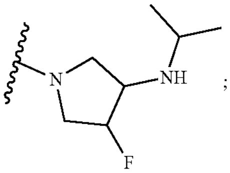 ;
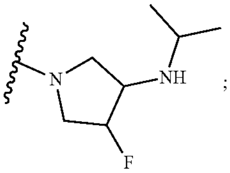 ;
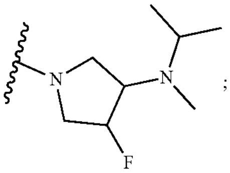 ;
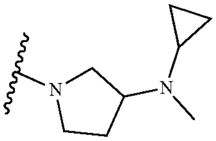 ;
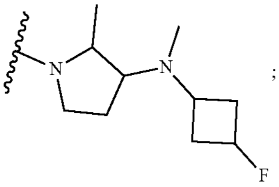 ;
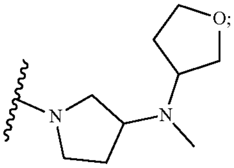
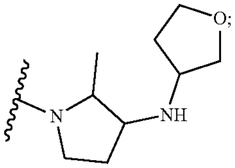
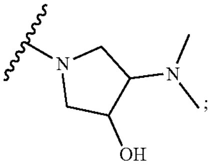
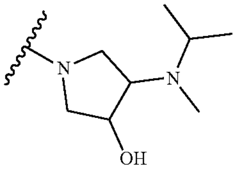 ;
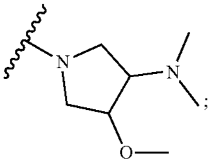
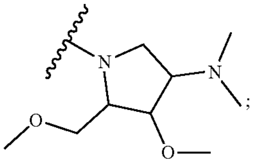
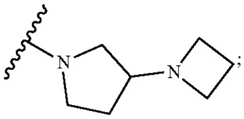
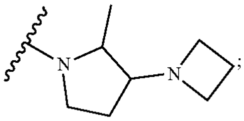
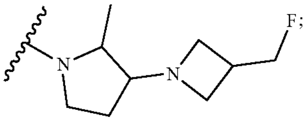
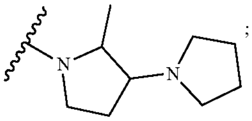 ;
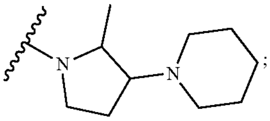
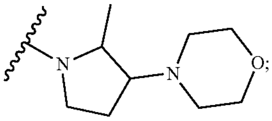
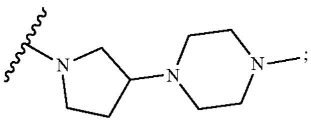
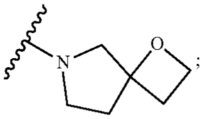
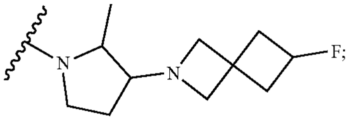

-continued

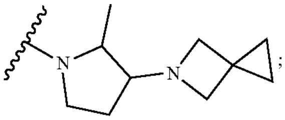
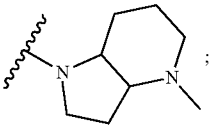 ;
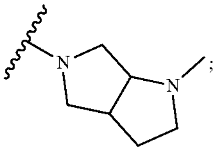
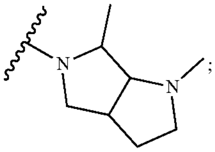 or
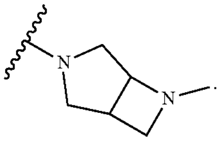

In an embodiment of a compound of Formula I or a pharmaceutically acceptable salt thereof, $R_4$ is a group of the formula

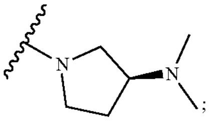
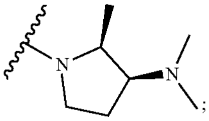
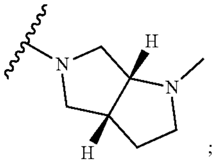 ;
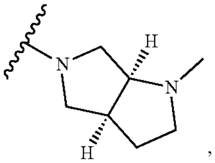 , or
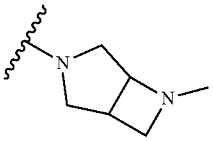 .

In an embodiment of a compound of Formula I or a pharmaceutically acceptable salt thereof, $R_4$ is a group of the formula

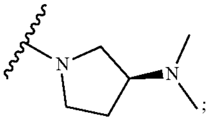
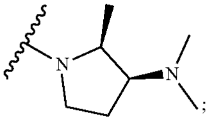
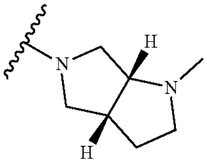 ; or
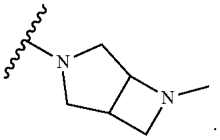 .

In an embodiment of a compound of Formula I or a pharmaceutically acceptable salt thereof, $R_4$ is a group of the formula

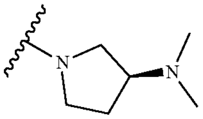; 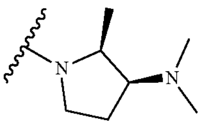; 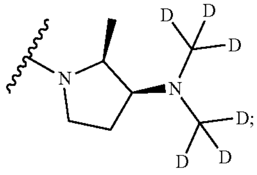; 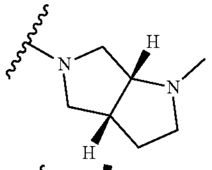; 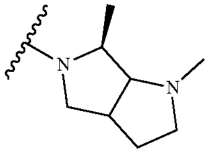 ; or 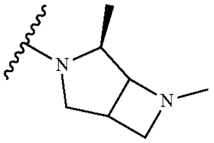 .

In an embodiment of a compound of Formula I or a pharmaceutically acceptable salt thereof, $R_4$ is a group of the formula

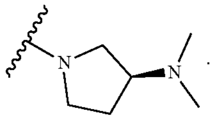 [SMILES: *N1CC[C@H](N(C)C)C1]

In an embodiment of a compound of Formula I or a pharmaceutically acceptable salt thereof $R_4$ is a group of the formula

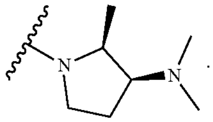 [SMILES: *N1CC[C@H](N(C)C)[C@@H]1C]

In an embodiment of a compound of Formula I, or a pharmaceutically acceptable salt thereof, $R_4$ is a group of the formula

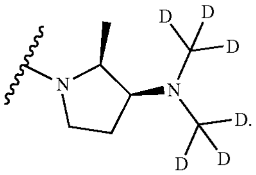

In an embodiment of a compound of Formula I or a pharmaceutically acceptable salt thereof, $R_4$ is a group of the formula

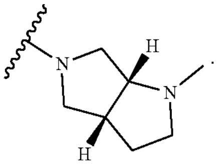 [SMILES: *N1C[C@H]2CCN(C)[C@H]2C1]

In an embodiment of a compound of Formula I or a pharmaceutically acceptable salt thereof, $R_4$ is a group of the formula

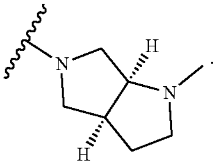 [SMILES: *N1C[C@@H]2CCN(C)[C@@H]2C1]

In an embodiment of a compound of Formula I, or a pharmaceutically acceptable salt thereof, $R_4$ is a group of the formula

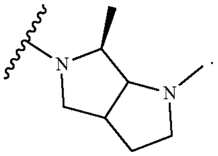 [SMILES: *N1CC2CCN(C)C2[C@@H]1C]

In an embodiment of a compound of Formula I or a pharmaceutically acceptable salt thereof, $R_4$ is a group of the formula

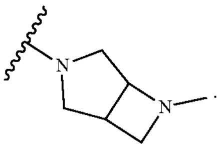 [SMILES: *N1CC2CN(C)C2C1]

In an embodiment of a compound of Formula I or a pharmaceutically acceptable salt thereof, $R_4$ is a group of the formula

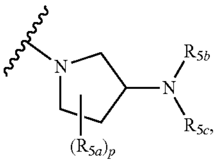

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; and p is 0, 1, or 2. In an embodiment, $R_{5a}$ is hydroxy or $C_{1-3}$ alkyl. In an embodiment, p is 1. In an embodiment, p is 2. In an embodiment, $R_{5b}$ is H, $C_{1-6}$ alkyl, $C_{3-5}$ cycloalkyl, or 3-, 4-, or 5-membered heterocycle, and $R_{5c}$ is H or $C_{1-6}$ alkyl. In an embodiment, $R_{5b}$ and $R_{5c}$ are each independently $C_{1-3}$ alkyl. In an embodiment, $R_4$ is a group of the formula:

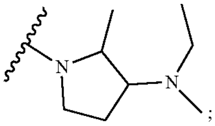
;
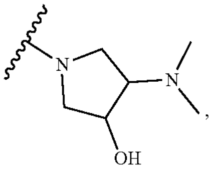
,

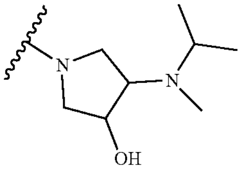
, or
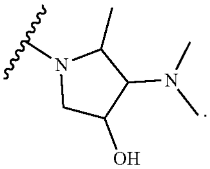
.

In an embodiment of a compound of Formula I or a pharmaceutically acceptable salt thereof, $R_4$ is a group of the formula

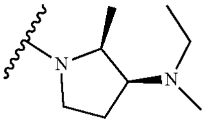
;
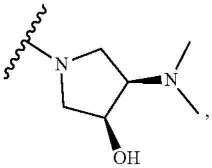
,

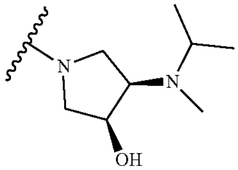
, or
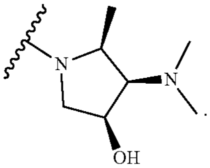
.

In an embodiment of a compound of Formula I or a pharmaceutically acceptable salt thereof, $R_4$ is a group of the formula

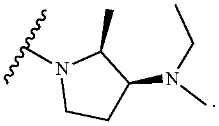 [SMILES: *N1CC[C@H](N(C)CC)[C@@H]1C]
.

In an embodiment of a compound of Formula I or a pharmaceutically acceptable salt thereof, $R_4$ is a group of the formula

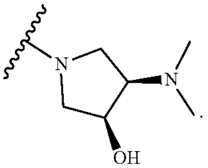 [SMILES: *N1C[C@@H](N(C)C)[C@@H](O)C1]
.

In an embodiment of a compound of Formula I or a pharmaceutically acceptable salt thereof, $R_4$ is a group of the formula

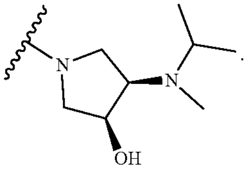 [SMILES: *N1C[C@@H](N(C)C(C)C)[C@@H](O)C1]
.

In an embodiment of a compound of Formula I or a pharmaceutically acceptable salt thereof, $R_4$ is a group of the formula

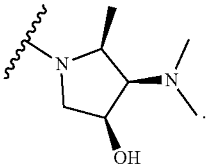 [SMILES: *N1C[C@H](O)[C@H](N(C)C)[C@@H]1C]
.

In an embodiment of a compound of Formula I or a pharmaceutically acceptable salt thereof, $R_4$ is a group of the formula

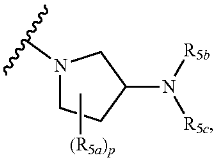

wherein $R_{5a}$ is halogen, hydroxy, $C_{1-3}$ alkyl, $C_{1-3}$ alkoxy, or $C_{1-3}$ alkoxy-$C_{1-3}$ alkyl; $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; and p is 0, 1, or 2. In an embodiment, $R_{5b}$ and $R_{5c}$ together with the nitrogen atom to which they are attached form an optionally substituted 4- or 5-membered heterocycle optionally containing a further heteroatom selected from N, O, and S; and p is 1. In an embodiment, $R_{5b}$ and $R_{5c}$ together with the nitrogen atom to which they are attached form a substituted 4- or 5-membered heterocycle; and p is 1. In an embodiment of a compound of Formula I or a pharmaceutically acceptable salt thereof, $R_4$ is a group of the formula

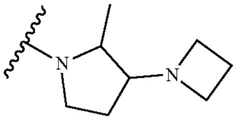
or
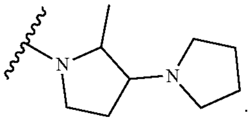
.

In an embodiment of a compound of Formula I or a pharmaceutically acceptable salt thereof, $R_4$ is a group of the formula

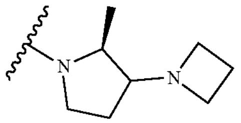

or

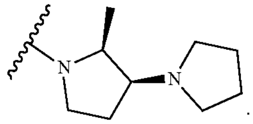

.

In an embodiment of a compound of Formula I or a pharmaceutically acceptable salt thereof, $R_4$ is a group of the formula

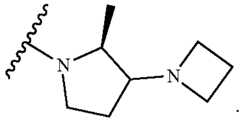 [SMILES: *N1CCC(N2CCC2)[C@@H]1C]

.

In an embodiment of a compound of Formula I or a pharmaceutically acceptable salt thereof, $R_4$ is a group of the formula

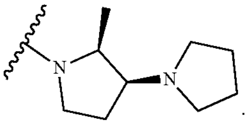 [SMILES: *N1CC[C@H](N2CCCC2)[C@@H]1C]

.

In an embodiment of a compound of Formula I or a pharmaceutically acceptable salt thereof, $R_4$ is a group of the formula

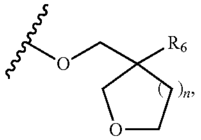

wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, $C_{1-3}$ dialkylamino (preferably dimethylamino); and n is 0 or 1. In an embodiment, $R_6$ is dimethylamino. In an embodiment, n is 1. In an embodiment, n is 0. In an embodiment, $R_4$ is a group of the formula

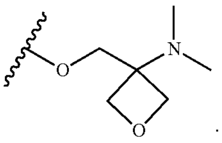 [SMILES: *OCC1(N(C)C)COC1]

.

In an embodiment of a compound of Formula I, or a pharmaceutically acceptable salt thereof, $R_4$ is a group of the formula

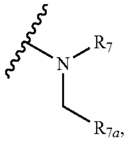

wherein $R_7$ is a $C_{1-3}$ alkyl; and $R_{7a}$ is a 4-, 5-, or 6-membered heterocycle optionally containing a further heteroatom selected from N, O, and S; or $R_7$ and $R_{7a}$ together with the atoms to which they are attached form a 4-, 5-, or 6-membered heterocyclic ring optionally containing a further heteroatom selected from N, O, and S.

In an embodiment of a compound of Formula I, or a pharmaceutically acceptable salt thereof, $R_4$ is a group of the formula

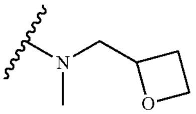

;

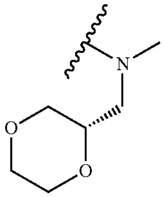

; or

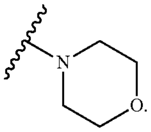

In an embodiment of a compound of Formula I, or a pharmaceutically acceptable salt thereof, $R_4$ is a group of the formula

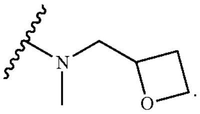 [SMILES: *N(C)CC1CCO1]

In an embodiment of a compound of Formula I, or a pharmaceutically acceptable salt thereof, $R_4$ is a group of the formula

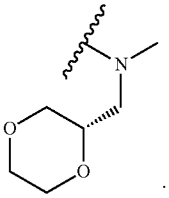 [SMILES: *N(C)C[C@H]1COCCO1]

.

In an embodiment of a compound of Formula I, or a pharmaceutically acceptable salt thereof, $R_4$ is a group of the formula

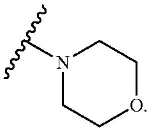 [SMILES: *N1CCOCC1]

The present invention also provides a compound of Formula Ia, Formula Ib, Formula Ic, Formula Id, Formula Ie, or Formula If:

Formula Ia

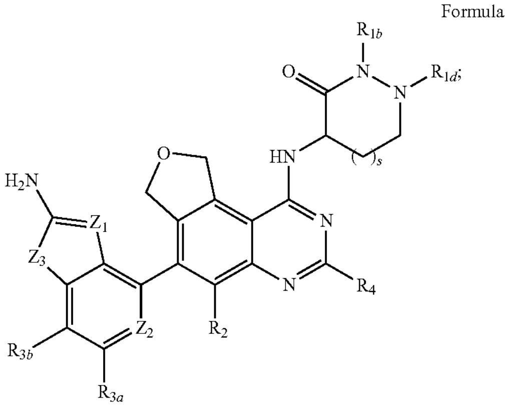

Formula Ib

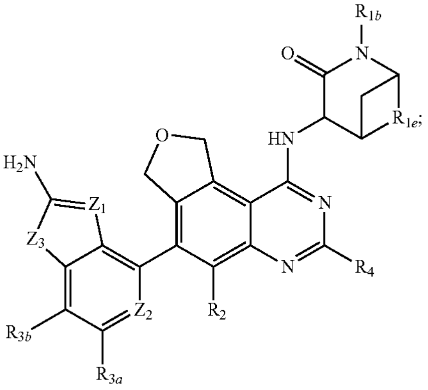

Formula Ic

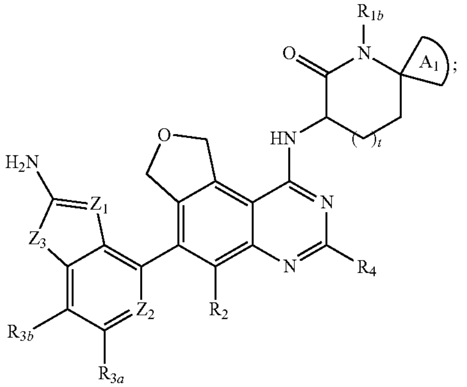

Formula Id

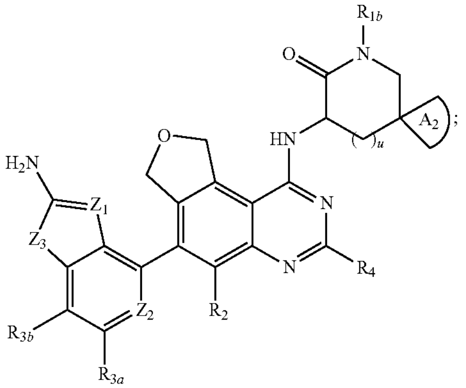

-continued

Formula Ie

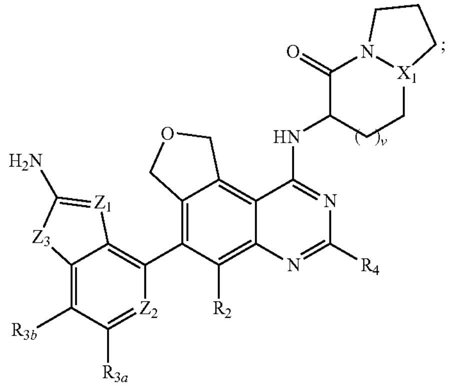

Formula If

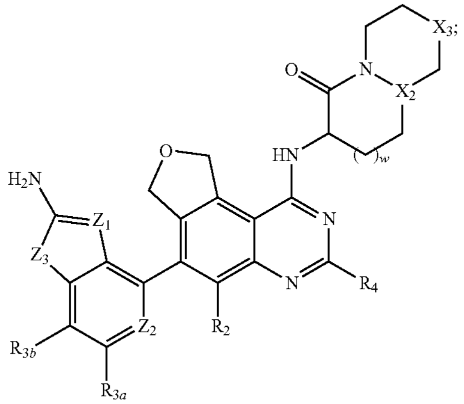

wherein $R_{1b}$, $R_{1d}$, $R_{1e}$, $R_2$, $R_{3a}$, $R_{3b}$, $R_4$, $Z_1$, $Z_2$, $Z_3$, $X_1$, $X_2$, $X_3$, Ring $A_1$, Ring $A_2$, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ia, Formula Ib, Formula Ic, Formula Id, Formula Ie, Formula If, Formula Ih, Formula II, Formula Ij, Formula Ik, or Formula Im:

Formula Ia

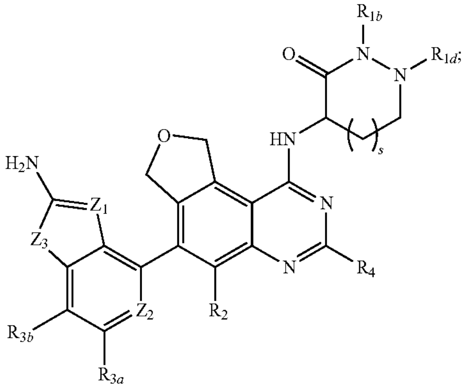

Formula Ib

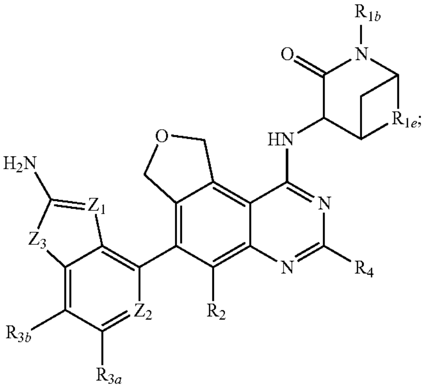

Formula Ic

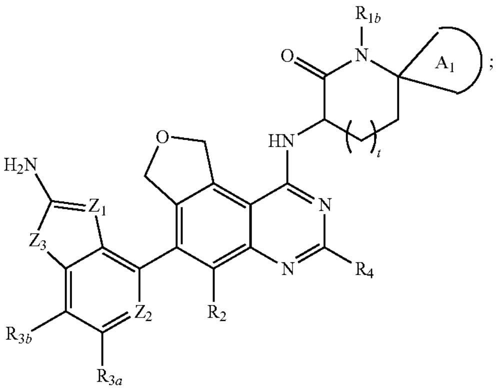

-continued
Formula Id
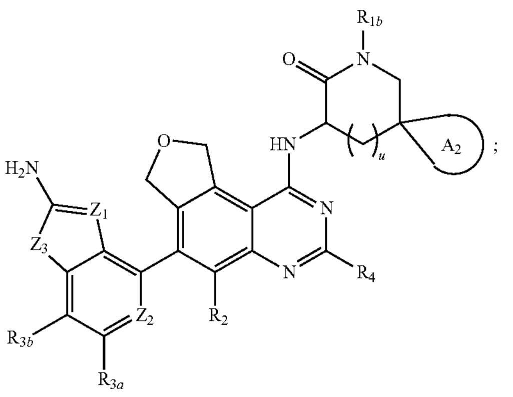
Formula Ie
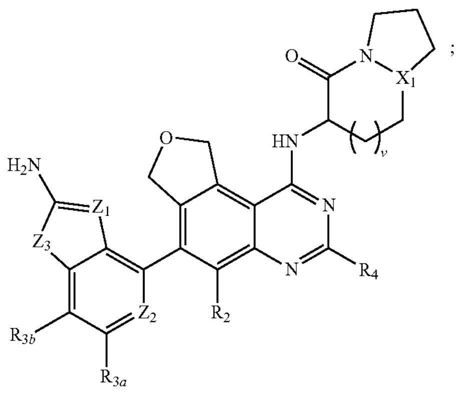
Formula If
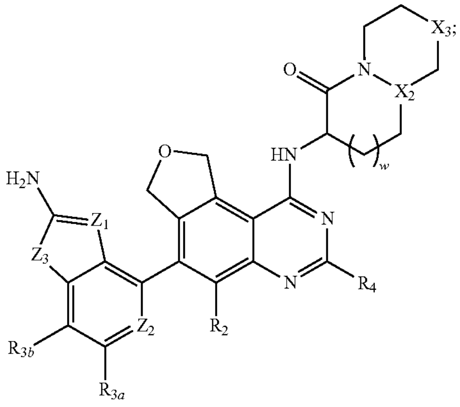
-continued
Formula Ih
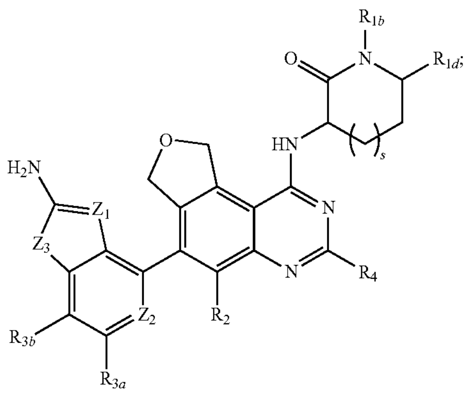
Formula Ii
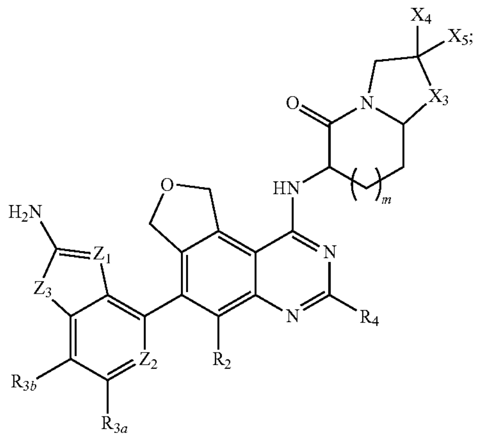
Formula Ij
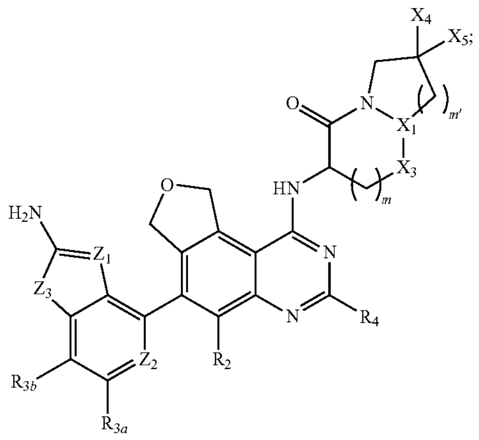

-continued

Formula Ik

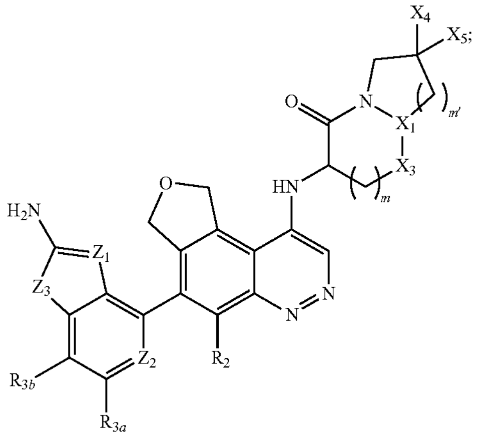

Formula Im

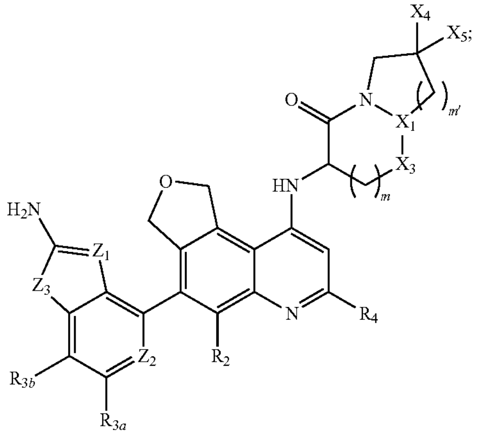

wherein $R_{1b}$, $R_{1d}$, $R_{1e}$, $R_2$, $R_{3a}$, $R_{3b}$, $R_4$, $Z_1$, $Z_2$, $Z_3$, $X_1$, $X_2$, $X_3$, $X_4$, $X_5$, Ring $A_1$, Ring $A_2$, m, m', s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, Rib is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1. In an embodiment, $Z_1$ is —C(CN)—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —S—, $R_2$ is Cl, and $R_{3c}$ is H. In an embodiment, $Z_1$ is —C(CN)—, $Z_2$ is —C($R_{3c}$)—, $Z_3$ is —S—, $R_2$ is F, and $R_{3c}$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In some embodiments, the compound is a compound of Formula Ia, Formula Ib, Formula Ic, Formula Id, Formula Ie, or Formula If. In some embodiments, the compound is a compound of Formula Ih, Formula Ii, Formula Ij, Formula Ik, or Formula Im.

The present invention also provides a compound of Formula Ia*, Formula Ib*, Formula Ic*, Formula Id*, Formula Ie*, or Formula If*

Formula Ia*

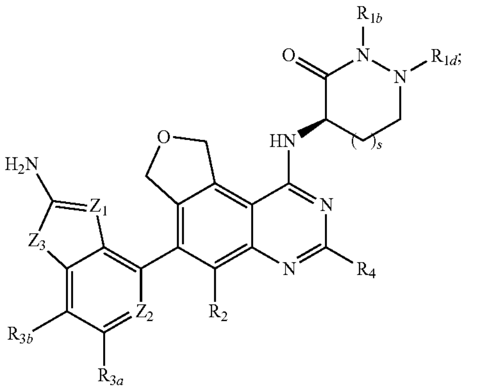

-continued

Formula Ib*

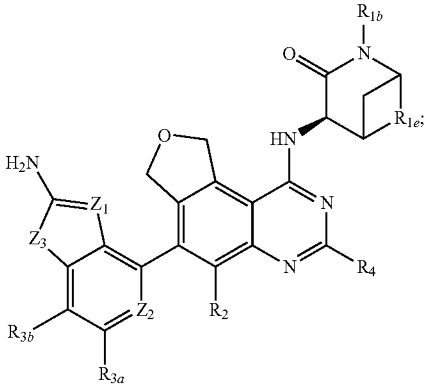

Formula Ic*

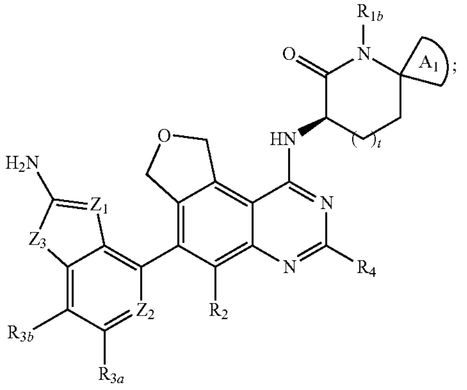

Formula Id*

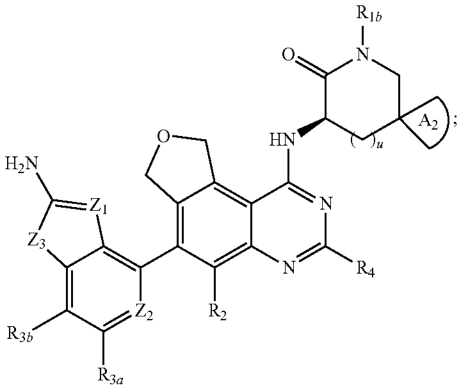

Formula Ie*

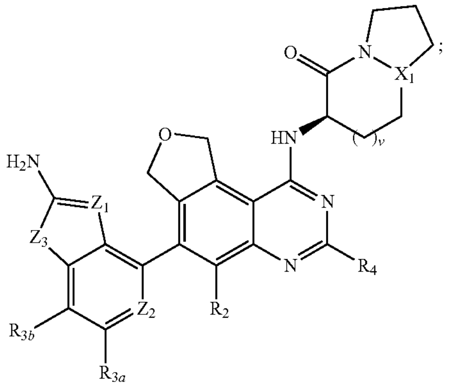

-continued

Formula If*

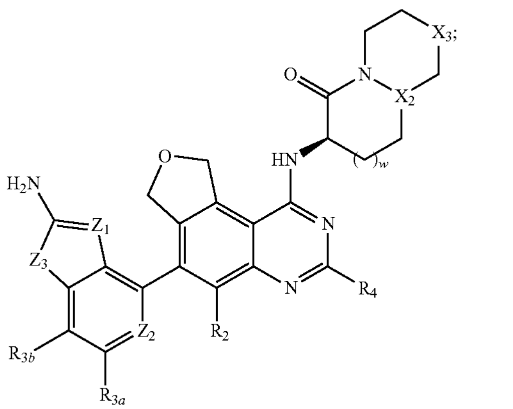

wherein $R_{1b}$, $R_{1d}$, $R_{1e}$, $R_2$, $R_{3a}$, $R_{3b}$, $R_4$, $Z_1$, $Z_2$, $Z_3$, $X_1$, $X_2$, $X_3$, Ring $A_1$, Ring $A_2$, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ia*, Formula Ib*, Formula Ic*, Formula Id*, Formula Ie*, Formula If*, Formula Ih*, Formula II*, Formula Ij*, Formula Ik*, or Formula Im*:
Formula Ia*
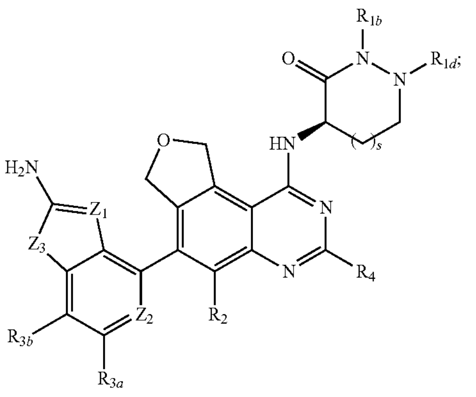
Formula Ib*
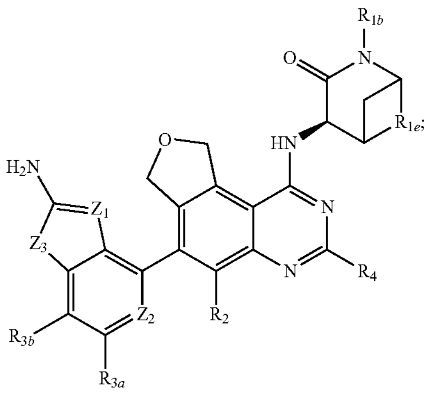
Formula Ic*
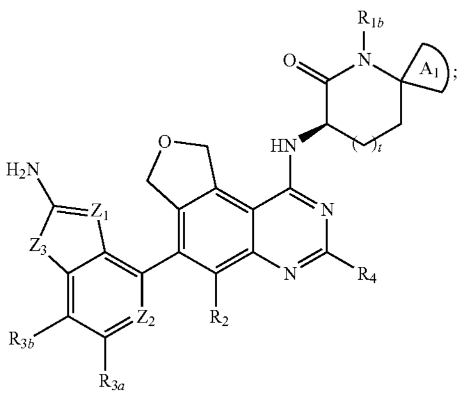
-continued
Formula Id*
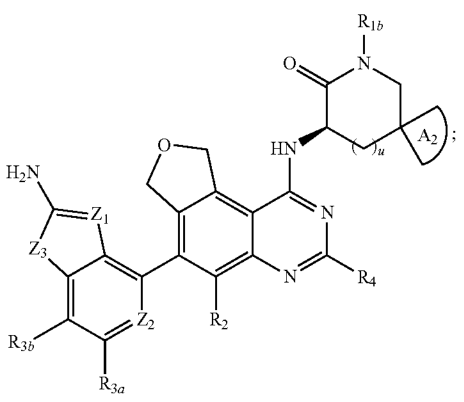
Formula Ie*
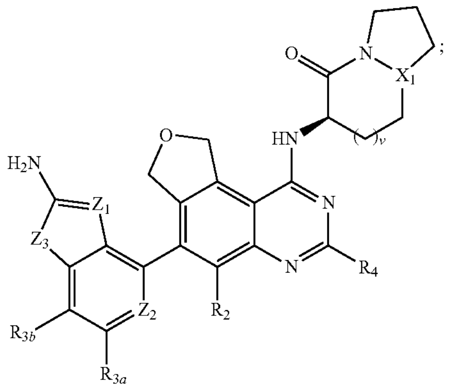
Formula If*
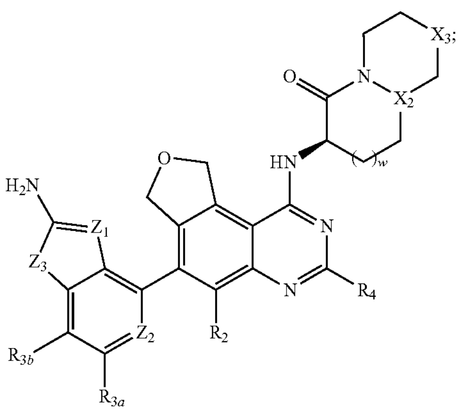
Formula Ih*
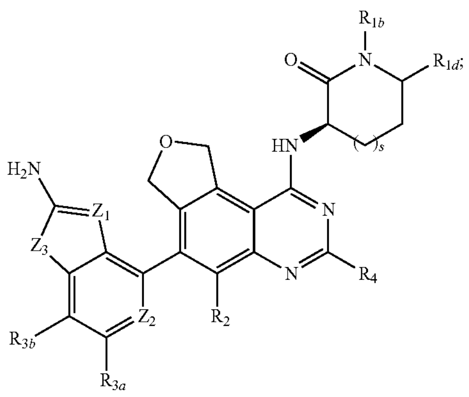

-continued

Formula Ii*

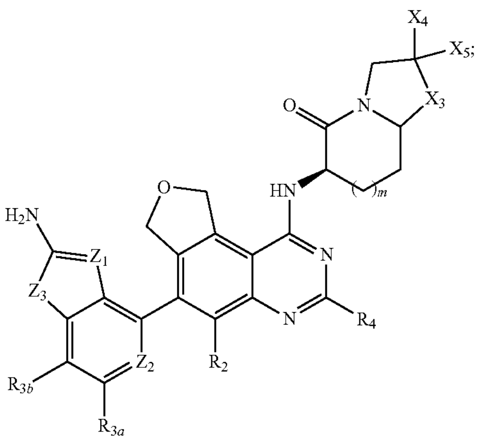

Formula Ij*

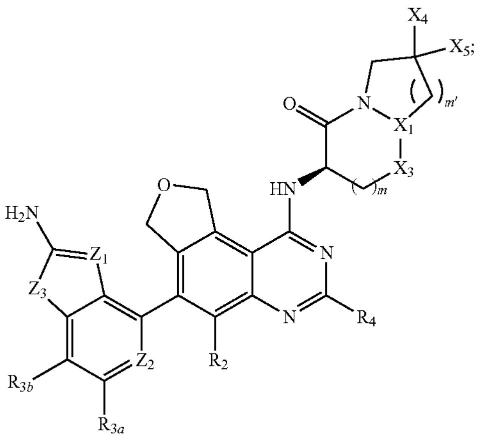

Formula Ik*

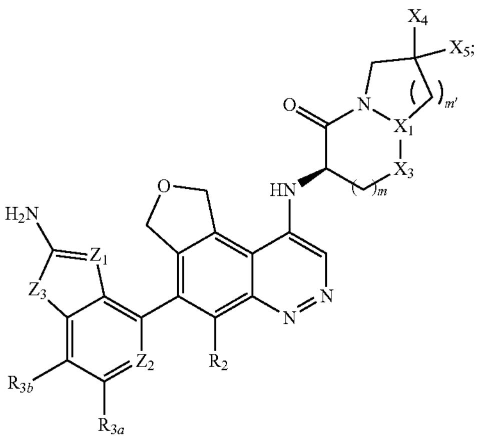

-continued

Formula Im*

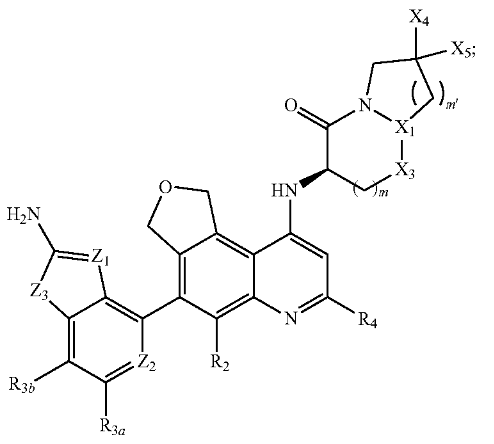

wherein $R_{1b}$, $R_{1d}$, $R_{1e}$, $R_2$, $R_{3a}$, $R_{3b}$, $R_4$, $Z_1$, $Z_2$, $Z_3$, $X_1$, $X_2$, $X_3$, $X_4$, $X_5$, Ring $A_1$, Ring $A_2$, m, m', s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ia-1, Formula Ib-1, Formula Ic-1, Formula Id-1, Formula Ie-1, or Formula If-1:

Formula Ia-1

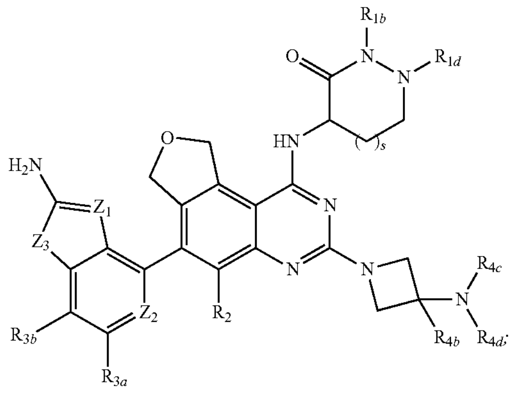

Formula Ib-1

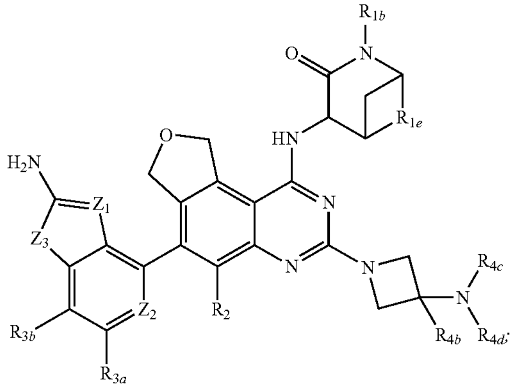

Formula Ic-1

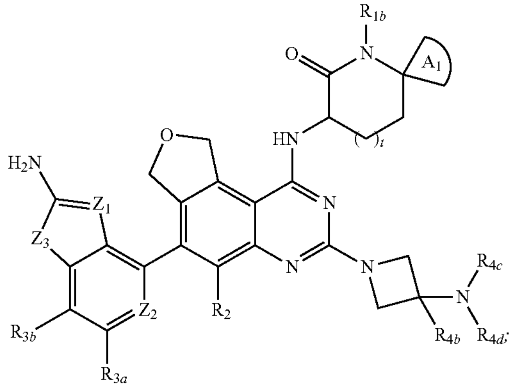

-continued

Formula Id-1

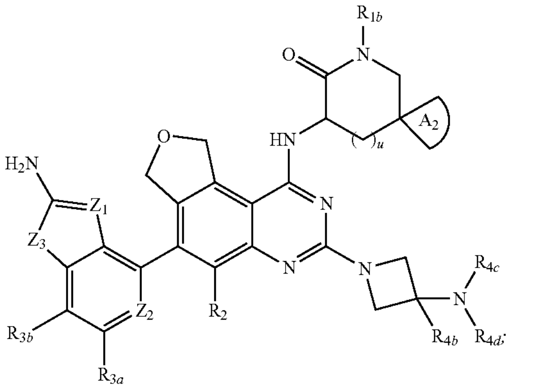

Formula Ie-1

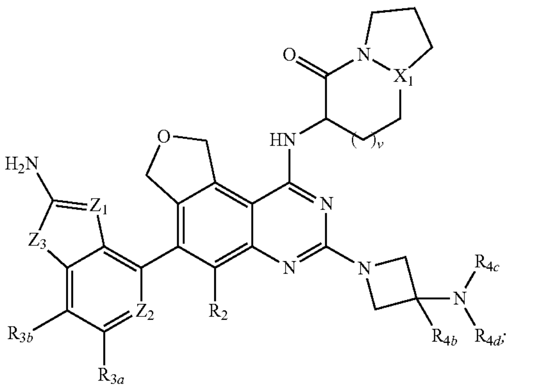

Formula If-1

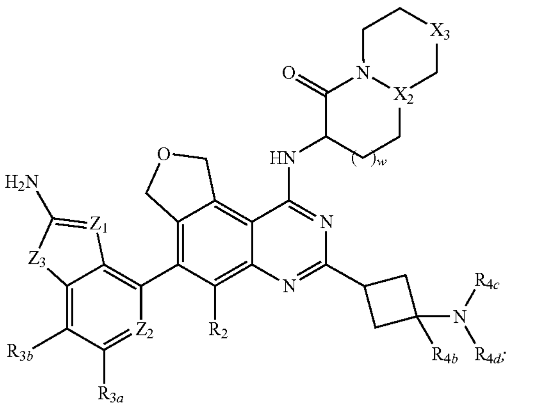

wherein $R_{1b}$, $R_{1d}$, $R_{1e}$, $R_2$, $R_{3a}$, $R_{3b}$, $R_{4b}$, $R_{4c}$, $R_{4d}$, $Z_1$, $Z_2$, $Z_3$, $X_1$, $X_2$, $X_3$, Ring $A_1$, Ring $A_2$, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ia*-1, Formula Ib*-1, Formula Ic*-1, Formula Id*-1, Formula Ie*-1, or Formula If*-1:

Formula Ia*-1

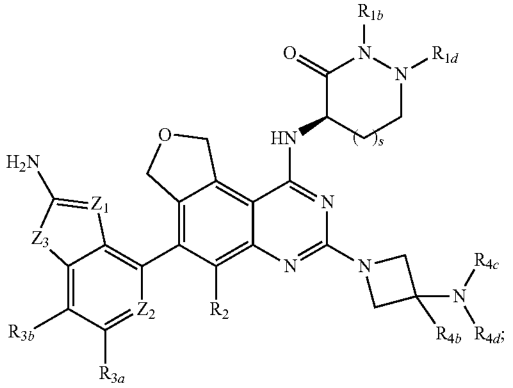

Formula Ib*-1

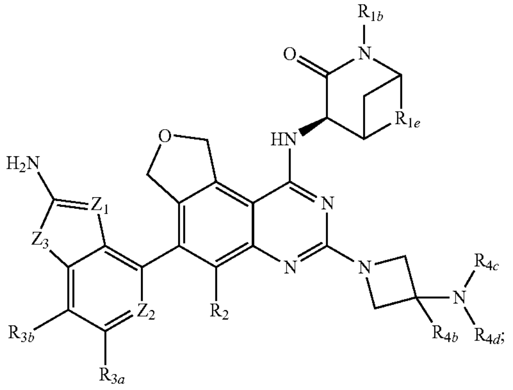

-continued

Formula Ic*-1

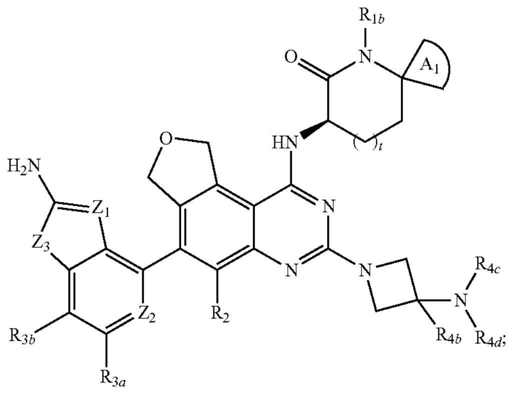

Formula Id*-1

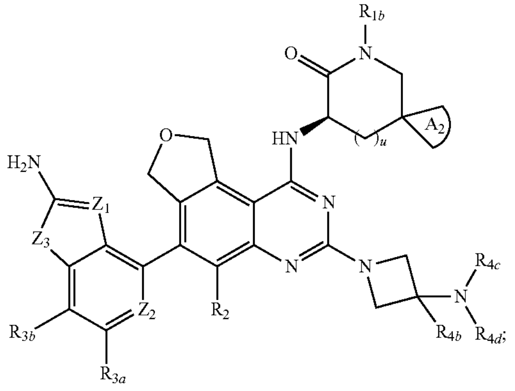

Formula Ie*-1

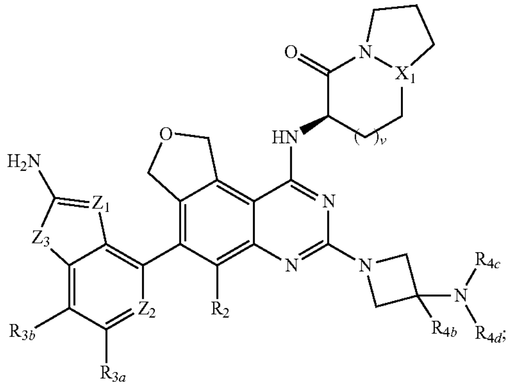

-continued

Formula If*-1

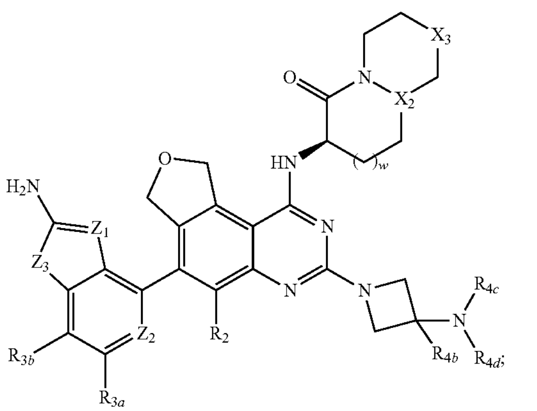

wherein $R_{1b}$, $R_{1d}$, $R_{1e}$, $R_2$, $R_{3a}$, $R_{3b}$, $R_{4b}$, $R_{4c}$, $R_{4d}$, $Z_1$, $Z_2$, $Z_3$, $X_1$, $X_2$, $X_3$, Ring $A_1$, Ring $A_2$, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—$R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ih-1:

Formula Ih-1

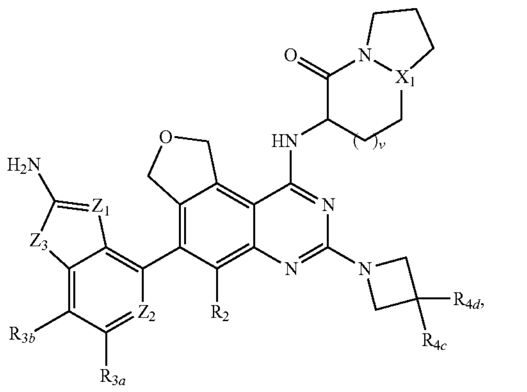

wherein $R_2$, $R_{3a}$, $R_{3b}$, $R_{4c}$, $R_{4d}$, $Z_1$, $Z_2$, $Z_3$, $X_1$, and v are as defined above, or a pharmaceutically acceptable salt thereof. In an embodiment, $R_{4c}$ and $R_{4d}$ together with the carbon atom to which they are attached form a 4-, 5-, or 6-membered heterocycle. In an embodiment, $R_{4c}$ and $R_{4d}$ together with the carbon atom to which they are attached form a 4-membered heterocycle. In an embodiment, $R_{4c}$ and $R_{4d}$ together with the carbon atom to which they are attached form a 5-membered heterocycle. In an embodiment, $R_{4c}$ and $R_{4d}$ together with the carbon atom to which they are attached form a 6-membered heterocycle. In an embodiment, $R_{4c}$ is hydroxy and $R_{4d}$ is $C_{1-3}$ haloalkyl. In an embodiment, $R_{4c}$ is hydroxy, $R_{4d}$ is fluoromethyl, and v is 1.

The present invention also provides a compound of Formula Ih*-1:

Formula Ih*-1

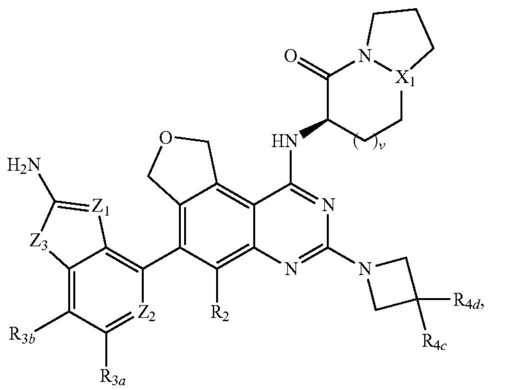

wherein $R_2$, $R_{3a}$, $R_{3b}$, $R_{4c}$, $R_{4d}$, $Z_1$, $Z_2$, $Z_3$, $X_1$, and v are as defined above, or a pharmaceutically acceptable salt thereof. In an embodiment, $R_{4c}$ and $R_{4d}$ together with the carbon atom to which they are attached form a 4-, 5-, or 6-membered heterocycle. In an embodiment, $R_{4c}$ and $R_{4d}$ together with the carbon atom to which they are attached form a 4-membered heterocycle. In an embodiment, $R_{4c}$ and $R_{4d}$ together with the carbon atom to which they are attached form a 5-membered heterocycle. In an embodiment, $R_{4c}$ and $R_{4d}$ together with the carbon atom to which they are attached form a 6-membered heterocycle. In an embodiment, $R_{4c}$ is hydroxy and $R_{4d}$ is $C_{1-3}$ haloalkyl. In an embodiment, $R_{4c}$ is hydroxy, $R_{4d}$ is fluoromethyl, and v is 1.

The present invention also provides a compound of Formula Ia-2, Formula Ib-2, Formula Ic-2, Formula Id-2, Formula Ie-2, or Formula If-2:

Formula Ia-2

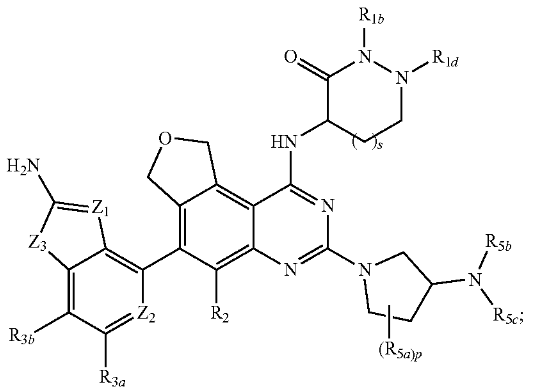

Formula Ib-2

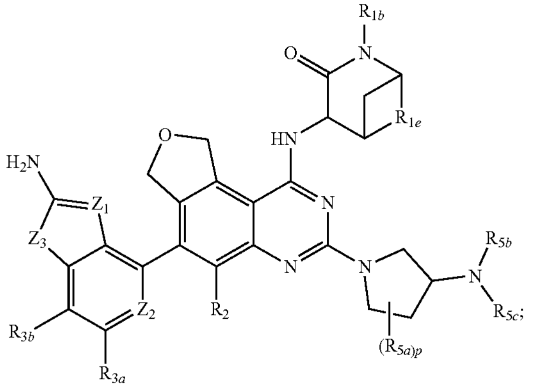

Formula Ic-2

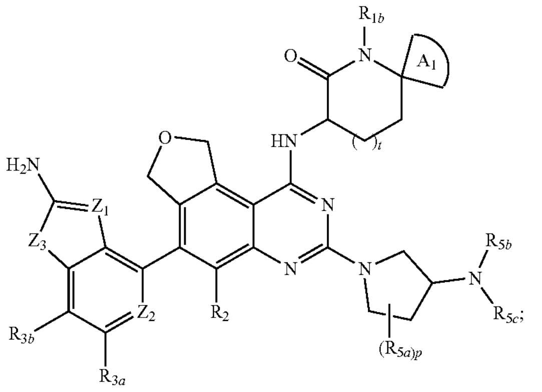

-continued

Formula Id-2

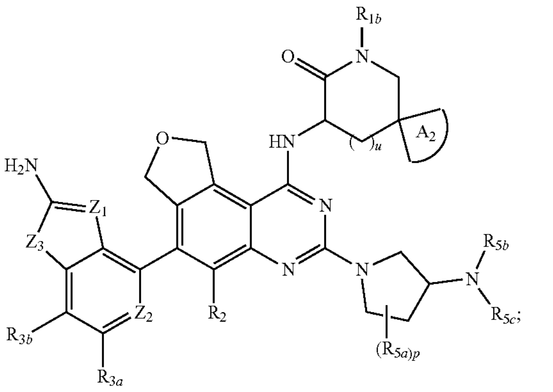

Formula Ie-2

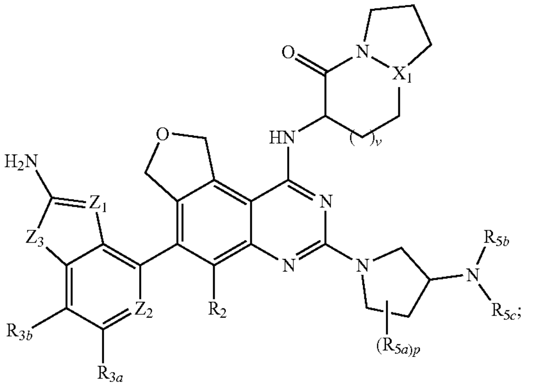

Formula If-2

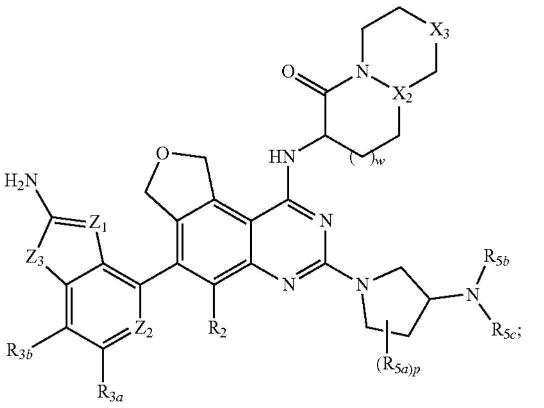

wherein $R_{1b}$, $R_{1d}$, $R_{1e}$, $R_2$, $R_{3a}$, $R_{3b}$, $R_{5a}$, $R_{5b}$, $R_{5c}$, $Z_1$, $Z_2$, $Z_3$, $X_1$, $X_2$, $X_3$, Ring $A_1$, Ring $A_2$, p, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ia*-2, Formula Ib*-2, Formula Ic*-2, Formula Id*-2, Formula Ie*-2, or Formula If*-2:

Formula Ia*-2

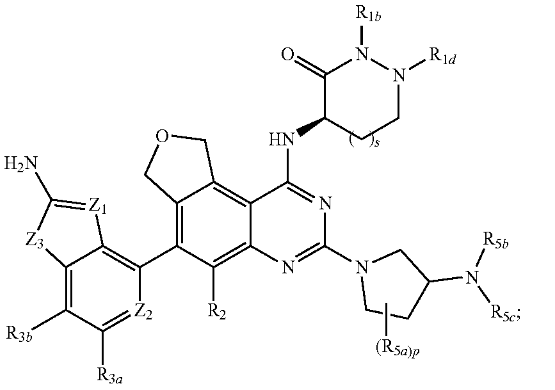

Formula Ib*-2

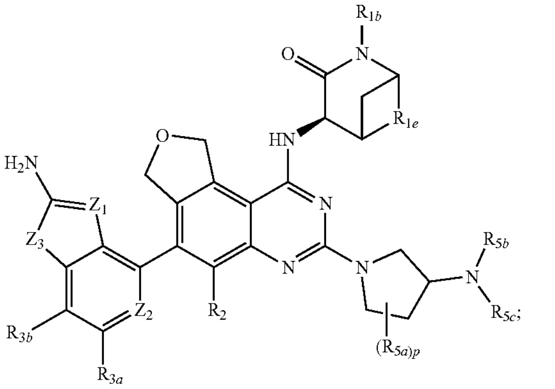

-continued

Formula Ic*-2

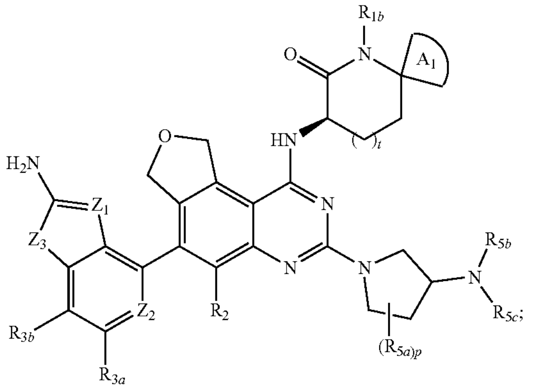

Formula Id*-2

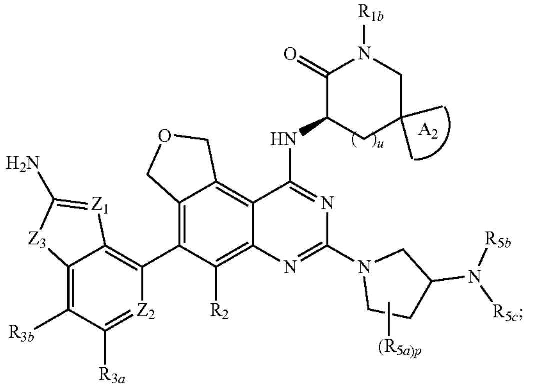

Formula Ie*-2

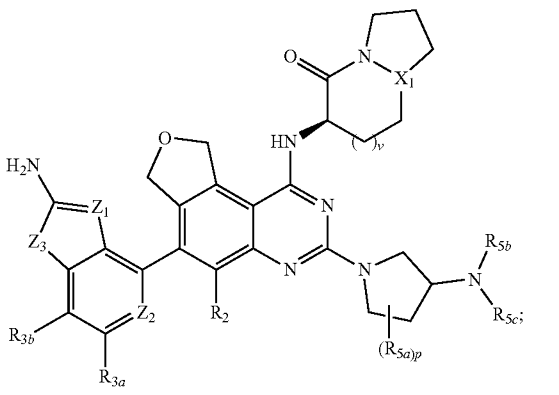

-continued

Formula If*-2

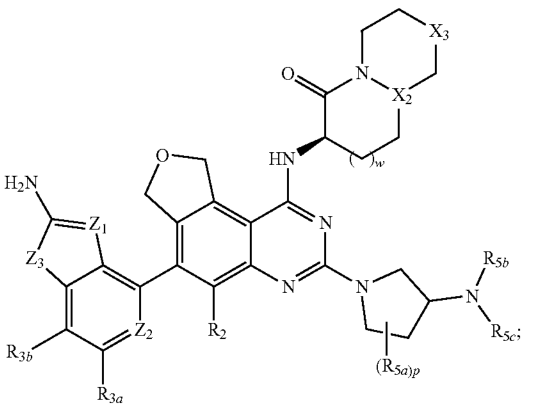

wherein $R_{1b}$, $R_{1d}$, $R_{1e}$, $R_2$, $R_{3a}$, $R_{3b}$, $R_{5a}$, $R_{5b}$, $R_{5c}$, $Z_1$, $Z_2$, $Z_3$, $X_1$, $X_2$, $X_3$, Ring $A_1$, Ring $A_2$, p, s, t, u, v, and w are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is Cl, and s, t, u, v, and w are 1. In an embodiment, $Z_1$ is —C(CN)—, $Z_2$ is —C($R_{3c}$)—, $Z_3$ is —S—, $R_2$ is F, and s, t, u, v, and w are 1. In an embodiment, $Z_1$ is —C(CN)—, $Z_2$ is —N—, $Z_3$ is —S—, $R_2$ is Cl, and s, t, u, v, and w are 1. In an embodiment, $Z_1$ is —C(CN)—, $Z_2$ is —N—, $Z_3$ is —S—, $R_2$ is F, and s, t, u, v, and w are 1. In an embodiment, $Z_1$ is —N—, $Z_2$ is —C($R_{3c}$)—, $Z_3$ is —S—, $R_2$ is Cl, and s, t, u, v, and w are 1. In an embodiment, $Z_1$ is —N—, $Z_2$ is —C($R_{3c}$)—, $Z_3$ is —S—, $R_2$ is F, and s, t, u, v, and w are 1. In an embodiment, $Z_1$ is —N—, $Z_2$ is —N—, $Z_3$ is —S—, $R_2$ is Cl, and s, t, u, v, and w are 1. In an embodiment, $Z_1$ is —N—, $Z_2$ is —N—, $Z_3$ is —S—, $R_2$ is F, and s, t, u, v, and w are 1. In an embodiment, $Z_1$ is —C(CN)—, $Z_2$ is —C($R_{3c}$)—, $Z_3$ is —O—, $R_2$ is Cl, and s, t, u, v, and w are 1. In an embodiment, $Z_1$ is —C(CN)—, $Z_2$ is —C($R_{3c}$)—, $Z_3$ is —O—, $R_2$ is F, and s, t, u, v, and w are 1. In an embodiment, $Z_1$ is —C(CN)—, $Z_2$ is —N—, $Z_3$ is —O—, $R_2$ is Cl, and s, t, u, v, and w are 1. In an embodiment, $Z_1$ is —C(CN)—, $Z_2$ is —N—, $Z_3$ is —O—, $R_2$ is F, and s, t, u, v, and w are 1. In an embodiment, $Z_1$ is —N—, $Z_2$ is —C($R_{3c}$)—, $Z_3$ is —O—, $R_2$ is Cl, and s, t, u, v, and w are 1. In an embodiment, $Z_1$ is —N—, $Z_2$ is —C($R_{3c}$)—, $Z_3$ is —O—, $R_2$ is F, and s, t, u, v, and w are 1. In an embodiment, $Z_1$ is —N—, $Z_2$ is —N—, $Z_3$ is —O—, $R_2$ is Cl, and s, t, u, v, and w are 1. In an embodiment, $Z_1$ is —N—, $Z_2$ is —N—, $Z_3$ is —O—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —S—, and $R_2$ is Cl. In an embodiment, $R_{1b}$ is methyl, $Z_1$ is —C(CN)—, $Z_2$ is —C($R_{3c}$)—, $Z_3$ is —S—, and $R_2$ is F. In an embodiment, $R_{1b}$ is methyl, $Z_1$ is —C(CN)—, $Z_2$ is —N—, $Z_3$ is —S—, and $R_2$ is Cl. In an embodiment, $R_{1b}$ is methyl, $Z_1$ is —C(CN)—, $Z_2$ is —N—, $Z_3$ is —S—, and $R_2$ is F. In an embodiment, $R_{1b}$ is methyl, $Z_1$ is —N—, $Z_2$ is —C($R_{3c}$)—, $Z_3$ is —S—, and $R_2$ is Cl. In an embodiment, $R_{1b}$ is methyl, $Z_1$ is —N—, $Z_2$ is —C($R_{3c}$)—, $Z_3$ is —S—, and $R_2$ is F. In an embodiment, $R_{1b}$ is hydrogen, $Z_1$ is —N—, $Z_2$ is —C($R_{3c}$)—, $Z_3$ is —S—, and $R_2$ is F. In an embodiment, $R_{1b}$ is methyl, $Z_1$ is —N—, $Z_2$ is —N—, $Z_3$ is —S—, and $R_2$ is Cl. In an embodiment, $R_{1b}$ is methyl, $Z_1$ is —N—, $Z_2$ is —N—, $Z_3$ is —S—, and $R_2$ is F. In an embodiment, $R_{1b}$ is methyl, $Z_1$ is —C(CN)—, $Z_2$ is —C($R_{3c}$)—, $Z_3$ is —O—, and $R_2$ is Cl. In an embodiment, $R_{1b}$ is methyl, $Z_1$ is —C(CN)—, $Z_2$ is —C($R_{3c}$)—, $Z_3$ is —O—, and $R_2$ is F. In an embodiment, $R_{1b}$ is methyl, $Z_1$ is —C(CN)—, $Z_2$ is —N—, $Z_3$ is —O—, and $R_2$ is Cl. In an embodiment, $R_{1b}$ is methyl, $Z_1$ is —C(CN)—, $Z_2$ is —N—, $Z_3$ is —O—, and $R_2$ is F. In an embodiment, $R_{1b}$ is methyl, $Z_1$ is —N—, $Z_2$ is —C($R_{3c}$)—, $Z_3$ is —O—, and $R_2$ is Cl. In an embodiment, $R_{1b}$ is methyl, $Z_1$ is —N—, $Z_2$ is —C($R_{3c}$)—, $Z_3$ is —O—, and $R_2$ is F. In an embodiment, $R_{1b}$ is methyl, $Z_1$ is —N—, $Z_2$ is —N—, $Z_3$ is —O—, and $R_2$ is Cl. In an embodiment, $R_{1b}$ is methyl, $Z_1$ is —N—, $Z_2$ is —N—, $Z_3$ is —O—, and $R_2$ is F. In an embodiment, $R_{1b}$ is methyl, $Z_1$ is —C(CN)—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —S—, $R_2$ is F, and s, t, u, v, and w are 1. In an embodiment, $R_{1b}$ is methyl, $Z_1$ is —C(CN)—, $Z_2$ is —N—, $Z_3$ is —S—, $R_2$ is Cl, and s, t, u, v, and w are 1. In an embodiment, $R_{1b}$ is methyl, $Z_1$ is —C(CN)—, $Z_2$ is —N—, $Z_3$ is —S—, $R_2$ is F, and s, t, u, v, and w are 1. In an embodiment, $R_{1b}$ is methyl, $Z_1$ is —N—, $Z_2$ is —C($R_{3c}$)—, $Z_3$ is —S—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —S—, $R_2$ is F, and s, t, u, v, and w are 1. In an embodiment, $R_{1b}$ is hydrogen, $Z_1$ is —N—, $Z_2$ is —C($R_{3c}$)—, $Z_3$ is —S—, $R_2$ is F, and s, t, u, v, and w are 1. In an embodiment, $R_{1b}$ is methyl, $Z_1$ is —N—, $Z_2$ is —N—, $Z_3$ is —S—, $R_2$ is Cl, and s, t, u, v, and w are 1. In an embodiment, $R_{1b}$ is methyl, $Z_1$ is —N—, $Z_2$ is —N—, $Z_3$ is —S—, $R_2$ is F, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —C(CN)—, $Z_2$ is —C($R_{3c}$)—, $Z_3$ is —O—, $R_2$ is F, and s, t, u, v, and w are 1. In an embodiment, $R_{1b}$ is methyl, $Z_1$ is —C(CN)—, $Z_2$ is —N—, $Z_3$ is —O—, $R_2$ is Cl, and s, t, u, v, and w are 1. In an embodiment, $R_{1b}$ is methyl, $Z_1$ is —C(CN)—, $Z_2$ is —N—, $Z_3$ is —O—, $R_2$ is F, and s, t, u, v, and w are 1. In an embodiment, $R_{1b}$ is methyl, $Z_1$ is —N—, $Z_2$ is —C($R_{3c}$)—, $Z_3$ is —O—, $R_2$ is Cl, and s, t, u, v, and w are 1. In an embodiment, $R_{1b}$ is methyl, $Z_1$ is —N—, $Z_2$ is —C($R_{3c}$)—, $Z_3$ is —O—, $R_2$ is F, and s, t, u, v, and w are 1. In an embodiment, $R_{1b}$ is methyl, $Z_1$ is —N—, $Z_2$ is —N—, $Z_3$ is —O—, $R_2$ is Cl, and s, t, u, v, and w are 1. In an embodiment, $R_{1b}$ is methyl, $Z_1$ is —N—, $Z_2$ is —N—, $Z_3$ is —O—, $R_2$ is F, and s, t, u, v, and w are 1.

The present invention also provides a compound of Formula Ig-2:

Formula Ig-2

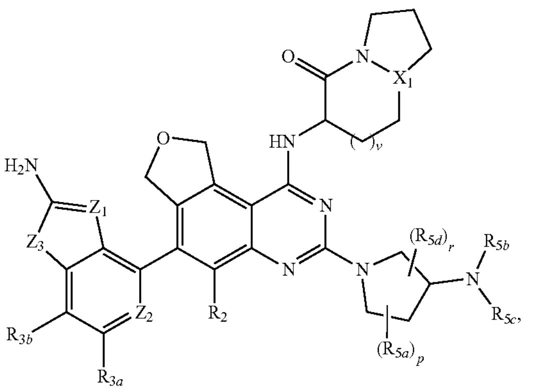

wherein $R_2$, $R_{3a}$, $R_{3b}$, $R_{5a}$, $R_{5b}$, $R_{5c}$, $R_{5d}$, $Z_1$, $Z_2$, $Z_3$, $X_1$, p, r, and v are as defined above, or a pharmaceutically acceptable salt thereof. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is N—, $Z_3$ is —S—, and $R_2$ is F. In an embodiment, $Z_1$ is —N—, $Z_2$ is N—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —C($R_{3c}$)—, $Z_3$ is —S—, $R_2$ is F, r is 0, and p and v are 1. In an embodiment, $Z_1$ is —N—, $Z_2$ is —C($R_{3c}$)—, $Z_3$ is —S—, $R_2$ is Cl, r is 0, and p and v are 1. In an embodiment, $Z_1$ is —N—, $Z_2$ is N—, $Z_3$ is —S—, $R_2$ is F, r is 0, and p and v are 1. In an embodiment, $Z_1$ is —N—, $Z_2$ is N—, $Z_3$ is —S—, $R_2$ is Cl, r is 0, and p and v are 1. In an embodiment, $Z_1$ is —N—, $Z_2$ is —C($R_{3c}$)—, $Z_3$ is —S—, $R_2$ is F, p' is 0, and p and v are 1. In an embodiment, $R_{5b}$ and $R_{5c}$ are each independently $C_{1-3}$ alkyl, $C_{1-3}$ alkyl substituted with one or more deuterium, or a $C_{3-5}$ cycloalkyl optionally substituted with halogen or a $C_{1-3}$ haloalkyl. In an embodiment, $R_{5b}$ and $R_{5c}$ together with the nitrogen atom to which they are attached form an optionally substituted 4-, 5-, or 6-membered heterocycle, wherein the heterocycle is optionally substituted with halogen, $C_{1-3}$ alkyl, or $C_{1-3}$ haloalkyl. In an embodiment, $R_{5b}$ and $R_{5c}$ together with the nitrogen atom to which they are attached form an optionally substituted 6-, 7-, or 8-membered spiro heterocycle, wherein the spiro heterocycle optionally contains a further heteroatom selected from N, O, and S, and wherein the spiro heterocycle is optionally substituted with halogen, $C_{1-3}$ alkyl, or $C_{1-3}$ haloalkyl. In an embodiment, $R_{5b}$ and $R_{5c}$ together with the nitrogen atom to which they are attached form an optionally substituted 6-membered spiro heterocycle, wherein the 6-membered spiro heterocycle optionally contains a further heteroatom selected from N, O, and S, and wherein the spiro heterocycle is optionally substituted with halogen. In an embodiment, $R_{5b}$ and $R_{5c}$ together with the nitrogen atom to which they are attached form an optionally substituted 7-membered spiro heterocycle, wherein the 7-membered spiro heterocycle optionally contains a further heteroatom selected from N, O, and S, and wherein the spiro heterocycle is optionally substituted with halogen. In an embodiment, $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-2}$ alkyl, and the 4-, 5-, or 6-membered fused ring is optionally further substituted with a $C_{1-2}$ alkyl.

The present invention also provides a compound of Formula Ig*-2:

Formula Ig*-2

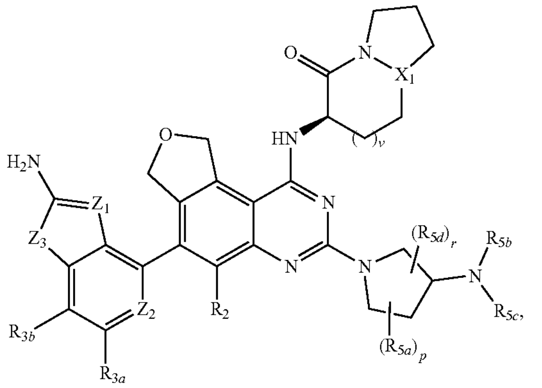

wherein $R_2$, $R_{3a}$, $R_{3b}$, $R_{5a}$, $R_{5b}$, $R_{5c}$, $R_{5d}$, $Z_1$, $Z_2$, $Z_3$, $X_1$, p, r, and v are as defined above, or a pharmaceutically acceptable salt thereof. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is N—, $Z_3$ is —S—, and $R_2$ is F. In an embodiment, $Z_1$ is —N—, $Z_2$ is N—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —C($R_{3c}$)—, $Z_3$ is —S—, $R_2$ is F, r is 0, and p and v are 1. In an embodiment, $Z_1$ is —N—, $Z_2$ is —C($R_{3c}$)—, $Z_3$ is —S—, $R_2$ is Cl, r is 0, and p and v are 1. In an embodiment, $Z_1$ is —N—, $Z_2$ is N—, $Z_3$ is —S—, $R_2$ is F, r is 0, and p and v are 1. In an embodiment, $Z_1$ is —N—, $Z_2$ is N—, $Z_3$ is —S—, $R_2$ is Cl, r is 0, and p and v are 1. In an embodiment, $Z_1$ is —N—, $Z_2$ is —C($R_{3c}$)—, $Z_3$ is —S—, $R_2$ is F, r is 0, and p and v are 1. In an embodiment, $R_{5b}$ and $R_{5c}$ are each independently $C_{1-3}$ alkyl, $C_{1-3}$ alkyl substituted with 1, 2, or 3 deuterium, or a $C_{3-5}$ cycloalkyl optionally substituted with halogen or $C_{1-3}$ haloalkyl. In an embodiment, $R_{5b}$ and $R_{5c}$ together with the nitrogen atom to which they are attached form an optionally substituted 4-, 5-, or 6-membered heterocycle, wherein the heterocycle is optionally substituted with one or more halogen, deuterium, $C_{1-3}$ alkyl, or $C_{1-3}$ haloalkyl. In an embodiment, $R_{5b}$ and $R_{5c}$ together with the nitrogen atom to which they are attached form an optionally substituted 6-, 7-, or 8-membered spiro heterocycle, wherein the spiro heterocycle optionally contains a further heteroatom selected from N, O, and S, and wherein the spiro heterocycle is optionally substituted with halogen, $C_{1-3}$ alkyl, or $C_{1-3}$ haloalkyl. In an embodiment, $R_{5b}$ and $R_{5c}$ together with the nitrogen atom to which they are attached form an optionally substituted 6-membered spiro heterocycle, wherein the 6-membered spiro heterocycle optionally contains a further heteroatom selected from N, O, and S, and wherein the spiro heterocycle is optionally substituted with halogen. In an embodiment, $R_{5b}$ and $R_{5c}$ together with the nitrogen atom to which they are attached form an optionally substituted 7-membered spiro heterocycle, wherein the 7-membered spiro heterocycle optionally contains a further heteroatom selected from N, O, and S, and wherein the spiro heterocycle is optionally substituted with halogen. In an embodiment, $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-2}$ alkyl, and the 4-, 5-, or 6-membered fused ring is optionally further substituted with a $C_{1-2}$ alkyl.

The present invention also provides a compound of Formula Ih-2:

Formula Ih-2

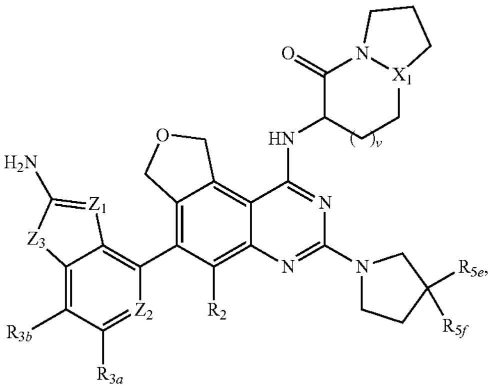

wherein $R_2$, $R_{3a}$, $R_{3b}$, $R_{5e}$, $R_{5f}$, $Z_1$, $Z_2$, $Z_3$, $X_1$, and v are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —C($R_{3c}$)—, $Z_3$ is —S—, $R_2$ is Cl, and v is 1. In an embodiment, $R_{5e}$ and $R_{5f}$ together with the carbon atom to which they are attached form a 4-, 5-, or 6-membered heterocycle. In an embodiment, $R_{5e}$ and $R_{5f}$ together with the carbon atom to which they are attached form a 4-membered heterocycle (e.g., oxetanyl). In an embodiment, $R_{5e}$ and $R_{5f}$ together with the carbon atom to which they are attached form a 5-membered heterocycle. In an embodiment, $R_{5e}$ and $R_{5f}$ together with the carbon atom to which they are attached form a 6-membered heterocycle.

The present invention also provides a compound of Formula Ih*-2:

Formula Ih*-2

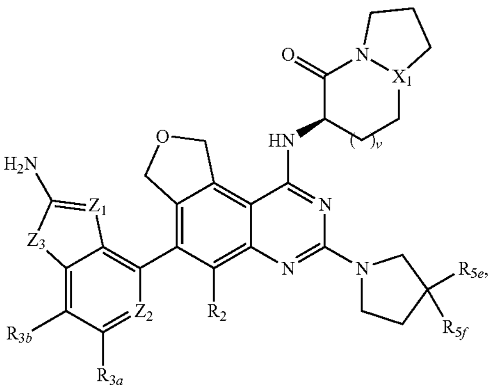

wherein $R_2$, $R_{3a}$, $R_{3b}$, $R_{5e}$, $R_{5f}$, $Z_1$, $Z_2$, $Z_3$, $X_1$, and v are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —C($R_{3c}$)—, $Z_3$ is —S—, $R_2$ is Cl, and v is 1. In an embodiment, $R_{5e}$ and $R_{5f}$ together with the carbon atom to which they are attached form a 4-, 5-, or 6-membered heterocycle. In an embodiment, $R_{5e}$ and $R_{5f}$ together with the carbon atom to which they are attached form a 4-membered heterocycle (e.g., oxetanyl). In an embodiment, $R_{5e}$ and $R_{5f}$ together with the carbon atom to which they are attached form a 5-membered heterocycle. In an embodiment, $R_{5e}$ and $R_{5f}$ together with the carbon atom to which they are attached form a 6-membered heterocycle.

The present invention also provides a compound of Formula Ia-3:

Formula Ia-3

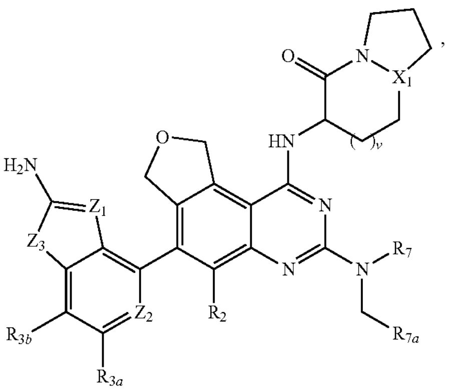

wherein $R_2$, $R_{3a}$, $R_{3b}$, $R_7$, $R_{7a}$, $Z_1$, $Z_2$, $Z_3$, $X_1$, and v are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 4-, 5-, or 6-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 4-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 5-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 6-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_7$ and $R_{7a}$ together with the atoms to which they are attached form a 4-, 5-, or 6-membered heterocyclic ring optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_7$ and $R_{7a}$ together with the atoms to which they are attached form a 6-membered heterocyclic ring optionally containing a further heteroatom selected from N, O, and S.

The present invention also provides a compound of Formula Ja*-3:

Formula Ia*-3

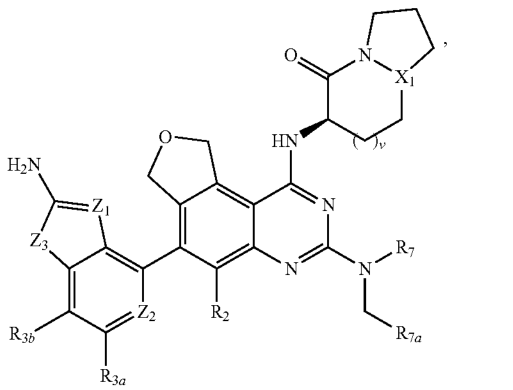

wherein $R_2$, $R_{3a}$, $R_{3b}$, $R_7$, $R_{7a}$, $Z_1$, $Z_2$, $Z_3$, $X_1$, and v are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 4-, 5-, or 6-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 4-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 5-membered heterocycle optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_{7a}$ is a 6-membered heterocycle optionally containing a further heteroatom selected from N, O, and S (e.g., 1,4-dioxanyl). In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_7$ and $R_{7a}$ together with the atoms to which they are attached form a 4-, 5-, or 6-membered heterocyclic ring optionally containing a further heteroatom selected from N, O, and S. In an embodiment, $Z_1$ is —C(CN)—, $Z_2$ is —C($R_{3c}$)—, $Z_3$ is —S—, $R_2$ is Cl, $R_7$ is a $C_{1-2}$ alkyl, and $R_7$ and $R_{7a}$ together with the atoms to which they are attached form a 6-membered heterocyclic ring optionally containing a further heteroatom selected from N, O, and S (e.g., morpholinyl).

The present invention also provides a compound of Formula Ig-1:

Formula Ig-1

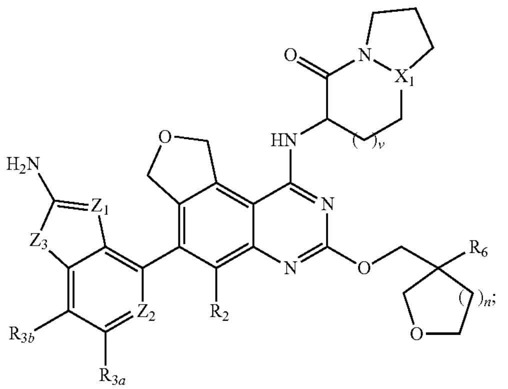

wherein $R_2$, $R_{3a}$, $R_{3b}$, $R_{3c}$, $R_6$, $Z_1$, $Z_2$, $Z_3$, $X_1$, v, and n are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is $C_1$, v is 1, and n is 0. In an embodiment, $Z_1$ is —C(CN)—, $Z_2$ is —C($R_{3c}$)—, $Z_3$ is —S—, $R_2$ is F, v is 1, and n is 0. In an embodiment, $Z_1$ is —C(CN)—, $Z_2$ is —N—, $Z_3$ is —S—, $R_2$ is Cl, v is 1, and n is 0. In an embodiment, $Z_1$ is —C(CN)—, $Z_2$ is —N—, $Z_3$ is —S—, $R_2$ is F, v is 1, and n is 0. In an embodiment, $Z_1$ is —C(CN)—, $Z_2$ is —N—, $Z_3$ is —S—, $R_2$ is F, v is 1, and n is 0. In an embodiment, $Z_1$ is —N—, $Z_2$ is —C($R_{3c}$)—, $Z_3$ is —S—, $R_2$ is F, v is 1, and n is 0.

The present invention also provides a compound of Formula Ig*-1:

Formula Ig*-1

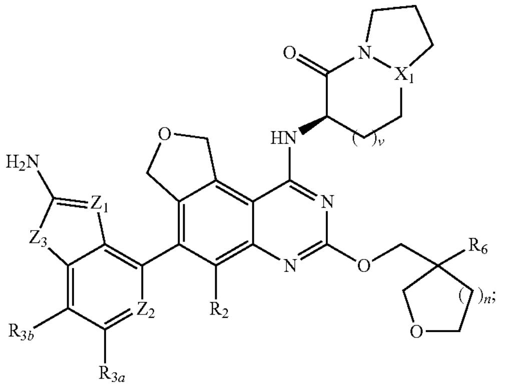

wherein $R_2$, $R_{3a}$, $R_{3b}$, $R_{3c}$, $R_6$, $Z_1$, $Z_2$, $Z_3$, $X_1$, v, and n are as defined above, or a pharmaceutically acceptable salt thereof. In an embodiment, $Z_1$ is —C(CN)—, $Z_2$ is —C($R_{3c}$)—, $Z_3$ is —S—, and $R_2$ is Cl. In an embodiment, $Z_1$ is —C(CN)—, $Z_2$ is —C($R_{3c}$)—, $Z_3$ is —S—, and $R_2$ is F. In an embodiment, $Z_1$ is —C(CN)—, $Z_2$ is —N—, $Z_3$ is —S—, and $R_2$ is Cl. In an embodiment, $Z_1$ is —C(CN)—, $Z_2$ is —N—, $Z_3$ is —S—, and $R_2$ is F. In an embodiment, $Z_1$ is —N—, $Z_2$ is —C($R_{3c}$)—, $Z_3$ is —S—, and $R_2$ is Cl. In an embodiment, $Z_1$ is —N—, $Z_2$ is —C($R_{3c}$)—, $Z_3$ is —S—, and $R_2$ is F. In an embodiment, $Z_1$ is —N—, $Z_2$ is —N—, $Z_3$ is —S—, and $R_2$ is Cl. In an embodiment, $Z_1$ is —N—, $Z_2$ is —N—, $Z_3$ is —S—, and $R_2$ is F. In an embodiment, $Z_1$ is —C(CN)—, $Z_2$ is —C($R_{3c}$)—, $Z_3$ is —O—, and $R_2$ is Cl. In an embodiment, $Z_1$ is —C(CN)—, $Z_2$ is —C($R_{3c}$)—, $Z_3$ is —O—, and $R_2$ is F. In an embodiment, $Z_1$ is —C(CN)—, $Z_2$ is —N—, $Z_3$ is —O—, and $R_2$ is Cl. In an embodiment, $Z_1$ is —C(CN)—, $Z_2$ is —N—, $Z_3$ is —O—, and $R_2$ is F. In an embodiment, $Z_1$ is —N—, $Z_2$ is —C($R_{3c}$)—, $Z_3$ is —O—, and $R_2$ is Cl. In an embodiment, $Z_1$ is —N—, $Z_2$ is —C($R_{3c}$)—, $Z_3$ is —O—, and $R_2$ is F. In an embodiment, $Z_1$ is —N—, $Z_2$ is —N—, $Z_3$ is —O—, and $R_2$ is Cl. In an embodiment, $Z_1$ is —N—, $Z_2$ is —N—, $Z_3$ is —O—, and $R_2$ is F. In an embodiment, $Z_1$ is —C(CN)—, $Z_2$ is —C($R_{3c}$)—, $Z_3$ is —S—, $R_2$ is $C_1$, v is 1, and n is 0. In an embodiment, $Z_1$ is —C(CN)—, $Z_2$ is —C($R_{3c}$)—, $Z_3$ is —S—, $R_2$ is F, v is 1, and n is 0. In an embodiment, $Z_1$ is —C(CN)—, $Z_2$ is —N—, $Z_3$ is —S—, $R_2$ is Cl, v is 1, and n is 0. In an embodiment, $Z_1$ is —C(CN)—, $Z_2$ is —N—, $Z_3$ is —S—, $R_2$ is F, v is 1, and n is 0. In an embodiment, $Z_1$ is —C(CN)—, $Z_2$ is —N—, $Z_3$ is —S—, $R_2$ is F, v is 1, and n is 0. In an embodiment, $Z_1$ is —N—, $Z_2$ is —C($R_3$)—, $Z_3$ is —S—, $R_2$ is F, v is 1, and n is 0.

References to Formula I should be understood to refer to compounds of Formula I together with any and all sub-formulae disclosed herein, including Formulae I', Ia, Ib, Ic, Id, Ie, If, Ih, Ii, Ij, Ik, Im, Ia*, Ib*, Ic*, Id*, Ie*, If*, Ih*, Ii*, Ij*, Ik*, Im*, Ia-1, Ib-1, Ic-1, Id-1, Ie-1, If-1, Ig-1, Ih-1, Ia*-1, Ib*-1, Ic*-1, Id*-1, Ie*-1, If*-1, Ig*-1, Ih*-1, Ia-2, Ib-2, Ic-2, Id-2, Ie-2, If-2, Ig-2, Ih-2, Ia*-2, Ib*-2, Ic*-2, Id*-2, Ie*-2, If*-2, Ig*-2, Ih*-2, Ia-3, or Ia*-3.

In the above embodiments of the compounds of Formula I, the chemical drawings are shown flat without chiral information. These compounds often have multiple chiral centers and are contemplated to exist in various forms with various combinations of chiral centers. Additionally, these compounds have various enantiomers, diastereomers, and atropisomers that can exist and are included herein.

In an embodiment of a compound of Formula I or a pharmaceutically acceptable salt thereof, the compound is an isotopic derivative of any one of the compounds described herein or a pharmaceutically acceptable salt thereof.

It is understood that the isotopic derivative can be prepared using any of a variety of art-recognized techniques. For example, the isotopic derivatives can generally be prepared by carrying out the procedures disclosed in the schemes and/or in the examples described herein or a pharmaceutically acceptable salt thereof, by substituting an isotopically labeled reagent for a non-isotopically labeled reagent.

In an embodiment of a compound of Formula I or a pharmaceutically acceptable salt thereof, the compound is a deuterium labeled compound of any one of the compounds described herein and pharmaceutically acceptable salts thereof. In a further embodiment of a compound of Formula I or a pharmaceutically acceptable salt thereof, the compound may be deuterated at one or more positions. Unless otherwise stated, when an atom is designated specifically as "H" or "hydrogen", the atom is understood to have hydrogen at its natural abundance isotopic composition. Also, unless otherwise stated, when an atom is designated specifically as "D" or "deuterium", the atom is understood to have deuterium at an abundance substantially greater than the natural abundance of deuterium, which is 0.015%.

The following are further numbered embodiments of the invention:

Embodiment 1. A compound of the formula:

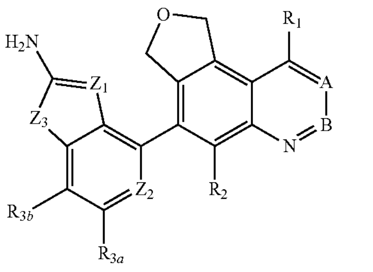

wherein:

A is —C(H)— or —N—;

B is —C($R_4$)— or —N—;

$R_1$ is a group of the formula

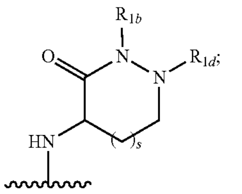

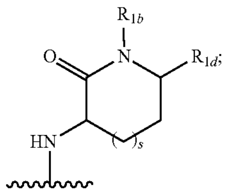

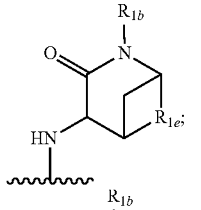

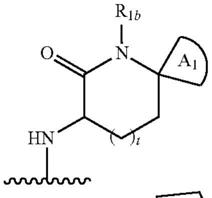

;

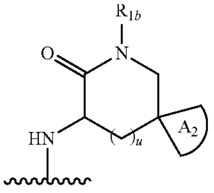

;

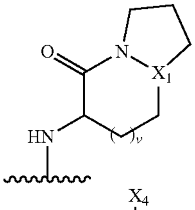

;

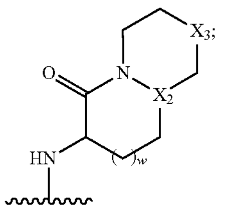

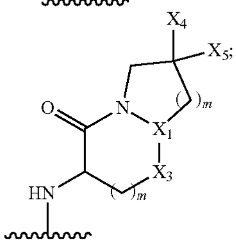

or

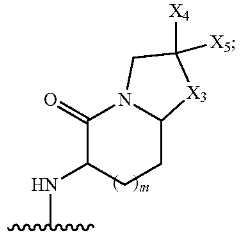

$R_{1b}$ is H or $C_{1-3}$ alkyl;

$R_{1d}$ is $C_{1-3}$ alkyl, $C_{1-3}$ haloalkyl, or $C_{3-4}$ cycloalkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

$X_4$ and $X_5$ are each independently $C_{1-3}$ alkyl, halogen, or H;

m, m', s, t, u, v, and w are each 0 or 1;

$R_2$ is halogen or $C_{1-3}$ alkyl;

$Z_1$ is —C(CN)— or —N—;

$Z_2$ is —C($R_{3c}$)— or —N—;

$Z_3$ is —O— or —S—;

$R_{3a}$, $R_{3b}$, and $R_{3c}$ are each independently H, halogen, or $C_{1-3}$ alkyl;

$R_4$ is H, $C_{1-3}$ alkyl, $C_{1-3}$ alkoxy optionally substituted with 1, 2, 3, or 4 substituents independently selected from hydroxyl and methyl, or $R_4$ is a group of the formula (i)

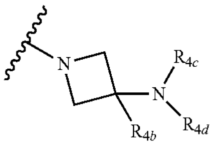

or

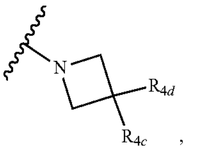

, wherein $R_{4b}$ is H or methyl; and $R_{4c}$ and $R_{4d}$ are each independently $C_{1-3}$ alkyl, hydroxyl, or $C_{1-3}$ haloalkyl; or $R_{4c}$ and $R_{4d}$ together with the nitrogen or carbon atom to which they are attached form a 4-, 5-, or 6-membered heterocycle; or (ii)

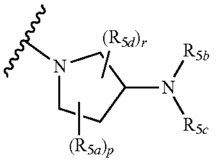

or

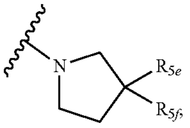

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5d}$ is $C_{1-3}$ alkyl;

$R_{5e}$ and $R_{5f}$ together with the carbon atom to which they are attached form a 4-, 5-, or 6-membered heterocycle;

$R_{5b}$ and $R_{5c}$ are each independently H, $C_{1-6}$ alkyl optionally substituted with one or more deuterium, $C_{3-5}$ cycloalkyl optionally substituted with halogen or $C_{1-3}$ haloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle or a 6-, 7-, or 8-membered spiro heterocycle, wherein each heterocycle or spiro heterocycle optionally contains a further heteroatom selected from N, O, and S, and wherein the heterocycle and the spiro heterocycle is each optionally substituted with one or more halogen, deuterium, $C_{1-3}$ alkyl, or $C_{1-3}$ haloalkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p and r are each 0, 1, or 2;

(iii)

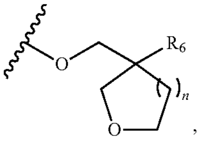

, wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, and $C_{1-3}$ dialkylamino; and n is O or 1; and (iv)

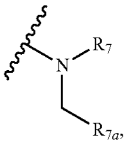

wherein $R_7$ is a $C_{1-3}$ alkyl; and $R_{7a}$ is a 4-, 5-, or 6-membered heterocycle optionally containing a further heteroatom selected from N, O, and S; or $R_7$ and $R_{7a}$ together with the atoms to which they are attached form a 4-, 5-, or 6-membered heterocyclic ring optionally containing a further heteroatom selected from N, O, and S;

or a pharmaceutically acceptable salt thereof.

Embodiment 2. A compound of the formula:

Formula I'

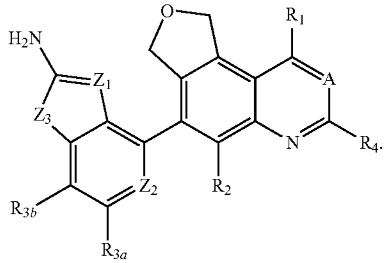

wherein:

$R_1$ is a group of the formula

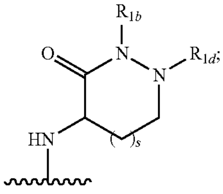

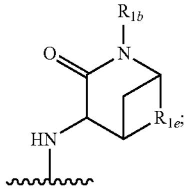

-continued

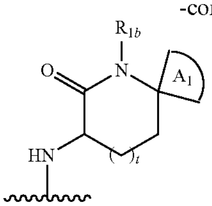
;
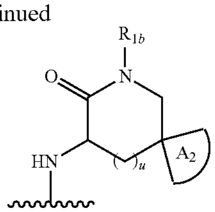
;
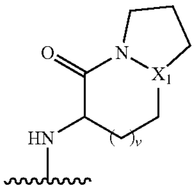
;
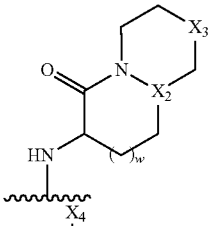
; or
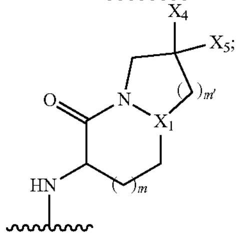

$R_{1b}$ is H or $C_{1-3}$ alkyl;

$R_{1d}$ is $C_{1-3}$ alkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

$X_4$ and $X_5$ are each independently $C_{1-3}$ alkyl, halogen, or H;

m, m', s, t, u, v, and w are each 0 or 1;

$R_2$ is halogen;

$Z_1$ is —C(CN)— or —N—;

$Z_2$ is —C($R_{3c}$)— or —N—;

$Z_3$ is —O— or —S—;

$R_{3a}$, $R_{3b}$, and $R_{3c}$ are each independently H or halogen;

$R_4$ is a group of the formula (i)

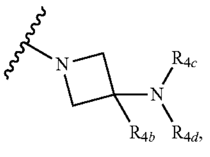

wherein $R_{4b}$ is H or methyl; and $R_{4c}$ and $R_{4d}$ are each independently $C_{1-3}$ alkyl; or (ii)

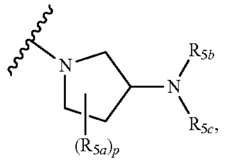

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p is 0, 1, or 2;

(iii)

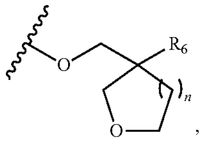

wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, and $C_{1-3}$ dialkylamino; and n is 0 or 1;

or a pharmaceutically acceptable salt thereof.

Embodiment 3. A compound of the formula:

Formula I'

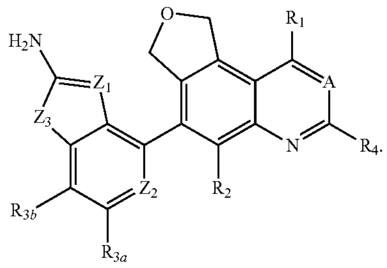

wherein:

$R_1$ is a group of the formula

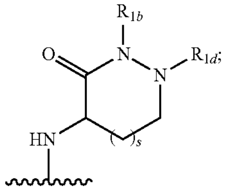
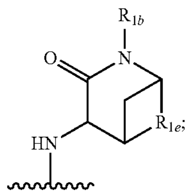

-continued

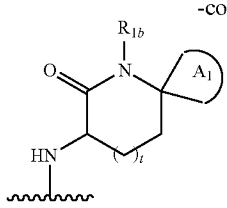 ; 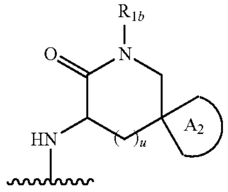 ;

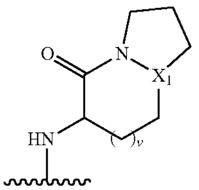 ; or 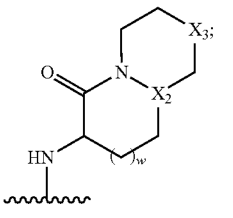

$R_{1b}$ is $C_{1-3}$ alkyl;

$R_{1d}$ is $C_{1-3}$ alkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

s, t, u, v, and w are each 0 or 1;

$R_2$ is halogen;

$Z_1$ is —C(CN)— or —N—;

$Z_2$ is —C($R_{3c}$)— or —N—;

$Z_3$ is —O— or —S—;

$R_{3a}$, $R_{3b}$, and $R_{3c}$ are each independently H or halogen;

$R_4$ is a group of the formula

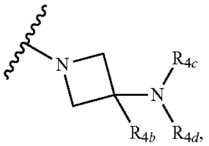

(i)

wherein $R_{4b}$ is H or methyl; and $R_{4c}$ and $R_{4d}$ are each independently $C_{1-3}$ alkyl; or

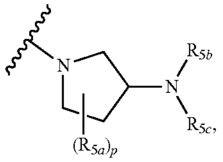

(ii)

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p is0 or 1;

or a pharmaceutically acceptable salt thereof.

Embodiment 4. The compound according to any one of embodiments 1-3, wherein $R_1$ is a group of formula

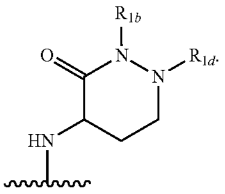

or a pharmaceutically acceptable salt thereof.

Embodiment 5. The compound according to embodiment 4, wherein $R_{1d}$ is methyl or ethyl, or a pharmaceutically acceptable salt thereof.

Embodiment 6. The compound according to embodiment 1, wherein $R_1$ is a group of formula

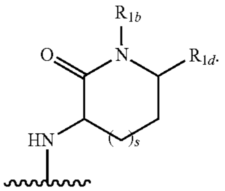

or a pharmaceutically acceptable salt thereof.

Embodiment 7. The compound according to embodiment 1 or 6, wherein $R_{1d}$ is methyl, ethyl, or difluoromethyl, or a pharmaceutically acceptable salt thereof.

Embodiment 8. The compound according to any one of embodiments 1-3, wherein $R_1$ is a group of formula

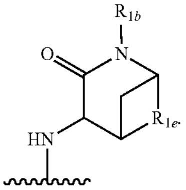

or a pharmaceutically acceptable salt thereof.

Embodiment 9. The compound according to embodiment 8, wherein $R_{1e}$ is methylene, or a pharmaceutically acceptable salt thereof.

Embodiment 10. The compound according to any one of embodiments 1-3, wherein $R_1$ is a group of formula

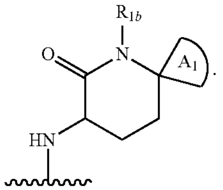

or a pharmaceutically acceptable salt thereof.

Embodiment 11. The compound according to embodiment 10, wherein Ring $A_1$ is $C_{3-4}$ cycloalkyl, or a pharmaceutically acceptable salt thereof.

Embodiment 12. The compound according to embodiment 10, wherein Ring $A_1$ is cyclopropyl, or a pharmaceutically acceptable salt thereof.

Embodiment 13. The compound according to embodiment 10, wherein Ring $A_1$ is cyclobutyl, or a pharmaceutically acceptable salt thereof.

Embodiment 14. The compound according to embodiment 10, wherein Ring $A_1$ is a 3- or 4-membered heterocycle containing a heteroatom selected from N, O, and S, or a pharmaceutically acceptable salt thereof.

Embodiment 15. The compound according to embodiment 10, wherein Ring $A_1$ is oxetanyl, or a pharmaceutically acceptable salt thereof.

Embodiment 16. The compound according to any one of embodiments 1-3, wherein $R_1$ is a group of formula

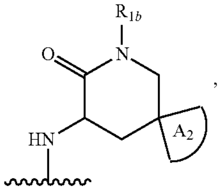

or a pharmaceutically acceptable salt thereof.

Embodiment 17. The compound according to embodiment 16, wherein Ring $A_2$ is $C_{3-4}$ cycloalkyl, or a pharmaceutically acceptable salt thereof.

Embodiment 18. The compound according to embodiment 16, wherein Ring $A_2$ is cyclopropyl, or a pharmaceutically acceptable salt thereof.

Embodiment 19. The compound according to embodiment 16, wherein Ring $A_2$ is cyclobutyl, or a pharmaceutically acceptable salt thereof.

Embodiment 20. The compound according to embodiment 16, wherein Ring $A_2$ is a 3- or 4-membered heterocycle containing a heteroatom selected from N, O, and S, or a pharmaceutically acceptable salt thereof.

Embodiment 21. The compound according to embodiment 16, wherein Ring $A_2$ is oxetanyl, or a pharmaceutically acceptable salt thereof.

Embodiment 22. The compound according to any one of embodiments 1 or 4-21, wherein A is —C(H)—, or a pharmaceutically acceptable salt thereof.

Embodiment 23. The compound according to any one of embodiments 1 or 4-21, wherein A is —N—, or a pharmaceutically acceptable salt thereof.

Embodiment 24. The compound according to any one of embodiments 1 or 4-23, wherein B is —C($R_4$)—, or a pharmaceutically acceptable salt thereof.

Embodiment 25. The compound according to any one of embodiments 1 or 4-23, wherein B is —N—, or a pharmaceutically acceptable salt thereof.

Embodiment 26. The compound according to any one of embodiments 1-25, wherein $R_{1b}$ is $C_{1-3}$ alkyl, or a pharmaceutically acceptable salt thereof.

Embodiment 27. The compound according to any one of embodiments 1-25, wherein $R_{1b}$ is methyl, or a pharmaceutically acceptable salt thereof.

Embodiment 28. The compound according to any one of embodiments 1-25, wherein $R_{1b}$ is hydrogen, or a pharmaceutically acceptable salt thereof.

Embodiment 29. The compound according to embodiment 1, wherein $R_1$ is a group of formula

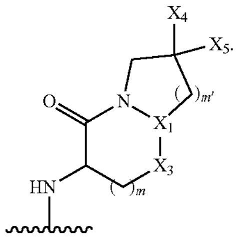

or a pharmaceutically acceptable salt thereof.

Embodiment 30. The compound according to embodiment 29, wherein $X_4$ and $X_5$ are fluoro, or a pharmaceutically acceptable salt thereof.

Embodiment 31. The compound according to embodiment 29 or 30, wherein $X_3$ is —O—, or a pharmaceutically acceptable salt thereof.

Embodiment 32. The compound according to embodiment 29 or 30, wherein $X_3$ is —$CH_2$—, or a pharmaceutically acceptable salt thereof.

Embodiment 33. The compound according to embodiment 1, wherein $R_1$ is a group of formula

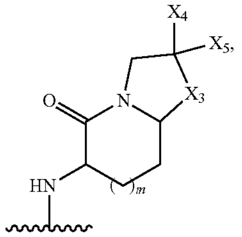

or a pharmaceutically acceptable salt thereof.

Embodiment 34. The compound according to embodiment 33, wherein $X_4$ is methyl and $X_5$ is hydrogen, or a pharmaceutically acceptable salt thereof.

Embodiment 35. The compound according to embodiment 33 or 34, wherein $X_3$ is —O—, or a pharmaceutically acceptable salt thereof.

Embodiment 36. The compound according to any one of embodiments 1-3, wherein $R_1$ is a group of formula

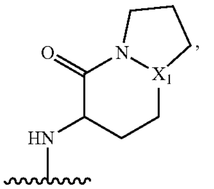

or a pharmaceutically acceptable salt thereof.

Embodiment 37. The compound according to embodiment 36, wherein $X_1$ is —CH—, or a pharmaceutically acceptable salt thereof.

Embodiment 38. The compound according to embodiment 36, wherein $X_1$ is —N—, or a pharmaceutically acceptable salt thereof.

Embodiment 39. The compound according to any one of embodiments 1-3, wherein $R_1$ is a group of formula

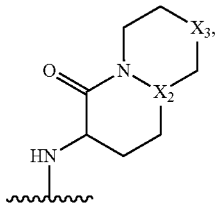

or a pharmaceutically acceptable salt thereof.

Embodiment 40. The compound according to embodiment 39, wherein $X_2$ is —CH—, or a pharmaceutically acceptable salt thereof.

Embodiment 41. The compound according to embodiment 39, wherein $X_2$ is —N—, or a pharmaceutically acceptable salt thereof.

Embodiment 42. The compound according to any one of embodiments 39-41, wherein $X_3$ is —$CH_2$—, or a pharmaceutically acceptable salt thereof.

Embodiment 43. The compound according to any one of embodiments 39-41, wherein $X_3$ is —O—, or a pharmaceutically acceptable salt thereof.

Embodiment 44. The compound according to any one of embodiments 1-3, wherein $R_1$ is a group of the formula

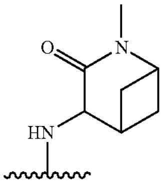 , 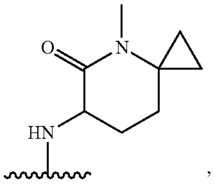 ,

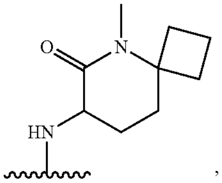 , 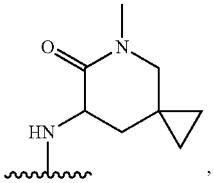 ,

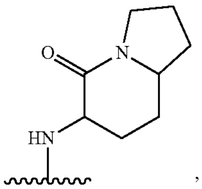 , 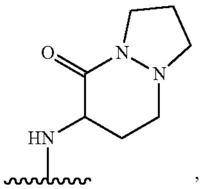 , or

-continued

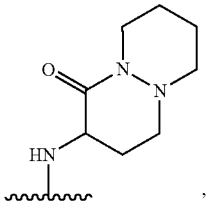 , or a pharmaceutically acceptable salt thereof.

Embodiment 45. The compound according to embodiment 44, wherein $R_1$ is a group of the formula

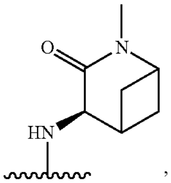 , 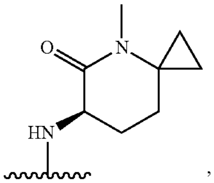 ,

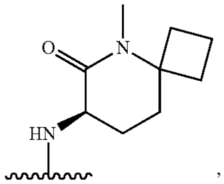 , 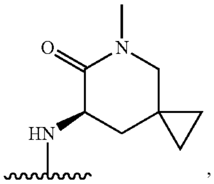 ,

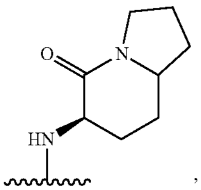 , 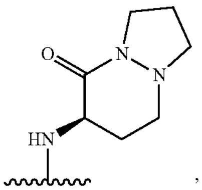 , or

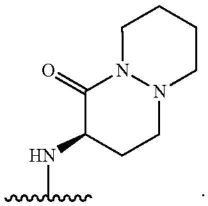 .

or a pharmaceutically acceptable salt thereof.

Embodiment 46. The compound according to embodiment 1, wherein $R_1$ is a group of the formula

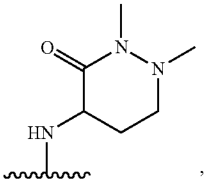 , 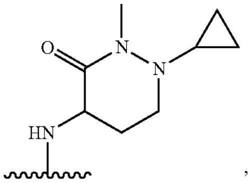 ,

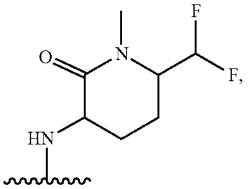 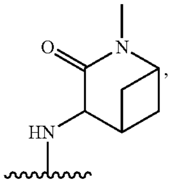

-continued
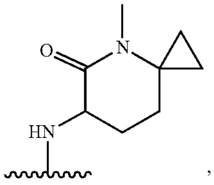,
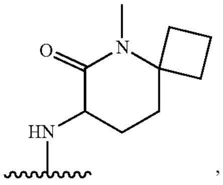,
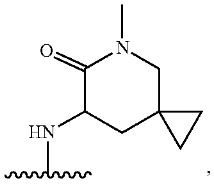,
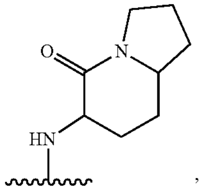,
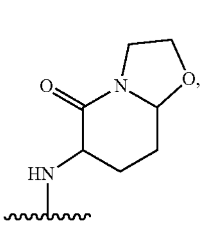
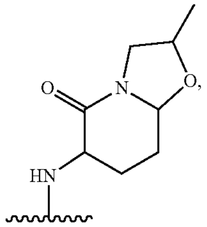,
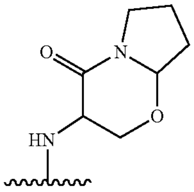
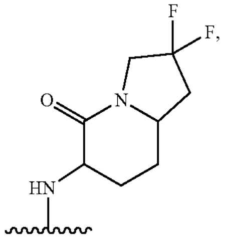
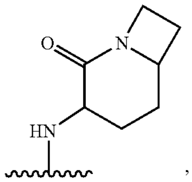,
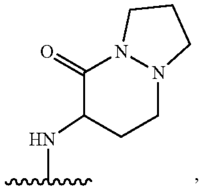,
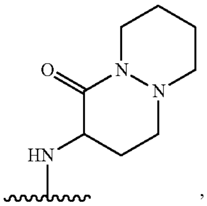,
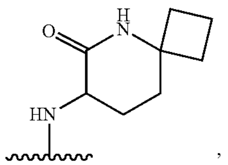,
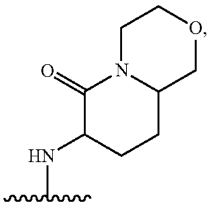 or
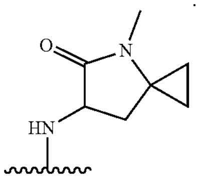.
pharmaceutically acceptable salt thereof.
Embodiment 47. The compound according to embodiment 1-2 or 46, wherein $R_1$ is a group of the formula
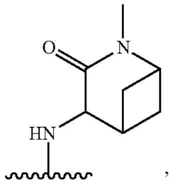,
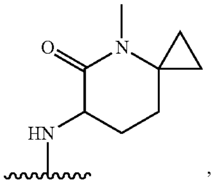,
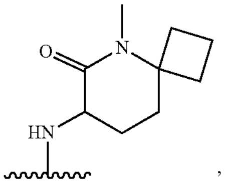,
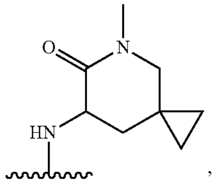,
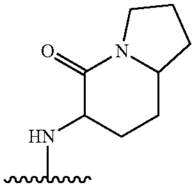
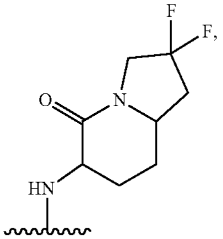
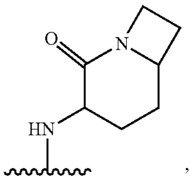,
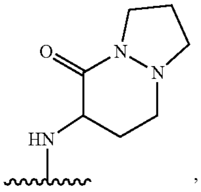,
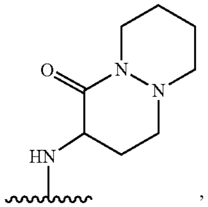,
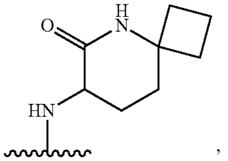,
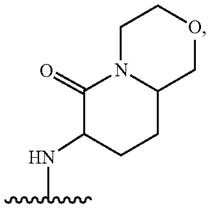 or
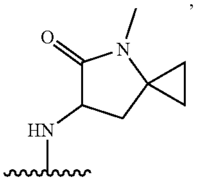,
pharmaceutically acceptable salt thereof.
Embodiment 48. The compound according to embodiment 46, wherein $R_1$ is a group of the formula
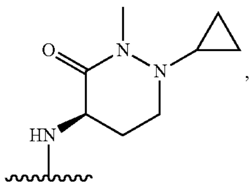,
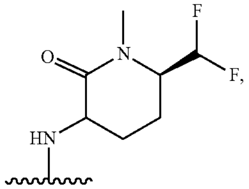

-continued

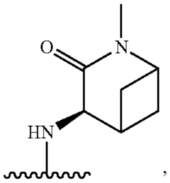 , 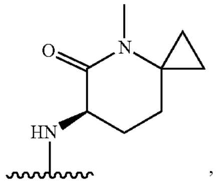 ,

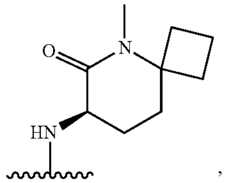 , 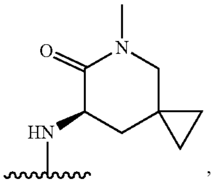 ,

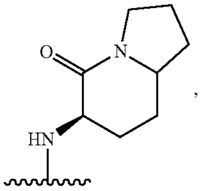 , 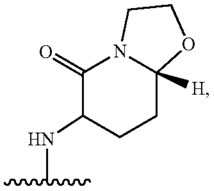

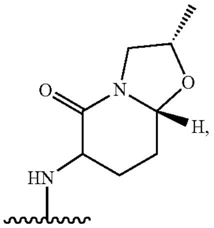 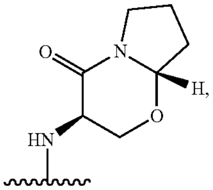 ,

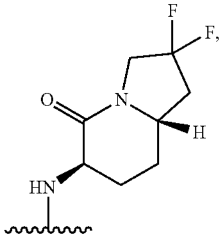 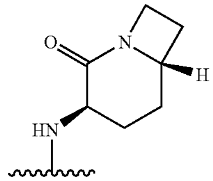

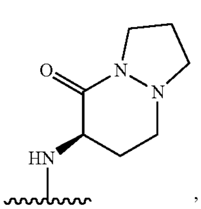 , 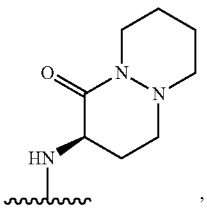 , or

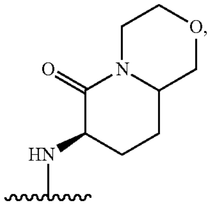

or a pharmaceutically acceptable salt thereof.

Embodiment 49. The compound according to embodiment 46 or 47, wherein $R_1$ is a group of the formula

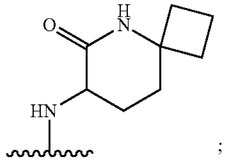 ; 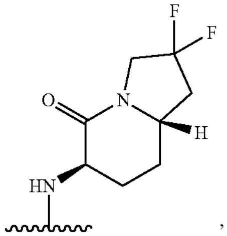 ,

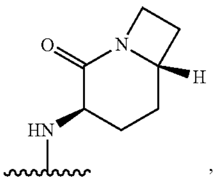 , 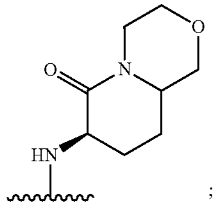 ; or

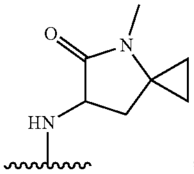 , or a pharmaceutically acceptable salt thereof.

Embodiment 50. The compound according to any one of embodiments 1-49, wherein $R_2$ is F or Cl, or a pharmaceutically acceptable salt thereof.

Embodiment 51. The compound according to any one of embodiments 1-50, wherein $R_2$ is F, or a pharmaceutically acceptable salt thereof.

Embodiment 52. The compound according to any one of embodiments 1-50, wherein $R_2$ is Cl, or a pharmaceutically acceptable salt thereof.

Embodiment 53. The compound according to embodiment 1, wherein $R_2$ is methyl, or a pharmaceutically acceptable salt thereof.

Embodiment 54. The compound according to any one of embodiments 1-53, wherein $Z_1$ is —C(CN)—, $Z_2$ is —C($R_{3c}$)—, $Z_3$ is —S—, and $R_{3a}$ is H, or a pharmaceutically acceptable salt thereof.

Embodiment 55. The compound according to embodiment 54, wherein $R_{3b}$ is halogen (preferably fluoro), and $R_{3c}$ is H, or a pharmaceutically acceptable salt thereof.

Embodiment 56. The compound according to embodiment 54, wherein $R_{3b}$ is H, and $R_{3c}$ is halogen (preferably fluoro), or a pharmaceutically acceptable salt thereof.

Embodiment 57. The compound according to embodiment 54, wherein $R_{3b}$ is halogen (preferably fluoro), and $R_{3c}$ is halogen (preferably fluoro), or a pharmaceutically acceptable salt thereof.

Embodiment 58. The compound according to any one of embodiments 1-53, wherein $Z_1$ is —C(CN)—, $Z_2$ is —N—, $Z_3$ is —S—, and $R_{3a}$ is H, or a pharmaceutically acceptable salt thereof.

Embodiment 59. The compound according to embodiment 58, wherein $R_{3b}$ is halogen (preferably fluoro), or a pharmaceutically acceptable salt thereof.

Embodiment 60. The compound according to any one of embodiments 1-53, wherein $Z_1$ is —N—, $Z_2$ is —C($R_{3c}$)—, $Z_3$ is —S—, and $R_{3a}$ is H, or a pharmaceutically acceptable salt thereof.

Embodiment 61. The compound according to embodiment 60, wherein $R_{3b}$ is halogen (preferably fluoro), and $R_{3c}$ is H, or a pharmaceutically acceptable salt thereof.

Embodiment 62. The compound according to embodiment 60, wherein $R_{3b}$ is H, and $R_{3c}$ is halogen (preferably fluoro), or a pharmaceutically acceptable salt thereof.

Embodiment 63. The compound according to embodiment 60, wherein $R_{3b}$ is halogen (preferably fluoro), and $R_{3c}$ is halogen (preferably fluoro), or a pharmaceutically acceptable salt thereof.

Embodiment 64. The compound according to embodiment 60, wherein $R_{3b}$ is H, and $R_{3c}$ is H, or a pharmaceutically acceptable salt thereof.

Embodiment 65. The compound according to any one of embodiments 1-53, wherein $Z_1$ is —N—, $Z_2$ is —N—, $Z_3$ is —S—, and $R_{3a}$ is H, or a pharmaceutically acceptable salt thereof.

Embodiment 66. The compound according to embodiment 65, wherein $R_{3b}$ is halogen (preferably fluoro), or a pharmaceutically acceptable salt thereof.

Embodiment 67. The compound according to any one of embodiments 1-53, wherein $Z_1$ is —N—, $Z_2$ is —C($R_{3c}$)—, $Z_3$ is —O—, and $R_{3a}$ is H, or a pharmaceutically acceptable salt thereof.

Embodiment 68. The compound according to embodiment 67, wherein $R_{3b}$ is hydrogen, or a pharmaceutically acceptable salt thereof.

Embodiment 69. The compound according to any one of embodiments 1-53, wherein $R_{3b}$ is fluoro or hydrogen, or a pharmaceutically acceptable salt thereof.

Embodiment 70. The compound according to any one of embodiments 1-53, wherein $R_{3b}$ is fluoro, or a pharmaceutically acceptable salt thereof.

Embodiment 71. The compound according to any one of embodiments 1 or 4-53, wherein $R_{3a}$ is methyl, or a pharmaceutically acceptable salt thereof.

Embodiment 72. The compound according to any one of embodiments 1-53, wherein $R_{3b}$ is hydrogen, or a pharmaceutically acceptable salt thereof.

Embodiment 73. The compound according to any one of embodiments 1 or 4-72, wherein $R_4$ is H, $C_{1-3}$ alkyl, or $C_{1-3}$ alkoxy optionally substituted with 1, 2, 3, or 4 substituents independently selected from hydroxyl and methyl, or a pharmaceutically acceptable salt thereof.

Embodiment 74. The compound according to embodiment 73, wherein $R_4$ is H, or a pharmaceutically acceptable salt thereof.

Embodiment 75. The compound according to any one of embodiments 1-72, wherein $R_4$ is a group of the formula

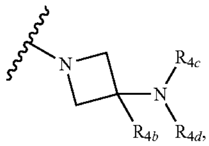

or a pharmaceutically acceptable salt thereof.

Embodiment 76. The compound according to embodiment 75, wherein $R_4$ is a group of the formula

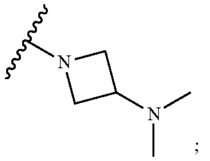 [SMILES: *N1CC(N(C)C)C1]
;
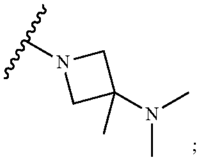
; or

-continued

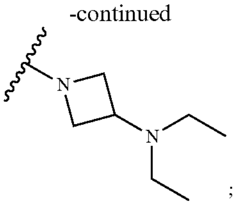
;

or a pharmaceutically acceptable salt thereof.

Embodiment 77. The compound according to embodiment 76, wherein $R_4$ is a group of the formula

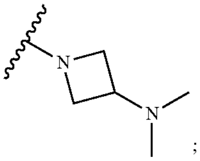
;

or a pharmaceutically acceptable salt thereof.

Embodiment 78. The compound according to any one of embodiments 1 or 4-72, wherein $R_4$ is a group of the formula

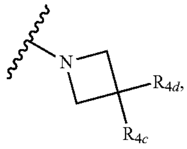

or a pharmaceutically acceptable salt thereof.

Embodiment 79. The compound according to embodiment 1 or 78, wherein $R_4$ is a group of the formula

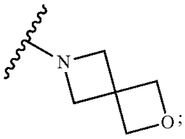
;
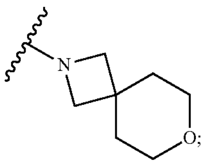
; or
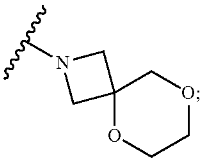
;

or a pharmaceutically acceptable salt thereof.

Embodiment 80. The compound according to any one of embodiments 1 or 4-72, wherein $R_4$ is a group of the formula

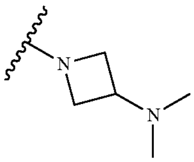
;
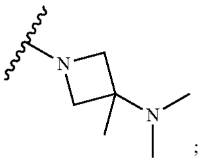
;

-continued

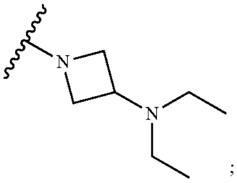
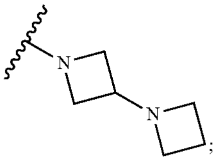
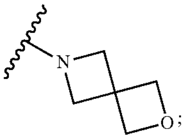
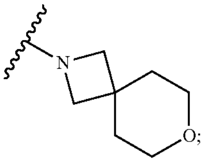
or
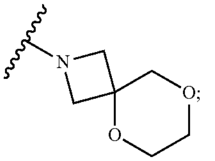

or a pharmaceutically acceptable salt thereof.

Embodiment 81. The compound according to any one of embodiments 1 or 4-72, wherein $R_4$ is a group of the formula

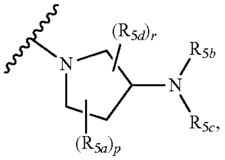

or a pharmaceutically acceptable salt thereof.

Embodiment 82. The compound according to embodiment 81, wherein $R_4$ is a group of the formula

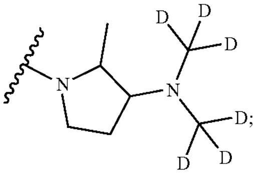
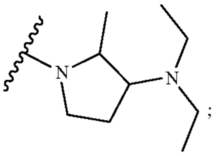
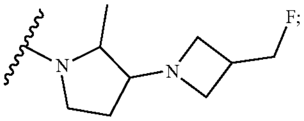
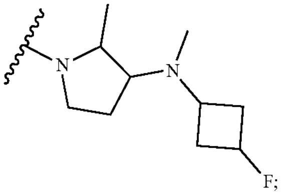

-continued

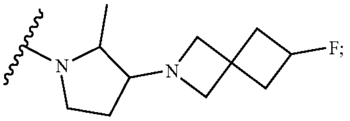
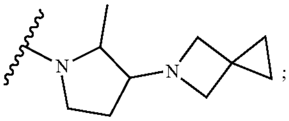
or
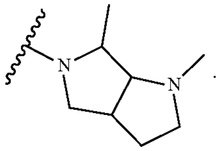

or a pharmaceutically acceptable salt thereof.

Embodiment 83. The compound according to any one of embodiments 1-72 or 81, wherein $R_4$ is a group of the formula

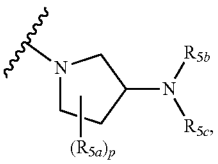

or a pharmaceutically acceptable salt thereof.

Embodiment 84. The compound according to embodiment 83, wherein $R_4$ is a group of the formula

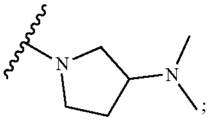
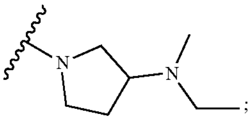
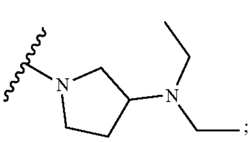
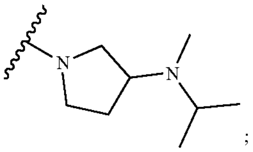
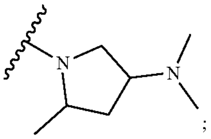
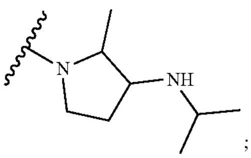
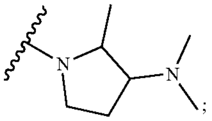
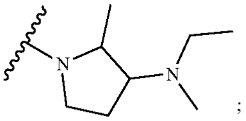
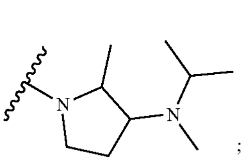
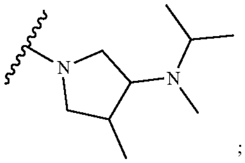

-continued
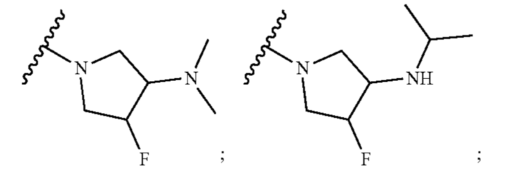
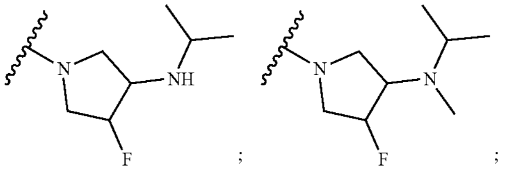
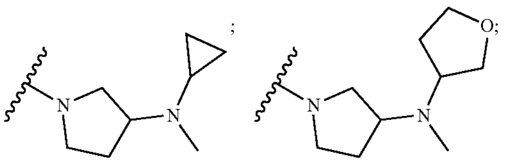
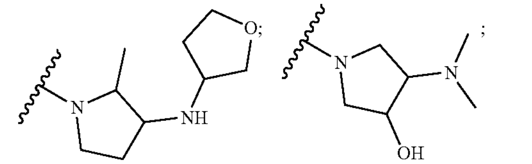
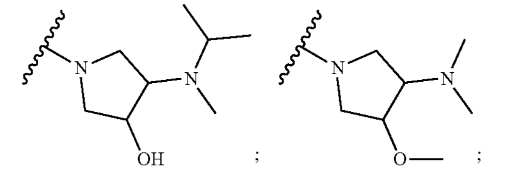
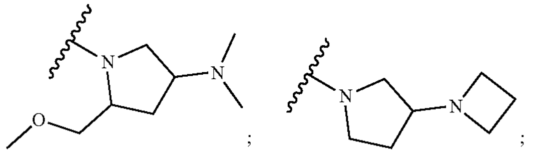
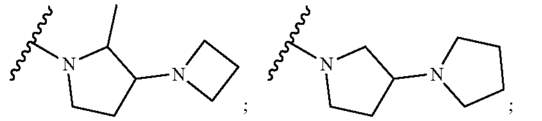
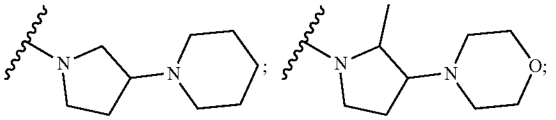
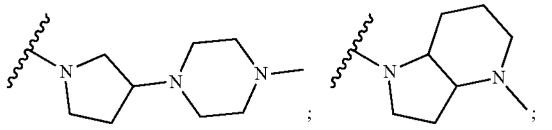
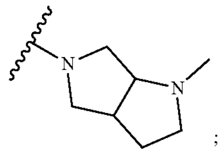
; or
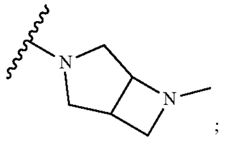
;
or a pharmaceutically acceptable salt thereof.
Embodiment 85. The compound according to embodiment 1, wherein $R_4$ is a group of the formula
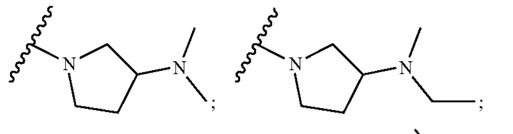
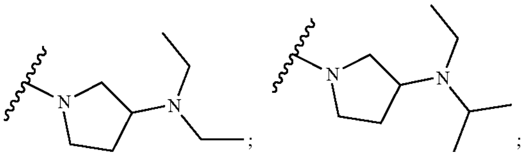
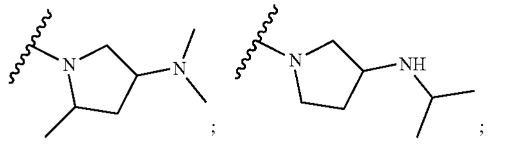
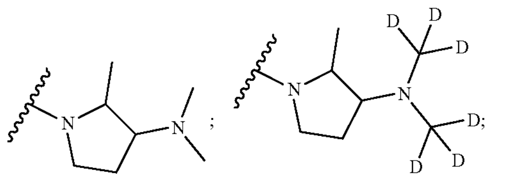
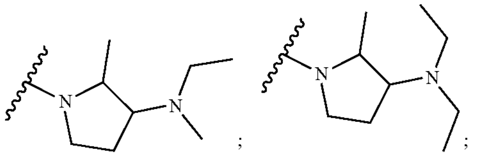
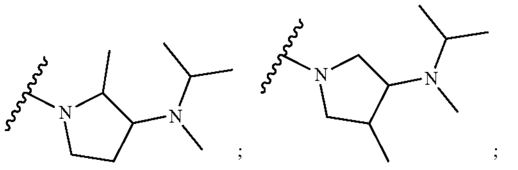
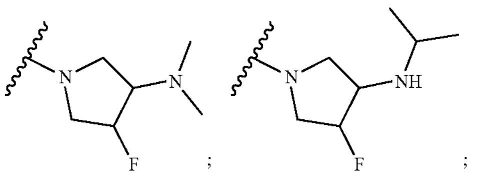
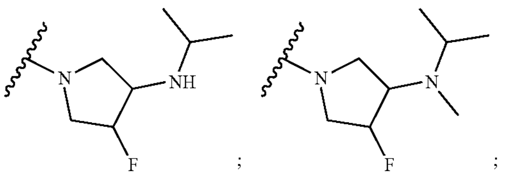
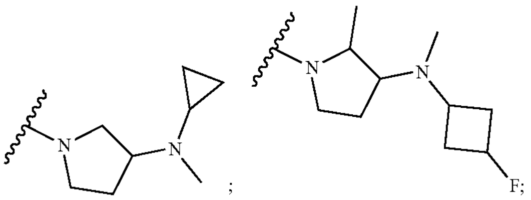
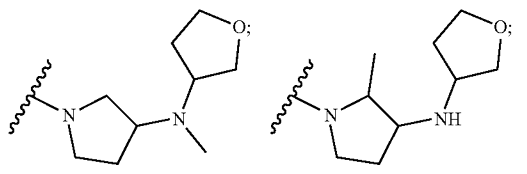

-continued

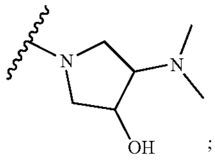 ; 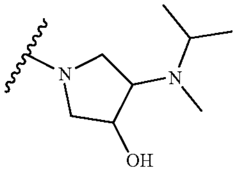 ;

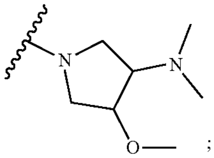 ; 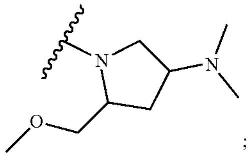 ;

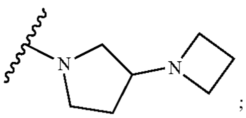 ; 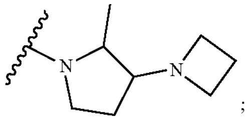 ;

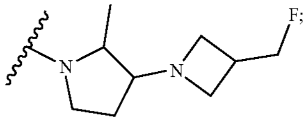 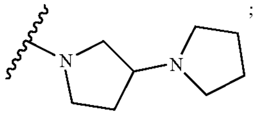 ;

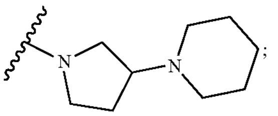 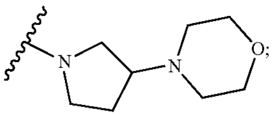

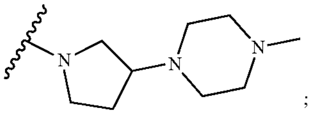 ; 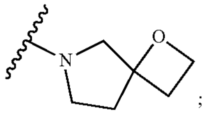 ;

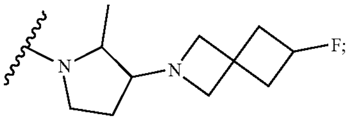

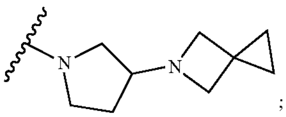 ; 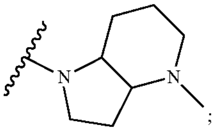 ;

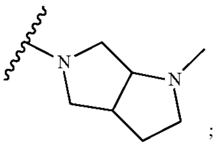 ; 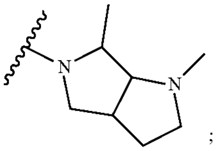 ; or

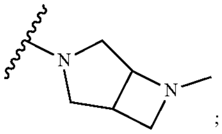 ;

or a pharmaceutically acceptable salt thereof.

Embodiment 86. The compound according to embodiment 84 or 85, wherein $R_4$ is a group of the formula

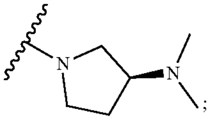 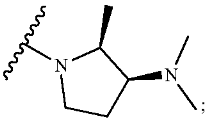

-continued

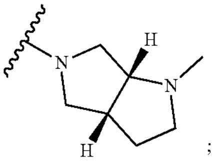 ; or 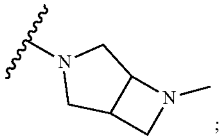 ;

or a pharmaceutically acceptable salt thereof.

Embodiment 87. The compound according to embodiment 84 or 85, wherein $R_4$ is a group of the formula

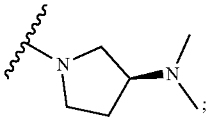 [SMILES: *N1CC[C@H](N(C)C)C1]

or a pharmaceutically acceptable salt thereof.

Embodiment 88. The compound according to embodiment 84 or 85, wherein $R_4$ is a group of the formula

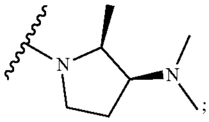 [SMILES: *N1CC[C@H](N(C)C)[C@@H]1C]

or a pharmaceutically acceptable salt thereof.

Embodiment 89. The compound according to embodiment 84 or 85, wherein $R_4$ is a group of the formula

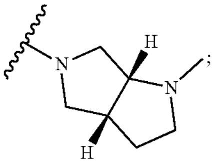 [SMILES: *N1C[C@H]2CCN(C)[C@H]2C1]

or a pharmaceutically acceptable salt thereof.

Embodiment 90. The compound according to embodiment 84 or 85, wherein $R_4$ is a group of the formula

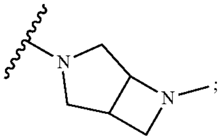 [SMILES: *N1CC2CN(C)C2C1]

or a pharmaceutically acceptable salt thereof.

Embodiment 91. The compound according to embodiment 84 or 85, wherein $R_4$ is a group of the formula

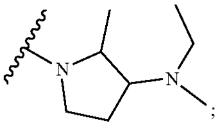 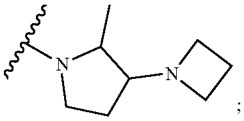

-continued

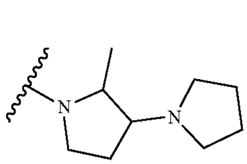 ; 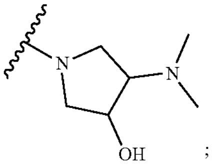 ;

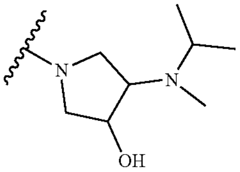 ; 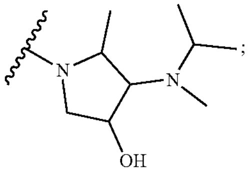 ;

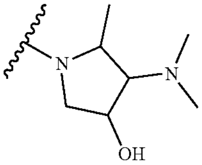 ; or 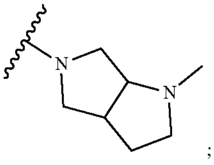 ;

or a pharmaceutically acceptable salt thereof.

Embodiment 92. The compound according to embodiment 84 or 85, wherein $R_4$ is a group of the formula

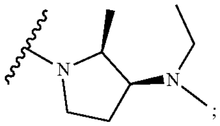 [SMILES: *N1CC[C@H](N(C)CC)[C@@H]1C] ; 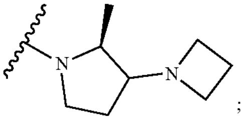 ;

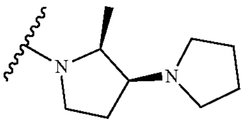 ; 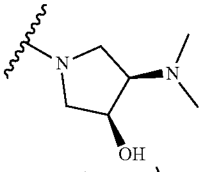 ;

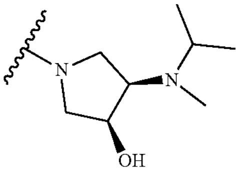 ; 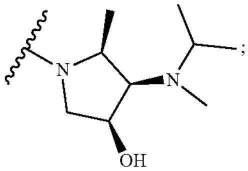 ;

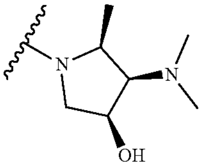 ; or 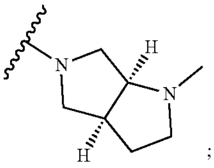 ;

or a pharmaceutically acceptable salt thereof.

Embodiment 93. The compound according to embodiment 84 or 85, wherein $R_4$ is a group of the formula

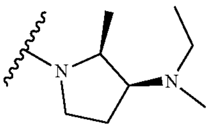 ;

Embodiment 94. The compound according to embodiment 84 or 85, wherein $R_4$ is a group of the formula

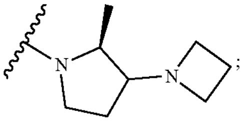 [SMILES: *N1CCC(N2CCC2)[C@@H]1C] ;

or a pharmaceutically acceptable salt thereof.

Embodiment 95. The compound according to embodiment 84 or 85, wherein $R_4$ is a group of the formula

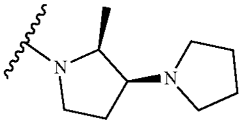 ;

or a pharmaceutically acceptable salt thereof.

Embodiment 96. The compound according to embodiment 84 or 85, wherein $R_4$ is a group of the formula

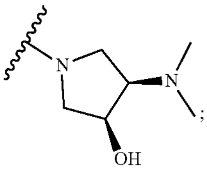 [SMILES: *N1C[C@@H](N(C)C)[C@@H](O)C1] ;

or a pharmaceutically acceptable salt thereof.

Embodiment 97. The compound according to embodiment 84 or 85, wherein $R_4$ is a group of the formula

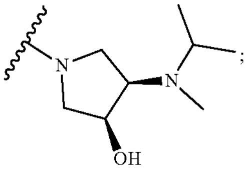 [SMILES: *N1C[C@@H](N(C)C(C)C)[C@@H](O)C1] ;

or a pharmaceutically acceptable salt thereof.

Embodiment 98. The compound according to embodiment 84 or 85, wherein $R_4$ is a group of the formula

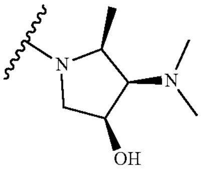 ;

or a pharmaceutically acceptable salt thereof.

Embodiment 99. The compound according to embodiment 84 or 85, wherein $R_4$ is a group of the formula

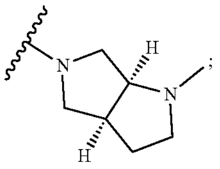 [SMILES: *N1C[C@@H]2CCN(C)[C@@H]2C1]

or a pharmaceutically acceptable salt thereof.

Embodiment 100. The compound according to any one of embodiments 1-2 or 4-72, wherein $R_4$ is a group of the formula

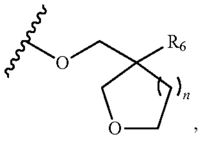

or a pharmaceutically acceptable salt thereof.

Embodiment 101. The compound according to embodiment 100, wherein n is 0, or a pharmaceutically acceptable salt thereof.

Embodiment 102. The compound according to embodiment 100, wherein $R_6$ is selected from $C_{1-3}$ alkyl, $C_{1-3}$ haloalkyl, and $C_{1-3}$ dialkylamino, or a pharmaceutically acceptable salt thereof.

Embodiment 103. The compound according to any one of embodiments 100-102, wherein $R_6$ is dimethylamino, or a pharmaceutically acceptable salt thereof.

Embodiment 104. The compound according to any one of embodiments 102-103, wherein $R_4$ is a group of the formula

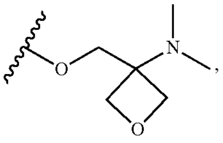 [SMILES: *OCC1(N(C)C)COC1]

or a pharmaceutically acceptable salt thereof.

Embodiment 105. The compound according to any one of embodiments 1 or 4-72, wherein $R_4$ is a group of the formula

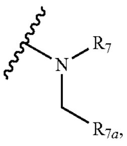

or a pharmaceutically acceptable salt thereof.

Embodiment 106. The compound according to embodiment 105, wherein $R_7$ is a $C_{1-3}$ alkyl; and $R_{7a}$ is a 4-, 5-, or 6-membered heterocycle optionally containing a further heteroatom selected from N, O, and S; or $R_7$ and $R_{7a}$ together with the atoms to which they are attached form a 4-, 5-, or 6-membered heterocyclic ring optionally containing a further heteroatom selected from N, O, and S.

Embodiment 107. The compound according to embodiment 105 or 106, wherein $R_4$ is a group of the formula

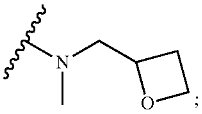
;
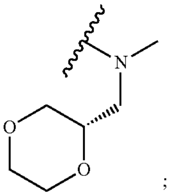
; or
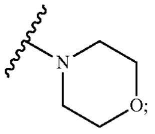

or a pharmaceutically acceptable salt thereof.

Embodiment 108. The compound according to any one of embodiments 1-3, wherein the compound is selected from

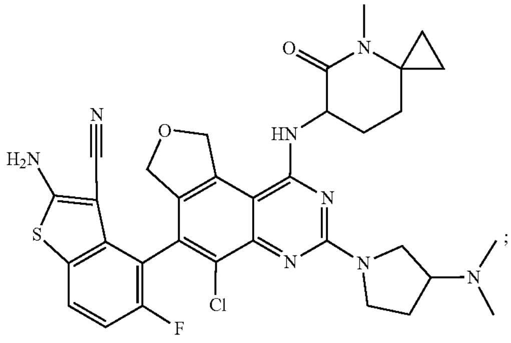
;
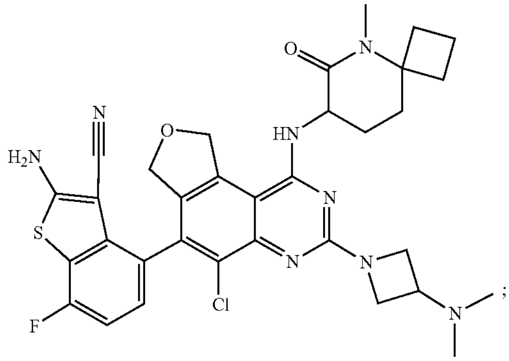
;
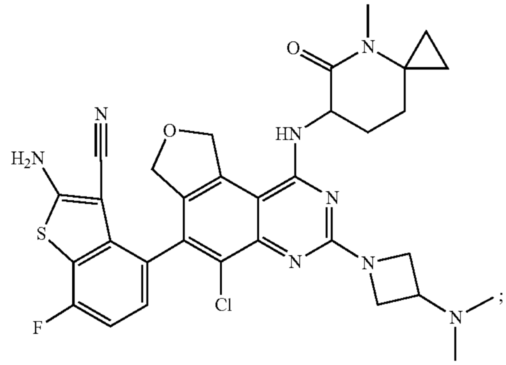
;

-continued
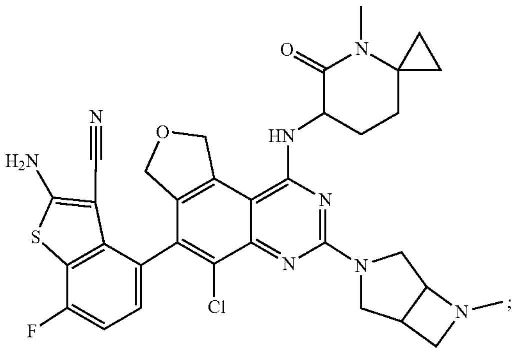
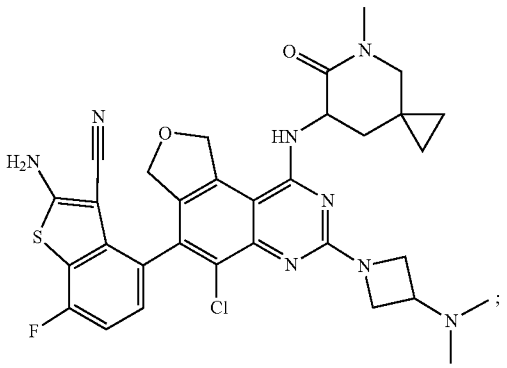
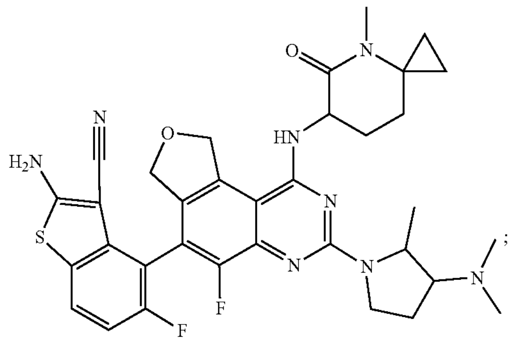
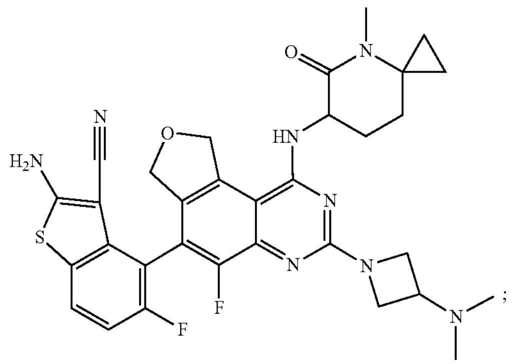
-continued
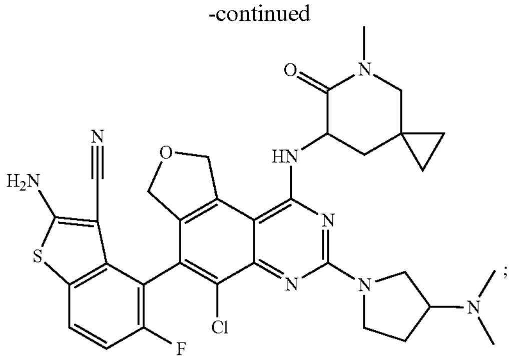
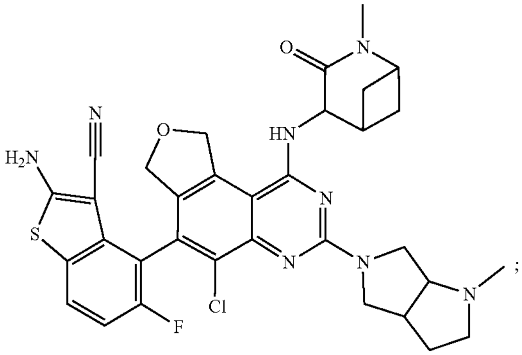
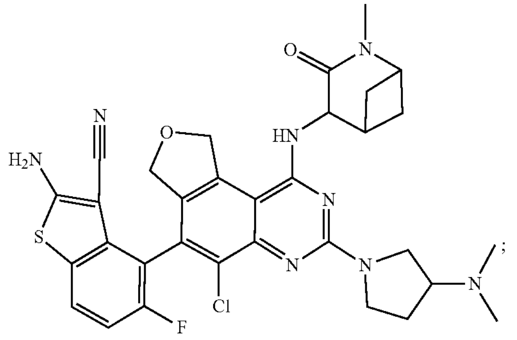
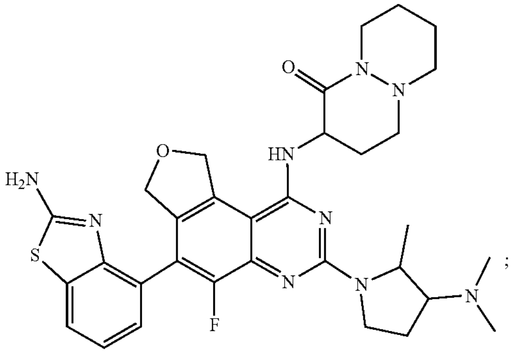
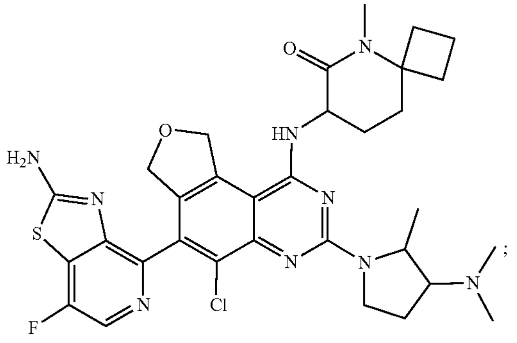

-continued
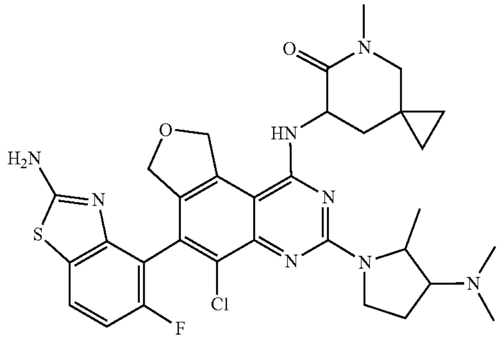
;
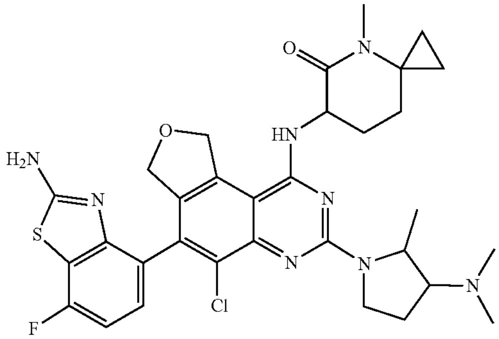
;
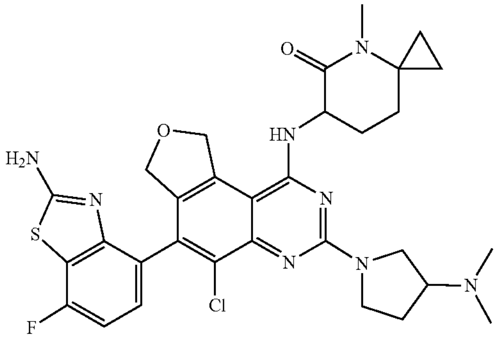
;
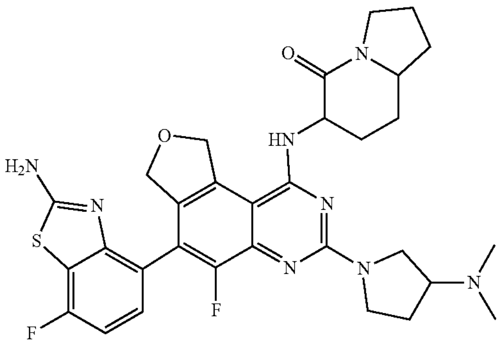
;
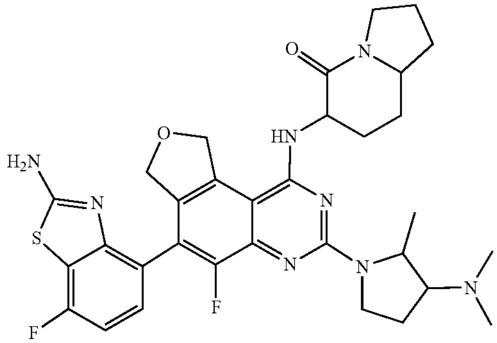
;
-continued
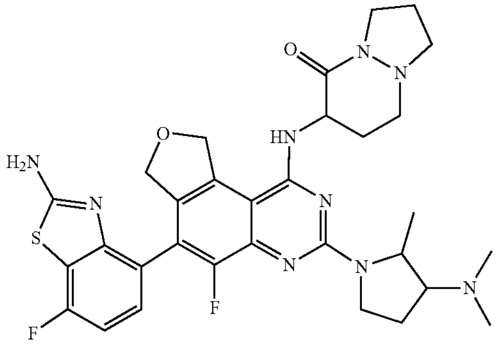
;
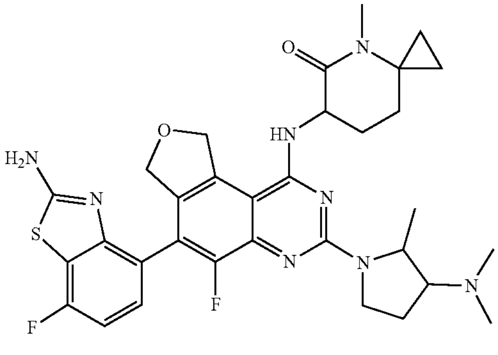
; and
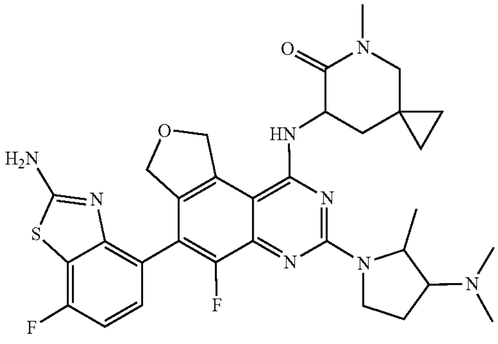
;
or a pharmaceutically acceptable salt thereof.
Embodiment 109. The compound according to any one of embodiments 1-3, or 108, wherein the compound is selected from
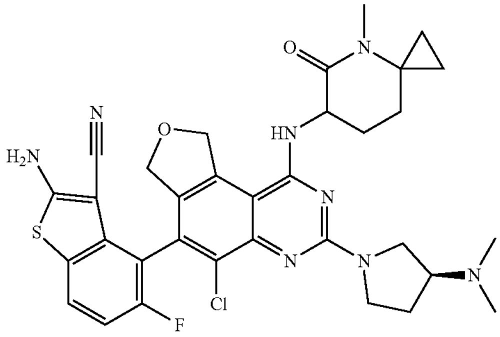
;

-continued
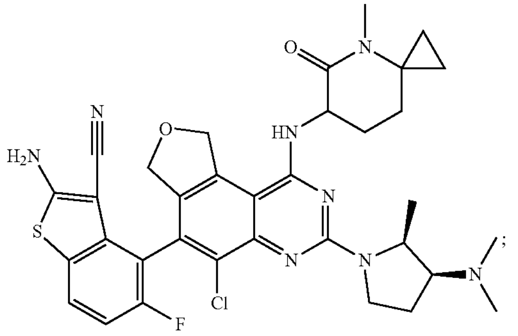
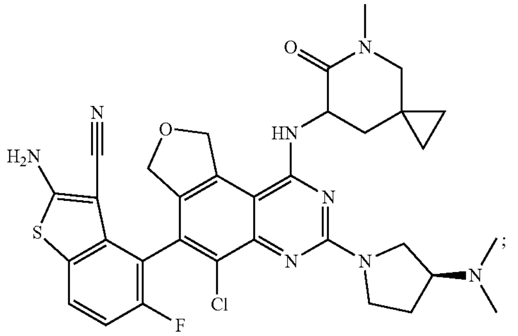
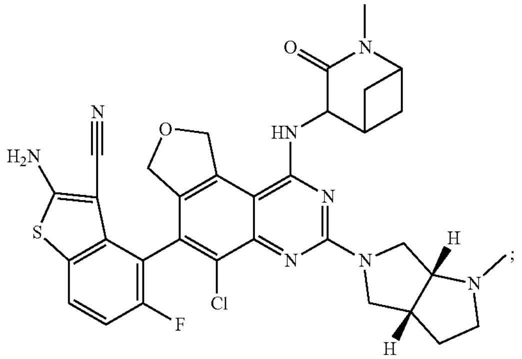
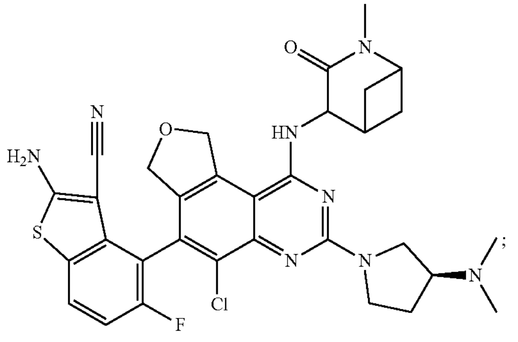
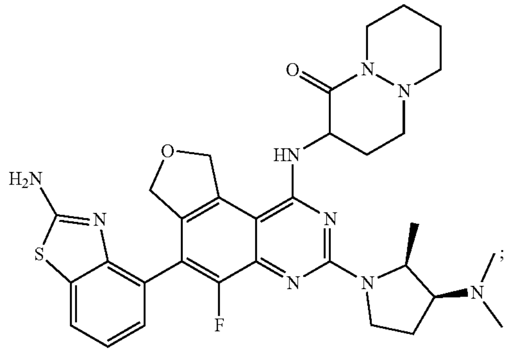
-continued
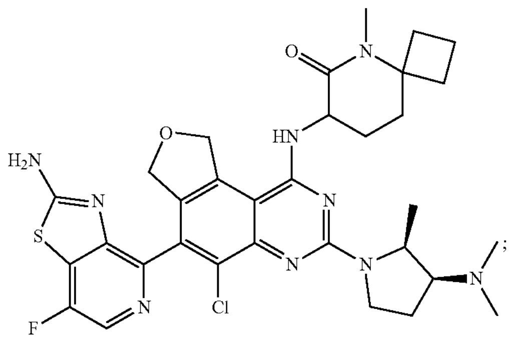
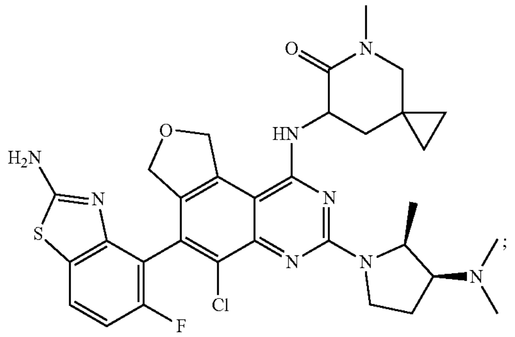
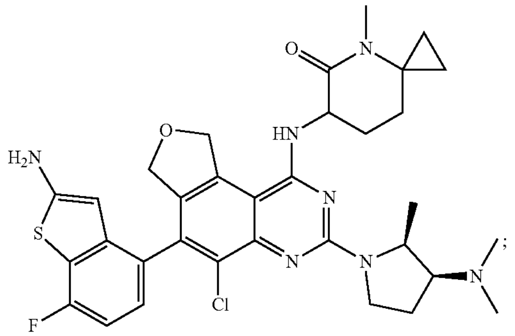
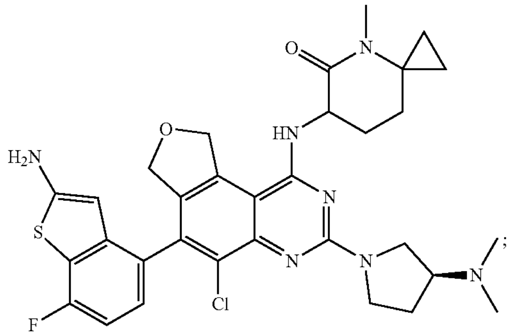
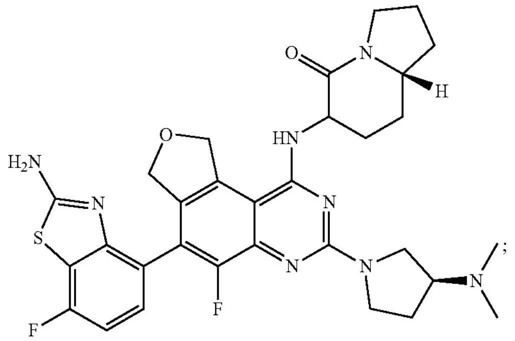

-continued
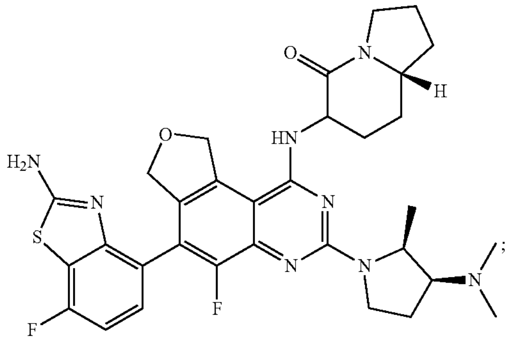
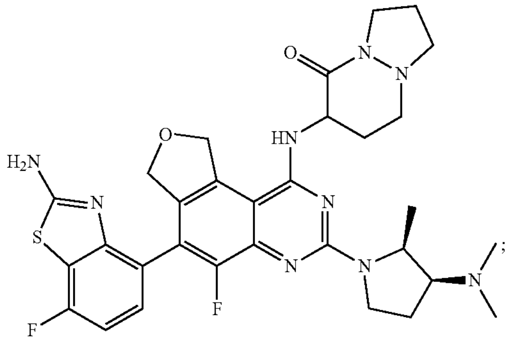
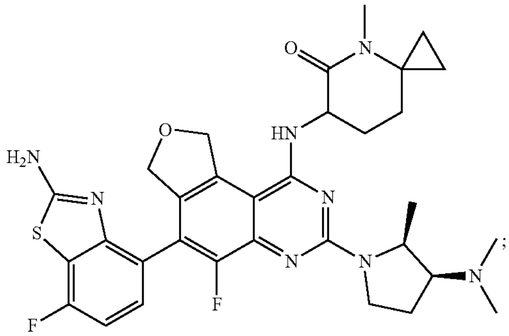
; and
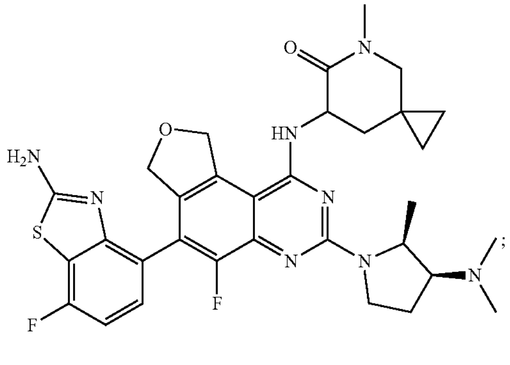 [SMILES: C[C@H]1[C@@H](N(C)C)CCN1c1nc(NC2CC3(CC3)CN(C)C2=O)c2c3c(c(-c4ccc(F)c5sc(N)nc45)c(F)c2n1)COC3]
or a pharmaceutically acceptable salt thereof.
Embodiment 110. The compound according to embodiment 1 or 2, wherein the compound is selected from
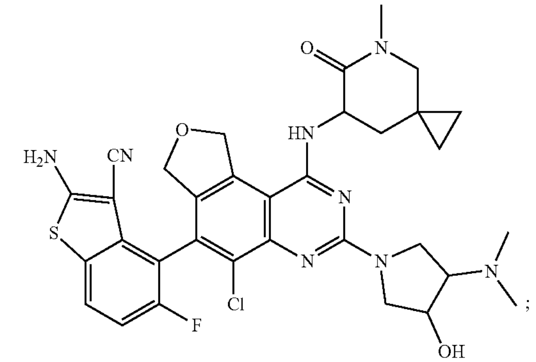
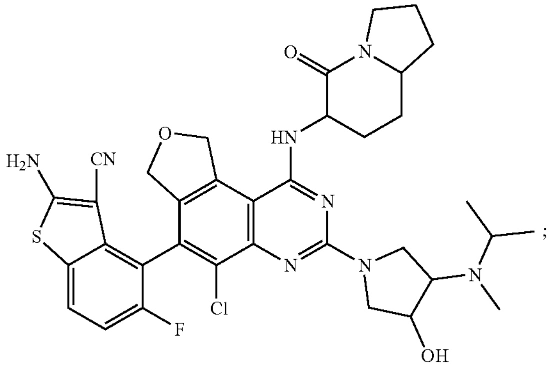
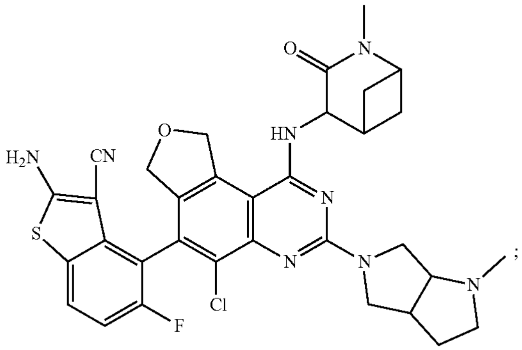
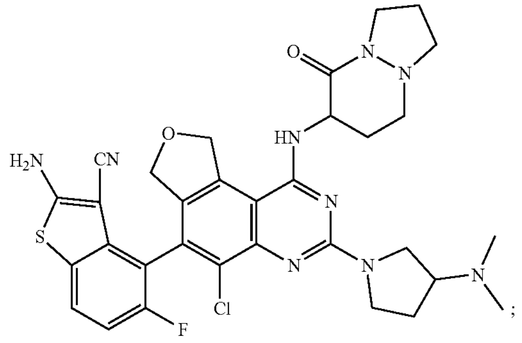

-continued
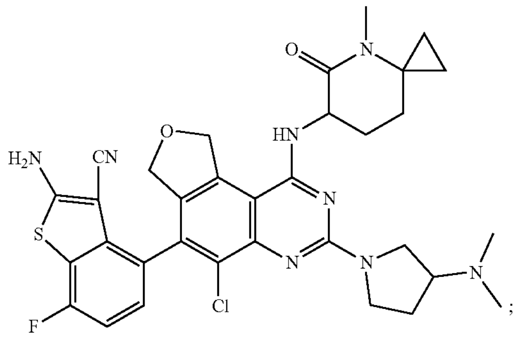
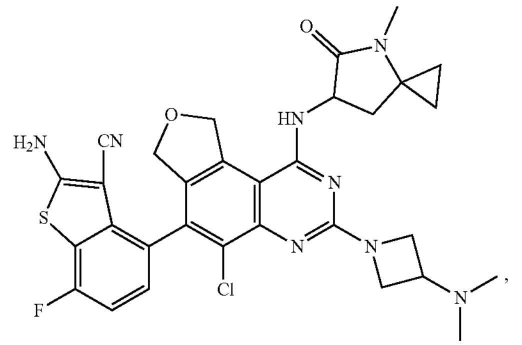
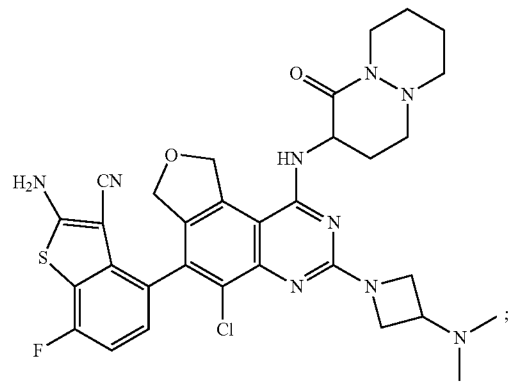
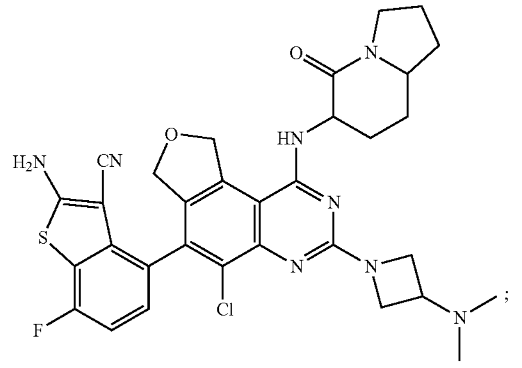
-continued
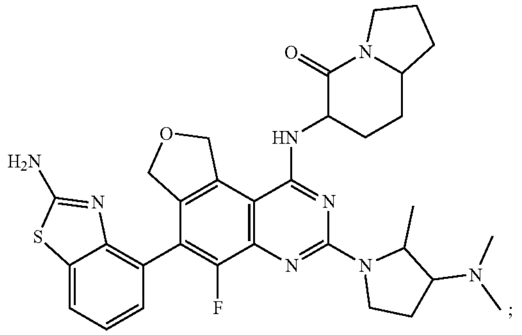
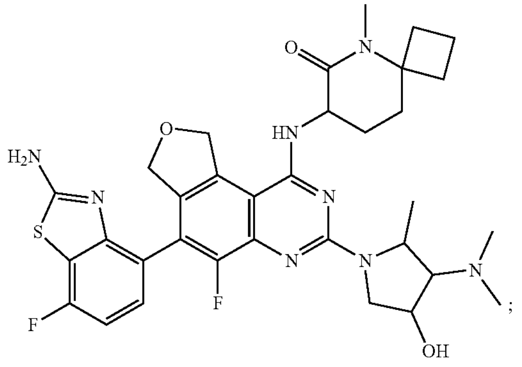
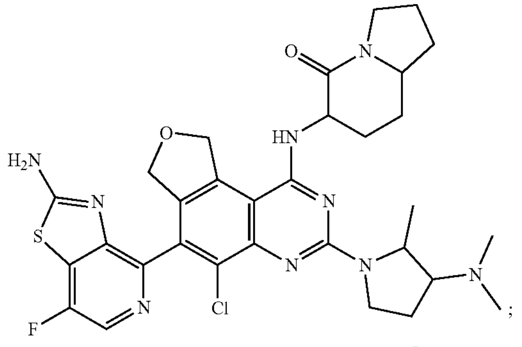
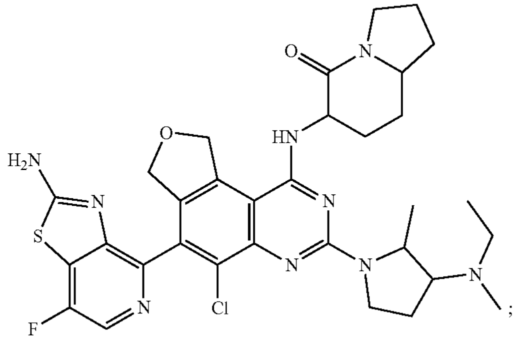
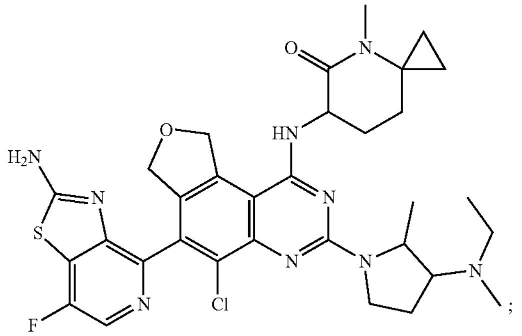

-continued
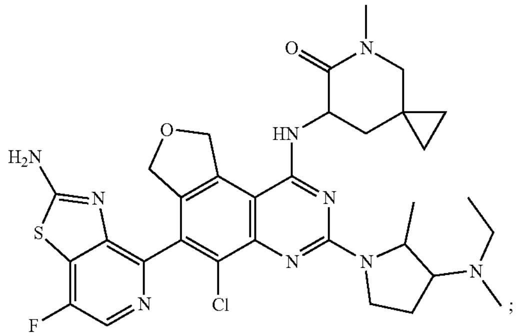
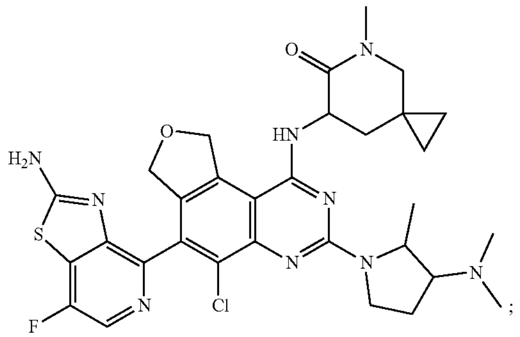
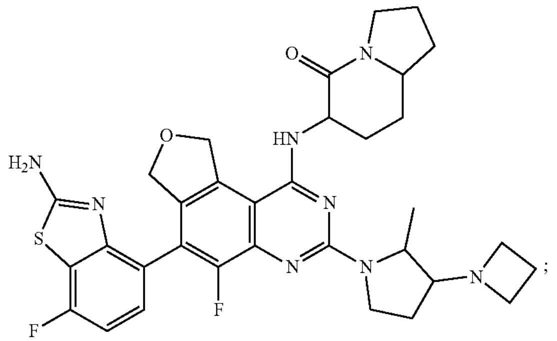
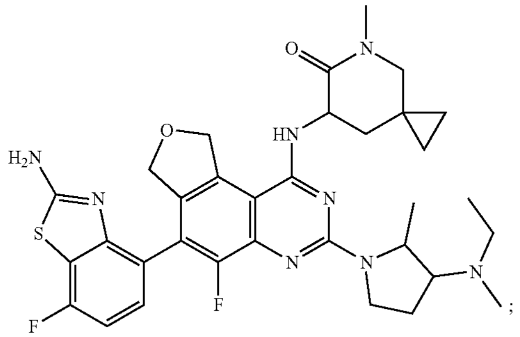
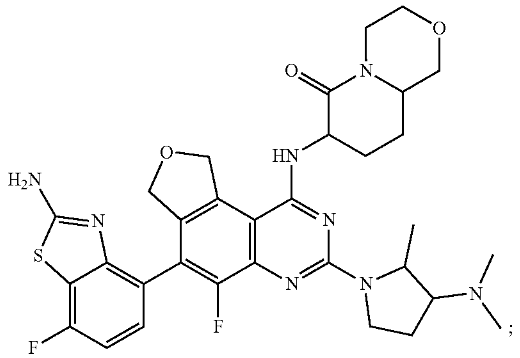
-continued
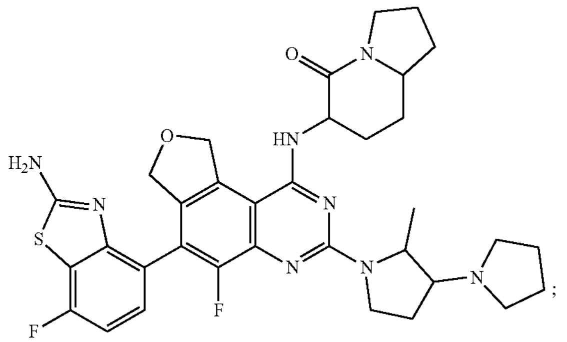
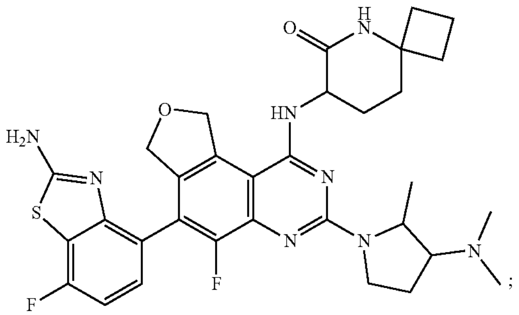
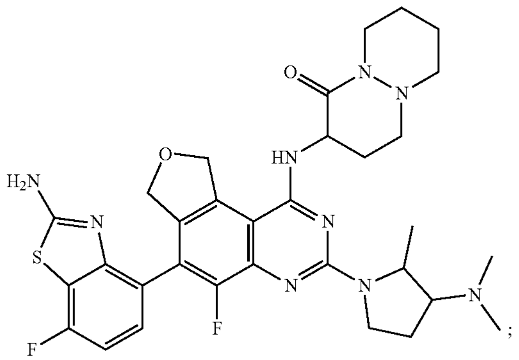
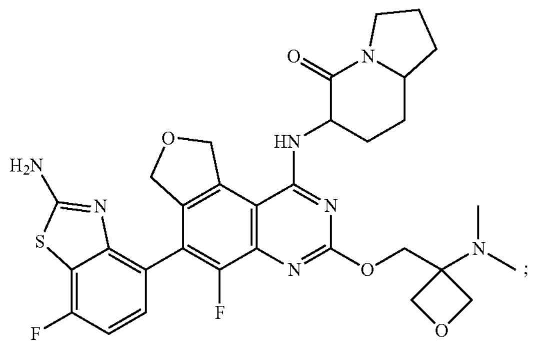
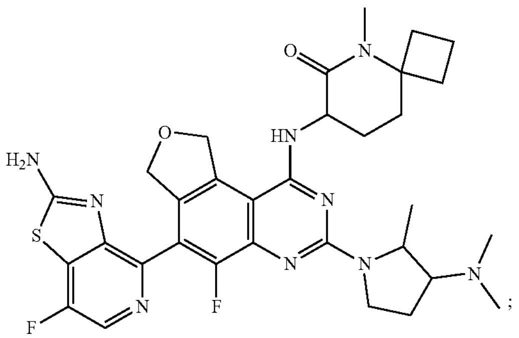

-continued
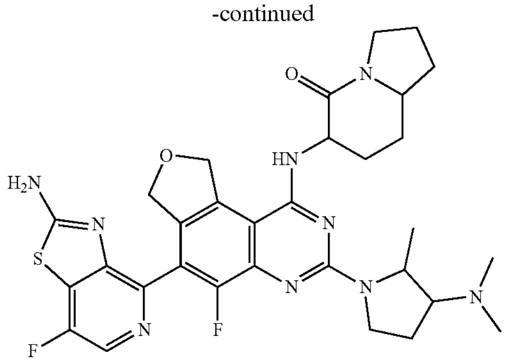
;
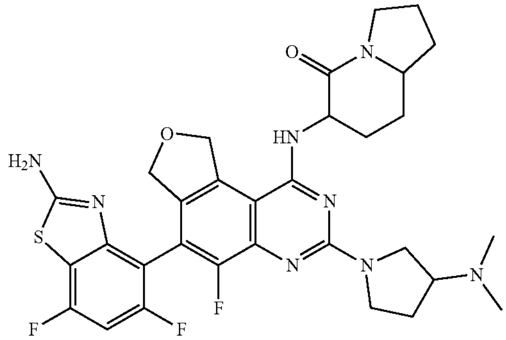
;
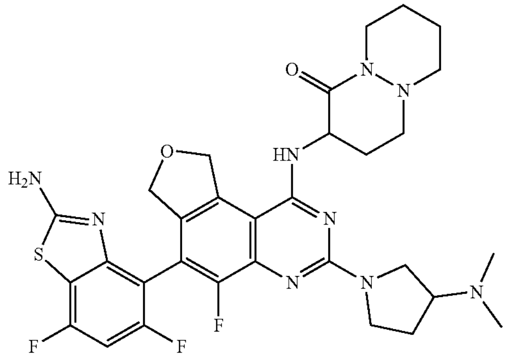
;
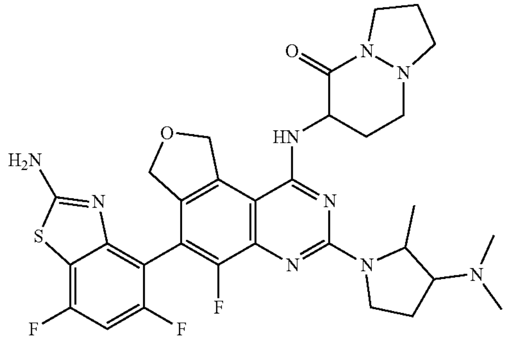
;
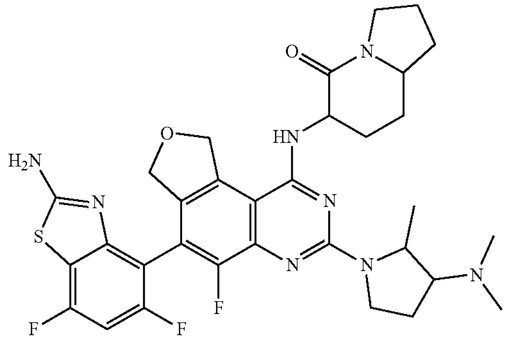
;
-continued
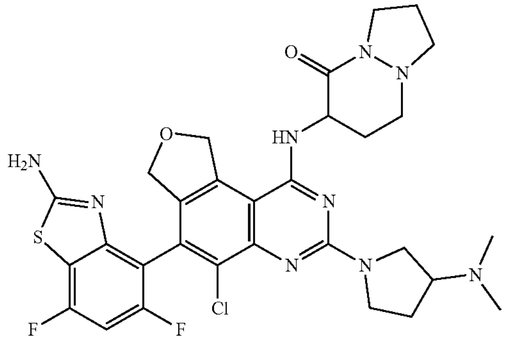
;
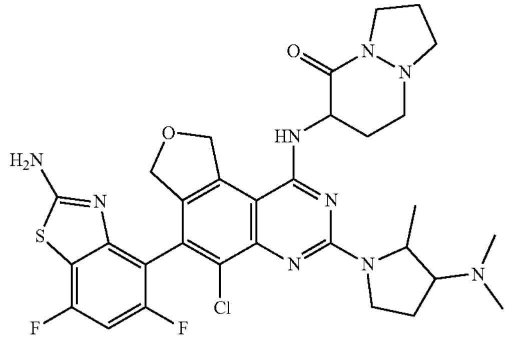
, and
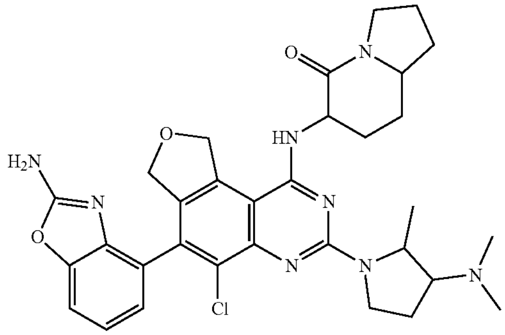
;
or a pharmaceutically acceptable salt thereof.
Embodiment 111. The compound according to any one of embodiments 1, 2, or 110, wherein the compound is selected from
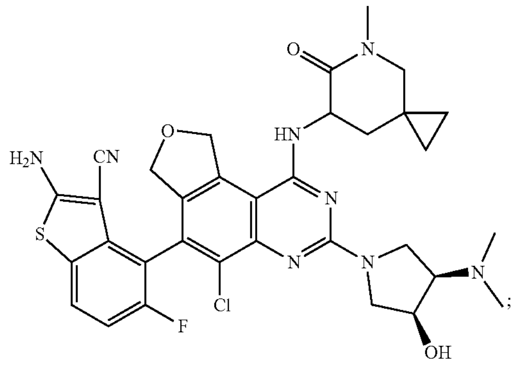
;

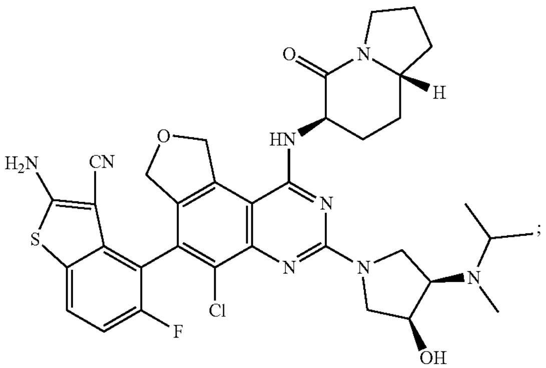
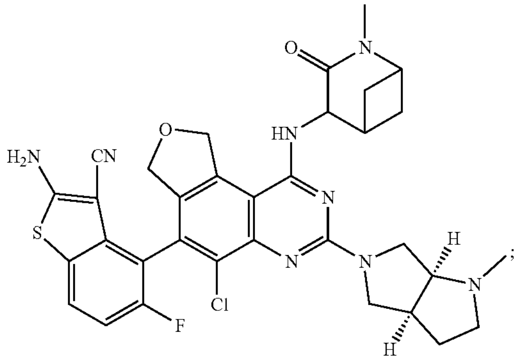
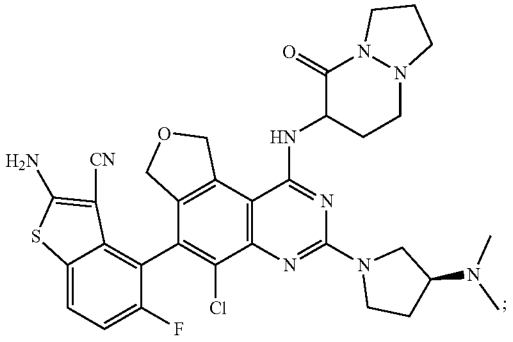
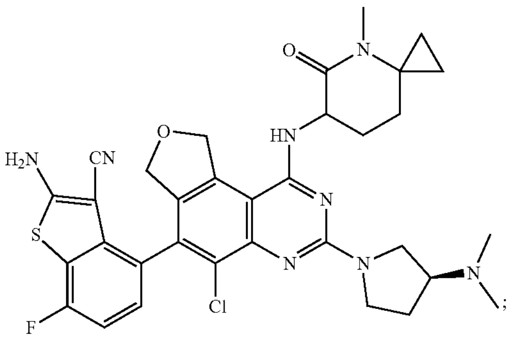
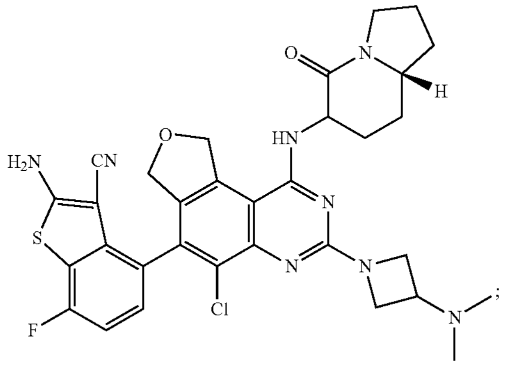
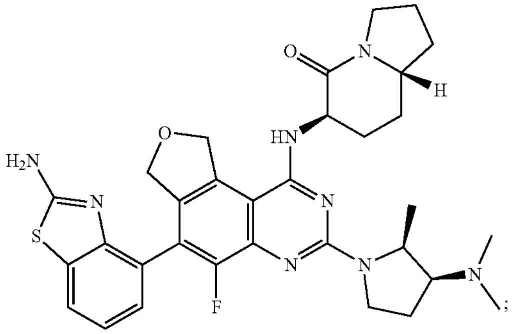
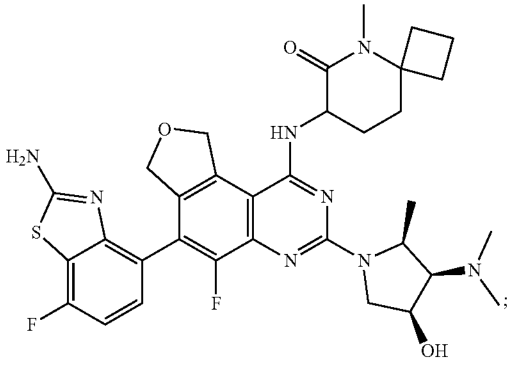
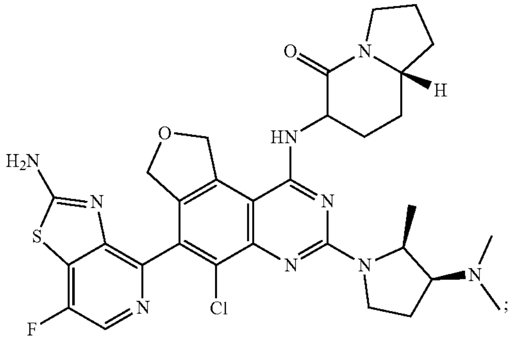

-continued
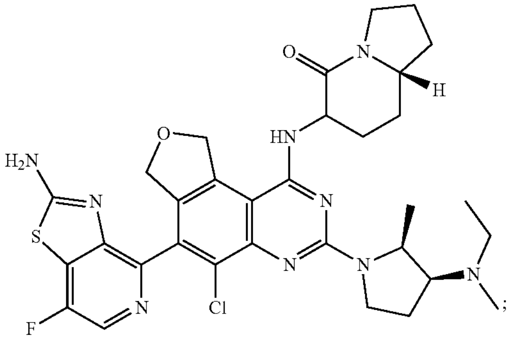
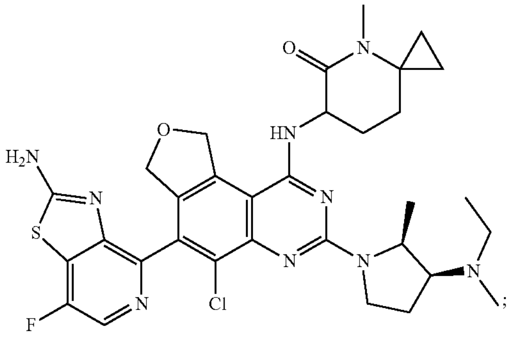
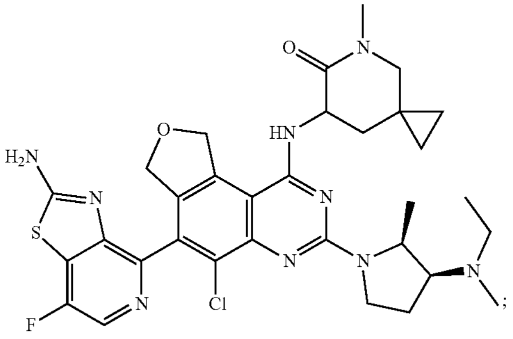
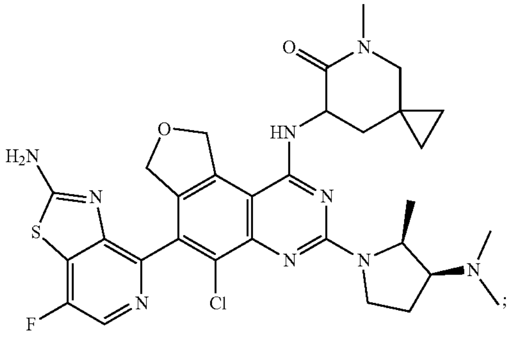
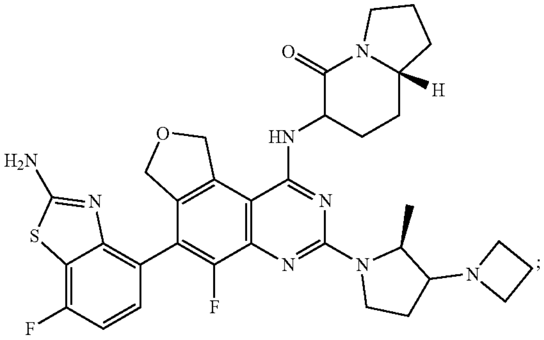
-continued
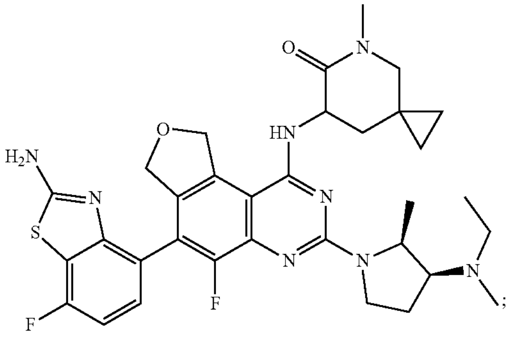
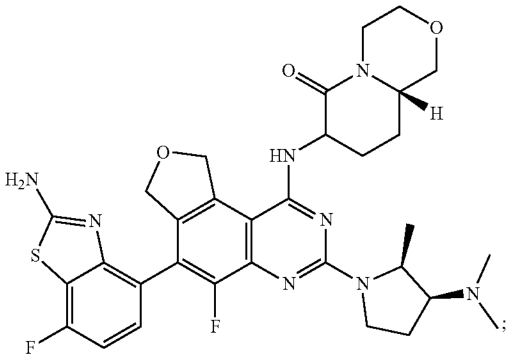
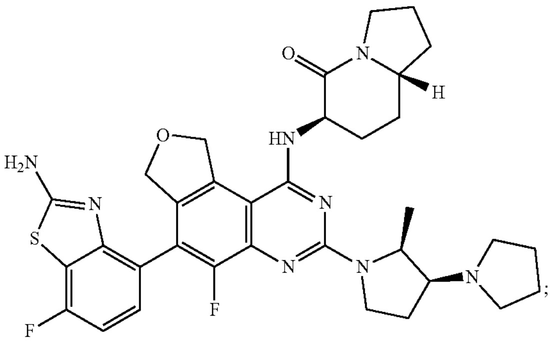
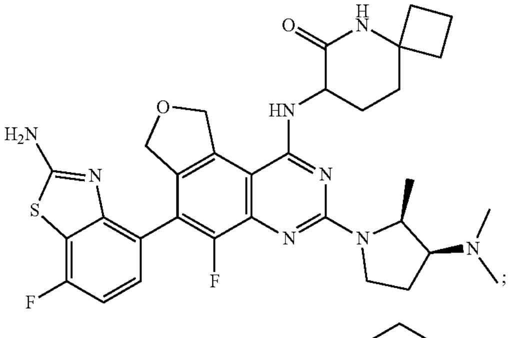
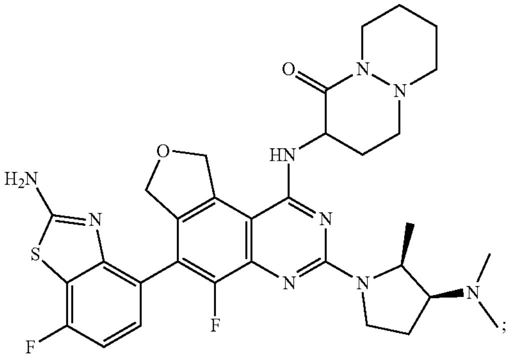

-continued
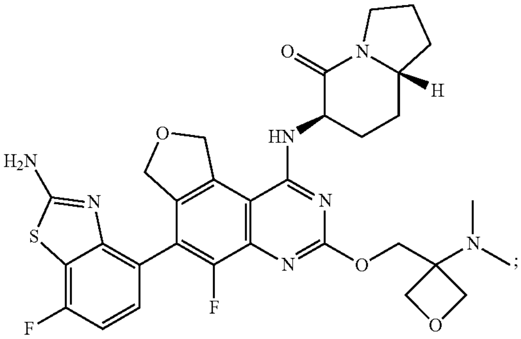
;
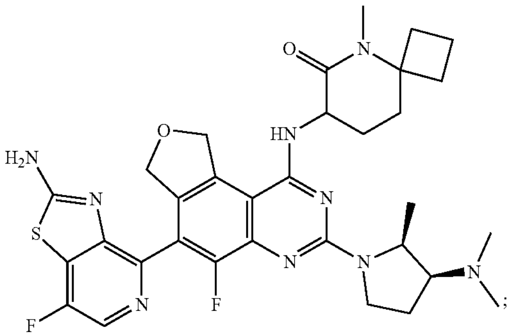
;
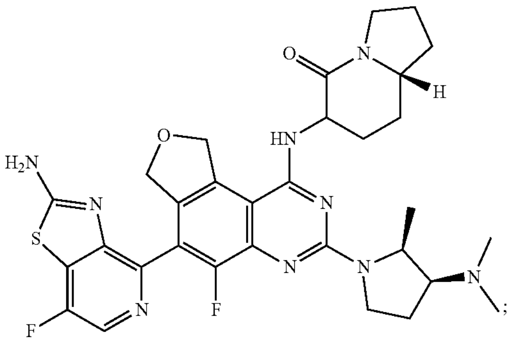
;
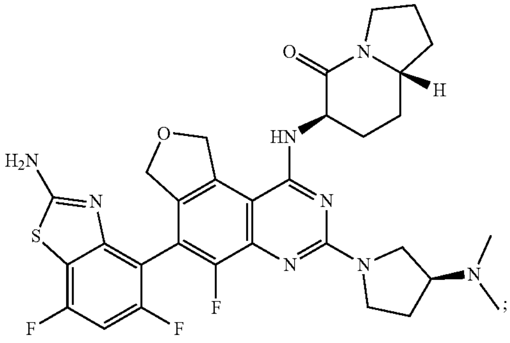
;
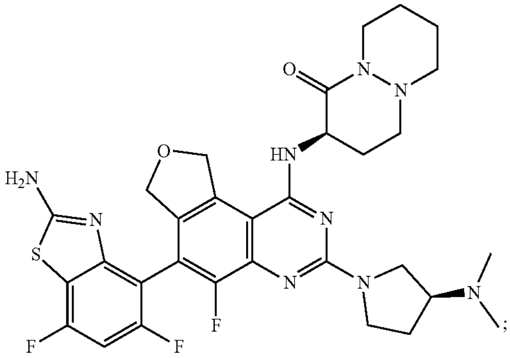
;
-continued
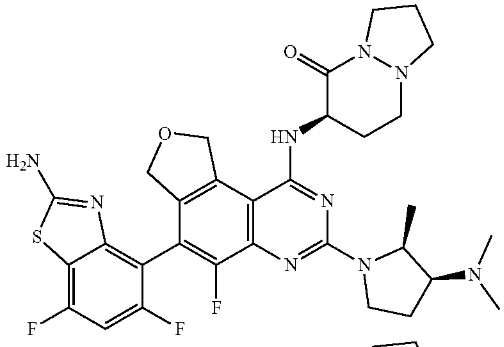
;
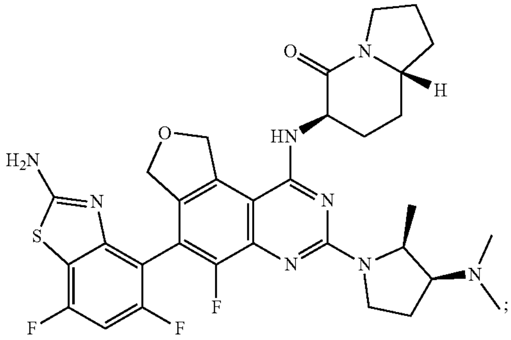
;
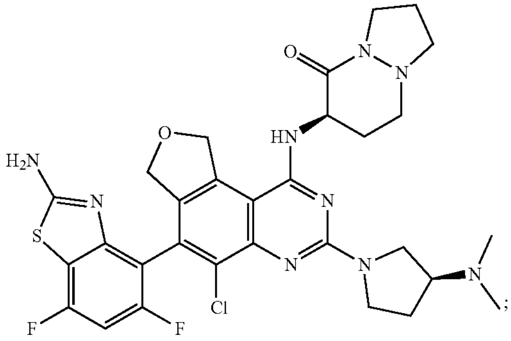
;
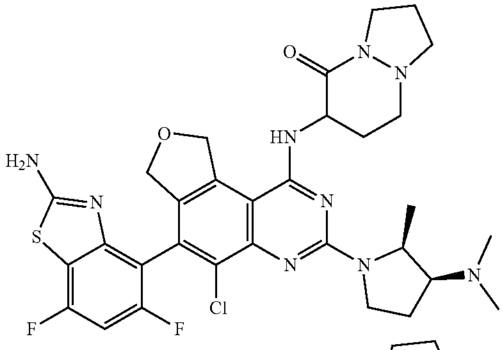
; and
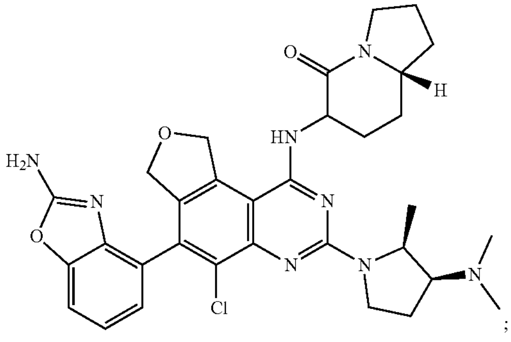
;
or a pharmaceutically acceptable salt thereof.

Embodiment 112. The compound according to embodiment 1, wherein the compound is selected from
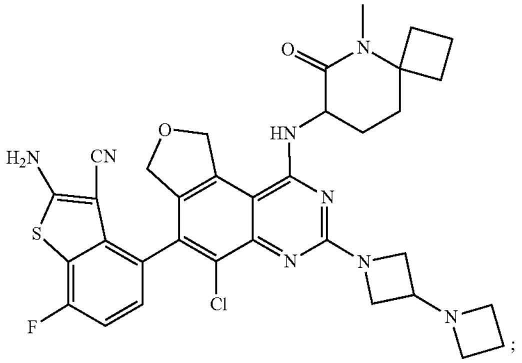
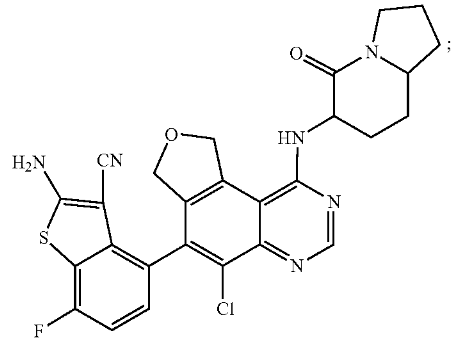
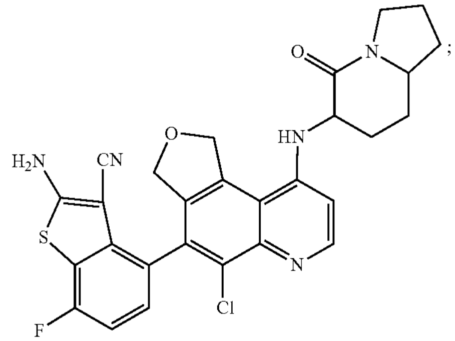
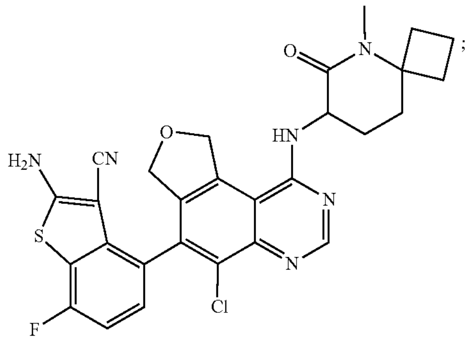
-continued
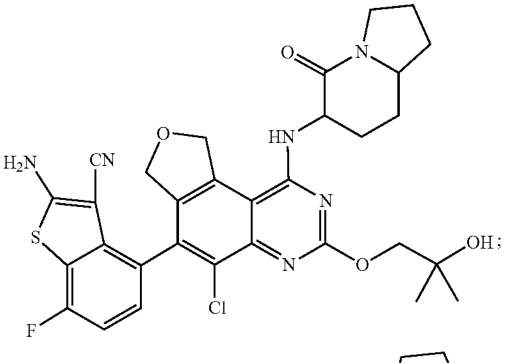
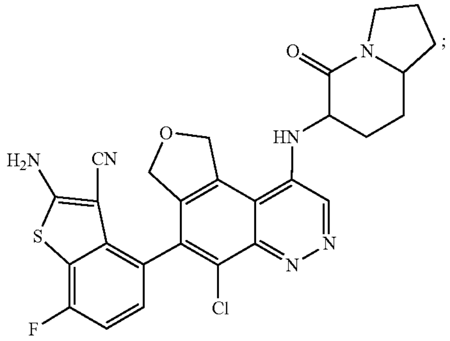
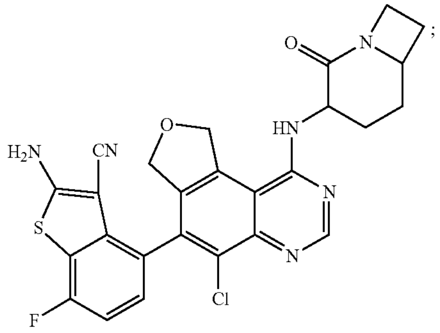
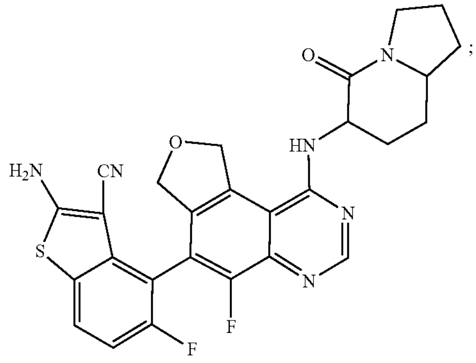
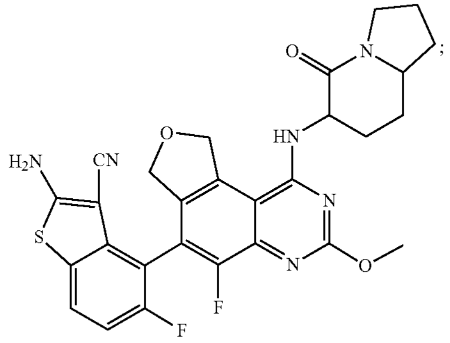

-continued
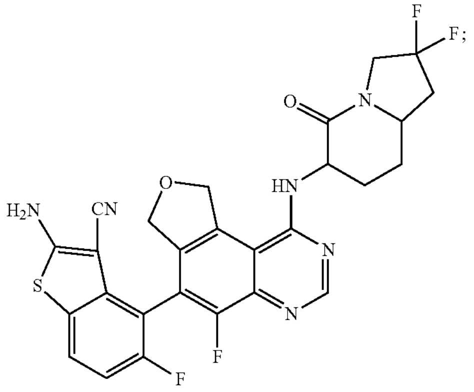
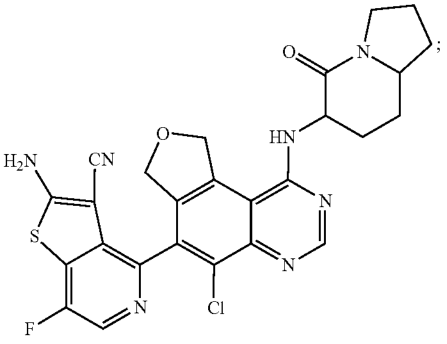
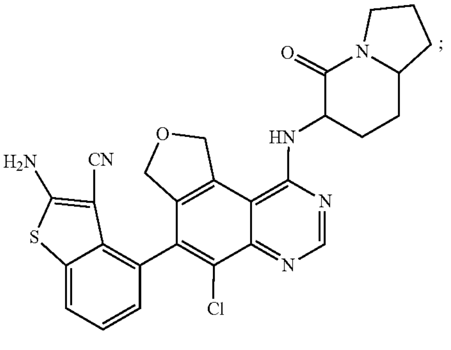
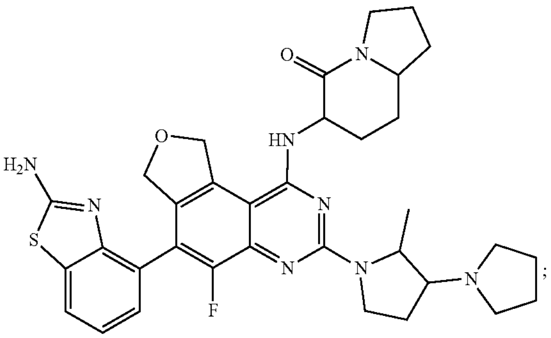
-continued
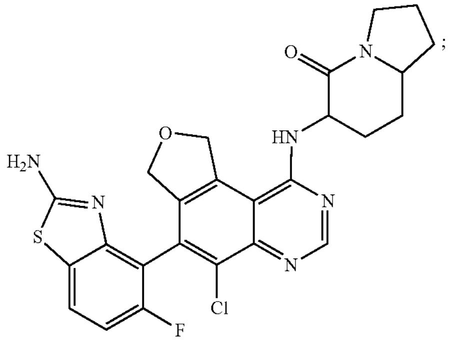
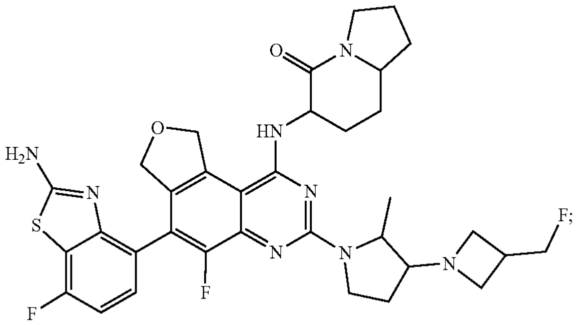
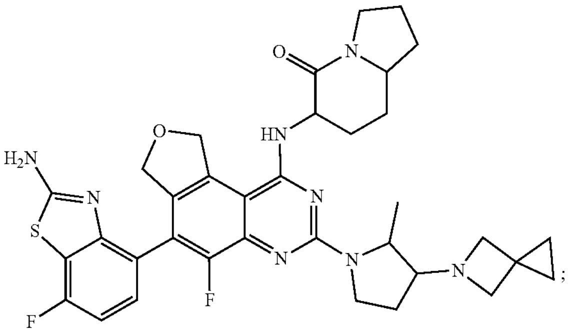
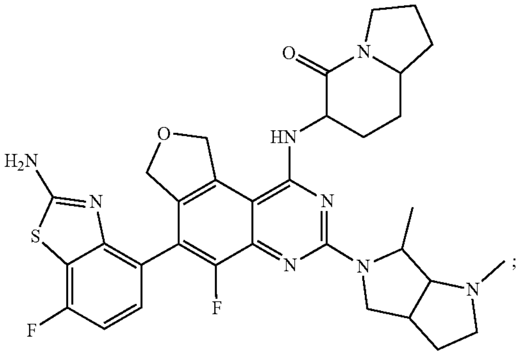
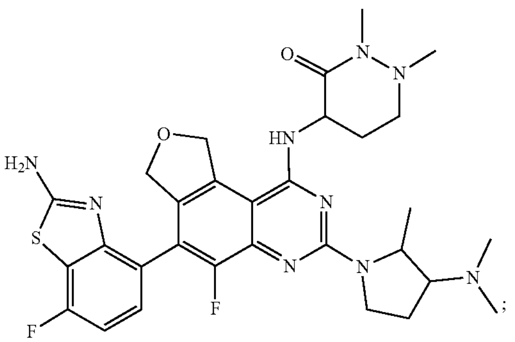

-continued
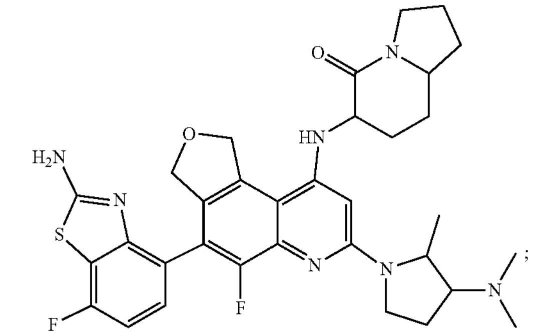
;
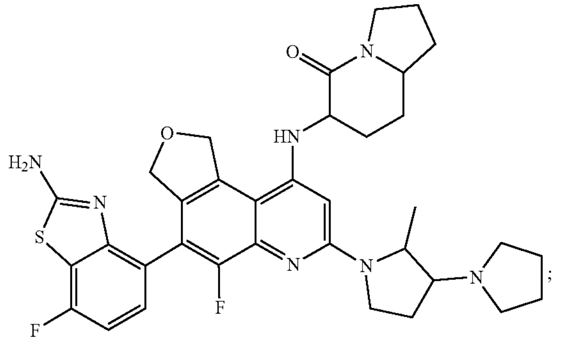
;
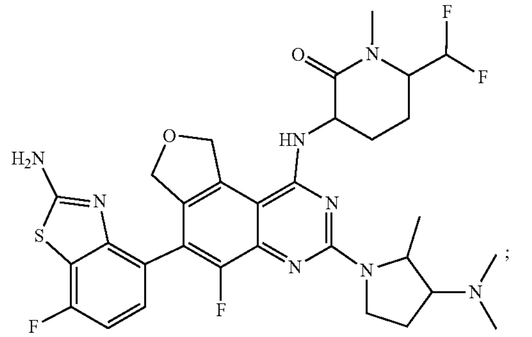
;
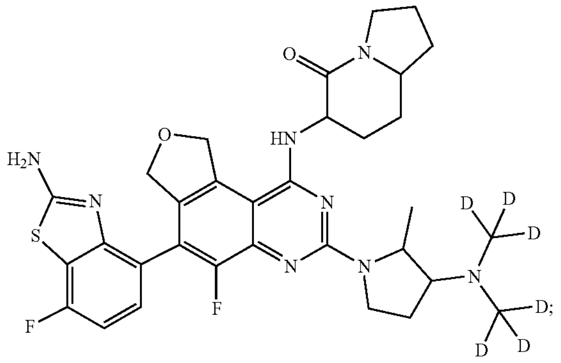
;
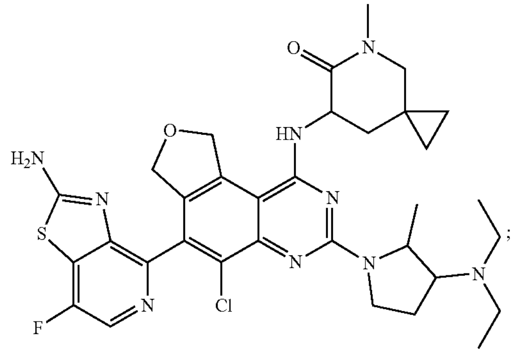
;
-continued
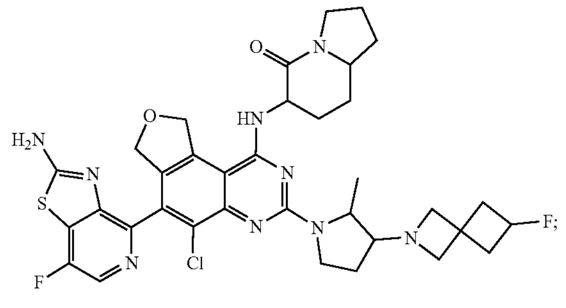
;
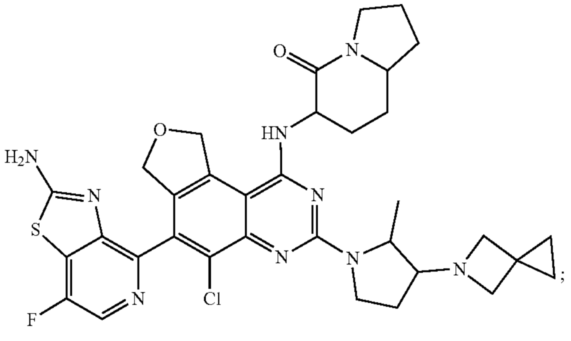
;
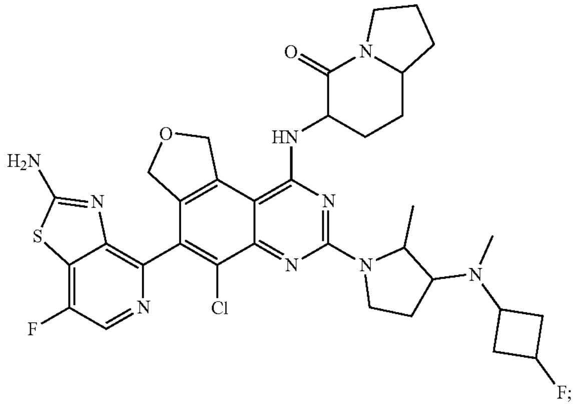
;
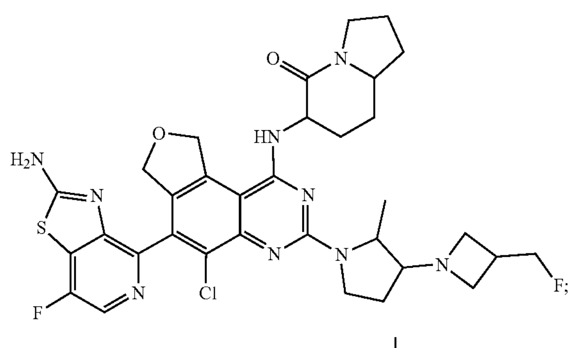
;
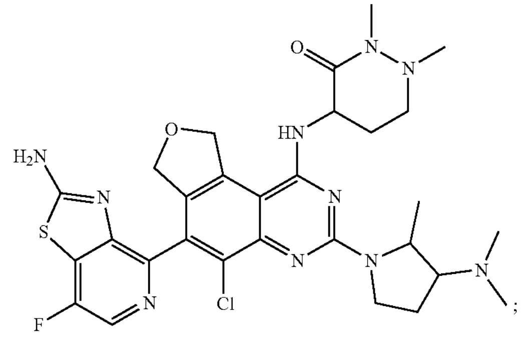
;

-continued
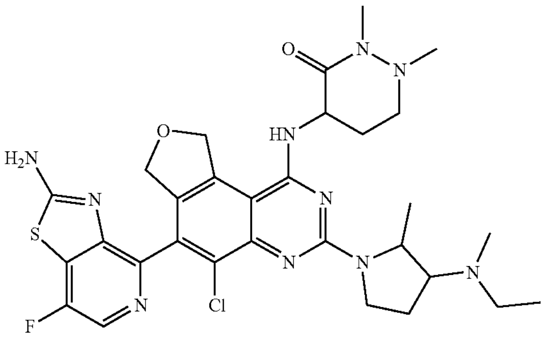
;
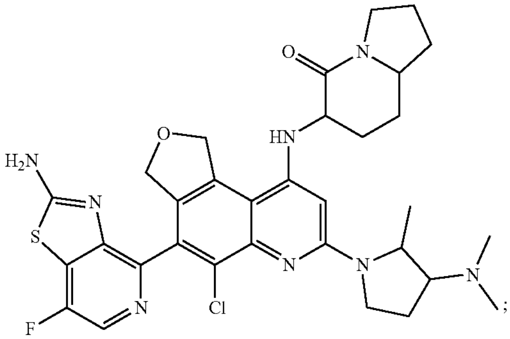
;
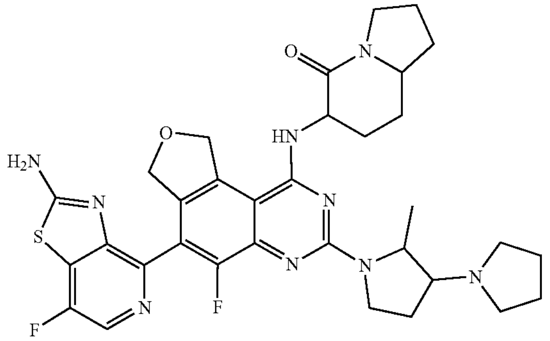
;
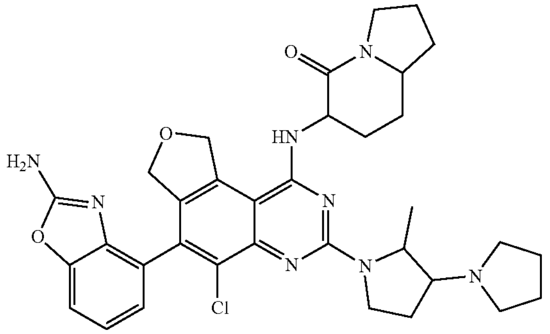
;
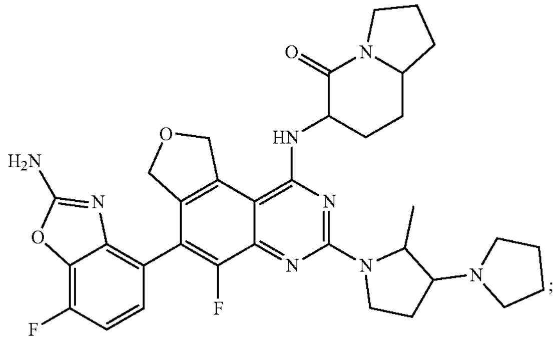
;
-continued
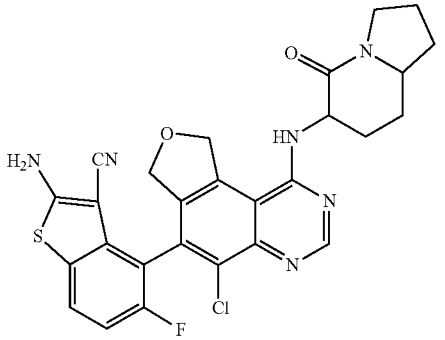
;
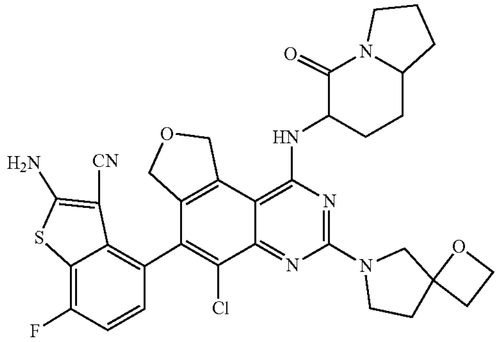
;
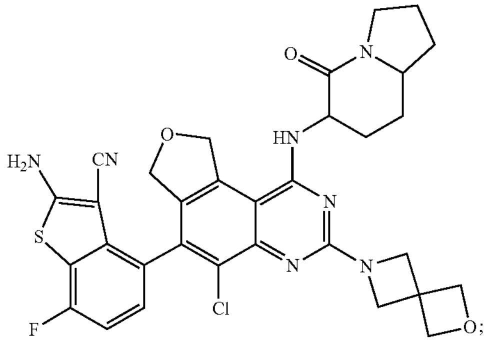
;
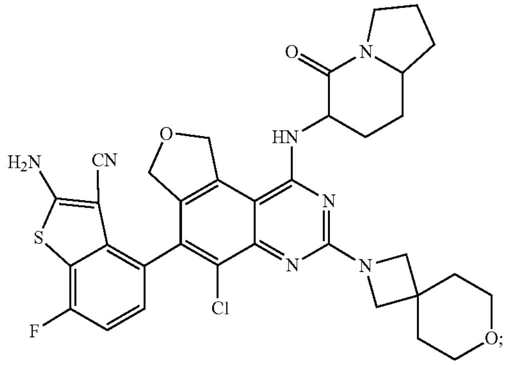
;

-continued
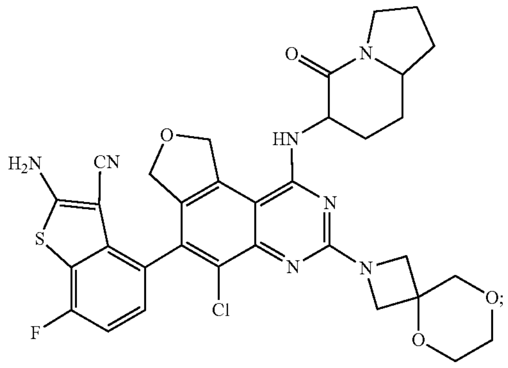
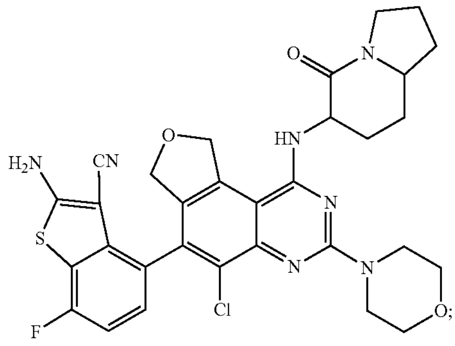
and
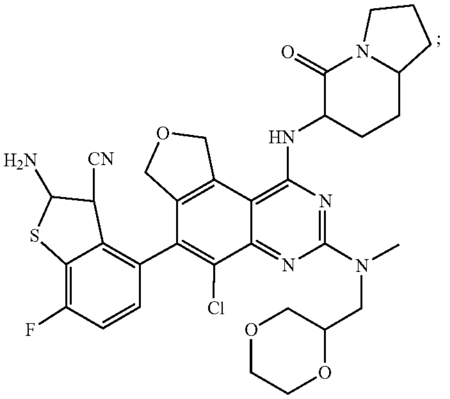
or a pharmaceutically acceptable salt thereof.
Embodiment 113. The compound according to embodiment 1 or 112, wherein the compound is selected from
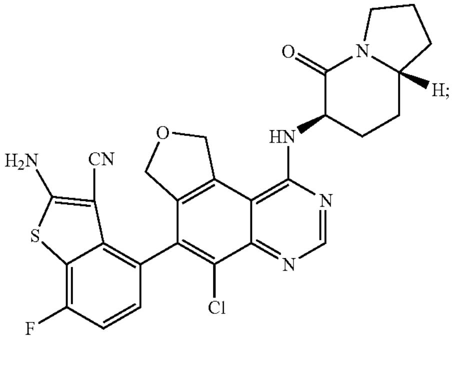
-continued
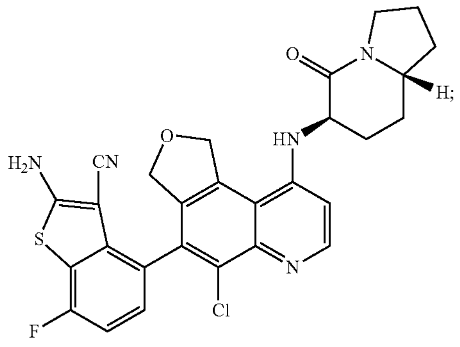
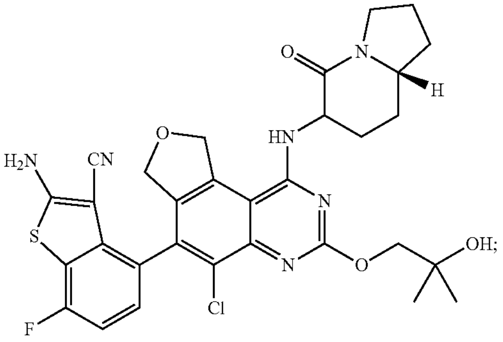
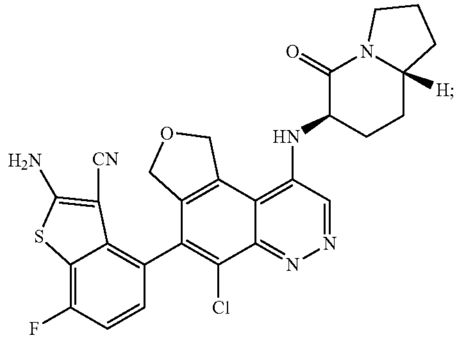
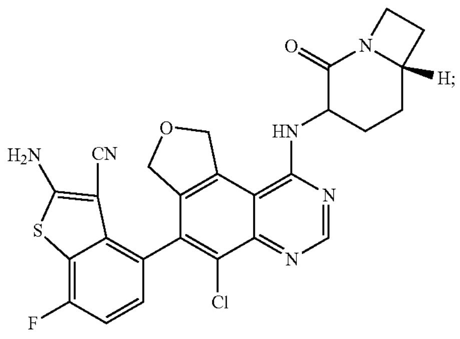
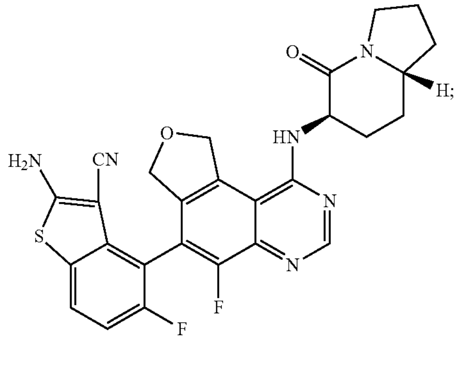

-continued
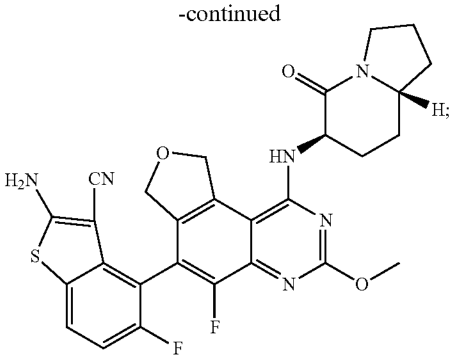
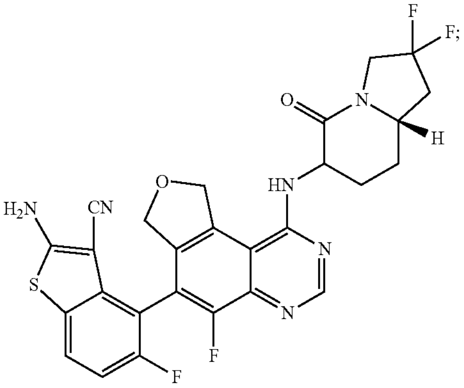
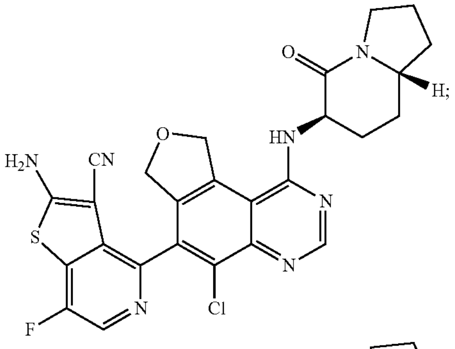
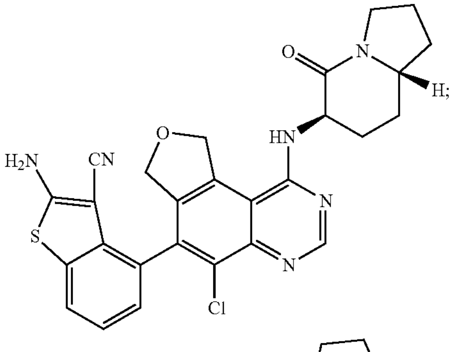
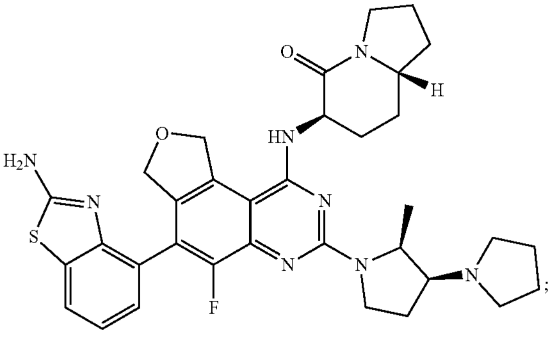
-continued
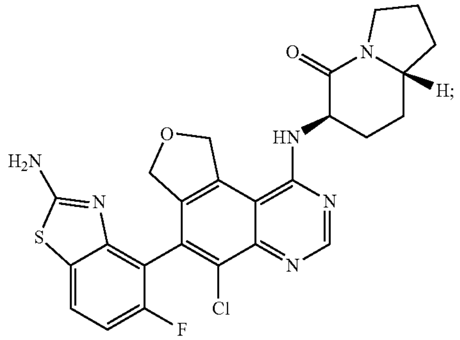
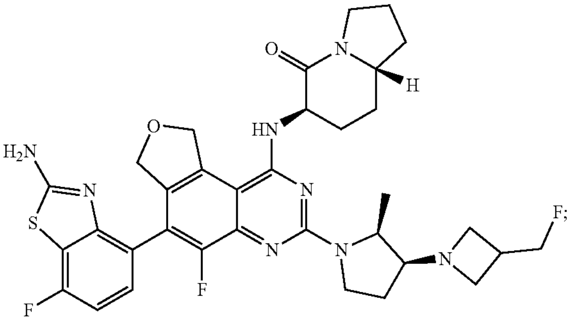
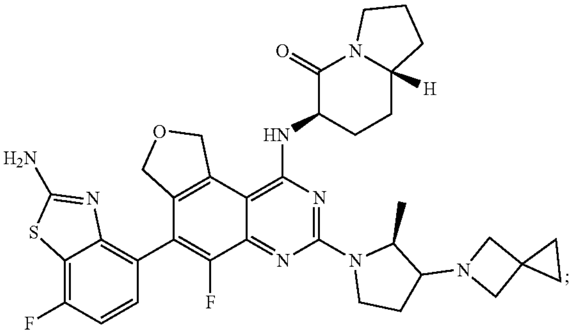
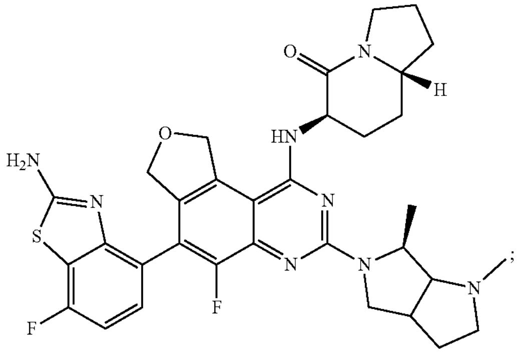
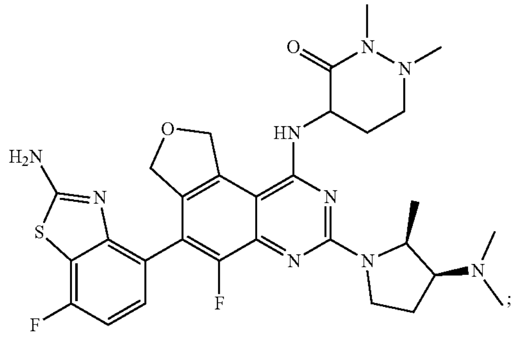

-continued
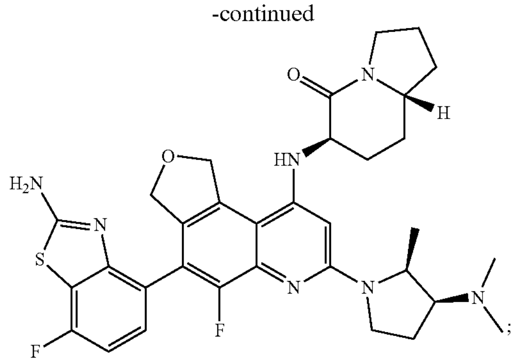
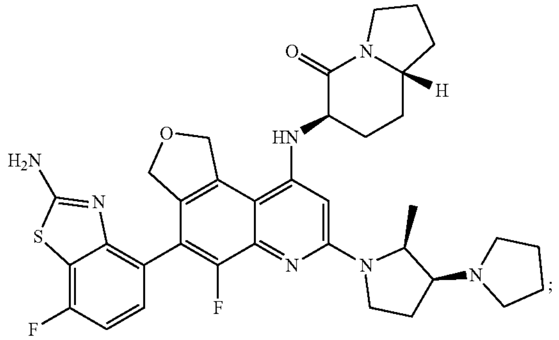
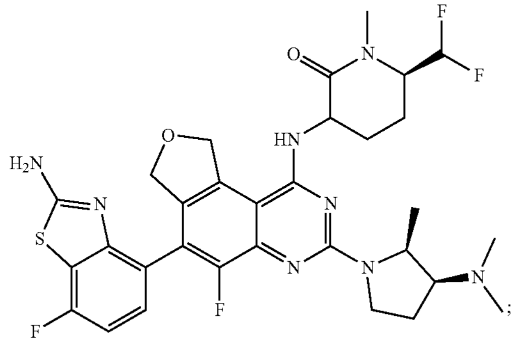
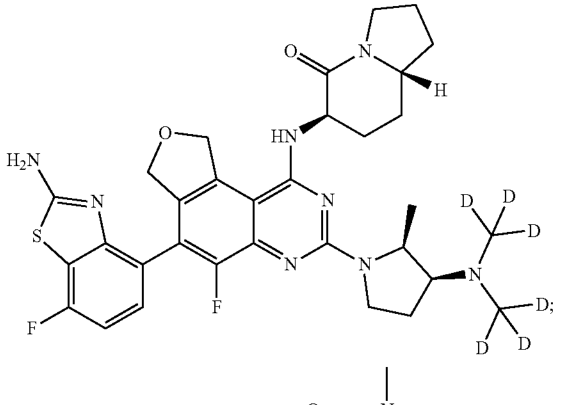
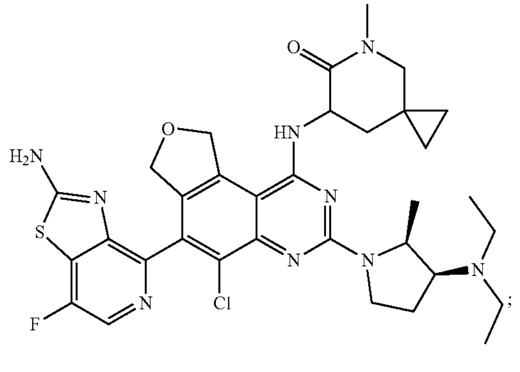
-continued
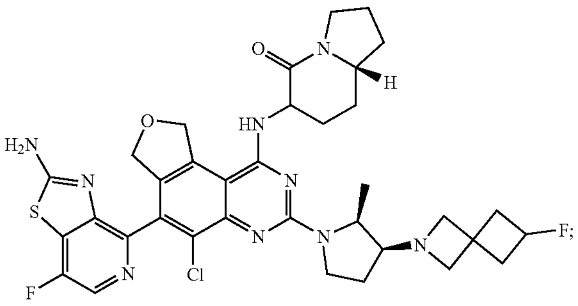
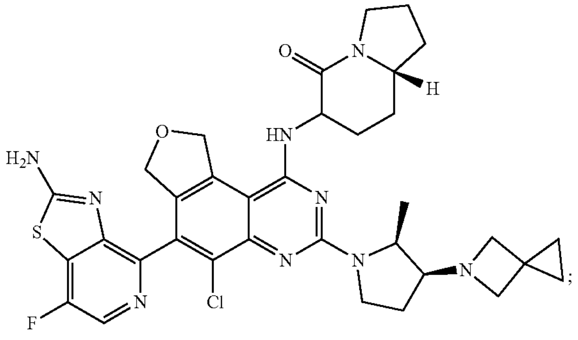
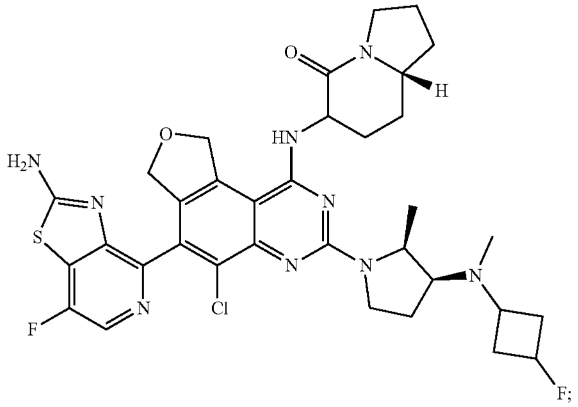
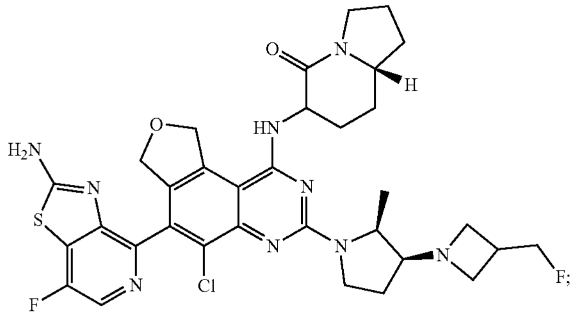
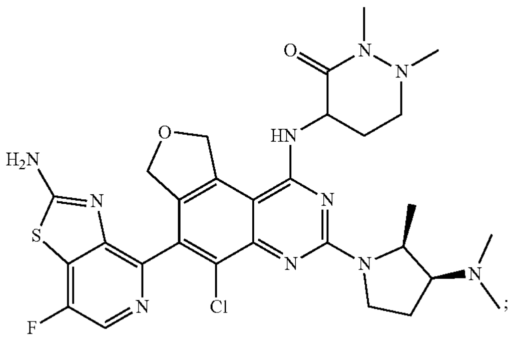

-continued
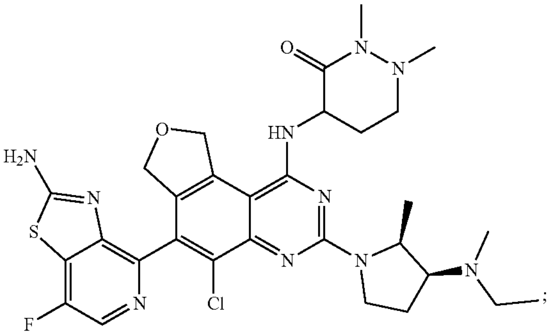
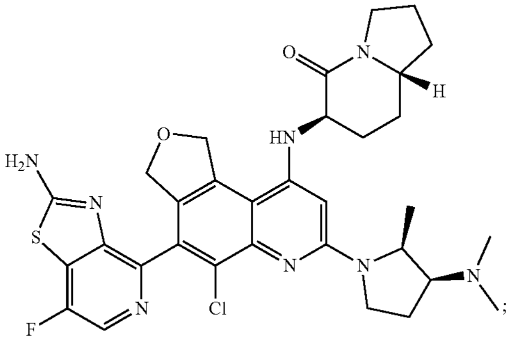
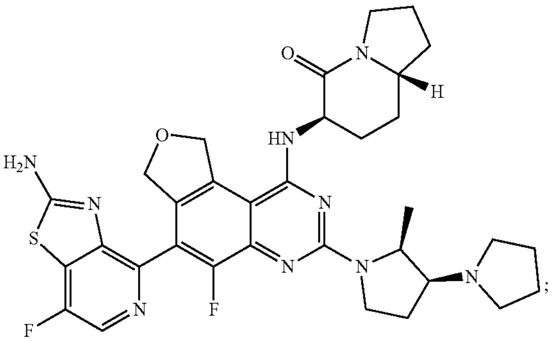
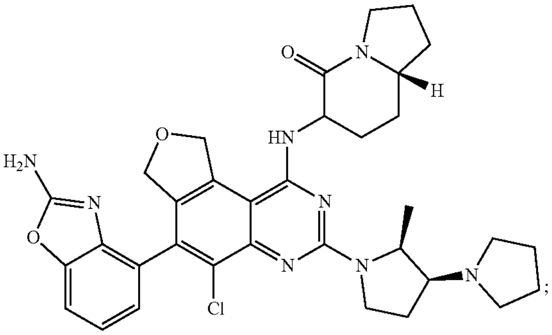
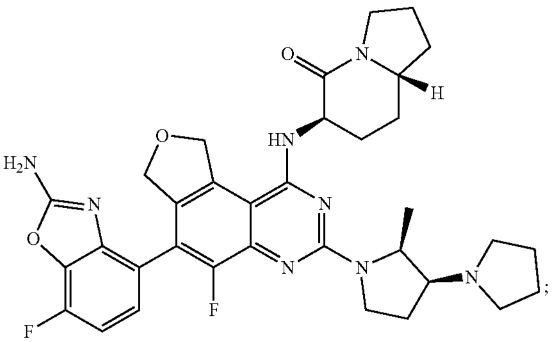
-continued
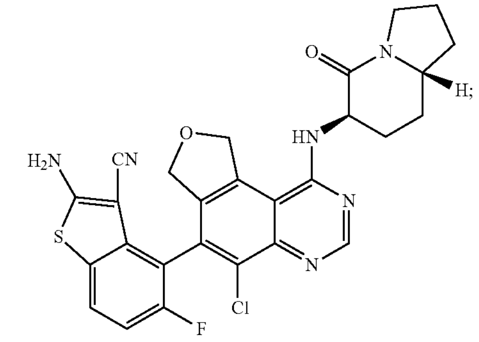
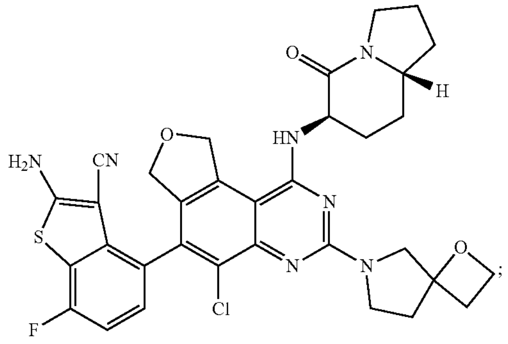
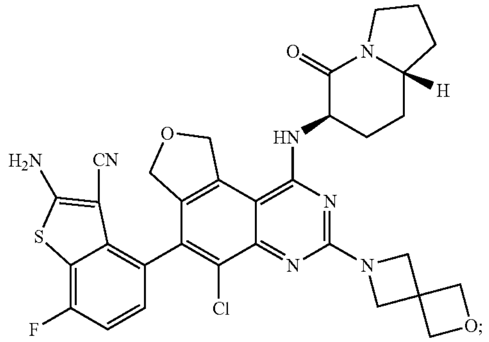
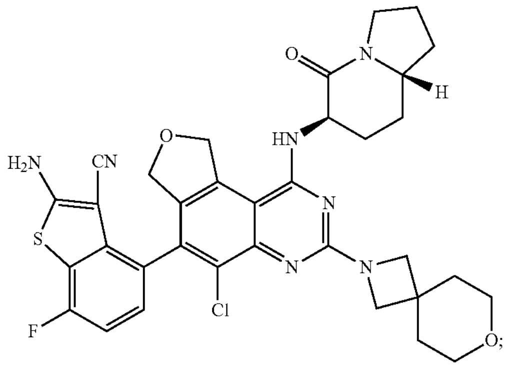

-continued

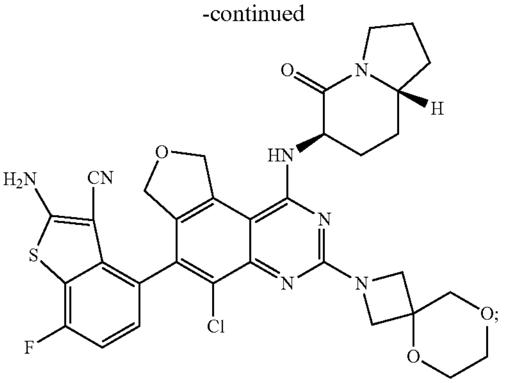

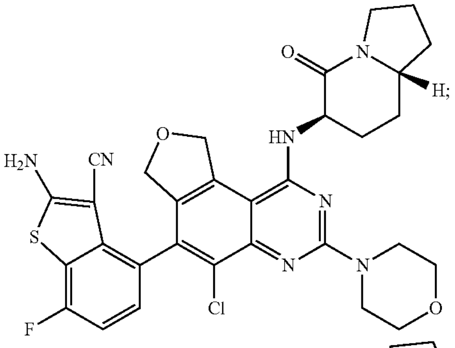

and

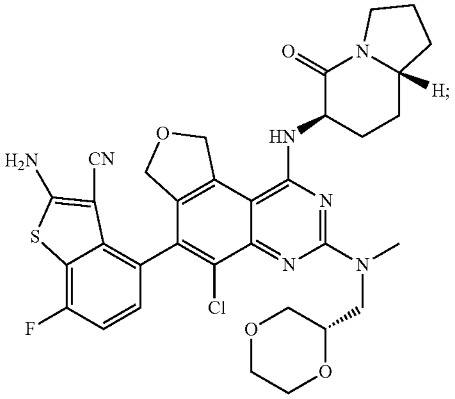

or a pharmaceutically acceptable salt thereof.

Embodiment 114. A pharmaceutical composition comprising a compound according to any one of embodiments 1-113, or a pharmaceutically acceptable salt thereof, and a pharmaceutically acceptable carrier, diluent or excipient.

Embodiment 115. A method of treating a patient with cancer, comprising administering to a patient in need thereof, an effective amount of a pharmaceutical composition according to embodiment 114, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

Embodiment 116. A method of treating a patient with cancer, comprising administering to a patient in need thereof, an effective amount of a compound according to any one of embodiments 1-113, or a pharmaceutically acceptable salt thereof, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

Embodiment 117. The method according to embodiment 115 or embodiment 116, wherein the patient has a cancer that was determined to have one or more cells expressing the KRAS G12V mutant protein prior to administration of the compound or a pharmaceutically acceptable salt thereof.

Embodiment 118. The method according to embodiment 115 or embodiment 116, wherein one or more cells express KRAS G12V mutant protein.

Embodiment 119. A method of treating a patient with a cancer that has a KRAS G12V mutation comprising administering to a patient in need thereof an effective amount of a compound according to any one of embodiments 1-113, or a pharmaceutically acceptable salt thereof.

Embodiment 120. The method according to embodiment 119, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

Embodiment 121. The method according to any one of embodiments 115-120, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

Embodiment 122. The compound, or a pharmaceutically acceptable salt thereof, according to any one of embodiments 1-113, for use in therapy.

Embodiment 123. The compound, or a pharmaceutically acceptable salt thereof, according to any one of embodiments 1-113, for use in the treatment of cancer.

Embodiment 124. The compound, or a pharmaceutically acceptable salt thereof, for use according to embodiment 123, wherein the cancer has a KRAS G12V mutation.

Embodiment 125. The compound, or a pharmaceutically acceptable salt thereof, for use according to embodiment 123 or embodiment 124, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

Embodiment 126. The compound, or a pharmaceutically acceptable salt thereof, according to any one of embodiments 1-113 for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer.

Embodiment 127. The method according to embodiment 121, or compound, or a pharmaceutically acceptable salt thereof, for use according to embodiment 126, wherein the patient is also administered an effective amount of a PD-1 inhibitor.

Embodiment 128. The method according to embodiment 121, or compound, or a pharmaceutically acceptable salt thereof, for use according to embodiment 126, wherein the patient is also administered an effective amount of a PD-L1 inhibitor.

Embodiment 129. The method according to embodiment 121, or compound, or a pharmaceutically acceptable salt thereof, for use according to embodiment 126, wherein the patient is also administered an effective amount of a CDK4/CDK6 inhibitor.

Embodiment 130. The method according to embodiment 121, or compound, or a pharmaceutically acceptable salt thereof, for use according to embodiment 126, wherein the patient is also administered an effective amount of an EGFR inhibitor.

Embodiment 131. The method according to embodiment 121, or compound, or a pharmaceutically acceptable salt thereof, for use according to embodiment 126, wherein the patient is also administered an effective amount of an ERK inhibitor.

Embodiment 132. The method according to embodiment 121, or compound, or a pharmaceutically acceptable salt thereof, for use according to embodiment 126, wherein the patient is also administered an effective amount of an Aurora A inhibitor.

Embodiment 133. The method according to embodiment 121, or compound, or a pharmaceutically acceptable salt thereof, for use according to embodiment 126, wherein the patient is also administered an effective amount of a SHP2 inhibitor.

Embodiment 134. The method according to embodiment 121, or compound, or a pharmaceutically acceptable salt thereof, for use according to embodiment 126, wherein the patient is also administered an effective amount of a platinum agent.

Embodiment 135. The method according to embodiment 121, or compound, or a pharmaceutically acceptable salt thereof, for use according to embodiment 126, wherein the patient is also administered an effective amount of pemetrexed, or pharmaceutically acceptable salts thereof.

Embodiment 136. The method according to any one of embodiments 115-121 or 127-135, or the compound, or a pharmaceutically acceptable salt thereof, for use according to any one of embodiments 123-135, wherein the cancer is non-small cell lung cancer.

Embodiment 137. The method according to any one of embodiments 115-121 or 127-135, or the compound, or a pharmaceutically acceptable salt thereof, for use according to any one of embodiments 123-135, wherein the cancer is colorectal cancer.

Embodiment 138. The method according to any one of embodiments 115-121 or 127-135, or the compound, or a pharmaceutically acceptable salt thereof, for use according to any one of embodiments 123-135, wherein the cancer is pancreatic cancer.

Embodiment 139. The method according to any one of embodiments 115-121 or 127-135, or the compound, or a pharmaceutically acceptable salt thereof, for use according to any one of embodiments 123-135, wherein the cancer is cervical cancer.

Embodiment 140. The method according to any one of embodiments 115-121 or 127-135, or the compound, or a pharmaceutically acceptable salt thereof, for use according to any one of embodiments 123-135, wherein the cancer is esophageal cancer.

Embodiment 141. The method according to any one of embodiments 115-121 or 127-135, or the compound, or a pharmaceutically acceptable salt thereof, for use according to any one of embodiments 123-135, wherein the cancer is endometrial cancer.

Embodiment 142. The method according to any one of embodiments 115-121 or 127-135, or the compound, or a pharmaceutically acceptable salt thereof, for use according to any one of embodiments 123-135, wherein the cancer is ovarian cancer.

Embodiment 143. The method according to any one of embodiments 115-121 or 127-135, or the compound, or a pharmaceutically acceptable salt thereof, for use according to any one of embodiments 123-135, wherein the cancer is cholangiocarcinoma.

Embodiment 144. The method according to any one of embodiments 115-121 or 127-135, or the compound, or a pharmaceutically acceptable salt thereof, for use according to any one of embodiments 123-135, wherein the cancer is stomach adenocarcinoma.

Embodiment 145. The method according to any one of embodiments 115-121 or 127-135, or the compound, or a pharmaceutically acceptable salt thereof, for use according to any one of embodiments 123-135, wherein the cancer is invasive ductal carcinoma.

Embodiment 146. The method according to any one of embodiments 115-121 or 127-135, or the compound, or a pharmaceutically acceptable salt thereof, for use according to any one of embodiments 123-135, wherein the cancer is uterine carcinosarcoma.

Embodiment 147. The method according to any one of embodiments 115-121 or 127-135, or the compound, or a pharmaceutically acceptable salt thereof, for use according to any one of embodiments 123-135, wherein the cancer is a germ cell tumor.

Embodiment 148. The method according to any one of embodiments 115-121 or 127-135, or the compound, or a pharmaceutically acceptable salt thereof, for use according to any one of embodiments 123-135, wherein the cancer is bladder cancer.

Embodiment 149. The method according to any one of embodiments 115-121 or 127-135, or the compound, or a pharmaceutically acceptable salt thereof, for use according to any one of embodiments 123-135, wherein the cancer is small bowel adenocarcinoma.

Embodiment 150. The method according to any one of embodiments 115-121 or 127-135, or the compound, or a pharmaceutically acceptable salt thereof, for use according to any one of embodiments 123-135, wherein the cancer is appendix cancer.

Embodiment 151. The method according to any one of embodiments 115-121 or 127-135, or the compound, or a pharmaceutically acceptable salt thereof, for use according to any one of embodiments 123-135, wherein the cancer is peritoneum cancer.

The chemical drawings in the compounds above contain indications of chiral aspects of the specific compounds shown. However, the chemical drawings in the compounds above do not contain all the possible chiral features of these compounds and the chiral indications shown are not intended to exclude changes to the chiral aspects shown. Thus, alternate chiral versions of the compounds as well as different combinations of chiral attributes are contemplated and included herein.

Further provided herein are methods of treating cancer, comprising administering to a patient in need thereof, an effective amount of a compound according to Formula I, or a pharmaceutically acceptable salt thereof. In this method, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. In this method, the cancer can more specifically be non-small cell lung cancer, pancreatic cancer, or colorectal cancer. In an embodiment the cancer can be non-small cell lung cancer. In an embodiment the cancer can be pancreatic cancer. In an embodiment the cancer can be colorectal cancer. In an embodiment the cancer can be stomach adenocarcinoma. In an embodiment the cancer can be invasive ductal carcinoma. In an embodiment the cancer can be uterine carcinosarcoma. In an embodiment the cancer can be germ cell tumors. In an embodiment the cancer can be bladder cancer. In an embodiment the cancer can be small bowel adenocarcinoma. In an embodiment the cancer can be appendix cancer. In an embodiment the cancer can be peritoneum cancer.

Also provided herein is a method of treating cancer, comprising administering to a patient in need thereof, an effective amount of a compound according to Formula I, or a pharmaceutically acceptable salt thereof, in which the cancer has one or more cells that express a mutant KRAS G12V protein. In this method, the cancer can be non-small cell lung cancer, pancreatic cancer, or colorectal cancer, in which the cancer has one or more cells that express a KRAS G12V mutant protein. In an embodiment, the cancer is non-small cell lung carcinoma in which the cancer has one or more cells that express a KRAS G12V mutant protein. In an embodiment, the cancer is mutant pancreatic cancer in which the cancer has one or more cells that express a KRAS G12V mutant protein. In an embodiment, the cancer is colorectal carcinoma in which the cancer has one or more cells that express a KRAS G12V mutant protein. This method also includes treating KRAS G12V mutant bearing cancers of other origins.

Further provided herein is a method of treating a patient with a cancer that has a KRAS G12V mutation comprising administering to a patient in need thereof an effective amount of a compound according to Formula I or a pharmaceutically acceptable salt thereof. In this method, the cancer that has a KRAS G12V mutation can be KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, and KRAS G12V mutant peritoneum cancer. In an embodiment the cancer that has a KRAS G12V mutation can be KRAS G12V mutant non-small cell lung cancer. In an embodiment the cancer that has a KRAS G12V mutation can be KRAS G12V mutant pancreatic cancer. In an embodiment the cancer that has a KRAS G12V mutation can be KRAS G12V mutant colorectal cancer.

Additionally provided herein is a method of modulating a mutant KRAS G12V enzyme in a patient in need thereof, by administering a compound according to Formula I, or a pharmaceutically acceptable salt thereof. In one embodiment this method comprises inhibiting a human mutant KRAS G12V enzyme.

Also provided herein is a method of treating cancer in a patient in need thereof, wherein the patient has a cancer that was determined to express the KRAS G12V mutant protein. The method comprises administering to a patient an effective amount of a compound according to Formula I, or a pharmaceutically acceptable salt thereof. The G12V mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12C, G12D, and/or G12V mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Further provided herein is a compound or a pharmaceutically acceptable salt thereof according to Formula I for use in therapy. The compound or a pharmaceutically acceptable salt thereof, can be for use in treating cancer. For this use in treating cancer, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer. In an embodiment, the cancer is non-small cell lung cancer. In an embodiment, the cancer is pancreatic cancer. In an embodiment, the cancer is cervical cancer. In an embodiment, the cancer is esophageal cancer. In an embodiment, the cancer is endometrial cancer. In an embodiment, the cancer is ovarian cancer. In an embodiment, the cancer is cholangiocarcinoma. In an embodiment, the cancer is colorectal cancer. In an embodiment, the cancer is stomach adenocarcinoma. In an embodiment, the cancer is invasive ductal carcinoma. In an embodiment, the cancer is uterine carcinosarcoma. In an embodiment, the cancer is germ cell tumors. In an embodiment, the cancer is bladder cancer. In an embodiment, the cancer is small bowel adenocarcinoma. In an embodiment, the cancer is appendix cancer. In an embodiment, the cancer is peritoneum cancer. The cancer can have one or more cancer cells that express the mutant KRAS G12V protein such as KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, or KRAS G12V mutant peritoneum cancer. Additionally, the cancer can be non-small cell lung cancer, and one or more cells express KRAS G12V mutant protein. Further, the cancer can be colorectal cancer, and one or more cells express KRAS G12V mutant protein. Additionally, the cancer can be pancreatic cancer, and one or more cells express KRAS G12V mutant protein. Further, the cancer can be KRAS G12V mutant cervical cancer, and one or more cells express KRAS G12V mutant protein. Additionally, the cancer can be KRAS G12V mutant esophageal cancer, and one or more cells express KRAS G12V mutant protein. Further, the cancer can be KRAS G12V mutant endometrial cancer, and one or more cells express KRAS G12V mutant protein. Additionally, the cancer can be KRAS G12V mutant ovarian cancer, and one or more cells express KRAS G12V mutant protein. Further, the cancer can be KRAS G12V mutant cholangiocarcinoma, and one or more cells express KRAS G12V mutant protein. Additionally, the cancer can be KRAS G12V mutant stomach adenocarcinoma, and one or more cells express KRAS G12V mutant protein. Further, the cancer can be KRAS G12V mutant invasive ductal carcinoma, and one or more cells express KRAS G12V mutant protein. Additionally, the cancer can be KRAS G12V mutant uterine carcinosarcoma, and one or more cells express KRAS G12V mutant protein. Further, the cancer can be KRAS G12V mutant germ cell tumors, and one or more cells express KRAS G12V mutant protein. Additionally, the cancer can be KRAS G12V mutant bladder cancer, and one or more cells express KRAS G12V mutant protein. Further, the cancer can be KRAS G12V mutant small bowel adenocarcinoma, and one or more cells express KRAS G12V mutant protein. Additionally, the cancer can be KRAS G12V mutant appendix cancer, and one or more cells express KRAS G12V mutant protein. Further, the cancer can be KRAS G12V mutant peritoneum cancer, and one or more cells express KRAS G12V mutant protein. The patient can have a cancer that was determined to have one or more cells expressing the KRAS G12V mutant protein prior to administration of the compound or a pharmaceutically acceptable salt thereof. The patient may have been treated with a different course of treatment prior to being treated as described herein.

The compounds provided herein according to Formula I, or a pharmaceutically acceptable salt thereof, may also be used in the manufacture of a medicament for treating cancer. When used in the manufacture of a medicament, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer. In an embodiment, the cancer is non-small cell lung cancer. In an embodiment, the cancer is pancreatic cancer. In an embodiment, the cancer is cervical cancer. In an embodiment, the cancer is esophageal cancer. In an embodiment, the cancer is endometrial cancer. In an embodiment, the cancer is ovarian cancer. In an embodiment, the cancer is cholangiocarcinoma. In an embodiment, the cancer is colorectal cancer. In an embodiment, the cancer is stomach adenocarcinoma. In an embodiment, the cancer is invasive ductal carcinoma. In an embodiment, the cancer is uterine carcinosarcoma. In an embodiment, the cancer is germ cell tumors. In an embodiment, the cancer is bladder cancer. In an embodiment, the cancer is small bowel adenocarcinoma. In an embodiment, the cancer is appendix cancer. In an embodiment, the cancer is peritoneum cancer. The cancer can have one or more cancer cells that express the mutant KRAS G12V protein. When the cancer cells express KRAS G12V protein, the cancer can be selected from KRAS G12V mutant lung cancer, KRAS G12V mutant pancreatic cancer, KRAS G12V mutant cervical cancer, KRAS G12V mutant esophageal cancer, KRAS G12V mutant endometrial cancer, KRAS G12V mutant ovarian cancer, KRAS G12V mutant cholangiocarcinoma, KRAS G12V mutant colorectal cancer, KRAS G12V mutant stomach adenocarcinoma, KRAS G12V mutant invasive ductal carcinoma, KRAS G12V mutant uterine carcinosarcoma, KRAS G12V mutant germ cell tumors, KRAS G12V mutant bladder cancer, KRAS G12V mutant small bowel adenocarcinoma, KRAS G12V mutant appendix cancer, and KRAS G12V mutant peritoneum cancer.

Also provided herein is a method of treating cancer, comprising administering to a patient in need thereof, an effective amount of a compound according to Formula I, or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRAS G12V protein. Further provided herein is a compound according to Formula I, or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to Formula I, or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to Formula I, or a pharmaceutically acceptable salt thereof, and a PD-1 or PD-L1 inhibitor, in which the cancer has one or more cells that express a mutant KRAS G12V protein. Further provided is a compound according to Formula I, or a pharmaceutically acceptable salt thereof, for use in simultaneous, separate, or sequential combination with a PD-1 or PD-L1 inhibitor, for use in the treatment of cancer. Additionally provided is a combination comprising a compound according to Formula I, or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab.

Also provided is a method of treating cancer, comprising administering to a patient in need thereof, an effective amount of a compound according to Formula I, or a pharmaceutically acceptable salt thereof, and a CDK4/CDK6 inhibitor, or a pharmaceutically acceptable salt thereof, in which the cancer has one or more cells that express a mutant KRAS G12V protein. Further provided is a compound according to Formula I, or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRAS G12V protein. Additionally provided is a combination comprising a compound according to Formula I, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRAS G12V protein. As used herein, the CDK4/CDK6 inhibitor can be abemaciclib; the CDK4/CDK6 inhibitor can be palbociclib; or the CDK4/CDK6 inhibitor can be ribociclib.

Also provided is a method of treating cancer, comprising administering to a patient in need thereof, an effective amount of a compound according to Formula I, or a pharmaceutically acceptable salt thereof, and an EGFR inhibitor, or a pharmaceutically acceptable salt thereof, in which the cancer has one or more cells that express a mutant KRAS G12V protein. Further provided is a compound according to Formula I, or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to Formula I, or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; or the EGFR inhibitor can be cetuximab.

Also provided is a method of treating cancer, comprising administering to a patient in need thereof, an effective amount of a compound according to Formula I, or a pharmaceutically acceptable salt thereof, and an ERK inhibitor, or a pharmaceutically acceptable salt thereof, in which the cancer has one or more cells that express a mutant KRAS G12V protein. Further provided is a compound according to Formula I, or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947.

Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRAS G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid: 2-methylpropan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

Also provided is a method of treating cancer, comprising administering to a patient in need thereof, an effective amount of a compound according to Formula I, or a pharmaceutically acceptable salt thereof, and a SHP2 inhibitor, in which the cancer has one or more cells that express a mutant KRAS G12V protein. Further provided is a compound according to Formula I, or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PHPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. This method also includes treating KRAS G12V mutant protein mutant bearing cancers of other origins.

Also provided is a method of treating cancer, comprising administering to a patient in need thereof, an effective amount of a compound according to Formula I, or a pharmaceutically acceptable salt thereof, and a platinum agent, in which the cancer has one or more cells that express a mutant KRAS G12V protein. Further provided is a compound according to Formula I, or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRAS G12V protein. Additionally provided is a combination comprising a compound according to Formula I, or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin.

Also provided is a method of treating cancer, comprising administering to a patient in need thereof, an effective amount of a compound according to Formula I, or a pharmaceutically acceptable salt thereof, and pemetrexed, in which the cancer has one or more cells that express a mutant KRAS G12V protein. Further provided is a compound according to Formula I, or a pharmaceutically acceptable salt thereof, for use in simultaneous, separate, or sequential combination with pemetrexed, for the treatment of cancer, in which the cancer has one or more cells that express a mutant KRAS G12V protein. Additionally provided is a combination comprising a compound according to Formula I, or a pharmaceutically acceptable salt thereof, and pemetrexed, for simultaneous, separate, or sequential use in the treatment of cancer, in which the cancer has one or more cells that express a mutant KRAS G12V protein.

As described above, the cancer can be lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer, in which the cancer has one or more cells that express a KRAS G12V mutant protein, or the cancer can be mutant lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, or peritoneum cancer, in which the cancer has one or more cells that express a KRAS G12V mutant protein. These methods also include treating KRAS G12V mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

Pharmaceutical compositions containing the compounds of Formula I as described herein may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in achieving a desired therapeutic result such as treating a disorder or disease, like a cancerous lesion or progression of abnormal cell growth and/or cell division. Factors considered in the determination of an effective amount or dose of a compound include: whether the compound or its salt will be administered; the co-administration of other agents, if used; the species of patient to be treated; the patient's size, age, gender, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Pharmaceutical compositions can be formulated as a tablet or capsule for oral administration, a solution for oral administration, or an injectable solution. The tablet, capsule, or solution can include a compound of the present invention in an amount effective for treating a patient in need of treatment with cancer.

As used herein, the terms "treating", "to treat", or "treatment", includes slowing, controlling, delaying, reducing, stopping, reversing, preventing, or ameliorating the progression or severity of an existing symptom, disorder, condition, which can include specifically slowing the growth of a cancerous lesion or progression of abnormal cell growth and/or cell division. Treating does not necessarily indicate a total elimination of all disorder or disease symptoms.

As used herein, the term "patient" refers to a mammal in need of treatment. Specifically, the patient can be a human that is in need of treatment with cancer, for example, KRAS G12V mutant protein mutant bearing cancers.

Certain abbreviations are defined as follows: "ACN" refers to acetonitrile; "AcOH" or "HOAc" refer to acetic acid; "aq." refers to aqueous; "conc." refers to concentrated; "DCM" refers to dichloromethane; "DIBAL-H" refers to diisobutylaluminum hydride; "DIEA" and "DIPEA" refer to N,N-diisopropyl ethylamine; "DMAP" refers to 4-dimethylaminopyridine; "DMEA" refers to N,N-dimethylethylamine; "DMF" refers to N,N-dimethylformamide; "DMSO" refers to dimethylsulfoxide; "ELISA" refers to enzyme-linked immunosorbent assay; "ERK" refers to extracellular signal-regulated kinases; "Et" refers to an ethyl group; "EtOAc" refers to ethyl acetate; "$Et_2O$" refers to diethyl ether; "EtOH" refers to ethanol; "FA" refers to formic acid; "FBS" refers to fetal bovine serum; "GDP" refers to guanosine diphosphate; "GTP" refers to guanosine triphosphate; "h" refers to hour or hours; "Hex" or "hex" refers to hexane or hexanes; "HPLC" refers to high-performance liquid chromatography; "IPA" refers to isopropyl alcohol; "IPAm" refers to isopropyl amine; "KOAc" refers to potassium acetate; "LC-ES/MS" refers to liquid chromatograph-electrospray mass spectrometry; "LC-MS" refers to liquid chromatography mass spectrometry; "LiHMDS" refers to lithium bis(trimethylsilyl)amide; "MAPK" refers to mitogen-activated protein kinases; "mCPBA" refers to 3-chloroperoxybenzoic acid; "Me" refers to a methyl group; "MeOH" refers to methanol; "min" refers to minute or minutes; "MTBE" refers to methyl tert-butyl ether; "NMP" refers to 1-methylpyrrolidin-2-one; "$Pd(OAc)_2$ refers to palladium (II) acetate; "RT" refers to room temperature; "sat." refers to saturated; "SCX" refers to strong cation exchange; "TBAF" refers to tetrabutylammonium fluoride; "tBu" refers to the tert-butyl group; "t-BuOH" refers to tert-butanol or tert-butyl alcohol; "TEA" refers to triethylamine; "TFA" refers to trifluoracetic acid; "THF" refers to tetrahydrofuran; "XantPhos" refers to 4,5-bis(diphenylphosphino)-9,9-dimethylxanthene; "XPhos" refers to 2-(dicyclohexylphosphino)-2',4',6'-tri-isopropyl-1,1'-biphenyl.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The molecules described herein include compounds that are atropisomers and which can exist in different conformations or as different rotomers. Atropisomers are compounds that exist in different conformations arising from restricted rotation about a single bond. Atropisomers can be isolated as separate chemical species if the energy barrier to rotation about the single bond is sufficiently high that the rate of interconversion is slow enough to allow the individual rotomers to be separated from each other. This description is intended to include all of the isomers, enantiomers, diastereomers, and atropisomers possible for the compounds disclosed herein or that could be made using the compounds disclosed herein. In the molecules described herein, only molecules in which the absolute conformation of a chiral center (or atropisomer conformation) is known have used naming conventions or chemical formula that are drawn to indicate the chirality or atropisomerism. Those of skill in the art will readily understand when other chiral centers are present in the molecules described herein and be able to identify the same.

Compounds of any one of Formula I that are chemically capable of forming salts are readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

The compounds of the present invention, or salts thereof, may be prepared by a variety of procedures, some of which are illustrated in the Schemes, Preparations, and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

Preparation 1 tert-Butyl (4-bromo-5-fluorobenzo[id]thiazol-2-yl) carbamate

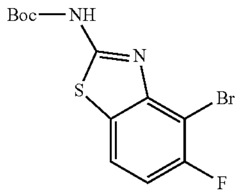 [SMILES: CC(C)(C)OC(=O)Nc1nc2c(Br)c(F)ccc2s1]

To a mixture of 4-bromo-5-fluorobenzo[d]thiazol-2-amine (10.6 g, 42.9 mmol) and di-tert-butyl dicarbonate (10.3 g, 47.2 mmol) in DCM (100 mL) was added 4-dimethylaminopyridine (0.262 g, 2.14 mmol). The mixture was stirred at room temperature overnight, then combined with diatomaceous earth. The crude material was purified on silica, eluting with 0-100% EtOAc in DCM to obtain the title compound (13.4 g, 90%) as an off-white solid. MS (ES) m/z=347 (M-1).

The following compounds in Table 1 were prepared in similar manner as described in Preparation 1. A base, such as triethylamine or diisopropylethylamine, may have been used. Various methods were used to purify the compounds, which would be apparent to one skilled in the art.

TABLE 1

| Preparation | Chemical Name | Structure | MS (ES) m/z (M + 1) |
|---|---|---|---|
| 2 | tert-Butyl (4-chloro-7-fluorothiazolo[4,5-c]pyridin-2-yl)carbamate | 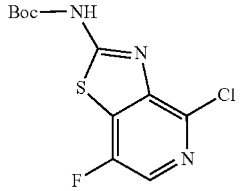 [SMILES: CC(C)(C)OC(=O)Nc1nc2c(Cl)ncc(F)c2s1] | 304 |

Preparation 3

(2-((tert-Butoxycarbonyl)amino)-5-fluorobenzo[d]thiazol-4-yl)boronic acid

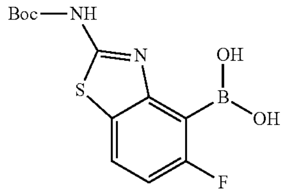 [SMILES: CC(C)(C)OC(=O)Nc1nc2c(B(O)O)c(F)ccc2s1]

Sodium hydride (60 wt % in mineral oil; 1.73 g, 43.2 mmol) was mixed with THF (100 mL) under argon and cooled to 0° C. A mixture of tert-butyl (4-bromo-5-fluorobenzo[d]thiazol-2-yl)carbamate (10.0 g, 28.8 mmol) in THF (35 mL) was added. The mixture was stirred at 0° C. for 30 min, cooled to −78° C., and n-butyllithium (2.5M in hexanes; 17.3 mL, 43.2 mmol) was slowly added. The mixture was stirred at −78° C. for 15 min, then triisopropyl borate (19.9 mL, 86.4 mmol) was slowly added. The mixture was stirred at −78° C. for 1 h, −40° C. for 1 h, −10° C. for 45 min, then slowly quenched with saturated aqueous ammonium chloride. The mixture was diluted with water (100 mL) and extracted with EtOAc (300 mL, 200 mL). The combined organics were dried over anhydrous $Na_2SO_4$, filtered, and concentrated under reduced pressure. The residue was diluted with hexanes, stirred at 50° C. for 30 min, cooled to room temperature, and filtered. The solids were washed with hexanes and dried under vacuum to obtain the title compound (7.2 g, 80%) as a white solid. MS (ES) m/z=313 (M+1).

Preparation 1A (2-((tert-Butoxycarbonyl)amino)benzo[d]oxazol-4-yl)boronic acid

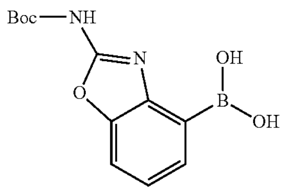 [SMILES: CC(C)(C)OC(=O)Nc1nc2c(B(O)O)cccc2o1]

tert-Butyl (4-bromobenzo[d]oxazol-2-yl)carbamate was used in a manner analogous to the method of Preparation 3 to afford the title compound (0.23 g, 69%) as a white solid. MS (ES) m/z=279 (M+1).

Preparation 4

Methyl 4-bromo-5-fluorobenzo[b]thiophene-2-carboxylate

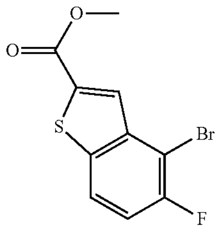

A solution of methyl thioglycolate (0.18 mL, 2.0 mmol, 1 eq.) in THF (5 mL) was flushed with $N_2$ and charged with NaH (60 mass %) in mineral oil (0.101 g, 2.53 mmol, 1.24 eq.) at RT. Gas evolution was observed, and a precipitate formed in the flask. The reaction was stirred at RT for 20 min. A solution of 2-bromo-3,6-difluorobenzaldehyde (0.475 g, 2.04 mmol) in THF (5 mL) was added slowly via syringe over ~2 min. The reaction was stirred at RT for 9 h. Additional methyl thioglycolate (0.1 mL, 1 mmol, 0.5 eq.) and sodium hydride (60 mass %) in mineral oil (0.050 g, 1.3 mmol, 0.6 eq.) were added and stirring was continued at RT for ~18 h. The mixture was diluted with EtOAc and washed with sat. aq. $NH_4Cl$ and brine. The organics were dried over anhydrous $Na_2SO_4$, filtered and concentrated. The residue was purified on silica, eluting with 2% MTBE/Hex to obtain the title compound (0.346 g, 59%) as a white solid. $^1H$ NMR (400 MHz, DMSO-$d_6$) δ 8.23-8.19 (dd, J=4.49, 8.9 Hz, 1H), 8.05 (s, 1H), 7.62 (t, J=9.0 Hz, 1H), 3.93 (s, 3H).

Preparation 5

4-Bromo-5-fluorobenzo[b]thiophene-2-carboxylic acid

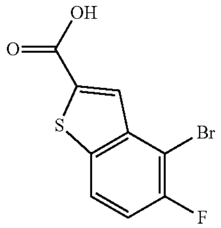 [SMILES: O=C(O)c1cc2c(Br)c(F)ccc2s1]

A solution of methyl 4-bromo-5-fluorobenzo[b]thiophene-2-carboxylate (19.2 g, 66.4 mmol, 1 eq.) in MeOH (130 mL) and THF (130 mL) was charged with 5N NaOH (66 mL, 330 mmol, 5 eq.) and stirred at RT for 40 min. The mixture was concentrated and $H_2O$ (500 mL) was added. The pH was adjusted to ~2 with 5N HCl. The mixture was extracted with EtOAc (2×500 mL) and the combined organic layers were dried over anhydrous $Na_2SO_4$, filtered and concentrated. The solids were dried under vacuum at 50° C. to afford the title compound (17.6 g, 96%) as a white solid. MS (ES) m/z=229 (M-1-$CO_2$).

Preparation 6 tert-Butyl (4-bromo-5-fluorobenzo[b]thiophen-2-yl) carbamate

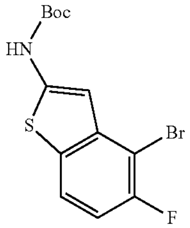 [SMILES: CC(C)(C)OC(=O)Nc1cc2c(Br)c(F)ccc2s1]

A solution of 4-bromo-5-fluorobenzo[b]thiophene-2-carboxylic acid (1.5 g, 5.5 mmol) in t-butanol (30 mL) was charged with TEA (1.5 mL, 11 mmol, 2.0 eq.) and diphenylphosphoryl azide (1.5 mL, 6.9 mmol, 1.3 eq.) and heated at 95° C. for 1 h. The mixture was cooled and concentrated. The residue was purified on silica, eluting with MTBE/Hex (4% to 20%) to obtain the title compound (0.987 g, 52%) as a white solid. MS (ES) m/z=290 (M+1).

Preparation 7 tert-Butyl (4-(5,5-dimethyl-1,3,2-dioxaborinan-2-yl)-5-fluorobenzo[b]thiophen-2-yl)carbamate

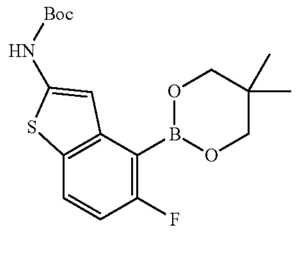 [SMILES: CC1(C)COB(c2c(F)ccc3sc(NC(=O)OC(C)(C)C)cc23)OC1]

A mixture of tert-butyl (4-bromo-5-fluorobenzo[b]thiophen-2-yl)carbamate (3.08 g, 8.90 mmol) and bis(neopentyl glycolato)diboron (4.02 g, 17.8 mmol, 2 eq.) and KOAc (2.62 g, 26.7 mmol, 3 eq.) in 1,4-dioxane (70 mL, 819.9 mmol) was sparged with $N_2$ for 20 min. To the mixture was added Pd(ddpf)$Cl_2$ (0.69 g, 0.90 mmol, 0.1 eq.). The reaction was sonicated for 3 min, then put through a vacuum/$N_2$ refill cycle (3×) and was heated at 100° C. for 3 h. The mixture was cooled to RT, filtered through diatomaceous earth and was rinsed with 1:4 EtOAc/Hex. The filtrate was concentrated and the residue was purified on silica (0-40% MTBE/Hex) to obtain the title compound (2.95 g, 87%) as a white solid. $^1$H NMR (400 MHz, DMSO-$d_6$) δ 10.81-10.79 (bs, 1H), 7.84-7.74 (dd, J=5.07, 8.59, 1H), 7.14 (s, 1H), 6.94-6.88 (m, 1H), 3.89 (bs, 4H), 1.49 (s, I0H), 1.03 (s, 6H).

Preparation 8 tert-Butyl (4-chloro-3-cyano-7-fluorothieno[3,2-c]pyridin-2-yl)carbamate

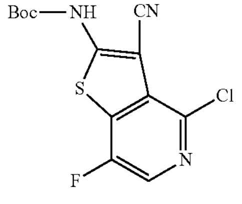 [SMILES: CC(C)(C)OC(=O)Nc1sc2c(F)cnc(Cl)c2c1C#N]

Ethyl (3-cyano-7-fluorothieno[3,2-c]pyridin-2-yl)carbamate. A solution of 2-(4-chloro-5-fluoropyridin-3-yl)acetonitrile (11.8 g, 56.1 mmol) in DMF (112 mL) was cooled to 0° C. Potassium tert-butoxide (7.00 g, 61.1 mmol) was added. After 15 min, ethoxycarbonyl isothiocyanate (7.45 mL, 61.8 mmol) was added dropwise. The reaction mixture was allowed to slowly warm to room temperature overnight. The reaction mixture was poured into a mixture of ice/water (1.5 L), stirred until all ice had melted, and filtered through diatomaceous earth. The solids were dried in a vacuum oven (60° C.) overnight and separated from the diatomaceous earth to give ethyl N-(3-cyano-7-fluoro-thieno[3,2-c]pyridin-2-yl)carbamate (11.9 g, 79%) as a solid. MS (ES) m/z=266 (M+1).

2-Amino-7-fluorothieno[3,2-c]pyridine-3-carbonitrile. A suspension of ethyl (3-cyano-7-fluorothieno[3,2-c]pyridin-2-yl)carbamate (11.9 g, 44.4 mmol) in DMSO (90 mL) was cooled to 0° C. NaOH (5 M in water, 90 mL) was added dropwise over 15 min. The reaction mixture was heated to 105° C. for 1 h, then cooled to room temperature. The reaction mixture was poured into a mixture of ice/water (1.8 L), stirred until all ice had melted, and filtered through diatomaceous earth. The solids were dried in a vacuum oven (50° C.) overnight and separated from the diatomaceous earth to give crude 2-amino-7-fluoro-thieno[3,2-c]pyridine-3-carbonitrile.

tert-Butyl (3-cyano-7-fluorothieno[3,2-c]pyridin-2-yl) carbamate. A mixture of crude 2-amino-7-fluorothieno[3,2-c]pyridine-3-carbonitrile (8.6 g, 44.4 mmol), DCM (90 mL), DMF (90 mL) and N,N-diisopropylethylamine (15.5 mL, 88.9 mmol) was cooled to 0° C. 4-dimethylaminopyridine (0.54 g, 4.42 mmol) and di-tert-butyl dicarbonate (14.6 g, 66.7 mmol) were added. The reaction mixture was stirred at room temperature for 2 h. The solvents were removed under reduced pressure and the remaining material was diluted with DCM (400 mL) and 5% aq. citric acid (250 mL). The aqueous phase was washed twice with DCM. The combined organic phases were washed with sat. aq. $NaHCO_3$, dried over $MgSO_4$, filtered, and concentrated to give tert-butyl N-(3-cyano-7-fluoro-thieno[3,2-c]pyridin-2-yl)carbamate (7.5 g, 58%) as a brown solid. MS (ES) m/z=294 (M+1).

2-((tert-Butoxycarbonyl)amino)-3-cyano-7-fluorothieno[3,2-c]pyridine 5-oxide. 3-Chloroperoxybenzoic acid (9.00 g, 40.2 mmol) was added to a solution of tert-butyl (3-cyano-7-fluorothieno[3,2-c]pyridin-2-yl)carbamate (7.85 g, 26.8 mmol) in DCM (180 mL). The reaction mixture was stirred at room temperature overnight, then cooled to 0° C. for −15 min. Solids were collected by filtration and dried in a vacuum oven (60° C.). The filtrate was diluted with MeOH and silica gel, concentrated, and the residue was purified on silica, eluting with 0-6% MeOH in DCM. Fractions containing desired material were combined with the solids from the filtration and concentrated to give tert-butyl N-(3-cyano-7-fluoro-5-oxido-thieno[3,2-c]pyridin-5-ium-2-yl)carbamate (7.26 g, 88%) as an off-white solid. MS (ES) m/z=310 (M+1).

tert-Butyl (4-chloro-3-cyano-7-fluorothieno[3,2-c]pyridin-2-yl)carbamate. A suspension of 2-((tert-butoxycarbonyl)amino)-3-cyano-7-fluorothieno[3,2-c]pyridine 5-oxide (5.27 g, 17.0 mmol) in 1,2-dichloroethane (34 mL) was cooled to 0° C. A solution of phosphoryl chloride (32 mL, 344 mmol) in 1,2-dichloroethane (34 mL) was added dropwise. The reaction mixture was stirred at room temperature for 30 min, at 45° C. for 90 min, and cooled to room temperature. The reaction mixture was diluted with 1,2-dichloroethane (100 mL) and added to a mixture of sat. aq. $NaHCO_3$ (500 mL), NaOH (5 M in water, 40 mL), and ice. Solid $NaHCO_3$ was added to the stirred mixture to maintain pH ~6-7. Once bubbling ceased, the phases were separated. The aqueous phase was extracted 3× with DCM. The combined organic phases were dried over $MgSO_4$ and filtered. The filtrate was diluted with MeOH and silica gel, concentrated, and the residue was purified on silica, eluting with 50-100% DCM in hexanes. Fractions containing desired material were concentrated to give the title compound (3.87 g, 69%) as a white solid. MS (ES) m/z=328 (M+1).

Preparation 9

5-Fluoroisobenzofuran-1(3H)-one

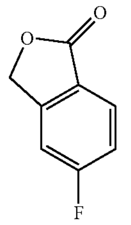 [SMILES: O=C1OCc2cc(F)ccc21]

To a stirred mixture of (2-bromo-5-fluorophenyl)methanol (500 g, 2.44 mol) and TEA (474.6 mL, 3.41 mol, 1.4 eq.) in ACN (2500 mL) was added $Pd(OAc)_2$ (10.95 g, 48.77 mmol, 0.02 eq.) and XantPhos (42.33 g, 73.16 mmol, 0.03 equiv.) at RT, then stirred for 3 days at 120° C. under 10 atm of carbon monoxide. The reaction was cooled to RT and concentrated. The residue was diluted with $H_2O$ (1,000 mL), then extracted with EtOAc (2×2000 mL). The combined organic layers were washed with brine (2×1,000 mL), dried over anhydrous $Na_2SO_4$, filtered and concentrated. The residue was triturated with 10:1 hexanes/EtOAc (1,100 mL) and then filtered. The filter cake was dried at 50° C. for ~18 h to obtain the title compound as a yellow solid (300 g, 81%). MS (ES) m/Vz=153 (M+1).

Preparation 10

4-Bromo-5-fluoro-6-nitroisobenzofuran-1(3H)-one

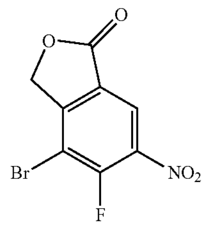 [SMILES: O=C1OCc2c1cc([N+](=O)[O-])c(F)c2Br]

To a stirred mixture of 5-fluoroisobenzofuran-1(3H)-one (300 g, 1.97 mol) in $H_2SO_4$ (1,500 mL) was added $HNO_3$ (273.38 g, 4.348 mol, 2.2 eq.) dropwise at 65° C. The reaction was stirred for 1 h then cooled to RT. 1,3-dibromo-5,5-dimethylimidazolidine-2,4-dione (2,255.43 g, 7.88 mol, 4 eq.) was added in portions over 20 min and was stirred at RT for ~18 h. The mixture was poured onto ice/water (pre-treated with 3 kg $Na_2SO_3$) and filtered. The filter cake was dissolved in EtOAc (3,000 mL), washed with sat. aq. $Na_2CO_3$ (2×1,000 mL), brine (2×1,000 mL), dried over anhydrous $Na_2SO_4$ and concentrated. The residue was triturated with 10:1 hexanes/EtOAc (660 mL) and was filtered and dried at 50° C. for ~18 h to obtain the title compound as a yellow solid (270 g, 49%) which was used in a subsequent step without further purification. $^1$H NMR (400 MHz, DMSO-$d_6$) δ 8.58 (s, 1H), 5.51 (s, 2H).

Preparation 11

4-Bromo-5-fluoro-6-nitro-1,3-dihydroisobenzofuran

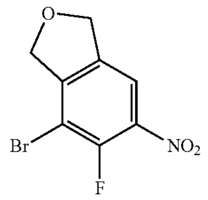

To a stirred mixture of 4-bromo-5-fluoro-6-nitroisobenzofuran-1(3H)-one (270 g, 978 mmol) in DCM (2,500 mL) was added DIBAL-H (1M in THF, 1,467 mL, 1.467 mol, 1.5 eq.) dropwise at −78° C. under $N_2$. The reaction was stirred for 5 h at −78° C., then was quenched with 5N NaOH (300 mL) at −78° C. The resulting mixture was allowed to warm to RT, then was concentrated. The residue was diluted with EtOAc (2,500 mL), washed with brine (2×1,000 mL) and dried over anhydrous $Na_2SO_4$ and concentrated. The residue was triturated with 10:1 hexanes/EtOAc (550 mL) and filtered. The solids were dried (190 g, 683.4 mmol) then dissolved in DCM (1,500 mL) and treated dropwise with $Et_3SiH$ (662 mL, 4.10 mol, 6 eq.) at 0° C. The reaction was stirred for 20 min at 0° C. TFA (152 mL, 2.05 mol, 3 eq.) was added dropwise at 0° C. The ice bath was removed, and the reaction was stirred at RT for ~18 h. The reaction was concentrated to an oil, which was diluted with EtOAc (2,000 mL), washed with sat. aq. $Na_2CO_3$ (2×500 mL) and brine (2×500 mL), dried over anhydrous $Na_2SO_4$, filtered and concentrated to obtain the title compound (110 g, 42%) which was used in a subsequent step without further purification. $^1$H NMR (400 MHz, DMSO-$d_6$) δ 8.16 (d, J=6.2 Hz, 1H), 5.18-5.15 (m, 2H), 5.11-5.06 (m, 2H).

Preparation 12

7-Bromo-6-fluoro-1,3-dihydroisobenzofuran-5-amine

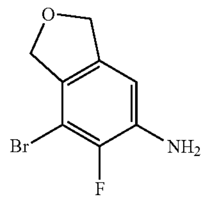 [SMILES: Nc1cc2c(c(Br)c1F)COC2]

To a stirred mixture of 4-bromo-5-fluoro-6-nitro-1,3-dihydroisobenzofuran (110 g, 420 mmol) and $NH_4Cl$ (112.3 g, 2.10 mol, 5 eq.) in EtOH (1,000 mL) and $H_2O$ (200 mL) was added Fe (117.22 g, 2.09 mol, 5 eq.) in portions at RT, then stirred for ~18 h at 80° C. The mixture was filtered and concentrated. The mixture was diluted with $H_2O$ (500 mL) and extracted with EtOAc (2×1,000 mL). The combined organic layers were washed with brine (2×500 mL), dried over anhydrous $Na_2SO_4$, filtered and concentrated. The residue was purified on silica (25% to 50% EtOAc/Hex) to afford the title compound (70 g, 72%) as a yellow solid. MS (ES) m/z=231 (M+1).

Preparation 13

(4-Chloro-1,2-phenylene)dimethanol

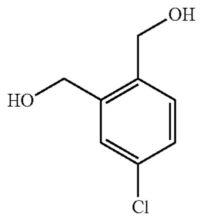

To a stirred mixture of $LiAlH_4$ (1.9 L, 2.74 mol, 2 eq., 2.5 M in THF) in THF (1 L) was added 4-chlorophthalic anhydride (250 g, 1.34 mol, 1.00 eq.) in THF (500 mL) dropwise at −20° C. under $N_2$. The resulting mixture was stirred for 30 min at 45° C. under $N_2$. The reaction was quenched by the addition of $H_2O$ (1.5 L) and 15% NaOH (500 mL) at RT. The mixture was filtered, and the filter cake was washed with MTBE (3×250 mL). The filtrate was extracted with MTBE (3×1.5 L). The combined organic layers were washed with brine (2×2 L) and dried over anhydrous $Na_2SO_4$. After filtration, the filtrate was concentrated under reduced pressure to obtain the title compound (219.5 g, 93%) as an off-white solid. $^1H$ NMR (300 MHz, DMSO-$d_6$) δ 7.45-7.36 (m, 2H), 7.28 (dd, J=8.2 Hz, 1H), 5.40-5.13 (m, 2H), 4.54 (s, 2H), 4.49 (s, 2H).

Preparation 14

5-Chloro-1,3-dihydroisobenzofuran

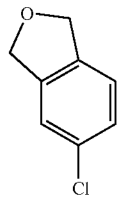

To a stirred mixture of (4-chloro-2-p enylene)dimethanol (219.5 g, 1.271 mol) and dimethyl carbonate (458.2 g, 5.082 mol, 4 eq.) in ACN (3 L) was added NaOMe (137.4 g, 2.544 mol, 2 eq.) in portions at RT. The resulting mixture was stirred for ~18 h at 80° C. under $N_2$. The mixture was concentrated under reduced pressure, diluted with $H_2O$ (2 L) and extracted with EtOAc (3×2 L). The combined organic layers were washed with brine (2×2 L) and dried over anhydrous $Na_2SO_4$. After filtration, the filtrate was concentrated under reduced pressure. The residue was purified on silica (10:1 to 8:1 hex/EtOAc) to obtain the title compound (165 g, 82%) as a light-brown solid. $^1H$ NMR (300 MHz, DMSO-$d_6$) δ 7.42-7.37 (m, 1H), 7.33 (d, J=1.4 Hz, 2H), 4.99 (s, 4H).

Preparation 15

5-Chloro-6-nitro-1,3-dihydroisobenzofuran

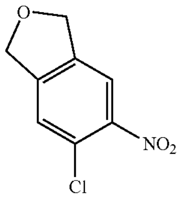 [SMILES: O=[N+]([O-])c1cc2c(cc1Cl)COC2]

A solution of 5-chloro-1,3-dihydroisobenzofuran (110 g, 712 mmol) in $H_2SO_4$ (700 mL) at −10° C. was charged with a solution of $KNO_3$ (64.74 g, 640 mmol, 0.9 eq.) in $H_2SO_4$ (200 mL) dropwise at −5° C.-0° C. The resulting mixture was stirred for additional 30 min at 0° C. and then was slowly added to stirred ice-cooled $H_2O$. The precipitated solids were collected by filtration and washed with $H_2O$ (3×1 L). The filter cake was dried in vacuo to afford the title compound (110 g, 77%) as a light-brown solid which was used in a subsequent step without further purification. $^1H$ NMR (400 MHz, DMSO-$d_6$) δ 8.05 (s, 1H), 7.75 (s, 1H), 5.07-5.02 (m, 4H).

Preparation 16

4-Bromo-5-chloro-6-nitro-1,3-dihydroisobenzofuran

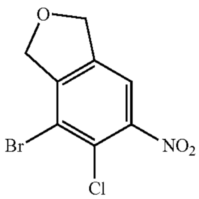 [SMILES: O=[N+]([O-])c1cc2c(c(Br)c1Cl)COC2]

To a stirred solution of 5-chloro-6-nitro-1,3-dihydroisobenzofuran (125 g, 626 mmol) in $H_2SO_4$ (700 mL) was added 1,3-dibromo-5,5-dimethylimidazolidine-2,4-dione (179.1 g, 626.3 mmol, 1 eq.) in portions at −10° C. The mixture was stirred for 1 h at −10° C. then slowly was added to stirred ice-cooled $H_2O$. The precipitated solids were collected by filtration and washed with $H_2O$ (3×0.5 L). The filter cake was dried in vacuo and purified on silica (10:1 to 5:1 Hex/EtOAc) to obtain the title compound (83.5 g, 47.9%) as a white solid.

$^1H$ NMR (300 MHz, DMSO-$d_6$) δ 8.07 (d, J=1.1 Hz, 1H), 5.19 (dt, J=2.3, 1.1 Hz, 2H), 5.08 (t, 2H).

Preparation 17

7-Bromo-6-chloro-1,3-dihydroisobenzofuran-5-amine

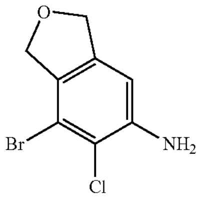 [SMILES: Nc1cc2c(c(Br)c1Cl)COC2]

To a stirred mixture of 4-bromo-5-chloro-6-nitro-1,3-dihydroisobenzofuran (37.0 g, 133 mmol) and $NH_4Cl$ (42.64 g, 797.2 mmol, 6 eq.) in EtOH (200 mL) and $H_2O$ (40 mL) was added Fe (44.52 g, 797.2 mmol, 6 equiv.) in portions at RT. The resulting mixture was stirred for ~18 h at 80° C. The resulting mixture was filtered hot and the filter cake was washed with EtOAc (3×500 mL). The filtrate was concentrated under reduced pressure and was purified on silica (15:1 to 10:1 Hex/EtOAc) to obtain the title compound (25 g, 76%) as a light-yellow solid. MS (ES) m/z=248 (M+1).

Preparation 1B

4-Bromo-7,9-dichloro-5-fluoro-1,3-dihydrofuro[3,4-f]quinoline

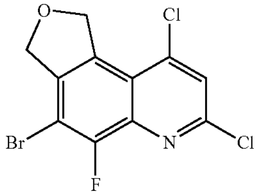 [SMILES: Fc1c(Br)c2c(c3c(Cl)cc(Cl)nc13)COC2]

A mixture of 7-bromo-6-fluoro-1,3-dihydroisobenzofuran-5-amine (5.00 g, 21.5 mmol), malonic acid (3.36 g, 32.3 mmol) and phosphoryl trichloride (19.9 mL, 215 mmol) was stirred for 15 h at 110° C., then cooled to room temperature. The mixture was diluted with cold water and extracted with DCM (3×200 mL). The combined organic layers were dried over magnesium sulfate and concentrated under reduced pressure. The residue was purified on silica, eluting with 0-100% ethyl acetate in heptane, to give the title compound (3.4 g, 47%) as a solid. MS (ES) m/z=336 (M+1).

Preparation 2B

4-Bromo-5,7,9-trichloro-1,3-dihydrofuro[3,4-f]quinoline

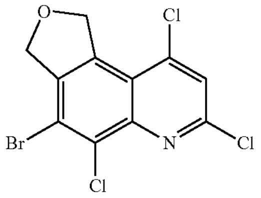 [SMILES: Clc1cc(Cl)c2c3c(c(Br)c(Cl)c2n1)COC3]

7-Bromo-6-chloro-1,3-dihydroisobenzofuran-5-amine was used in a manner analogous to the method of Preparation 1B to afford the title compound (2.0 g, 28%) as a yellow solid. MS (ES) m/z=352 (M+1).

Preparation 3B

4-Bromo-5-chloro-1,3-dihydrofuro[3,4-f]quinolin-9-ol

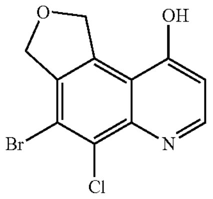 [SMILES: Oc1ccnc2c(Cl)c(Br)c3c(c12)COC3]

5-(((7-Bromo-6-chloro-1,3-dihydroisobenzofuran-5-yl)amino)methylene)-2,2-dimethyl-1,3-dioxane-4,6-dione: A mixture of 2,2-dimethyl-1,3-dioxane-4,6-dione (13 g, 89 mmol) and trimethoxymethane (180 mL, 1.64 mol) was stirred for 2 h at 100° C., then cooled to room temperature. 7-bromo-6-chloro-1,3-dihydroisobenzofuran-5-amine (20 g, 80 mmol) was added and the mixture was stirred for 18 h at 100° C., then cooled to room temperature. The mixture was filtered. The solids were washed with methanol and dried to give 5-(((7-bromo-6-chloro-1,3-dihydroisobenzofuran-5-yl)amino)methylene)-2,2-dimethyl-1,3-dioxane-4,6-dione (31.4 g, 97%) as an orange solid. MS (ES) m/z=402 (M+1).

4-Bromo-5-chloro-1,3-dihydrofuro[3,4-f]quinolin-9-ol: A mixture of 5-(((7-bromo-6-chloro-1,3-dihydroisobenzofuran-5-yl)amino)methylene)-2,2-dimethyl-1,3-dioxane-4,6-dione (10 g, 25 mmol) and oxydibenzene (100 mL, 629 mmol) was stirred for 30 min at 203° C., then cooled to room temperature. Heptane (300 mL) was added and the mixture was filtered. The solids were washed with heptane and dried to give the title compound (6.9 g, 92%) as a brown solid. $^1H$ NMR (400 MHz, DMSO-d6) δ ppm 5.03 (t, J=2.69 Hz, 2H) 5.55 (t, J=2.69 Hz, 2H) 6.12 (d, J=7.50 Hz, 1H) 7.81-7.86 (m, 1H) 11.37-11.50 (m, 1H).

Preparation 4B

4-Bromo-5,9-dichloro-1,3-dihydrofuro[3,4-f]cinnoline

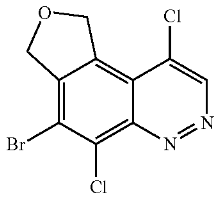 [SMILES: Clc1c(Br)c2c(c3c(Cl)cnnc13)COC2]

7-Bromo-6-chloro-4-((trimethylsilyl)ethynyl)-1,3-dihydroisobenzofuran-5-amine: A solution of cuprous iodide (0.560 g, 2.94 mmol) and ethynyl-trimethyl-silane (1.88 g, 19.1 mmol) in triethylamine (45 mL) was sparged with argon. Bis-(triphenylphosphino)-palladous chloride (1.03 g, 1.47 mmol) was added and the mixture was allowed to stir at room temperature for 30 min. 7-Bromo-6-chloro-4-iodo-1,3-dihydroisobenzofuran-5-amine (prepared as in WO/2023183585; 5.50 g, 14.7 mmol) was added. The reaction vessel was sealed and the mixture was heated for 2 h at 90° C. The mixture was filtered through anhydrous sodium sulfate and the solids were washed with ethyl acetate. The combined filtrates were concentrated under reduced pressure. The residue was purified on silica, eluting with 0-60% ethyl acetate in DCM, to give 7-bromo-6-chloro-4-((trimethylsilyl)ethynyl)-1,3-dihydroisobenzofuran-5-amine (4.58 g, 90%) as a yellow solid. MS (ES) m/z=344 (M+1).

4-Bromo-5-chloro-1,3-dihydrofuro[3,4-f]cinnolin-9-ol: A suspension of 7-bromo-6-chloro-4-((trimethylsilyl)ethynyl)-1,3-dihydroisobenzofuran-5-amine (1.31 g, 3.80 mmol) in HCl (conc aqueous; 15 mL) was slowly treated with sodium nitrite (3.0 M in water; 1.58 mL, 4.75 mmol). The reaction vessel was sealed and the mixture was heated for 30 min at 80° C. The mixture was poured into a stirring mixture of ice and water. The resulting mixture was stirred for 20 min as the ice melted. The resulting suspension was filtered to give 4-bromo-5-chloro-1,3-dihydrofuro[3,4-f]cinnolin-9-ol (0.94 g, 73%) as a tan solid. MS (ES) m/z=301 (M+1).

4-Bromo-5,9-dichloro-1,3-dihydrofuro[3,4-f]cinnoline: A solution of 4-bromo-5-chloro-1,3-dihydrofuro[3,4-f]cinnolin-9-ol (0.94 g, 3.10 mmol) in DCM (10 mL) was treated with chloromethylene(dimethyl)ammonium chloride (0.834 g, 6.51 mmol). The mixture was allowed to stir at room temperature for 15 min. The mixture was concentrated under reduced pressure. The resulting solids were suspended in water (40 mL), sonicated (10 min), and filtered. The solids were washed with water (20 mL) and heptane:methyl tert-butyl ether (4:1; 30 mL), then dried to give the title compound (0.92 g, 93%) as a brown solid. MS (ES) m/z=319 (M+1).

Preparation 18

Ethyl N-[(7-bromo-6-fluoro-1,3-dihydroisobenzofuran-5-yl)carbamothioyl]carbamate

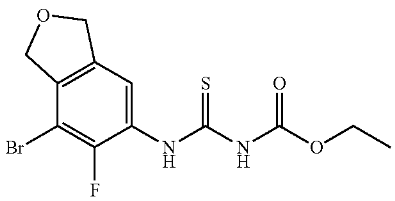 [SMILES: CCOC(=O)NC(=S)Nc1cc2c(c(Br)c1F)COC2]

A solution of 7-bromo-6-fluoro-1,3-dihydroisobenzofuran-5-amine (20.4 g, 87.9 mmol) in DCM (550 mL) was charged with ethoxycarbonyl isothiocyanate (9.7 mL, 82 mmol, 0.93 eq.) slowly via addition funnel and subsequently stirred at RT for ~4 h. The solids were filtered. The filtrate was concentrated, suspended in DCM (100 mL) and hexanes (350 mL) and stirred at RT. The resultant filtered solids and previous filtered solids were dried under vacuum at 50° C. for 2 h. The batches were combined to obtain the title compound (32.6 g, quantitative) as a white solid. MS (ES) m/z=363 (M+1).

Preparation 19

Ethyl N-[(7-bromo-6-chloro-1,3-dihydroisobenzofuran-5-yl)carbamothioyl]carbamate

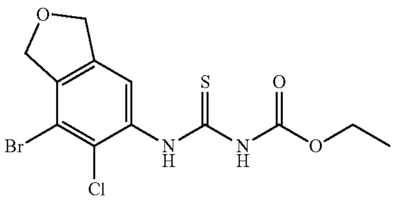 [SMILES: CCOC(=O)NC(=S)Nc1cc2c(c(Br)c1Cl)COC2]

7-Bromo-6-chloro-1,3-dihydroisobenzofuran-5-amine was used in a manner analogous to the method of Preparation 18 to afford the title compound (14 g, 92%) as a white solid. MS (ES) m/z=379 (M+1).

Preparation 20

Ethyl (((7-bromo-6-fluoro-1,3-dihydroisobenzofuran-5-yl)amino)(ethylthio)methylene)carbamate

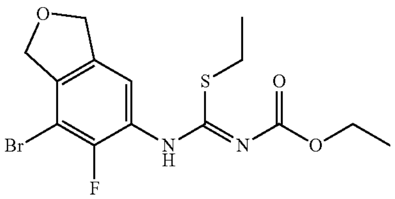 [SMILES: CCOC(=O)/N=C(/Nc1cc2c(c(Br)c1F)COC2)SCC]

A 2L 3-necked RBF, equipped with an overhead stirrer, dropping funnel and thermocouple was charged with a suspension of ethyl N-[(7-bromo-6-fluoro-1,3-dihydroisobenzofuran-5-yl)carbamothioyl]carbamate (32.6 g, 89.8 mmol) and acetone (450 mL). To this was added solid $K_2CO_3$ (37.2 g, 269 mmol, 3.00 eq.) in several portions, followed by the dropwise addition of EtI (7.2 mL, 90 mmol, 1.0 eq.) over 20 min. The mixture was stirred at RT for ~18 h. The solids were filtered and the filtrate was concentrated and partitioned between DCM (500 mL) and $H_2O$ (500 mL). The organics were further washed with brine and dried over anhydrous $Na_2SO_4$, filtered and concentrated. The residue was purified on silica (0 to 30% EtOAc/Hex) to obtain the title compound (30.9 g, 85.6%) as a white solid. MS (ES) m/z=391 (M+1).

Preparation 21

Ethyl (((7-bromo-6-chloro-1,3-dihydroisobenzofuran-5-yl)amino)(ethylthio)methylene)carbamate

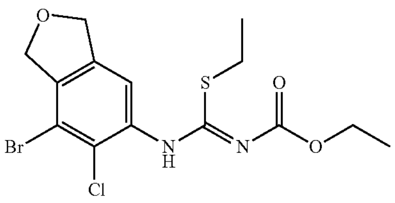 [SMILES: CCOC(=O)/N=C(/Nc1cc2c(c(Br)c1Cl)COC2)SCC]

Ethyl N-[(7-bromo-6-chloro-1,3-dihydroisobenzofuran-5-yl)carbamothioyl]carbamate was used in a manner analogous to the method of Preparation 20 to afford the title compound (15.4 g, crude) as a brown solid. MS (ES) m/z=407 (M+1).

Preparation 22

6-Bromo-3-(ethylthio)-5-fluoro-7,9-dihydrofuro[3,4-f]quinazolin-1-ol

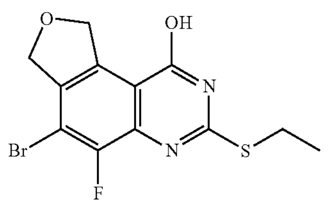 [SMILES: CCSc1nc(O)c2c3c(c(Br)c(F)c2n1)COC3]

A 2 L 4-necked RBF was equipped with an overhead stirrer, dropping funnel, $N_2$ inlet and thermocouple and was purged with $N_2$. NMP (anhydrous, 300 mL) was added. The mixture was heated to 175° C. In a second flask, ethyl (((7-bromo-6-fluoro-1,3-dihydroisobenzofuran-5-yl)amino)(ethylthio)methylene)carbamate (22.63 g, 57.83 mmol) and NMP (anhydrous, 100 mL) were combined and stirred under $N_2$ until a homogeneous solution was obtained. When the first flask had reached 175° C., the contents of the second flask were poured into the dropping funnel and were added dropwise but rapidly to the hot NMP. After 30 min, the heat was turned off and the reaction cooled to 45° C. $H_2O$ (500 mL) was slowly added and the mixture was stirred at RT for 1 h. The solids were filtered, rinsed with $H_2O$ (300 mL) and dried under vacuum at 50° C. for ~18 h to afford the title compound (15.2 g, 73%) as an off-white solid. MS (ES) m/z=363 (M+1).

Preparation 23

6-Bromo-5-chloro-3-(ethylthio)-7,9-dihydrofuro[3,4-f]quinazolin-1-ol

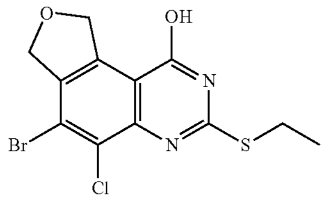

Ethyl (((7-bromo-6-chloro-1,3-dihydroisobenzofuran-5-yl)amino)(ethylthio)methylene)carbamate was used in a manner analogous to the method of Preparation 22 to afford the title compound (11.4 g, 86%) as a white solid. MS (ES) m/z=361 (M+1).

Preparation 24

6-Bromo-3-(ethylthio)-5-fluoro-2-((2-(trimethylsilyl)ethoxy)methyl)-7,9-dihydrofuro[3,4-f]quinazolin-1(2H)-one

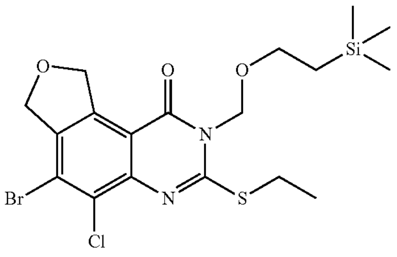 [SMILES: CCSc1nc2c(Cl)c(Br)c3c(c2c(=O)n1COCC[Si](C)(C)C)COC3]

A mixture of 6-bromo-3-(ethylthio)-5-fluoro-7,9-dihydrofuro[3,4-f]quinazolin-1-ol (30.1 g, 87.3 mmol) in DMF was heated to ~70° C. to dissolve the solids, then cooled to 40° C. To the mixture was added diisopropylethylamine (30.4 mL, 175 mmol) and 2-(chloromethoxyethyl)trimethyl silane (23.2 mL, 131 mmol). The reaction mixture was stirred for 1 h at 40° C., then cooled to room temperature and diluted with water (1 L) and EtOAc (500 mL). The layers were separated and the organic layer was washed with brine (2×500 mL), dried over magnesium sulfate, filtered, and concentrated under reduced pressure to give the crude title compound (49.2 g, 85% purity) as a yellow oil. MS (ES) m/z=475 (M+1).

Preparation 25

6-Bromo-5-chloro-3-(ethylthio)-2-((2-(trimethylsilyl)ethoxy)methyl)-7,9-dihydrofuro[3,4-f]quinazolin-1(2H)-one

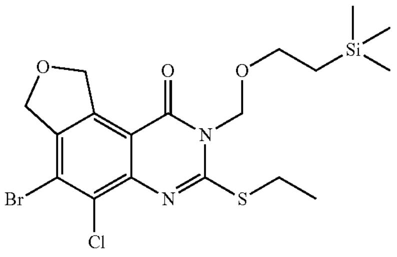 [SMILES: CCSc1nc2c(Cl)c(Br)c3c(c2c(=O)n1COCC[Si](C)(C)C)COC3]

6-Bromo-5-chloro-3-(ethylthio)-7,9-dihydrofuro[3,4-f]quinazolin-1-ol was used in a manner analogous to the method of Preparation 24 to afford the title compound (10.5 g, 96%) as a pink solid. MS (ES) m/z=491 (M+1).

Preparation 26

6-Bromo-1-chloro-3-(ethylthio)-5-fluoro-7,9-dihydrofuro[3,4-f]quinazoline

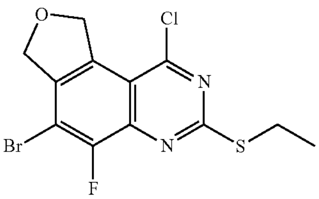

A 5 L 3-necked RBF, equipped with a dropping funnel, thermocouple and an overhead stirrer was charged with a solution of DMF (50 mL, 646 mmol, 4 eq.) in DCM (1,000 mL) and was placed in an ice/water bath and cooled to −4° C. Oxalyl chloride (50.0 mL, 576 mmol, 4 eq.) was added dropwise via addition funnel over −40 min. When the addition was complete, the reaction was stirred at −4° C. for 15 min. Solid 6-bromo-3-(ethylthio)-5-fluoro-7,9-dihydrofuro[3,4-f]quinazolin-1-ol (50.4 g, 140 mmol) was added in several portions to the reaction mixture and the resulting suspension was stirred at −4° C. for 30 min. The ice bath was removed and the reaction was allowed to warm to RT and stir for 1 h. Then $H_2O$ (1 L) was added and the mixture was stirred for 15 min. The mixture was partitioned and the organic layer was washed with brine (1 L) and dried over anhydrous $Na_2SO_4$, filtered and concentrated. The residue was purified on silica, eluting with DCM/Hex (60% to 90%) to obtain the title compound (45.1 g, 89%) as a white solid. MS (ES) m/z=363 (M+1).

Preparation 27

6-Bromo-1,5-dichloro-3-(ethylthio)-7,9-dihydrofuro[3,4-f]quinazoline

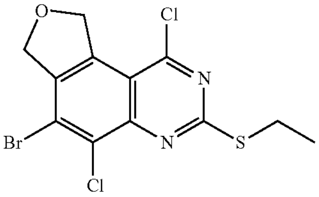 [SMILES: CCSc1nc(Cl)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 26 to afford the title compound (0.81 g, 77%) as a yellow solid. MS (ES) m/z=382 (M+1).

Preparation 28 tert-Butyl (3-cyano-4-(3-(ethylthio)-5-fluoro-1-hydroxy-7,9-dihydrofuro[3,4-f]quinazolin-6-yl)-7-fluorobenzo[b]thiophen-2-yl)carbamate

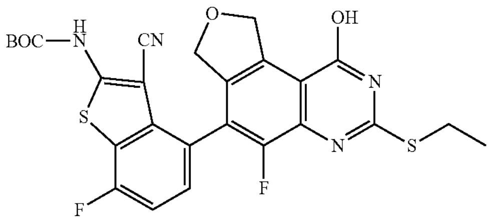 [SMILES: CCSc1nc(O)c2c3c(c(-c4ccc(F)c5sc(NC(=O)OC(C)(C)C)c(C#N)c45)c(F)c2n1)COC3]

6-Bromo-3-(ethylthio)-5-fluoro-7,9-dihydrofuro[3,4-f]quinazolin-1-ol (0.80 g, 2.32 mmol), tert-butyl (3-cyano-4-(5,5-dimethyl-1,3,2-dioxaborinan-2-yl)-7-fluorobenzo[b]thiophen-2-yl)carbamate (1.12 g, 2.78 mmol) and cesium carbonate (2.27 g, 6.95 mmol) were combined in DMF (12 mL) and the mixture was degassed by sparging with argon for 10 min. Dichloro[bis(2-(diphenylphosphino)phenyl)ether]palladium(II) (Pd-117, 0.166 g, 0.232 mmol) was added and the mixture was heated to 100° C. After 24 h, the mixture was concentrated under reduced pressure. The residue was purified on silica, eluting with 0-10% MeOH in DCM to obtain the title compound (0.96 g, 74%) as a yellow solid. MS (ES) m/z=557 (M+1).

The following compounds in Table 2 were prepared in similar manner as described in Preparation 28. Different coupling conditions, such as base, ligands, or palladium sources, may have been substituted. Various methods were used to purify the compounds, which would be apparent to one skilled in the art.

TABLE 2

| Preparation | Chemical Name | Structure | MS (ES) m/z (M + 1) |
|---|---|---|---|
| 29 | tert-Butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate | 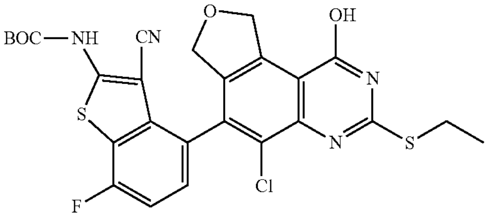 [SMILES: CCSc1nc(O)c2c3c(c(-c4ccc(F)c5sc(NC(=O)OC(C)(C)C)c(C#N)c45)c(Cl)c2n1)COC3] | 573 |

TABLE 2-continued

| Preparation | Chemical Name | Structure | MS (ES) m/z (M + 1) |
|---|---|---|---|
| 30 [1] | tert-Butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate, Atropisomer 2 | 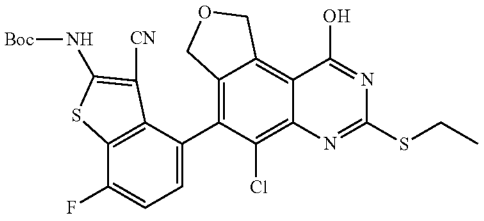 | 573 |
| 31 | tert-Butyl (4-(3-(ethylthio)-5-fluoro-1-hydroxy-7,9-dihydrofuro[3,4-f]quinazolin-6-yl)-5-fluorobenzo[b]thiophen-2-yl)carbamate | 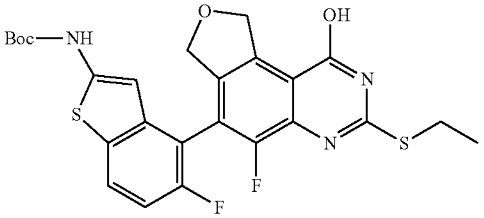 [SMILES: CCSc1nc(O)c2c3c(c(-c4c(F)ccc5sc(NC(=O)OC(C)(C)C)cc45)c(F)c2n1)COC3] | 532 |
| 32 [2] | tert-Butyl (4-(3-(ethylthio)-5-fluoro-1-oxo-2-((2-(trimethylsilyl)ethoxy)methyl)-1,2,7,9-tetrahydrofuro[3,4-f]quinazolin-6-yl)-5-fluorobenzo[b]thiophen-2-yl)carbamate, Atropisomer 1 | 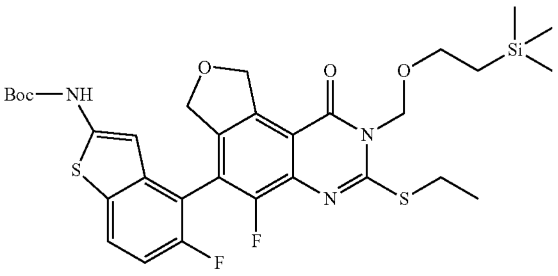 [SMILES: CCSc1nc2c(F)c(-c3c(F)ccc4sc(NC(=O)OC(C)(C)C)cc34)c3c(c2c(=O)n1COCC[Si](C)(C)C)COC3] | 662 |
| 33 | tert-Butyl (4-(5-chloro-3-(ethylthio)-1-oxo-2-((2-(trimethylsilyl)ethoxy)methyl)-1,2,7,9-tetrahydrofuro[3,4-f]quinazolin-6-yl)-5-fluorobenzo[b]thiophen-2-yl)carbamate | 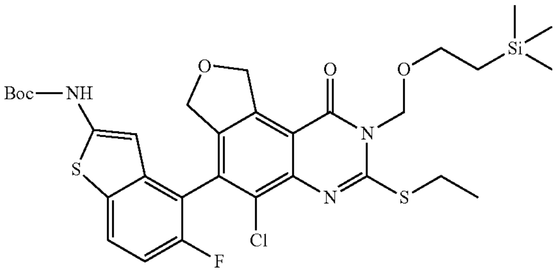 | 678 |
| 34 [3] | tert-Butyl (4-(5-chloro-3-(ethylthio)-1-oxo-2-((2-(trimethylsilyl)ethoxy)methyl)-1,2,7,9-tetrahydrofuro[3,4-f]quinazolin-6-yl)-5-fluorobenzo[b]thiophen-2-yl)carbamate, Atropisomer 1 | 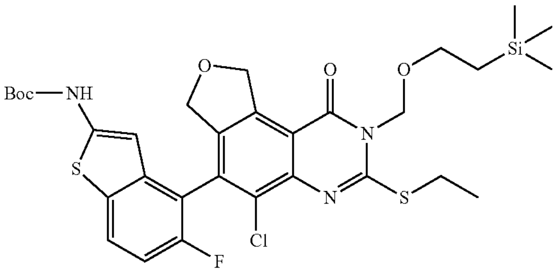 | 678 |

TABLE 2-continued

| Preparation | Chemical Name | Structure | MS (ES) m/z (M + 1) |
|---|---|---|---|
| 35 | tert-Butyl (4-(5-chloro-3-(ethylthio)-1-oxo-2-((2-(trimethylsilyl)ethoxy) methyl)-1,2,7,9-tetrahydrofuro[3,4-f]quinazolin-6-yl)-7-fluorobenzo[d]thiazol-2-yl)carbamate | 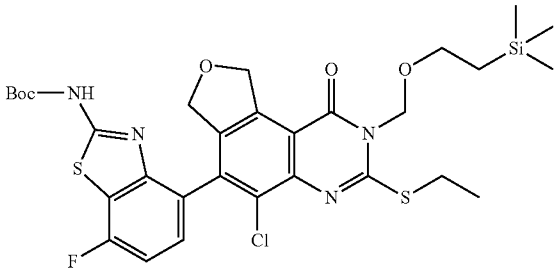 [SMILES: CCSc1nc2c(Cl)c(-c3ccc(F)c4sc(NC(=O)OC(C)(C)C)nc34)c3c(c2c(=O)n1COCC[Si](C)(C)C)COC3] | 679 |
| 5B | tert-Butyl (4-(5-chloro-9-hydroxy-1,3-dihydrofuro[3,4-f]quinolin-4-yl)-3-cyano-7-fluorobenzo[b]thiophen-2-yl)carbamate | 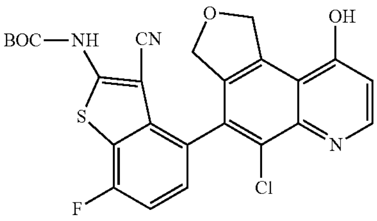 [SMILES: CC(C)(C)OC(=O)Nc1sc2c(F)ccc(-c3c4c(c5c(O)ccnc5c3Cl)COC4)c2c1C#N] | 512 |
| 6B [4] | tert-Butyl (4-(5-chloro-3-(ethylthio)-1-oxo-2-((2-(trimethylsilyl)ethoxy) methyl)-1,2,7,9-tetrahydrofuro[3,4-f]quinazolin-6-yl)-3-cyano-7-fluorobenzo[b]thiophen-2-yl)carbamate, Atropisomer 1 | 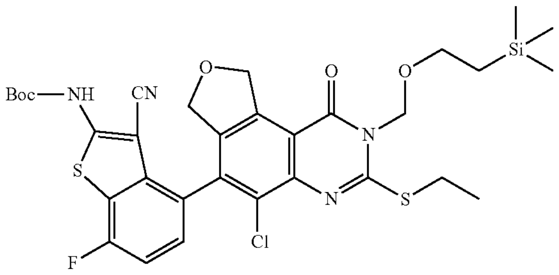 [SMILES: CCSc1nc2c(Cl)c(-c3ccc(F)c4sc(NC(=O)OC(C)(C)C)c(C#N)c34)c3c(c2c(=O)n1COCC[Si](C)(C)C)COC3] | 703 |
| 7B | tert-Butyl (4-(3-(ethylthio)-5-fluoro-1-oxo-2-((2-(trimethylsilyl)ethoxy) methyl)-1,2,7,9-tetrahydrofuro[3,4-f]quinazolin-6-yl)-7-fluorobenzo[d]thiazol-2-yl)carbamate | 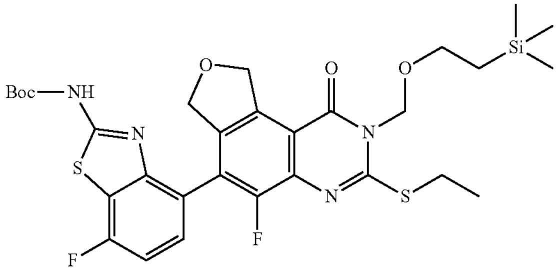 [SMILES: CCSc1nc2c(F)c(-c3ccc(F)c4sc(NC(=O)OC(C)(C)C)nc34)c3c(c2c(=O)n1COCC[Si](C)(C)C)COC3] | 663 |
| 8B [5] | tert-Butyl (4-(5-chloro-3-(ethylthio)-1-oxo-2-((2-(trimethylsilyl)ethoxy) methyl)-1,2,7,9-tetrahydrofuro[3,4-f]quinazolin-6-yl)-3-cyano-7-fluorothieno[3,2-c]pyridin-2-yl)carbamate | 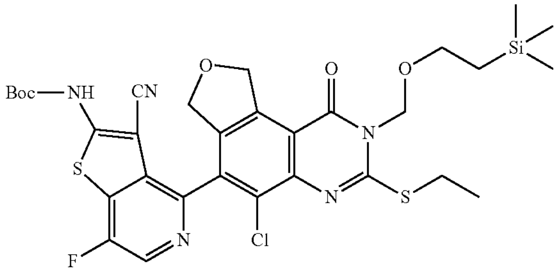 [SMILES: CCSc1nc2c(Cl)c(-c3ncc(F)c4sc(NC(=O)OC(C)(C)C)c(C#N)c34)c3c(c2c(=O)n1COCC[Si](C)(C)C)COC3] | 648 |

[1] Prep-Chiral-HPLC; Phenomenex Lux Cellulose-5, 30 x 150 mm, 18-30% (1:1 methanol:ethanol) in heptane, 42.5 mL/min

[2] Chiral SFC; Chiralpak IC, 50 x 250 mm, 25% (methanol w/ 0.2% dimethylethylamine) in $CO_2$, 300 g/min

[3] Chiral SFC; Chiralpak IC, 20 x 250 mm, 25% (isopropanol w/ 0.5% dimethylethylamine) in $CO_2$, 80 mL/min

[4] Chiral SFC; ColumnTek Enantiocel C4-5, 30 x 250 mm, 40% methanol in $CO_2$, 75 mL/min

[5] Prepared in similar manner as described in Preparation 73

Preparation 9B tert-Butyl (4-(9-bromo-5-chloro-1,3-dihydrofuro[3,4-f]quinolin-4-yl)-3-cyano-7-fluorobenzo[b]thiophen-2-yl)carbamate

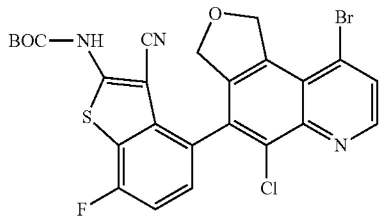 [SMILES: CC(C)(C)OC(=O)Nc1sc2c(F)ccc(-c3c4c(c5c(Br)ccnc5c3Cl)COC4)c2c1C#N]

4-(2-((tert-Butoxycarbonyl)amino)-3-cyano-7-fluorobenzo[b]thiophen-4-yl)-5-chloro-1,3-dihydrofuro[3,4-f]quinolin-9-yl trifluoromethanesulfonate: 1,1,1-Trifluoro-N-phenyl-N—((trifluoromethyl)sulfonyl)methanesulfonamide (8.4 g, 23 mmol) was added to a suspension of tert-butyl (4-(5-chloro-9-hydroxy-1,3-dihydrofuro[3,4-f]quinolin-4-yl)-3-cyano-7-fluorobenzo[b]thiophen-2-yl)carbamate (10 g, 20 mmol) and triethylamine (8.2 mL, 59 mmol) in acetonitrile (60 mL). The mixture was stirred for 2 h at room temperature, then concentrated under reduced pressure. The residue was purified on silica, eluting with 0-100% ethyl acetate in heptane, to give 4-(2-((tert-butoxycarbonyl)amino)-3-cyano-7-fluorobenzo[b]thiophen-4-yl)-5-chloro-1,3-dihydrofuro[3,4-f]quinolin-9-yl trifluoromethanesulfonate (10.1 g, 80%). MS (ES) m/z=644 (M+1).

tert-Butyl (4-(9-bromo-5-chloro-1,3-dihydrofuro[3,4-f]quinolin-4-yl)-3-cyano-7-fluorobenzo[b]thiophen-2-yl)carbamate: A mixture of 4-(2-((tert-butoxycarbonyl)amino)-3-cyano-7-fluorobenzo[b]thiophen-4-yl)-5-chloro-1,3-dihydrofuro[3,4-f]quinolin-9-yl trifluoromethanesulfonate (3.74 g, 5.81 mmol) and lithium bromide (10.1 g, 116 mmol) in acetonitrile (20 mL) was stirred for 75 min at 40° C. The mixture was concentrated under reduced pressure. The residue was diluted with DCM and saturated aqueous sodium chloride. The organic layer was concentrated under reduced pressure. The residue was purified on silica, eluting with 0-100% ethyl acetate in heptane, to give the title compound (2.82 g, 85%) as a white solid. MS (ES) m/z=574 (M+1).

Preparation 10B tert-Butyl (4-(5-chloro-1-oxo-2-((2-(trimethylsilyl)ethoxy)methyl)-1,2,7,9-tetrahydrofuro[3,4-f]quinazolin-6-yl)-3-cyano-7-fluorobenzo[b]thiophen-2-yl)carbamate

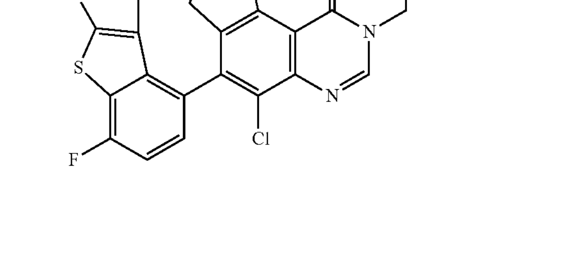

A mixture of tert-butyl (4-(5-chloro-3-(ethylthio)-1-oxo-2-((2-(trimethylsilyl)ethoxy)methyl)-1,2,7,9-tetrahydrofuro[3,4-f]quinazolin-6-yl)-3-cyano-7-fluorobenzo[b]thiophen-2-yl)carbamate, Atropisomer 1 (0.500 g, 0.711 mmol) and palladium(II)chloride (6.30 mg, 0.036 mmol) in THF (5 mL) was sparged with argon. Triethylsilane (0.165 g, 0.227 mmol) was added and the reaction vessel was sealed and stirred for 5 h at room temperature. The mixture was filtered. The filtrate was concentrated under reduced pressure to give the crude title compound (0.46 g). MS (ES) m/z=643 (M+1). Clean atropisomer, chiral purification from Preparation 6B.

Preparation 36 tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate

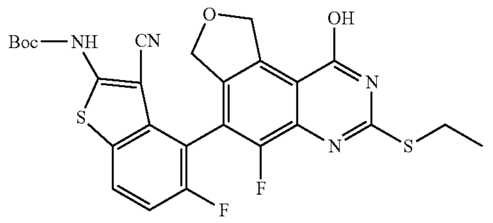

A mixture of tert-butyl (4-(3-(ethylthio)-5-fluoro-1-hydroxy-7,9-dihydrofuro[3,4-f]quinazolin-6-yl)-5-fluorobenzo[b]thiophen-2-yl)carbamate (0.750 g, 1.41 mmol) and acetonitrile (10 mL) was stirred at −40° C. Sulfurisocyanatidic chloride (0.184 mL, 2.12 mmol) was slowly added and the mixture was allowed to warm to 0° C. After consumption of the starting material (monitored by LCMS), the mixture was cooled to 0° C. DMF (4 mL) was slowly added. Upon reaction completion (monitored by LCMS), the mixture was diluted with DCM (20 mL) and saturated aq. ammonium chloride (20 mL). The layers were separated and the aqueous layer was extracted with DCM (3×30 mL). The combined organics were passed through a hydrophobic frit and concentrated under reduced pressure to obtain the crude title compound. MS (ES) m/z=557 (M+1).

The following compounds in Table 3 were prepared in similar manner as described in Preparation 36. Various methods were used to purify the compounds, which would be apparent to one skilled in the art.

TABLE 3

| Preparation | Chemical Name | Structure | MS (ES) m/z (M + 1) |
|---|---|---|---|
| 37 [1] | tert-Butyl (3-cyano-4-(3-(ethylthio)-5-fluoro-1-oxo-2-((2-(trimethylsilyl)ethoxy) methyl)-1,2,7,9-tetrahydrofuro[3,4-f]quinazolin-6-yl)-5-fluorobenzo[b]thiophen-2-yl)carbamate | 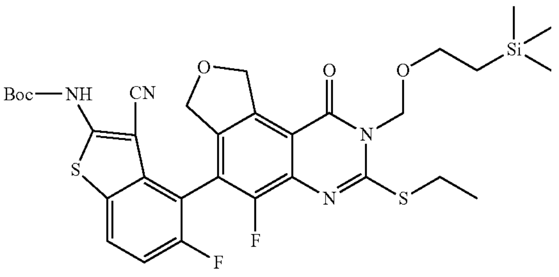 [SMILES: CCSc1nc2c(F)c(-c3c(F)ccc4sc(NC(=O)OC(C)(C)C)c(C#N)c34)c3c(c2c(=O)n1COCC[Si](C)(C)C)COC3] | 687 |
| 38 | tert-Butyl (4-(5-chloro-3-(ethylthio)-1-oxo-2-((2-(trimethylsilyl)ethoxy) methyl)-1,2,7,9-tetrahydrofuro[3,4-f]quinazolin-6-yl)-3-cyano-5-fluorobenzo[b]thiophen-2-yl)carbamate | 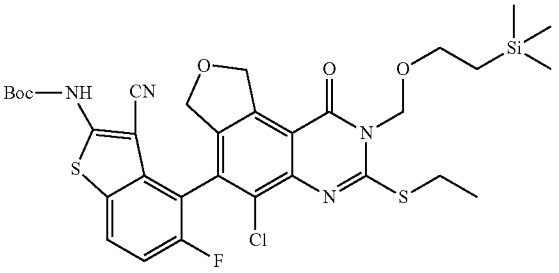 | 703 |
| 39 [2] | tert-Butyl (4-(5-chloro-3-(ethylthio)-1-oxo-2-((2-(trimethylsilyl)ethoxy) methyl)-1,2,7,9-tetrahydrofuro[3,4-f]quinazolin-6-yl)-3-fluorobenzo[b]thiophen-cyano-5-2-yl)carbamate | 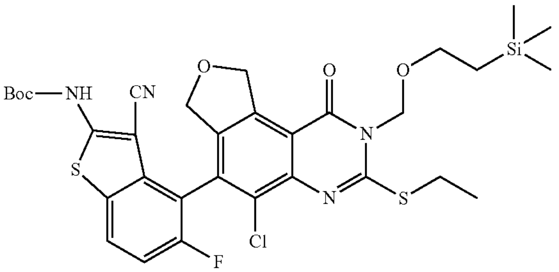 | 703 |

[1] Clean atropisomer, chiral purification from Preparation 32

[2] Clean atropisomer, chiral purification from Preparation 34

Preparation 40 tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate

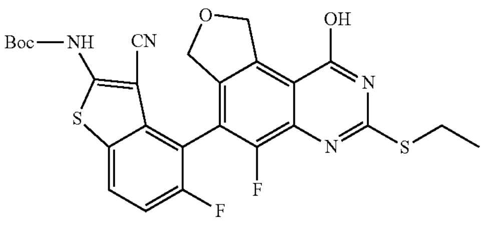 [SMILES: CCSc1nc(O)c2c3c(c(-c4c(F)ccc5sc(NC(=O)OC(C)(C)C)c(C#N)c45)c(Cl)c2n1)COC3]

To a mixture of tert-butyl (3-cyano-4-(3-(ethylthio)-5-fluoro-1-oxo-2-((2-(trimethylsilyl)ethoxy)methyl)-1,2,7,9-tetrahydrofuro[3,4-f]quinazolin-6-yl)-5-fluorobenzo[b]thiophen-2-yl)carbamate (19.2 g, 26.3 mmol) in THF (192 mL) was added activated molecular sieves (4 angstrom, 38 g), followed by tetrabutylammonium fluoride (1M in THF, 105 mL, 105 mmol). The reaction mixture was heated for 9 h at a bath temperature of 80° C., then cooled to room temperature. Additional activated molecular sieves (4 angstrom, 17 g) were added, and the reaction mixture was heated overnight at a bath temperature of 80° C., then cooled to room temperature. The mixture was filtered and the filter cake was washed with EtOAc. The combined filtrates were concentrated under reduced pressure, diluted with 2-methyltetrahydrofuran (300 mL), and washed with water (3×300 mL). The combined aqueous layers were extracted with 2-methyltetrahydrofuran (300 mL). The combined organic layers were washed with 5% aqueous citric acid (300 mL), dried over magnesium sulfate, filtered, and concentrated under reduced pressure. The crude material was purified on silica, eluting with 0-60% EtOAc in cyclohexane to obtain the title compound (9.42 g) as a yellow foam. MS (ES) nVz=557 (M+1). Clean atropisomer, chiral purification from Preparation 32.

The following compounds in Table 4 were prepared in similar manner as described in Preparation 40. Different deprotection conditions, such as cesium fluoride in DMF, may have been substituted. Various methods were used to purify the compounds, which would be apparent to one skilled in the art.

TABLE 4

| Preparation | Chemical Name | Structure | MS (ES) m/z (M + 1) |
|---|---|---|---|
| 41 | tert-Butyl (4-(5-chloro-3-(ethylthio)-1-hydroxy-7,9-dihydrofuro[3,4-f]quinazolin-6-yl)-3-cyano-5-fluorobenzo[b]thiophen-2-yl)carbamate | 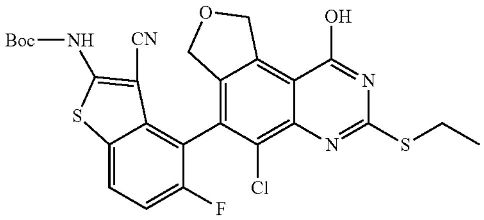 [SMILES: CCSc1nc(O)c2c3c(c(-c4c(F)ccc5sc(NC(=O)OC(C)(C)C)c(C#N)c45)c(Cl)c2n1)COC3] | 573 |
| 42 [1] | tert-Butyl (4-(5-chloro-3-(ethylthio)-1-hydroxy-7,9-dihydrofuro[3,4-f]quinazolin-6-yl)-3-cyano-5-fluorobenzo[b]thiophen-2-yl)carbamate | 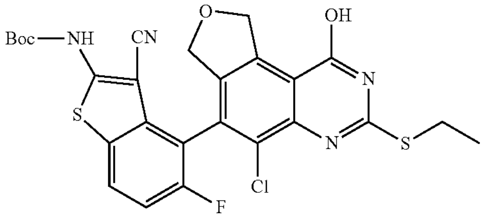 | 573 |
| 43 | tert-Butyl (4-(5-chloro-3-(ethylthio)-1-hydroxy-7,9-dihydrofuro[3,4-f]quinazolin-6-yl)-7-fluorobenzo[d]thiazol-2-yl)carbamate | 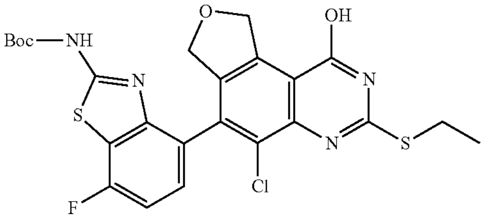 [SMILES: CCSc1nc(O)c2c3c(c(-c4ccc(F)c5sc(NC(=O)OC(C)(C)C)nc45)c(Cl)c2n1)COC3] | 549 |
| 11B [2] | tert-Butyl (4-(5-chloro-1-hydroxy-7,9-dihydrofuro[3,4-f]quinazolin-6-yl)-3-cyano-7-fluorobenzo[b]thiophen-2-yl)carbamate | 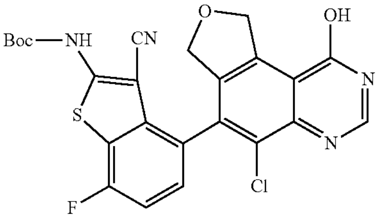 [SMILES: CC(C)(C)OC(=O)Nc1sc2c(F)ccc(-c3c4c(c5c(O)ncnc5c3Cl)COC4)c2c1C#N] | 513 |
| 12B | tert-Butyl (4-(5-chloro-3-(ethylthio)-1-hydroxy-7,9-dihydrofuro[3,4-f]quinazolin-6-yl)-3-cyano-7-fluorothieno[3,2-c]pyridin-2-yl)carbamate | 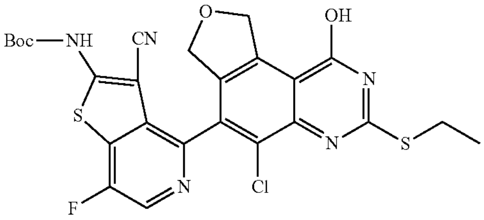 [SMILES: CCSc1nc(O)c2c3c(c(-c4ncc(F)c5sc(NC(=O)OC(C)(C)C)c(C#N)c45)c(Cl)c2n1)COC3] | 574 |
| 13B | tert-Butyl (4-(3-(ethylthio)-5-fluoro-1-hydroxy-7,9-dihydrofuro[3,4-f]quinazolin-6-yl)-7-fluorobenzo[d]thiazol-2-yl)carbamate | 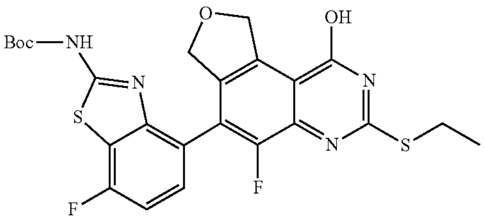 [SMILES: CCSc1nc(O)c2c3c(c(-c4ccc(F)c5sc(NC(=O)OC(C)(C)C)nc45)c(F)c2n1)COC3] | 533 |

[1] Clean atropisomer, chiral purification from Preparation 34

[2] Clean atropisomer, chiral purification from Preparation 6B

The following compounds in Table 5 were prepared in similar manner as described in Preparation 26. Various methods were used to purify the compounds, which would be apparent to one skilled in the art.

TABLE 5

| Preparation | Chemical Name | Structure | MS (ES) m/z (M + 1) |
|---|---|---|---|
| 44 [1] | tert-Butyl (3-cyano-4-(1,5-dichloro-3-(ethylthio)-7,9-dihydrofuro[3,4-f]quinazolin-6-yl)-7-fluorobenzo[b]thiophen-2-yl)carbamate | 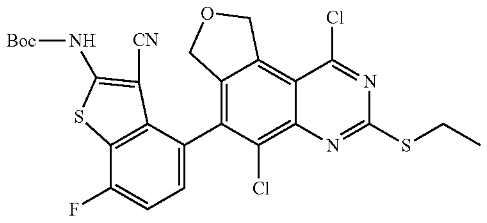 [SMILES: CCSc1nc(Cl)c2c3c(c(-c4ccc(F)c5sc(NC(=O)OC(C)(C)C)c(C#N)c45)c(Cl)c2n1)COC3] | 591 |
| 45 | tert-Butyl (4-(1-chloro-3-(ethylthio)-5-fluoro-7,9-dihydrofuro[3,4-f]quinazolin-6-yl)-3-cyano-5-fluorobenzo[b]thiophen-2-yl)carbamate | 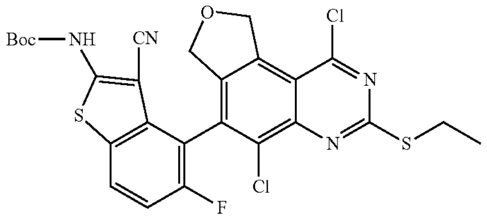 [SMILES: CCSc1nc(Cl)c2c3c(c(-c4c(F)ccc5sc(NC(=O)OC(C)(C)C)c(C#N)c45)c(Cl)c2n1)COC3] | 575 |
| 46 | tert-Butyl (3-cyano-4-(1,5-dichloro-3-(ethylthio)-7,9-dihydrofuro[3,4-f]quinazolin-6-yl)-5-fluorobenzo[b]thiophen-2-yl)carbamate | 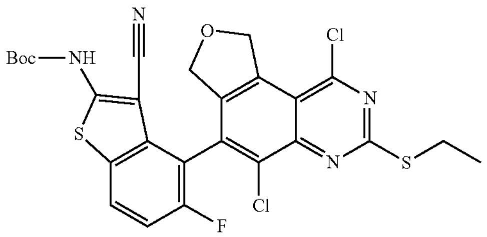 [SMILES: CCSc1nc(Cl)c2c3c(c(-c4c(F)ccc5sc(NC(=O)OC(C)(C)C)c(C#N)c45)c(Cl)c2n1)COC3] | 591 |
| 47 [2] | tert-Butyl (3-cyano-4-(1,5-dichloro-3-(ethylthio)-7,9-dihydrofuro[3,4-f]quinazolin-6-yl)-5-fluorobenzo[b]thiophen-2-yl)carbamate | 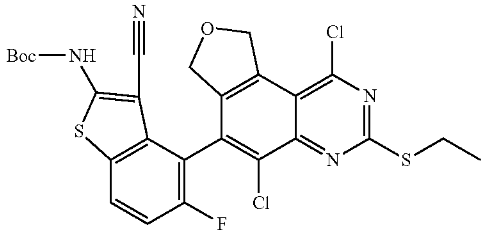 [SMILES: CCSc1nc(Cl)c2c3c(c(-c4c(F)ccc5sc(NC(=O)OC(C)(C)C)c(C#N)c45)c(Cl)c2n1)COC3] | 591 |
| 48 | tert-Butyl (4-(1,5-dichloro-3-(ethylthio)-7,9-dihydrofuro[3,4-f]quinazolin-6-yl)-7-fluorobenzo[d]thiazol-2-yl)carbamate | 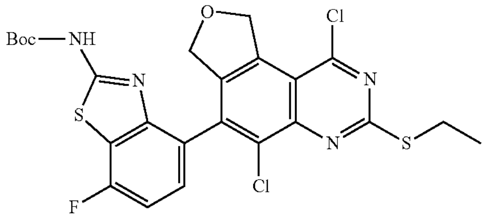 [SMILES: CCSc1nc(Cl)c2c3c(c(-c4ccc(F)c5sc(NC(=O)OC(C)(C)C)nc45)c(Cl)c2n1)COC3] | 567 |
| 14B | tert-Butyl (3-cyano-4-(1,5-dichloro-3-(ethylthio)-7,9-dihydrofuro[3,4-f]quinazolin-6-yl)-7-fluorothieno [3,2-c]pyridin-2-yl)carbamate | 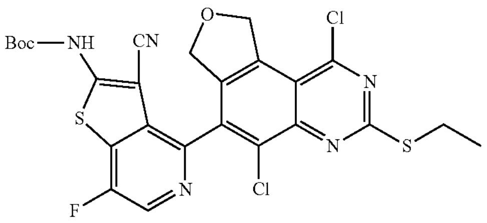 [SMILES: CCSc1nc(Cl)c2c3c(c(-c4ncc(F)c5sc(NC(=O)OC(C)(C)C)c(C#N)c45)c(Cl)c2n1)COC3] | 592 |

[1] Clean atropisomer, chiral purification from Preparation 30

[2] Clean atropisomer, chiral purification from Preparation 34

Preparation 49

6-Amino-4-methyl-4-azaspiro[2.5]octan-5-one

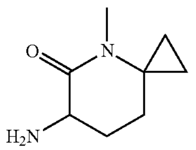

4-Methyl-4-azaspiro[2.5]octan-5-one. To a solution of 4-azaspiro[2.5]octan-5-one (5.00 g, 40.0 mmol) in THF (30 mL) was added sodium hydride (60 wt % in mineral oil; 1.92 g, 47.9 mmol). The mixture was stirred at room temperature for 30 min, then cooled to 0° C. A solution of iodomethane (3.73 mL, 59.9 mmol) in THF (5 mL) was added dropwise and the mixture was stirred at 0° C. for 5 min, then warmed to room temperature and stirred for 16 h. The mixture was diluted with water (5 mL) and extracted with EtOAc and DCM. The combined organics were dried over anhydrous $Na_2SO_4$ and concentrated under reduced pressure to give crude 4-methyl-4-azaspiro [2.5]octan-5-one (3.03 g, 55%) as a light yellow oil. MS (ES) m/z=140 (M+1).

6-Chloro-4-methyl-4-azaspiro[2.5]octan-5-one. A solution of 4-methyl-4-azaspiro[2.5]octan-5-one (3.03 g, 21.8 mmol) in THF (50 mL) was cooled to −78° C. Lithium diisopropylamide (2.0 M in THF/heptane/ethylbenzene; 14.2 mL, 28.4 mmol) was added. The mixture was stirred at −78° C. for 20 min, then a solution of tosyl chloride (12.45 g, 65.3 mmol) in THF (5 mL) was slowly added. The mixture was stirred at −78° C. for 90 min. The mixture was diluted with water and extracted with DCM. The organics were dried over anhydrous $Na_2SO_4$, followed by reversed phase purification (C18 column), eluting with 0-100% acetonitrile in (0.1% formic acid in water), to obtain 6-chloro-4-methyl-4-azaspiro[2.5]octan-5-one (2.33 g, 62%) as a yellow oil. MS (ES) m/z=174 (M+1).

6-Amino-4-methyl-4-azaspiro[2.5]octan-5-one. A solution of 6-chloro-4-azaspiro[2.5]octan-5-one (7.02 g, 40.4 mmol) in acetonitrile (5 mL) and ammonium hydroxide (10 mL) was heated under microwave irradiation at 80° C. for 22 h. The mixture was concentrated under reduced pressure to give the title compound (5.8 g, crude) as a brown solid. MS (ES) m/z=155 (M+1).

The following compounds in Table 6 were prepared in similar manner as described in Preparation 49. Various methods were used to purify the compounds, which would be apparent to one skilled in the art.

TABLE 6

| Preparation | Chemical Name | Structure | MS (ES) m/z (M + 1) |
|---|---|---|---|
| 50 | 7-Amino-5-methyl-5-azaspiro[3.5]nonan-6-one | 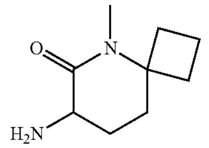 | 169 |
| 51 | 7-Amino-5-methyl-5-azaspiro[2.5]octan-6-one | 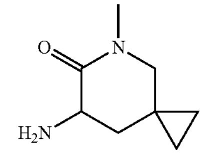 | 155 |
| 2A | 6-Amino-4-methyl-4-azaspiro[2.4]heptan-5-one | 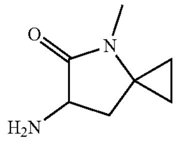 | 141 |
| 15B | (6R)-3-Amino-6-(difluoromethyl)-1-methylpiperidin-2-one | 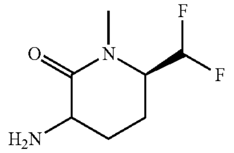 | 179 |

Preparation 3A

7-Amino-5-azaspiro[3.5]nonan-6-one

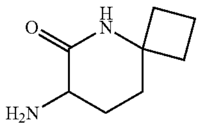

tert-Butyl 6-oxo-5-azaspiro[3.5]nonane-5-carboxylate. To a solution of 5-azaspiro[3.5]nonanone (0.500 g, 3.59 mmol) in THF (10 mL) was added di-tert-butyl dicarbonate (1.02 g, 4.67 mmol) and 4-dimethylaminopyridine (0.088 g, 0.718 mmol). The mixture was stirred at 65° C. for 12 h, then concentrated under reduced pressure. The residue was purified by reversed phase purification (C18 column), eluting with 0-100% acetonitrile in (0.1% formic acid in water), to obtain tert-butyl 6-oxo-5-azaspiro[3.5]nonane-5-carboxylate (0.610 g, 71%) as a brown oil. MS (ES) m/z=184 (M+1-tBu).

tert-Butyl 7-chloro-6-oxo-5-azaspiro[3.5]nonane-5-carboxylate. tert-Butyl 6-oxo-5-azaspiro[3.5]nonane-5-carboxylate was used in a manner analogous to the method of Preparation 49 (Step 6-chloro-4-methyl-4-azaspiro[2.5]octan-5-one) to afford tert-butyl 7-chloro-6-oxo-5-azaspiro[3.5]nonane-5-carboxylate (0.28 g, 78%) as a yellow oil. MS (ES) m/z=218 (M+1-tBu).

7-Chloro-5-azaspiro[3.5]nonan-6-one. A mixture of tert-butyl 7-chloro-6-oxo-5-azaspiro[3.5]nonane-5-carboxylate in DCM (3 mL) was treated with HCl solution (3 mL) and stirred at room temperature for 3 h. The mixture was concentrated under reduced pressure to give crude 7-chloro-5-azaspiro[3.5]nonan-6-one as a white solid. MS (ES) m/z=174 (M+1).

7-Amino-5-azaspiro[3.5]nonan-6-one. 7-Chloro-5-azaspiro[3.5]nonan-6-one was used in a manner analogous to the method of Preparation 49 (Step 6-amino-4-methyl-4-azaspiro[2.5]octan-5-one) to afford the title compound (0.24 g) as a yellow solid. MS (ES) m/z=155 (M+1).

Preparation 52

4-Amino-2-methyl-2-azabicyclo[3.1.1]heptan-3-one dihydrochloride

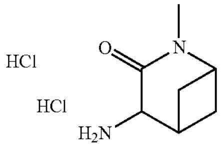

2-Methyl-2-azabicyclo[3.1.1]heptan-3-one. Sodium hydride (60 wt % in mineral oil 0.346 g, 8.64 mmol) was added to a solution of 2-azabicyclo[3.1.1]heptan-3-one (0.800 g, 7.20 mmol) in THF (15 mL). The mixture was stirred at 25° C. for 30 min, then cooled to 0° C. A solution of iodomethane (0.67 mL, 10.8 mmol) in THF (0.3 mL) was added dropwise. The mixture was stirred at 0° C. for 5 min, then at 25° C. for 16 h. Diluted with water (5 mL) and extracted with EtOAc, then DCM. The combined organics were dried over anhydrous $Na_2SO_4$ and concentrated under reduced pressure to give crude 2-methyl-2-azabicyclo[3.1.1]heptan-3-one as a light yellow oil. MS (ES) m/z=126 (M+1).

Methyl 2-methyl-3-oxo-2-azabicyclo[3.1.1]heptane-4-carboxylate. To a −78° C. solution of 2-methyl-2-azabicyclo[3.1.1]heptan-3-one (1.09 g, 8.71 mmol) in THF (60 mL) was added lithium diisopropylamide (2.0 M in THF/heptane/ethylbenzene; 8.71 mL, 17.4 mmol). The mixture was stirred at −78° C. for 30 min. Methyl chloroformate (0.81 mL, 10.5 mmol) was added and the mixture was stirred at −78° C. for 2 h. The mixture was quenched with water, warmed to RT, and extracted with EtOAc, then DCM. The combined organics were concentrated under reduced pressure to give crude methyl 2-methyl-3-oxo-2-azabicyclo[3.1.1]heptane-4-carboxylate (1.37 g, 86%) as a light yellow oil. MS (ES) m/z=184 (M+1).

2-Methyl-3-oxo-2-azabicyclo[3.1.1]heptane-4-carboxamide. To a mixture of methyl 2-methyl-3-oxo-2-azabicyclo[3.1.1]heptane-4-carboxylate (1.37 g, 7.47 mmol) in ammoniated methanol (7M; 53.4 mL, 374 mmol) was added sodium methoxide (0.404 g, 7.47 mmol). The mixture was stirred at 45° C. for 5 h, then cooled. The mixture was concentrated under reduced pressure. The residue was diluted with water, followed by reversed phase purification (C18 column), eluting with 0-100% acetonitrile in (0.1% formic acid in water), to obtain 2-methyl-3-oxo-2-azabicyclo[3.1.1]heptane-4-carboxamide (0.904 g, 72%) as a yellow solid. MS (ES) m/z=169 (M+1).

Methyl (2-methyl-3-oxo-2-azabicyclo[3.1.1]heptan-4-yl) carbamate. To a mixture of 2-methyl-3-oxo-2-azabicyclo[3.1.1]heptane-4-carboxamide (1.04 g, 6.20 mmol) and THF (15 mL) was added (diacetoxyiodo)benzene (2.20 g, 6.82 mmol). The mixture was stirred at 25° C. for 20 min, then concentrated under reduced pressure. MeOH (15 mL) was added and the mixture was stirred at 70° C. for 1 h. The mixture was concentrated under reduced pressure to give crude methyl (2-methyl-3-oxo-2-azabicyclo[3.1.1]heptan-4-yl)carbamate as a light yellow oil. MS (ES) m/z=199 (M+1).

tert-Butyl (methoxycarbonyl)(2-methyl-3-oxo-2-azabicyclo[3.1.1]heptan-4-yl)carbamate. To a solution of methyl (2-methyl-3-oxo-2-azabicyclo[3.1.1]heptan-4-yl)carbamate (1.23 g, 6.21 mmol) in THF (12 mL) was added di-tert-butyl dicarbonate (2.71 g, 12.4 mmol) and dimethylaminopyridine (0.227 g, 1.86 mmol). The mixture was stirred at 65° C. for 4 h, then concentrated under reduced pressure. The residue was purified on silica, eluting with 60-100% EtOAc in heptane to obtain tert-butyl (methoxycarbonyl)(2-methyl-3-oxo-2-azabicyclo[3.1.1]heptan-4-yl)carbamate (0.571 g, 31%) as a brown oil. MS (ES) m/z=199 (M+1, −Boc).

tert-Butyl (2-methyl-3-oxo-2-azabicyclo[3.1.1]heptan-4-yl)carbamate. To a 0° C. solution of tert-butyl (methoxycarbonyl)(2-methyl-3-oxo-2-azabicyclo[3.1.1]heptan-4-yl)carbamate (0.571 g, 1.91 mmol) in MeOH (5 mL) was added sodium methoxide (0.031 g, 0.57 mmol). The mixture was stirred at 0° C. for 20 min, then 25° C. for 12 h. The mixture was quenched with ice and diluted with brine. The mixture was extracted with EtOAc, then DCM. The combined organics were dried over anhydrous $Na_2SO_4$ and concentrated under reduced pressure to give crude tert-butyl (2-methyl-3-oxo-2-azabicyclo[3.1.1]heptan-4-yl)carbamate. MS (ES) m/z=185 (M+1, -tert-butyl).

4-Amino-2-methyl-2-azabicyclo[3.1.1]heptan-3-one dihydrochloride. HCl (4M in 1,4-dioxane; 3 mL) was added to a solution of tert-butyl (2-methyl-3-oxo-2-azabicyclo[3.1.1]heptan-4-yl)carbamate (0.460 g, 1.91 mmol) in DCM (3 mL). The mixture was stirred at RT for 6 h, then concentrated under reduced pressure to give the title compound (0.400 g, 98%). MS (ES) m/z=141 (M+1, free base).

Preparation 4A

4-Amino-2-methyl-2-azabicyclo[3.1.1]heptan-3-one hydrochloride

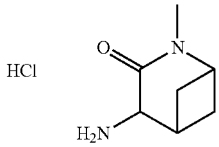

The title compound was made in a manner analogous to the method of Preparation 52. MS (ES) m/z=141 (M+1, free base).

Preparation 53

(8aR)-6-Aminohexahydroindolizin-5(1H)-one dihydrochloride

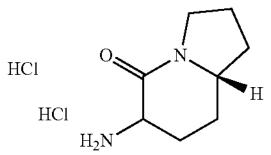

tert-Butyl (R)-2-(2-bromoethyl)pyrrolidine-1-carboxylate. To a mixture of tert-butyl (R)-2-(2-hydroxyethyl)pyrrolidine-1-carboxylate (10 g, 46 mmol) in THF (200 mL) was added carbon tetrabromide (23 g, 70 mmol). The mixture was stirred at 0° C. for 10 min, then triphenylphosphine (18 g, 70 mmol) was added. The mixture was stirred at RT for 10 min, then quenched with saturated aqueous sodium bicarbonate (100 mL). The organic layer was dried over anhydrous $Na_2SO_4$ and concentrated under reduced pressure. The residue was purified on silica, eluting with 5-75% EtOAc in heptane to obtain tert-butyl (R)-2-(2-bromoethyl)pyrrolidine-1-carboxylate (7.4 g, 57%) as a colorless oil.

Dimethyl (S)-2-(2-(1-(tert-butoxycarbonyl)pyrrolidin-2-yl)ethyl)malonate. To a mixture of dimethyl malonate (7.0 g, 53 mmol) in THF (100 mL) was added sodium hydride (60 wt % in mineral oil; 2.1 g, 53 mmol). The mixture was stirred at RT for 15 min. A solution of tert-butyl (R)-2-(2-bromoethyl)pyrrolidine-1-carboxylate (7.4 g, 27 mmol) in THF (100 mL) was added dropwise. The mixture was stirred at 75° C. for 20 h, then cooled and quenched with acetic acid (1.5 mL, 27 mmol). The mixture was diluted with chloroform (150 mL) and water (100 mL). The organic layer was passed through a hydrophobic frit and concentrated under reduced pressure. The residue was purified on silica, eluting with 5-100% EtOAc in heptane to obtain dimethyl (S)-2-(2-(1-(tert-butoxycarbonyl)pyrrolidin-2-yl)ethyl)malonate (7.0 g, 80%).

Dimethyl (S)-2-(2-(pyrrolidin-2-yl)ethyl)malonate hydrochloride. Acetyl chloride (30 mL, 430 mmol) was added dropwise to MeOH (20 mL) at 0° C. The mixture was stirred at 0° C. for 5 min, then a solution of dimethyl (S)-2-(2-(1-(tert-butoxycarbonyl)pyrrolidin-2-yl)ethyl)malonate (7.0 g, 21 mmol) in MeOH (5 mL) was added. The mixture was stirred at RT for 24 h. The mixture was concentrated under reduced pressure to give crude dimethyl (S)-2-(2-(pyrrolidin-2-yl)ethyl)malonate hydrochloride.

Methyl (8aS)-5-oxooctahydroindolizine-6-carboxylate. A mixture of dimethyl (S)-2-(2-(pyrrolidin-2-yl)ethyl)malonate hydrochloride (4.9 g, 18 mmol) and triethylamine (7.7 mL, 55 mmol) in DCM (100 mL) was stirred at RT for 24 h. The mixture was diluted with DCM (50 mL) and saturated aqueous sodium bicarbonate (75 mL). The organic layer was passed through a hydrophobic frit and concentrated under reduced pressure to give methyl (8aS)-5-oxooctahydroindolizine-6-carboxylate (1.8:1 mix of diastereomers; 2.6 g, 71%). MS (ES) m/z=198 (M+1).

(8aS)-5-Oxooctahydroindolizine-6-carboxamide. To a mixture of methyl (8aS)-5-oxooctahydroindolizine-6-carboxylate (2.7 g, 14 mmol) in ammoniated methanol (7M; 60 mL, 420 mmol) was added sodium methoxide (0.74 g, 14 mmol). The mixture was stirred at 45° C. for 5 h, then cooled. The mixture was concentrated under reduced pressure. The residue was purified on silica, eluting with 1-20% MeOH in DCM to obtain (8aS)-5-oxooctahydroindolizine-6-carboxamide (1.2 g, 48%) as a colorless oil.

tert-Butyl ((8aR)-5-oxooctahydroindolizin-6-yl)carbamate. To a mixture of (8aS)-5-oxooctahydroindolizine-6-carboxamide (5.7 g, 31 mmol), THF (75 mL) and tert-butanol (100 mL) was added (diacetoxyiodo)benzene (11 g, 34 mmol). The mixture was stirred at RT for 20 min, then 70° C. overnight. The mixture was concentrated under reduced pressure. The residue was purified on silica, eluting with 0-10% MeOH in DCM to obtain tert-butyl ((8aR)-5-oxooctahydroindolizin-6-yl)carbamate (7.0 g, 88%) as a colorless oil. MS (ES) m/z=255 (M+1).

(8aR)-6-Aminohexahydroindolizin-5(1H)-one dihydrochloride. HCl (4M in 1,4-dioxane; 3 mL) was added to a solution of tert-butyl ((8aR)-5-oxooctahydroindolizin-6-yl) carbamate (0.270 g, 1.06 mmol) in DCM (3 mL). The mixture was stirred at RT for 6 h, then concentrated under reduced pressure to give the title compound (0.241 g, 100%). MS (ES) n/Vz=155 (M+1, free base).

Preparation 5A (8aR)-6-Aminohexahydroindolizin-5(1H)-one hydrochloride

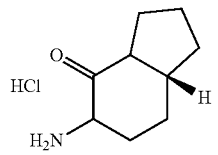

The title compound was made in a manner analogous to the method of Preparation 53 (the (6R,8aR) diastereomer is predominant). MS (ES) m/z=155 (M+1, free base).

Preparation 6A (9aS)-7-Aminohexahydropyrido[2,1-c][1,4]oxazin-6(1H)-one hydrochloride

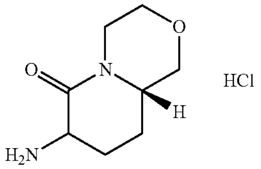

tert-Butyl (S)-3-(2-hydroxyethyl)morpholine-4-carboxylate was used in a manner analogous to the method of Preparation 53 to afford the title compound (the (7R,9aS) diastereomer is predominant; 0.44 g). MS (ES) m/z=171 (M+1, free base).

Preparation 54

6-Aminotetrahydro-1H-pyrazolo[1,2-a]pyridazin-5(6H)-one trihydrochloride

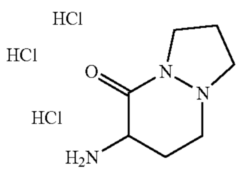 [SMILES: Cl ; Cl ; Cl ; NC1CCN2CCCN2C1=O]

tert-Butyl (4-hydroxy-1-oxo-1-(pyrazolidin-1-yl)butan-2-yl)carbamate. A solution of tert-butyl (R)-(2-oxotetrahydrofuran-3-yl)carbamate (5.00 g, 24.8 mmol) and pyrazolidine dihydrochloride (3.60 g, 24.8 mmol) in chloroform (34 mL) was treated with triethylamine (13.9 mL, 99.4 mmol). The mixture was stirred at 70° C. for 16 h, cooled to RT, and concentrated under reduced pressure. The residue was purified on silica, eluting with 0-10% MeOH in DCM to obtain tert-butyl (4-hydroxy-1-oxo-1-(pyrazolidin-1-yl)butan-2-yl) carbamate (enriched toward (R) enantiomer; 3.51 g, 52%) as a colorless oil. MS (ES) m/z=274 (M+1).

tert-Butyl (5-oxohexahydro-1H-pyrazolo[1,2-a]pyridazin-6-yl)carbamate. A mixture of tert-butyl (4-hydroxy-1-oxo-1-(pyrazolidin-1-yl)butan-2-yl)carbamate (enriched toward (R) enantiomer; 2.51 g, 9.18 mmol) and 2-(tributylphosphoranylidene)acetonitrile (2.44 g, 10.1 mmol) in toluene (23 mL) was stirred at 100° C. for 15 h, cooled to RT, and concentrated under reduced pressure. The residue was purified on silica, eluting with 0-10% MeOH in DCM to obtain tert-butyl (5-oxohexahydro-1H-pyrazolo[1,2-a]pyridazin-6-yl)carbamate (enriched toward (R) enantiomer; 1.96 g, 84%) as a light yellow solid. MS (ES) m/z=256 (M+1).

6-Aminotetrahydro-1H-pyrazolo[1,2-a]pyridazin-5(6H)-one trihydrochloride. HCl (4M in 1,4-dioxane; 18.9 mL) was added to a solution of tert-butyl (5-oxohexahydro-1H-pyrazolo[1,2-a]pyridazin-6-yl)carbamate (enriched toward (R) enantiomer; 1.93 g, 7.56 mmol) in DCM (19 mL). The mixture was stirred at RT for 31 h, then concentrated under reduced pressure. The solids were dried under vacuum to give the title compound (enriched toward (R) enantiomer; 2.00 g, 100%). MS (ES) m/Vz=156 (M+1, free base).

Preparation 7A

6-Aminotetrahydro-1H-pyrazolo[1,2-a]pyridazin-5(6H)-one dihydrochloride

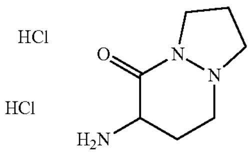 [SMILES: Cl ; Cl ; NC1CCN2CCCN2C1=O]

The title compound was made in a manner analogous to the method of Preparation 54 (the (R) enantiomer is predominant). MS (ES) m/z=156 (M+1, free base).

Preparation 55

2-Aminohexahydropyridazino[1,2-a]pyridazin-1(2H)-one trihydrochloride

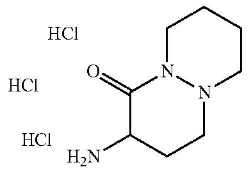 [SMILES: Cl ; Cl ; Cl ; NC1CCN2CCCCN2C1=O]

Hexahydropyridazine dihydrochloride was used in a manner analogous to the method of Preparation 54 to afford the title compound (enriched toward (R) enantiomer; 4.08 g). MS (ES) m/z=170 (M+1, free base).

Preparation 8A

2-Aminohexahydropyridazino[1,2-a]pyridazin-1(2H)-one dihydrochloride

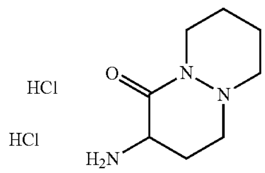 [SMILES: Cl ; Cl ; NC1CCN2CCCCN2C1=O]

The title compound was made in a manner analogous to the method of Preparation 54 (the (R) enantiomer is predominant). MS (ES) m/z=170 (M+1, free base).

Preparation 16B (6R,8aR)-6-Aminohexahydroindolizin-5(1H)-one hydrochloride

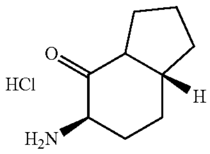 [SMILES: Cl ; N[C@@H]1CC[C@H]2CCCC2C1=O]

tert-Butyl ((6R,8aR)-5-oxooctahydroindolizin-6-yl)carbamate: tert-Butyl ((8aR)-5-oxooctahydroindolizin-6-yl) carbamate (6.85 kg, 26.9 mol) was combined with dichloromethane:hexanes (1:50; 35 L). The mixture was filtered to give tert-butyl ((6R,8aR)-5-oxooctahydroindolizin-6-yl)carbamate (998 g, 14%) as an off-white solid. MS (ES) m/z=255 (M+1).

(6R,8aR)-6-Aminohexahydroindolizin-5(1H)-one hydrochloride: tert-Butyl ((6R,8aR)-5-oxooctahydroindolizin-6-yl)carbamate (27 g, 0.11 mol) was stirred in HCl (4 M in ethyl acetate; 270 mL, 1.1 mol) overnight. The mixture was concentrated under reduced pressure and the solids were dried to give the title compound (20 g, 99%) as a white solid. $^1$H NMR (400 MHz, MeOD) δ 3.91 (dd, J=12.1, 6.3 Hz, 1H), 3.69-3.43 (m, 3H), 2.39 (dddd, J=12.8, 6.5, 4.1, 2.7 Hz, 1H), 2.29 (dq, J=13.6, 3.6 Hz, 1H), 2.19-2.12 (m, 1H), 2.11-1.98 (m, 1H), 1.98-1.83 (m, 2H), 1.71-1.46 (m, 2H).

Preparation 17B (6S)-3-Amino-1-azabicyclo[4.2.0]octan-2-one 2,2,2-trifluoroacetate

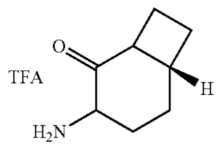

tert-Butyl (2S)-2-(3-(bis(tert-butoxycarbonyl)amino)-4-methoxy-4-oxobutyl)azetidine-1-carboxylate: A solution of dipotassium phosphate (28.9 g, 166 mmol), (R)-2-(1-(tert-butoxycarbonyl)azetidin-2-yl)acetic acid (23.1 g, 108 mmol) 1.3 eq), methyl 2-[bis(tert-butoxycarbonyl)amino] prop-2-enoate (25 g, 83.0 mmol), and Ir[dF(CF3)ppy]$_2$ (dtbpy)(PF$_6$) (2.33 g, 2.07 mmol) in DMF (1.25 L) was circulated through a photoreactor (light source 450 nm, 2400W) for 12 h. The mixture was diluted with ice water (1 L) and extracted with ethyl acetate (3×500 mL). The combined organic phases were washed with saturated aqueous sodium chloride (3×300 mL). The organic phase was dried over anhydrous sodium sulfate and the solvent was concentrated under reduced pressure. The residue was purified on silica, eluting with 0-20% ethyl acetate in hexanes, to give tert-butyl (2S)-2-(3-(bis(tert-butoxycarbonyl)amino)-4-methoxy-4-oxobutyl)azetidine-1-carboxylate (19.8 g, 45%) as a yellow gummy material.

Methyl 2-amino-4-((S)-azetidin-2-yl)butanoate bis-2,2,2-trifluoroacetate: To a solution of tert-butyl (2S)-2-(3-(bis (tert-butoxycarbonyl)amino)-4-methoxy-4-oxobutyl)azetidine-1-carboxylate (15.0 g, 31.7 mmol) in DCM (150 mL) was added trifluoroacetic acid (35.4 mL, 476 mmol) at 0° C. The mixture was stirred at 25° C. for 4 h, then concentrated under reduced pressure. The residue was diluted with DCM (80 mL) and concentrated under reduced pressure to give methyl 2-amino-4-((S)-azetidin-2-yl)butanoate bis-2,2,2-trifluoroacetate (12.71 g, 100%) as a yellow gummy material.

(6S)-3-Amino-1-azabicyclo[4.2.0]octan-2-one: To a solution of methyl 2-amino-4-((S)-azetidin-2-yl)butanoate bis-2,2,2-trifluoroacetate (12.71 g, 31.7 mmol) in water (120 mL) and methanol (120 mL) at 0° C. was added potassium carbonate (18.6 g, 135 mmol). The mixture was stirred at 0° C. for 15 min and 25° C. for 12 h. Potassium carbonate (4.39 g, 31.7 mmol) was added at 0° C. and the mixture was stirred at 25° C. for 24 h. The mixture was concentrated under reduced pressure to give crude (6S)-3-amino-1-azabicyclo [4.2.0]octan-2-one as a yellow oil.

tert-Butyl ((6S)-2-oxo-1-azabicyclo[4.2.0]octan-3-yl)carbamate, Isomers 1 and 2: To a solution of the crude (6S)-3-amino-1-azabicyclo[4.2.0]octan-2-one in THF (20 mL) was added di-tert-butyl dicarbonate (12.3 g, 56.5 mmol) at 0° C. over 5 min. The mixture was stirred at 0° C. for 5 min and 25° C. for 16 h. The mixture was concentrated under reduced pressure. The residue was purified on silica, eluting with 0-60% ethyl acetate in DCM, followed by chiral HPLC separation, to give tert-butyl ((6S)-2-oxo-1-azabicyclo [4.2.0]octan-3-yl)carbamate, Isomer 1 (5.0 g) and Isomer 2 (5.3 g). MS (ES) m/z=241 (M+1), for both. Isomer 1 elutes before Isomer 2 on Chiral SFC (ChiralPak AD-3, 4.6×100 mm, 5-40% (ethanol w/0.2% methylamine) in $CO_2$, 2.8 mL/min). Isomer refers to a clean isomer at the 3-position of the azabicyclooctanone.

(6S)-3-Amino-1-azabicyclo[4.2.0]octan-2-one 2,2,2-trifluoroacetate: tert-Butyl ((6S)-2-oxo-1-azabicyclo[4.2.0]octan-3-yl)carbamate, Isomer 2 (0.500 g, 2.08 mmol) and trifluoroacetic acid (1.60 mL, 20.8 mmol) were stirred in DCM (10 mL) for 24 h. The mixture was concentrated under reduced pressure and the material dried to give the title compound (single diastereomer; 0.53 g, 100%) as a colorless oil. $^1$H NMR (400 MHz, $CDCl_3$) δ 4.81-4.64 (m, 1H), 4.25 (q, J=8.9 Hz, 1H), 4.20-4.09 (m, 1H), 4.00 (dd, J=11.5, 6.5 Hz, 1H), 2.50-2.38 (m, 3H), 2.22-2.13 (m, 1H), 2.07-1.92 (m, 1H), 1.88-1.74 (m, 1H).

Preparation 18B (8aS)-6-Amino-2,2-difluorohexahydroindolizin-5(1H)-one hydrochloride

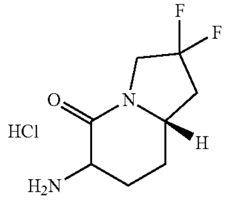 [SMILES: Cl ; NC1CC[C@H]2CC(F)(F)CN2C1=O]

(S)-2-(1-(tert-Butoxycarbonyl)-4,4-difluoropyrrolidin-2-yl)acetic acid was used in a manner analogous to the method of Preparation 17B to afford tert-butyl ((8aS)-2,2-difluoro-5-oxooctahydroindolizin-6-yl)carbamate, Isomer 1 (5.5 g) and Isomer 2 (5.5 g). Isomer 1 elutes before Isomer 2 on Chiral SFC (ChiralPak AD-3, 4.6×100 mm, 5-40% (isopropanol w/0.2% methylamine) in $CO_2$, 2.8 mL/min). Isomer refers to a clean isomer at the 6-position of the hexahydroindolizinone. Isomer 2 was used in a manner analogous to the method of Preparation 17B to give the title compound (single diastereomer; 1.5 g) as a white solid. $^1$H NMR (400 MHz, MeOD) δ 4.11-3.92 (m, 3H), 3.73 (ddd, J=19.4, 14.0, 5.7 Hz, 1H), 2.68-2.52 (m, 1H), 2.49-2.16 (m, 2H), 2.04-1.89 (m, 1H), 1.80 (tdd, J=13.7, 10.8, 2.3 Hz, 1H).

Preparation 19B

4-Amino-1,2-dimethyltetrahydropyridazin-3(2H)-one

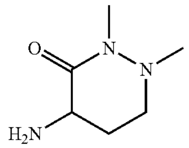

Benzyl (1-(1,2-dimethylhydrazineyl)-4-hydroxy-1-oxobutan-2-yl)carbamate: To a stirred solution of benzyl (R)-(2-oxotetrahydrofuran-3-yl)carbamate (6.00 g, 25.5 mmol) and 1,2-dimethylhydrazine hydrochloride (10.2 g, 76.5 mmol) in tetrahydrofuran (150 mL) was added triethylamine (33.6 g, 332 mmol) dropwise at room temperature under nitrogen. The mixture was stirred at 80° C. for 24 h, then filtered. The solids were washed with ethyl acetate (200 mL). The combined filtrates were concentrated under reduced pressure. The residue was purified by reversed phase purification (C18 column), eluting with 25-35% acetonitrile in (10 mM ammonium bicarbonate in water), to give benzyl (1-(1,2-dimethylhydrazineyl)-4-hydroxy-1-oxobutan-2-yl)carbamate (6.05 g, 80%) as a colorless oil. MS (ES) m/z=296 (M+1).

Benzyl (1,2-dimethyl-3-oxohexahydropyridazin-4-yl)carbamate: A solution of benzyl (1-(1,2-dimethylhydrazineyl)-4-hydroxy-1-oxobutan-2-yl)carbamate (5.50 g, 18.6 mmol) and 2-(tributyl-lambda5-phosphanylidene)acetonitrile (45.0 g, 186 mmol) in toluene (150 mL) was stirred at 100° C. for 1.5 h under nitrogen. The mixture was concentrated under reduced pressure. The residue was purified on silica, eluting with 14-25% (7:3 ethyl acetate:methanol) in DCM, followed by reversed phase purification (C18 column), eluting with 25-35% acetonitrile in (0.1% formic acid in water), to give benzyl (1,2-dimethyl-3-oxohexahydropyridazin-4-yl)carbamate (1.5 g, 29%) as a yellow solid. MS (ES) m/z=278 (M+1).

4-Amino-1,2-dimethyltetrahydropyridazin-3(2H)-one: To a stirred solution of benzyl (1,2-dimethyl-3-oxohexahydropyridazin-4-yl)carbamate (1.5 g, 5.41 mmol) in methanol (50 mL) was added palladium hydroxide (Pd 20% on carbon powder, nominally 50% water; 1.2 g) in portions at room temperature under nitrogen. The mixture was stirred at room temperature for 2 h under hydrogen, then filtered. The solids were washed with methanol (200 mL). The combined filtrates were concentrated under reduced pressure to give the crude title compound (0.85 g) as a yellow oil. $^1$H NMR (300 MHz, DMSO-d6) δ 3.28 (t, 1H), 3.06 (dd, 2H), 2.91 (s, 3H), 2.59 (s, 3H), 2.11 (ddt, 1H), 1.81 (ddt,1H).

Preparation 20B tert-Butyl (4-(5-chloro-9-(((6R,8aR)-5-oxooctahydroindolizin-6-yl)amino)-1,3-dihydrofuro[3,4-f]quinolin-4-yl)-3-cyano-7-fluorobenzo[b]thiophen-2-yl) carbamate

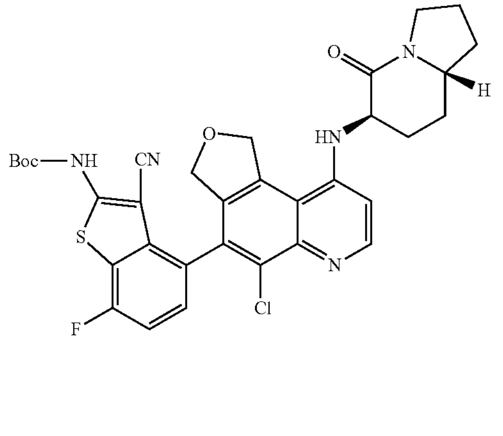

A mixture of tert-butyl (4-(9-bromo-5-chloro-1,3-dihydrofuro[3,4-f]quinolin-4-yl)-3-cyano-7-fluorobenzo[b]thiophen-2-yl)carbamate (0.152 g, 0.264 mmol), (6R,8aR)-6-aminohexahydroindolizin-5(1H)-one hydrochloride (0.151 g, 0.793 mmol), cesium carbonate (0.172 g, 0.529 mmol), 2,2'-bis(diphenylphosphaneyl)-1,1'-binaphthalene (0.020 g, 0.032 mmol), and tris(dibenzylideneacetone)dipalladium(0) (0.029 g, 0.032 mmol) in toluene (2.40 mL) was stirred for 16 h at 100° C. The mixture was diluted with water and extracted with DCM (2×50 mL). The combined organic layers were dried over anhydrous sodium sulfate, filtered, and concentrated under reduced pressure. The residue was purified on silica, eluting with 0-15% methanol in DCM, to give the title compound (0.16 g, 93%). MS (ES) m/z=648 (M+1).

Preparation 21B tert-Butyl (3-cyano-4-(3-(ethylthio)-5-fluoro-1-(((6R,8aR)-5-oxooctahydroindolizin-6-yl)amino)-7,9-dihydrofuro[3,4-f]quinazolin-6-yl)-5-fluorobenzo[b]thiophen-2-yl)carbamate

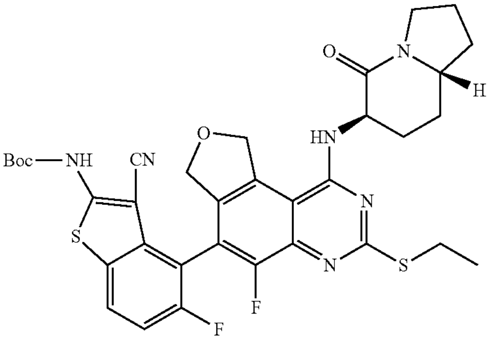 [SMILES: CCSc1nc(N[C@@H]2CC[C@H]3CCCN3C2=O)c2c3c(c(-c4c(F)ccc5sc(NC(=O)OC(C)(C)C)c(C#N)c45)c(Cl)c2n1)COC3]

BOP—Cl (CAS #68641-49-6; 0.274 g, 1.08 mmol) was added to a solution of tert-butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate (4.1 g, 7.2 mmol) and diisopropylethylamine (0.469 mL, 2.69 mmol). The mixture was stirred for 1 h at 60° C. (6R,8aR)-6-Amino-hexahydroindolizin-5(1H)-one hydrochloride (0.257 g, 1.35 mmol) was added and the mixture was stirred for 2 h at 60° C. The mixture was concentrated under reduced pressure, diluted with DCM (150 mL), and washed with saturated aqueous sodium bicarbonate (3×100 mL). The organic layer was dried over anhydrous sodium sulfate, filtered, and concentrated under reduced pressure. The residue was purified on silica, eluting with 0-100% ethyl acetate in DCM, to give the title compound (0.515 g, 83%) as a yellow solid. MS (ES) m/z=693 (M+1). Clean atropisomer, chiral purification from Preparation 32.

The following compounds in Table 7 were prepared in similar manner as described in Preparation 21B. Various methods were used to purify the compounds, which would be apparent to one skilled in the art.

TABLE 7

| Preparation | Chemical Name | Structure | MS (ES) m/z (M + 1) |
|---|---|---|---|
| 22B [2] | tert-Butyl (4-(5-chloro-3-(ethylthio)-1-(((6R,8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate | 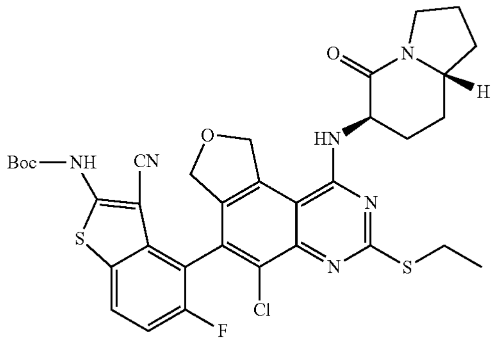 | 709 |
| 23B [1] | tert-Butyl (4-(5-chloro-3-(ethylthio)-1-(((6R,8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 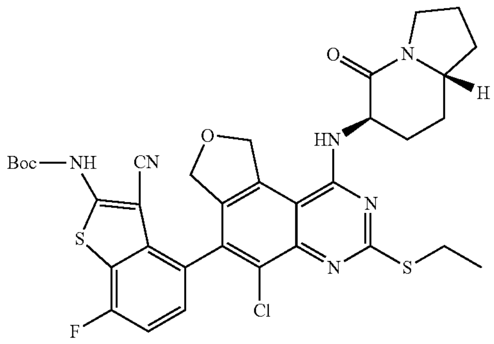 | 709 |
| 24B | tert-Butyl (4-(5-chloro-3-(ethylthio)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 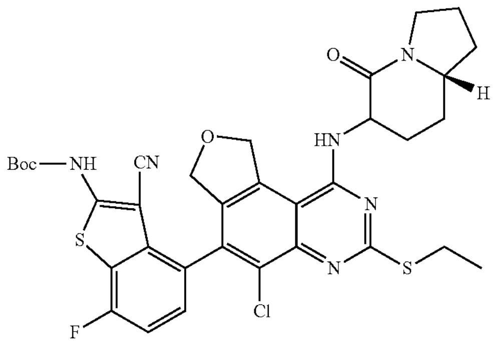 [SMILES: CCSc1nc(NC2CC[C@H]3CCCN3C2=O)c2c3c(c(-c4ccc(F)c5sc(NC(=O)OC(C)(C)C)c(C#N)c45)c(Cl)c2n1)COC3] | 709 |
| 25B [4,5] | tert-Butyl (3-cyano-4-(1-(((8aS)-2,2-difluoro-5-oxooctahydroindolizin-6-yl)amino)-3-(ethylthio)-5-fluoro-7,9-dihydrofuro[3,4-f]quinazolin-6-yl)-5-fluorobenzo[b]thiophen-2-yl)carbamate | 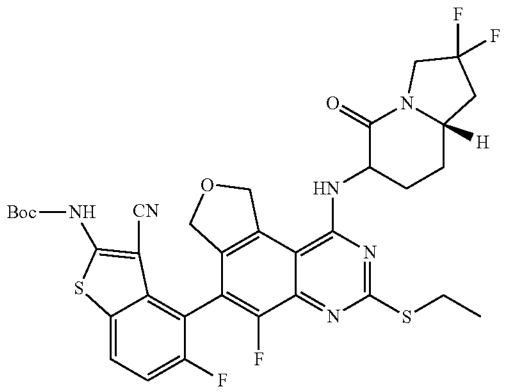 [SMILES: CCSc1nc(NC2CC[C@H]3CC(F)(F)CN3C2=O)c2c3c(c(-c4c(F)ccc5sc(NC(=O)OC(C)(C)C)c(C#N)c45)c(F)c2n1)COC3] | 729 |

TABLE 7-continued

| Preparation | Chemical Name | Structure | MS (ES) m/z (M + 1) |
|---|---|---|---|
| 26B [6,7] | tert-Butyl (4-(5-chloro-1-(((6S)-2-oxo-1-azabicyclo[4.2.0]octan-3-f]quinazolin-6-yl)-3-dihydrofuro[3,4-yl)amino)-7,9-cyano-7-fluorobenzo[b]thiophen-2-yl)carbamate | 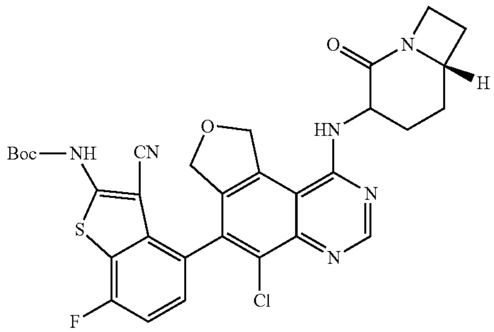 [SMILES: CC(C)(C)OC(=O)Nc1sc2c(F)ccc(-c3c4c(c5c(NC6CC[C@H]7CCN7C6=O)ncnc5c3Cl)COC4)c2c1C#N] | 635 |

[1] Clean atropisomer, chiral purification from Preparation 30
[2] Clean atropisomer, chiral purification from Preparation 34
[3] A predominant chiral center is present based on starting material from Preparation 53, 54, 55, 5A, 6A, 7A, or 8A
[4] Clean atropisomer, chiral purification from Preparation 32
[5] Clean isomer at the 6-position of the hexahydroindolizinone, chiral purification from Preparation 18B
[6] Clean atropisomer, chiral purification from Preparation 6B
[7] Clean isomer at the 3-position of the azabicyclooctanone, chiral purification from Preparation 17B

Preparation 56 tert-Butyl (4-(5-chloro-3-(ethylthio)-1-((4-methyl-5-oxo-4-azaspiro[2.5]octan-6-yl)amino)-7,9-dihydrofuro[3,4-f]quinazolin-6-yl)-3-cyano-5-fluorobenzo[b]thiophen-2-yl)carbamate

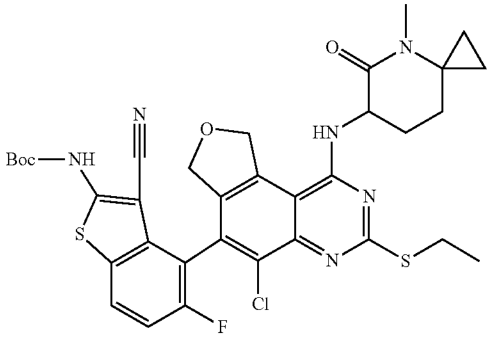 [SMILES: CCSc1nc(NC2CCC3(CC3)N(C)C2=O)c2c3c(c(-c4c(F)ccc5sc(NC(=O)OC(C)(C)C)c(C#N)c45)c(Cl)c2n1)COC3]

To a mixture of tert-butyl (3-cyano-4-(1,5-dichloro-3-(ethylthio)-7,9-dihydrofuro[3,4-f]quinazolin-6-yl)-5-fluorobenzo[b]thiophen-2-yl)carbamate (0.206 g, 0.348 mmol) and 6-amino-4-methyl-4-azaspiro[2.5]octan-5-one (0.161 g, 1.04 mmol) in acetonitrile (4 mL) was added diisopropylethylamine (0.30 mL, 1.74 mmol). The mixture was stirred at rt. After 16 h, the mixture was concentrated under reduced pressure. The residue was purified on silica, eluting with 0-100% EtOAc in heptane to obtain the title compound (0.107 g, 43%) as a white solid. MS (ES) nVz=709 (M+1).

The following compounds in Table 8 were prepared in similar manner as described in Preparation 56. Various methods were used to purify the compounds, which would be apparent to one skilled in the art.

TABLE 8

| Preparation | Chemical Name | Structure | MS (ES) m/z (M + 1) |
|---|---|---|---|
| 57[1] | tert-Butyl (4-(5-chloro-3-(ethylthio)-1-((5-methyl-6-oxo-5-azaspiro[3.5]nonan-7-yl)amino)-7,9-dihydrofuro[3,4-f]quinazolin-6-yl)-3-cyano-7-fluorobenzo[b]thiophen-2-yl)carbamate | 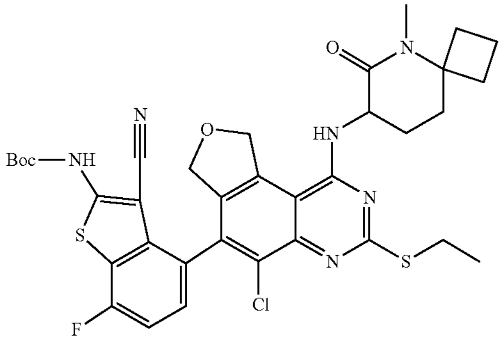 [SMILES: CCSc1nc(NC2CCC3(CCC3)N(C)C2=O)c2c3c(c(-c4ccc(F)c5sc(NC(=O)OC(C)(C)C)c(C#N)c45)c(Cl)c2n1)COC3] | 723 |

TABLE 8-continued

| Preparation | Chemical Name | Structure | MS (ES) m/z (M + 1) |
|---|---|---|---|
| 58[1] | tert-Butyl (4-(5-chloro-3-(ethylthio)-1-((4-methyl-5-oxo-4-azaspiro[2.5]octan-6-yl)amino)-7,9-dihydrofuro[3,4-f]quinazolin-6-yl)-3-cyano-7-fluorobenzo[b]thiophen-2-yl)carbamate | 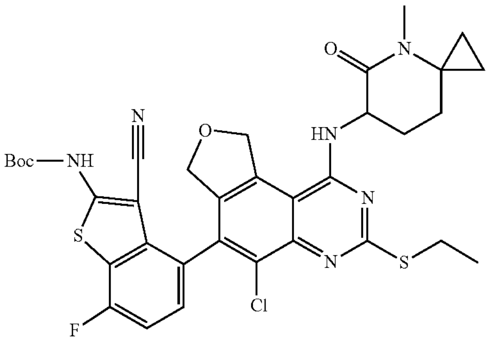 [SMILES: CCSc1nc(NC2CCC3(CC3)N(C)C2=O)c2c3c(c(-c4ccc(F)c5sc(NC(=O)OC(C)(C)C)c(C#N)c45)c(Cl)c2n1)COC3] | 709 |
| 59[1] | tert-Butyl (4-(5-chloro-3-(ethylthio)-1-((5-methyl-6-oxo-5-azaspiro[2.5]octan-7-yl)amino)-7,9-dihydrofuro[3,4-f]quinazolin-6-yl)-3-cyano-7-fluorobenzo[b]thiophen-2-yl)carbamate | 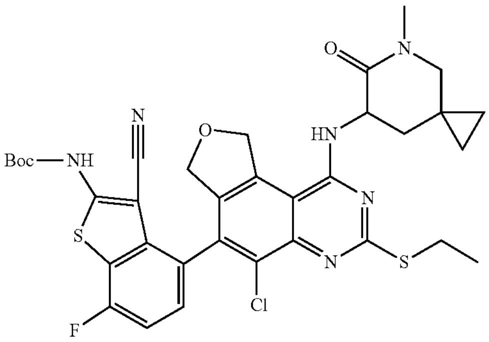 [SMILES: CCSc1nc(NC2CC3(CC3)CN(C)C2=O)c2c3c(c(-c4ccc(F)c5sc(NC(=O)OC(C)(C)C)c(C#N)c45)c(Cl)c2n1)COC3] | 709 |
| 60 | tert-Butyl (3-cyano-4-(3-(ethylthio)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophen-2-yl)carbamate | 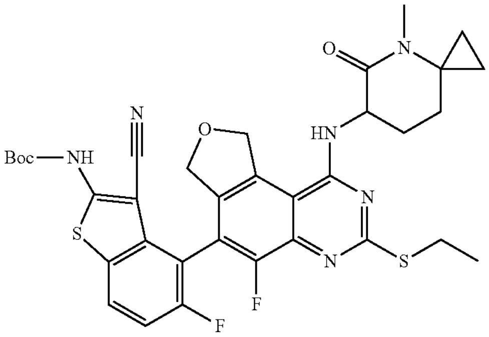 [SMILES: CCSc1nc(NC2CCC3(CC3)N(C)C2=O)c2c3c(c(-c4c(F)ccc5sc(NC(=O)OC(C)(C)C)c(C#N)c45)c(F)c2n1)COC3] | 693 |
| 61 | tert-Butyl (4-(5-chloro-3-(ethylthio)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 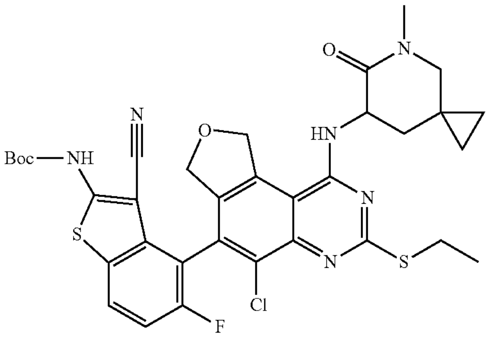 [SMILES: CCSc1nc(NC2CC3(CC3)CN(C)C2=O)c2c3c(c(-c4c(F)ccc5sc(NC(=O)OC(C)(C)C)c(C#N)c45)c(Cl)c2n1)COC3] | 709 |

TABLE 8-continued

| Preparation | Chemical Name | Structure | MS (ES) m/z (M + 1) |
| --- | --- | --- | --- |
| 62[2] | tert-Butyl (4-(5-chloro-3-(ethylthio)-1-((2-methyl-3-oxo-2-azabicyclo[3.1.1]heptan-4-yl)amino)-7,9-dihydrofuro[3,4-f]quinazolin-6-yl)-3-cyano-5-fluorobenzo[b]thiophen-2-yl)carbamate | 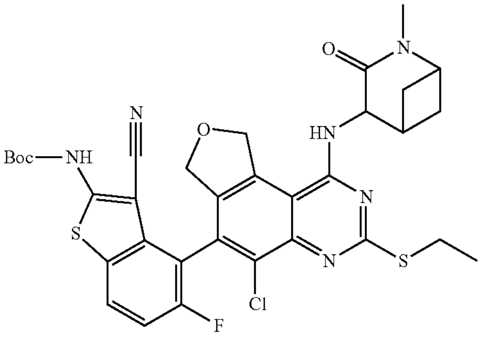 [SMILES: CCSc1nc(NC2C(=O)N(C)C3CC2C3)c2c3c(c(-c4c(F)ccc5sc(NC(=O)OC(C)(C)C)c(C#N)c45)c(Cl)c2n1)COC3] | 695 |
| 63 | 7-((6-Bromo-5-chloro-3-(ethylthio)-7,9-dihydrofuro[3,4-f]quinazolin-1-yl)amino)-5-methyl-5-azaspiro[3.5]nonan-6-one | 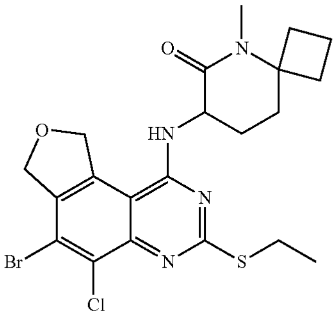 [SMILES: CCSc1nc(NC2CCC3(CCC3)N(C)C2=O)c2c3c(c(Br)c(Cl)c2n1)COC3] | 511 |
| 64 | 7-((6-Bromo-5-chloro-3-(ethylthio)-7,9-dihydrofuro[3,4-f]quinazolin-1-yl)amino)-5-methyl-5-azaspiro[2.5]octan-6-one | 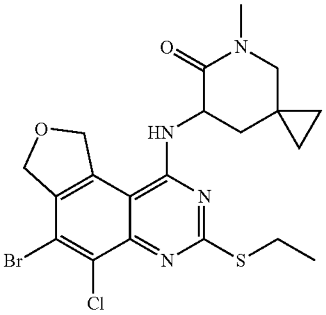 [SMILES: CCSc1nc(NC2CC3(CC3)CN(C)C2=O)c2c3c(c(Br)c(Cl)c2n1)COC3] | 497 |
| 65 | tert-Butyl (4-(5-chloro-3-(ethylthio)-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 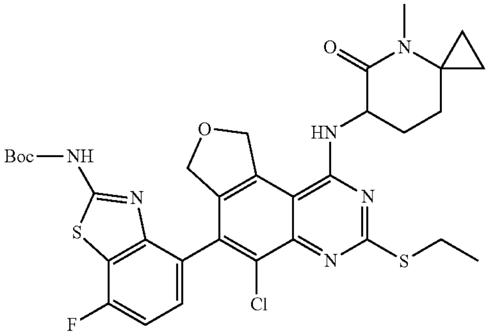 [SMILES: CCSc1nc(NC2CCC3(CC3)N(C)C2=O)c2c3c(c(-c4ccc(F)c5sc(NC(=O)OC(C)(C)C)nc45)c(Cl)c2n1)COC3] | 685 |

TABLE 8-continued

| Preparation | Chemical Name | Structure | MS (ES) m/z (M + 1) |
|---|---|---|---|
| 66 | (8aR)-6-((6-Bromo-3-(ethylthio)-5-fluoro-7,9-dihydrofuro[3,4-f]quinazolin-1-yl)amino) hexahydroindolizin-5(1H)-one | 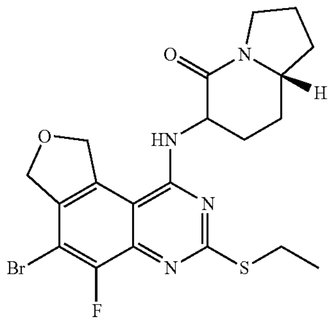 [SMILES: CCSc1nc(NC2CC[C@H]3CCCN3C2=O)c2c3c(c(Br)c(F)c2n1)COC3] | 481 |
| 67 | 6-((6-Bromo-3-(ethylthio)-5-fluoro-7,9-dihydrofuro[3,4-f]quinazolin-1-yl)amino)-4-methyl-4-azaspiro[2.5]octan-5-one | 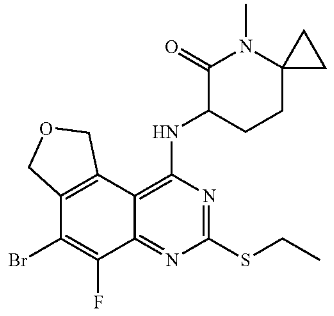 [SMILES: CCSc1nc(NC2CCC3(CC3)N(C)C2=O)c2c3c(c(Br)c(F)c2n1)COC3] | 483 |
| 68 | 7-((6-Bromo-3-(ethylthio)-5-fluoro-7,9-dihydrofuro[3,4-f]quinazolin-1-yl)amino)-5-methyl-5-azaspiro[2.5]octan-6-one | 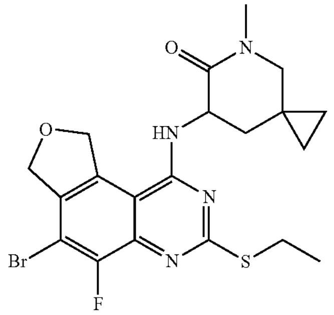 [SMILES: CCSc1nc(NC2CC3(CC3)CN(C)C2=O)c2c3c(c(Br)c(F)c2n1)COC3] | 483 |
| 9A[2] | tert-Butyl (4-(5-chloro-3-(ethylthio)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 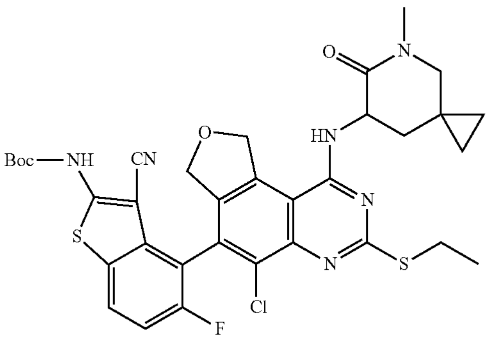 [SMILES: CCSc1nc(NC2CC3(CC3)CN(C)C2=O)c2c3c(c(-c4c(F)ccc5sc(NC(=O)OC(C)(C)C)c(C#N)c45)c(Cl)c2n1)COC3] | 709 |

TABLE 8-continued

| Preparation | Chemical Name | Structure | MS (ES) m/z (M + 1) |
|---|---|---|---|
| 10A[1] | tert-Butyl (4-(5-chloro-3-(ethylthio)-1-((4-methyl-5-oxo-4-azaspiro[2.4]heptan-6-yl)amino)-7,9-dihydrofuro[3,4-f]quinazolin-6-yl)-3-cyano-7-fluorobenzo[b]thiophen-2-yl)carbamate | 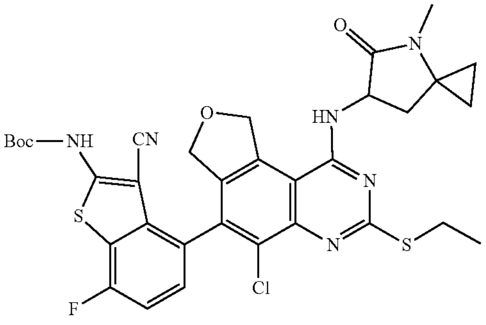 [SMILES: CCSc1nc(NC2CC3(CC3)N(C)C2=O)c2c3c(c(-c4ccc(F)c5sc(NC(=O)OC(C)(C)C)c(C#N)c45)c(Cl)c2n1)COC3] | 695 |
| 11A[1] | tert-Butyl (4-(5-chloro-3-(ethylthio)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 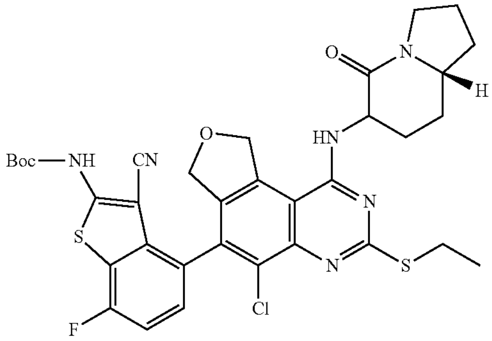 [SMILES: CCSc1nc(NC2CC[C@H]3CCCN3C2=O)c2c3c(c(-c4ccc(F)c5sc(NC(=O)OC(C)(C)C)c(C#N)c45)c(Cl)c2n1)COC3] | 709 |
| 12A | 7-((6-Bromo-3-(ethylthio)-5-fluoro-7,9-dihydrofuro[3,4-f]quinazolin-1-yl)amino)-5-methyl-5-azaspiro[3.5]nonan-6-one | 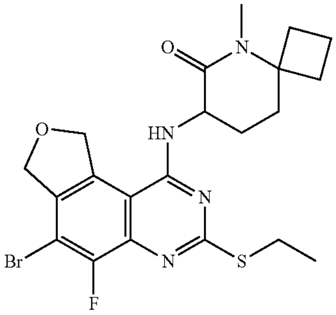 [SMILES: CCSc1nc(NC2CCC3(CCC3)N(C)C2=O)c2c3c(c(Br)c(F)c2n1)COC3] | 495 |
| 13A[3] | (8aR)-6-((6-Bromo-5-chloro-3-(ethylthio)-7,9-dihydrofuro[3,4-f]quinazolin-1-yl)amino) hexahydroindolizin-5(1H)-one, Isomer 1 | 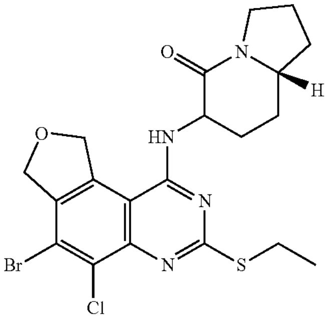 | 497 |

TABLE 8-continued

| Preparation | Chemical Name | Structure | MS (ES) m/z (M + 1) |
|---|---|---|---|
| 14A[3] | (8aR)-6-((6-Bromo-5-chloro-3-(ethylthio)-7,9-dihydrofuro[3,4-f]quinazolin-1-yl)amino) hexahydroindolizin-5(1H)-one, Isomer 2 | 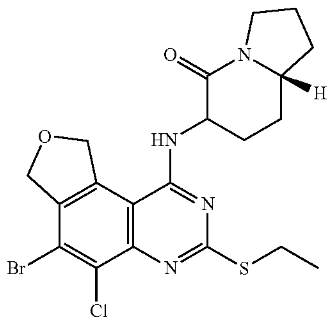 | 497 |
| 15A | 6-((6-Bromo-5-chloro-3-(ethylthio)-7,9-dihydrofuro[3,4-f]quinazolin-1-yl)amino)-4-methyl-4-azaspiro[2.5]octan-5-one | 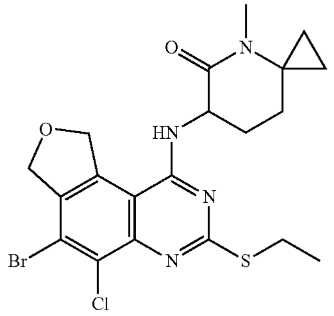 [SMILES: CCSc1nc(NC2CCC3(CC3)N(C)C2=O)c2c3c(c(Br)c(Cl)c2n1)COC3] | 497 |
| 16A[4] | (9aS)-7-((6-Bromo-3-(ethylthio)-5-fluoro-7,9-dihydrofuro[3,4-f]quinazolin-1-yl)amino)hexahydropyrido [2,1-c][1,4]oxazin-6(1H)-one | 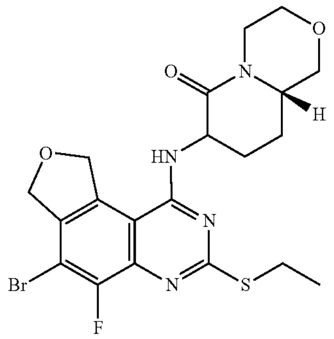 [SMILES: CCSc1nc(NC2CC[C@H]3COCCN3C2=O)c2c3c(c(Br)c(F)c2n1)COC3] | 497 |
| 17A | 7-((6-Bromo-3-(ethylthio)-5-fluoro-7,9-dihydrofuro[3,4-f]quinazolin-1-yl)amino)-5-azaspiro[3.5]nonan-6-one | 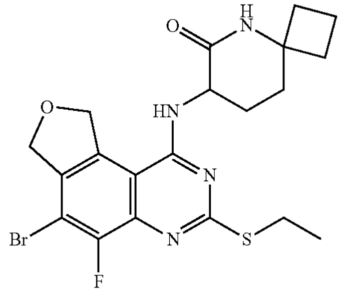 [SMILES: CCSc1nc(NC2CCC3(CCC3)NC2=O)c2c3c(c(Br)c(F)c2n1)COC3] | 481 |

TABLE 8-continued

| Preparation | Chemical Name | Structure | MS (ES) m/z (M + 1) |
|---|---|---|---|
| 18A[2,4] | tert-Butyl (4-(5-chloro-3-(ethylthio)-1-(((8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate | 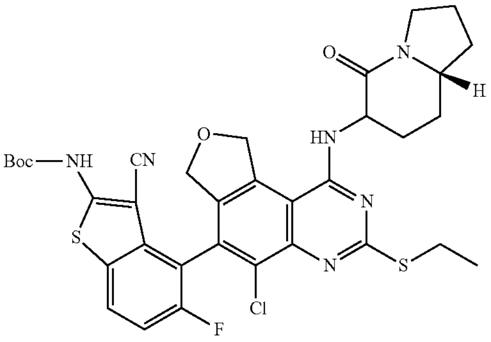 [SMILES: CCSc1nc(NC2CC[C@H]3CCCN3C2=O)c2c3c(c(-c4c(F)ccc5sc(NC(=O)OC(C)(C)C)c(C#N)c45)c(Cl)c2n1)COC3] | 709 |
| 19A[4] | (8aR)-6-((6-bromo-3-(ethylthio)-5-fluoro-7,9-dihydrofuro[3,4-f]quinazolin-1-yl)amino) hexahydroindolizin-5(1H)-one | 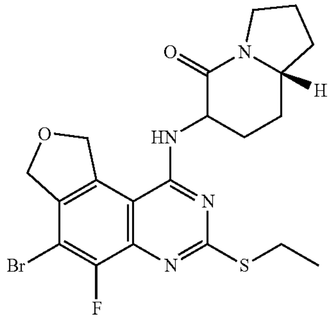 [SMILES: CCSc1nc(NC2CC[C@H]3CCCN3C2=O)c2c3c(c(Br)c(F)c2n1)COC3] | 481 |
| 27B | tert-Butyl (4-(5-chloro-3-(ethylthio)-1-(((6R,8aR)-5-oxooctahydroindolizin-6-yl)amino)-7,9-dihydrofuro[3,4-f]quinazolin-6-yl)-3-cyano-7-fluorothieno[3,2-c]pyridin-2-yl)carbamate | 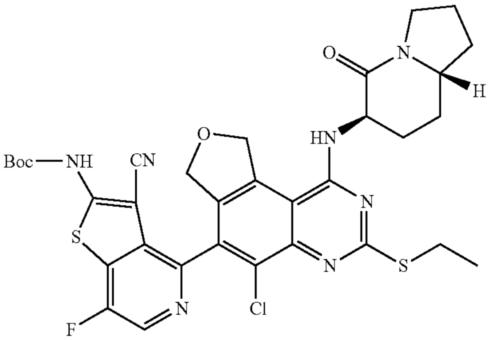 [SMILES: CCSc1nc(N[C@@H]2CC[C@H]3CCCN3C2=O)c2c3c(c(-c4ncc(F)c5sc(NC(=O)OC(C)(C)C)c(C#N)c45)c(Cl)c2n1)COC3] | 710 |
| 28B | (6R,8aR)-6-((6-Bromo-5-chloro-3-(ethylthio)-7,9-dihydrofuro[3,4-f]quinazolin-1-yl)amino) hexahydroindolizin-5(1H)-one | 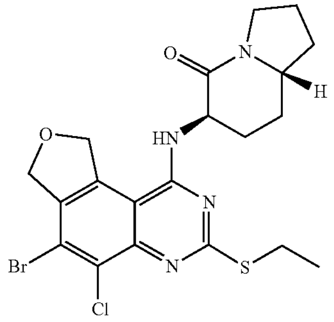 [SMILES: CCSc1nc(N[C@@H]2CC[C@H]3CCCN3C2=O)c2c3c(c(Br)c(Cl)c2n1)COC3] | 497 |

TABLE 8-continued

| Preparation | Chemical Name | Structure | MS (ES) m/z (M + 1) |
|---|---|---|---|
| 29B | (6R,8aR)-6-((4-Bromo-7-chloro-5-fluoro-1,3-dihydrofuro[3,4-f]quinolin-9-yl)amino) hexahydroindolizin-5(1H)-one | 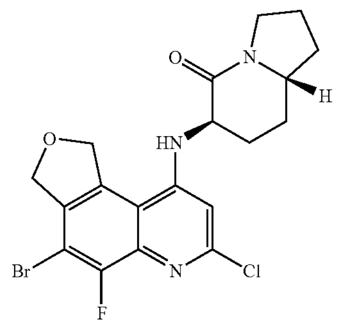 | 454 |
| 30B | (6R)-3-((6-Bromo-3-(ethylthio)-5-fluoro-7,9-dihydrofuro[3,4-f]quinazolin-1-yl)amino)-6-(difluoromethyl)-1-methylpiperidin-2-one | 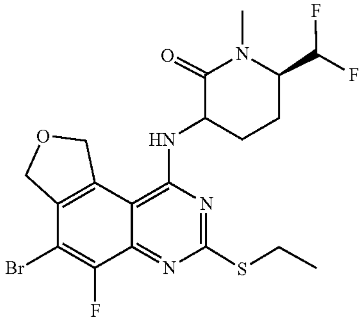 [SMILES: CCSc1nc(NC2CC[C@H](C(F)F)N(C)C2=O)c2c3c(c(Br)c(F)c2n1)COC3] | 505 |
| 31B | (6R,8aR)-6-((4-Bromo-5,7-dichloro-1,3-dihydrofuro[3,4-f]quinolin-9-yl)amino) hexahydroindolizin-5(1H)-one | 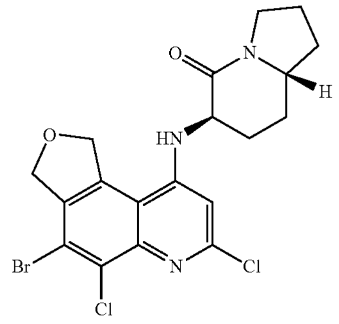 [SMILES: O=C1[C@H](Nc2cc(Cl)nc3c(Cl)c(Br)c4c(c23)COC4)CC[C@H]2CCCN12] | 472 |

[1]Clean atropisomer, chiral purification from Preparation 30

[2]Clean atropisomer, chiral purification from Preparation 34

[3]Normal Phase; silica, 0-100% EtOAc in DCM, Isomer refers to a clean isomer at the 6-position of the hexahydroindolizinone

[4]A predominant chiral center is present based on starting material from Preparation 53, 54, 55, 5A, 6A, 7A, or 8A The following compounds in Table 9 were prepared in similar manner as described in Preparation 28. Different coupling conditions, such as base, ligands, or palladium sources, may have been substituted. Various methods were used to purify the compounds, which would be apparent to one skilled in the art.

TABLE 9

| Preparation | Chemical Name | Structure | MS (ES) m/z (M + 1) |
| --- | --- | --- | --- |
| 69 | tert-Butyl (4-(5-chloro-3-(ethylthio)-1-((5-methyl-6-oxo-5-azaspiro[2.5]octan-7-yl)amino)-7,9-dihydrofuro[3,4-f]quinazolin-6-yl)-5-fluorobenzo[d]thiazol-2-yl)carbamate | 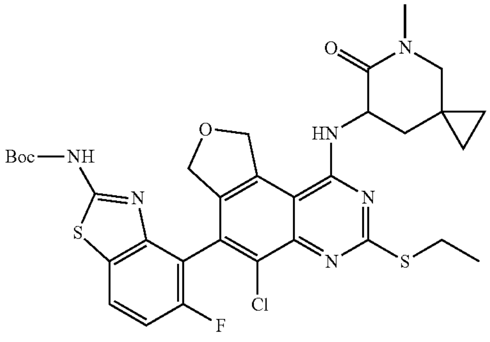 [SMILES: CCSc1nc(NC2CC3(CC3)CN(C)C2=O)c2c3c(c(-c4c(F)ccc5sc(NC(=O)OC(C)(C)C)nc45)c(Cl)c2n1)COC3] | 685 |
| 70 | tert-Butyl (4-(3-(ethylthio)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate | 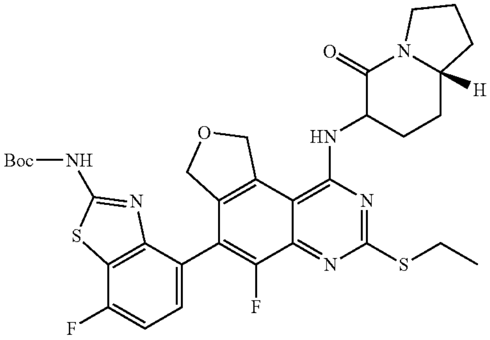 [SMILES: CCSc1nc(NC2CC[C@H]3CCCN3C2=O)c2c3c(c(-c4ccc(F)c5sc(NC(=O)OC(C)(C)C)nc45)c(F)c2n1)COC3] | 669 |
| 71 | tert-Butyl (4-(3-(ethylthio)-5-fluoro-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 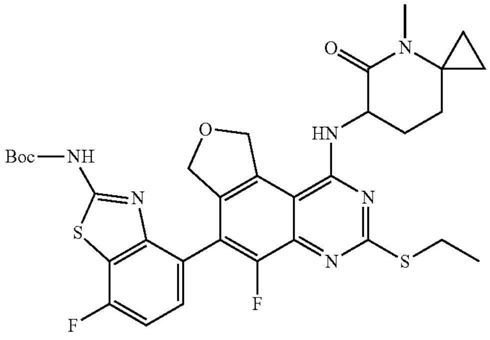 | 669 |
| 72 | tert-Butyl (4-(3-(ethylthio)-5-fluoro-1-((5-methyl-6-oxo-5-azaspiro[2.5]octan-7-yl)amino)-7,9-dihydrofuro[3,4-f]quinazolin-6-yl)-7-fluorobenzo[d]thiazol-2-yl)carbamate | 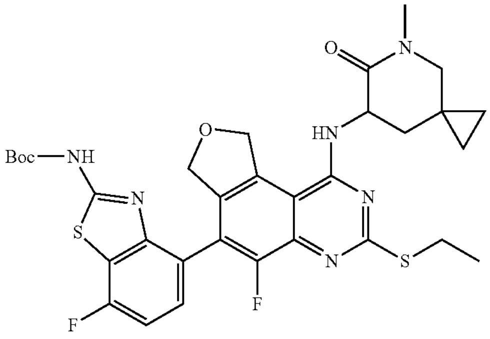 [SMILES: CCSc1nc(NC2CC3(CC3)CN(C)C2=O)c2c3c(c(-c4ccc(F)c5sc(NC(=O)OC(C)(C)C)nc45)c(F)c2n1)COC3] | 669 |

TABLE 9-continued

| Preparation | Chemical Name | Structure | MS (ES) m/z (M + 1) |
| --- | --- | --- | --- |
| 20A | tert-Butyl (4-(3-(ethylthio)-5-fluoro-1-((5-methyl-6-oxo-5-azaspiro[3.5]nonan-7-yl)amino)-7,9-dihydrofuro[3,4-f]quinazolin-6-yl)-7-fluorobenzo[d]thiazol-2-yl)carbamate | 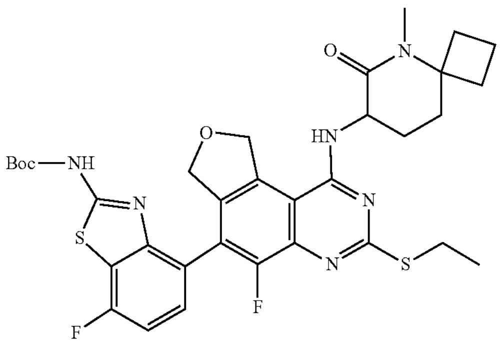 [SMILES: CCSc1nc(NC2CCC3(CCC3)N(C)C2=O)c2c3c(c(-c4ccc(F)c5sc(NC(=O)OC(C)(C)C)nc45)c(F)c2n1)COC3] | 683 |
| 21A[1] | tert-Butyl (4-(3-(ethylthio)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate | 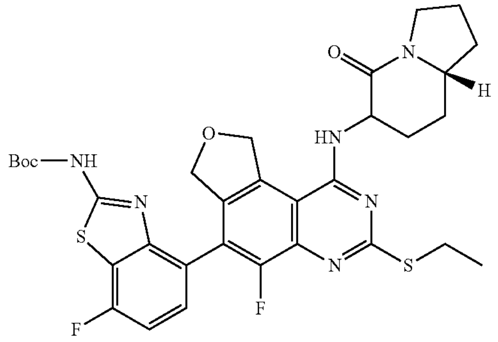 [SMILES: CCSc1nc(NC2CC[C@H]3CCCN3C2=O)c2c3c(c(-c4ccc(F)c5sc(NC(=O)OC(C)(C)C)nc45)c(F)c2n1)COC3] | 669 |

[1]A predominant chiral center is present based on starting material from Preparation 53, 54, 55, 5A, 6A, 7A, or 8A Preparation 73 tert-Butyl (4-(5-chloro-3-(ethylthio)-1-((5-methyl-6-oxo-5-azaspiro[3.5]nonan-7-yl)amino)-7,9-dihydrofuro[3,4-f]quinazolin-6-yl)-7-fluorothiazolo[4,5-c]pyridin-2-yl)carbamate

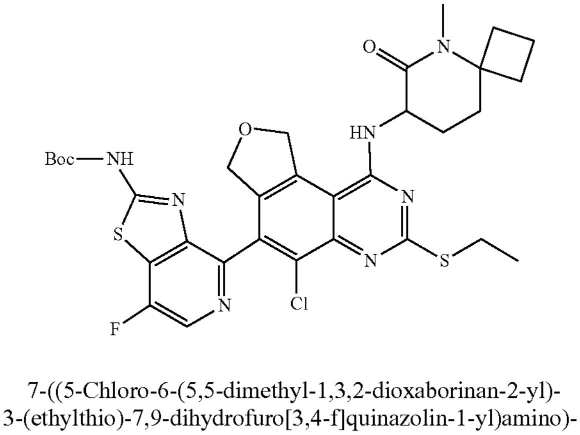

7-((5-Chloro-6-(5,5-dimethyl-1,3,2-dioxaborinan-2-yl)-3-(ethylthio)-7,9-dihydrofuro[3,4-f]quinazolin-1-yl)amino)-5-methyl-5-azaspiro[3.5]nonan-6-one. To a solution of 7-((6-bromo-5-chloro-3-(ethylthio)-7,9-dihydrofuro[3,4-f]quinazolin-1-yl)amino)-5-methyl-5-azaspiro[3.5]nonan-6-one (0.292 g, 0.570 mmol), 5,5,5',5'-tetramethyl-2,2'-bi(1,3,2-dioxaborinane) (0.258 g, 1.14 mmol), and potassium acetate (0.168 g, 1.71 mmol) in 1,4-dioxane (5 mL) was added Pd-117 (CAS 205319-06-8; 0.012 g, 0.017 mmol). The mixture was stirred at 80° C. for 16 h, cooled, and filtered. The solids were washed with 1,4-dioxane (3×60 mL). The combined filtrates were concentrated under reduced pressure. The residue was purified on silica, eluting with 0-60% MeOH in DCM to obtain 7-((5-chloro-6-(5,5-dimethyl-1,3,2-dioxaborinan-2-yl)-3-(ethylthio)-7,9-dihydrofuro[3,4-f]quinazolin-1-yl)amino)-5-methyl-5-azaspiro[3.5]nonan-6-one (0.331 g) as a white solid. MS (ES) m/z=477 (M+1, boronic acid).

tert-Butyl (4-(5-chloro-3-(ethylthio)-1-((5-methyl-6-oxo-5-azaspiro[3.5]nonan-7-yl)amino)-7,9-dihydrofuro[3,4-f]quinazolin-6-yl)-7-fluorothiazolo[4,5-c]pyridin-2-yl)carbamate. To a mixture of tert-butyl (4-chloro-7-fluorothiazolo[4,5-c]pyridin-2-yl)carbamate (0.316 g, 1.04 mmol), 7-((5-chloro-6-(5,5-dimethyl-1,3,2-dioxaborinan-2-yl)-3-(ethylthio)-7,9-dihydrofuro[3,4-f]quinazolin-1-yl)amino)-5-methyl-5-azaspiro[3.5]nonan-6-one (0.331 g, 0.570 mmol), 2-(dicyclohexylphosphanyl)-2',4',6'-tris(isopropyl)biphenyl (0.033 g, 0.069 mmol), and XPhos Pd(crotyl)$C_1$ (CAS 1798782-02-1; 0.047 g, 0.069 mmol) in 1,4-dioxane (5 mL) was added a solution of dipotassium phosphate (0.362 g, 2.08 mmol) in water (1 mL). The mixture was degassed (direct nitrogen sparge) for 5 min, stirred at 80° C. for 16 h, and concentrated under reduced pressure. The residue was purified on silica, eluting with 0-100% ethyl acetate in heptane to obtain the title compound (0.276 g, 57%). MS (ES) m/z=700 (M+1).

The following compounds in Table 10 were prepared in similar manner as described in Preparation 73. Different coupling conditions, such as base, ligands, or palladium sources, may have been substituted. Various methods were used to purify the compounds, which would be apparent to one skilled in the art.

TABLE 10

| Preparation | Chemical Name | Structure | MS (ES) m/z (M + 1) |
|---|---|---|---|
| 22A | tert-Butyl (4-(5-chloro-3-(ethylthio)-1-((5-methyl-6-oxo-5-azaspiro[2.5]octan-7-yl)amino)-7,9-dihydrofuro[3,4-f]quinazolin-6-yl)-7-fluorothiazolo[4,5-c]pyridin-2-yl) carbamate | 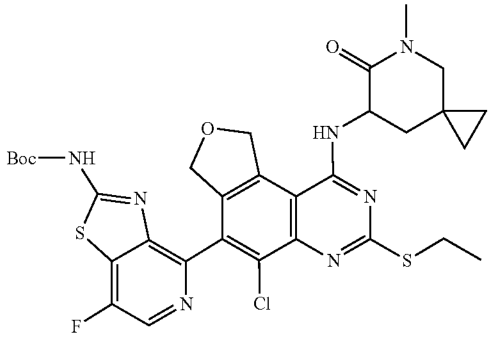 [SMILES: CCSc1nc(NC2CC3(CC3)CN(C)C2=O)c2c3c(c(-c4ncc(F)c5sc(NC(=O)OC(C)(C)C)nc45)c(Cl)c2n1)COC3] | 686 |

Preparation 23A (6R,8aR)-6-((6-Bromo-3-(ethylthio)-5-fluoro-7,9-dihydrofuro[3,4-f]quinazolin-1-yl)amino)hexahydroindolizin-5(1H)-one

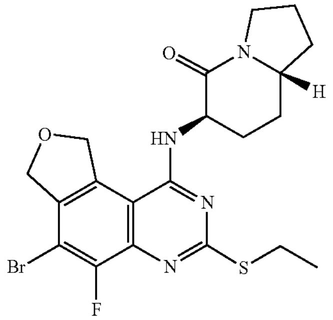 [SMILES: CCSc1nc(N[C@@H]2CC[C@H]3CCCN3C2=O)c2c3c(c(Br)c(F)c2n1)COC3]

To a solution of (8aR)-6-((6-bromo-3-(ethylthio)-5-fluoro-7,9-dihydrofuro[3,4-f]quinazolin-1-yl)amino)hexahydroindolizin-5(1H)-one (21.8 g, 45.2 mmol) in MeOH (400 mL) was added potassium carbonate (12.5 g, 90.5 mmol). The mixture was stirred at 40° C. for 16 h, then concentrated under reduced pressure. The residue was diluted with water (200 mL) and filtered to obtain the title compound (18.2 g, 84%) as a yellow solid. MS (ES) m/z=481 (M+1).

Preparation 74 tert-Butyl (4-(5-chloro-3-(ethylsulfonyl)-1-((4-methyl-5-oxo-4-azaspiro[2.5]octan-6-yl)amino)-7,9-dihydrofuro[3,4-f]quinazolin-6-yl)-3-cyano-5-fluorobenzo[b]thiophen-2-yl)carbamate

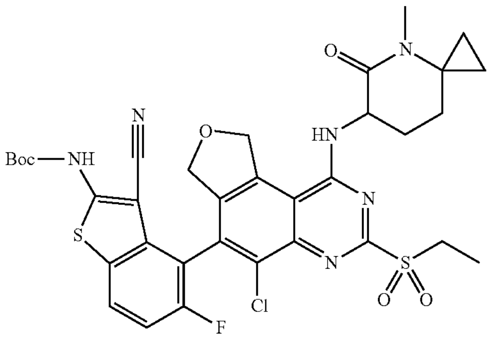 [SMILES: CCS(=O)(=O)c1nc(NC2CCC3(CC3)N(C)C2=O)c2c3c(c(-c4c(F)ccc5sc(NC(=O)OC(C)(C)C)c(C#N)c45)c(Cl)c2n1)COC3]

To a solution of tert-butyl (4-(5-chloro-3-(ethylthio)-1-((4-methyl-5-oxo-4-azaspiro[2.5]octan-6-yl)amino)-7,9-dihydrofuro[3,4-f]quinazolin-6-yl)-3-cyano-5-fluorobenzo[b]thiophen-2-yl)carbamate (0.107 g, 0.150 mmol) in DCM (5 mL) was added mCPBA (70 wt %; 0.081 g, 0.330 mmol) portionwise at 0° C. The mixture was stirred at 0° C. for 30 min, then at room temperature for 2 h. The mixture was concentrated under reduced pressure. The crude material was purified on silica, eluting with 0-100% EtOAc in DCM to obtain the title compound (0.115 g, 100%) as a light yellow solid. MS (ES) nvz=741 (M+1).

The following compounds in Table 11 were prepared in similar manner as described in Preparation 74. Different oxidation conditions, such as hydrogen peroxide and hexaammonium heptamolybdate tetrahydrate in ethanol and DCM, may have been substituted. Various methods were used to purify the compounds, which would be apparent to one skilled in the art.

TABLE 11

| Preparation | Chemical Name | Structure | MS (ES) m/z (M + 1) |
|---|---|---|---|
| 75[1] | tert-Butyl (4-(5-chloro-3-(ethylsulfonyl)-1-((5-methyl-6-oxo-5-azaspiro[3.5]nonan-7-yl)amino)-7,9-dihydrofuro[3,4-f]quinazolin-6-yl)-3-cyano-7-fluorobenzo[b]thiophen-2-yl)carbamate | 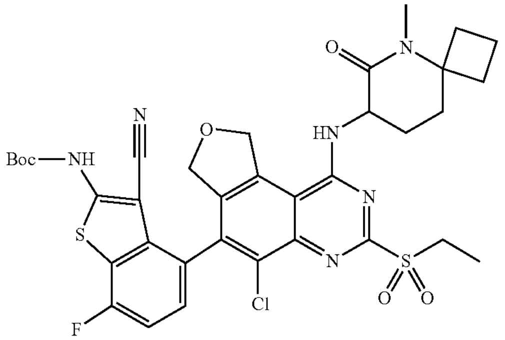 [SMILES: CCS(=O)(=O)c1nc(NC2CCC3(CCC3)N(C)C2=O)c2c3c(c(-c4ccc(F)c5sc(NC(=O)OC(C)(C)C)c(C#N)c45)c(Cl)c2n1)COC3] | 755 |
| 76[1] | tert-Butyl (4-(5-chloro-3-(ethylsulfonyl)-1-((4-methyl-5-oxo-4-azaspiro[2.5]octan-6-yl)amino)-7,9-dihydrofuro[3,4-f]quinazolin-6-yl)-3-cyano-7-fluorobenzo[b]thiophen-2-yl)carbamate | 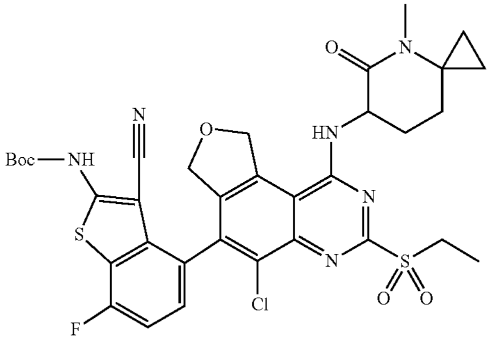 [SMILES: CCS(=O)(=O)c1nc(NC2CCC3(CC3)N(C)C2=O)c2c3c(c(-c4ccc(F)c5sc(NC(=O)OC(C)(C)C)c(C#N)c45)c(Cl)c2n1)COC3] | 741 |
| 77[1] | tert-Butyl (4-(5-chloro-3-(ethylsulfonyl)-1-((5-methyl-6-oxo-5-azaspiro[2.5]octan-7-yl)amino)-7,9-dihydrofuro[3,4-f]quinazolin-6-yl)-3-cyano-7-fluorobenzo[b]thiophen-2-yl)carbamate | 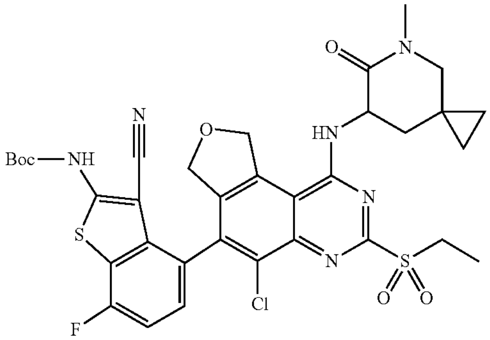 [SMILES: CCS(=O)(=O)c1nc(NC2CC3(CC3)CN(C)C2=O)c2c3c(c(-c4ccc(F)c5sc(NC(=O)OC(C)(C)C)c(C#N)c45)c(Cl)c2n1)COC3] | 741 |
| 78 | tert-Butyl (3-cyano-4-(3-(ethylsulfonyl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophen-2-yl)carbamate | 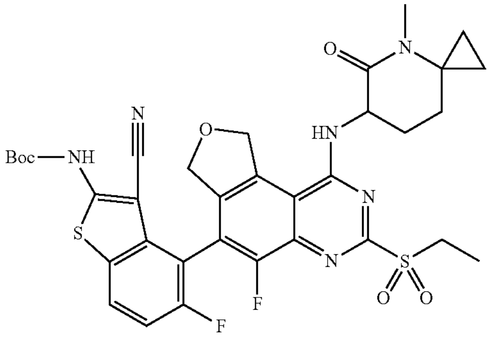 [SMILES: CCS(=O)(=O)c1nc(NC2CCC3(CC3)N(C)C2=O)c2c3c(c(-c4c(F)ccc5sc(NC(=O)OC(C)(C)C)c(C#N)c45)c(F)c2n1)COC3] | 725 |

TABLE 11-continued

| Preparation | Chemical Name | Structure | MS (ES) m/z (M + 1) |
|---|---|---|---|
| 79 | tert-Butyl (4-(5-chloro-3-(ethylsulfonyl)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 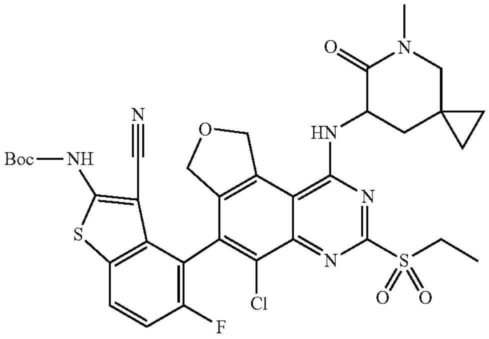 [SMILES: CCS(=O)(=O)c1nc(NC2CC3(CC3)CN(C)C2=O)c2c3c(c(-c4c(F)ccc5sc(NC(=O)OC(C)(C)C)c(C#N)c45)c(Cl)c2n1)COC3] | 741 |
| 80[2] | tert-Butyl (4-(5-chloro-3-(ethylsulfonyl)-1-((2-methyl-3-oxo-2-azabicyclo[3.1.1]heptan-4-yl)amino)-7,9-dihydrofuro[3,4-f]quinazolin-6-yl)-3-cyano-5-fluorobenzo[b]thiophen-2-yl)carbamate | 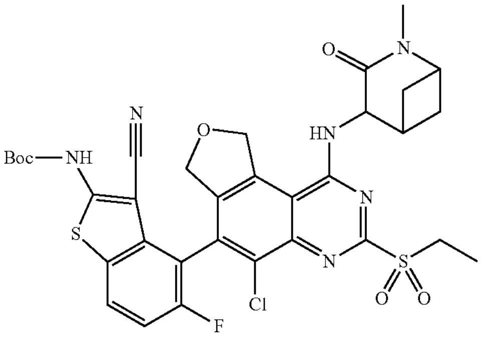 [SMILES: CCS(=O)(=O)c1nc(NC2C(=O)N(C)C3CC2C3)c2c3c(c(-c4c(F)ccc5sc(NC(=O)OC(C)(C)C)c(C#N)c45)c(Cl)c2n1)COC3] | 727 |
| 81 | 6-Bromo-3-(ethylsulfonyl)-5-fluoro-7,9-dihydrofuro[3,4-f]quinazolin-1-ol | 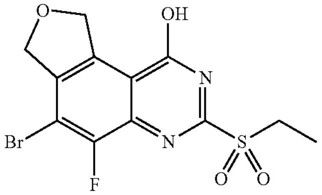 [SMILES: CCS(=O)(=O)c1nc(O)c2c3c(c(Br)c(F)c2n1)COC3] | 377 |
| 82 | tert-Butyl (4-(5-chloro-3-(ethylsulfonyl)-1-((5-methyl-6-oxo-5-azaspiro[3.5]nonan-7-yl)amino)-7,9-dihydrofuro[3,4-f]quinazolin-6-yl)-7-fluorothiazolo[4,5-c]pyridin-2-yl)carbamate | 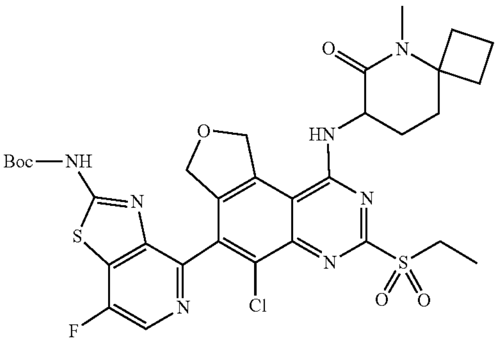 [SMILES: CCS(=O)(=O)c1nc(NC2CCC3(CCC3)N(C)C2=O)c2c3c(c(-c4ncc(F)c5sc(NC(=O)OC(C)(C)C)nc45)c(Cl)c2n1)COC3] | 732 |

TABLE 11-continued

| Preparation | Chemical Name | Structure | MS (ES) m/z (M + 1) |
|---|---|---|---|
| 83 | tert-Butyl (4-(5-chloro-3-(ethylsulfonyl)-1-((5-methyl-6-oxo-5-azaspiro[2.5]octan-7-yl)amino)-7,9-dihydrofuro[3,4-f]quinazolin-6-yl)-5-fluorobenzo[d]thiazol-2-yl)carbamate | 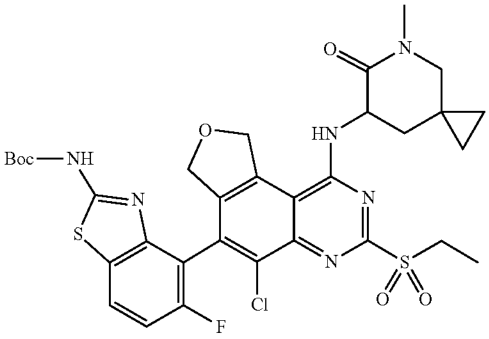 [SMILES: CCS(=O)(=O)c1nc(NC2CC3(CC3)CN(C)C2=O)c2c3c(c(-c4c(F)ccc5sc(NC(=O)OC(C)(C)C)nc45)c(Cl)c2n1)COC3] | 717 |
| 84 | tert-Butyl (4-(5-chloro-3-(ethylsulfonyl)-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 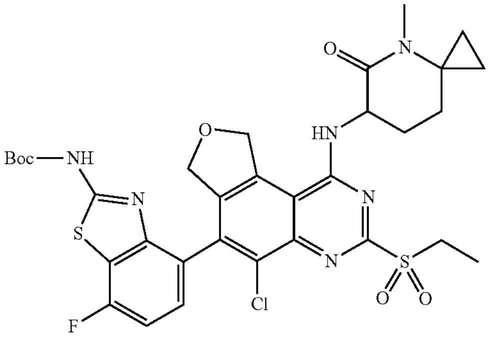 [SMILES: CCS(=O)(=O)c1nc(NC2CCC3(CC3)N(C)C2=O)c2c3c(c(-c4ccc(F)c5sc(NC(=O)OC(C)(C)C)nc45)c(Cl)c2n1)COC3] | 717 |
| 85[3] | tert-Butyl (4-(3-(ethylsulfonyl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate, Enantiomer 1 | 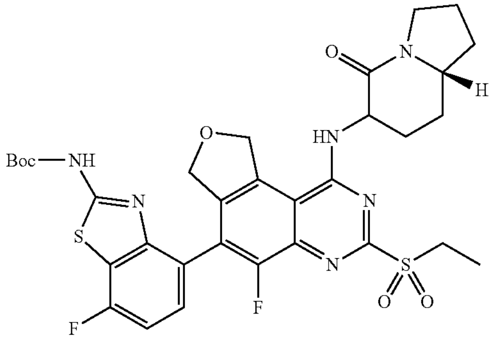 [SMILES: CCS(=O)(=O)c1nc(NC2CC[C@H]3CCCN3C2=O)c2c3c(c(-c4ccc(F)c5sc(NC(=O)OC(C)(C)C)nc45)c(F)c2n1)COC3] | 701 |
| 86[3] | tert-Butyl (4-(3-(ethylsulfonyl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate, Enantiomer 2 | 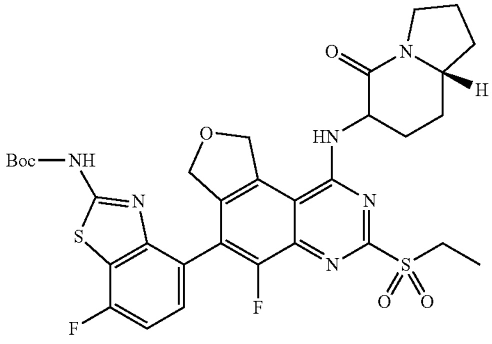 [SMILES: CCS(=O)(=O)c1nc(NC2CC[C@H]3CCCN3C2=O)c2c3c(c(-c4ccc(F)c5sc(NC(=O)OC(C)(C)C)nc45)c(F)c2n1)COC3] | 701 |

TABLE 11-continued

| Preparation | Chemical Name | Structure | MS (ES) m/z (M + 1) |
|---|---|---|---|
| 87 | tert-Butyl (4-(3-(ethylsulfonyl)-5-fluoro-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 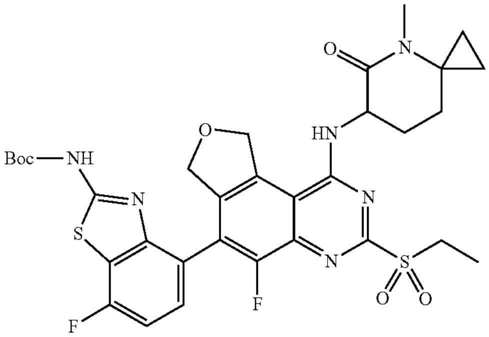 [SMILES: CCS(=O)(=O)c1nc(NC2CCC3(CC3)N(C)C2=O)c2c3c(c(-c4ccc(F)c5sc(NC(=O)OC(C)(C)C)nc45)c(F)c2n1)COC3] | 701 |
| 88 | tert-Butyl (4-(3-(ethylsulfonyl)-5-fluoro-1-((5-methyl-6-oxo-5-azaspiro[2.5]octan-7-yl)amino)-7,9-dihydrofuro[3,4-f]quinazolin-6-yl)-7-fluorobenzo[d]thiazol-2-yl)carbamate | 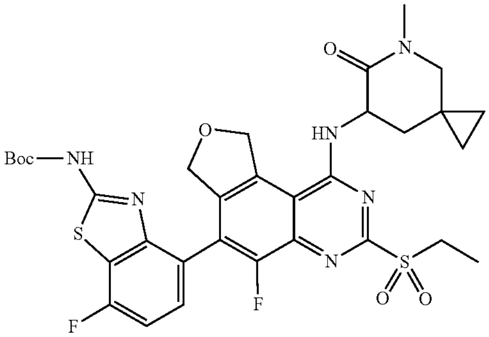 [SMILES: CCS(=O)(=O)c1nc(NC2CC3(CC3)CN(C)C2=O)c2c3c(c(-c4ccc(F)c5sc(NC(=O)OC(C)(C)C)nc45)c(F)c2n1)COC3] | 701 |
| 24A[2] | tert-Butyl (4-(5-chloro-3-(ethylsulfonyl)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 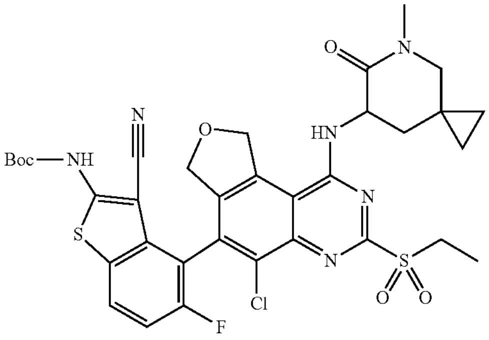 [SMILES: CCS(=O)(=O)c1nc(NC2CC3(CC3)CN(C)C2=O)c2c3c(c(-c4c(F)ccc5sc(NC(=O)OC(C)(C)C)c(C#N)c45)c(Cl)c2n1)COC3] | 741 |
| 25A[2] | tert-Butyl (4-(5-chloro-3-(ethylsulfonyl)-1-hydroxy-7,9-dihydrofuro[3,4-f]quinazolin-6-yl)-3-cyano-5-fluorobenzo[b]thiophen-2-yl)carbamate | 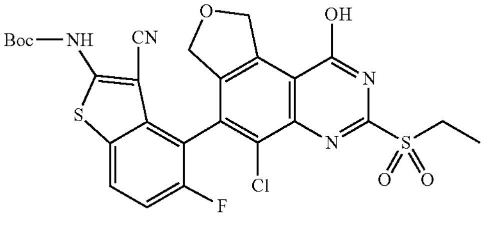 [SMILES: CCS(=O)(=O)c1nc(O)c2c3c(c(-c4c(F)ccc5sc(NC(=O)OC(C)(C)C)c(C#N)c45)c(Cl)c2n1)COC3] | 605 |

TABLE 11-continued

| Prepar-ation | Chemical Name | Structure | MS (ES) m/z (M + 1) |
|---|---|---|---|
| 26A[1] | tert-Butyl (4-(5-chloro-3-(ethylsulfonyl)-1-((4-methyl-5-oxo-4-azaspiro[2.4]heptan-6-yl)amino)-7,9-dihydrofuro[3,4-f]quinazolin-6-yl)-3-cyano-7-fluorobenzo[b]thiophen-2-yl)carbamate | 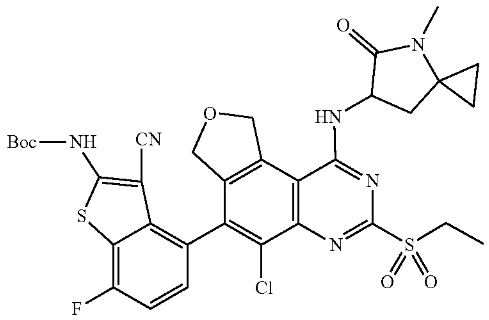 [SMILES: CCS(=O)(=O)c1nc(NC2CC3(CC3)N(C)C2=O)c2c3c(c(-c4ccc(F)c5sc(NC(=O)OC(C)(C)C)c(C#N)c45)c(Cl)c2n1)COC3] | 727 |
| 27A[1] | tert-Butyl (4-(5-chloro-3-(ethylsulfonyl)-1-hydroxy-7,9-dihydrofuro[3,4-f]quinazolin-6-yl)-3-cyano-7-fluorobenzo[b]thiophen-2-yl)carbamate | 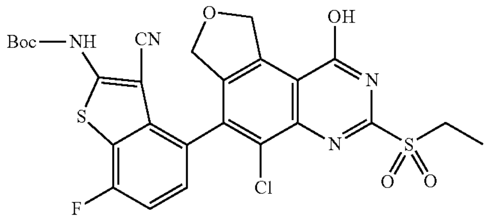 [SMILES: CCS(=O)(=O)c1nc(O)c2c3c(c(-c4ccc(F)c5sc(NC(=O)OC(C)(C)C)c(C#N)c45)c(Cl)c2n1)COC3] | 605 |
| 28A[1,4] | tert-Butyl (4-(5-chloro-3-(ethylsulfonyl)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate, Isomer 1 | 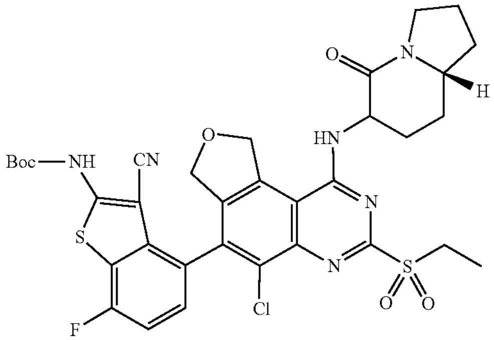 [SMILES: CCS(=O)(=O)c1nc(NC2CC[C@H]3CCCN3C2=O)c2c3c(c(-c4ccc(F)c5sc(NC(=O)OC(C)(C)C)c(C#N)c45)c(Cl)c2n1)COC3] | 741 |
| 29A[1,4] | tert-Butyl (4-(5-chloro-3-(ethylsulfonyl)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate, Isomer 2 | 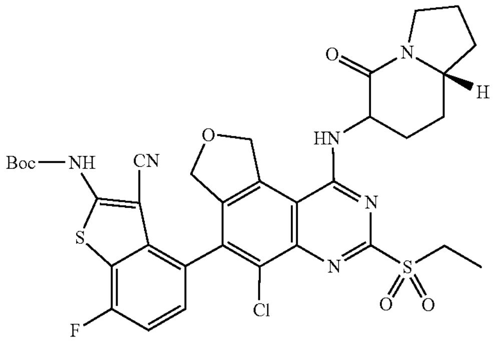 [SMILES: CCS(=O)(=O)c1nc(NC2CC[C@H]3CCCN3C2=O)c2c3c(c(-c4ccc(F)c5sc(NC(=O)OC(C)(C)C)c(C#N)c45)c(Cl)c2n1)COC3] | 741 |

TABLE 11-continued

| Preparation | Chemical Name | Structure | MS (ES) m/z (M + 1) |
|---|---|---|---|
| 30A | tert-Butyl (4-(3-(ethylsulfonyl)-5-fluoro-1-((5-methyl-6-oxo-5-azaspiro[3.5]nonan-7-yl)amino)-7,9-dihydrofuro[3,4-f]quinazolin-6-yl)-7-fluorobenzo[d]thiazol-2-yl)carbamate | 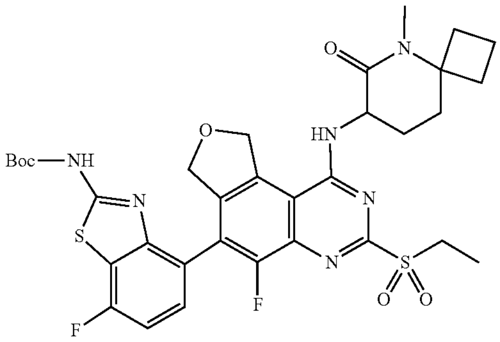 [SMILES: CCS(=O)(=O)c1nc(NC2CCC3(CCC3)N(C)C2=O)c2c3c(c(-c4ccc(F)c5sc(NC(=O)OC(C)(C)C)nc45)c(F)c2n1)COC3] | 715 |
| 31A[5] | (8aR)-6-((6-Bromo-5-chloro-3-(ethylsulfonyl)-7,9-dihydrofuro[3,4-f]quinazolin-1-yl)amino) hexahydroindolizin-5(1H)-one | 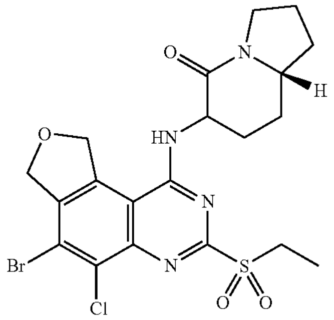 [SMILES: CCS(=O)(=O)c1nc(NC2CC[C@H]3CCCN3C2=O)c2c3c(c(Br)c(Cl)c2n1)COC3] | 529 |
| 32A[6] | (8aR)-6-((6-Bromo-5-chloro-3-(ethylsulfonyl)-7,9-dihydrofuro[3,4-f]quinazolin-1-yl)amino) hexahydroindolizin-5(1H)-one | 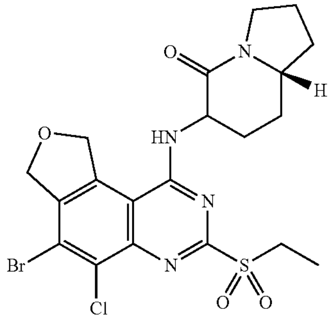 [SMILES: CCS(=O)(=O)c1nc(NC2CC[C@H]3CCCN3C2=O)c2c3c(c(Br)c(Cl)c2n1)COC3] | 529 |
| 33A | 6-((6-Bromo-5-chloro-3-(ethylsulfonyl)-7,9-dihydrofuro[3,4-f]quinazolin-1-yl)amino)-4-methyl-4-azaspiro[2.5]octan-5-one | 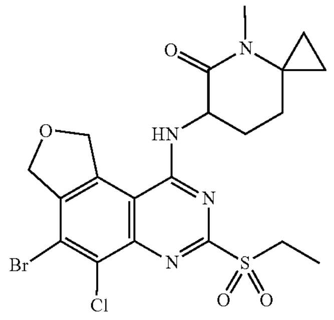 [SMILES: CCS(=O)(=O)c1nc(NC2CCC3(CC3)N(C)C2=O)c2c3c(c(Br)c(Cl)c2n1)COC3] | 529 |

TABLE 11-continued

| Prepar-ation | Chemical Name | Structure | MS (ES) m/z (M + 1) |
|---|---|---|---|
| 34A | 7-((6-Bromo-5-chloro-3-(ethylsulfonyl)-7,9-dihydrofuro[3,4-f]quinazolin-1-yl)amino)-5-methyl-5-azaspiro[2.5]octan-6-one | 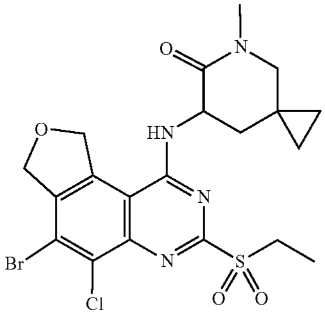 [SMILES: CCS(=O)(=O)c1nc(NC2CC3(CC3)CN(C)C2=O)c2c3c(c(Br)c(Cl)c2n1)COC3] | 529 |
| 35A | tert-Butyl (4-(5-chloro-3-(ethylsulfonyl)-1-((5-methyl-6-oxo-5-azaspiro[2.5]octan-7-yl)amino)-7,9-dihydrofuro[3,4-f]quinazolin-6-yl)-7-fluorothiazolo[4,5-c]pyridin-2-yl)carbamate | 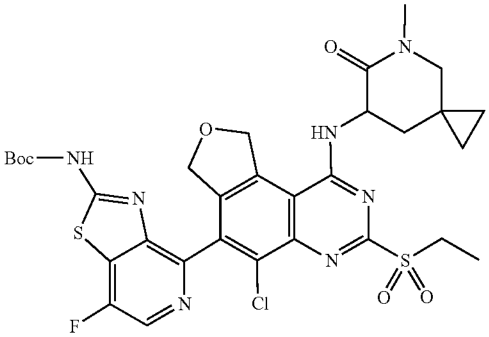 [SMILES: CCS(=O)(=O)c1nc(NC2CC3(CC3)CN(C)C2=O)c2c3c(c(-c4ncc(F)c5sc(NC(=O)OC(C)(C)C)nc45)c(Cl)c2n1)COC3] | 718 |
| 36A[7] | (9aS)-7-((6-Bromo-3-(ethylsulfonyl)-5-fluoro-7,9-dihydrofuro[3,4-f]quinazolin-1-yl)amino)hexahydropyrido[2,1-c][1,4]oxazin-6(1H)-one | 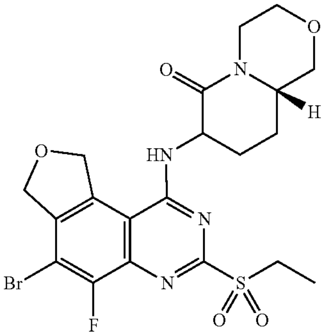 [SMILES: CCS(=O)(=O)c1nc(NC2CC[C@H]3COCCN3C2=O)c2c3c(c(Br)c(F)c2n1)COC3] | 529 |
| 37A | (6R,8aR)-6-((6-Bromo-3-(ethylsulfonyl)-5-fluoro-7,9-dihydrofuro[3,4-f]quinazolin-1-yl)amino)hexahydroindolizin-5(1H)-one | 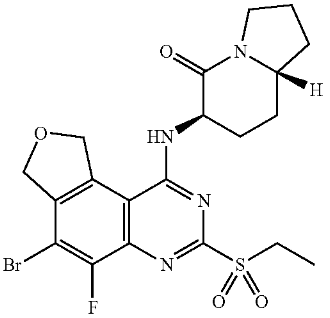 [SMILES: CCS(=O)(=O)c1nc(N[C@@H]2CC[C@H]3CCCN3C2=O)c2c3c(c(Br)c(F)c2n1)COC3] | 513 |

TABLE 11-continued

| Preparation | Chemical Name | Structure | MS (ES) m/z (M + 1) |
|---|---|---|---|
| 38A | 7-((6-Bromo-3-(ethylsulfonyl)-5-fluoro-7,9-dihydrofuro[3,4-f]quinazolin-1-yl)amino)-5-azaspiro[3.5]nonan-6-one | 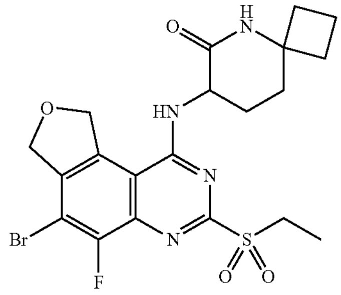 [SMILES: CCS(=O)(=O)c1nc(NC2CCC3(CCC3)NC2=O)c2c3c(c(Br)c(F)c2n1)COC3] | 513 |
| 39A | 7-((6-Bromo-3-(ethylsulfonyl)-5-fluoro-7,9-dihydrofuro[3,4-f]quinazolin-1-yl)amino)-5-methyl-5-azaspiro[3.5]nonan-6-one | 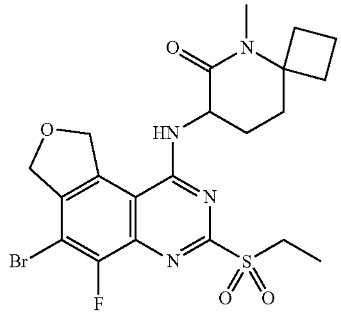 [SMILES: CCS(=O)(=O)c1nc(NC2CCC3(CCC3)N(C)C2=O)c2c3c(c(Br)c(F)c2n1)COC3] | 527 |
| 40A | 6-Bromo-5-chloro-3-(ethylsulfonyl)-7,9-dihydrofuro[3,4-f]quinazolin-1-ol | 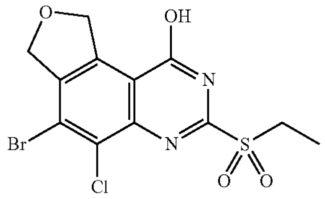 [SMILES: CCS(=O)(=O)c1nc(O)c2c3c(c(Br)c(Cl)c2n1)COC3] | 392 |
| 41A[2,7] | tert-Butyl (4-(5-chloro-3-(ethylsulfonyl)-1-(((8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate | 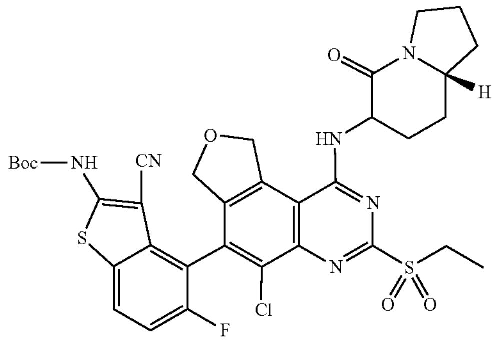 [SMILES: CCS(=O)(=O)c1nc(NC2CC[C@H]3CCCN3C2=O)c2c3c(c(-c4c(F)ccc5sc(NC(=O)OC(C)(C)C)c(C#N)c45)c(Cl)c2n1)COC3] | 741 |
| 42A[7] | (8aR)-6-((6-Bromo-3-(ethylsulfonyl)-5-fluoro-7,9-dihydrofuro[3,4-f]quinazolin-1-yl)amino)hexahydroindolizin-5(1H)-one | 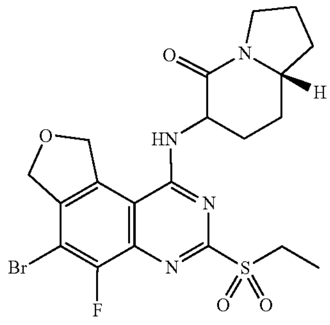 [SMILES: CCS(=O)(=O)c1nc(NC2CC[C@H]3CCCN3C2=O)c2c3c(c(Br)c(F)c2n1)COC3] | 513 |

TABLE 11-continued

| Preparation | Chemical Name | Structure | MS (ES) m/z (M + 1) |
| --- | --- | --- | --- |
| 43A[7] | tert-Butyl (4-(3-(ethylsulfonyl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate | 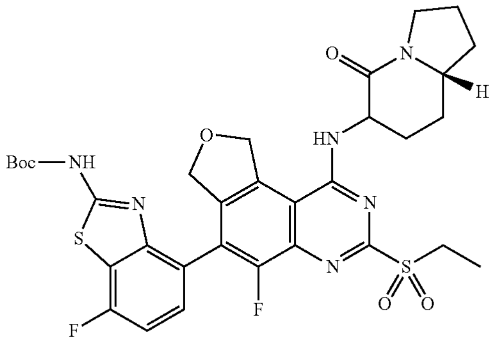 [SMILES: CCS(=O)(=O)c1nc(NC2CC[C@H]3CCCN3C2=O)c2c3c(c(-c4ccc(F)c5sc(NC(=O)OC(C)(C)C)nc45)c(F)c2n1)COC3] | 701 |
| 32B[2] | tert-Butyl (4-(5-chloro-3-(ethylsulfonyl)-1-(((6R,8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate | 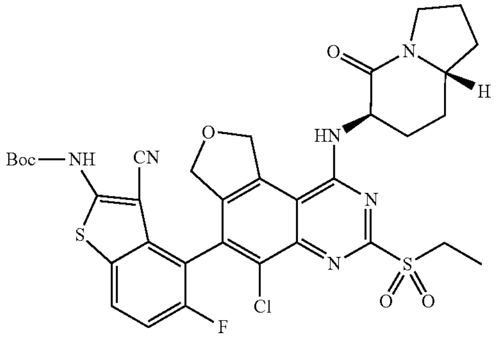 [SMILES: CCS(=O)(=O)c1nc(N[C@@H]2CC[C@H]3CCCN3C2=O)c2c3c(c(-c4c(F)ccc5sc(NC(=O)OC(C)(C)C)c(C#N)c45)c(Cl)c2n1)COC3] | 741 |
| 33B[1] | tert-Butyl (4-(5-chloro-3-(ethylsulfonyl)-1-(((6R,8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 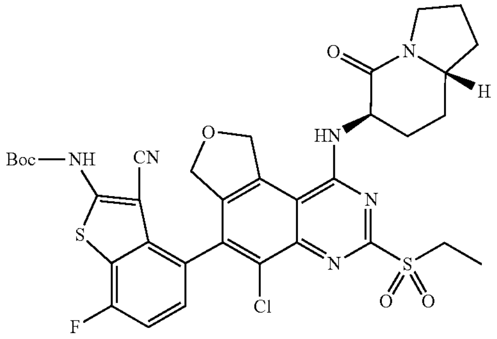 [SMILES: CCS(=O)(=O)c1nc(N[C@@H]2CC[C@H]3CCCN3C2=O)c2c3c(c(-c4ccc(F)c5sc(NC(=O)OC(C)(C)C)c(C#N)c45)c(Cl)c2n1)COC3] | 741 |
| 34B[1,7] | tert-Butyl (4-(5-chloro-3-(ethylsulfonyl)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 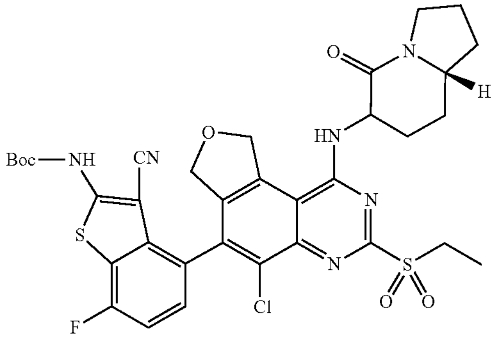 [SMILES: CCS(=O)(=O)c1nc(NC2CC[C@H]3CCCN3C2=O)c2c3c(c(-c4ccc(F)c5sc(NC(=O)OC(C)(C)C)c(C#N)c45)c(Cl)c2n1)COC3] | 741 |

TABLE 11-continued

| Preparation | Chemical Name | Structure | MS (ES) m/z (M + 1) |
| --- | --- | --- | --- |
| 35B[8] | tert-Butyl (3-cyano-4-(3-(ethylsulfonyl)-5-fluoro-1-(((6R,8aR)-5-oxooctahydroindolizin-6-yl)amino)-7,9-dihydrofuro[3,4-f]quinazolin-6-yl)-5-fluorobenzo[b]thiophen-2-yl)carbamate | 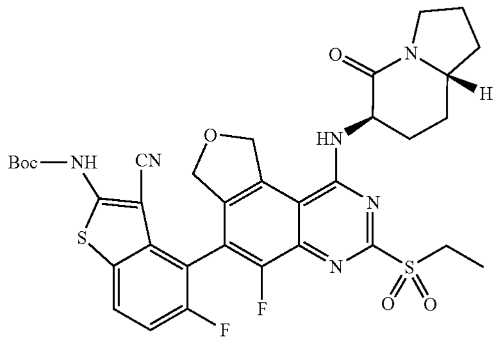 [SMILES: CCS(=O)(=O)c1nc(N[C@@H]2CC[C@H]3CCCN3C2=O)c2c3c(c(-c4c(F)ccc5sc(NC(=O)OC(C)(C)C)c(C#N)c45)c(F)c2n1)COC3] | 725 |
| 36B[8,9] | tert-Butyl (3-cyano-4-(1-(((8aS)-2,2-difluoro-5-oxooctahydroindolizin-6-yl)amino)-3-(ethylsulfonyl)-5-fluoro-7,9-dihydrofuro[3,4-f]quinazolin-6-yl)-5-fluorobenzo[b]thiophen-2-yl)carbamate | 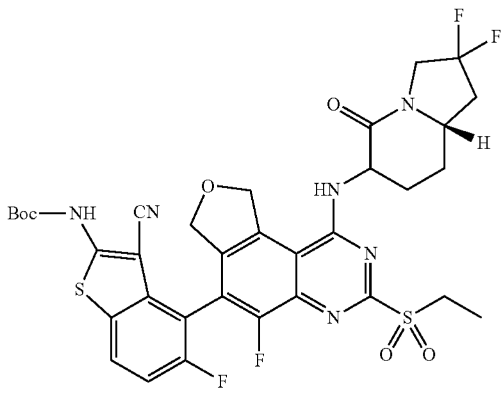 [SMILES: CCS(=O)(=O)c1nc(NC2CC[C@H]3CC(F)(F)CN3C2=O)c2c3c(c(-c4c(F)ccc5sc(NC(=O)OC(C)(C)C)c(C#N)c45)c(F)c2n1)COC3] | 761 |
| 37B | tert-Butyl (4-(5-chloro-3-(ethylsulfonyl)-1-(((6R,8aR)-5-oxooctahydroindolizin-6-yl)amino)-7,9-dihydrofuro[3,4-f]quinazolin-6-yl)-3-cyano-7-fluorothieno[3,2-c]pyridin-2-yl)carbamate | 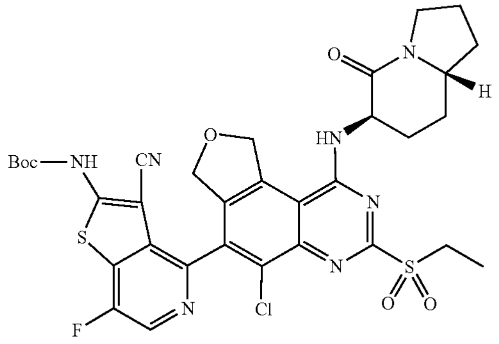 [SMILES: CCS(=O)(=O)c1nc(N[C@@H]2CC[C@H]3CCCN3C2=O)c2c3c(c(-c4ncc(F)c5sc(NC(=O)OC(C)(C)C)c(C#N)c45)c(Cl)c2n1)COC3] | 742 |
| 38B | (6R,8aR)-6-((6-Bromo-5-chloro-3-(ethylsulfonyl)-7,9-dihydrofuro[3,4-f]quinazolin-1-yl)amino)hexahydroindolizin-5(1H)-one | 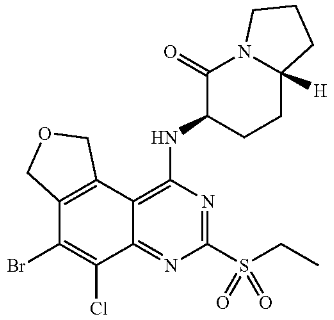 [SMILES: CCS(=O)(=O)c1nc(N[C@@H]2CC[C@H]3CCCN3C2=O)c2c3c(c(Br)c(Cl)c2n1)COC3] | 529 |

TABLE 11-continued

| Preparation | Chemical Name | Structure | MS (ES) m/z (M + 1) |
|---|---|---|---|
| 39B | tert-Butyl (4-(3-(ethylsulfonyl)-5-fluoro-1-hydroxy-7,9-dihydrofuro[3,4-f]quinazolin-6-yl)-7-fluorobenzo[d]thiazol-2-yl)carbamate | 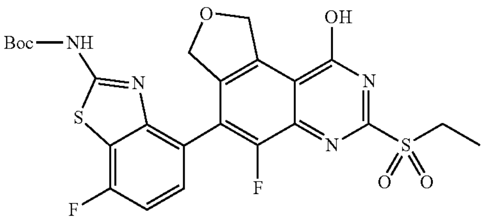 [SMILES: CCS(=O)(=O)c1nc(O)c2c3c(c(-c4ccc(F)c5sc(NC(=O)OC(C)(C)C)nc45)c(F)c2n1)COC3] | 563 (M − 1) |
| 40B | (6R)-3-((6-Bromo-3-(ethylsulfonyl)-5-fluoro-7,9-dihydrofuro[3,4-f]quinazolin-1-yl)amino)-6-(difluoromethyl)-1-methylpiperidin-2-one | 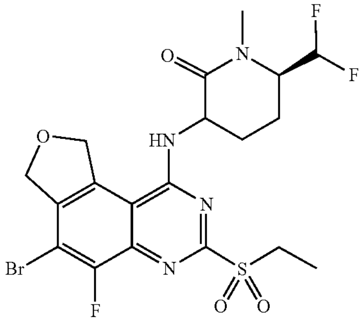 [SMILES: CCS(=O)(=O)c1nc(NC2CC[C@H](C(F)F)N(C)C2=O)c2c3c(c(Br)c(F)c2n1)COC3] | 537 |

[1]Clean atropisomer, chiral purification from Preparation 30
[2]Clean atropisomer, chiral purification from Preparation 34
[3]Normal Phase; silica, 0-100% EtOAc in DCM
[4]Normal Phase; silica, 0-100% EtOAc in DCM, Isomer refers to a clean isomer at the 6-position of the hexahydroindolizinone
[5]Clean isomer at the 6-position of the hexahydroindolizinone, chiral purification from Preparation 13A
[6]Clean isomer at the 6-position of the hexahydroindolizinone, chiral purification from Preparation 14A
[7]A predominant chiral center is present based on starting material from Preparation 53, 54, 55, 5A, 6A, 7A, or 8A
[8]Clean atropisomer, chiral purification from Preparation 32
[9]Clean isomer at the 6-position of the hexahydroindolizinone, chiral purification from Preparation 18B

Preparation 89 tert-Butyl 6-methyl-3,6-diazabicyclo[3.2.0]heptane-3-carboxylate

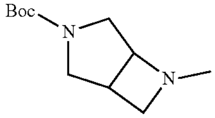

tert-Butyl 3,6-diazabicyclo[3.2.0]heptane-3-carboxylate (mix of cis isomers; 0.300 g, 1.51 mmol), formaldehyde (37 wt %; 0.737 g, 9.08 mmol), and sodium triacetoxyborohydride (1.92 g, 9.08 mmol) were dissolved in methanol (6 mL). The mixture was heated at 50° C. After 18 h, the mixture was cooled, concentrated under reduced pressure, and diluted with saturated aqueous sodium bicarbonate (20 mL). The mixture was extracted with EtOAc (3×50 mL). The combined organic layers were washed with brine (25 mL), dried over anhydrous $Na_2SO_4$, filtered, and concentrated under reduced pressure to give the crude title compound (mix of cis isomers; 0.365 g) as a colorless oil. MS (ES) m/z=213 (M+1).

The following compounds in Table 12 were prepared in similar manner as described in Preparation 89. Different reductive amination conditions, such as sodium cyanoborohydride with sodium dihydrogen phosphate, may have been substituted. Various methods were used to purify the compounds, which would be apparent to one skilled in the art.

TABLE 12

| Preparation | Chemical Name | Structure | MS (ES) m/z (M + 1) |
|---|---|---|---|
| 90 | tert-Butyl (2S,3S)-3-(dimethylamino)-2-methylpyrrolidine-1-carboxylate | 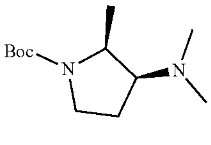 [SMILES: C[C@H]1[C@@H](N(C)C)CCN1C(=O)OC(C)(C)C] | 229 |

TABLE 12-continued

| Preparation | Chemical Name | Structure | MS (ES) m/z (M + 1) |
|---|---|---|---|
| 91 | tert-Butyl (3aR,6aR)-1-methylhexahydropyrrolo [3,4-b]pyrrole-5(1H)-carboxylate | 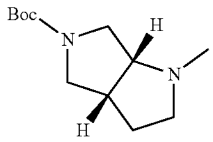 [SMILES: CN1CC[C@@H]2CN(C(=O)OC(C)(C)C)C[C@@H]21] | 227 |
| 44A | tert-Butyl (3aS,6aS)-1-methylhexahydropyrrolo [3,4-b]pyrrole-5(1H)-carboxylate | 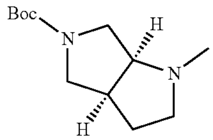 [SMILES: CN1CC[C@H]2CN(C(=O)OC(C)(C)C)C[C@H]21] | 227 |
| 45A | tert-Butyl (3R,4S)-3-(dimethylamino)-4-hydroxypyrrolidine-1-carboxylate | 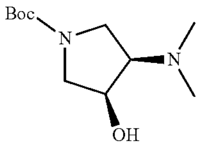 [SMILES: CN(C)[C@@H]1CN(C(=O)OC(C)(C)C)C[C@@H]1O] | |
| 46A | tert-Butyl (3S,4R)-3-hydroxy-4-(isopropylamino)pyrrolidine-1-carboxylate | 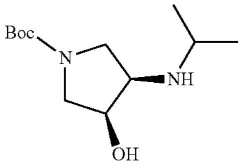 [SMILES: CC(C)N[C@@H]1CN(C(=O)OC(C)(C)C)C[C@@H]1O] | |
| 47A | tert-Butyl (3S,4R)-3-hydroxy-4-(isopropyl(methyl)amino) pyrrolidine-1-carboxylate | 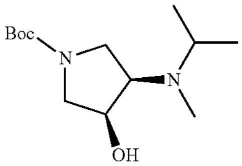 [SMILES: CC(C)N(C)[C@@H]1CN(C(=O)OC(C)(C)C)C[C@@H]1O] | 259 |
| 41B[1,2] | tert-Butyl (2S,3S)-2-methyl-3-((methyl-d3)amino)pyrrolidine-1-carboxylate | 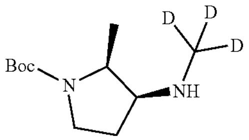 [SMILES: [2H]C([2H])([2H])N[C@H]1CCN(C(=O)OC(C)(C)C)[C@H]1C] | |
| 42B[1] | tert-Butyl (2S,3S)-3-(bis(methyl-d3)amino)-2-methylpyrrolidine-1-carboxylate | 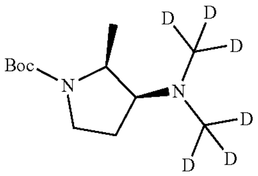 [SMILES: [2H]C([2H])([2H])N([C@H]1CCN(C(=O)OC(C)(C)C)[C@H]1C)C([2H])([2H])[2H]] | 235 |
| 43B[3] | tert-Butyl (2S,3S)-3-(ethylamino)-2-methylpyrrolidine-1-carboxylate | 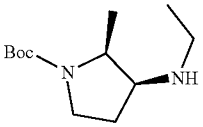 [SMILES: CCN[C@H]1CCN(C(=O)OC(C)(C)C)[C@H]1C] | |
| 44B | tert-Butyl (2S,3S)-3-(diethylamino)-2-methylpyrrolidine-1-carboxylate | 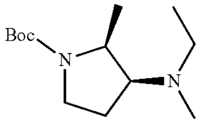 | 257 |

TABLE 12-continued

| Preparation | Chemical Name | Structure | MS (ES) m/z (M + 1) |
|---|---|---|---|
| 45B | tert-Butyl (6S)-1,6-dimethylhexahydropyrrolo [3,4-b]pyrrole-5(1H)-carboxylate | 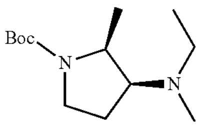 [SMILES: CCN(C)[C@H]1CCN(C(=O)OC(C)(C)C)[C@H]1C] | 241 |

[1]Reaction used deuterated formaldehyde, deuterated acetic acid, and sodium cyanoborodeuteride in methanol
[2]Not isolated; generated and consumed in the synthesis of Preparation 42B
[3]Not isolated; generated and consumed in the synthesis of Preparation 44B

Preparation 48A tert-Butyl (2S,4S)-4-((tert-butyldimethylsilyl)oxy)-2-methyl-3-oxopyrrolidine-1-carboxylate

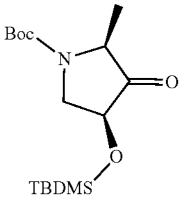

To a solution of DMSO (2.03 mL, 28.6 mmol) in DCM (60 mL) was added oxalyl chloride (2M in DCM; 7.15 mL, 14.3 mmol) at −78° C. under nitrogen. The mixture was stirred at −78° C. for 1 h, then tert-butyl (2S,3S,4S)-4-((tert-butyldimethylsilyl)oxy)-3-hydroxy-2-methylpyrrolidine-1-carboxylate (2.37 g, 7.15 mmol) in DCM (10 mL) was added. Triethylamine (5.98 mL, 42.9 mmol) was added. The mixture was stirred at −78° C. for 10 min, then at 25° C. for 45 min. The mixture was diluted with water and extracted with DCM (3×30 mL). The combined organic layers were washed with brine, dried over anhydrous $Na_2SO_4$, filtered, and concentrated under reduced pressure to give the crude title compound as an orange oil. MS (ES) m/z=274 (M+1-tBu).

Preparation 49A tert-Butyl (2S,3S)-3-(ethyl(methyl)amino)-2-methylpyrrolidine-1-carboxylate

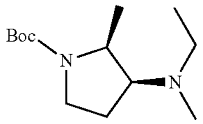 [SMILES: CCN(C)[C@H]1CCN(C(=O)OC(C)(C)C)[C@H]1C]

To a solution of tert-butyl (S)-2-methyl-3-oxopyrrolidine-1-carboxylate (1.00 g, 5.02 mmol), acetic acid (0.287 mL, 5.02 mmol), and N-methylethanamine (0.445 g, 7.53 mmol) in DCM (5 mL) was added sodium triacetoxyborohydride (1.70 g, 8.03 mmol) portionwise. The mixture was stirred at room temperature. After 22 h, the mixture was cooled to 0° C. and quenched with aqueous sodium bicarbonate. The two layers were separated. The aqueous layer was extracted with DCM. The combined organic layers were washed with brine, dried over anhydrous $Na_2SO_4$, filtered, and concentrated under reduced pressure. The residue was purified by reversed phase purification (C18 column), eluting with 0-100% acetonitrile in (0.1% formic acid in water), to give the title compound (1.32 g) as a colorless oil. MS (ES) m/z=243 (M+1).

Preparation 50A tert-Butyl (2S,3R,4S)-4-((tert-butyldimethylsilyl)oxy)-3-(dimethylamino)-2-methylpyrrolidine-1-carboxylate

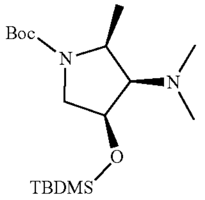

tert-Butyl (2S,4S)-4-((tert-butyldimethylsilyl)oxy)-2-methyl-3-oxopyrrolidine-1-carboxylate and dimethylamine were used in a manner analogous to the method of Preparation 49A to afford the title compound (1.12 g) as a yellow oil. MS (ES) m/z=359 (M+1).

Preparation 51A tert-Butyl (2S)-3-(azetidin-1-yl)-2-methylpyrrolidine-1-carboxylate

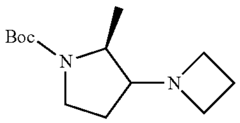 [SMILES: C[C@H]1C(N2CCC2)CCN1C(=O)OC(C)(C)C]

tert-Butyl (S)-2-methyl-3-oxopyrrolidine-1-carboxylate and azetidine were used in a manner analogous to the method ofPreparation 49A to afford the title compound (0.60 g, 99%) as a yellow oil. MS (ES) nVz=241 (M+1).

The following compounds in Table 13 were prepared in similar manner as described in Preparation 49A. Various methods were used to purify the compounds, which would be apparent to one skilled in the art.

TABLE 13

| Preparation | Chemical Name | Structure | MS (ES) m/z (M + 1) |
|---|---|---|---|
| 46B | tert-Butyl (2S,3S)-3-(3-(fluoromethyl)azetidin-1-yl)-2-methylpyrrolidine-1-carboxylate | 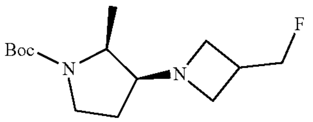 [SMILES: C[C@H]1[C@@H](N2CC(CF)C2)CCN1C(=O)OC(C)(C)C] | 273 |
| 47B | tert-Butyl (2S)-2-methyl-3-(5-azaspiro[2.3]hexan-5-yl)pyrrolidine-1-carboxylate | 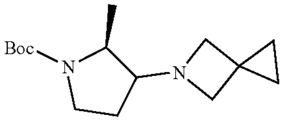 [SMILES: C[C@H]1C(N2CC3(CC3)C2)CCN1C(=O)OC(C)(C)C] | 267 |
| 48B | tert-Butyl (2S,3S)-3-(6-fluoro-2-azaspiro[3.3]heptan-2-yl)-2-methylpyrrolidine-1-carboxylate | 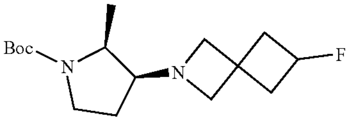 [SMILES: C[C@H]1[C@@H](N2CC3(CC(F)C3)C2)CCN1C(=O)OC(C)(C)C] | 299 |
| 49B | tert-Butyl (2S,3S)-2-methyl-3-(5-azaspiro[2.3]hexan-5-yl)pyrrolidine-1-carboxylate | 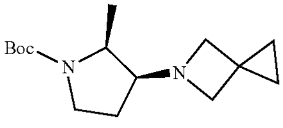 [SMILES: C[C@H]1[C@@H](N2CC3(CC3)C2)CCN1C(=O)OC(C)(C)C] | 267 |
| 50B | tert-Butyl (2S,3S)-3-((3-fluorocyclobutyl)(methyl)amino)-2-methylpyrrolidine-1-carboxylate | 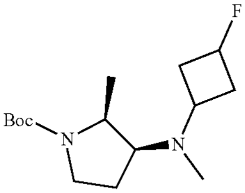 [SMILES: C[C@H]1[C@@H](N(C)C2CC(F)C2)CCN1C(=O)OC(C)(C)C] | 287 |

Preparation 52A tert-Butyl (2’S,3’S)-2'-methyl-[1,3'-bipyrrolidine]-1'-carboxylate

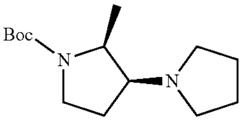 [SMILES: C[C@H]1[C@@H](N2CCCC2)CCN1C(=O)OC(C)(C)C]

tert-Butyl (2S,3S)-3-amino-2-methylpyrrolidine-1-carboxylate (2.5 g, 12 mmol), potassium iodide (1.0 g, 6.2 mmol), 1,4-dibromobutane (4.0 g, 19 mmol), and potassium carbonate (8.6 g, 62 mmol) were combined in acetonitrile (50 mL). The mixture was stirred at 70° C. overnight. The mixture was filtered through diatomaceous earth and the filtrate was concentrated under reduced pressure to give the crude title compound (3.0 g, 94%). MS (ES) m/z=255 (M+1).

Preparation 92

6-Methyl-3,6-diazabicyclo[3.2.0]heptane dihydrochloride

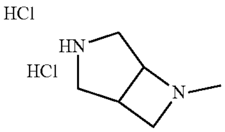

To a mixture of tert-butyl 6-methyl-3,6-diazabicyclo[3.2.0]heptane-3-carboxylate (mix of cis isomers; 0.370 g, 1.74 mmol) in DCM (3 mL) was added HCl (4M in 1,4-dioxane; 3 mL). The mixture was stirred at room temperature. After 6 h, the mixture was concentrated under reduced pressure to give the crude title compound (mix of cis isomers; 0.300 g) as a yellow solid. MS (ES) m/z=113 (M+1).

The following compounds in Table 14 were prepared in similar manner as described in Preparation 92. Different acidic conditions, such as trifluoroacetic acid, may have been substituted. Various methods were used to purify the compounds, which would be apparent to one skilled in the art.

TABLE 14

| Preparation | Chemical Name | Structure | MS (ES) m/z (M + 1) |
|---|---|---|---|
| 93 | (2S,3S)-N,N,2-Trimethylpyrrolidin-3-amine dihydrochloride | 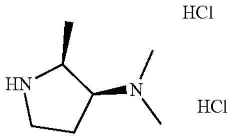 | 129 |
| 94 | (2S,3S)-N,N,2-Trimethylpyrrolidin-3-amine | 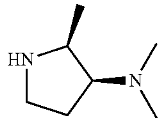 | 129 |
| 95 | (3aR,6aR)-1-Methyloctahydropyrrolo[3,4-b]pyrrole dihydrochloride | 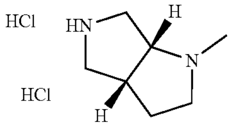 | 127 |
| 53A | (3aS,6aS)-1-Methyloctahydropyrrolo[3,4-b]pyrrole dihydrochloride | 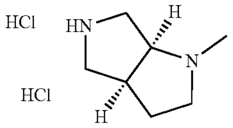 | 127 |
| 54A | (2S,3S)-N-Ethyl-N,2-dimethylpyrrolidin-3-amine dihydrochloride | 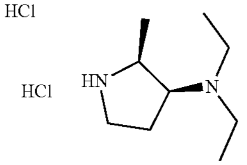 | 143 |
| 55A | (2S,3S)-N-Ethyl-N,2-dimethylpyrrolidin-3-amine | 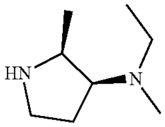 | 143 |
| 56A | (3S,4R)-4-(Dimethylamino)pyrrolidin-3-ol dihydrochloride | 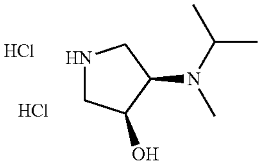 | 131 |
| 57A | (3S,4R)-4-(Isopropyl(methyl)amino)pyrrolidin-3-ol dihydrochloride | 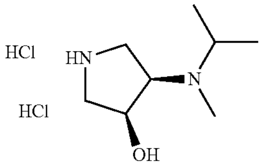 | 159 |
| 58A | (2S,3R,4S)-4-((tert-Butyldimethylsilyl)oxy)-N,N,2-trimethylpyrrolidin-3-amine dihydrochloride | 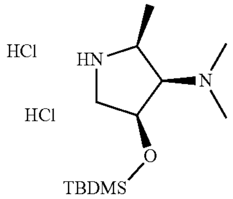 | 259 |

TABLE 14-continued

| Preparation | Chemical Name | Structure | MS (ES) m/z (M + 1) |
|---|---|---|---|
| 59A | (2S)-3-(Azetidin-1-yl)-2-methylpyrrolidine dihydrochloride | 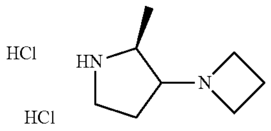 | 141 |
| 60A | (2'S,3'S)-2'-Methyl-1,3'-bipyrrolidine dihydrochloride | 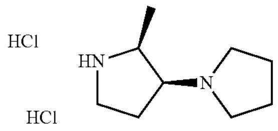 | 155 |
| 51B | (2S,3S)-3-(3-(Fluoromethyl)azetidin-1-yl)-2-methylpyrrolidine | 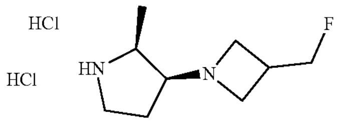 | 173 |
| 52B | 5-((2S)-2-Methylpyrrolidin-3-yl)-5-azaspiro[2.3]hexane dihydrochloride | 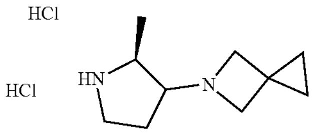 | 167 |
| 53B | (2S,3S)-2-Methyl-N,N-bis(methyl-d3)pyrrolidin-3-amine dihydrochloride | 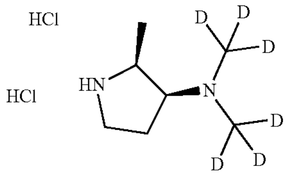 | 135 |
| 54B | (2S,3S)-N,N-Diethyl-2-methylpyrrolidin-3-amine | 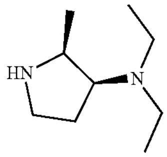 | 157 |
| 55B | 6-Fluoro-2-((2S,3S)-2-methylpyrrolidin-3-yl)-2-azaspiro[3.3]heptane dihydrochloride | 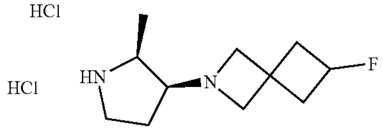 | 199 |
| 56B | 5-((2S,3S)-2-Methylpyrrolidin-3-yl)-5-azaspiro[2.3]hexane dihydrochloride | 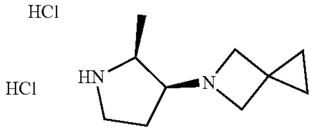 | 167 |
| 57B | (2S,3S)-N-(3-Fluorocyclobutyl)-N,2-dimethylpyrrolidin-3-amine dihydrochloride | 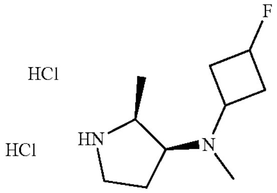 | 187 |

TABLE 14-continued

| Preparation | Chemical Name | Structure | MS (ES) m/z (M + 1) |
|---|---|---|---|
| 58B | (6S)-1,6-Dimethyloctahydropyrrolo[3,4-b]pyrrole dihydrochloride | 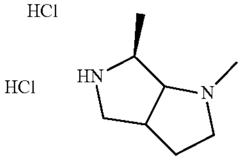 | 141 |

Preparation 59B

(6R,8aR)-6-((4-Bromo-7-((2S,3S)-3-(dimethylamino)-2-methylpyrrolidin-1-yl)-5-fluoro-1,3-dihydrofuro[3,4-f]quinolin-9-yl)amino)hexahydroindolizin-5(1H)-one

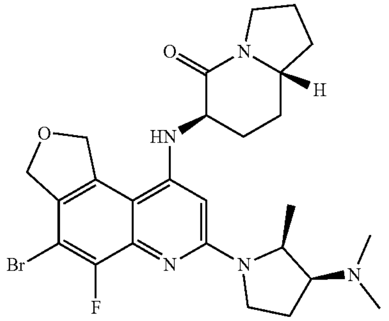 [SMILES: C[C@H]1[C@@H](N(C)C)CCN1c1cc(N[C@@H]2CC[C@H]3CCCN3C2=O)c2c3c(c(Br)c(F)c2n1)COC3]

To a mixture of (6R,8aR)-6-((4-bromo-7-chloro-5-fluoro-1,3-dihydrofuro[3,4-f]quinolin-9-yl)amino)hexahydroindolizin-5(1H)-one (0.083 g, 0.183 mmol), (2S,3S)—N,N,2-trimethylpyrrolidin-3-amine dihydrochloride (0.128 g, 0.639 mmol), and CsF (0.028 g, 0.183 mmol) in NMP (0.913 mL) was added diisopropylethylamine (0.32 mL, 1.83 mmol). The mixture was heated at 110° C. for 32 h, then cooled to room temperature and diluted with water. The mixture was purified by reversed phase purification (C18 column), eluting with 0-100% acetonitrile in (0.1% formic acid in water), to obtain the title compound (0.070 g, 70%). MS (ES) m/z=546 (M+1).

The following compounds in Table 15 were prepared in similar manner as described in Preparation 59B. Various methods were used to purify the compounds, which would be apparent to one skilled in the art.

TABLE 15

| Prep | Chemical Name | Structure | MS (ES) m/z (M + 1) |
|---|---|---|---|
| 60B | (6R,8aR)-6-((4-Bromo-5-fluoro-7-((2'S,3'S)-2'-methyl-[1,3'-bipyrrolidin]-1'-yl)-1,3-dihydrofuro[3,4-f]quinolin-9-yl)amino)hexahydroindolizin-5(1H)-one | 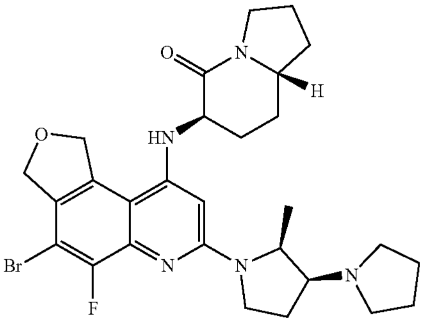 [SMILES: C[C@H]1[C@@H](N2CCCC2)CCN1c1cc(N[C@@H]2CC[C@H]3CCCN3C2=O)c2c3c(c(Br)c(F)c2n1)COC3] | 572 |

TABLE 15-continued

| Prep | Chemical Name | Structure | MS (ES) m/z (M + 1) |
| --- | --- | --- | --- |
| 61B | (6R,8aR)-6-((4-Bromo-5-chloro-7-((2S,3S)-3-(dimethylamino)-2-methylpyrrolidin-1-yl)-1,3-dihydrofuro[3,4-f]quinolin-9-yl)amino)hexahydroindolizin-5(1H)-one | 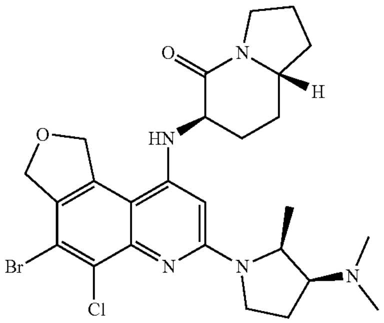 [SMILES: C[C@H]1[C@@H](N(C)C)CCN1c1cc(N[C@@H]2CC[C@H]3CCCN3C2=O)c2c3c(c(Br)c(Cl)c2n1)COC3] | 562 |

Preparation 96 tert-Butyl (4-(3-((2S,3S)-3-(dimethylamino)-2-methylpyrrolidin-1-yl)-5-fluoro-1-((5-methyl-6-oxo-5-azaspiro[2.5]octan-7-yl)amino)-7,9-dihydrofuro[3,4-f]quinazolin-6-yl)-7-fluorobenzo[d]thiazol-2-yl)carbamate

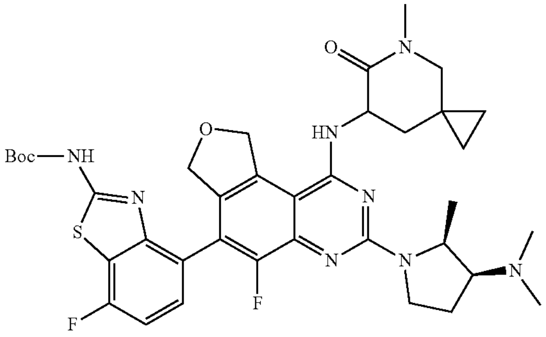 [SMILES: C[C@H]1[C@@H](N(C)C)CCN1c1nc(NC2CC3(CC3)CN(C)C2=O)c2c3c(c(-c4ccc(F)c5sc(NC(=O)OC(C)(C)C)nc45)c(F)c2n1)COC3]

tert-Butyl (4-(3-(ethylsulfonyl)-5-fluoro-1-((5-methyl-6-oxo-5-azaspiro[2.5]octan-7-yl)amino)-7,9-dihydrofuro[3,4-f]quinazolin-6-yl)-7-fluorobenzo[d]thiazol-2-yl)carbamate (0.080 g, 0.11 mmol) was mixed with diisopropylethylamine (0.30 mL, 1.7 mmol), (2S,3S)—N,N,2-trimethylpyrrolidin-3-amine dihydrochloride (0.11 g, 0.57 mmol), CsF (0.017 g, 0.11 mmol), and acetonitrile (3 mL). The mixture was heated at 70° C. for 16 h. The mixture was concentrated under reduced pressure. The residue was purified on silica, eluting with 0-40% MeOH in DCM to obtain the title compound (0.072 g, 86%) as a yellow solid. MS (ES) n/z=735 (M+1).

The following compounds in Table 16 were prepared in similar manner as described in Preparation 96. Different bases may have been substituted. Various methods were used to purify the compounds, which would be apparent to one skilled in the art.

TABLE 16

| Prep | Chemical Name | Structure | MS (ES) m/z (M + 1) |
| --- | --- | --- | --- |
| 97 | tert-Butyl (4-(5-chloro-3-((S)-3-(dimethylamino)pyrrolidin-1-yl)-1-((4-methyl-5-oxo-4-azaspiro[2.5]octan-6-yl)amino)-7,9-dihydrofuro[3,4-f]quinazolin-6-yl)-3-cyano-5-fluorobenzo[b]thiophen-2-yl)carbamate | 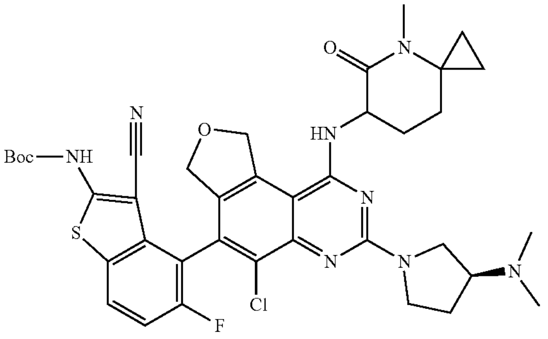 [SMILES: CN(C)[C@H]1CCN(c2nc(NC3CCC4(CC4)N(C)C3=O)c3c4c(c(-c5c(F)ccc6sc(NC(=O)OC(C)(C)C)c(C#N)c56)c(Cl)c3n2)COC4)C1] | 761 |

TABLE 16-continued

| Prep | Chemical Name | Structure | MS (ES) m/z (M + 1) |
|---|---|---|---|
| 98[1] | tert-Butyl (4-(5-chloro-3-(3-(dimethylamino)azetidin-1-yl)-1-((5-methyl-6-oxo-5-azaspiro[3.5]nonan-7-yl)amino)-7,9-dihydrofuro[3,4-f]quinazolin-6-yl)-3-cyano-7-fluorobenzo[b]thiophen-2-yl)carbamate | 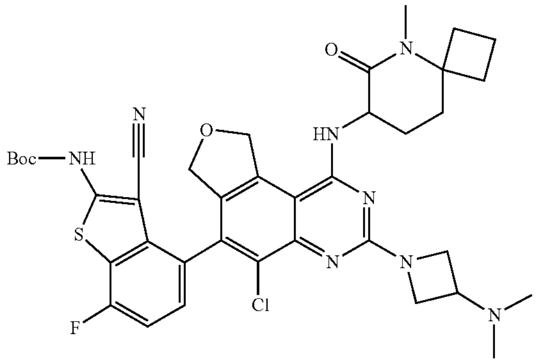 [SMILES: CN(C)C1CN(c2nc(NC3CCC4(CCC4)N(C)C3=O)c3c4c(c(-c5ccc(F)c6sc(NC(=O)OC(C)(C)C)c(C#N)c56)c(Cl)c3n2)COC4)C1] | 761 |
| 99[1] | tert-Butyl (4-(5-chloro-3-(3-(dimethylamino)azetidin-1-yl)-1-((4-methyl-5-oxo-4-azaspiro[2.5]octan-6-yl)amino)-7,9-dihydrofuro[3,4-f]quinazolin-6-yl)-3-cyano-7-fluorobenzo[b]thiophen-2-yl)carbamate | 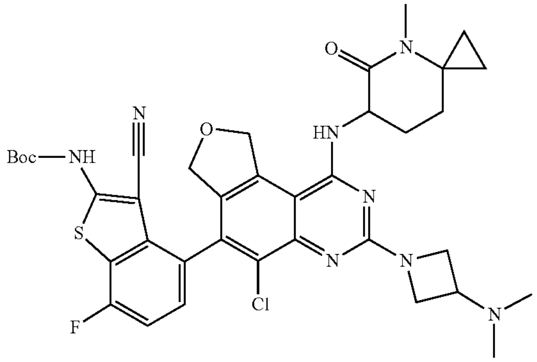 [SMILES: CN(C)C1CN(c2nc(NC3CCC4(CC4)N(C)C3=O)c3c4c(c(-c5ccc(F)c6sc(NC(=O)OC(C)(C)C)c(C#N)c56)c(Cl)c3n2)COC4)C1] | 747 |
| 100[1,4] | diazabicyclo[3.2.0]heptan-3-yl)-tert-Butyl (4-(5-chloro-1-((4-methyl-5-oxo-4-azaspiro[2.5]octan-6-yl)amino)-3-(6-methyl-3,6-7,9-dihydrofuro[3,4-f]quinazolin-6-yl)-3-cyano-7-fluorobenzo[b]thiophen-2-yl)carbamate | 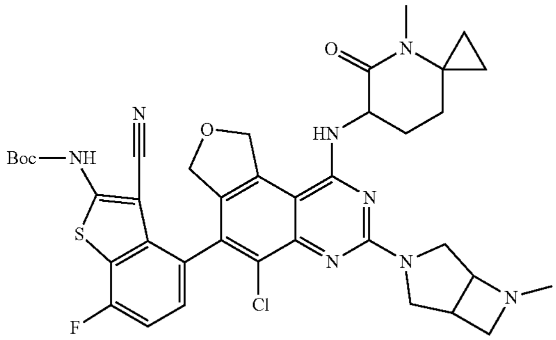 [SMILES: CN1CC2CN(c3nc(NC4CCC5(CC5)N(C)C4=O)c4c5c(c(-c6ccc(F)c7sc(NC(=O)OC(C)(C)C)c(C#N)c67)c(Cl)c4n3)COC5)CC21] | 759 |
| 101[1] | tert-Butyl (4-(5-chloro-3-(3-(dimethylamino)azetidin-1-yl)-1-((5-methyl-6-oxo-5-azaspiro[2.5]octan-7-yl)amino)-7,9-dihydrofuro[3,4-f]quinazolin-6-yl)-3-cyano-7-fluorobenzo[b]thiophen-2-yl)carbamate | 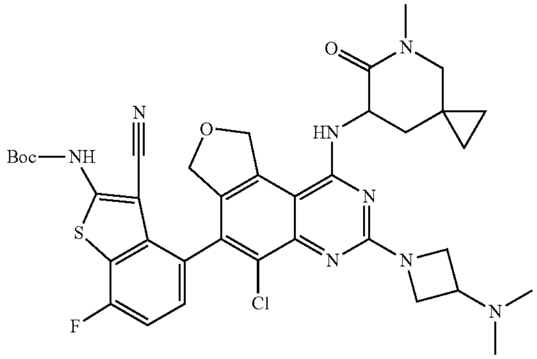 [SMILES: CN1CC2(CC2)CC(Nc2nc(N3CC(N(C)C)C3)nc3c(Cl)c(-c4ccc(F)c5sc(NC(=O)OC(C)(C)C)c(C#N)c45)c4c(c23)COC4)C1=O] | 747 |

TABLE 16-continued

| Prep | Chemical Name | Structure | MS (ES) m/z (M + 1) |
| --- | --- | --- | --- |
| 102 | tert-Butyl (3-cyano-4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophen-2-yl)carbamate | 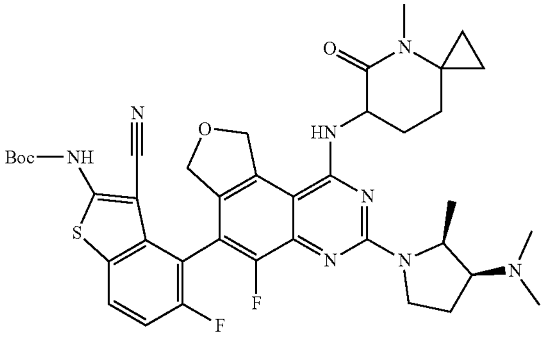 [SMILES: C[C@H]1[C@@H](N(C)C)CCN1c1nc(NC2CCC3(CC3)N(C)C2=O)c2c3c(c(-c4c(F)ccc5sc(NC(=O)OC(C)(C)C)c(C#N)c45)c(F)c2n1)COC3] | 759 |
| 103 | tert-Butyl (3-cyano-4-(3-(3-(dimethylamino)azetidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophen-2-yl)carbamate | 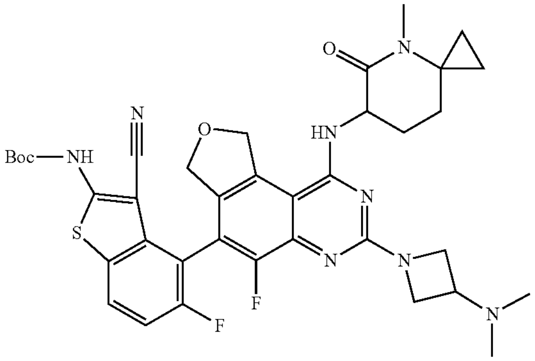 [SMILES: CN(C)C1CN(c2nc(NC3CCC4(CC4)N(C)C3=O)c3c4c(c(-c5c(F)ccc6sc(NC(=O)OC(C)(C)C)c(C#N)c56)c(F)c3n2)COC4)C1] | 731 |
| 104 | tert-Butyl (4-(5-chloro-3-((S)-3-(dimethylamino)pyrrolidin-1-yl)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 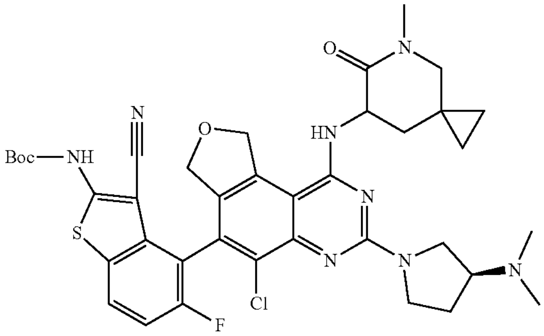 [SMILES: CN1CC2(CC2)CC(Nc2nc(N3CC[C@H](N(C)C)C3)nc3c(Cl)c(-c4c(F)ccc5sc(NC(=O)OC(C)(C)C)c(C#N)c45)c4c(c23)COC4)C1=O] | 761 |
| 105[2] | tert-Butyl (4-(5-chloro-1-((2-methyl-3-oxo-2-azabicyclo[3.1.1]heptan-4-yl)amino)-3-((3aR,6aR)-1-methylhexahydropyrrolo[3,4-b]pyrrol-5(1H)-yl)-7,9-dihydrofuro[3,4-f]quinazolin-6-yl)-3-cyano-5-fluorobenzo[b]thiophen-2-yl)carbamate | 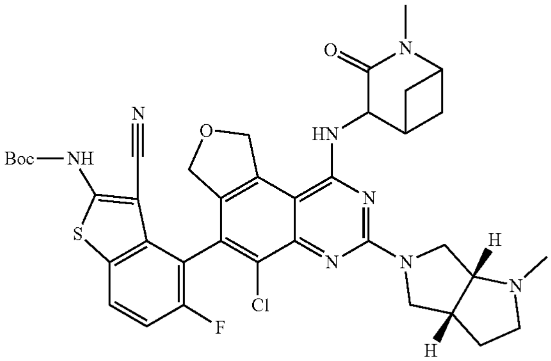 [SMILES: CN1C(=O)C(Nc2nc(N3C[C@H]4CCN(C)[C@H]4C3)nc3c(Cl)c(-c4c(F)ccc5sc(NC(=O)OC(C)(C)C)c(C#N)c45)c4c(c23)COC4)C2CC1C2] | 759 |

TABLE 16-continued

| Prep | Chemical Name | Structure | MS (ES) m/z (M + 1) |
|---|---|---|---|
| 106[2] | tert-Butyl (4-(5-chloro-3-((S)-3-(dimethylamino)pyrrolidin-1-yl)-1-((2-methyl-3-oxo-2-azabicyclo[3.1.1]heptan-4-yl)amino)-7,9-dihydrofuro[3,4-f]quinazolin-6-yl)-3-cyano-5-fluorobenzo[b]thiophen-2-yl)carbamate | 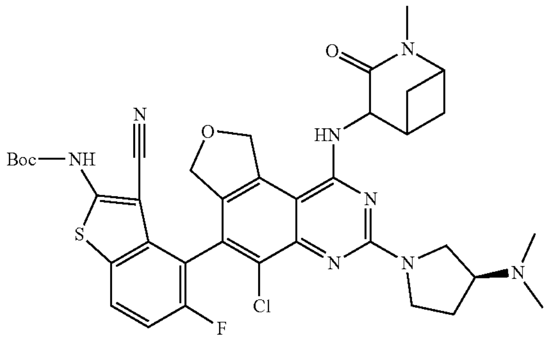 [SMILES: CN1C(=O)C(Nc2nc(N3CC[C@H](N(C)C)C3)nc3c(Cl)c(-c4c(F)ccc5sc(NC(=O)OC(C)(C)C)c(C#N)c45)c4c(c23)COC4)C2CC1C2] | 747 |
| 107 | 6-Bromo-3-((2S,3S)-3-(dimethylamino)-2-methylpyrrolidin-1-yl)-5-fluoro-7,9-dihydrofuro[3,4-f]quinazolin-1-ol | 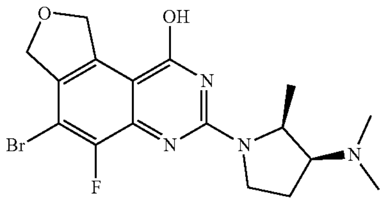 [SMILES: C[C@H]1[C@@H](N(C)C)CCN1c1nc(O)c2c3c(c(Br)c(F)c2n1)COC3] | 411 |
| 108 | tert-Butyl (4-(5-chloro-3-((2S,3S)-3-(dimethylamino)-2-methylpyrrolidin-1-yl)-1-((5-methyl-6-oxo-5-azaspiro[3.5]nonan-7-yl)amino)-7,9-dihydrofuro[3,4-f]quinazolin-6-yl)-7-fluorothiazolo[4,5-c]pyridin-2-yl)carbamate | 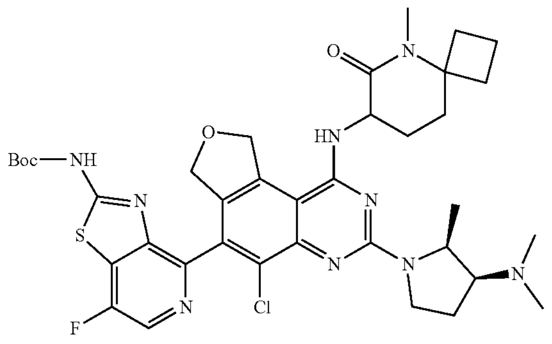 [SMILES: C[C@H]1[C@@H](N(C)C)CCN1c1nc(NC2CCC3(CCC3)N(C)C2=O)c2c3c(c(-c4ncc(F)c5sc(NC(=O)OC(C)(C)C)nc45)c(Cl)c2n1)COC3] | 766 |
| 109[2] | tert-Butyl (4-(5-chloro-3-((2S,3S)-3-(dimethylamino)-2-methylpyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[d]thiazol-2-yl)carbamate | 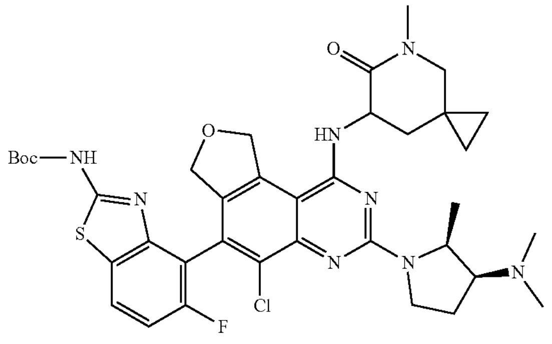 [SMILES: C[C@H]1[C@@H](N(C)C)CCN1c1nc(NC2CC3(CC3)CN(C)C2=O)c2c3c(c(-c4c(F)ccc5sc(NC(=O)OC(C)(C)C)nc45)c(Cl)c2n1)COC3] | 751 |

TABLE 16-continued

| Prep | Chemical Name | Structure | MS (ES) m/z (M + 1) |
|---|---|---|---|
| 110 | tert-Butyl (4-(5-chloro-3-((2S,3S)-3-(dimethylamino)-2-methylpyrrolidin-1-yl)-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 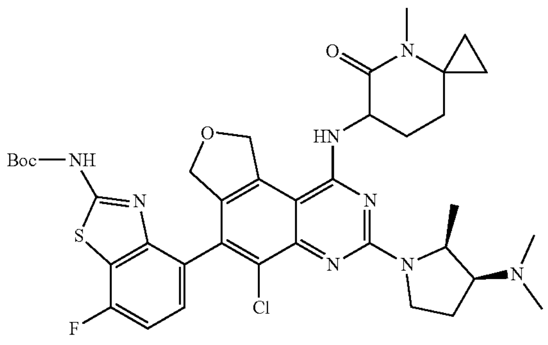 [SMILES: C[C@H]1[C@@H](N(C)C)CCN1c1nc(NC2CCC3(CC3)N(C)C2=O)c2c3c(c(-c4ccc(F)c5sc(NC(=O)OC(C)(C)C)nc45)c(Cl)c2n1)COC3] | 751 |
| 111 | tert-Butyl (4-(5-chloro-3-((S)-3-(dimethylamino)pyrrolidin-1-yl)-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 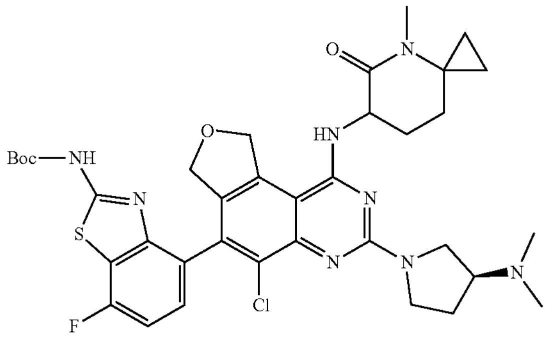 [SMILES: CN(C)[C@H]1CCN(c2nc(NC3CCC4(CC4)N(C)C3=O)c3c4c(c(-c5ccc(F)c6sc(NC(=O)OC(C)(C)C)nc56)c(Cl)c3n2)COC4)C1] | 737 |
| 112[3] | tert-Butyl (4-(3-((S)-3-(dimethylamino)pyrrolidin-1-yl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate | 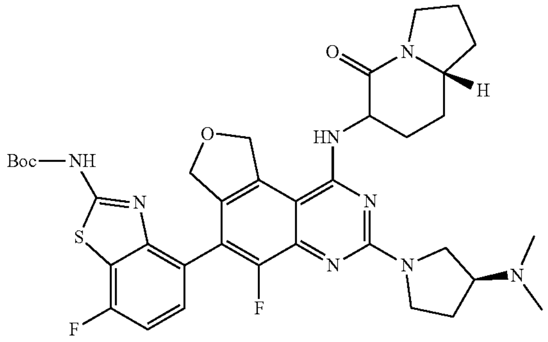 [SMILES: CN(C)[C@H]1CCN(c2nc(NC3CC[C@H]4CCCN4C3=O)c3c4c(c(-c5ccc(F)c6sc(NC(=O)OC(C)(C)C)nc56)c(F)c3n2)COC4)C1] | 721 |
| 113[3] | tert-Butyl (4-(3-((2S,3S)-3-(dimethylamino)-2-methylpyrrolidin-1-yl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate | 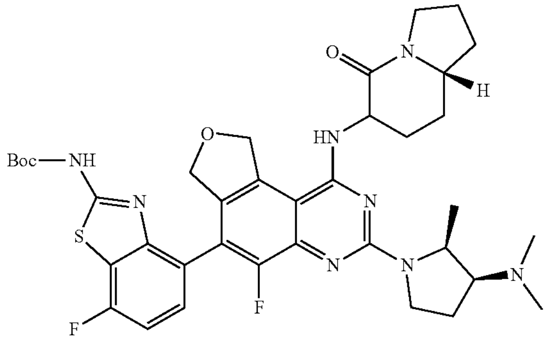 [SMILES: C[C@H]1[C@@H](N(C)C)CCN1c1nc(NC2CC[C@H]3CCCN3C2=O)c2c3c(c(-c4ccc(F)c5sc(NC(=O)OC(C)(C)C)nc45)c(F)c2n1)COC3] | 735 |

TABLE 16-continued

| Prep | Chemical Name | Structure | MS (ES) m/z (M + 1) |
|---|---|---|---|
| 114 | tert-Butyl (4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-7-fluorobenzo[d]thiazol-2-yl)carbamate | 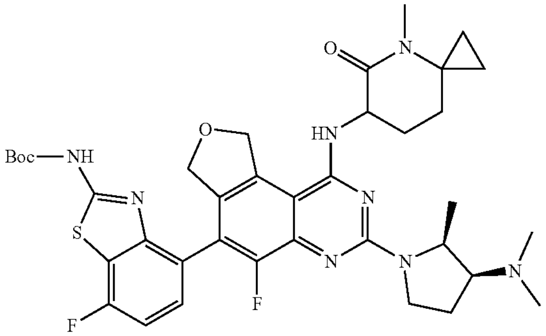 [SMILES: C[C@H]1[C@@H](N(C)C)CCN1c1nc(NC2CCC3(CC3)N(C)C2=O)c2c3c(c(-c4ccc(F)c5sc(NC(=O)OC(C)(C)C)nc45)c(F)c2n1)COC3] | 735 |
| 61A[2] | tert-Butyl (4-(5-chloro-3-((3R,4S)-3-(dimethylamino)-4-hydroxypyrrolidin-1-yl)-1-((5-methyl-6-oxo-5-azaspiro[2.5]octan-7-yl)amino)-7,9-dihydrofuro[3,4-f]quinazolin-6-yl)-3-cyano-5-fluorobenzo[b]thiophen-2-yl)carbamate | 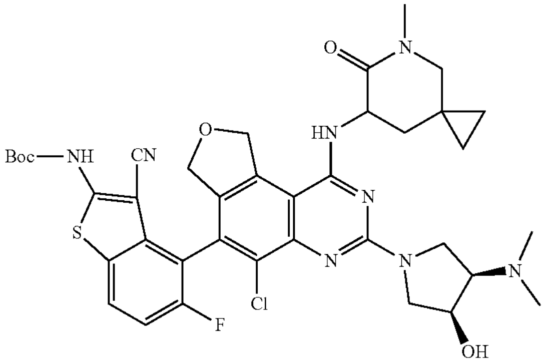 [SMILES: CN1CC2(CC2)CC(Nc2nc(N3C[C@@H](N(C)C)[C@@H](O)C3)nc3c(Cl)c(-c4c(F)ccc5sc(NC(=O)OC(C)(C)C)c(C#N)c45)c4c(c23)COC4)C1=O] | 777 |
| 62A[2] | tert-Butyl (4-(5-chloro-1-((2-methyl-3-oxo-2-azabicyclo[3.1.1]heptan-4-yl)amino)-3-((3aS,6aS)-1-methylhexahydropyrrolo[3,4-b]pyrrol-5(1H)-yl)-7,9-dihydrofuro[3,4-f]quinazolin-6-yl)-3-cyano-5-fluorobenzo[b]thiophen-2-yl)carbamate | 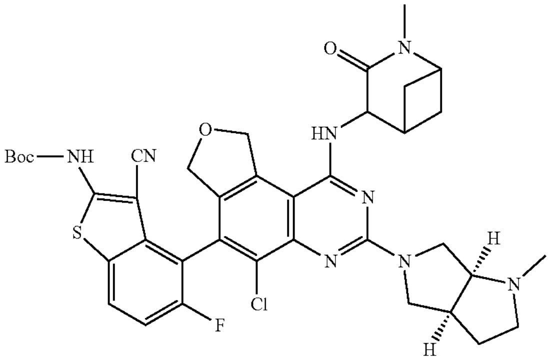 [SMILES: CN1C(=O)C(Nc2nc(N3C[C@@H]4CCN(C)[C@@H]4C3)nc3c(Cl)c(-c4c(F)ccc5sc(NC(=O)OC(C)(C)C)c(C#N)c45)c4c(c23)COC4)C2CC1C2] | 759 |
| 63A[2] | tert-Butyl (4-(5-chloro-3-((S)-3-(dimethylamino)pyrrolidin-1-yl)-1-hydroxy-7,9-dihydrofuro[3,4-f]quinazolin-6-yl)-3-cyano-5-fluorobenzo[b]thiophen-2-yl)carbamate | 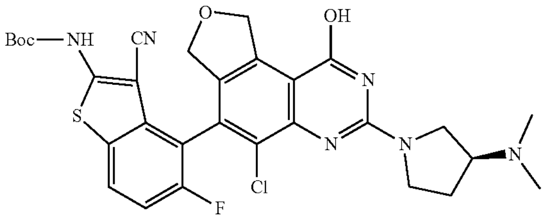 [SMILES: CN(C)[C@H]1CCN(c2nc(O)c3c4c(c(-c5c(F)ccc6sc(NC(=O)OC(C)(C)C)c(C#N)c56)c(Cl)c3n2)COC4)C1] | 625 |

TABLE 16-continued

| Prep | Chemical Name | Structure | MS (ES) m/z (M + 1) |
|---|---|---|---|
| 64A[1] | tert-Butyl (4-(5-chloro-3-((S)-3-(dimethylamino)pyrrolidin-1-yl)-1-((4-methyl-5-oxo-4-azaspiro[2.5]octan-6-yl)amino)-7,9-dihydrofuro[3,4-f]quinazolin-6-yl)-3-cyano-7-fluorobenzo[b]thiophen-2-yl)carbamate | 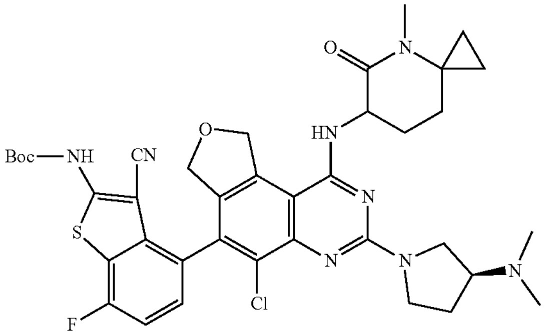 [SMILES: CN(C)[C@H]1CCN(c2nc(NC3CCC4(CC4)N(C)C3=O)c3c4c(c(-c5ccc(F)c6sc(NC(=O)OC(C)(C)C)c(C#N)c56)c(Cl)c3n2)COC4)C1] | 761 |
| 65A[1] | tert-Butyl (4-(5-chloro-3-(3-(dimethylamino)azetidin-1-yl)-1-((4-methyl-5-oxo-4-azaspiro[2.4]heptan-6-yl)amino)-7,9-dihydrofuro[3,4-f]quinazolin-6-yl)-3-cyano-7-fluorobenzo[b]thiophen-2-yl)carbamate | 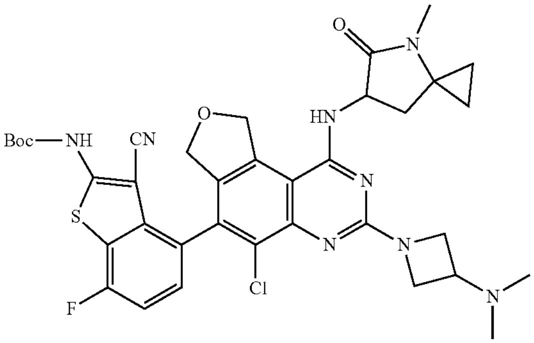 [SMILES: CN(C)C1CN(c2nc(NC3CC4(CC4)N(C)C3=O)c3c4c(c(-c5ccc(F)c6sc(NC(=O)OC(C)(C)C)c(C#N)c56)c(Cl)c3n2)COC4)C1] | 733 |
| 66A[1] | tert-Butyl (4-(5-chloro-3-(3-(dimethylamino)azetidin-1-yl)-1-hydroxy-7,9-dihydrofuro[3,4-f]quinazolin-6-yl)-3-cyano-7-fluorobenzo[b]thiophen-2-yl)carbamate | 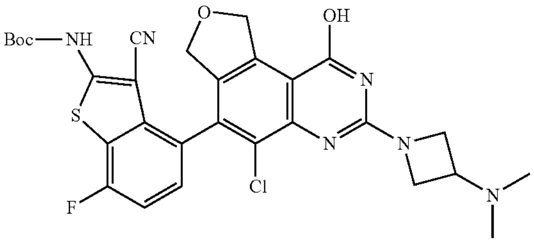 [SMILES: CN(C)C1CN(c2nc(O)c3c4c(c(-c5ccc(F)c6sc(NC(=O)OC(C)(C)C)c(C#N)c56)c(Cl)c3n2)COC4)C1] | 611 |
| 67A[1,5] | tert-Butyl (4-(5-chloro-3-(3-(dimethylamino)azetidin-1-yl)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 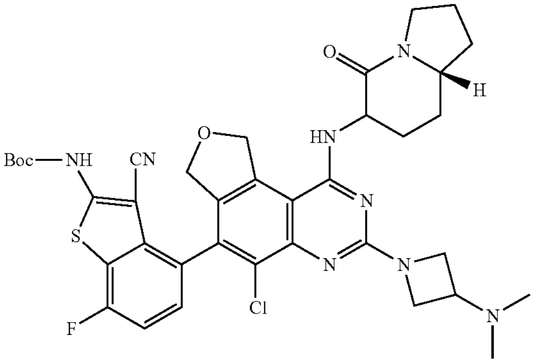 [SMILES: CN(C)C1CN(c2nc(NC3CC[C@H]4CCCN4C3=O)c3c4c(c(-c5ccc(F)c6sc(NC(=O)OC(C)(C)C)c(C#N)c56)c(Cl)c3n2)COC4)C1] | 747 |

TABLE 16-continued

| Prep | Chemical Name | Structure | MS (ES) m/z (M + 1) |
|---|---|---|---|
| 68A[1,6] | tert-Butyl (4-(5-chloro-3-(3-(dimethylamino)azetidin-1-yl)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 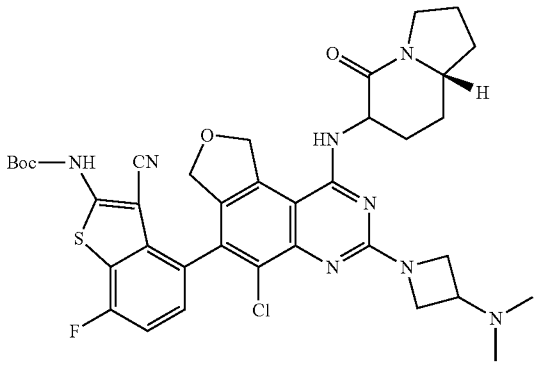 [SMILES: CN(C)C1CN(c2nc(NC3CC[C@H]4CCCN4C3=O)c3c4c(c(-c5ccc(F)c6sc(NC(=O)OC(C)(C)C)c(C#N)c56)c(Cl)c3n2)COC4)C1] | 747 |
| 69A | tert-Butyl (4-(3-((2S,3R,4S)-3-(dimethylamino)-4-hydroxy-2-methylpyrrolidin-1-yl)-5-fluoro-1-((5-methyl-6-oxo-5-azaspiro[3.5]nonan-7-yl)amino)-7,9-dihydrofuro[3,4-f]quinazolin-6-yl)-7-fluorobenzo[d]thiazol-2-yl)carbamate | 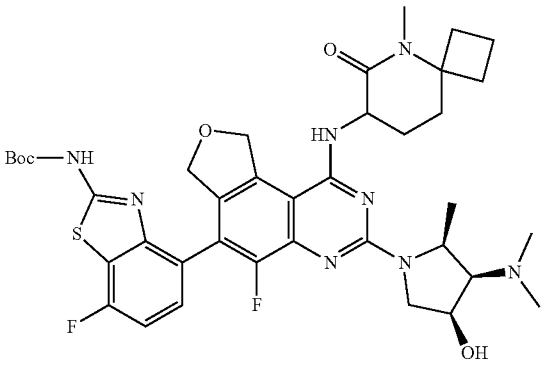 [SMILES: C[C@H]1[C@@H](N(C)C)[C@@H](O)CN1c1nc(NC2CCC3(CCC3)N(C)C2=O)c2c3c(c(-c4ccc(F)c5sc(NC(=O)OC(C)(C)C)nc45)c(F)c2n1)COC3] | 765 |
| 70A[7] | (8aR)-6-((6-Bromo-5-chloro-3-((2S,3S)-3-(dimethylamino)-2-methylpyrrolidin-1-yl)-7,9-dihydrofuro[3,4-f]quinazolin-1-yl)amino)hexahydroindolizin-5(1H)-one | 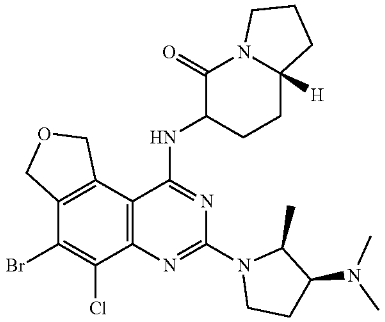 [SMILES: C[C@H]1[C@@H](N(C)C)CCN1c1nc(NC2CC[C@H]3CCCN3C2=O)c2c3c(c(Br)c(Cl)c2n1)COC3] | 563 |
| 71A[8] | (8aR)-6-((6-Bromo-5-chloro-3-((2S,3S)-3-(dimethylamino)-2-methylpyrrolidin-1-yl)-7,9-dihydrofuro[3,4-f]quinazolin-1-yl)amino)hexahydroindolizin-5(1H)-one | 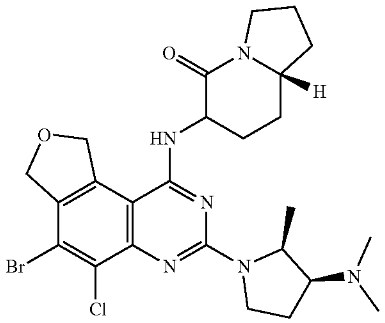 | 563 |

TABLE 16-continued

| Prep | Chemical Name | Structure | MS (ES) m/z (M + 1) |
|---|---|---|---|
| 72A[8] | (8aR)-6-((6-Bromo-5-chloro-3-((2S,3S)-3-(ethyl(methyl)amino)-2-methylpyrrolidin-1-yl)-7,9-dihydrofuro[3,4-f]quinazolin-1-yl)amino)hexahydroindolizin-5(1H)-one | 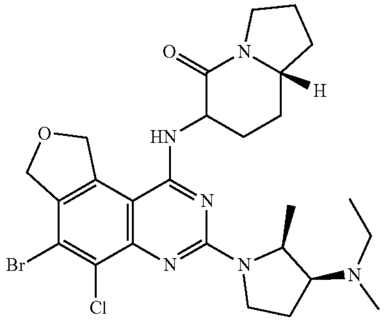 [SMILES: CCN(C)[C@H]1CCN(c2nc(NC3CC[C@H]4CCCN4C3=O)c3c4c(c(Br)c(Cl)c3n2)COC4)[C@H]1C] | 577 |
| 73A | 6-((6-Bromo-5-chloro-3-((2S,3S)-3-(ethyl(methyl)amino)-2-methylpyrrolidin-1-yl)-7,9-dihydrofuro[3,4-f]quinazolin-1-yl)amino)-4-methyl-4-azaspiro[2.5]octan-5-one | 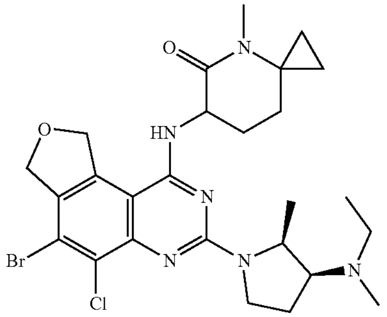 [SMILES: CCN(C)[C@H]1CCN(c2nc(NC3CCC4(CC4)N(C)C3=O)c3c4c(c(Br)c(Cl)c3n2)COC4)[C@H]1C] | 577 |
| 74A | 7-((6-Bromo-5-chloro-3-((2S,3S)-3-(ethyl(methyl)amino)-2-methylpyrrolidin-1-yl)-7,9-dihydrofuro[3,4-f]quinazolin-1-yl)amino)-5-methyl-5-azaspiro[2.5]octan-6-one | 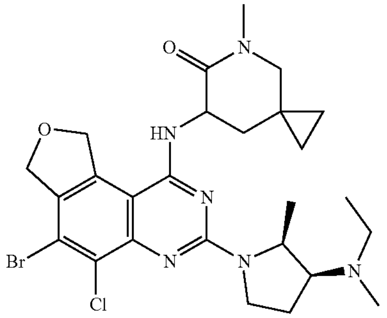 [SMILES: CCN(C)[C@H]1CCN(c2nc(NC3CC4(CC4)CN(C)C3=O)c3c4c(c(Br)c(Cl)c3n2)COC4)[C@H]1C] | 577 |
| 75A | tert-Butyl (4-(5-chloro-3-((2S,3S)-3-(dimethylamino)-2-methylpyrrolidin-1-yl)-1-((5-methyl-6-oxo-5-azaspiro[2.5]octan-7-yl)amino)-7,9-dihydrofuro[3,4-f]quinazolin-6-yl)-7-fluorothiazolo[4,5-c]pyridin-2-yl)carbamate | 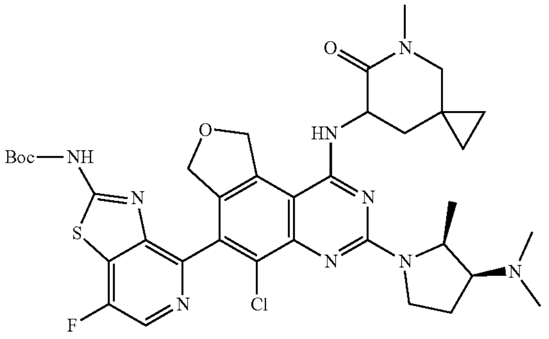 [SMILES: C[C@H]1[C@@H](N(C)C)CCN1c1nc(NC2CC3(CC3)CN(C)C2=O)c2c3c(c(-c4ncc(F)c5sc(NC(=O)OC(C)(C)C)nc45)c(Cl)c2n1)COC3] | 752 |

TABLE 16-continued

| Prep | Chemical Name | Structure | MS (ES) m/z (M + 1) |
|---|---|---|---|
| 76A[3,9] | tert-Butyl (4-(3-((2S)-3-(azetidin-1-yl)-2-methylpyrrolidin-1-yl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate, Isomer 1 | 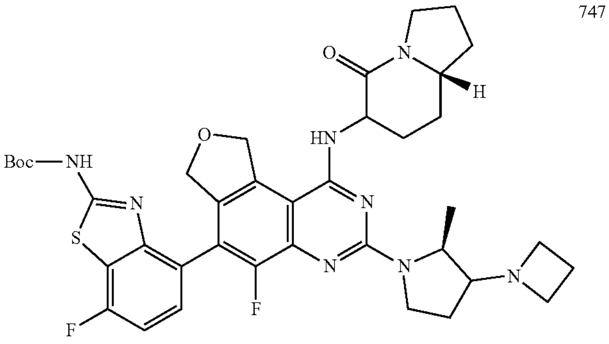 | 747 |
| 77A[3,9] | tert-Butyl (4-(3-((2S)-3-(azetidin-1-yl)-2-methylpyrrolidin-1-yl)-5-fluoro-1-(((8aR)-5-oxooctahydroindolizin-6-yl)amino)-7,9-dihydrofuro[3,4-f]quinazolin-6-yl)-7-fluorobenzo[d]thiazol-2-yl)carbamate, Isomer 2 | 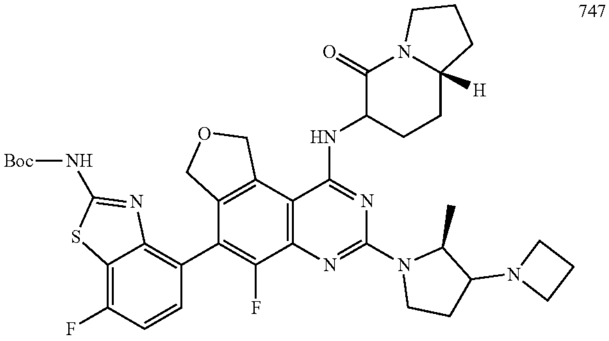 | 747 |
| 78A | tert-Butyl (4-(3-((2S,3S)-3-(ethyl(methyl)amino)-2-methylpyrrolidin-1-yl)-5-fluoro-1-((5-methyl-6-oxo-5-azaspiro[2.5]octan-7-yl) amino)-7,9-dihydrofuro[3,4-f]quinazolin-6-yl)-7-fluorobenzo[d]thiazol-2-yl)carbamate | 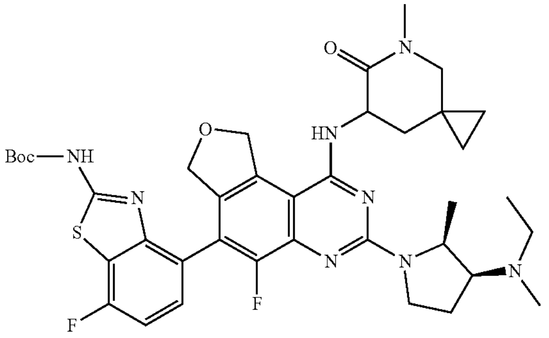 [SMILES: CCN(C)[C@H]1CCN(c2nc(NC3CC4(CC4)CN(C)C3=O)c3c4c(c(-c5ccc(F)c6sc(NC(=O)OC(C)(C)C)nc56)c(F)c3n2)COC4)[C@H]1C] | 749 |
| 79A[10] | (9aS)-7-((6-Bromo-3-((2S,3S)-3-(dimethylamino)-2-methylpyrrolidin-1-yl)-5-fluoro-7,9-dihydrofuro[3,4-f]quinazolin-1-yl)amino)hexahydropyrido [2,1-c][1,4]oxazin-6(1H)-one | 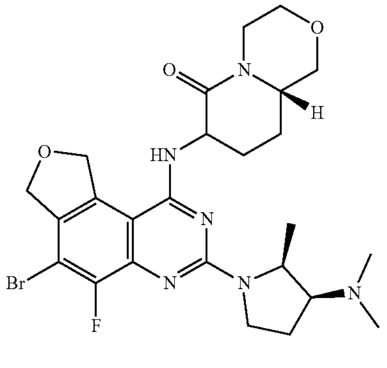 [SMILES: C[C@H]1[C@@H](N(C)C)CCN1c1nc(NC2CC[C@H]3COCCN3C2=O)c2c3c(c(Br)c(F)c2n1)COC3] | 563 |

TABLE 16-continued

| Prep | Chemical Name | Structure | MS (ES) m/z (M + 1) |
|---|---|---|---|
| 80A | (6R,8aR)-6-((6-Bromo-5-fluoro-3-((2'S,3'S)-2'-methyl-[1,3'-bipyrrolidin]-1'-yl)-7,9-dihydrofuro[3,4-f]quinazolin-1-yl)amino)hexahydroindolizin-5(1H)-one | 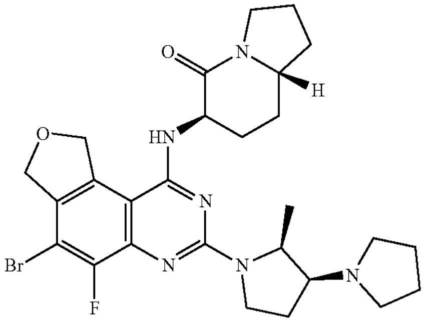 [SMILES: C[C@H]1[C@@H](N2CCCC2)CCN1c1nc(N[C@@H]2CC[C@H]3CCCN3C2=O)c2c3c(c(Br)c(F)c2n1)COC3] | 573 |
| 81A | 7-((6-Bromo-3-((2S,3S)-3-(dimethylamino)-2-methylpyrrolidin-1-yl)-5-fluoro-7,9-dihydrofuro[3,4-f]quinazolin-1-yl)amino)-5-azaspiro [3.5]nonan-6-one | 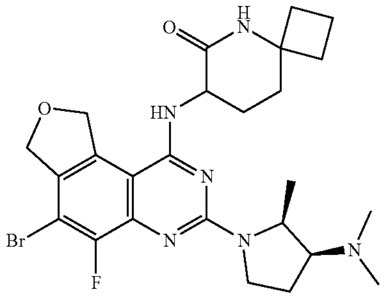 [SMILES: C[C@H]1[C@@H](N(C)C)CCN1c1nc(NC2CCC3(CCC3)NC2=O)c2c3c(c(Br)c(F)c2n1)COC3] | 547 |
| 82A | 7-((6-Bromo-3-((2S,3S)-3-(dimethylamino)-2-methylpyrrolidin-1-yl)-5-fluoro-7,9-dihydrofuro[3,4-f]quinazolin-1-yl)amino)-5-methyl-5-azaspiro[3.5]nonan-6-one | 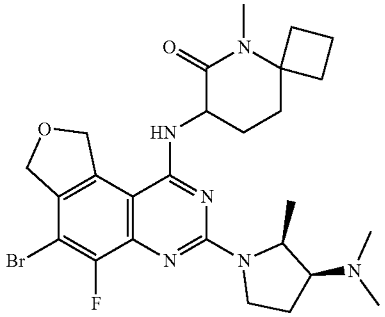 [SMILES: C[C@H]1[C@@H](N(C)C)CCN1c1nc(NC2CCC3(CCC3)N(C)C2=O)c2c3c(c(Br)c(F)c2n1)COC3] | 561 |
| 83A | (S)-6-Bromo-3-(3-(dimethylamino)pyrrolidin-1-yl)-5-fluoro-7,9-dihydrofuro[3,4-f]quinazolin-1-ol | 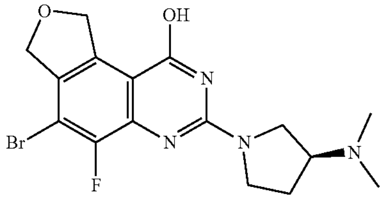 [SMILES: CN(C)[C@H]1CCN(c2nc(O)c3c4c(c(Br)c(F)c3n2)COC4)C1] | 397 |
| 84A | (S)-6-Bromo-5-chloro-3-(3-(dimethylamino)pyrrolidin-1-yl)-7,9-dihydrofuro[3,4-f]quinazolin-1-ol | 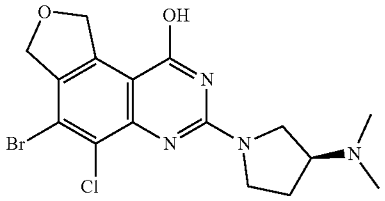 [SMILES: CN(C)[C@H]1CCN(c2nc(O)c3c4c(c(Br)c(Cl)c3n2)COC4)C1] | 413 |

TABLE 16-continued

| Prep | Chemical Name | Structure | MS (ES) m/z (M + 1) |
|---|---|---|---|
| 85A | 6-Bromo-5-chloro-3-((2S,3S)-3-(dimethylamino)-2-methylpyrrolidin-1-yl)-7,9-dihydrofuro[3,4-f]quinazolin-1-ol | 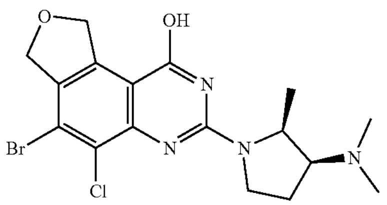 [SMILES: C[C@H]1[C@@H](N(C)C)CCN1c1nc(O)c2c3c(c(Br)c(Cl)c2n1)COC3] | 427 |
| 86A[2,10] | tert-Butyl (4-(5-chloro-3-((3S,4R)-3-hydroxy-4-(isopropyl(methyl)amino)pyrrolidin-1-yl)-1-(((8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate | 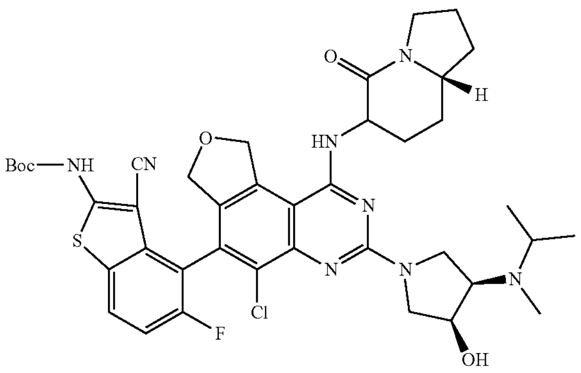 [SMILES: CC(C)N(C)[C@@H]1CN(c2nc(NC3CC[C@H]4CCCN4C3=O)c3c4c(c(-c5c(F)ccc6sc(NC(=O)OC(C)(C)C)c(C#N)c56)c(Cl)c3n2)COC4)C[C@@H]1O] | 805 |
| 87A[10] | (8aR)-6-((6-Bromo-3-((2S,3S)-3-(dimethylamino)-2-methylpyrrolidin-1-yl)-5-fluoro-7,9-dihydrofuro[3,4-f]quinazolin-1-yl)amino)hexahydroindolizin-5(1H)-one | 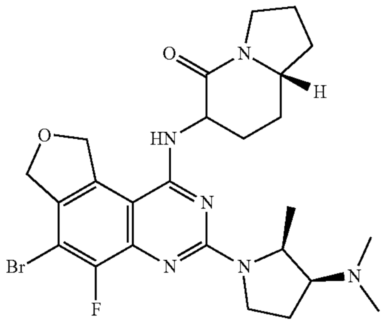 [SMILES: C[C@H]1[C@@H](N(C)C)CCN1c1nc(NC2CC[C@H]3CCCN3C2=O)c2c3c(c(Br)c(F)c2n1)COC3] | 547 |
| 88A[10,11] | tert-Butyl (4-(3-((3-(dimethylamino)oxetan-3-yl)methoxy)-5-fluoro-1-(((6R,8aR)-5-oxooctahydroindolizin-6-yl)amino)-7,9-dihydrofuro[3,4-f]quinazolin-6-yl)-7-fluorobenzo[d]thiazol-2-yl)carbamate | 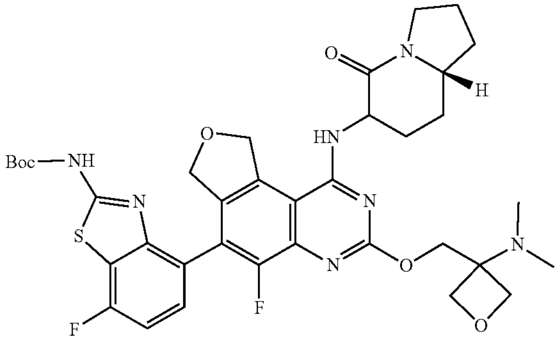 [SMILES: CN(C)C1(COc2nc(NC3CC[C@H]4CCCN4C3=O)c3c4c(c(-c5ccc(F)c6sc(NC(=O)OC(C)(C)C)nc56)c(F)c3n2)COC4)COC1] | 738 |

TABLE 16-continued

| Prep | Chemical Name | Structure | MS (ES) m/z (M + 1) |
|---|---|---|---|
| 89A[10] | (8aR)-6-((6-Bromo-3-((S)-3-(dimethylamino)pyrrolidin-1-yl)-5-fluoro-7,9-dihydrofuro[3,4-f]quinazolin-1-yl)amino)hexahydroindolizin-5(1H)-one | 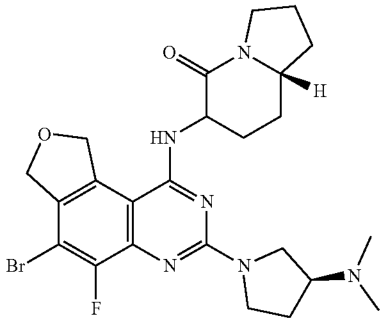 [SMILES: CN(C)[C@H]1CCN(c2nc(NC3CC[C@H]4CCCN4C3=O)c3c4c(c(Br)c(F)c3n2)COC4)C1] | 533 |
| 62B[1] | tert-Butyl (4-(3-([1,3'-biazetidin]-1'-yl)-5-chloro-1-((5-methyl-6-oxo-5-azaspiro [3.5]nonan-7-yl)amino)-7,9-dihydrofuro[3,4-f]quinazolin-6-yl)-3-cyano-7-fluorobenzo[b]thiophen-2-yl)carbamate | 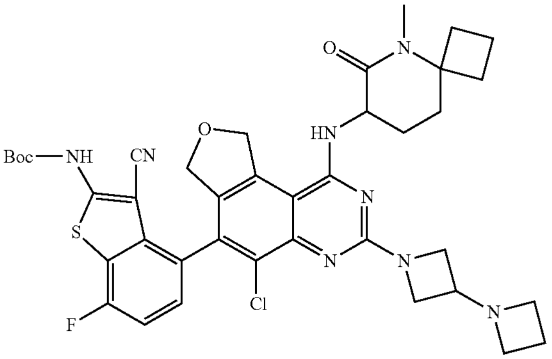 [SMILES: CN1C(=O)C(Nc2nc(N3CC(N4CCC4)C3)nc3c(Cl)c(-c4ccc(F)c5sc(NC(=O)OC(C)(C)C)c(C#N)c45)c4c(c23)COC4)CCC12CCC2] | 773 |
| 63B[1,10] | tert-Butyl (4-(5-chloro-3-(2-hydroxy-2-methylpropoxy)-1-(((8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate | 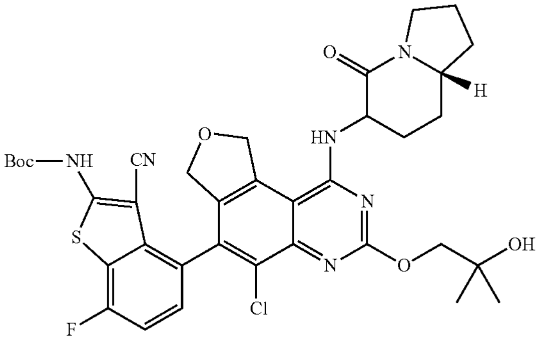 [SMILES: CC(C)(O)COc1nc(NC2CC[C@H]3CCCN3C2=O)c2c3c(c(-c4ccc(F)c5sc(NC(=O)OC(C)(C)C)c(C#N)c45)c(Cl)c2n1)COC3] | 737 |
| 64B | (6R,8aR)-6-((6-Bromo-5-fluoro-3-((2S,3S)-3-(3-(fluoromethyl)azetidin-1-yl)-2-methylpyrrolidin-1-yl)-7,9-dihydrofuro[3,4-f]quinazolin-1-yl)amino)hexahydroindolizin-5(1H)-one | 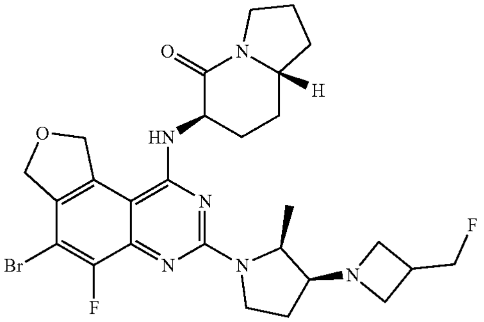 [SMILES: C[C@H]1[C@@H](N2CC(CF)C2)CCN1c1nc(N[C@@H]2CC[C@H]3CCCN3C2=O)c2c3c(c(Br)c(F)c2n1)COC3] | 591 |

TABLE 16-continued

| Prep | Chemical Name | Structure | MS (ES) m/z (M + 1) |
|---|---|---|---|
| 65B | (6R,8aR)-6-((6-Bromo-5-fluoro-3-((2S)-2-methyl-3-(5-azaspiro[2.3]hexan-5-yl)pyrrolidin-1-yl)-7,9-dihydrofuro[3,4-f]quinazolin-1-yl)amino)hexahydroindolizin-5(1H)-one | 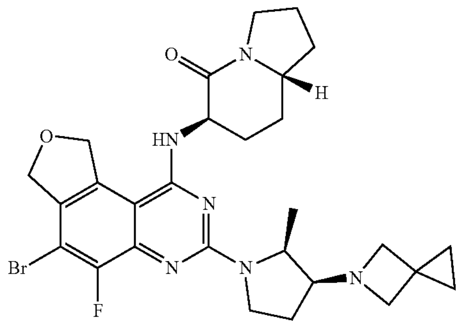 [SMILES: C[C@H]1[C@@H](N2CC3(CC3)C2)CCN1c1nc(N[C@@H]2CC[C@H]3CCCN3C2=O)c2c3c(c(Br)c(F)c2n1)COC3] | 585 |
| 66B | (6R,8aR)-6-((6-Bromo-3-((6S)-1,6-dimethylhexahydropyrrolo[3,4-b]pyrrol-5(1H)-yl)-5-fluoro-7,9-dihydrofuro[3,4-f]quinazolin-1-yl)amino)hexahydroindolizin-5(1H)-one | 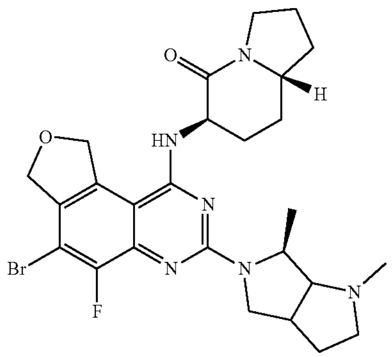 [SMILES: C[C@H]1C2C(CCN2C)CN1c1nc(N[C@@H]2CC[C@H]3CCCN3C2=O)c2c3c(c(Br)c(F)c2n1)COC3] | 559 |
| 67B | tert-Butyl (4-(3-((2S,3S)-3-(dimethylamino)-2-methylpyrrolidin-1-yl)-5-fluoro-1-hydroxy-7,9-dihydrofuro[3,4-f]quinazolin-6-yl)-7-fluorobenzo[d]thiazol-2-yl)carbamate | 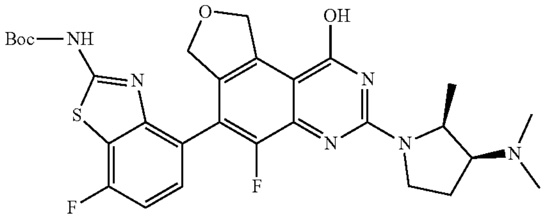 [SMILES: C[C@H]1[C@@H](N(C)C)CCN1c1nc(O)c2c3c(c(-c4ccc(F)c5sc(NC(=O)OC(C)(C)C)nc45)c(F)c2n1)COC3] | 599 |
| 68B | (6R)-3-((6-Bromo-3-((2S,3S)-3-(dimethylamino)-2-methylpyrrolidin-1-yl)-5-fluoro-7,9-dihydrofuro[3,4-f]quinazolin-1-yl)amino)-6-(difluoromethyl)-1-methylpiperidin-2-one | 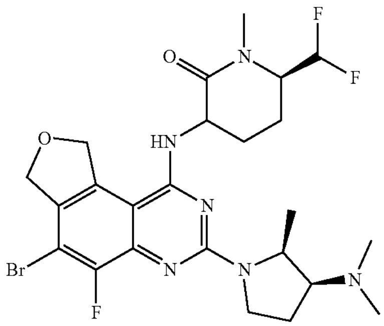 [SMILES: C[C@H]1[C@@H](N(C)C)CCN1c1nc(NC2CC[C@H](C(F)F)N(C)C2=O)c2c3c(c(Br)c(F)c2n1)COC3] | 571 |

TABLE 16-continued

| Prep | Chemical Name | Structure | MS (ES) m/z (M + 1) |
| --- | --- | --- | --- |
| 69B | (6R,8aR)-6-((3-((2S,3S)-3-(Bis(methyl-d3)amino)-2-methylpyrrolidin-1-yl)-6-bromo-5-fluoro-7,9-dihydrofuro[3,4-f]quinazolin-1-yl)amino)hexahydroindolizin-5(1H)-one | 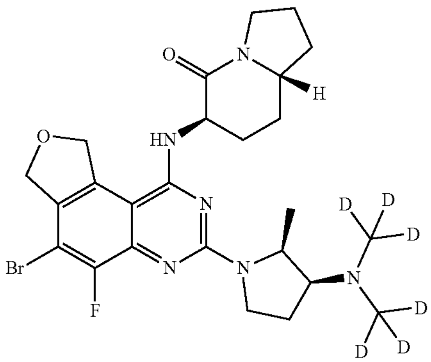 [SMILES: [2H]C([2H])([2H])N([C@H]1CCN(c2nc(N[C@@H]3CC[C@H]4CCCN4C3=O)c3c4c(c(Br)c(F)c3n2)COC4)[C@H]1C)C([2H])([2H])[2H]] | 553 |
| 70B | 7-((6-Bromo-5-chloro-3-((2S,3S)-3-(diethylamino)-2-methylpyrrolidin-1-yl)-7,9-dihydrofuro[3,4-f]quinazolin-1-yl)amino)-5-methyl-5-azaspiro [2.5]octan-6-one | 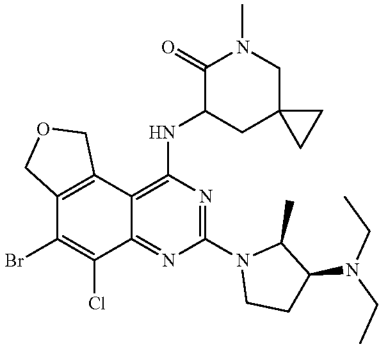 [SMILES: CCN(CC)[C@H]1CCN(c2nc(NC3CC4(CC4)CN(C)C3=O)c3c4c(c(Br)c(Cl)c3n2)COC4)[C@H]1C] | 591 |
| 71B[8] | (8aR)-6-((6-Bromo-5-chloro-3-((2S,3S)-3-(6-fluoro-2-azaspiro[3.3]heptan-2-yl)-2-methylpyrrolidin-1-yl)-7,9-dihydrofuro[3,4-f]quinazolin-1-yl)amino)hexahydroindolizin-5(1H)-one | 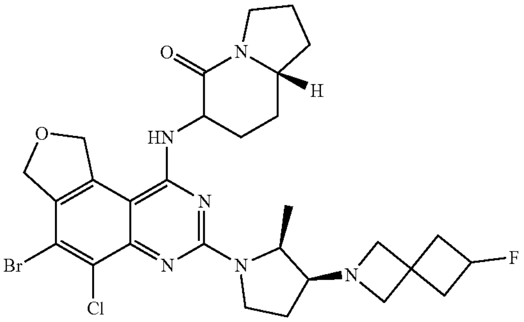 [SMILES: C[C@H]1[C@@H](N2CC3(CC(F)C3)C2)CCN1c1nc(NC2CC[C@H]3CCCN3C2=O)c2c3c(c(Br)c(Cl)c2n1)COC3] | 633 |
| 72B[8] | (8aR)-6-((6-Bromo-5-chloro-3-((2S,3S)-2-methyl-3-(5-azaspiro[2.3]hexan-5-yl)pyrrolidin-1-yl)-7,9-dihydrofuro[3,4-f]quinazolin-1-yl)amino)hexahydroindolizin-5(1H)-one | 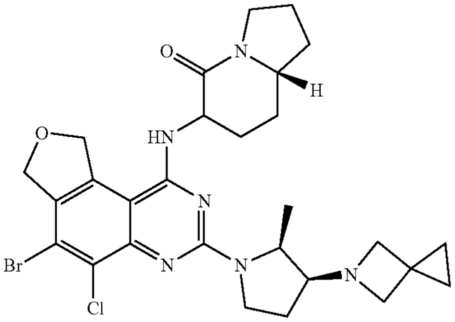 [SMILES: C[C@H]1[C@@H](N2CC3(CC3)C2)CCN1c1nc(NC2CC[C@H]3CCCN3C2=O)c2c3c(c(Br)c(Cl)c2n1)COC3] | 601 |

TABLE 16-continued

| Prep | Chemical Name | Structure | MS (ES) m/z (M + 1) |
|---|---|---|---|
| 73B[8] | (8aR)-6-((6-Bromo-5-chloro-3-((2S,3S)-3-((3-fluorocyclobutyl)(methyl)amino)-2-methylpyrrolidin-1-yl)-7,9-dihydrofuro[3,4-f]quinazolin-1-yl)amino)hexahydroindolizin-5(1H)-one | 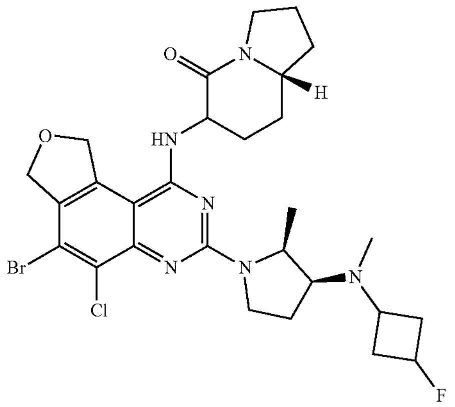 [SMILES: C[C@H]1[C@@H](N(C)C2CC(F)C2)CCN1c1nc(NC2CC[C@H]3CCCN3C2=O)c2c3c(c(Br)c(Cl)c2n1)COC3] | 621 |
| 74B[8] | (8aR)-6-((6-Bromo-5-chloro-3-((2S,3S)-3-(3-(fluoromethyl)azetidin-1-yl)-2-methylpyrrolidin-1-yl)-7,9-dihydrofuro[3,4-f]quinazolin-1-yl)amino)hexahydroindolizin-5(1H)-one | 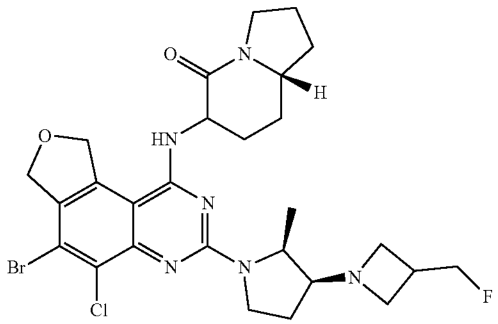 [SMILES: C[C@H]1[C@@H](N2CC(CF)C2)CCN1c1nc(NC2CC[C@H]3CCCN3C2=O)c2c3c(c(Br)c(Cl)c2n1)COC3] | 607 |
| 75B | 6-Bromo-5-chloro-3-((2S,3S)-3-(ethyl(methyl)amino)-2-methylpyrrolidin-1-yl)-7,9-dihydrofuro[3,4-f]quinazolin-1-ol | 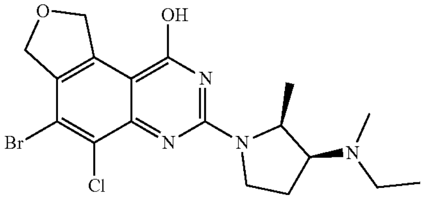 [SMILES: CCN(C)[C@H]1CCN(c2nc(O)c3c4c(c(Br)c(Cl)c3n2)COC4)[C@H]1C] | 441 |
| 76B[8] | (8aR)-6-((6-Bromo-5-chloro-3-((2'S,3'S)-2'-methyl-[1,3'-bipyrrolidin]-1'-yl)-7,9-dihydrofuro[3,4-f]quinazolin-1-yl)amino)hexahydroindolizin-5(1H)-one | 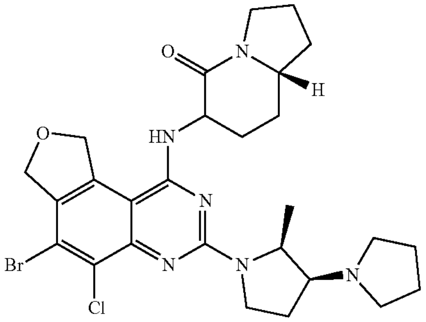 [SMILES: C[C@H]1[C@@H](N2CCCC2)CCN1c1nc(NC2CC[C@H]3CCCN3C2=O)c2c3c(c(Br)c(Cl)c2n1)COC3] | 589 |

[1]Clean atropisomer, chiral purification from Preparation 30
[2]Clean atropisomer, chiral purification from Preparation 34
[3]Clean enantiomer at the 6-position of the hexahydroindolizinone, chiral purification from Preparation 86
[4]Mix of cis isomers
[5]Clean isomer at the 6-position of the hexahydroindolizinone, chiral purification from Preparation 28A
[6]Clean isomer at the 6-position of the hexahydroindolizinone, chiral purification from Preparation 29A
[7]Clean isomer at the 6-position of the hexahydroindolizinone, chiral purification from Preparation 13A
[8]Clean isomer at the 6-position of the hexahydroindolizinone, chiral purification from Preparation 14A
[9]Normal Phase; silica, 0-40% MeOH in DCM, Isomer refers to a clean isomer at the 3-position of the pyrrolidine
[10]A predominant chiral center is present based on starting material from Preparation 53, 54, 55, 5A, 6A, 7A, or 8A
[11]Lithium bis(trimethylsilyl)amide was used as base The following compounds in Table 17 were prepared in similar manner as described in Preparation 26. Various methods were used to purify the compounds, which would be apparent to one skilled in the art.

TABLE 17

| Preparation | Chemical Name | Structure | MS (ES) m/z (M + 1) |
|---|---|---|---|
| 90A[1] | tert-Butyl (3-cyano-4-(1,5-dichloro-3-(3-(dimethylamino)-azetidin-1-yl)-7,9-dihydrofuro[3,4-f]quinazolin-6-yl)-7-fluorobenzo[b]thiophen-2-yl)carbamate | 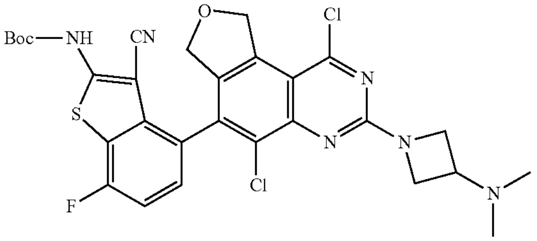 [SMILES: CN(C)C1CN(c2nc(Cl)c3c4c(c(-c5ccc(F)c6sc(NC(=O)OC(C)(C)C)c(C#N)c56)c(Cl)c3n2)COC4)C1] | 629 |

[1]Clean atropisomer, chiral purification from Preparation 30

The following compounds in Table 18 were prepared in similar manner as described in Preparation 56. Different bases may have been substituted. Various methods were used to purify the compounds, which would be apparent to one skilled in the art.

TABLE 18

| Preparation | Chemical Name | Structure | MS (ES) m/z (M + 1) |
|---|---|---|---|
| 91A[1] | tert-Butyl (4-(5-chloro-3-(3-(dimethylamino)-azetidin-1-yl)-1-((1-oxooctahydropyridazino[1,2-a]pyridazin-2-yl)-amino)-7,9-dihydrofuro[3,4-f]quinazolin-6-yl)-3-cyano-7-fluorobenzo[b]thiophen-2-yl)carbamate | 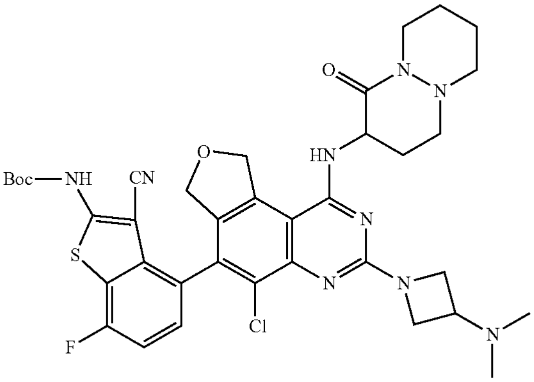 [SMILES: CN(C)C1CN(c2nc(NC3CCN4CCCCN4C3=O)c3c4c(c(-c5ccc(F)c6sc(NC(=O)OC(C)(C)C)c(C#N)c56)c(Cl)c3n2)COC4)C1] | 762 |
| 77B | (6R,8aR)-6-((4-Bromo-5-chloro-1,3-dihydro-furo[3,4-f]cinnolin-9-yl)amino)hexahydro-indolizin-5(1H)-one | 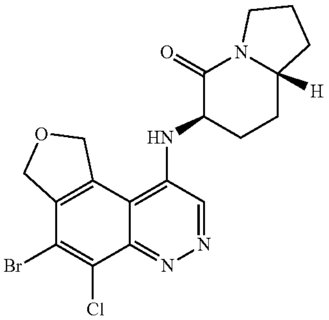 [SMILES: O=C1[C@H](Nc2cnnc3c(Cl)c(Br)c4c(c23)COC4)CC[C@H]2CCCN12] | 437 |

TABLE 18-continued

| Preparation | Chemical Name | Structure | MS (ES) m/z (M + 1) |
|---|---|---|---|
| 78B[2] | 4-((6-Bromo-5-chloro-3-((2S,3S)-3-(dimethylamino)-2-methylpyrrolidin-1-yl)-7,9-dihydrofuro[3,4-f]quinazolin-1-yl)amino)-1,2-dimethyltetrahydropyridazin-3(2H)-one, Isomer 2 | 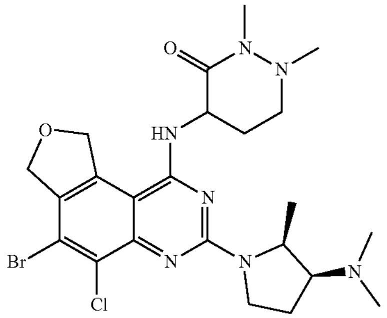 [SMILES: C[C@H]1[C@@H](N(C)C)CCN1c1nc(NC2CCN(C)N(C)C2=O)c2c3c(c(Br)c(Cl)c2n1)COC3] | 552 |
| 79B[3] | 4-((6-Bromo-5-chloro-3-((2S,3S)-3-(ethyl(methyl)amino)-2-methylpyrrolidin-1-yl)-7,9-dihydrofuro[3,4-f]quinazolin-1-yl)amino)-1,2-dimethyltetrahydropyridazin-3(2H)-one, Isomer 2 | 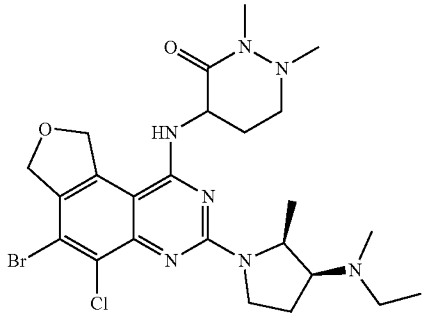 [SMILES: CCN(C)[C@H]1CCN(c2nc(NC3CCN(C)N(C)C3=O)c3c4c(c(Br)c(Cl)c3n2)COC4)[C@H]1C] | 566 |

[1]Clean atropisomer, chiral purification from Preparation 30

[2]Chiral SFC; ChiralPak AD, 30 x 250 mm, 50% (isopropanol w/20 mM ammonia) in $CO_2$, 100 mL/min, Isomer refers to a clean isomer at the 4-position of the pyridazinone.

[3]Chiral SFC; ChiralPak IK, 30 x 250 mm, 50% (3:1 isopropanol:dichlorometane w/20 mM ammonia) in $CO_2$, 100 mL/min, Isomer refers to a clean isomer at the 4-position of the pyridazinone.

Preparation 115

2-((6-Bromo-3-((2S,3S)-3-(dimethylamino)-2-methylpyrrolidin-1-yl)-5-fluoro-7,9-dihydrofuro[3,4-f]quinazolin-1-yl)amino)hexahydropyridazino[1,2-a]pyridazin-1(2H)-one

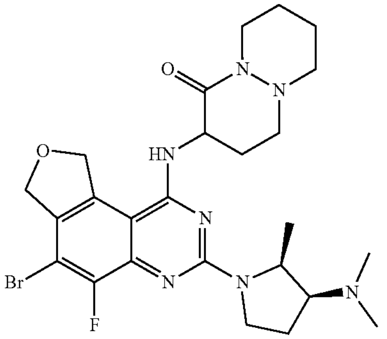 [SMILES: C[C@H]1[C@@H](N(C)C)CCN1c1nc(NC2CCN3CCCCN3C2=O)c2c3c(c(Br)c(F)c2n1)COC3]

To a mixture of 6-bromo-3-((2S,3S)-3-(dimethylamino)-2-methylpyrrolidin-1-yl)-5-fluoro-7,9-dihydrofuro[3,4-f]quinazolin-1-ol (0.129 g, 0.314 mmol) and (benzotriazol-1-yloxy)tripyrrolidinophosphoniumhexafluorophosphate (0.326 g, 0.627 mmol) in acetonitrile (2.6 mL) was added diisopropylethylamine (0.55 mL, 3.14 mmol). The mixture was stirred at RT for 1 h, then 2-aminohexahydropyridazino[1,2-a]pyridazin-1(2H)-one trihydrochloride (enriched toward (R) enantiomer; 0.306 g, 1.10 mmol) was added. The mixture was stirred at RT for 2.5 h, then concentrated under reduced pressure. The crude material was purified on silica, eluting with 10% MeOH in DCM to obtain the title compound (enriched toward (R) enantiomer; 0.176 g, 100%) as an off-white solid. MS (ES) m/z=564 (M+1).

The following compounds in Table 19 were prepared in similar manner as described in Preparation 115. Various methods were used to purify the compounds, which would be apparent to one skilled in the art.

TABLE 19

| Preparation | Chemical Name | Structure | MS (ES) m/z (M + 1) |
|---|---|---|---|
| 116[1] | 6-((6-Bromo-3-((2S,3S)-3-(dimethylamino)-2-methylpyrrolidin-1-yl)-5-fluoro-7,9-dihydro-furo[3,4-f]quinazolin-1-yl)amino)tetrahydro-1H-pyrazolo[1,2-a]pyrid-azin-5(6H)-one | 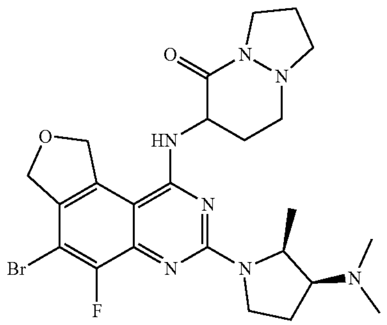 [SMILES: C[C@H]1[C@@H](N(C)C)CCN1c1nc(NC2CCN3CCCN3C2=O)c2c3c(c(Br)c(F)c2n1)COC3] | 550 |
| 92A[2] | tert-Butyl (4-(5-chloro-3-((S)-3-(dimethylamino)-pyrrolidin-1-yl)-1-((5-oxohexahydro-1H-pyr-azolo[1,2-a]pyridazin-6-yl)amino)-7,9-dihydro-furo[3,4-f]quinazolin-6-yl)-3-cyano-5-fluoro-benzo[b]thiophen-2-yl)-carbamate | 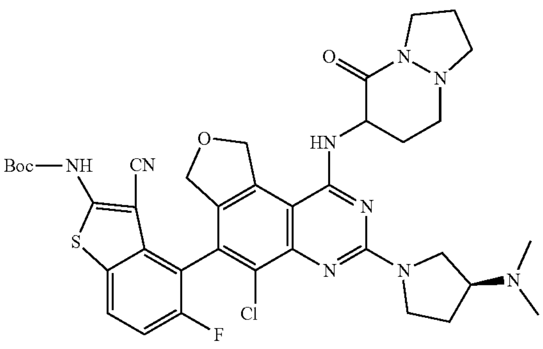 [SMILES: CN(C)[C@H]1CCN(c2nc(NC3CCN4CCCN4C3=O)c3c4c(c(-c5c(F)ccc6sc(NC(=O)OC(C)(C)C)c(C#N)c56)c(Cl)c3n2)COC4)C1] | 762 |
| 93A | (8aR)-6-((6-Bromo-3-((2S,3S)-3-(dimethyl-amino)-2-methylpyr-rolidin-1-yl)-5-fluoro-7,9-dihydrofuro[3,4-f]quinazolin-1-yl)amino)-hexahydroindolizin-5(1H)-one | 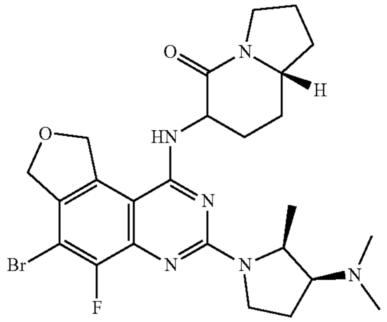 [SMILES: C[C@H]1[C@@H](N(C)C)CCN1c1nc(NC2CC[C@H]3CCCN3C2=O)c2c3c(c(Br)c(F)c2n1)COC3] | 547 |
| 94A[3] | 2-((6-Bromo-3-((S)-3-(dimethylamino)pyrrol-idin-1-yl)-5-fluoro-7,9-dihydrofuro[3,4-f]quin-azolin-1-yl)amino)hexa-hydropyridazino[1,2-a]pyridazin-1(2H)-one | 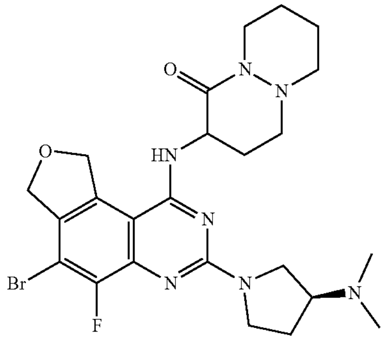 [SMILES: CN(C)[C@H]1CCN(c2nc(NC3CCN4CCCCN4C3=O)c3c4c(c(Br)c(F)c3n2)COC4)C1] | 548 |

TABLE 19-continued

| Preparation | Chemical Name | Structure | MS (ES) m/z (M + 1) |
|---|---|---|---|
| 95A[3] | 6-((6-Bromo-3-((2S,3S)-3-(dimethylamino)-2-methylpyrrolidin-1-yl)-5-fluoro-7,9-dihydro-furo[3,4-f]quinazolin-1-yl)amino)tetrahydro-1H-pyrazolo[1,2-a]pyrid-azin-5(6H)-one | 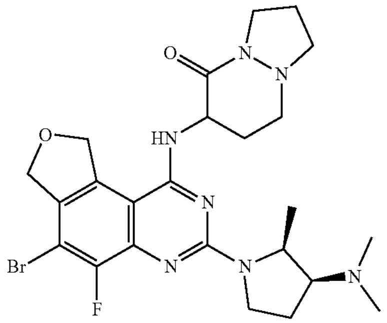 [SMILES: C[C@H]1[C@@H](N(C)C)CCN1c1nc(NC2CCN3CCCN3C2=O)c2c3c(c(Br)c(F)c2n1)COC3] | 548 |
| 96A[3] | 6-((6-Bromo-5-chloro-3-((S)-3-(dimethylamino)-pyrrolidin-1-yl)-7,9-dihydrofuro[3,4-f]quin-azolin-1-yl)amino)tetra-hydro-1H-pyrazolo[1,2-a]pyridazin-5(6H)-one | 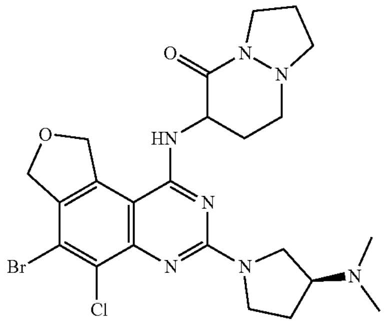 [SMILES: CN(C)[C@H]1CCN(c2nc(NC3CCN4CCCN4C3=O)c3c4c(c(Br)c(Cl)c3n2)COC4)C1] | 550 |
| 97A[3] | 6-((6-Bromo-5-chloro-3-((2S,3S)-3-(dimethyl-amino)-2-methylpyrrol-idin-1-yl)-7,9-dihydro-furo[3,4-f]quinazolin-1-yl)amino)tetrahydro-1H-pyrazolo[1,2-a]pyrid-azin-5(6H)-one | 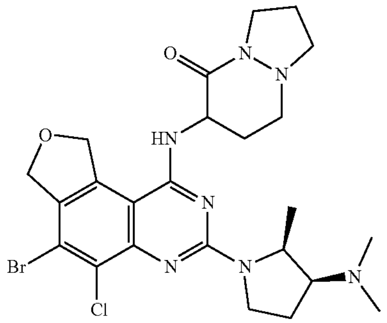 [SMILES: C[C@H]1[C@@H](N(C)C)CCN1c1nc(NC2CCN3CCCN3C2=O)c2c3c(c(Br)c(Cl)c2n1)COC3] | 564 |
| 80B | tert-Butyl (4-(1-((1,2-dimethyl-3-oxohexa-hydropyridazin-4-yl)-amino)-3-((2S,3S)-3-(dimethylamino)-2-methylpyrrolidin-1-yl)-5-fluoro-7,9-dihydro-furo[3,4-f]quinazolin-6-yl)-7-fluorobenzo[d]thiazol-2-yl)carbamate | 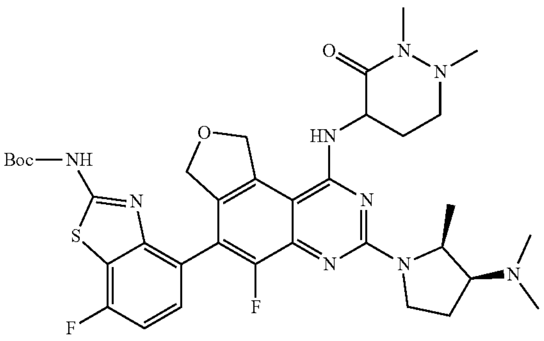 [SMILES: C[C@H]1[C@@H](N(C)C)CCN1c1nc(NC2CCN(C)N(C)C2=O)c2c3c(c(-c4ccc(F)c5sc(NC(=O)OC(C)(C)C)nc45)c(F)c2n1)COC3] | 724 |

[1]enriched toward (R) enantiomer
[2]Clean atropisomer, chiral purification from Preparation 34
[3]A predominant chiral center is present based on starting material from Preparation 53, 54, 55, 5A, 6A, 7A, or 8A The following compounds in Table 20 were prepared in similar manner as described in Preparation 28. Different coupling conditions, such as base, ligands, or palladium sources, may have been substituted. Various methods were used to purify the compounds, which would be apparent to one skilled in the art.

TABLE 20

| Preparation | Chemical Name | Structure | MS (ES) m/z (M + 1) |
|---|---|---|---|
| 117[1] | tert-Butyl (4-(3-((2S,3S)-3-(dimethylamino)-2-methylpyrrolidin-1-yl)-5-fluoro-1-((1-oxoocta-hydropyridazino[1,2-a] pyridazin-2-yl)amino)-7,9-dihydrofuro[3,4-f] quinazolin-6-yl)benzo [d]thiazol-2-yl)carbamate | 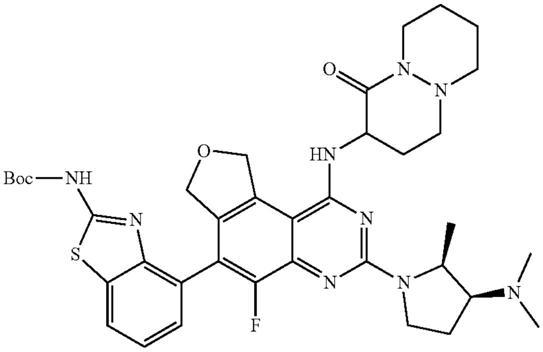 [SMILES: C[C@H]1[C@@H](N(C)C)CCN1c1nc(NC2CCN3CCCCN3C2=O)c2c3c(c(-c4cccc5sc(NC(=O)OC(C)(C)C)nc45)c(F)c2n1)COC3] | 732 |
| 118[1] | tert-Butyl (4-(3-((2S,3S)-3-(dimethylamino)-2-methylpyrrolidin-1-yl)-5-fluoro-1-((5-oxohexa-hydro-1H-pyrazolo[1,2-a]pyridazin-6-yl)amino)-7,9-dihydrofuro[3,4-f] quinazolin-6-yl)-7-fluorobenzo[d]thiazol-2-yl)carbamate | 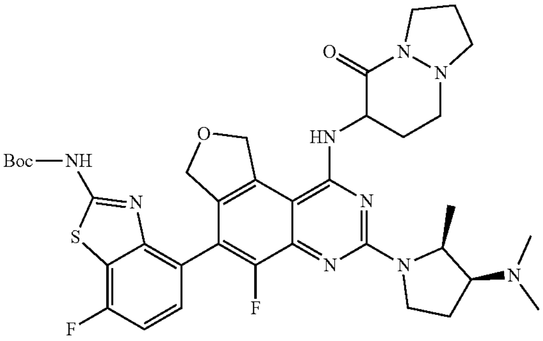 [SMILES: C[C@H]1[C@@H](N(C)C)CCN1c1nc(NC2CCN3CCCN3C2=O)c2c3c(c(-c4ccc(F)c5sc(NC(=O)OC(C)(C)C)nc45)c(F)c2n1)COC3] | 736 |
| 98A[2] | tert-Butyl (4-(3-((2S,3S)-3-(dimethylamino)-2-methylpyrrolidin-1-yl)-5-fluoro-1-(((9aS)-6-oxooctahydropyrido [2,1-c][1,4]oxazin-7-yl)-amino)-7,9-dihydrofuro [3,4-f]quinazolin-6-yl)-7-fluorobenzo[d]thiazol-2-yl)carbamate | 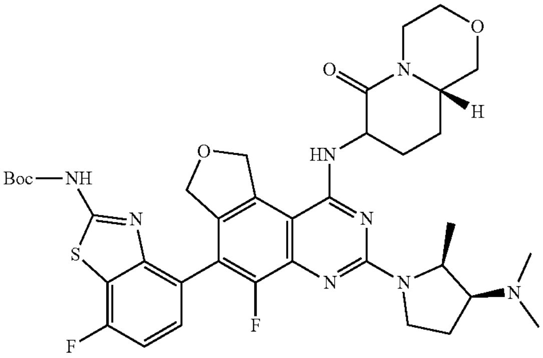 [SMILES: C[C@H]1[C@@H](N(C)C)CCN1c1nc(NC2CC[C@H]3COCCN3C2=O)c2c3c(c(-c4ccc(F)c5sc(NC(=O)OC(C)(C)C)nc45)c(F)c2n1)COC3] | 751 |
| 99A | tert-Butyl (7-fluoro-4-(5-fluoro-3-((2'S,3'S)-2'-methyl-[1,3'-bipyrrol-idin]-1'-yl)-1-(((6R,8aR)-5-oxooctahydroindolizin-6-yl)amino)-7,9-dihydro-furo[3,4-f]quinazolin-6-yl)benzo[d]thiazol-2-yl)carbamate | 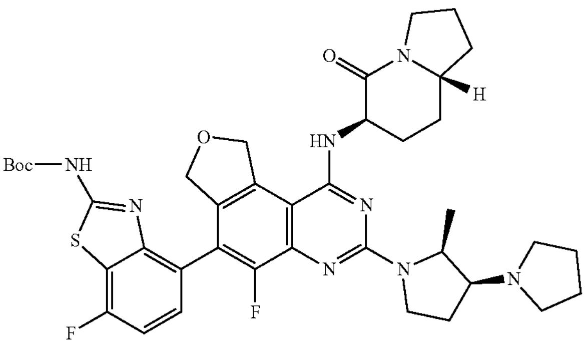 [SMILES: C[C@H]1[C@@H](N2CCCC2)CCN1c1nc(N[C@@H]2CC[C@H]3CCCN3C2=O)c2c3c(c(-c4ccc(F)c5sc(NC(=O)OC(C)(C)C)nc45)c(F)c2n1)COC3] | 761 |

TABLE 20-continued

| Preparation | Chemical Name | Structure | MS (ES) m/z (M + 1) |
|---|---|---|---|
| 100A | tert-Butyl (4-(3-((2S,3S)-3-(dimethylamino)-2-methylpyrrolidin-1-yl)-5-fluoro-1-((6-oxo-5-azaspiro[3.5]nonan-7-yl)amino)-7,9-dihydro-furo[3,4-f]quinazolin-6-yl)-7-fluorobenzo[d]thiazol-2-yl)carbamate | 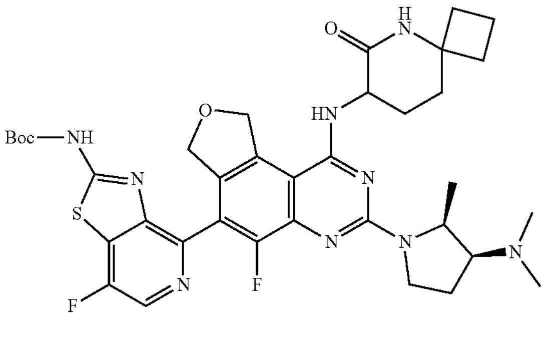 [SMILES: C[C@H]1[C@@H](N(C)C)CCN1c1nc(NC2CCC3(CCC3)NC2=O)c2c3c(c(-c4ncc(F)c5sc(NC(=O)OC(C)(C)C)nc45)c(F)c2n1)COC3] | 735 |
| 101A[2] | tert-Butyl (4-(3-((2S,3S)-3-(dimethylamino)-2-methylpyrrolidin-1-yl)-5-fluoro-1-((1-oxoocta-hydropyridazino[1,2-a]pyridazin-2-yl)amino)-7,9-dihydrofuro[3,4-f]quinazolin-6-yl)-7-fluorobenzo[d]thiazol-2-yl)carbamate | 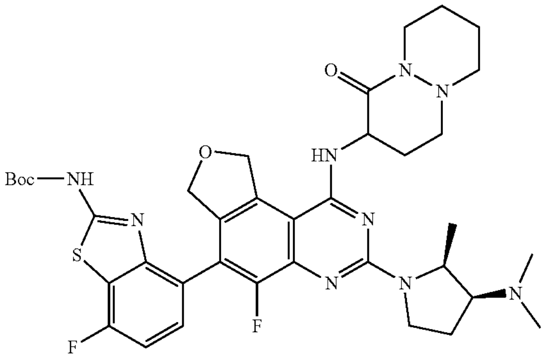 [SMILES: C[C@H]1[C@@H](N(C)C)CCN1c1nc(NC2CCN3CCCCN3C2=O)c2c3c(c(-c4ccc(F)c5sc(NC(=O)OC(C)(C)C)nc45)c(F)c2n1)COC3] | 750 |
| 102A[2] | tert-Butyl (4-(3-((S)-3-(dimethylamino)pyrrolidin-1-yl)-5-fluoro-1-((1-oxooctahydro-pyridazino[1,2-a]pyridazin-2-yl)amino)-7,9-dihydrofuro[3,4-f]quinazolin-6-yl)-5,7-difluorobenzo[d]thiazol-2-yl)carbamate | 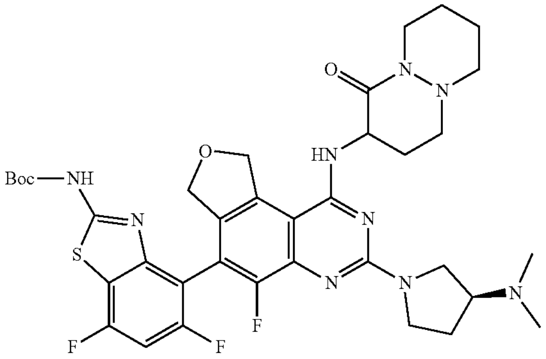 [SMILES: CN(C)[C@H]1CCN(c2nc(NC3CCN4CCCCN4C3=O)c3c4c(c(-c5c(F)cc(F)c6sc(NC(=O)OC(C)(C)C)nc56)c(F)c3n2)COC4)C1] | 754 |
| 103A[2] | tert-Butyl (4-(3-((2S,3S)-3-(dimethylamino)-2-methylpyrrolidin-1-yl)-5-fluoro-1-((5-oxohexa-hydro-1H-pyrazolo[1,2-a]pyridazin-6-yl)amino)-7,9-dihydrofuro[3,4-f]quinazolin-6-yl)-5,7-difluorobenzo[d]thiazol-2-yl)carbamate | 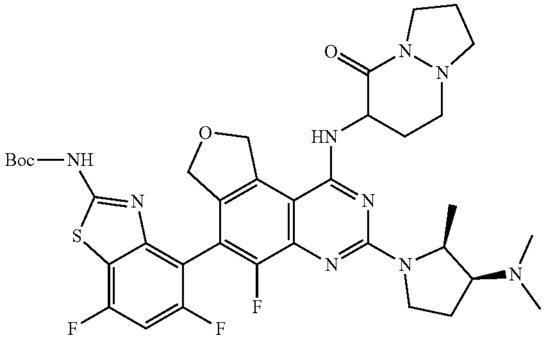 [SMILES: C[C@H]1[C@@H](N(C)C)CCN1c1nc(NC2CCN3CCCN3C2=O)c2c3c(c(-c4c(F)cc(F)c5sc(NC(=O)OC(C)(C)C)nc45)c(F)c2n1)COC3] | 754 |

TABLE 20-continued

| Preparation | Chemical Name | Structure | MS (ES) m/z (M + 1) |
|---|---|---|---|
| 104A[2] | tert-Butyl (4-(5-chloro-3-((S)-3-(dimethyl-amino)pyrrolidin-1-yl)-1-((5-oxohexahydro-1H-pyrazolo[1,2-a]pyridazin-6-yl)-amino)-7,9-dihydrofuro[3,4-f]quinazolin-6-yl)-5,7-difluorobenzo[d]thiazol-2-yl)carbamate | 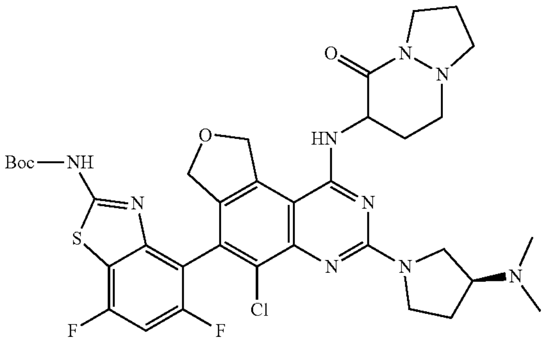 [SMILES: CN(C)[C@H]1CCN(c2nc(NC3CCN4CCCN4C3=O)c3c4c(c(-c5c(F)cc(F)c6sc(NC(=O)OC(C)(C)C)nc56)c(Cl)c3n2)COC4)C1] | 756 |
| 105A[2] | tert-Butyl (4-(5-chloro-3-((2S,3S)-3-(dimethyl-amino)-2-methylpyrrol-idin-1-yl)-1-((5-oxo-hexahydro-1H-pyrazolo[1,2-a]pyridazin-6-yl)-amino)-7,9-dihydrofuro[3,4-f]quinazolin-6-yl)-5,7-difluorobenzo[d]thiazol-2-yl)carbamate | 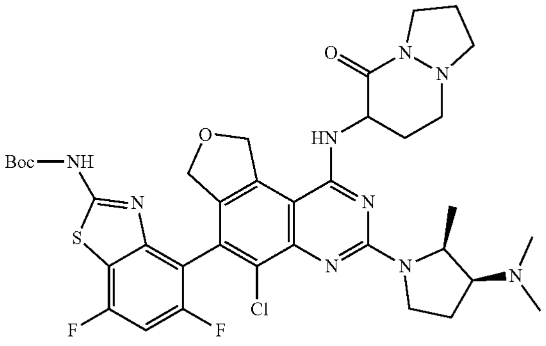 [SMILES: C[C@H]1[C@@H](N(C)C)CCN1c1nc(NC2CCN3CCCN3C2=O)c2c3c(c(-c4c(F)cc(F)c5sc(NC(=O)OC(C)(C)C)nc45)c(Cl)c2n1)COC3] | 770 |
| 106A[2] | tert-Butyl (4-(3-((2S,3S)-3-(dimethylamino)-2-methylpyrrolidin-1-yl)-5-fluoro-1-(((8aR)-5-oxooctahydroindolizin-6-yl)amino)-7,9-dihydro-furo[3,4-f]quinazolin-6-yl)benzo[d]thiazol-2-yl)carbamate | 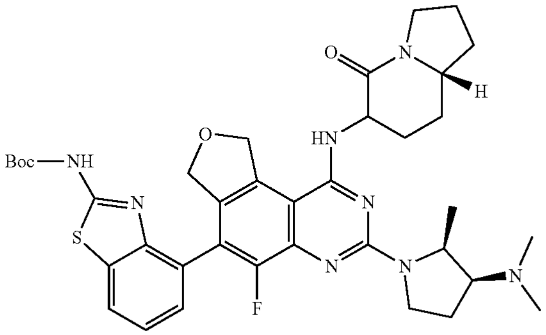 [SMILES: C[C@H]1[C@@H](N(C)C)CCN1c1nc(NC2CC[C@H]3CCCN3C2=O)c2c3c(c(-c4cccc5sc(NC(=O)OC(C)(C)C)nc45)c(F)c2n1)COC3] | 717 |
| 107A[2] | tert-Butyl (4-(3-((S)-3-(dimethylamino)pyrrol-idin-1-yl)-5-fluoro-1-(((8aR)-5-oxoocta-hydroindolizin-6-yl)-amino)-7,9-dihydro-furo[3,4-f]quinazolin-6-yl)-5,7-difluoro-benzo[d]thiazol-2-yl)-carbamate | 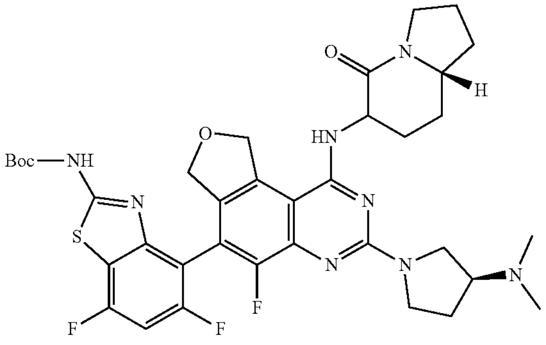 [SMILES: CN(C)[C@H]1CCN(c2nc(NC3CC[C@H]4CCCN4C3=O)c3c4c(c(-c5c(F)cc(F)c6sc(NC(=O)OC(C)(C)C)nc56)c(F)c3n2)COC4)C1] | 739 |

TABLE 20-continued

| Preparation | Chemical Name | Structure | MS (ES) m/z (M + 1) |
|---|---|---|---|
| 108A[2] | tert-Butyl (4-(3-((2S,3S)-3-(dimethylamino)-2-methylpyrrolidin-1-yl)-5-fluoro-1-(((8aR)-5-oxooctahydroindolizin-6-yl)amino)-7,9-dihydro-furo[3,4-f]quinazolin-6-yl)-5,7-difluorobenzo [d]thiazol-2-yl)carbamate | 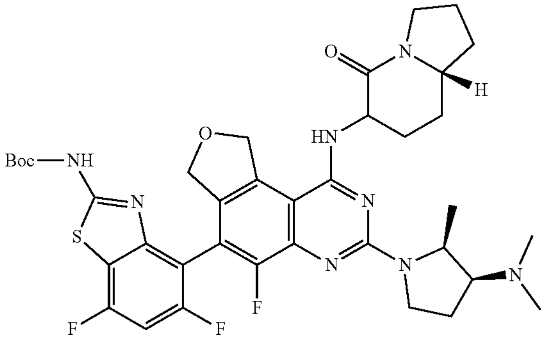 [SMILES: C[C@H]1[C@@H](N(C)C)CCN1c1nc(NC2CC[C@H]3CCCN3C2=O)c2c3c(c(-c4c(F)cc(F)c5sc(NC(=O)OC(C)(C)C)nc45)c(F)c2n1)COC3] | 753 |
| 81B | tert-Butyl (4-(5-chloro-9-(((6R,8aR)-5-oxoocta-hydroindolizin-6-yl)-amino)-1,3-dihydro-furo[3,4-f]cinnolin-4-yl)-3-cyano-7-fluoro-benzo[b]thiophen-2-yl)-carbamate | 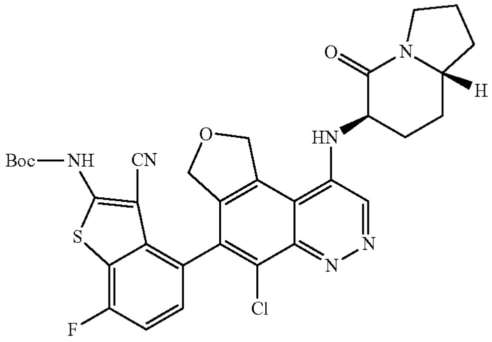 | 649 |
| 82B | tert-Butyl (4-(5-fluoro-3-((2'S,3'S)-2'-methyl-[1,3'-bipyrrolidin]-1'-yl)-1-(((6R,8aR)-5-oxooctahydroindolizin-6-yl)amino)-7,9-dihydrofuro[3,4-f] quinazolin-6-yl)benzo [d]thiazol-2-yl)-carbamate | 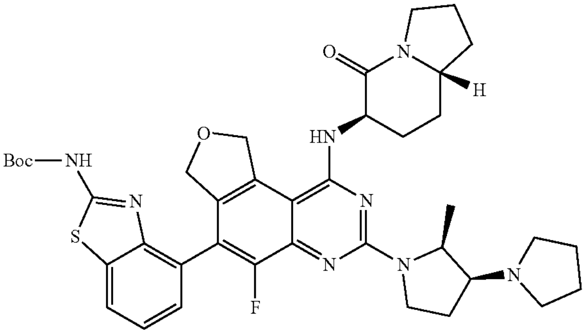 [SMILES: C[C@H]1[C@@H](N2CCCC2)CCN1c1nc(N[C@@H]2CC[C@H]3CCCN3C2=O)c2c3c(c(-c4cccc5sc(NC(=O)OC(C)(C)C)nc45)c(F)c2n1)COC3] | 743 |
| 83B | tert-Butyl (7-fluoro-4-(5-fluoro-3-((2S,3S)-3-(3-(fluoromethyl)azet-idin-1-yl)-2-methyl-pyrrolidin-1-yl)-1-(((6R,8aR)-5-oxoocta-hydroindolizin-6-yl)-amino)-7,9-dihydro-furo[3,4-f]quinazolin-6-yl)benzo[d]thiazol-2-yl)carbamate | 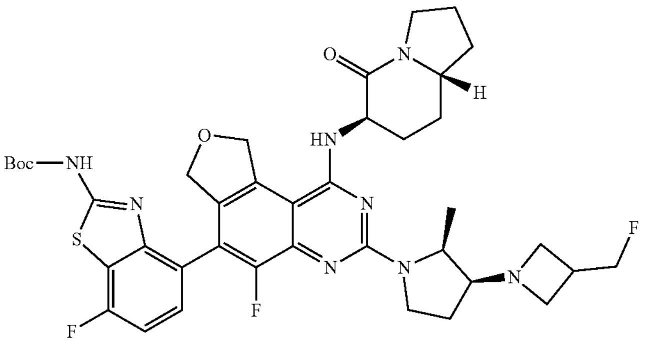 [SMILES: C[C@H]1[C@@H](N2CC(CF)C2)CCN1c1nc(N[C@@H]2CC[C@H]3CCCN3C2=O)c2c3c(c(-c4ccc(F)c5sc(NC(=O)OC(C)(C)C)nc45)c(F)c2n1)COC3] | 779 |

TABLE 20-continued

| Preparation | Chemical Name | Structure | MS (ES) m/z (M + 1) |
| --- | --- | --- | --- |
| 84B[3] | tert-Butyl (7-fluoro-4-(5-fluoro-3-((2S)-2-methyl-3-(5-azaspiro[2.3]hexan-5-yl)-pyrrolidin-1-yl)-1-(((6R,8aR)-5-oxooctahydroindolizin-6-yl)-amino)-7,9-dihydro-furo[3,4-f]quinazolin-6-yl)benzo[d]thiazol-2-yl)carbamate, Isomer 1 | 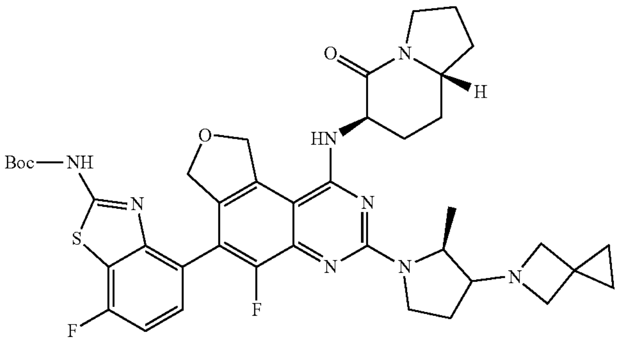 [SMILES: C[C@H]1C(N2CC3(CC3)C2)CCN1c1nc(N[C@@H]2CC[C@H]3CCCN3C2=O)c2c3c(c(-c4ccc(F)c5sc(NC(=O)OC(C)(C)C)nc45)c(F)c2n1)COC3] | 773 |
| 85B[3] | tert-Butyl (7-fluoro-4-(5-fluoro-3-((2S)-2-methyl-3-(5-azaspiro[2.3]hexan-5-yl)-pyrrolidin-1-yl)-1-(((6R,8aR)-5-oxooctahydroindolizin-6-yl)-amino)-7,9-dihydro-furo[3,4-f]quinazolin-6-yl)benzo[d]thiazol-2-yl)carbamate, Isomer 2 | 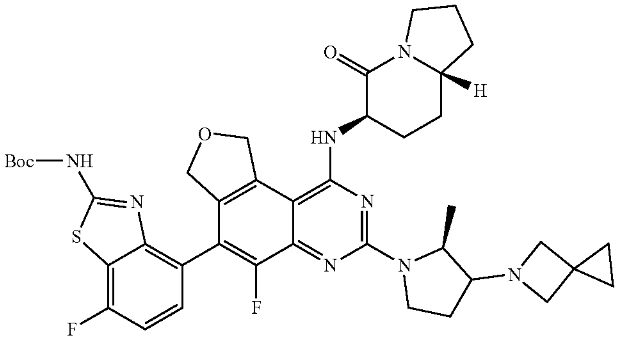 [SMILES: C[C@H]1C(N2CC3(CC3)C2)CCN1c1nc(N[C@@H]2CC[C@H]3CCCN3C2=O)c2c3c(c(-c4ccc(F)c5sc(NC(=O)OC(C)(C)C)nc45)c(F)c2n1)COC3] | 773 |
| 86B | tert-Butyl (4-(3-((6S)-1,6-dimethylhexahydropyrrolo[3,4-b]pyrrol-5(1H)-yl)-5-fluoro-1-(((6R,8aR)-5-oxooctahydroindolizin-6-yl)amino)-7,9-dihydrofuro[3,4-f]quinazolin-6-yl)-7-fluorobenzo[d]thiazol-2-yl)carbamate | 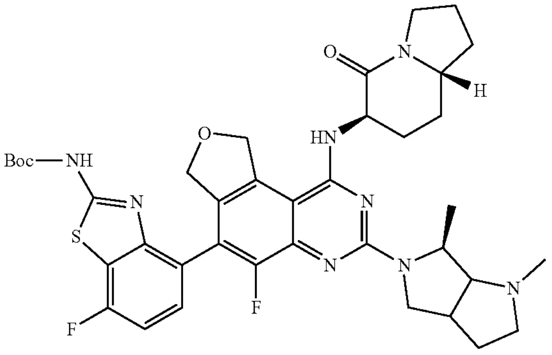 [SMILES: C[C@H]1C2C(CCN2C)CN1c1nc(N[C@@H]2CC[C@H]3CCCN3C2=O)c2c3c(c(-c4ccc(F)c5sc(NC(=O)OC(C)(C)C)nc45)c(F)c2n1)COC3] | 747 |
| 87B | tert-Butyl (4-(7-((2S,3S)-3-(dimethylamino)-2-methylpyrrolidin-1-yl)-5-fluoro-9-(((6R,8aR)-5-oxooctahydroindolizin-6-yl)amino)-1,3-dihydrofuro[3,4-f]quinolin-4-yl)-7-fluorobenzo[d]thiazol-2-yl)carbamate | 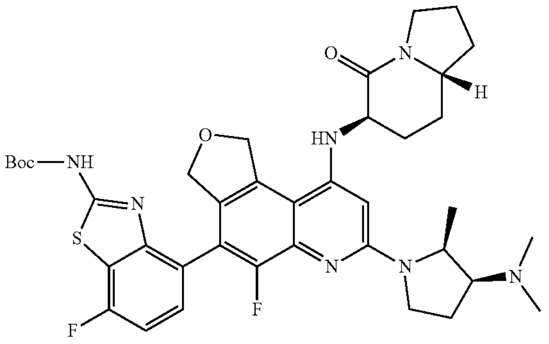 [SMILES: C[C@H]1[C@@H](N(C)C)CCN1c1cc(N[C@@H]2CC[C@H]3CCCN3C2=O)c2c3c(c(-c4ccc(F)c5sc(NC(=O)OC(C)(C)C)nc45)c(F)c2n1)COC3] | 734 |

TABLE 20-continued

| Preparation | Chemical Name | Structure | MS (ES) m/z (M + 1) |
|---|---|---|---|
| 88B | tert-Butyl (7-fluoro-4-(5-fluoro-7-((2'S,3'S)-2'-methyl-[1,3'-bipyrrolidin]-1'-yl)-9-(((6R,8aR)-5-oxooctahydroindolizin-6-yl)-amino)-1,3-dihydrofuro[3,4-f]quinolin-4-yl)benzo[d]thiazol-2-yl)carbamate | 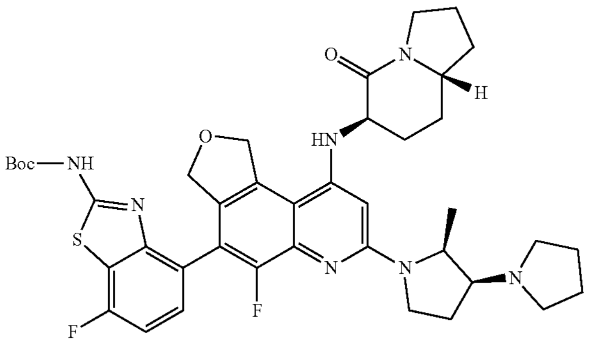 [SMILES: C[C@H]1[C@@H](N2CCCC2)CCN1c1cc(N[C@@H]2CC[C@H]3CCCN3C2=O)c2c3c(c(-c4ccc(F)c5sc(NC(=O)OC(C)(C)C)nc45)c(F)c2n1)COC3] | 760 |
| 89B | tert-Butyl (4-(1-(((6R)-6-(difluoromethyl)-1-methyl-2-oxopiperidin-3-yl)amino)-3-((2S,3S)-3-(dimethylamino)-2-methylpyrrolidin-1-yl)-5-fluoro-7,9-dihydrofuro[3,4-f]quinazolin-6-yl)-7-fluorobenzo[d]thiazol-2-yl)carbamate | 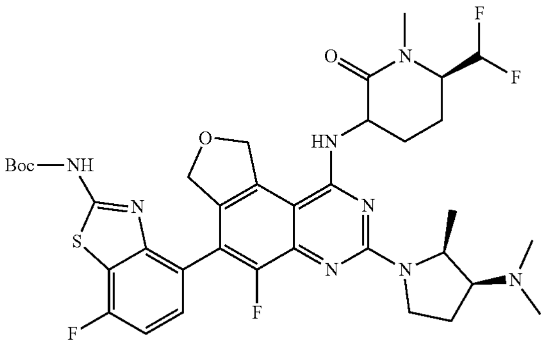 [SMILES: C[C@H]1[C@@H](N(C)C)CCN1c1nc(NC2CC[C@H](C(F)F)N(C)C2=O)c2c3c(c(-c4ccc(F)c5sc(NC(=O)OC(C)(C)C)nc45)c(F)c2n1)COC3] | 759 |
| 90B | tert-Butyl (4-(3-((2S,3S)-3-(bis(methyl-d3)amino)-2-methylpyrrolidin-1-yl)-5-fluoro-1-(((6R,8aR)-5-oxooctahydroindolizin-6-yl)amino)-7,9-dihydrofuro[3,4-f]quinazolin-6-yl)-7-fluorobenzo[d]thiazol-2-yl)carbamate | 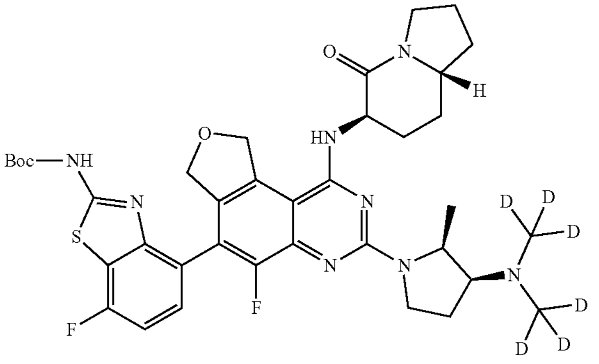 [SMILES: [2H]C([2H])([2H])N([C@H]1CCN(c2nc(N[C@@H]3CC[C@H]4CCCN4C3=O)c3c4c(c(-c5ccc(F)c6sc(NC(=O)OC(C)(C)C)nc56)c(F)c3n2)COC4)[C@H]1C)C([2H])([2H])[2H]] | 741 |

[1]enriched toward (R) enantiomer

[2]A predominant chiral center is present based on starting material from Preparation 53, 54, 55, 5A, 6A, 7A, or 8A

[3]Normal Phase; silica, 0-10% methanol in dichloromethane, Isomer refers to a clean diastereomer on the pyrrolidine The following compounds in Table 21 were prepared in similar manner as described in Preparation 73. Different coupling conditions, such as base, ligands, or palladium sources, may have been substituted. Various methods were used to purify the compounds, which would be apparent to one skilled in the art.

TABLE 21

| Preparation | Chemical Name | Structure | MS (ES) m/z (M + 1) |
|---|---|---|---|
| 109A[1] | tert-Butyl (4-(5-chloro-3-((2S,3S)-3-(dimethyl-amino)-2-methylpyrrol-idin-1-yl)-1-(((8aR)-5-oxooctahydroindolizin-6-yl)amino)-7,9-dihydro-furo[3,4-f]quinazolin-6-yl)-7-fluorothiazolo [4,5-c]pyridin-2-yl) carbamate | 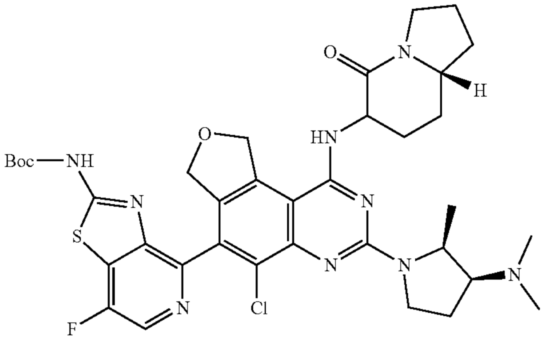 [SMILES: C[C@H]1[C@@H](N(C)C)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 752 |
| 110A[2] | tert-Butyl (4-(5-chloro-3-((2S,3S)-3-(dimethyl-amino)-2-methylpyrrol-idin-1-yl)-1-(((8aR)-5-oxooctahydroindolizin-6-yl)amino)-7,9-dihydrofuro[3,4-f]quin-azolin-6-yl)-7-fluoro-thiazolo[4,5-c]pyridin-2-yl)carbamate | 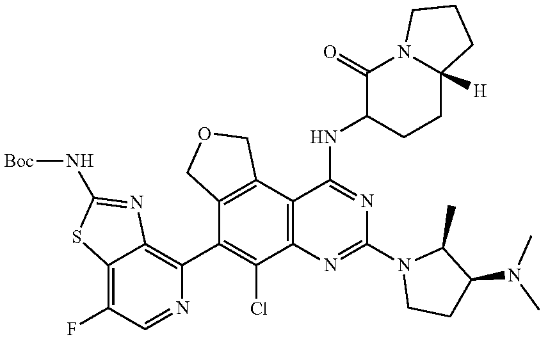 [SMILES: C[C@H]1[C@@H](N(C)C)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 752 |
| 111A[2] | tert-Butyl (4-(5-chloro-3-((2S,3S)-3-(ethyl-(methyl)amino)-2-methylpyrrolidin-1-yl)-1-(((8aR)-5-oxo-octahydroindolizin-6-yl)amino)-7,9-dihydro-furo[3,4-f]quinazolin-6-yl)-7-fluorothiazolo [4,5-c]pyridin-2-yl)-carbamate | 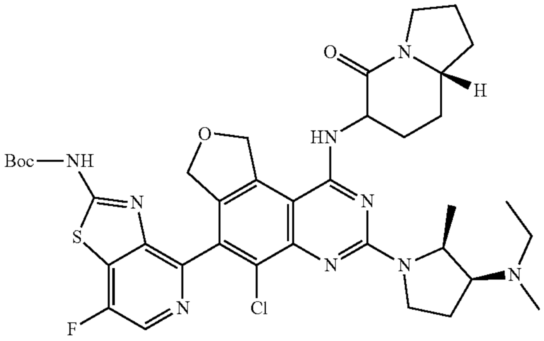 [SMILES: CCN(C)[C@H]1CCN(c2nc(NC3CC[C@H]4CCCN4C3=O)c3c4c(c(-c5ncc(F)c6sc(NC(=O)OC(C)(C)C)nc56)c(Cl)c3n2)COC4)[C@H]1C] | 766 |
| 112A[3] | tert-Butyl (4-(5-chloro-3-((2S,3S)-3-(ethyl-(methyl)amino)-2-methylpyrrolidin-1-yl)-1-((4-methyl-5-oxo-4-azaspiro[2.5]octan-6-yl)-amino)-7,9-dihydrofuro [3,4-f]quinazolin-6-yl)-7-fluorothiazolo[4,5-c] pyridin-2-yl)carbamate, Isomer 1 | 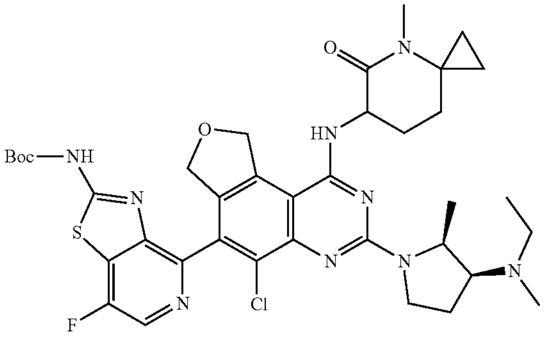 [SMILES: CCN(C)[C@H]1CCN(c2nc(NC3CCC4(CC4)N(C)C3=O)c3c4c(c(-c5ncc(F)c6sc(NC(=O)OC(C)(C)C)nc56)c(Cl)c3n2)COC4)[C@H]1C] | 766 |

TABLE 21-continued

| Preparation | Chemical Name | Structure | MS (ES) m/z (M + 1) |
|---|---|---|---|
| 113A[3] | tert-Butyl (4-(5-chloro-3-((2S,3S)-3-(ethyl-(methyl)amino)-2-methylpyrrolidin-1-yl)-1-((4-methyl-5-oxo-4-azaspiro[2.5]octan-6-yl)-amino)-7,9-dihydrofuro[3,4-f]quinazolin-6-yl)-7-fluorothiazolo[4,5-c]pyridin-2-yl)carbamate, Isomer 2 | 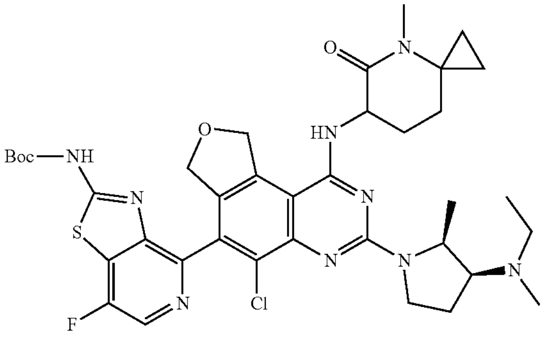 [SMILES: CCN(C)[C@H]1CCN(c2nc(NC3CCC4(CC4)N(C)C3=O)c3c4c(c(-c5ncc(F)c6sc(NC(=O)OC(C)(C)C)nc56)c(Cl)c3n2)COC4)[C@H]1C] | 766 |
| 114A | tert-Butyl (4-(5-chloro-3-((2S,3S)-3-(ethyl-(methyl)amino)-2-methylpyrrolidin-1-yl)-1-((5-methyl-6-oxo-5-azaspiro[2.5]octan-7-yl)-amino)-7,9-dihydrofuro[3,4-f]quinazolin-6-yl)-7-fluorothiazolo[4,5-c]pyridin-2-yl)carbamate | 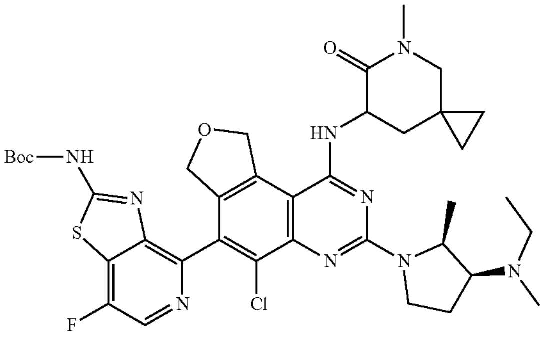 [SMILES: CCN(C)[C@H]1CCN(c2nc(NC3CC4(CC4)CN(C)C3=O)c3c4c(c(-c5ncc(F)c6sc(NC(=O)OC(C)(C)C)nc56)c(Cl)c3n2)COC4)[C@H]1C] | 766 |
| 115A | tert-Butyl (4-(3-((2S,3S)-3-(dimethylamino)-2-methylpyrrolidin-1-yl)-5-fluoro-1-((5-methyl-6-oxo-5-azaspiro[3.5]nonan-7-yl)amino)-7,9-dihydrofuro[3,4-f]quin-azolin-6-yl)-7-fluoro-thiazolo[4,5-c]pyridin-2-yl)carbamate | 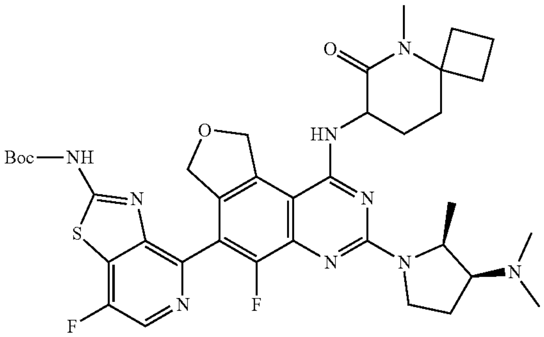 [SMILES: C[C@H]1[C@@H](N(C)C)CCN1c1nc(NC2CCC3(CCC3)N(C)C2=O)c2c3c(c(-c4ncc(F)c5sc(NC(=O)OC(C)(C)C)nc45)c(F)c2n1)COC3] | 750 |
| 116A | tert-Butyl (4-(3-((2S,3S)-3-(dimethylamino)-2-methylpyrrolidin-1-yl)-5-fluoro-1-(((8aR)-5-oxooctahydroindolizin-6-yl)amino)-7,9-dihydro-furo[3,4-f]quinazolin-6-yl)-7-fluorothiazolo[4,5-c]pyridin-2-yl)-carbamate | 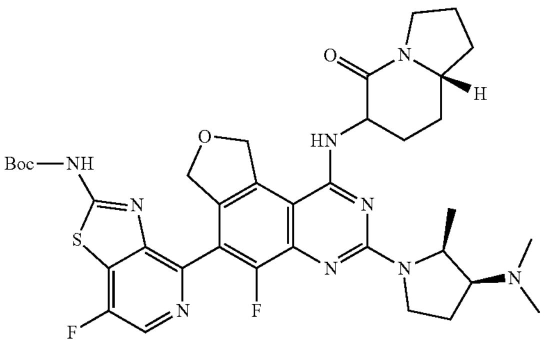 [SMILES: C[C@H]1[C@@H](N(C)C)CCN1c1nc(NC2CC[C@H]3CCCN3C2=O)c2c3c(c(-c4ncc(F)c5sc(NC(=O)OC(C)(C)C)nc45)c(F)c2n1)COC3] | 736 |

TABLE 21-continued

| Preparation | Chemical Name | Structure | MS (ES) m/z (M + 1) |
|---|---|---|---|
| 91B | tert-Butyl (4-(5-chloro-3-((2S,3S)-3-(diethyl-amino)-2-methyl-pyrrolidin-1-yl)-1-((5-methyl-6-oxo-5-aza-spiro[2.5]octan-7-yl)-amino)-7,9-dihydro-furo[3,4-f]quinazolin-6-yl)-7-fluorothiazolo [4,5-c]pyridin-2-yl)-carbamate | 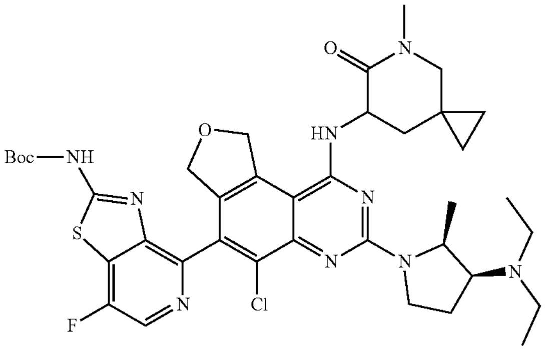 [SMILES: CCN(CC)[C@H]1CCN(c2nc(NC3CC4(CC4)CN(C)C3=O)c3c4c(c(-c5ncc(F)c6sc(NC(=O)OC(C)(C)C)nc56)c(Cl)c3n2)COC4)[C@H]1C] | 780 |
| 92B[2] | tert-Butyl (4-(5-chloro-3-((2S,3S)-3-(6-fluoro-2-azaspiro[3.3]heptan-2-yl)-2-methylpyrrol-idin-1-yl)-1-(((8aR)-5-oxooctahydroindolizin-6-yl)amino)-7,9-dihydrofuro[3,4-f] quinazolin-6-yl)-7-fluorothiazolo[4,5-c] pyridin-2-yl)carbamate | 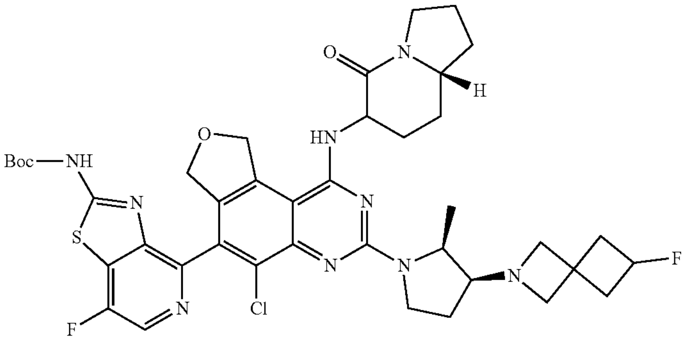 [SMILES: C[C@H]1[C@@H](N2CC3(CC(F)C3)C2)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 822 |
| 93B[2] | tert-Butyl (4-(5-chloro-3-((2S,3S)-2-methyl-3-(5-azaspiro[2.3]hexan-5-yl)pyrrolidin-1-yl)-1-(((8aR)-5-oxoocta-hydroindolizin-6-yl)-amino)-7,9-dihydro-furo[3,4-f]quinazolin-6-yl)-7-fluorothiazolo [4,5-c]pyridin-2-yl)-carbamate | 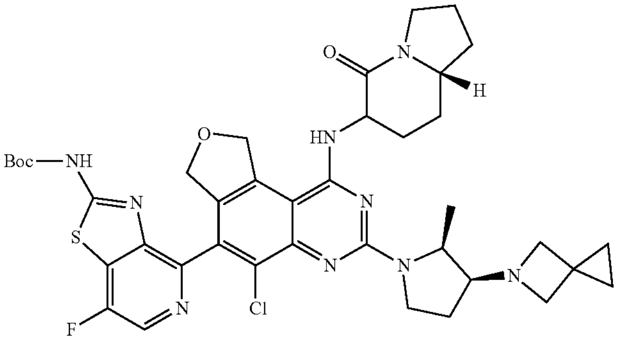 [SMILES: C[C@H]1[C@@H](N2CC3(CC3)C2)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 790 |
| 94B[2] | tert-Butyl (4-(5-chloro-3-((2S,3S)-3-((3-fluoro-cyclobutyl)(methyl)-amino)-2-methylpyr-rolidin-1-yl)-1-(((8aR)-5-oxooctahydroindoli-zin-6-yl)amino)-7,9-dihydrofuro[3,4-f] quinazolin-6-yl)-7-fluorothiazolo[4,5-c] pyridin-2-yl)carbamate | 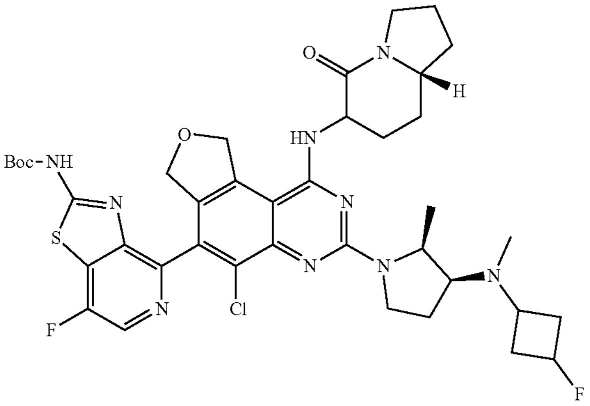 [SMILES: C[C@H]1[C@@H](N(C)C2CC(F)C2)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 810 |

TABLE 21-continued

| Preparation | Chemical Name | Structure | MS (ES) m/z (M + 1) |
| --- | --- | --- | --- |
| 95B[2] | tert-Butyl (4-(5-chloro-3-((2S,3S)-3-(3-(fluoromethyl)azetidin-1-yl)-2-methylpyrrolidin-1-yl)-1-(((8aR)-5-oxooctahydroindolizin-6-yl)amino)-7,9-dihydrofuro[3,4-f]quinazolin-6-yl)-7-fluorothiazolo[4,5-c]pyridin-2-yl)carbamate | 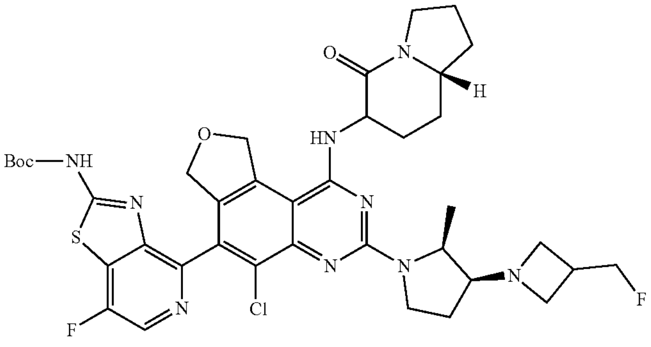 [SMILES: C[C@H]1[C@@H](N2CC(CF)C2)CCN1c1nc(NC2CC[C@H]3CCCN3C2=O)c2c3c(c(-c4ncc(F)c5sc(NC(=O)OC(C)(C)C)nc45)c(Cl)c2n1)COC3] | 796 |
| 96B[4] | tert-Butyl (4-(5-chloro-1-((1,2-dimethyl-3-oxohexahydropyridazin-4-yl)amino)-3-((2S,3S)-3-(dimethylamino)-2-methylpyrrolidin-1-yl)-7,9-dihydrofuro[3,4-f]quinazolin-6-yl)-7-fluorothiazolo[4,5-c]pyridin-2-yl)carbamate | 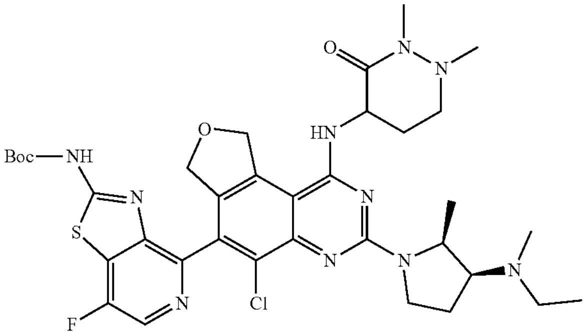 [SMILES: CCN(C)[C@H]1CCN(c2nc(NC3CCN(C)N(C)C3=O)c3c4c(c(-c5ncc(F)c6sc(NC(=O)OC(C)(C)C)nc56)c(Cl)c3n2)COC4)[C@H]1C] | 741 |
| 97B[5] | tert-Butyl (4-(5-chloro-1-((1,2-dimethyl-3-oxohexahydropyridazin-4-yl)amino)-3-((2S,3S)-3-(ethyl(methyl)amino)-2-methylpyrrolidin-1-yl)-7,9-dihydrofuro[3,4-f]quinazolin-6-yl)-7-fluorothiazolo[4,5-c]pyridin-2-yl)carbamate | 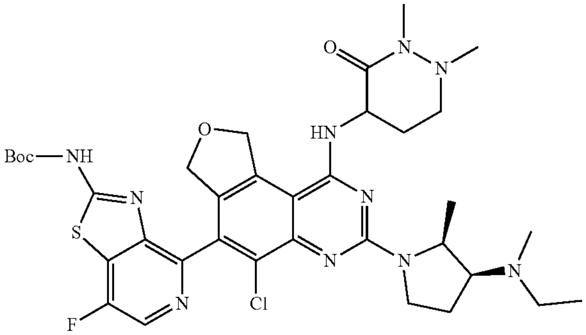 [SMILES: CCN(C)[C@H]1CCN(c2nc(NC3CCN(C)N(C)C3=O)c3c4c(c(-c5ncc(F)c6sc(NC(=O)OC(C)(C)C)nc56)c(Cl)c3n2)COC4)[C@H]1C] | 755 |
| 98B | tert-Butyl (4-(5-chloro-7-((2S,3S)-3-(dimethylamino)-2-methylpyrrolidin-1-yl)-9-(((6R,8aR)-5-oxooctahydroindolizin-6-yl)amino)-1,3-dihydrofuro[3,4-f]quinolin-4-yl)-7-fluorothiazolo[4,5-c]pyridin-2-yl)carbamate | 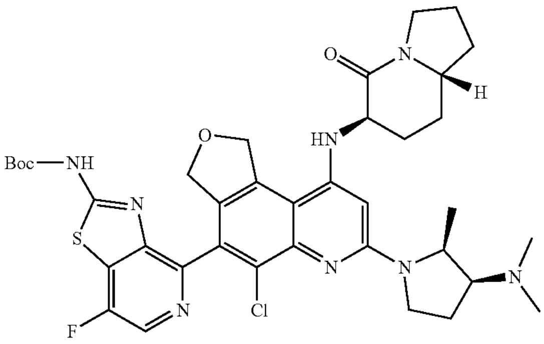 [SMILES: C[C@H]1[C@@H](N(C)C)CCN1c1cc(N[C@@H]2CC[C@H]3CCCN3C2=O)c2c3c(c(-c4ncc(F)c5sc(NC(=O)OC(C)(C)C)nc45)c(Cl)c2n1)COC3] | 751 |

TABLE 21-continued

| Preparation | Chemical Name | Structure | MS (ES) m/z (M + 1) |
|---|---|---|---|
| 99B | tert-Butyl (7-fluoro-4-(5-fluoro-3-((2'S,3'S)-2'-methyl-[1,3'-bipyrrolidin]-1'-yl)-1-(((6R,8aR)-5-oxooctahydroindolizin-6-yl)amino)-7,9-dihydrofuro[3,4-f]quinazolin-6-yl)thiazolo[4,5-c]pyridin-2-yl)carbamate | 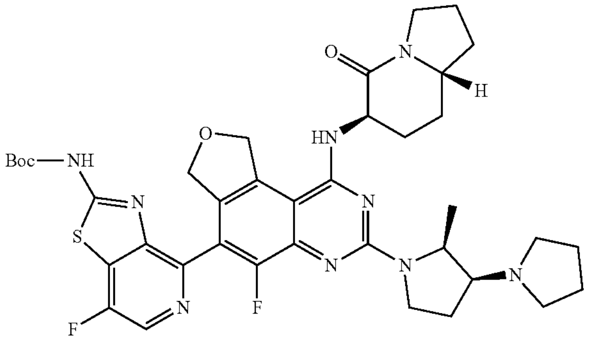 [SMILES: C[C@H]1[C@@H](N2CCCC2)CCN1c1nc(N[C@@H]2CC[C@H]3CCCN3C2=O)c2c3c(c(-c4ncc(F)c5sc(NC(=O)OC(C)(C)C)nc45)c(F)c2n1)COC3] | 762 |

[1]Clean isomer at the 6-position of the hexahydroindolizinone, chiral purification from Preparation 13A
[2]Clean isomer at the 6-position of the hexahydroindolizinone, chiral purification from Preparation 14A
[3]Chiral SFC; Chiralcel OD, 20 x 250 mm, 20% (isopropanol w/0.5% dimethylethylamine) in $CO_2$, 80 mL/min, Isomer refers to a clean isomer at the 6-position of the azaspirooctanone.
[4]Clean isomer at the 4-position of the pyridazinone, chiral purification from Preparation 78B
[5]Clean isomer at the 4-position of the pyridazinone, chiral purification from Preparation 79B

Preparation 100B

2-Amino-4-(5-chloro-3-(ethylsulfonyl)-1-(((6R,8aR)-5-oxooctahydroindolizin-6-yl)amino)-7,9-dihydrofuro[3,4-f]quinazolin-6-yl)-5-fluorobenzo[b]thiophene-3-carbonitrile

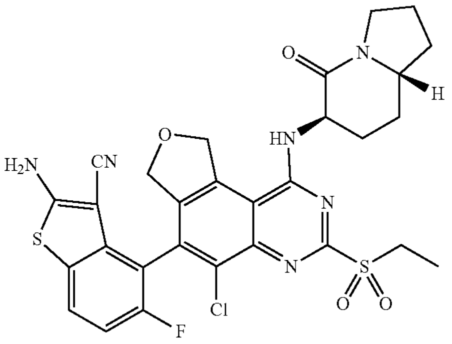 [SMILES: CCS(=O)(=O)c1nc(N[C@@H]2CC[C@H]3CCCN3C2=O)c2c3c(c(-c4c(F)ccc5sc(N)c(C#N)c45)c(Cl)c2n1)COC3]

tert-Butyl (4-(5-chloro-3-(ethylsulfonyl)-1-(((6R,8aR)-5-oxooctahydroindolizin-6-yl)amino)-7,9-dihydrofuro[3,4-f]quinazolin-6-yl)-3-cyano-5-fluorobenzo[b]thiophen-2-yl)carbamate (0.200 g, 0.270 mmol) was diluted with acetonitrile (1.80 mL) and HCl (3M in cyclopentyl methyl ether; 0.45 mL, 1.35 mmol). The mixture was stirred for 16 h at room temperature. The mixture was concentrated under reduced pressure to obtain the title compound (0.17 g, 98%) as a yellow solid. MS (ES) m/z=641 (M+1). Clean atropisomer, chiral purification from Preparation 34.

The following compounds in Table 22 were prepared in similar manner as described in Preparation 100B. Various methods were used to purify the compounds, which would be apparent to one skilled in the art.

TABLE 22

| Preparation | Chemical Name | Structure | MS (ES) m/z (M + 1) |
|---|---|---|---|
| 101B[1] | 2-Amino-4-(5-chloro-3-(ethylsulfonyl)-1-(((6R,8aR)-5-oxooctahydroindolizin-6-yl)amino)-7,9-dihydrofuro[3,4-f]quinazolin-6-yl)-7-fluorobenzo[b]thiophene-3-carbonitrile | 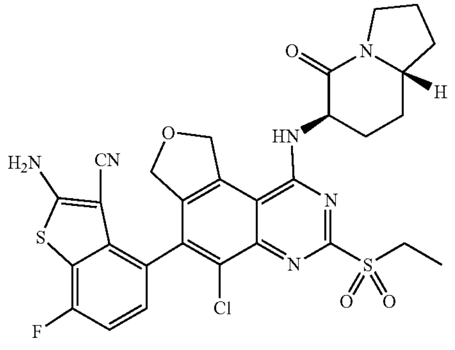 [SMILES: CCS(=O)(=O)c1nc(N[C@@H]2CC[C@H]3CCCN3C2=O)c2c3c(c(-c4ccc(F)c5sc(N)c(C#N)c45)c(Cl)c2n1)COC3] | 641 |

[1]Clean atropisomer, chiral purification from Preparation 30

Preparation 102B tert-Butyl (4-(5-chloro-1-(((6R,8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate

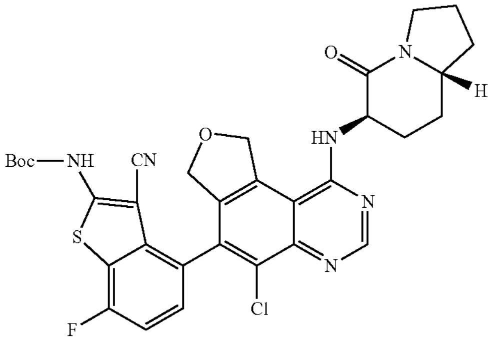 [SMILES: CC(C)(C)OC(=O)Nc1sc2c(F)ccc(-c3c4c(c5c(N[C@@H]6CC[C@H]7CCCN7C6=O)ncnc5c3Cl)COC4)c2c1C#N]

A mixture of tert-butyl (4-(5-chloro-3-(ethylsulfonyl)-1-(((6R,8aR)-5-oxooctahydroindolizin-6-yl)amino)-7,9-dihydrofuro[3,4-f]quinazolin-6-yl)-3-cyano-7-fluorobenzo[b]thiophen-2-yl)carbamate (0.050 g, 0.067 mmol) and sodium borohydride (0.0064 g, 0.17 mmol) in DCM (1 mL) and isopropanol (1 mL) was stirred for 40 minl at room temperature. The mixture was concentrated underreduced pressure. The residue was diluted with DCM and saturated aqueous sodium bicarbonate. The organic layer was concentrated under reduced pressure to obtain the crude title compound (0.044 g) as a white solid. MS (ES) m/z=651 (M+1). Clean atropisomer, chiral purification from Preparation 30.

The following compounds in Table 23 were prepared in similar manner as described in Preparation 102B. Various methods were used to purify the compounds, which would be apparent to one skilled in the art.

TABLE 23

| Preparation | Chemical Name | Structure | MS (ES) m/z (M + 1) |
|---|---|---|---|
| 103B[1] | tert-Butyl (4-(5-chloro-1-((5-methyl-6-oxo-5-azaspiro[3.5]nonan-7-yl)amino)-7,9-dihydrofuro[3,4-f]quinazolin-6-yl)-3-cyano-7-fluorobenzo[b]thiophen-2-yl)carbamate | 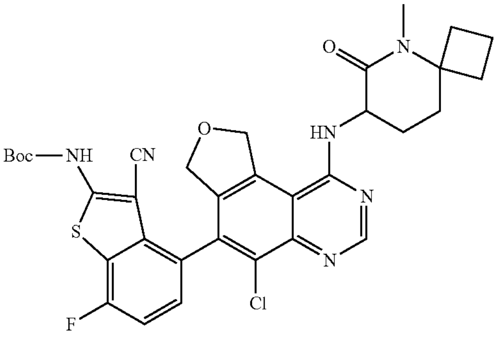 [SMILES: CN1C(=O)C(Nc2ncnc3c(Cl)c(-c4ccc(F)c5sc(NC(=O)OC(C)(C)C)c(C#N)c45)c4c(c23)COC4)CCC12CCC2] | 663 |
| 104B[2] | tert-Butyl (3-cyano-5-fluoro-4-(5-fluoro-1-(((6R,8aR)-5-oxooctahydroindolizin-6-yl)amino)-7,9-dihydrofuro[3,4-f]quinazolin-6-yl)benzo[b]thiophen-2-yl)carbamate | 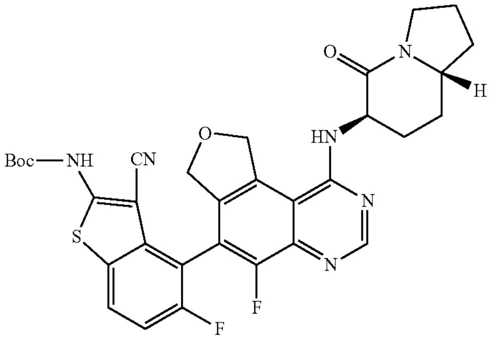 [SMILES: CC(C)(C)OC(=O)Nc1sc2ccc(F)c(-c3c4c(c5c(N[C@@H]6CC[C@H]7CCCN7C6=O)ncnc5c3F)COC4)c2c1C#N] | 633 |

TABLE 23-continued

| Preparation | Chemical Name | Structure | MS (ES) m/z (M + 1) |
|---|---|---|---|
| 105B[2,3] | tert-Butyl (3-cyano-5-fluoro-4-(5-fluoro-3-methoxy-1-(((6R,8aR)-5-oxooctahydroindolizin-6-yl)amino)-7,9-dihydrofuro[3,4-f]quinazolin-6-yl)benzo[b]thiophen-2-yl)carbamate | 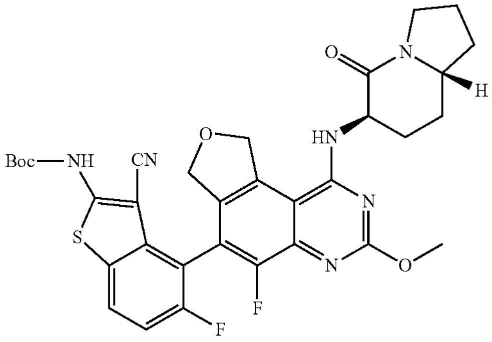 [SMILES: COc1nc(N[C@@H]2CC[C@H]3CCCN3C2=O)c2c3c(c(-c4c(F)ccc5sc(NC(=O)OC(C)(C)C)c(C#N)c45)c(F)c2n1)COC3] | 663 |
| 106B[2,4] | tert-Butyl (3-cyano-4-(1-(((8aS)-2,2-difluoro-5-oxooctahydroindolizin-6-yl)amino)-5-fluoro-7,9-dihydrofuro[3,4-f]quinazolin-6-yl)-5-fluorobenzo[b]thiophen-2-yl)carbamate | 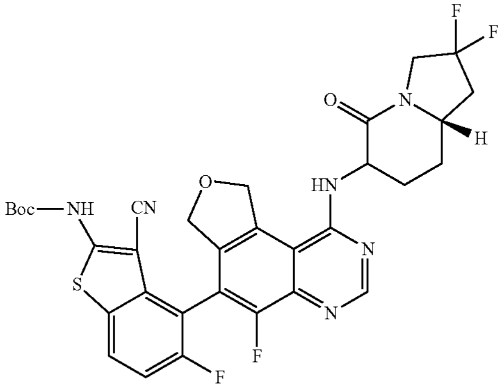 [SMILES: CC(C)(C)OC(=O)Nc1sc2ccc(F)c(-c3c4c(c5c(NC6CC[C@H]7CC(F)(F)CN7C6=O)ncnc5c3F)COC4)c2c1C#N] | 669 |
| 107B | tert-Butyl (4-(5-chloro-1-(((6R,8aR)-5-oxooctahydroindolizin-6-yl)-amino)-7,9-dihydro-furo[3,4-f]quinazolin-6-yl)-3-cyano-7-fluoro-thieno[3,2-c]pyridin-2-yl)carbamate | 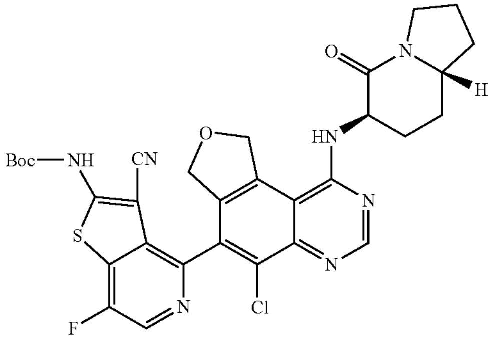 | 650 |
| 108B | (6R,8aR)-6-((6-Bromo-5-chloro-7,9-dihydro-furo[3,4-f]quinazolin-1-yl)amino)hexahydro-indolizin-5(1H)-one | 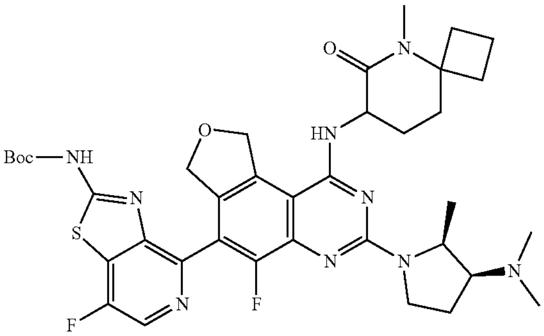 [SMILES: C[C@H]1[C@@H](N(C)C)CCN1c1nc(NC2CCC3(CCC3)N(C)C2=O)c2c3c(c(-c4ncc(F)c5sc(NC(=O)OC(C)(C)C)nc45)c(F)c2n1)COC3] | 437 |

[1]Clean atropisomer, chiral purification from Preparation 30

[2]Clean atropisomer, chiral purification from Preparation 32

[3]Byproduct from Preparation 104B. Methanol was used in the reaction.

[4]Clean isomer at the 6-position of the hexahydroindolizinone, chiral purification from Preparation 18B The following compounds in Table 24 were prepared in similar manner as described in Preparation 28. Different coupling conditions, such as base, ligands, or palladium sources, may have been substituted. Various methods were used to purify the compounds, which would be apparent to one skilled in the art.

TABLE 24

| Preparation | Chemical Name | Structure | MS (ES) m/z (M + 1) |
|---|---|---|---|
| 109B | tert-Butyl (4-(5-chloro-1-(((6R,8aR)-5-oxooctahydroindolizin-6-yl)-amino)-7,9-dihydrofuro [3,4-f]quinazolin-6-yl)-3-cyanobenzo[b]thiophen-2-yl)carbamate | 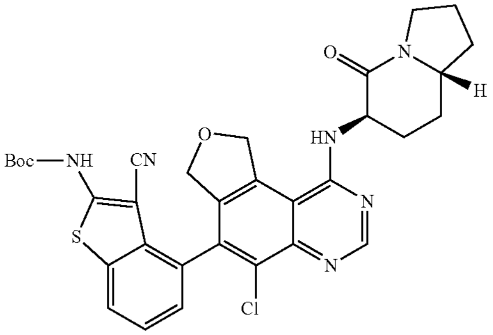 [SMILES: CC(C)(C)OC(=O)Nc1sc2cccc(-c3c4c(c5c(N[C@@H]6CC[C@H]7CCCN7C6=O)ncnc5c3Cl)COC4)c2c1C#N] | 631 |
| 110B | tert-Butyl (4-(5-chloro-1-(((6R,8aR)-5-oxooctahydroindolizin-6-yl)-amino)-7,9-dihydrofuro [3,4-f]quinazolin-6-yl)-5-fluorobenzo[d]thiazol-2-yl)carbamate | 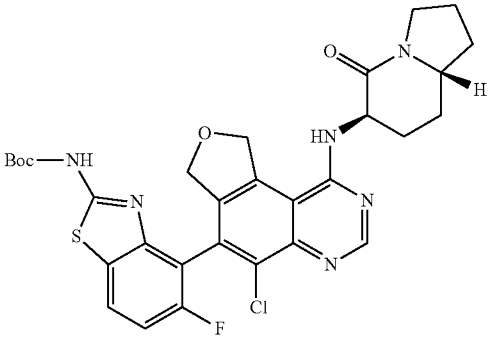 [SMILES: CC(C)(C)OC(=O)Nc1nc2c(-c3c4c(c5c(N[C@@H]6CC[C@H]7CCCN7C6=O)ncnc5c3Cl)COC4)c(F)ccc2s1] | 625 |

Examples 1-4

2-Amino-4-(5-chloro-3-((S)-3-(dimethylamino)pyrrolidin-1-yl)-1-((4-methyl-5-oxo-4-azaspiro[2.5] octan-6-yl)amino)-7,9-dihydrofuro[3,4-f]quinazolin-6-yl)-5-fluorobenzo[b]thiophene-3-carbonitrile, Diastereomers 1-4

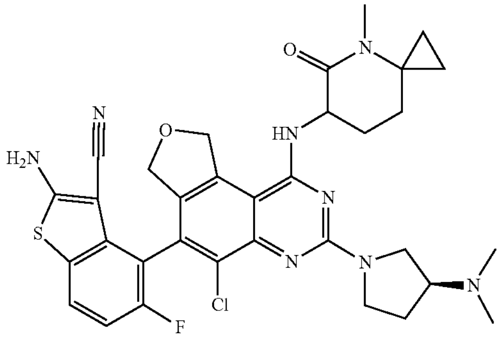 [SMILES: CN(C)[C@H]1CCN(c2nc(NC3CCC4(CC4)N(C)C3=O)c3c4c(c(-c5c(F)ccc6sc(N)c(C#N)c56)c(Cl)c3n2)COC4)C1]

tert-Butyl (4-(5-chloro-3-((S)-3-(dimethylamino)pyrrolidin-1-yl)-1-((4-methyl-5-oxo-4-azaspiro[2.5]octan-6-yl) amino)-7,9-dihydrofuro [3,4-f]quinazolin-6-yl)-3-cyano-5-fluorobenzo[b]thiophen-2-yl)carbamate (0.082 g, 0.11 mmol) was added to a mixture of DCM (1 mL) and trifluoroacetic acid (1 mL). The mixture was stirred at room temperature. After 1 h, the mixture was concentrated under reduced pressure and diluted with aqueous ammonium hydroxide and DCM. The layers were separated and the organic layer was concentrated under reduced pressure. The residue was purified by reversed phase purification (C18 column), eluting with 40-100% acetonitrile in (10 mM ammonium acetate in 95:5 water:methanol), to give the four title diastereomer compounds (0.017 g, 0.013 g, 0.014 g, 0.014 g; 81%). Diastereomer refers to both a clean atropisomer and a clean isomer on the piperidinone. MS (ES) m/z=661 (M+1), for all four compounds.

The following compounds in Table 25 were prepared in similar manner as described in Examples 1-4. Different acidic conditions, such as HCl in 1,4-dioxane, may have been substituted. Various methods were used to purify the compounds, which would be apparent to one skilled in the art. Isomer separation methods may be found as footnotes.

TABLE 25

| Example | Chemical Name | Structure | MS (ES) m/z (M +1) |
|---|---|---|---|
| 5[1,4] | 2-Amino-4-(5-chloro-3-(3-(dimethylamino)azetidin-1-yl)-1-((5-methyl-6-oxo-5-azaspiro[3.5]nonan-7-yl)amino)-7,9-dihydrofuro[3,4-f]quinazolin-6-yl)-7-fluorobenzo[b]thiophene-3-carbonitrile, Enantiomer 1 (Isomer 1) | 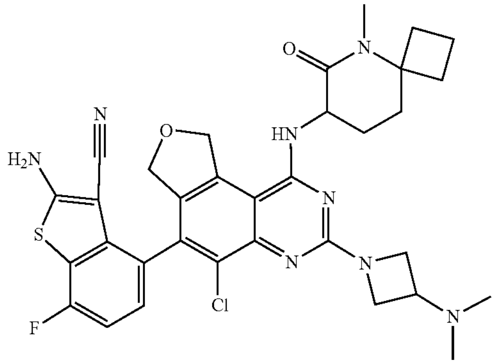 [SMILES: CN(C)C1CN(c2nc(NC3CCC4(CCC4)N(C)C3=O)c3c4c(c(-c5ccc(F)c6sc(N)c(C#N)c56)c(Cl)c3n2)COC4)C1] | 661 |
| 6[1,4] | 2-Amino-4-(5-chloro-3-(3-(dimethylamino)azetidin-1-yl)-1-((5-methyl-6-oxo-5-azaspiro[3.5]nonan-7-yl)amino)-7,9-dihydrofuro[3,4-f]quinazolin-6-yl)-7-fluorobenzo[b]thiophene-3-carbonitrile, Enantiomer 2 (Isomer 2) | 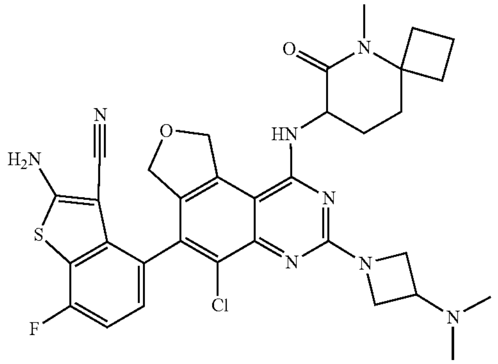 [SMILES: CN(C)C1CN(c2nc(NC3CCC4(CCC4)N(C)C3=O)c3c4c(c(-c5ccc(F)c6sc(N)c(C#N)c56)c(Cl)c3n2)COC4)C1] | 661 |
| 7[1,5] | 2-Amino-4-(5-chloro-3-(3-(dimethylamino)azetidin-1-yl)-1-((4-methyl-5-oxo-4-azaspiro[2.5]octan-6-yl)amino)-7,9-dihydrofuro[3,4-f]quinazolin-6-yl)-7-fluorobenzo[b]thiophene-3-carbonitrile, Enantiomer 1 (Isomer 1) | 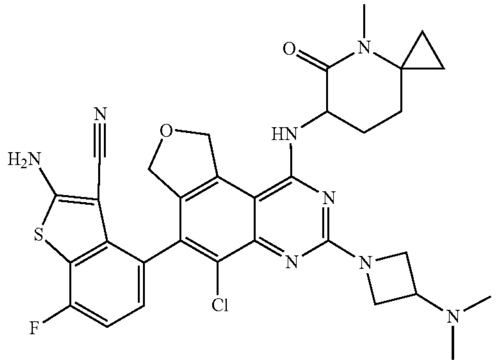 [SMILES: CN(C)C1CN(c2nc(NC3CCC4(CC4)N(C)C3=O)c3c4c(c(-c5ccc(F)c6sc(N)c(C#N)c56)c(Cl)c3n2)COC4)C1] | 647 |
| 8[1,5] | 2-Amino-4-(5-chloro-3-(3-(dimethylamino)azetidin-1-yl)-1-((4-methyl-5-oxo-4-azaspiro[2.5]octan-6-yl)amino)-7,9-dihydrofuro[3,4-f]quinazolin-6-yl)-7-fluorobenzo[b]thiophene-3-carbonitrile, Enantiomer 2 (Isomer 2) | 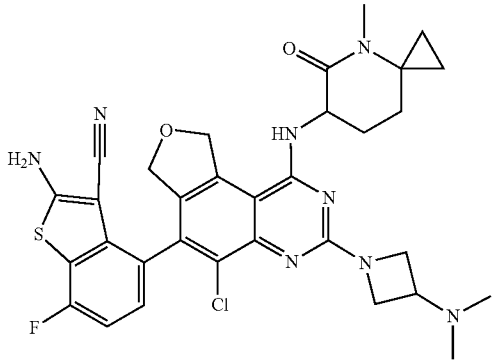 [SMILES: CN(C)C1CN(c2nc(NC3CCC4(CC4)N(C)C3=O)c3c4c(c(-c5ccc(F)c6sc(N)c(C#N)c56)c(Cl)c3n2)COC4)C1] | 647 |

TABLE 25-continued

| Example | Chemical Name | Structure | MS (ES) m/z (M +1) |
|---|---|---|---|
| 9[1,6] | 2-Amino-4-(5-chloro-1-((4-methyl-5-oxo-4-azaspiro[2.5]octan-6-yl)amino)-3-(6-methyl-3,6-diazabicyclo[3.2.0]heptan-3-yl)-7,9-dihydrofuro[3,4-f]quinazolin-6-yl)-7-fluorobenzo[b]thiophene-3-carbonitrile, Enantiomer 1 (Isomer 1) | 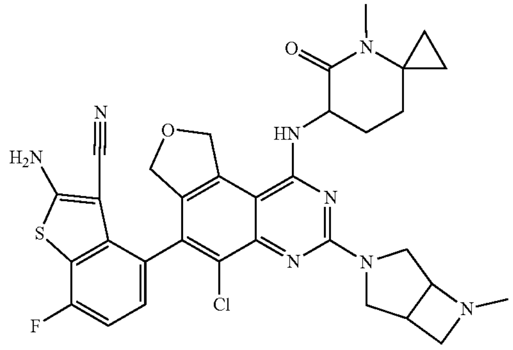 [SMILES: CN1CC2CN(c3nc(NC4CCC5(CC5)N(C)C4=O)c4c5c(c(-c6ccc(F)c7sc(N)c(C#N)c67)c(Cl)c4n3)COC5)CC21] | 659 |
| 10[1,6] | 2-Amino-4-(5-chloro-1-((4-methyl-5-oxo-4-azaspiro[2.5]octan-6-yl)amino)-3-(6-methyl-3,6-diazabicyclo[3.2.0]heptan-3-yl)-7,9-dihydrofuro[3,4-f]quinazolin-6-yl)-7-fluorobenzo[b]thiophene-3-carbonitrile, Enantiomer 2 (Isomer 2) | 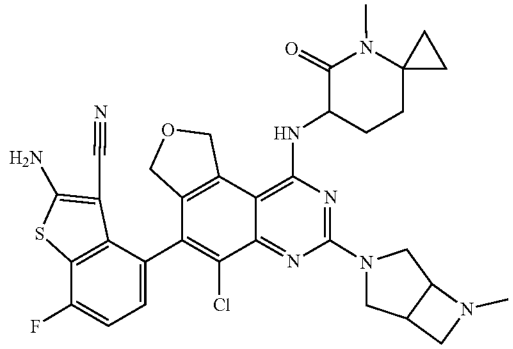 [SMILES: CN1CC2CN(c3nc(NC4CCC5(CC5)N(C)C4=O)c4c5c(c(-c6ccc(F)c7sc(N)c(C#N)c67)c(Cl)c4n3)COC5)CC21] | 659 |
| 11[1,7] | 2-Amino-4-(5-chloro-3-(3-(dimethylamino)azetidin-1-yl)-1-((5-methyl-6-oxo-5-azaspiro[2.5]octan-7-yl)amino)-7,9-dihydrofuro[3,4-f]quinazolin-6-yl)-7-fluorobenzo[b]thiophene-3-carbonitrile, Enantiomer 1 (Isomer 1) | 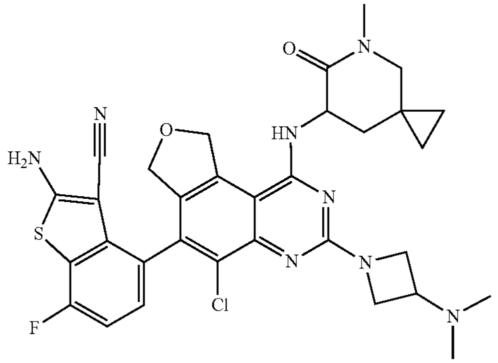 [SMILES: CN1CC2(CC2)CC(Nc2nc(N3CC(N(C)C)C3)nc3c(Cl)c(-c4ccc(F)c5sc(N)c(C#N)c45)c4c(c23)COC4)C1=O] | 647 |
| 12[1,7] | 2-Amino-4-(5-chloro-3-(3-(dimethylamino)azetidin-1-yl)-1-((5-methyl-6-oxo-5-azaspiro[2.5]octan-7-yl)amino)-7,9-dihydrofuro[3,4-f]quinazolin-6-yl)-7-fluorobenzo[b]thiophene-3-carbonitrile, Enantiomer 2 (Isomer 2) | 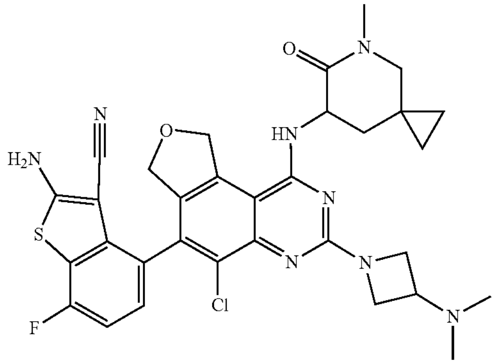 [SMILES: CN1CC2(CC2)CC(Nc2nc(N3CC(N(C)C)C3)nc3c(Cl)c(-c4ccc(F)c5sc(N)c(C#N)c45)c4c(c23)COC4)C1=O] | 647 |

TABLE 25-continued

| Example | Chemical Name | Structure | MS (ES) m/z (M +1) |
|---|---|---|---|
| 13[8] | 2-Amino-4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 1 | 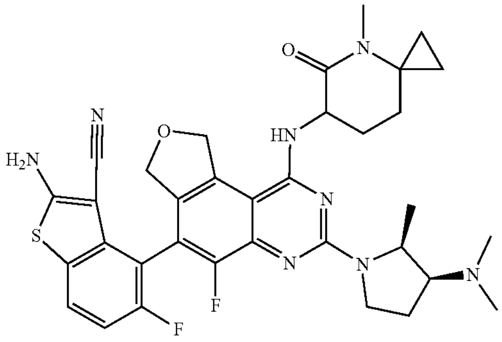 [SMILES: C[C@H]1[C@@H](N(C)C)CCN1c1nc(NC2CCC3(CC3)N(C)C2=O)c2c3c(c(-c4c(F)ccc5sc(N)c(C#N)c45)c(F)c2n1)COC3] | 659 |
| 14[8] | 2-Amino-4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 2 | 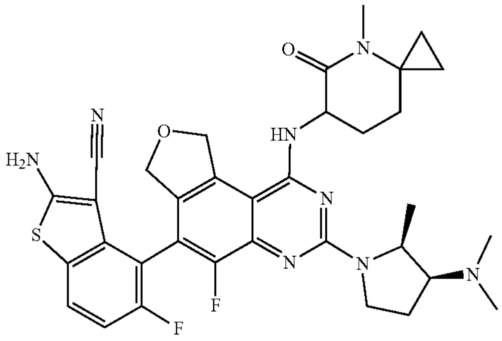 [SMILES: C[C@H]1[C@@H](N(C)C)CCN1c1nc(NC2CCC3(CC3)N(C)C2=O)c2c3c(c(-c4c(F)ccc5sc(N)c(C#N)c45)c(F)c2n1)COC3] | 659 |
| 15[8] | 2-Amino-4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 3 | 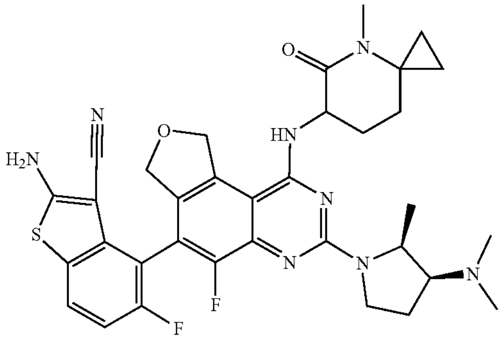 [SMILES: C[C@H]1[C@@H](N(C)C)CCN1c1nc(NC2CCC3(CC3)N(C)C2=O)c2c3c(c(-c4c(F)ccc5sc(N)c(C#N)c45)c(F)c2n1)COC3] | 659 |
| 16[8] | 2-Amino-4-(3-((2S,3S)-3-(dimethylamino)-2-methylpyrrolidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 4 | 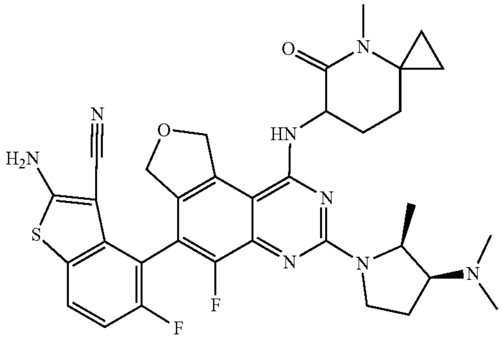 [SMILES: C[C@H]1[C@@H](N(C)C)CCN1c1nc(NC2CCC3(CC3)N(C)C2=O)c2c3c(c(-c4c(F)ccc5sc(N)c(C#N)c45)c(F)c2n1)COC3] | 659 |

TABLE 25-continued

| Example | Chemical Name | Structure | MS (ES) m/z (M +1) |
|---|---|---|---|
| 17[9] | 2-Amino-4-(3-(3-(dimethylamino)azetidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 1 | 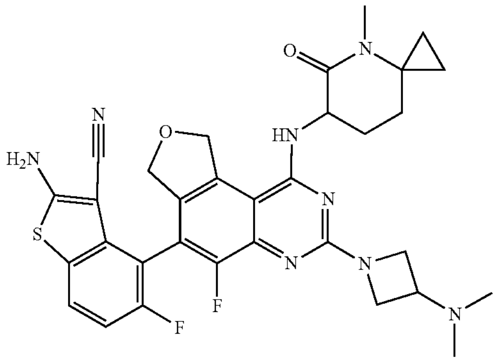 [SMILES: CN(C)C1CN(c2nc(NC3CCC4(CC4)N(C)C3=O)c3c4c(c(-c5c(F)ccc6sc(N)c(C#N)c56)c(F)c3n2)COC4)C1] | 631 |
| 18[9] | 2-Amino-4-(3-(3-(dimethylamino)azetidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 2 | 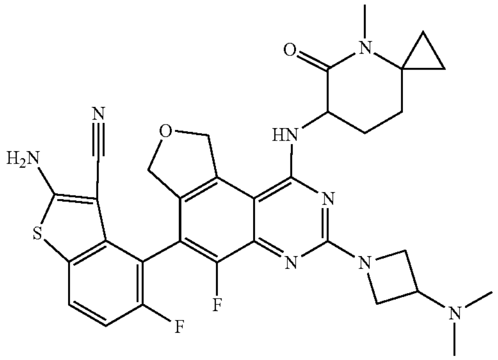 [SMILES: CN(C)C1CN(c2nc(NC3CCC4(CC4)N(C)C3=O)c3c4c(c(-c5c(F)ccc6sc(N)c(C#N)c56)c(F)c3n2)COC4)C1] | 631 |
| 19[9] | 2-Amino-4-(3-(3-(dimethylamino)azetidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diasteromer 3 | 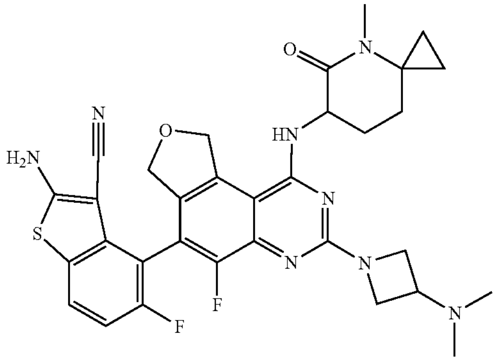 [SMILES: CN(C)C1CN(c2nc(NC3CCC4(CC4)N(C)C3=O)c3c4c(c(-c5c(F)ccc6sc(N)c(C#N)c56)c(F)c3n2)COC4)C1] | 631 |
| 20[9] | 2-Amino-4-(3-(3-(dimethylamino)azetidin-1-yl)-5-fluoro-1-((4-methyl-5-oxo-4-azaspiro[2.5]octan-6-yl)amino)-7,9-dihydrofuro[3,4-f]quinazolin-6-yl)-5-fluorobenzo[b]thiophene-3-carbonitrile, Diastereomer 4 | 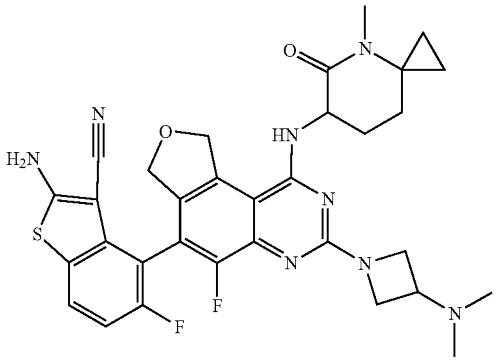 [SMILES: CN(C)C1CN(c2nc(NC3CCC4(CC4)N(C)C3=O)c3c4c(c(-c5c(F)ccc6sc(N)c(C#N)c56)c(F)c3n2)COC4)C1] | 631 |

TABLE 25-continued

| Example | Chemical Name | Structure | MS (ES) m/z (M +1) |
|---|---|---|---|
| 21[10] | 2-Amino-4-(5-chloro-3-((S)-3-(dimethylamino) pyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Diastereomer 1 | 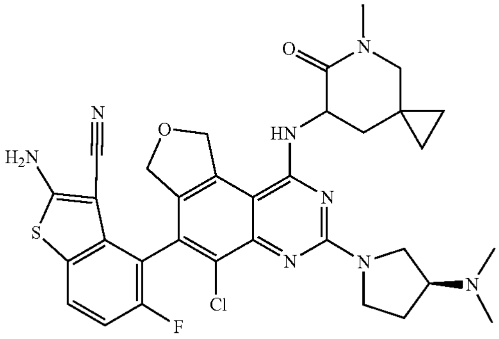 [SMILES: CN1CC2(CC2)CC(Nc2nc(N3CC[C@H](N(C)C)C3)nc3c(Cl)c(-c4c(F)ccc5sc(N)c(C#N)c45)c4c(c23)COC4)C1=O] | 661 |
| 22[10] | 2-Amino-4-(5-chloro-3-((S)-3-(dimethylamino)pyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Diastereomer 2 | 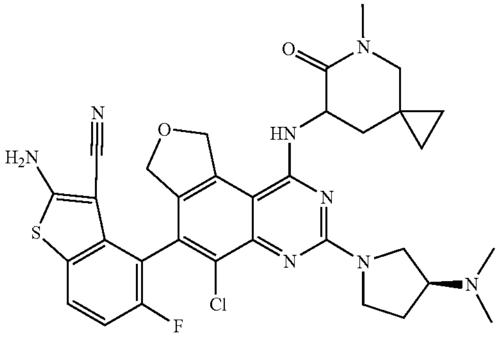 [SMILES: CN1CC2(CC2)CC(Nc2nc(N3CC[C@H](N(C)C)C3)nc3c(Cl)c(-c4c(F)ccc5sc(N)c(C#N)c45)c4c(c23)COC4)C1=O] | 661 |
| 23[10] | 2-Amino-4-(5-chloro-3-((S)-3-(dimethylamino)pyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Diastereomer 3 | 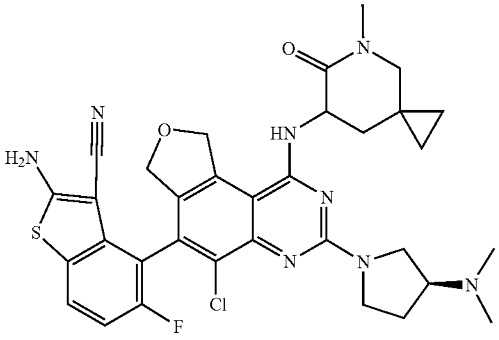 [SMILES: CN1CC2(CC2)CC(Nc2nc(N3CC[C@H](N(C)C)C3)nc3c(Cl)c(-c4c(F)ccc5sc(N)c(C#N)c45)c4c(c23)COC4)C1=O] | 661 |
| 24[10] | 2-Amino-4-(5-chloro-3-((S)-3-(dimethylamino)pyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Diastereomer 4 | 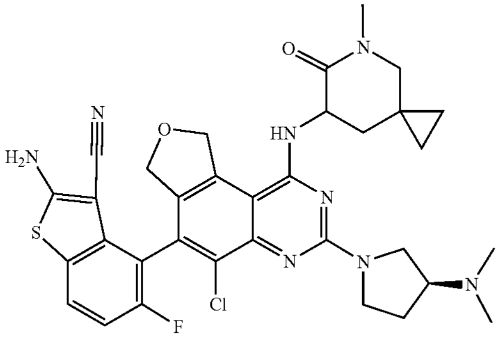 [SMILES: CN1CC2(CC2)CC(Nc2nc(N3CC[C@H](N(C)C)C3)nc3c(Cl)c(-c4c(F)ccc5sc(N)c(C#N)c45)c4c(c23)COC4)C1=O] | 661 |

TABLE 25-continued

| Example | Chemical Name | Structure | MS (ES) m/z (M +1) |
|---|---|---|---|
| 25[2,11] | 2-Amino-4-(5-chloro-1-((2-methyl-3-oxo-2-azabicyclo[3.1.1]heptan-4-yl)amino)-3-((3aR,6aR)-1-methylhexahydropyrrolo[3,4-b]pyrrol-5(1H)-yl)-7,9-dihydrofuro[3,4-f]quinazolin-6-yl)-5-fluorobenzo[b]thiophene-3-carbonitrile, Enantiomer 1 (Isomer 1) | 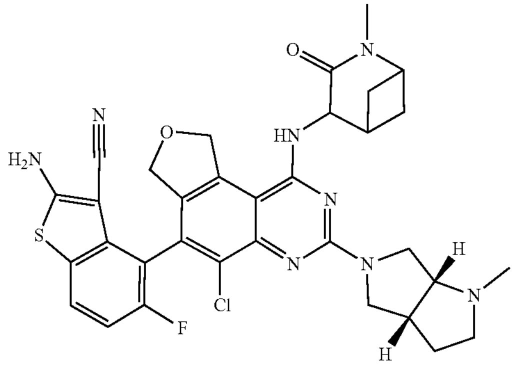 [SMILES: CN1C(=O)C(Nc2nc(N3C[C@H]4CCN(C)[C@H]4C3)nc3c(Cl)c(-c4c(F)ccc5sc(N)c(C#N)c45)c4c(c23)COC4)C2CC1C2] | 659 |
| 26[2,11] | 2-Amino-4-(5-chloro-1-((2-methyl-3-oxo-2-azabicyclo[3.1.1]heptan-4-yl)amino)-3-((3aR,6aR)-1-methylhexahydropyrrolo[3,4-b]pyrrol-5(1H)-yl)-7,9-dihydrofuro[3,4-f]quinazolin-6-yl)-5-fluorobenzo[b]thiophene-3-carbonitrile, Enantiomer 2 (Isomer 2) | 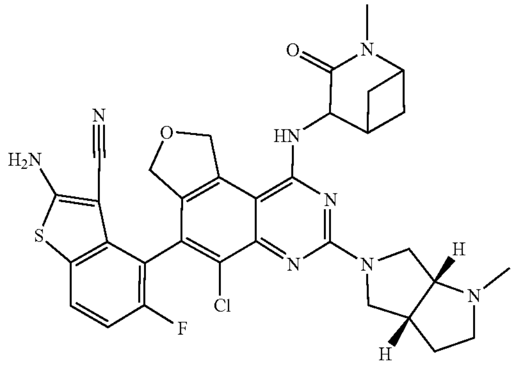 [SMILES: CN1C(=O)C(Nc2nc(N3C[C@H]4CCN(C)[C@H]4C3)nc3c(Cl)c(-c4c(F)ccc5sc(N)c(C#N)c45)c4c(c23)COC4)C2CC1C2] | 659 |
| 27[2,12] | 2-Amino-4-(5-chloro-3-((S)-3-(dimethylamino)pyrrolidin-1-yl)-1-((2-methyl-3-oxo-2-azabicyclo[3.1.1]heptan-4-yl)amino)-7,9-dihydrofuro[3,4-f]quinazolin-6-yl)-5-fluorobenzo[b]thiophene-3-carbonitrile, Enantiomer 1 (Isomer 1) | 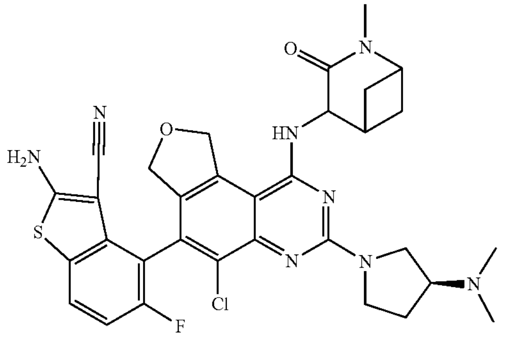 [SMILES: CN1C(=O)C(Nc2nc(N3CC[C@H](N(C)C)C3)nc3c(Cl)c(-c4c(F)ccc5sc(N)c(C#N)c45)c4c(c23)COC4)C2CC1C2] | 647 |
| 28[2,12] | 2-Amino-4-(5-chloro-3-((S)-3-(dimethylamino)pyrrolidin-1-yl)-1-((2-methyl-3-oxo-2-azabicyclo[3.1.1]heptan-4-yl)amino)-7,9-dihydrofuro[3,4-f]quinazolin-6-yl)-5-fluorobenzo[b]thiophene-3-carbonitrile, Enantiomer 2 (Isomer 2) | 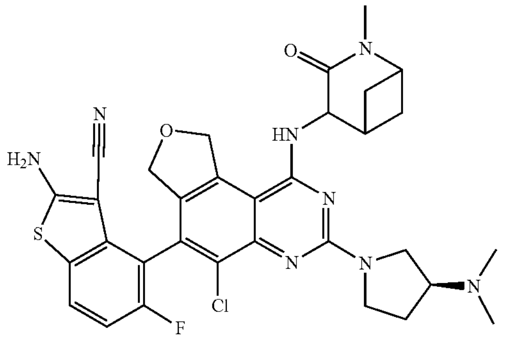 [SMILES: CN1C(=O)C(Nc2nc(N3CC[C@H](N(C)C)C3)nc3c(Cl)c(-c4c(F)ccc5sc(N)c(C#N)c45)c4c(c23)COC4)C2CC1C2] | 647 |

TABLE 25-continued

| Example | Chemical Name | Structure | MS (ES) m/z (M +1) |
|---|---|---|---|
| 29[13] | 2-((6-(2-Aminobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-pyridazino[1,2-a]pyridazin-1(2H)-one, Enantiomer 1 (Isomer 1) | 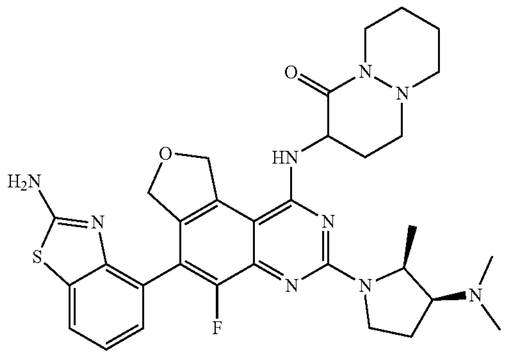 [SMILES: C[C@H]1[C@@H](N(C)C)CCN1c1nc(NC2CCN3CCCCN3C2=O)c2c3c(c(-c4cccc5sc(N)nc45)c(F)c2n1)COC3] | 632 |
| 30[13] | 2-((6-(2-Aminobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-pyridazino[1,2-a]pyridazin-1(2H)-one, Enantiomer 2 (Isomer 2) | 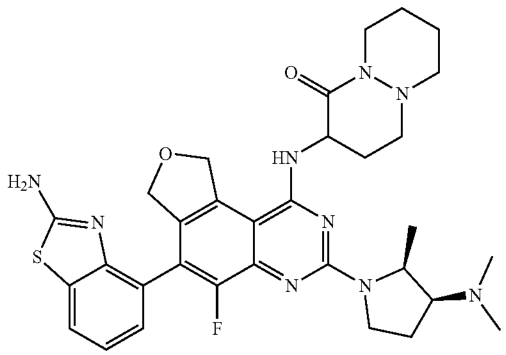 [SMILES: C[C@H]1[C@@H](N(C)C)CCN1c1nc(NC2CCN3CCCCN3C2=O)c2c3c(c(-c4cccc5sc(N)nc45)c(F)c2n1)COC3] | 632 |
| 31[14] | 7-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[3.5]nonan-6-one, Enantiomer 1 (Isomer 1) | 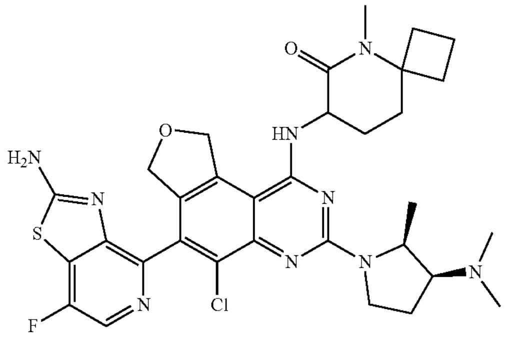 [SMILES: C[C@H]1[C@@H](N(C)C)CCN1c1nc(NC2CCC3(CCC3)N(C)C2=O)c2c3c(c(-c4ncc(F)c5sc(N)nc45)c(Cl)c2n1)COC3] | 666 |
| 32[14] | 7-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[3.5]nonan-6-one, Enantiomer 2 (Isomer 2) | 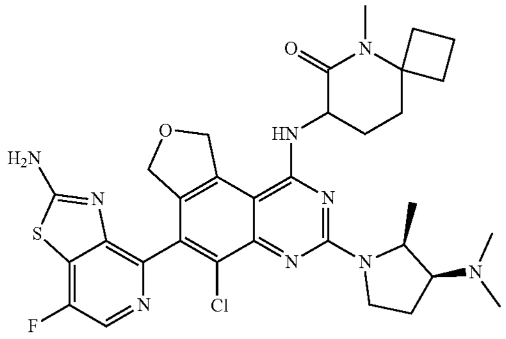 [SMILES: C[C@H]1[C@@H](N(C)C)CCN1c1nc(NC2CCC3(CCC3)N(C)C2=O)c2c3c(c(-c4ncc(F)c5sc(N)nc45)c(Cl)c2n1)COC3] | 666 |

TABLE 25-continued

| Example | Chemical Name | Structure | MS (ES) m/z (M +1) |
|---|---|---|---|
| 33[15] | 7-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Diastereomer 1 | 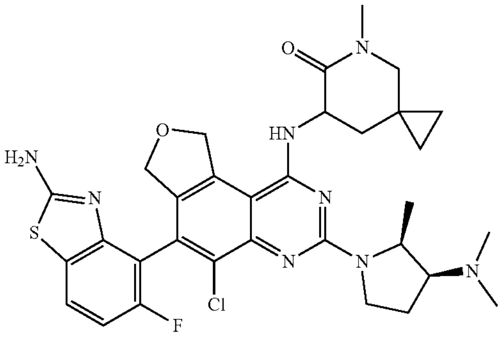 [SMILES: C[C@H]1[C@@H](N(C)C)CCN1c1nc(NC2CC3(CC3)CN(C)C2=O)c2c3c(c(-c4c(F)ccc5sc(N)nc45)c(Cl)c2n1)COC3] | 651 |
| 34[15] | 7-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Diastereomer 2 | 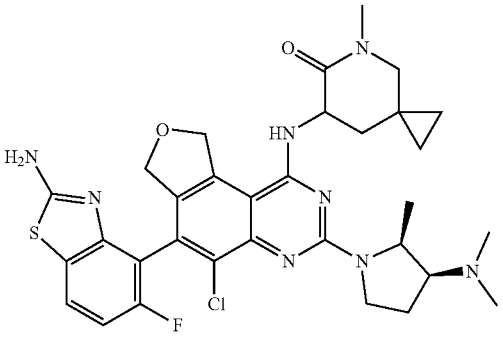 [SMILES: C[C@H]1[C@@H](N(C)C)CCN1c1nc(NC2CC3(CC3)CN(C)C2=O)c2c3c(c(-c4c(F)ccc5sc(N)nc45)c(Cl)c2n1)COC3] | 651 |
| 35[15] | 7-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Diastereomer 3 | 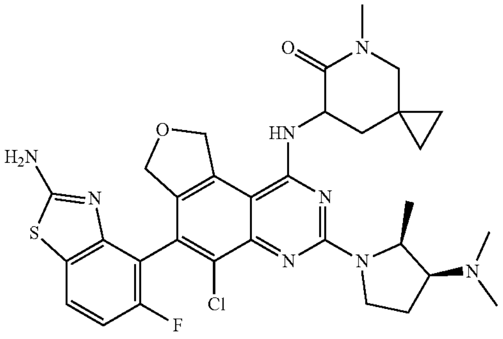 [SMILES: C[C@H]1[C@@H](N(C)C)CCN1c1nc(NC2CC3(CC3)CN(C)C2=O)c2c3c(c(-c4c(F)ccc5sc(N)nc45)c(Cl)c2n1)COC3] | 651 |
| 36[15] | 7-((6-(2-Amino-5-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Diastereomer 4 | 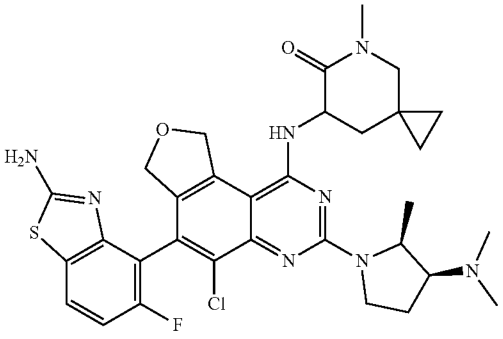 [SMILES: C[C@H]1[C@@H](N(C)C)CCN1c1nc(NC2CC3(CC3)CN(C)C2=O)c2c3c(c(-c4c(F)ccc5sc(N)nc45)c(Cl)c2n1)COC3] | 651 |

TABLE 25-continued

| Example | Chemical Name | Structure | MS (ES) m/z (M +1) |
|---|---|---|---|
| 37[16] | 6-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-4-methyl-4-azaspiro[2.5]octan-5-one, Diastereomer 1 | 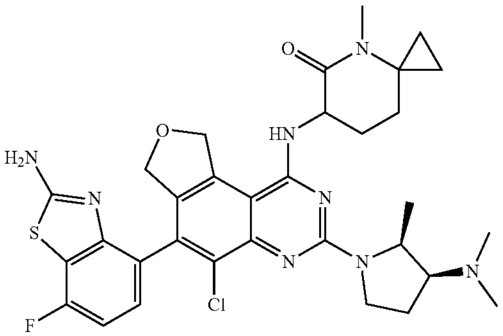 [SMILES: C[C@H]1[C@@H](N(C)C)CCN1c1nc(NC2CCC3(CC3)N(C)C2=O)c2c3c(c(-c4ccc(F)c5sc(N)nc45)c(Cl)c2n1)COC3] | 651 |
| 38[16] | 6-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-4-methyl-4-azaspiro[2.5]octan-5-one, Diastereomer 2 | 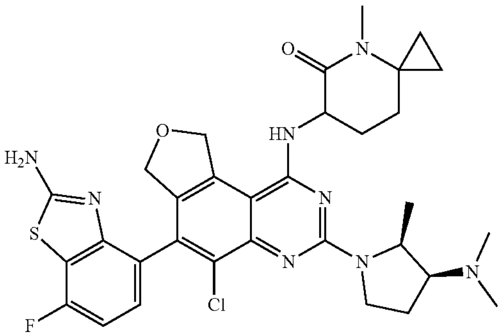 [SMILES: C[C@H]1[C@@H](N(C)C)CCN1c1nc(NC2CCC3(CC3)N(C)C2=O)c2c3c(c(-c4ccc(F)c5sc(N)nc45)c(Cl)c2n1)COC3] | 651 |
| 39[16] | 6-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-4-methyl-4-azaspiro[2.5]octan-5-one, Diasteromer 3 | 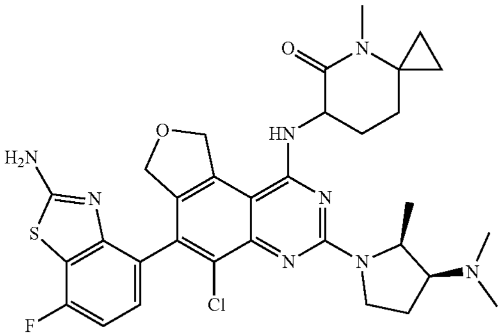 [SMILES: C[C@H]1[C@@H](N(C)C)CCN1c1nc(NC2CCC3(CC3)N(C)C2=O)c2c3c(c(-c4ccc(F)c5sc(N)nc45)c(Cl)c2n1)COC3] | 651 |
| 40[16] | 6-((6-(2-Amino-7-fluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)-4-methyl-4-azaspiro[2.5]octan-5-one, Diastereomer 4 | 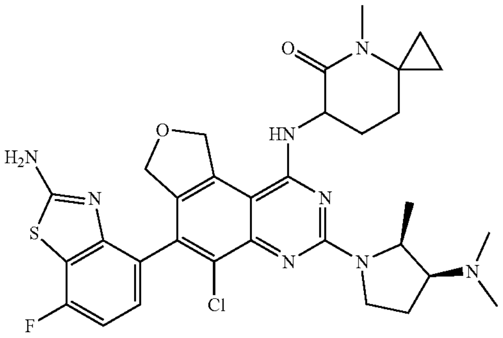 [SMILES: C[C@H]1[C@@H](N(C)C)CCN1c1nc(NC2CCC3(CC3)N(C)C2=O)c2c3c(c(-c4ccc(F)c5sc(N)nc45)c(Cl)c2n1)COC3] | 651 |

TABLE 25-continued

| Example | Chemical Name | Structure | MS (ES) m/z (M +1) |
|---|---|---|---|
| 41[17] | 6-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-4-methyl-4-azaspiro[2.5]octan-5-one, Diastereomer 1 | 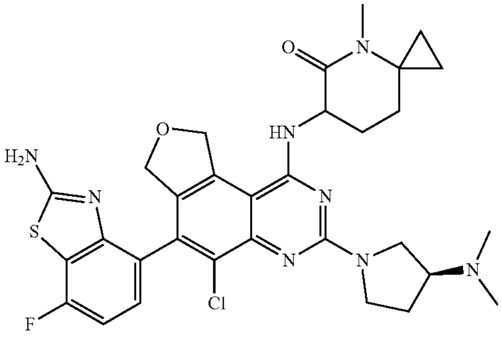 [SMILES: CN(C)[C@H]1CCN(c2nc(NC3CCC4(CC4)N(C)C3=O)c3c4c(c(-c5ccc(F)c6sc(N)nc56)c(Cl)c3n2)COC4)C1] | 637 |
| 42[17] | 6-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-4-methyl-4-azaspiro[2.5]octan-5-one, Diastereomer 2 | 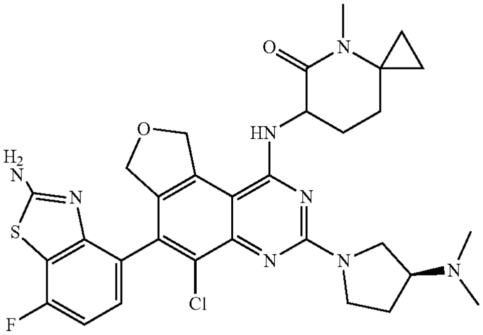 [SMILES: CN(C)[C@H]1CCN(c2nc(NC3CCC4(CC4)N(C)C3=O)c3c4c(c(-c5ccc(F)c6sc(N)nc56)c(Cl)c3n2)COC4)C1] | 637 |
| 43[17] | 6-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-4-methyl-4-azaspiro[2.5]octan-5-one, Diastereomer 3 | 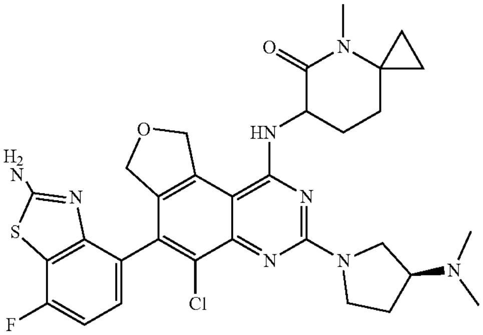 [SMILES: CN(C)[C@H]1CCN(c2nc(NC3CCC4(CC4)N(C)C3=O)c3c4c(c(-c5ccc(F)c6sc(N)nc56)c(Cl)c3n2)COC4)C1] | 637 |
| 44[17] | 6-((6-(2-Amino-7-fluorobenzo[d]thiazol-4-yl)-5-chloro-3-((S)-3-(dimethylamino)pyrrolidin-1-yl)-7,9-dihydrofuro[3,4-f]quinazolin-1-yl)amino)-4-methyl-4-azaspiro[2.5]octan-5-one, Diastereomer 4 | 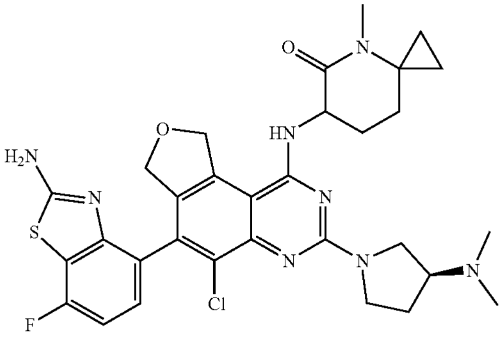 [SMILES: CN(C)[C@H]1CCN(c2nc(NC3CCC4(CC4)N(C)C3=O)c3c4c(c(-c5ccc(F)c6sc(N)nc56)c(Cl)c3n2)COC4)C1] | 637 |

TABLE 25-continued

| Example | Chemical Name | Structure | MS (ES) m/z (M +1) |
| --- | --- | --- | --- |
| 45[3] | (8aR)-6-((6-(2-Amino-7-fluorobenzo[d]thiazol-4-yl)-3-((S)-3-(dimethylamino)pyrrolidin-1-yl)-5-fluoro-7,9-dihydrofuro[3,4-f]quinazolin-1-yl)amino)hexahydro-indolizin-5(1H)-one | 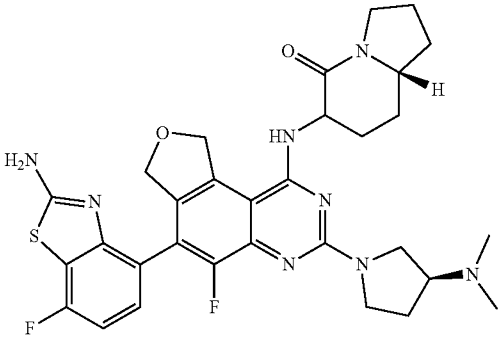 [SMILES: CN(C)[C@H]1CCN(c2nc(NC3CC[C@H]4CCCN4C3=O)c3c4c(c(-c5ccc(F)c6sc(N)nc56)c(F)c3n2)COC4)C1] | 621 |
| 46[3] | (8aR)-6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-indolizin-5(1H)-one | 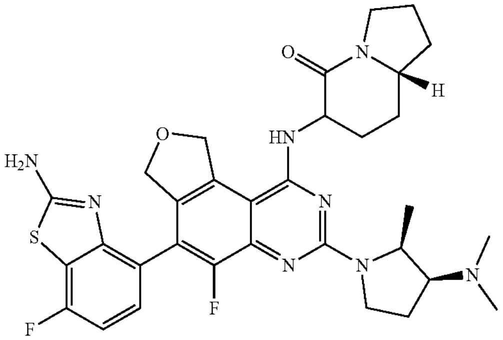 [SMILES: C[C@H]1[C@@H](N(C)C)CCN1c1nc(NC2CC[C@H]3CCCN3C2=O)c2c3c(c(-c4ccc(F)c5sc(N)nc45)c(F)c2n1)COC3] | 635 |
| 47[18] | 6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one | 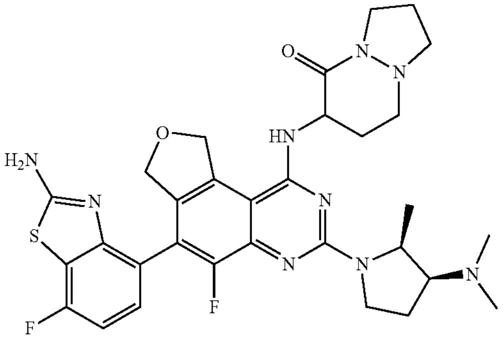 [SMILES: C[C@H]1[C@@H](N(C)C)CCN1c1nc(NC2CCN3CCCN3C2=O)c2c3c(c(-c4ccc(F)c5sc(N)nc45)c(F)c2n1)COC3] | 636 |
| 48[19] | 6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one, Enantiomer 1 (Isomer 1) | 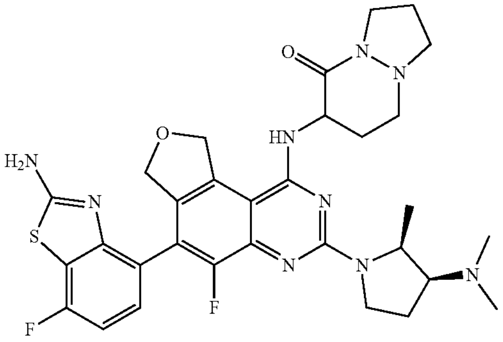 [SMILES: C[C@H]1[C@@H](N(C)C)CCN1c1nc(NC2CCN3CCCN3C2=O)c2c3c(c(-c4ccc(F)c5sc(N)nc45)c(F)c2n1)COC3] | 636 |

TABLE 25-continued

| Example | Chemical Name | Structure | MS (ES) m/z (M +1) |
|---|---|---|---|
| 49[19] | 6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one, Enantiomer 2 (Isomer 2) | 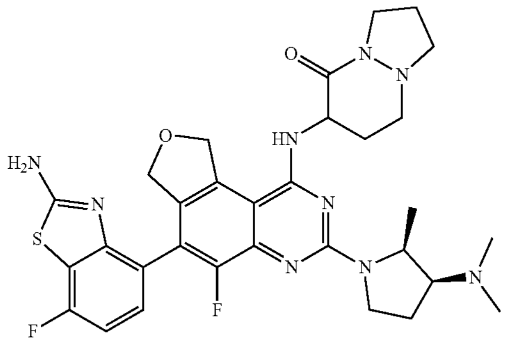 [SMILES: C[C@H]1[C@@H](N(C)C)CCN1c1nc(NC2CCN3CCCN3C2=O)c2c3c(c(-c4ccc(F)c5sc(N)nc45)c(F)c2n1)COC3] | 636 |
| 50[20] | 6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-4-methyl-4-azaspiro[2.5]octan-5-one, Enantiomer 1 (Isomer 1) | 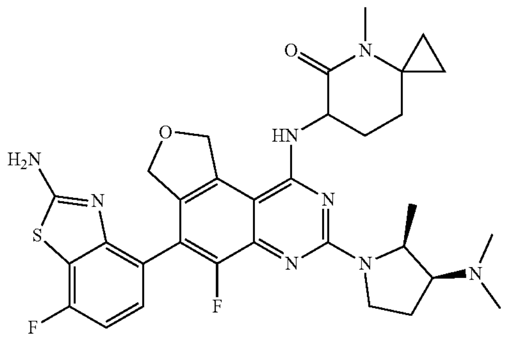 [SMILES: C[C@H]1[C@@H](N(C)C)CCN1c1nc(NC2CCC3(CC3)N(C)C2=O)c2c3c(c(-c4ccc(F)c5sc(N)nc45)c(F)c2n1)COC3] | 635 |
| 51[20] | 6-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-4-methyl-4-azaspiro[2.5]octan-5-one, Enantiomer 2 (Isomer 2) | 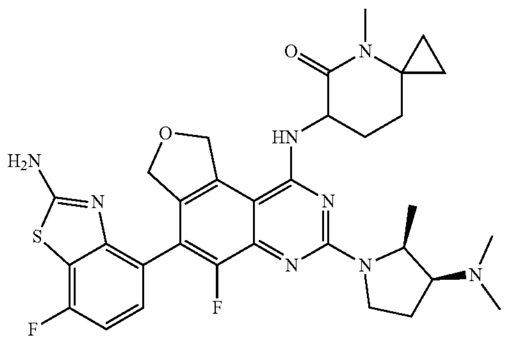 [SMILES: C[C@H]1[C@@H](N(C)C)CCN1c1nc(NC2CCC3(CC3)N(C)C2=O)c2c3c(c(-c4ccc(F)c5sc(N)nc45)c(F)c2n1)COC3] | 635 |
| 52[21] | 7-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-5-methyl-5-azaspiro[2.5]octan-6-one, Enantiomer 1 (Isomer 1) | 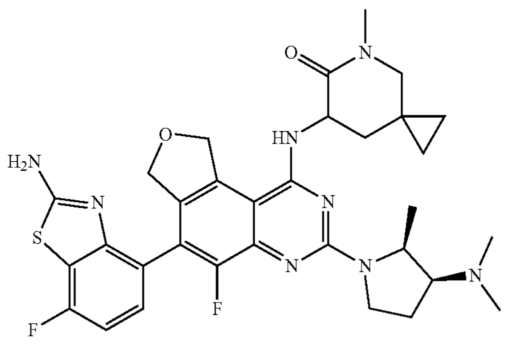 [SMILES: C[C@H]1[C@@H](N(C)C)CCN1c1nc(NC2CC3(CC3)CN(C)C2=O)c2c3c(c(-c4ccc(F)c5sc(N)nc45)c(F)c2n1)COC3] | 635 |

TABLE 25-continued

| Example | Chemical Name | Structure | MS (ES) m/z (M +1) |
|---|---|---|---|
| 53[21] | 7-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-5-methyl-5-azaspiro[2.5]octan-6-one, Enantiomer 2 (Isomer 2) | 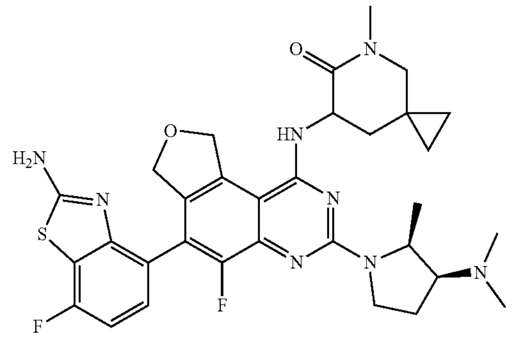 [SMILES: C[C@H]1[C@@H](N(C)C)CCN1c1nc(NC2CC3(CC3)CN(C)C2=O)c2c3c(c(-c4ccc(F)c5sc(N)nc45)c(F)c2n1)COC3] | 635 |
| 54[2,22] | 2-Amino-4-(5-chloro-3-((3R,4S)-3-(dimethylamino)-4-hydroxypyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Isomer 1 | 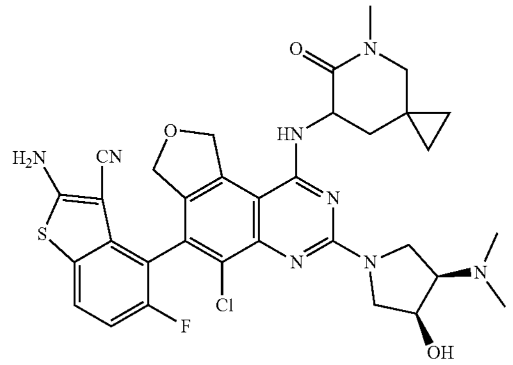 [SMILES: CN1CC2(CC2)CC(Nc2nc(N3C[C@@H](N(C)C)[C@@H](O)C3)nc3c(Cl)c(-c4c(F)ccc5sc(N)c(C#N)c45)c4c(c23)COC4)C1=O] | 677 |
| 55[2,22] | 2-Amino-4-(5-chloro-3-((3R,4S)-3-(dimethylamino)-4-hydroxypyrrolidin-1-yl)-1-((5-methyl-6-oxo-5-azaspiro[2.5]octan-7-yl)amino)-7,9-dihydrofuro[3,4-f]quinazolin-6-yl)-5-fluorobenzo[b]thiophene-3-carbonitrile, Isomer 2 | 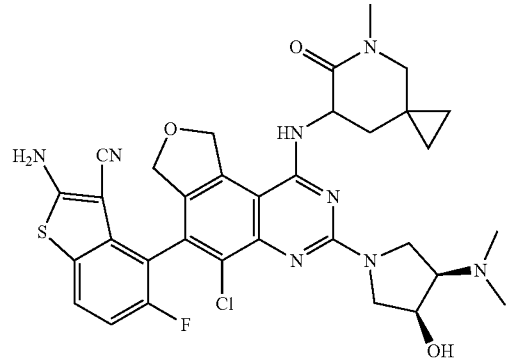 [SMILES: CN1CC2(CC2)CC(Nc2nc(N3C[C@@H](N(C)C)[C@@H](O)C3)nc3c(Cl)c(-c4c(F)ccc5sc(N)c(C#N)c45)c4c(c23)COC4)C1=O] | 677 |
| 56[2] | 2-Amino-4-(5-chloro-3-((3S,4R)-3-hydroxy-4-(isopropyl(methyl)amino)pyrrolidin-1-yl)-1-(((6R,8aR)-5-oxooctahydroindolizin-6-yl)amino)-7,9-dihydrofuro[3,4-f]quinazolin-6-yl)-5-fluorobenzo[b]thiophene-3-carbonitrile | 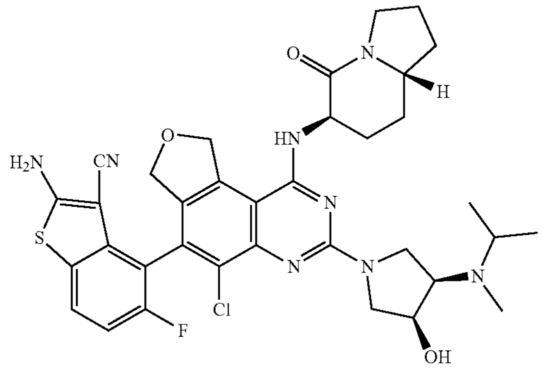 [SMILES: CC(C)N(C)[C@@H]1CN(c2nc(N[C@@H]3CC[C@H]4CCCN4C3=O)c3c4c(c(-c5c(F)ccc6sc(N)c(C#N)c56)c(Cl)c3n2)COC4)C[C@@H]1O] | 705 |

TABLE 25-continued

| Example | Chemical Name | Structure | MS (ES) m/z (M +1) |
|---|---|---|---|
| 57[2,23] | 2-Amino-4-(5-chloro-1-((2-methyl-3-oxo-2-azabicyclo[3.1.1]heptan-4-yl)amino)-3-((3aS,6aS)-1-methylhexahydropyrrolo[3,4-b]pyrrol-5(1H)-yl)-7,9-dihydrofuro[3,4-f]quinazolin-6-yl)-5-fluorobenzo[b]thiophene-3-carbonitrile, Isomer 1 | 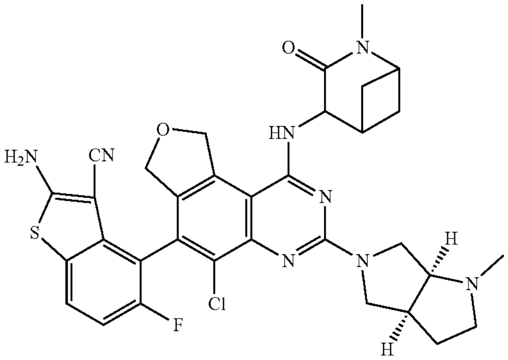 [SMILES: CN1C(=O)C(Nc2nc(N3C[C@@H]4CCN(C)[C@@H]4C3)nc3c(Cl)c(-c4c(F)ccc5sc(N)c(C#N)c45)c4c(c23)COC4)C2CC1C2] | 659 |
| 58[2,23] | 2-Amino-4-(5-chloro-1-((2-methyl-3-oxo-2-azabicyclo[3.1.1]heptan-4-yl)amino)-3-((3aS,6aS)-1-methylhexahydropyrrolo[3,4-b]pyrrol-5(1H)-yl)-7,9-dihydrofuro[3,4-f]quinazolin-6-yl)-5-fluorobenzo[b]thiophene-3-carbonitrile, Isomer 2 | 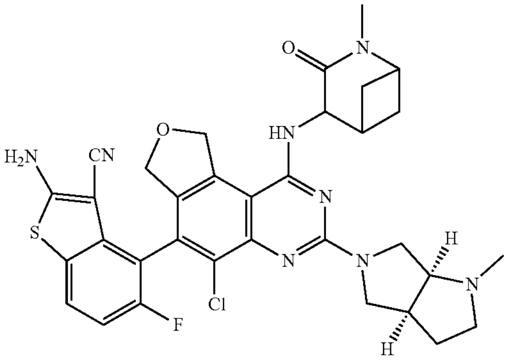 [SMILES: CN1C(=O)C(Nc2nc(N3C[C@@H]4CCN(C)[C@@H]4C3)nc3c(Cl)c(-c4c(F)ccc5sc(N)c(C#N)c45)c4c(c23)COC4)C2CC1C2] | 659 |
| 59[2,24] | 2-Amino-4-(5-chloro-3-((S)-3-(dimethylamino)pyrrolidin-1-yl)-1-((5-oxohexahydro-1H-pyrazolo[1,2-a]pyridazin-6-yl)amino)-7,9-dihydrofuro[3,4-f]quinazolin-6-yl)-5-fluorobenzo[b]thiophene-3-carbonitrile, Isomer 1 | 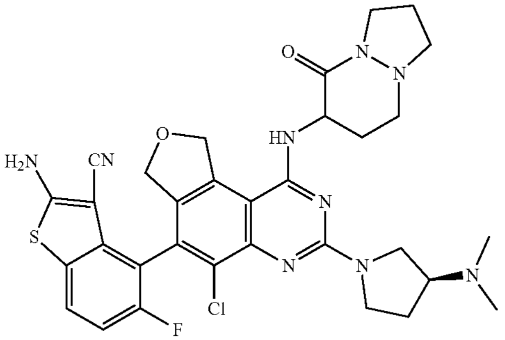 [SMILES: CN(C)[C@H]1CCN(c2nc(NC3CCN4CCCN4C3=O)c3c4c(c(-c5c(F)ccc6sc(N)c(C#N)c56)c(Cl)c3n2)COC4)C1] | 662 |
| 60[2,24] | 2-Amino-4-(5-chloro-3-((S)-3-(dimethylamino)pyrrolidin-1-yl)-1-((5-oxohexahydro-1H-pyrazolo[1,2-a]pyridazin-6-yl)amino)-7,9-dihydrofuro[3,4-f]quinazolin-6-yl)-5-fluorobenzo[b]thiophene-3-carbonitrile, Isomer 2 | 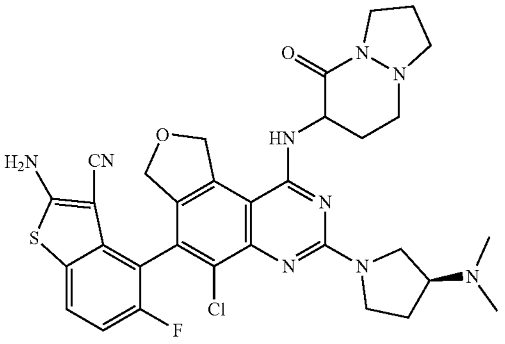 [SMILES: CN(C)[C@H]1CCN(c2nc(NC3CCN4CCCN4C3=O)c3c4c(c(-c5c(F)ccc6sc(N)c(C#N)c56)c(Cl)c3n2)COC4)C1] | 662 |

TABLE 25-continued

| Example | Chemical Name | Structure | MS (ES) m/z (M +1) |
|---|---|---|---|
| 61[1,25] | 2-Amino-4-(5-chloro-3-((S)-3-(dimethylamino)pyrrolidin-1-yl)-1-((4-methyl-5-oxo-4-azaspiro[2.5]octan-6-yl)amino)-7,9-dihydrofuro[3,4-f]quinazolin-6-yl)-7-fluorobenzo[b]thiophene-3-carbonitrile, Isomer 1 | 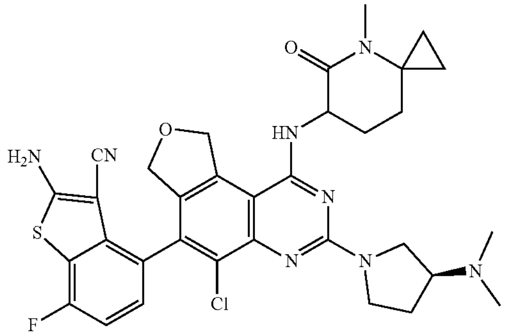 [SMILES: CN(C)[C@H]1CCN(c2nc(NC3CCC4(CC4)N(C)C3=O)c3c4c(c(-c5ccc(F)c6sc(N)c(C#N)c56)c(Cl)c3n2)COC4)C1] | 661 |
| 62[1,25] | 2-Amino-4-(5-chloro-3-((S)-3-(dimethylamino)pyrrolidin-1-yl)-1-((4-methyl-5-oxo-4-azaspiro[2.5]octan-6-yl)amino)-7,9-dihydrofuro[3,4-f]quinazolin-6-yl)-7-fluorobenzo[b]thiophene-3-carbonitrile, Isomer 2 | 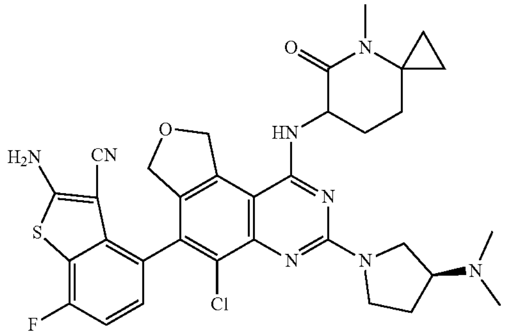 [SMILES: CN(C)[C@H]1CCN(c2nc(NC3CCC4(CC4)N(C)C3=O)c3c4c(c(-c5ccc(F)c6sc(N)c(C#N)c56)c(Cl)c3n2)COC4)C1] | 661 |
| 63[1,26] | 2-Amino-4-(5-chloro-3-(3-(dimethylamino)azetidin-1-yl)-1-((4-methyl-5-oxo-4-azaspiro[2.4]heptan-6-yl)amino)-7,9-dihydrofuro[3,4-f]quinazolin-6-yl)-7-fluorobenzo[b]thiophene-3-carbonitrile, Isomer 1 | 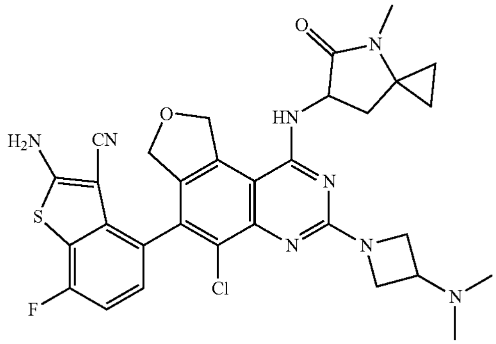 [SMILES: CN(C)C1CN(c2nc(NC3CC4(CC4)N(C)C3=O)c3c4c(c(-c5ccc(F)c6sc(N)c(C#N)c56)c(Cl)c3n2)COC4)C1] | 633 |
| 64[1,26] | 2-Amino-4-(5-chloro-3-(3-(dimethylamino)azetidin-1-yl)-1-((4-methyl-5-oxo-4-azaspiro[2.4]heptan-6-yl)amino)-7,9-dihydrofuro[3,4-f]quinazolin-6-yl)-7-fluorobenzo[b]thiophene-3-carbonitrile, Isomer 2 | 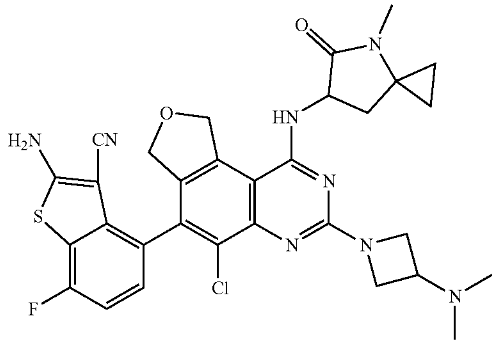 [SMILES: CN(C)C1CN(c2nc(NC3CC4(CC4)N(C)C3=O)c3c4c(c(-c5ccc(F)c6sc(N)c(C#N)c56)c(Cl)c3n2)COC4)C1] | 633 |

TABLE 25-continued

| Example | Chemical Name | Structure | MS (ES) m/z (M +1) |
|---|---|---|---|
| 65[1,27] | 2-Amino-4-(5-chloro-3-(3-(dimethylamino)azetidin-1-yl)-1-((1-oxooctahydropyridazino[1,2-a]pyridazin-2-yl)amino)-7,9-dihydrofuro[3,4-f]quinazolin-6-yl)-7-fluorobenzo[b]thiophene-3-carbonitrile, Isomer 1 | 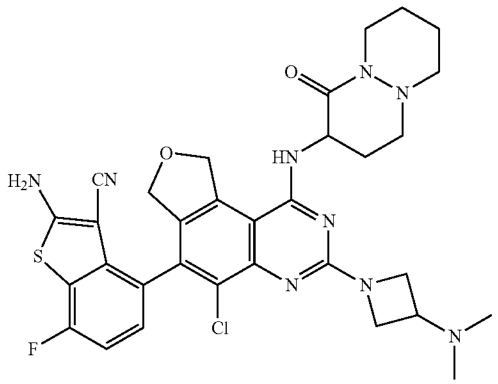 [SMILES: CN(C)C1CN(c2nc(NC3CCN4CCCCN4C3=O)c3c4c(c(-c5ccc(F)c6sc(N)c(C#N)c56)c(Cl)c3n2)COC4)C1] | 662 |
| 66[1,27] | 2-Amino-4-(5-chloro-3-(3-(dimethylamino)azetidin-1-yl)-1-((1-oxooctahydropyridazino[1,2-a]pyridazin-2-yl)amino)-7,9-dihydrofuro[3,4-f]quinazolin-6-yl)-7-fluorobenzo[b]thiophene-3-carbonitrile, Isomer 2 | 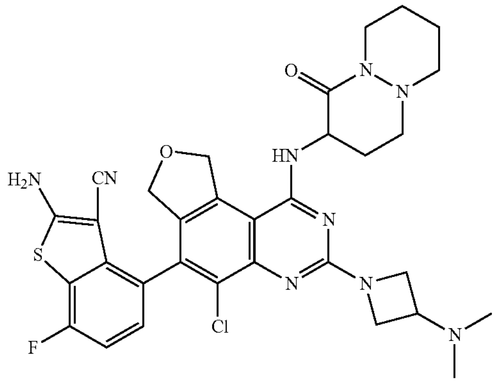 [SMILES: CN(C)C1CN(c2nc(NC3CCN4CCCCN4C3=O)c3c4c(c(-c5ccc(F)c6sc(N)c(C#N)c56)c(Cl)c3n2)COC4)C1] | 662 |
| 67[1,28] | 2-Amino-4-(5-chloro-3-(3-(dimethylamino)azetidin-1-yl)-1-(((8aR)-5-oxooctahydroindolizin-6-yl)amino)-7,9-dihydrofuro[3,4-f]quinazolin-6-yl)-7-fluorobenzo[b]thiophene-3-carbonitrile | 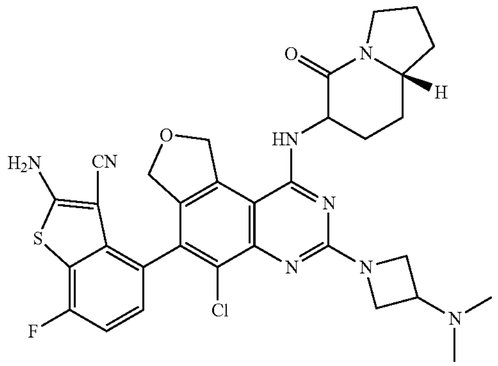 [SMILES: CN(C)C1CN(c2nc(NC3CC[C@H]4CCCN4C3=O)c3c4c(c(-c5ccc(F)c6sc(N)c(C#N)c56)c(Cl)c3n2)COC4)C1] | 647 |
| 68[1,29] | 2-Amino-4-(5-chloro-3-(3-(dimethylamino)azetidin-1-yl)-1-(((8aR)-5-oxooctahydroindolizin-6-yl)amino)-7,9-dihydrofuro[3,4-f]quinazolin-6-yl)-7-fluorobenzo[b]thiophene-3-carbonitrile | 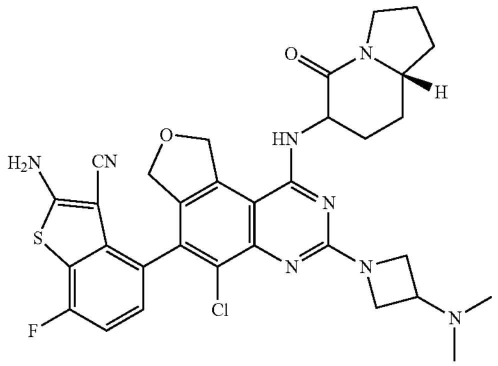 [SMILES: CN(C)C1CN(c2nc(NC3CC[C@H]4CCCN4C3=O)c3c4c(c(-c5ccc(F)c6sc(N)c(C#N)c56)c(Cl)c3n2)COC4)C1] | 647 |

TABLE 25-continued

| Example | Chemical Name | Structure | MS (ES) m/z (M +1) |
|---|---|---|---|
| 69 | (6R,8aR)-6-((6-(2-Aminobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-indolizin-5(1H)-one | 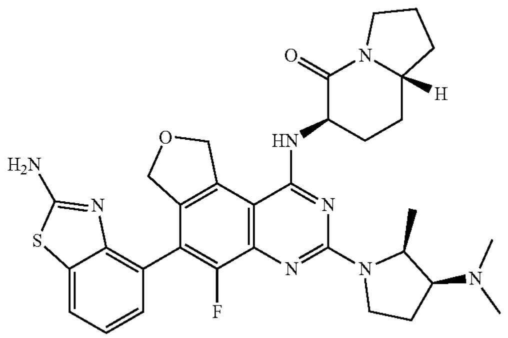 [SMILES: C[C@H]1[C@@H](N(C)C)CCN1c1nc(N[C@@H]2CC[C@H]3CCCN3C2=O)c2c3c(c(-c4cccc5sc(N)nc45)c(F)c2n1)COC3] | 617 |
| 70[30] | 7-((6-(2-Amino-7-fluorobenzo[d]thiazol-4-yl)-3-((2S,3R,4S)-3-(dimethylamino)-4-hydroxy-2-methylpyrrolidin-1-yl)-5-fluoro-7,9-dihydrofuro[3,4-f]quinazolin-1-yl)amino)-5-methyl-5-azaspiro[3.5]nonan-6-one, Isomer 1 | 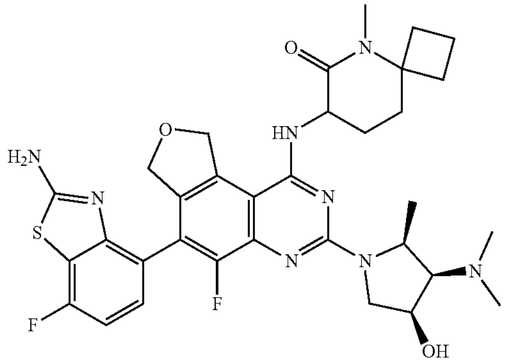 [SMILES: C[C@H]1[C@@H](N(C)C)[C@@H](O)CN1c1nc(NC2CCC3(CCC3)N(C)C2=O)c2c3c(c(-c4ccc(F)c5sc(N)nc45)c(F)c2n1)COC3] | 665 |
| 71[30] | 7-((6-(2-Amino-7-fluorobenzo[d]thiazol-4-yl)-3-((2S,3R,4S)-3-(dimethylamino)-4-hydroxy-2-methylpyrrolidin-1-yl)-5-fluoro-7,9-dihydrofuro[3,4-f]quinazolin-1-yl)amino)-5-methyl-5-azaspiro[3.5]nonan-6-one, Isomer 2 | 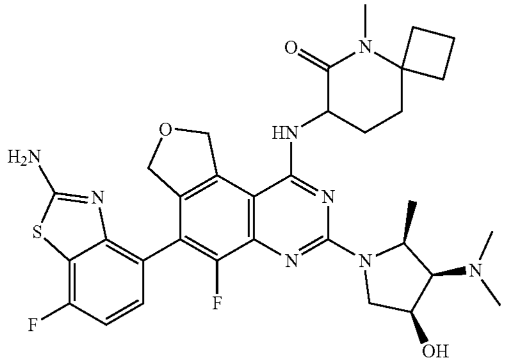 [SMILES: C[C@H]1[C@@H](N(C)C)[C@@H](O)CN1c1nc(NC2CCC3(CCC3)N(C)C2=O)c2c3c(c(-c4ccc(F)c5sc(N)nc45)c(F)c2n1)COC3] | 665 |
| 72[31] | (8aR)-6-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)hexahydro-indolizin-5(1H)-one | 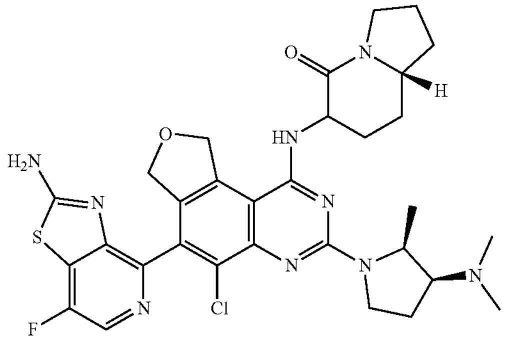 [SMILES: C[C@H]1[C@@H](N(C)C)CCN1c1nc(NC2CC[C@H]3CCCN3C2=O)c2c3c(c(-c4ncc(F)c5sc(N)nc45)c(Cl)c2n1)COC3] | 652 |

TABLE 25-continued

| Example | Chemical Name | Structure | MS (ES) m/z (M +1) |
|---|---|---|---|
| 73[32] | (8aR)-6-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)hexahydro-indolizin-5(1H)-one | 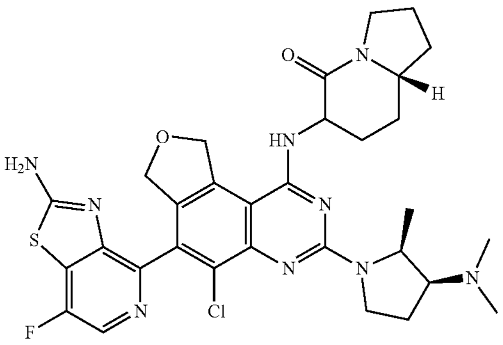 [SMILES: C[C@H]1[C@@H](N(C)C)CCN1c1nc(NC2CC[C@H]3CCCN3C2=O)c2c3c(c(-c4ncc(F)c5sc(N)nc45)c(Cl)c2n1)COC3] | 652 |
| 74[32] | (8aR)-6-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)hexahydro-indolizin-5(1H)-one | 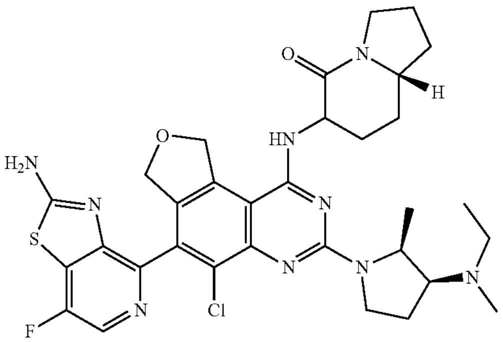 [SMILES: CCN(C)[C@H]1CCN(c2nc(NC3CC[C@H]4CCCN4C3=O)c3c4c(c(-c5ncc(F)c6sc(N)nc56)c(Cl)c3n2)COC4)[C@H]1C] | 666 |
| 75[33] | 6-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-4-methyl-4-azaspiro[2.4]octan-5-one | 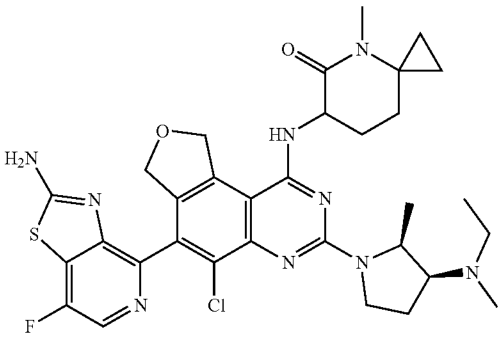 [SMILES: CCN(C)[C@H]1CCN(c2nc(NC3CCC4(CC4)N(C)C3=O)c3c4c(c(-c5ncc(F)c6sc(N)nc56)c(Cl)c3n2)COC4)[C@H]1C] | 666 |
| 76[34] | 6-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-4-methyl-4-azaspiro[2.5]octan-5-one | 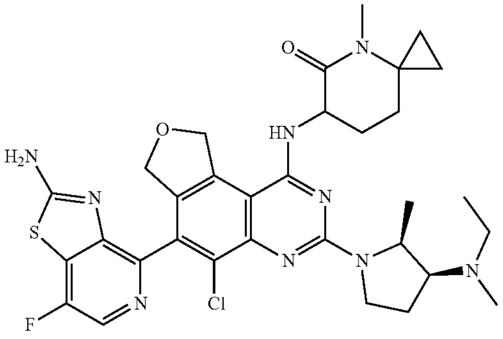 [SMILES: CCN(C)[C@H]1CCN(c2nc(NC3CCC4(CC4)N(C)C3=O)c3c4c(c(-c5ncc(F)c6sc(N)nc56)c(Cl)c3n2)COC4)[C@H]1C] | 666 |

TABLE 25-continued

| Example | Chemical Name | Structure | MS (ES) m/z (M +1) |
|---|---|---|---|
| 77[35] | 7-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-5-methyl-5-azaspiro[2.5]octan-6-one, Isomer 1 | 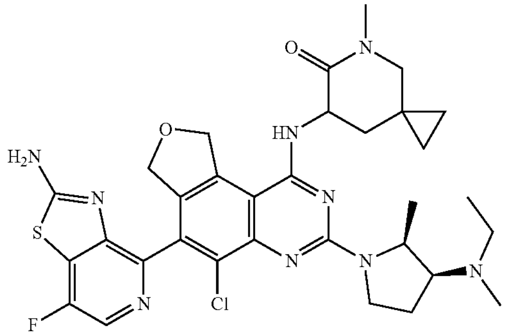 [SMILES: CCN(C)[C@H]1CCN(c2nc(NC3CC4(CC4)CN(C)C3=O)c3c4c(c(-c5ncc(F)c6sc(N)nc56)c(Cl)c3n2)COC4)[C@H]1C] | 666 |
| 78[35] | 7-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-5-methyl-5-azaspiro[2.5]octan-6-one, Isomer 2 | 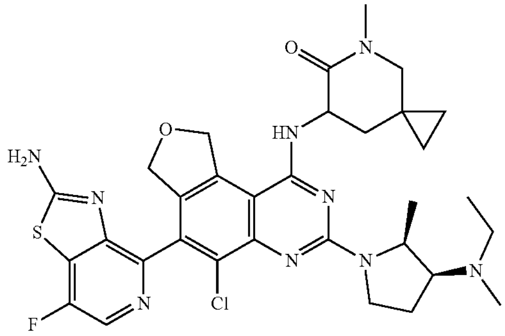 | 666 |
| 79[36] | 7-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Isomer 1 | 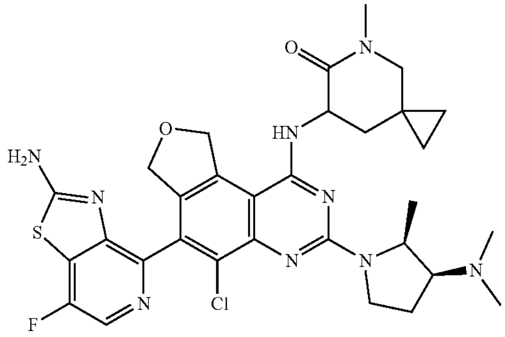 [SMILES: C[C@H]1[C@@H](N(C)C)CCN1c1nc(NC2CC3(CC3)CN(C)C2=O)c2c3c(c(-c4ncc(F)c5sc(N)nc45)c(Cl)c2n1)COC3] | 652 |
| 80[36] | 7-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-5-methyl-5-azaspiro[2.5]octan-6-one, Isomer 2 | 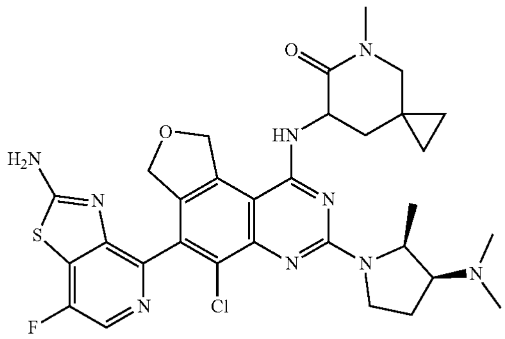 [SMILES: C[C@H]1[C@@H](N(C)C)CCN1c1nc(NC2CC3(CC3)CN(C)C2=O)c2c3c(c(-c4ncc(F)c5sc(N)nc45)c(Cl)c2n1)COC3] | 652 |

TABLE 25-continued

| Example | Chemical Name | Structure | MS (ES) m/z (M +1) |
|---|---|---|---|
| 81[3,37] | (8aR)-6-((6-(2-Amino-7-fluorobenzo[d]thiazol-4-yl)-3-((2S)-3-(azetidin-1-yl)-2-methylpyrrolidin-1-yl)-5-fluoro-7,9-dihydrofuro[3,4-f]quinazolin-1-yl)amino)hexahydroindolizin-5(1H)-one | 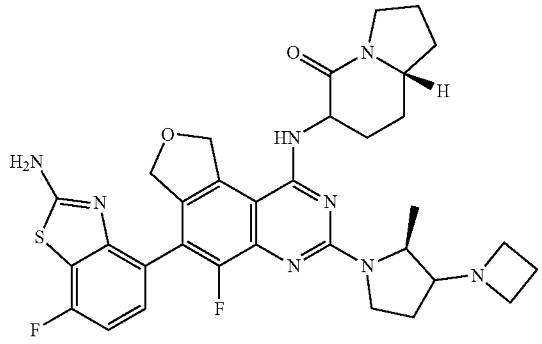 [SMILES: C[C@H]1C(N2CCC2)CCN1c1nc(NC2CC[C@H]3CCCN3C2=O)c2c3c(c(-c4ccc(F)c5sc(N)nc45)c(F)c2n1)COC3] | 647 |
| 82[3,38] | (8aR)-6-((6-(2-Amino-7-fluorobenzo[d]thiazol-4-yl)-3-((2S)-3-(azetidin-1-yl)-2-methylpyrrolidin-1-yl)-5-fluoro-7,9-dihydrofuro[3,4-f]quinazolin-1-yl)amino)hexahydro-indolizin-5(1H)-one | 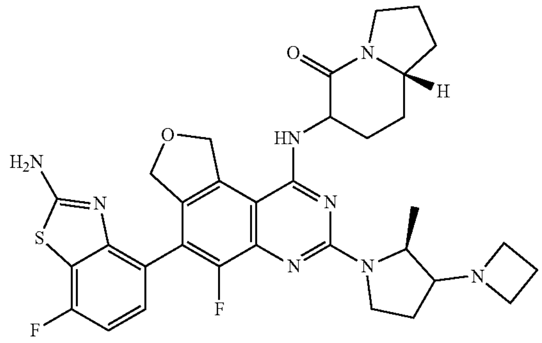 [SMILES: C[C@H]1C(N2CCC2)CCN1c1nc(NC2CC[C@H]3CCCN3C2=O)c2c3c(c(-c4ccc(F)c5sc(N)nc45)c(F)c2n1)COC3] | 647 |
| 83[39] | 7-((6-(2-Amino-7-fluorobenzo[d]thiazol-4-yl)-3-((2S,3S)-3-(ethyl(methyl)amino)-2-methylpyrrolidin-1-yl)-5-fluoro-7,9-dihydrofuro[3,4-f]quinazolin-1-yl)amino)-5-methyl-5-azaspiro[2.5]octan-6-one, Isomer 1 | 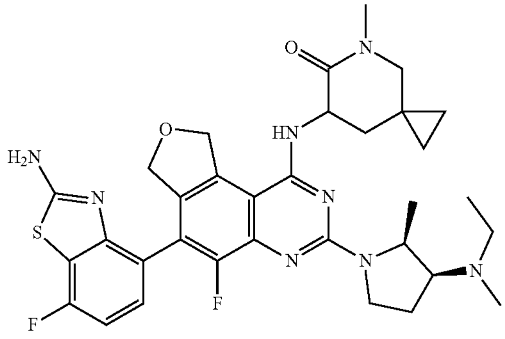 [SMILES: CCN(C)[C@H]1CCN(c2nc(NC3CC4(CC4)CN(C)C3=O)c3c4c(c(-c5ccc(F)c6sc(N)nc56)c(F)c3n2)COC4)[C@H]1C] | 649 |
| 84[39] | 7-((6-(2-Amino-7-fluorobenzo[d]thiazol-4-yl)-3-((2S,3S)-3-(ethyl(methyl)amino)-2-methylpyrrolidin-1-yl)-5-fluoro-7,9-dihydrofuro[3,4-f]quinazolin-1-yl)amino)-5-methyl-5-azaspiro[2.5]octan-6-one, Isomer 2 | 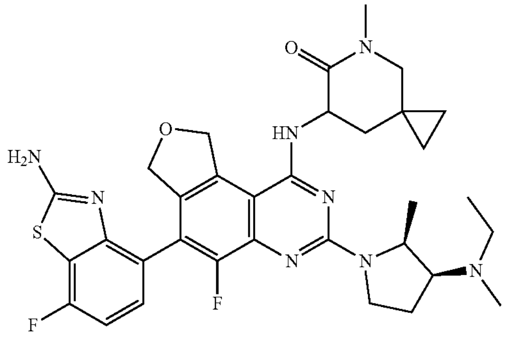 [SMILES: CCN(C)[C@H]1CCN(c2nc(NC3CC4(CC4)CN(C)C3=O)c3c4c(c(-c5ccc(F)c6sc(N)nc56)c(F)c3n2)COC4)[C@H]1C] | 649 |

TABLE 25-continued

| Example | Chemical Name | Structure | MS (ES) m/z (M +1) |
|---|---|---|---|
| 85[40] | (9aS)-7-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f] quinazolin-1-yl)amino) hexahydropyrido[2,1-c] [1,4]oxazin-6(1H)-one | 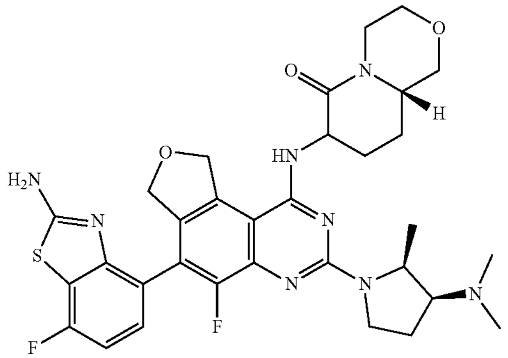 [SMILES: C[C@H]1[C@@H](N(C)C)CCN1c1nc(NC2CC[C@H]3COCCN3C2=O)c2c3c(c(-c4ccc(F)c5sc(N)nc45)c(F)c2n1)COC3] | 651 |
| 86 | (6R,8aR)-6-((6-(2-Amino-7-fluorobenzo[d]thiazol-4-yl)-5-fluoro-3-((2'S,3'S)-2'-methyl-[1,3'-bipyrrolidin]-1'-yl)-7,9-dihydrofuro[3,4-f]quinazolin-1-yl)amino)hexahydro-indolizin-5(1H)-one | 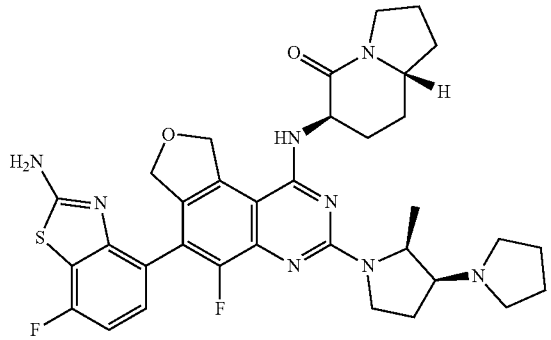 [SMILES: C[C@H]1[C@@H](N2CCCC2)CCN1c1nc(N[C@@H]2CC[C@H]3CCCN3C2=O)c2c3c(c(-c4ccc(F)c5sc(N)nc45)c(F)c2n1)COC3] | 661 |
| 87[41] | 7-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-5-azaspiro[3.5]nonan-6-one, Isomer 1 | 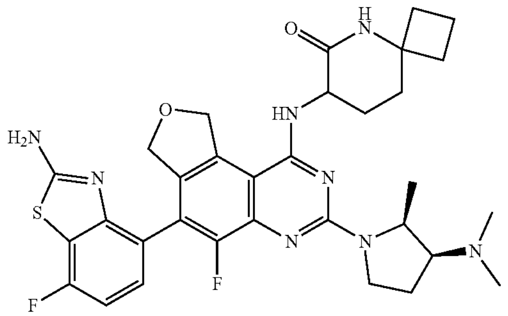 | 635 |
| 88[41] | 7-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-5-azaspiro[3.5]nonan-6-one, Isomer 2 | 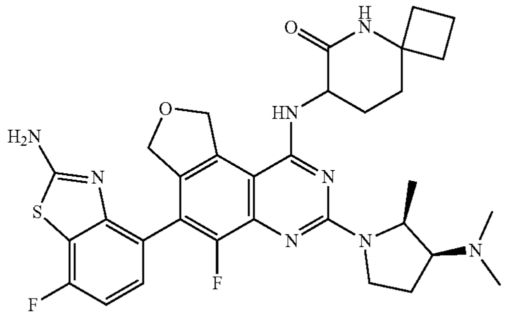 [SMILES: C[C@H]1[C@@H](N(C)C)CCN1c1nc(NC2CCC3(CCC3)NC2=O)c2c3c(c(-c4ccc(F)c5sc(N)nc45)c(F)c2n1)COC3] | 635 |

TABLE 25-continued

| Example | Chemical Name | Structure | MS (ES) m/z (M +1) |
|---|---|---|---|
| 89[42] | 2-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f] quinazolin-1-yl) amino)hexahydro-pyridazino[1,2-a]pyridazin-1(2H)-one, Isomer 1 | 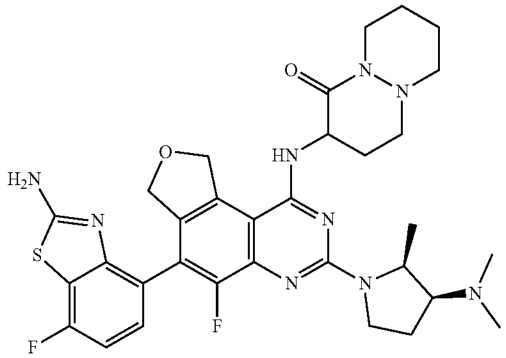 [SMILES: C[C@H]1[C@@H](N(C)C)CCN1c1nc(NC2CCN3CCCCN3C2=O)c2c3c(c(-c4ccc(F)c5sc(N)nc45)c(F)c2n1)COC3] | 650 |
| 90[42] | 2-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-pyridazino[1,2-a]pyridazin-1(2H)-one, Isomer 2 | 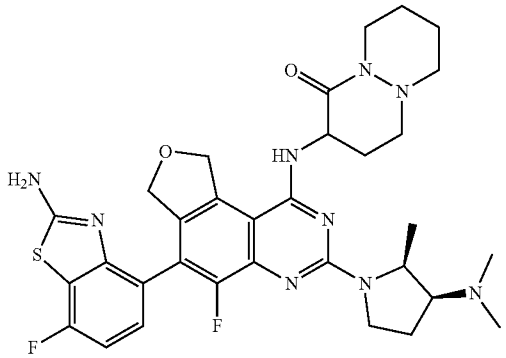 [SMILES: C[C@H]1[C@@H](N(C)C)CCN1c1nc(NC2CCN3CCCCN3C2=O)c2c3c(c(-c4ccc(F)c5sc(N)nc45)c(F)c2n1)COC3] | 650 |
| 91 | (6R,8aR)-6-((6-(2-Amino-7-fluorobenzo[d]thiazol-4-yl)-3-((3-(dimethylamino)oxetan-3-yl)methoxy)-5-fluoro-7,9-dihydrofuro[3,4-f]quinazolin-1-yl)amino)hexahydro-indolizin-5(1H)-one | 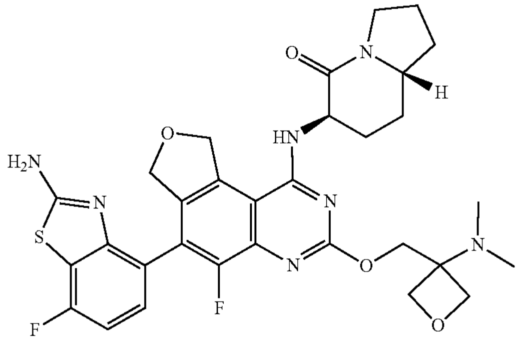 [SMILES: CN(C)C1(COc2nc(N[C@@H]3CC[C@H]4CCCN4C3=O)c3c4c(c(-c5ccc(F)c6sc(N)nc56)c(F)c3n2)COC4)COC1] | 638 |
| 92[43] | 7-((6-(2-Amino-7-fluorothiazolo[4,5-c]pyridin-4-yl)-3-((2S,3S)-3-(dimethylamino)-2-methylpyrrolidin-1-yl)-5-fluoro-7,9-dihydrofuro[3,4-f]quinazolin-1-yl)amino)-5-methyl-5-azaspiro[3.5]nonan-6-one, Isomer 1 | 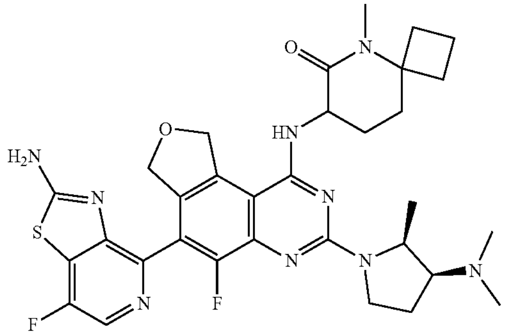 [SMILES: C[C@H]1[C@@H](N(C)C)CCN1c1nc(NC2CCC3(CCC3)N(C)C2=O)c2c3c(c(-c4ncc(F)c5sc(N)nc45)c(F)c2n1)COC3] | 650 |

TABLE 25-continued

| Example | Chemical Name | Structure | MS (ES) m/z (M +1) |
|---|---|---|---|
| 93[43] | 7-((6-(2-Amino-7-fluorothiazolo[4,5-c]pyridin-4-yl)-3-((2S,3S)-3-(dimethylamino)-2-methylpyrrolidin-1-yl)-5-fluoro-7,9-dihydrofuro[3,4-f]quinazolin-1-yl)amino)-5-methyl-5-azaspiro[3.5]nonan-6-one, Isomer 2 | 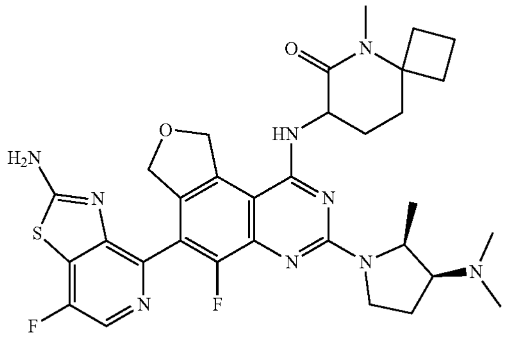 [SMILES: C[C@H]1[C@@H](N(C)C)CCN1c1nc(NC2CCC3(CCC3)N(C)C2=O)c2c3c(c(-c4ncc(F)c5sc(N)nc45)c(F)c2n1)COC3] | 650 |
| 94[44] | (8aR)-6-((6-(2-Amino-7-fluorothiazolo[4,5-c]pyridin-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-indolizin-5(1H)-one, Isomer 1 | 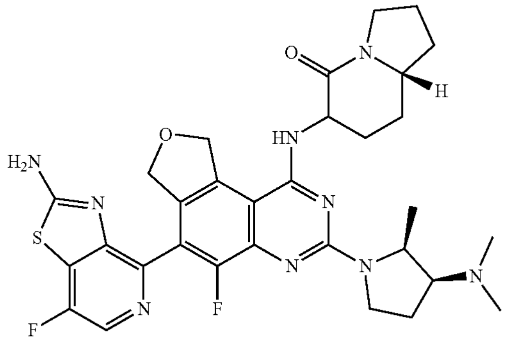 [SMILES: C[C@H]1[C@@H](N(C)C)CCN1c1nc(NC2CC[C@H]3CCCN3C2=O)c2c3c(c(-c4ncc(F)c5sc(N)nc45)c(F)c2n1)COC3] | 636 |
| 95[44] | (8aR)-6-((6-(2-Amino-7-fluorothiazolo[4,5-c]pyridin-4-yl)-3-((2S,3S)-3-(dimethylamino)-2-methylpyrrolidin-1-yl)-5-fluoro-7,9-dihydrofuro[3,4-f]quinazolin-1-yl)amino)hexahydro-indolizin-5(1H)-one, Isomer 2 | 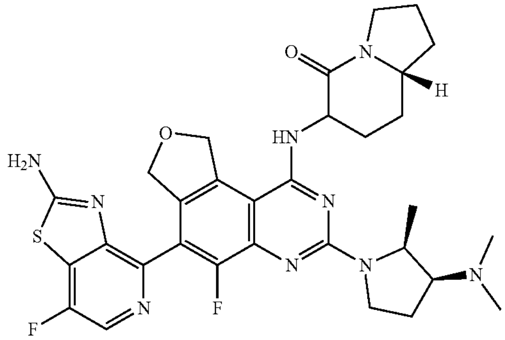 [SMILES: C[C@H]1[C@@H](N(C)C)CCN1c1nc(NC2CC[C@H]3CCCN3C2=O)c2c3c(c(-c4ncc(F)c5sc(N)nc45)c(F)c2n1)COC3] | 636 |
| 96[45] | (6R,8aR)-6-((6-(2-Amino-5,7-difluorobenzo[d]thiazol-4-yl)-3-((S)-3-(dimethylamino)pyrrolidin-1-yl)-5-fluoro-7,9-dihydrofuro[3,4-f] quinazolin-1-yl)amino) hexahydroindolizin-5(1H)-one, Isomer 1 | 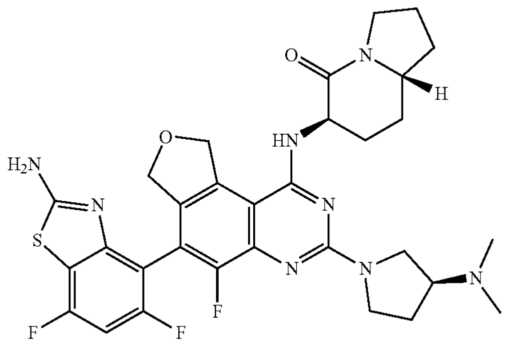 [SMILES: CN(C)[C@H]1CCN(c2nc(N[C@@H]3CC[C@H]4CCCN4C3=O)c3c4c(c(-c5c(F)cc(F)c6sc(N)nc56)c(F)c3n2)COC4)C1] | 639 |

TABLE 25-continued

| Example | Chemical Name | Structure | MS (ES) m/z (M +1) |
|---|---|---|---|
| 97[45] | (6R,8aR)-6-((6-(2-Amino-5,7-difluorobenzo[d]thiazol-4-yl)-3-((S)-3-(dimethylamino)pyrrolidin-1-yl)-5-fluoro-7,9-dihydrofuro[3,4-f]quinazolin-1-yl)amino)hexahydro-indolizin-5(1H)-one, Isomer 2 | 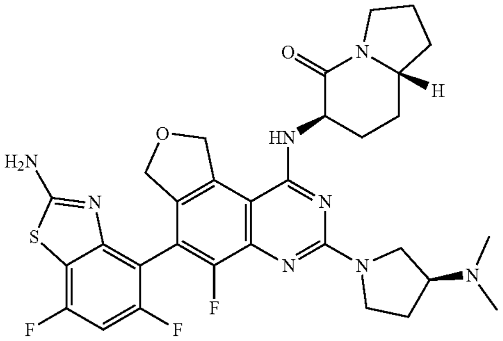 [SMILES: CN(C)[C@H]1CCN(c2nc(N[C@@H]3CC[C@H]4CCCN4C3=O)c3c4c(c(-c5c(F)cc(F)c6sc(N)nc56)c(F)c3n2)COC4)C1] | 639 |
| 98[46] | (2R)-2-((6-(2-Amino-5,7-difluorobenzo[d]thiazol-4-yl)-3-((S)-3-(dimethylamino)pyrrolidin-1-yl)-5-fluoro-7,9-dihydrofuro[3,4-f]quinazolin-1-yl)amino)hexahydro-pyridazino[1,2-a] pyridazin-1(2H)-one, Isomer 1 | 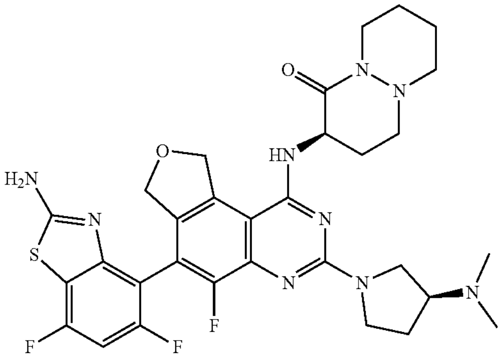 [SMILES: CN(C)[C@H]1CCN(c2nc(N[C@@H]3CCN4CCCCN4C3=O)c3c4c(c(-c5c(F)cc(F)c6sc(N)nc56)c(F)c3n2)COC4)C1] | 654 |
| 99[46] | (2R)-2-((6-(2-Amino-5,7-difluorobenzo[d]thiazol-4-yl)-3-((S)-3-(dimethylamino)pyrrolidin-1-yl)-5-fluoro-7,9-dihydrofuro[3,4-f]quinazolin-1-yl)amino)hexahydro-pyridazino[1,2-a]pyridazin-1(2H)-one, Isomer 2 | 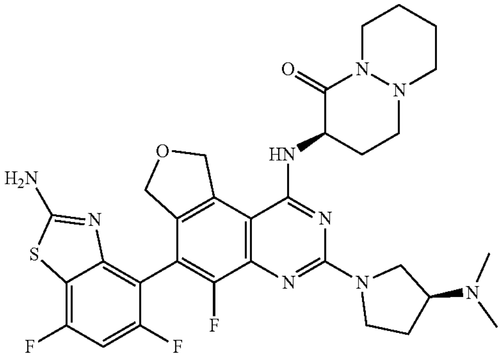 [SMILES: CN(C)[C@H]1CCN(c2nc(N[C@@H]3CCN4CCCCN4C3=O)c3c4c(c(-c5c(F)cc(F)c6sc(N)nc56)c(F)c3n2)COC4)C1] | 654 |
| 100[47] | (6R)-6-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one, Isomer 1 | 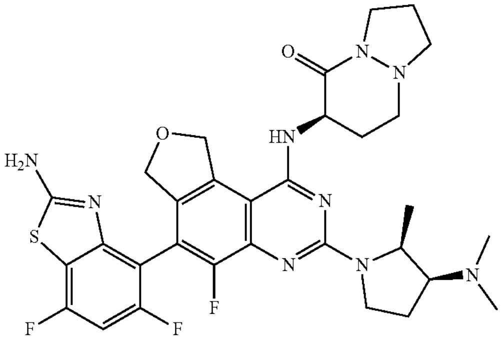 [SMILES: C[C@H]1[C@@H](N(C)C)CCN1c1nc(N[C@@H]2CCN3CCCN3C2=O)c2c3c(c(-c4c(F)cc(F)c5sc(N)nc45)c(F)c2n1)COC3] | 654 |

TABLE 25-continued

| Example | Chemical Name | Structure | MS (ES) m/z (M +1) |
|---|---|---|---|
| 101[47] | (6R)-6-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one, Isomer 2 | 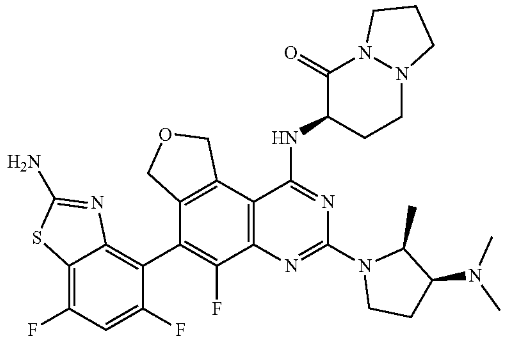 [SMILES: C[C@H]1[C@@H](N(C)C)CCN1c1nc(N[C@@H]2CCN3CCCN3C2=O)c2c3c(c(-c4c(F)cc(F)c5sc(N)nc45)c(F)c2n1)COC3] | 654 |
| 102[48] | (6R)-6-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)tetrahydro-1H-pyrazolo[1,2-a]pyridazin-5(6H)-one, Isomer 2 | 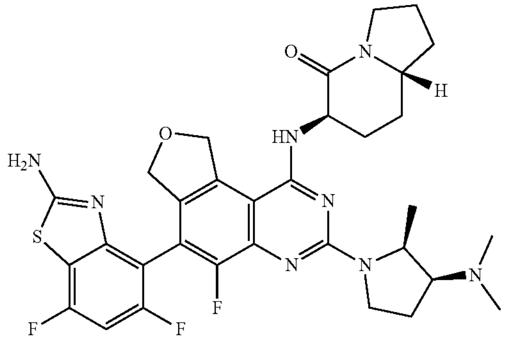 [SMILES: C[C@H]1[C@@H](N(C)C)CCN1c1nc(N[C@@H]2CC[C@H]3CCCN3C2=O)c2c3c(c(-c4c(F)cc(F)c5sc(N)nc45)c(F)c2n1)COC3] | 653 |
| 103[48] | (6R,8aR)-6-((6-(2-Amino-5,7-difluorobenzo[d]thiazol-4-yl)-3-((2S,3S)-3-(dimethylamino)-2-methylpyrrolidin-1-yl)-5-fluoro-7,9-dihydrofuro[3,4-f] quinazolin-1-yl)amino) hexahydroindolizin-5(1H)-one, Isomer 1 | 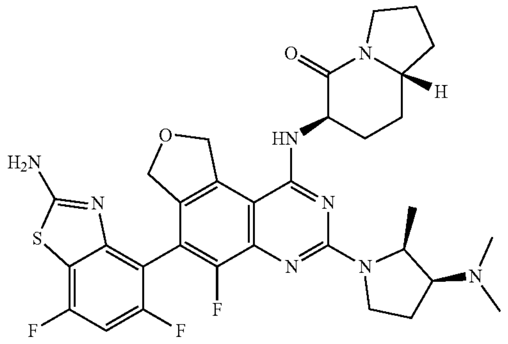 [SMILES: C[C@H]1[C@@H](N(C)C)CCN1c1nc(N[C@@H]2CC[C@H]3CCCN3C2=O)c2c3c(c(-c4c(F)cc(F)c5sc(N)nc45)c(F)c2n1)COC3] | 653 |
| 104[49] | (6R)-6-((6-(2-Amino-5,7-difluorobenzo[d]thiazol-4-yl)-5-chloro-3-((S)-3-(dimethylamino)pyrrolidin-1-yl)-7,9-dihydrofuro[3,4-f]quinazolin-1-yl)amino)tetrahydro-1H-pyrazolo[1,2-a]pyridazin-5(6H)-one, Isomer 1 | 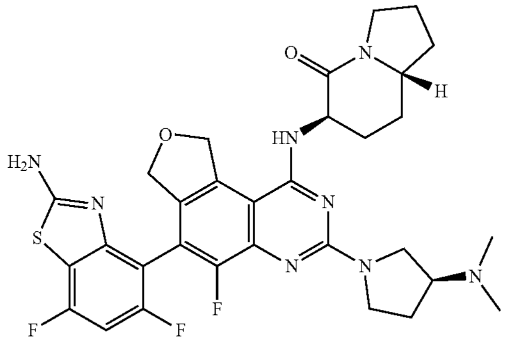 [SMILES: CN(C)[C@H]1CCN(c2nc(N[C@@H]3CC[C@H]4CCCN4C3=O)c3c4c(c(-c5c(F)cc(F)c6sc(N)nc56)c(F)c3n2)COC4)C1] | 656 |

TABLE 25-continued

| Example | Chemical Name | Structure | MS (ES) m/z (M +1) |
|---|---|---|---|
| 105[49] | (6R)-6-((6-(2-Amino-5,7-difluorobenzo[d]thiazol-4-yl)-5-chloro-3-((S)-3-(dimethylamino)pyrrolidin-1-yl)-7,9-dihydrofuro[3,4-f]quinazolin-1-yl)amino)tetrahydro-1H-pyrazolo[1,2-a]pyridazin-5(6H)-one, Isomer 2 | 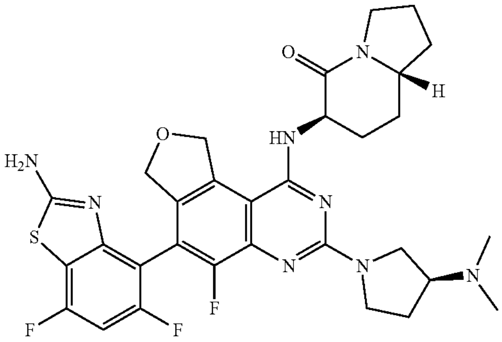 [SMILES: CN(C)[C@H]1CCN(c2nc(N[C@@H]3CC[C@H]4CCCN4C3=O)c3c4c(c(-c5c(F)cc(F)c6sc(N)nc56)c(F)c3n2)COC4)C1] | 656 |
| 106[50] | 6-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)tetrahydro-1H-pyrazolo[1,2-a]pyridazin-5(6H)-one, Diastereomer 1 | 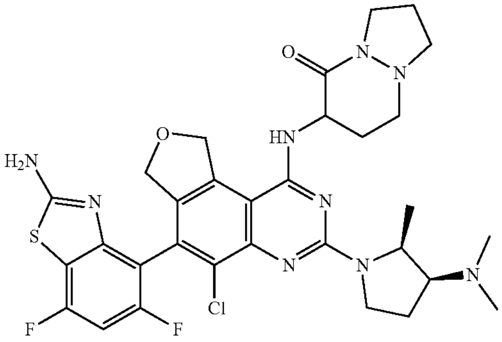 [SMILES: C[C@H]1[C@@H](N(C)C)CCN1c1nc(NC2CCN3CCCN3C2=O)c2c3c(c(-c4c(F)cc(F)c5sc(N)nc45)c(Cl)c2n1)COC3] | 670 |
| 107[50] | 6-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)tetrahydro-1H-pyrazolo[1,2-a]pyridazin-5(6H)-one, Diastereomer 2 | 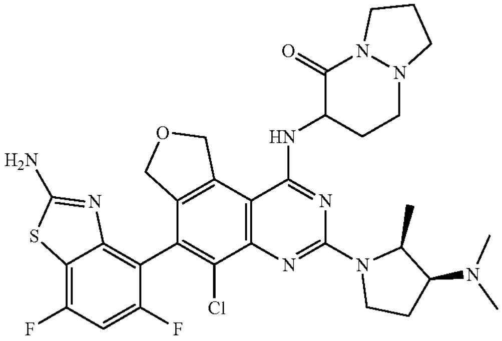 [SMILES: C[C@H]1[C@@H](N(C)C)CCN1c1nc(NC2CCN3CCCN3C2=O)c2c3c(c(-c4c(F)cc(F)c5sc(N)nc45)c(Cl)c2n1)COC3] | 670 |
| 108[50] | 6-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)tetrahydro-1H-pyrazolo[1,2-a]pyridazin-5(6H)-one, Diastereomer 3 | 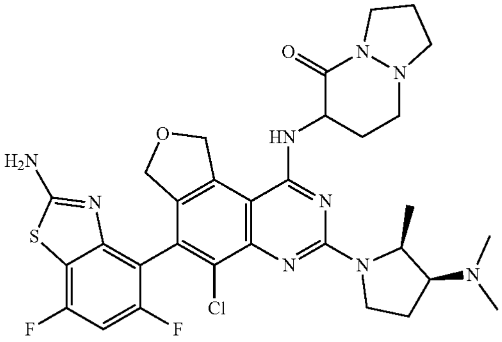 [SMILES: C[C@H]1[C@@H](N(C)C)CCN1c1nc(NC2CCN3CCCN3C2=O)c2c3c(c(-c4c(F)cc(F)c5sc(N)nc45)c(Cl)c2n1)COC3] | 670 |

TABLE 25-continued

| Example | Chemical Name | Structure | MS (ES) m/z (M +1) |
|---|---|---|---|
| 109[50] | 6-((6-(2-Amino-5,7-difluorobenzo[d]thiazol-4-yl)-5-chloro-3-((2S,3S)-3-(dimethylamino)-2-methylpyrrolidin-1-yl)-7,9-dihydrofuro[3,4-f]quinazolin-1-yl)amino)tetrahydro-1H-pyrazolo[1,2-a]pyridazin-5(6H)-one, Diastereomer 4 | 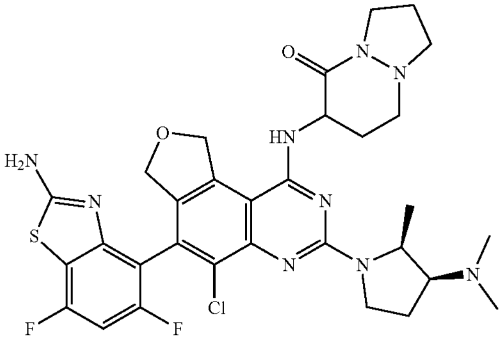 [SMILES: C[C@H]1[C@@H](N(C)C)CCN1c1nc(NC2CCN3CCCN3C2=O)c2c3c(c(-c4c(F)cc(F)c5sc(N)nc45)c(Cl)c2n1)COC3] | 670 |
| 1B[1,51] | 4-(3-([1,3'-Biazetidin]-1'-yl)-5-chloro-1-((5-methyl-6-oxo-5-azaspiro[3.5]nonan-7-yl)amino)-7,9-dihydrofuro[3,4-f]quinazolin-6-yl)-2-amino)-7-fluorobenzo[b]thiophene-3-carbonitrile, Isomer 1 | 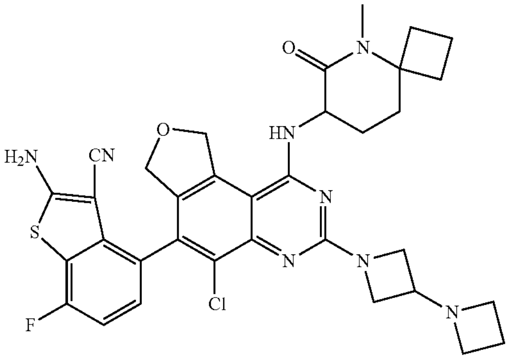 [SMILES: CN1C(=O)C(Nc2nc(N3CC(N4CCC4)C3)nc3c(Cl)c(-c4ccc(F)c5sc(N)c(C#N)c45)c4c(c23)COC4)CCC12CCC2] | 673 |
| 2B[1,51] | 4-(3-([1,3'-Biazetidin]-1'-yl)-5-chloro-1-((5-methyl-6-oxo-5-azaspiro[3.5]nonan-7-yl)amino)-7,9-dihydrofuro[3,4-f]quinazolin-6-yl)-2-amino-7-fluorobenzo[b]thiophene-3-carbonitrile, Isomer 2 | 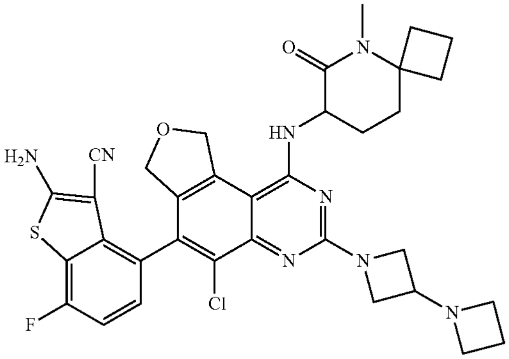 [SMILES: CN1C(=O)C(Nc2nc(N3CC(N4CCC4)C3)nc3c(Cl)c(-c4ccc(F)c5sc(N)c(C#N)c45)c4c(c23)COC4)CCC12CCC2] | 673 |
| 3B[1] | 2-Amino-4-(5-chloro-1-(((6R,8aR)-5-oxooctahydroindolizin-6-yl)amino)-7,9-dihydrofuro[3,4-f]quinazolin-6-yl)-7-fluorobenzo[b]thiophene-3-carbonitrile | 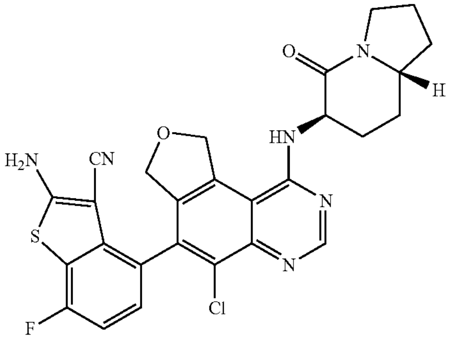 [SMILES: N#Cc1c(N)sc2c(F)ccc(-c3c4c(c5c(N[C@@H]6CC[C@H]7CCCN7C6=O)ncnc5c3Cl)COC4)c12] | 549 |

TABLE 25-continued

| Example | Chemical Name | Structure | MS (ES) m/z (M +1) |
| --- | --- | --- | --- |
| 4B[52] | 2-Amino-4-(5-chloro-9-(((6R,8aR)-5-oxooctahydroindolizin-6-yl)amino)-1,3-dihydrofuro[3,4-f]quinolin-4-yl)-7-fluorobenzo[b]thiophene-3-carbonitrile, Isomer 1 | 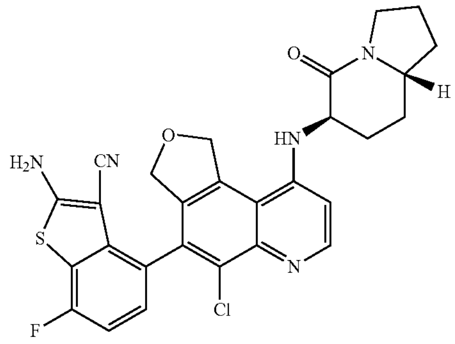 [SMILES: N#Cc1c(N)sc2c(F)ccc(-c3c4c(c5c(N[C@@H]6CC[C@H]7CCCN7C6=O)ccnc5c3Cl)COC4)c12] | 548 |
| 5B[52] | 2-Amino-4-(5-chloro-9-(((6R,8aR)-5-oxooctahydroindolizin-6-yl)amino)-1,3-dihydrofuro[3,4-f]quinolin-4-yl)-7-fluorobenzo[b]thiophene-3-carbonitrile, Isomer 2 | 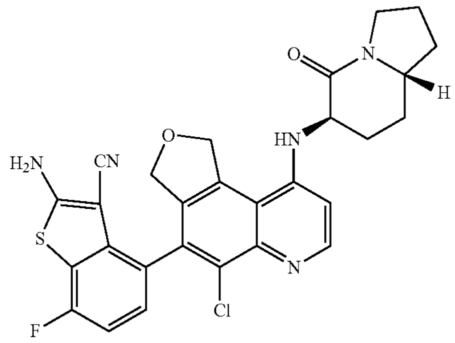 [SMILES: N#Cc1c(N)sc2c(F)ccc(-c3c4c(c5c(N[C@@H]6CC[C@H]7CCCN7C6=O)ccnc5c3Cl)COC4)c12] | 548 |
| 6B[1,53] | 2-Amino-4-(5-chloro-1-((5-methyl-6-oxo-5-azaspiro[3.5]nonan-7-yl)amino)-7,9-dihydrofuro[3,4-f]quinazolin-6-yl)-7-fluorobenzo[b]thiophene-3-carbonitrile, Isomer 1 | 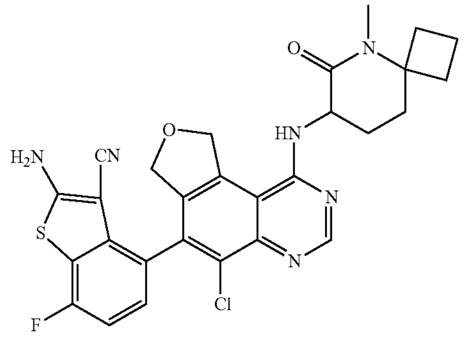 [SMILES: CN1C(=O)C(Nc2ncnc3c(Cl)c(-c4ccc(F)c5sc(N)c(C#N)c45)c4c(c23)COC4)CCC12CCC2] | 563 |
| 7B[1,53] | 2-Amino-4-(5-chloro-1-((5-methyl-6-oxo-5-azaspiro[3.5]nonan-7-yl)amino)-7,9-dihydrofuro[3,4-f]quinazolin-6-yl)-7-fluorobenzo[b]thiophene-3-carbonitrile, Isomer 2 | 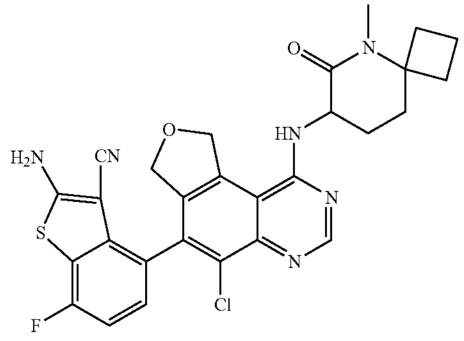 [SMILES: CN1C(=O)C(Nc2ncnc3c(Cl)c(-c4ccc(F)c5sc(N)c(C#N)c45)c4c(c23)COC4)CCC12CCC2] | 563 |

TABLE 25-continued

| Example | Chemical Name | Structure | MS (ES) m/z (M +1) |
|---|---|---|---|
| 8B[1,54] | 2-Amino-4-(5-chloro-3-(2-hydroxy-2-methylpropoxy)-1-(((8aR)-5-oxooctahydroindolizin-6-yl)amino)-7,9-dihydrofuro[3,4-f]quinazolin-6-yl)-7-fluorobenzo[b]thiophene-3-carbonitrile, Isomer 1 | 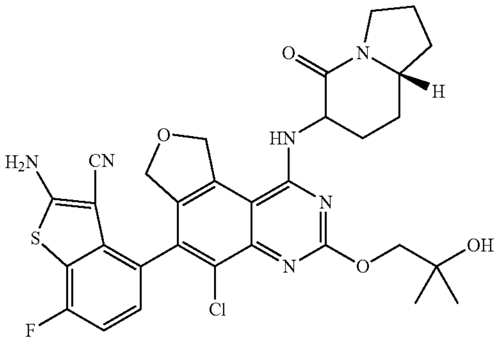 [SMILES: CC(C)(O)COc1nc(NC2CC[C@H]3CCCN3C2=O)c2c3c(c(-c4ccc(F)c5sc(N)c(C#N)c45)c(Cl)c2n1)COC3] | 637 |
| 9B[1,54] | 2-Amino-4-(5-chloro-3-(2-hydroxy-2-methylpropoxy)-1-(((8aR)-5-oxooctahydroindolizin-6-yl)amino)-7,9-dihydrofuro[3,4-f]quinazolin-6-yl)-7-fluorobenzo[b]thiophene-3-carbonitrile, Isomer 2 | 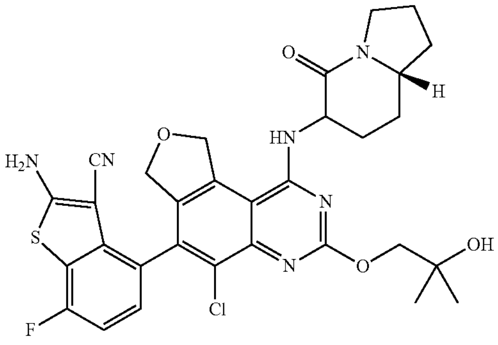 [SMILES: CC(C)(O)COc1nc(NC2CC[C@H]3CCCN3C2=O)c2c3c(c(-c4ccc(F)c5sc(N)c(C#N)c45)c(Cl)c2n1)COC3] | 637 |
| 10B[55] | 2-Amino-4-(5-chloro-9-(((6R,8aR)-5-oxooctahydroindolizin-6-yl)amino)-1,3-dihydrofuro[3,4-f]cinnolin-4-yl)-7-fluorobenzo[b]thiophene-3-carbonitrile, Isomer 1 | 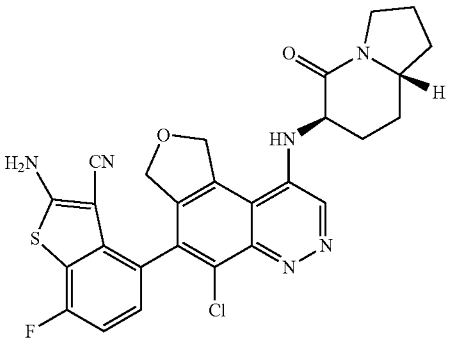 | 549 |
| 11B[55] | 2-Amino-4-(5-chloro-9-(((6R,8aR)-5-oxooctahydroindolizin-6-yl)amino)-1,3-dihydrofuro[3,4-f]cinnolin-4-yl)-7-fluorobenzo[b]thiophene-3-carbonitrile, Isomer 2 | 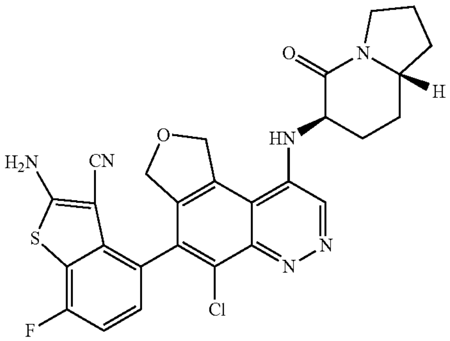 | 549 |

TABLE 25-continued

| Example | Chemical Name | Structure | MS (ES) m/z (M +1) |
|---|---|---|---|
| 12B[56,57] | 2-Amino-4-(5-chloro-1-(((6S)-2-oxo-1-azabicyclo[4.2.0]octan-3-yl)amino)-7,9-dihydrofuro[3,4-f]quinazolin-6-yl)-7-fluorobenzo[b]thiophene-3-carbonitrile | 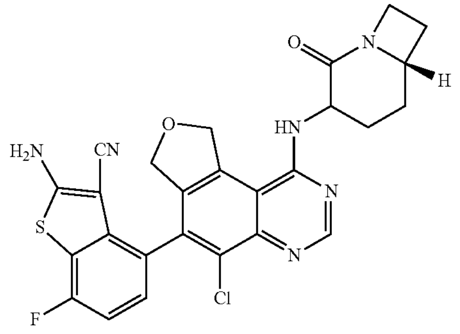 [SMILES: N#Cc1c(N)sc2c(F)ccc(-c3c4c(c5c(NC6CC[C@H]7CCN7C6=O)ncnc5c3Cl)COC4)c12] | 535 |
| 13B[58] | 2-Amino-5-fluoro-4-(5-fluoro-1-(((6R,8aR)-5-oxooctahydroindolizin-6-yl)amino)-7,9-dihydrofuro[3,4-f]quinazolin-6-yl)benzo[b]thiophene-3-carbonitrile | 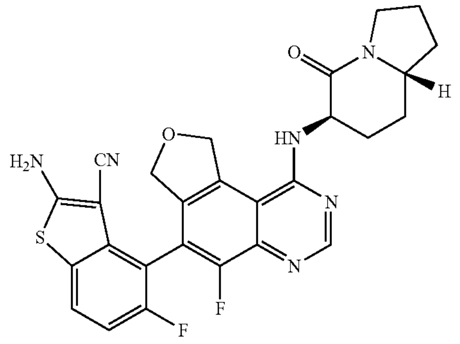 [SMILES: N#Cc1c(N)sc2ccc(F)c(-c3c4c(c5c(N[C@@H]6CC[C@H]7CCCN7C6=O)ncnc5c3F)COC4)c12] | 533 |
| 14B[58] | 2-Amino-5-fluoro-4-(5-fluoro-3-methoxy-1-(((6R,8aR)-5-oxooctahydroindolizin-6-yl)amino)-7,9-dihydrofuro[3,4-f]quinazolin-6-yl)benzo[b]thiophene-3-carbonitrile | 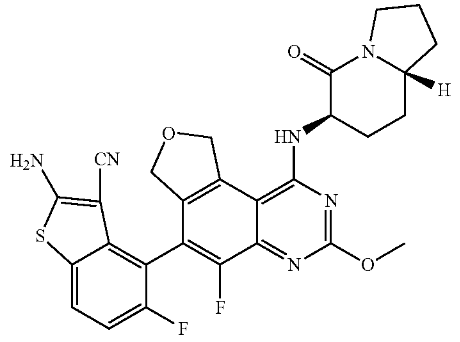 [SMILES: COc1nc(N[C@@H]2CC[C@H]3CCCN3C2=O)c2c3c(c(-c4c(F)ccc5sc(N)c(C#N)c45)c(F)c2n1)COC3] | 563 |
| 15B[58,59] | 2-Amino-4-(1-(((8aS)-2,2-difluoro-5-oxooctahydroindolizin-6-yl)amino)-5-fluoro-7,9-dihydrofuro[3,4-f]quinazolin-6-yl)-5-fluorobenzo[b]thiophene-3-carbonitrile | 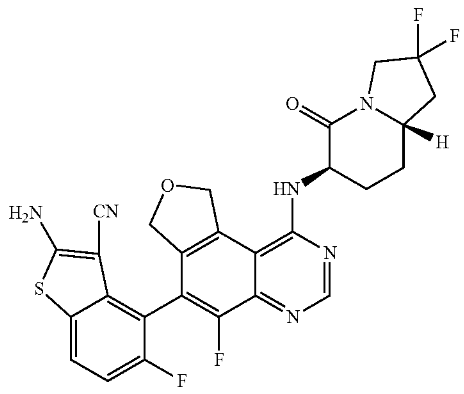 [SMILES: N#Cc1c(N)sc2ccc(F)c(-c3c4c(c5c(N[C@@H]6CC[C@H]7CC(F)(F)CN7C6=O)ncnc5c3F)COC4)c12] | 569 |

TABLE 25-continued

| Example | Chemical Name | Structure | MS (ES) m/z (M +1) |
|---|---|---|---|
| 16B[60] | 2-Amino-4-(5-chloro-1-(((6R,8aR)-5-oxooctahydroindolizin-6-yl)amino)-7,9-dihydrofuro[3,4-f]quinazolin-6-yl)-7-fluorothieno[3,2-c]pyridine-3-carbonitrile, Isomer 1 | 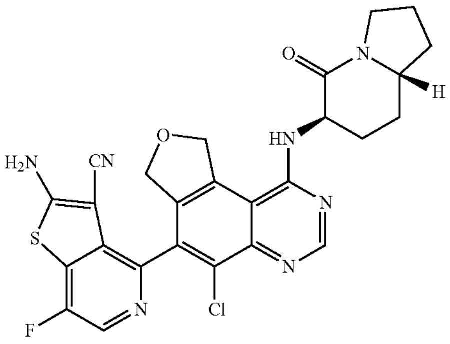 [SMILES: N#Cc1c(N)sc2c(F)cnc(-c3c4c(c5c(N[C@@H]6CC[C@H]7CCCN7C6=O)ncnc5c3Cl)COC4)c12] | 550 |
| 17B[60] | 2-Amino-4-(5-chloro-1-(((6R,8aR)-5-oxooctahydroindolizin-6-yl)amino)-7,9-dihydrofuro[3,4-f]quinazolin-6-yl)-7-fluorothieno[3,2-c]pyridine-3-carbonitrile, Isomer 2 | 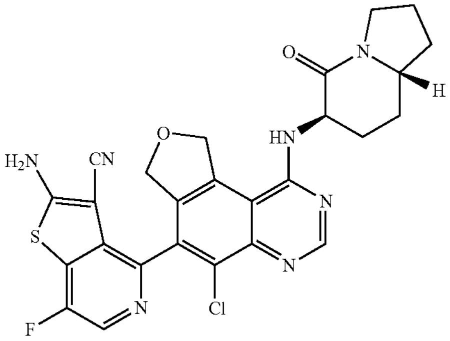 [SMILES: N#Cc1c(N)sc2c(F)cnc(-c3c4c(c5c(N[C@@H]6CC[C@H]7CCCN7C6=O)ncnc5c3Cl)COC4)c12] | 550 |
| 18B[61] | 2-Amino-4-(5-chloro-1-(((6R,8aR)-5-oxooctahydroindolizin-6-yl)amino)-7,9-dihydrofuro[3,4-f]quinazolin-6-yl)benzo[b]thiophene-3-carbonitrile, Isomer 1 | 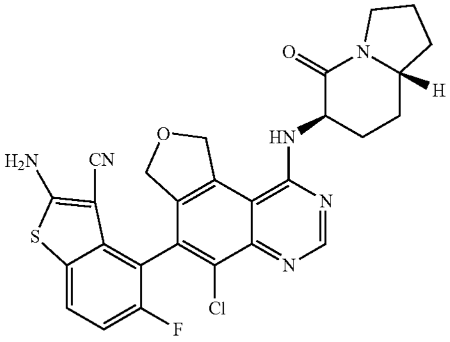 [SMILES: N#Cc1c(N)sc2ccc(F)c(-c3c4c(c5c(N[C@@H]6CC[C@H]7CCCN7C6=O)ncnc5c3Cl)COC4)c12] | 531 |
| 19B[61] | 2-Amino-4-(5-chloro-1-(((6R,8aR)-5-oxooctahydroindolizin-6-yl)amino)-7,9-dihydrofuro[3,4-f]quinazolin-6-yl)benzo[b]thiophene-3-carbonitrile, Isomer 2 | 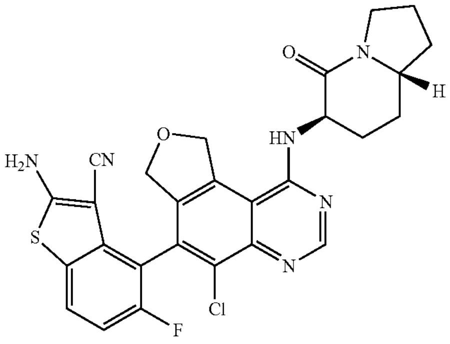 [SMILES: N#Cc1c(N)sc2ccc(F)c(-c3c4c(c5c(N[C@@H]6CC[C@H]7CCCN7C6=O)ncnc5c3Cl)COC4)c12] | 531 |

TABLE 25-continued

| Example | Chemical Name | Structure | MS (ES) m/z (M +1) |
| --- | --- | --- | --- |
| 20B | (6R,8aR)-6-((6-(2-Aminobenzo[d]thiazol-4-yl)-5-fluoro-3-((2'S,3'S)-2'-methyl-[1,3'-bipyrrolidin]-1'-yl)-7,9-dihydrofuro[3,4-f]quinazolin-1-yl)amino)hexahydro-indolizin-5(1H)-one | 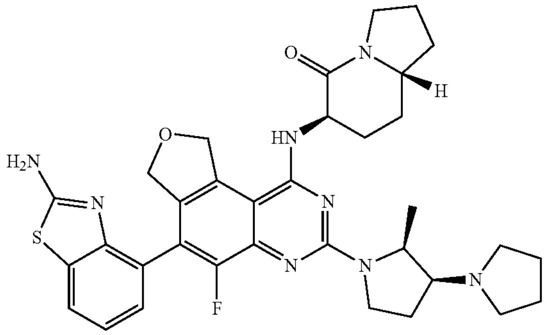 [SMILES: C[C@H]1[C@@H](N2CCCC2)CCN1c1nc(N[C@@H]2CC[C@H]3CCCN3C2=O)c2c3c(c(-c4cccc5sc(N)nc45)c(F)c2n1)COC3] | 643 |
| 21B[62] | (6R,8aR)-6-((6-(2-Amino-5-fluorobenzo[d]thiazol-4-yl)-5-chloro-7,9-dihydrofuro[3,4-f]quinazolin-1-yl)amino)hexahydro-indolizin-5(1H)-one, Isomer 1 | 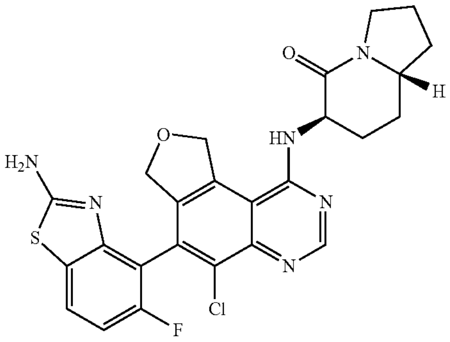 [SMILES: Nc1nc2c(-c3c4c(c5c(N[C@@H]6CC[C@H]7CCCN7C6=O)ncnc5c3Cl)COC4)c(F)ccc2s1] | 525 |
| 22B[62] | (6R,8aR)-6-((6-(2-Amino-5-fluorobenzo[d]thiazol-4-yl)-5-chloro-7,9-dihydrofuro[3,4-f]quinazolin-1-yl)amino)hexahydro-indolizin-5(1H)-one, Isomer 2 | 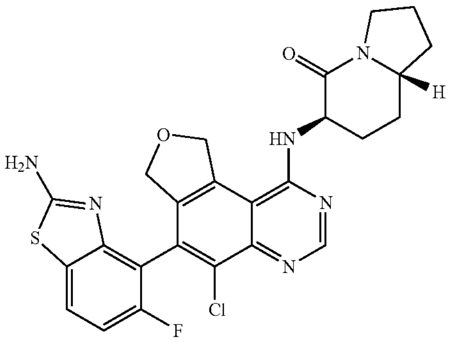 [SMILES: Nc1nc2c(-c3c4c(c5c(N[C@@H]6CC[C@H]7CCCN7C6=O)ncnc5c3Cl)COC4)c(F)ccc2s1] | 525 |
| 23B | (6R,8aR)-6-((6-(2-Amino-7-fluorobenzo[d]thiazol-4-yl)-5-fluoro-3-((2S,3S)-3-(3-(fluoromethyl)azetidin-1-yl)-2-methylpyrrolidin-1-yl)-7,9-dihydrofuro[3,4-f]quinazolin-1-yl)amino)hexahydro-indolizin-5(1H)-one | 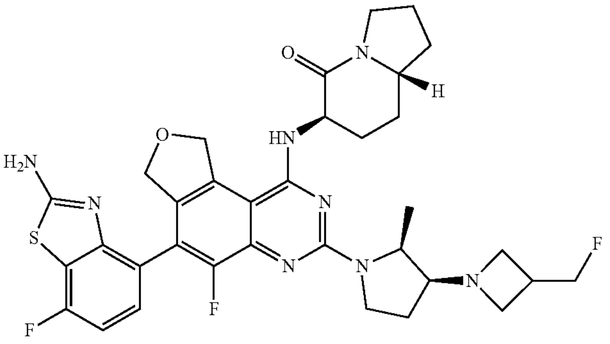 [SMILES: C[C@H]1[C@@H](N2CC(CF)C2)CCN1c1nc(N[C@@H]2CC[C@H]3CCCN3C2=O)c2c3c(c(-c4ccc(F)c5sc(N)nc45)c(F)c2n1)COC3] | 679 |

TABLE 25-continued

| Example | Chemical Name | Structure | MS (ES) m/z (M +1) |
|---|---|---|---|
| 24B[63] | (6R,8aS)-6-((6-(2-Amino-7-fluorobenzo[d]thiazol-4-yl)-5-fluoro-3-((2S)-2-methyl-3-(5-azaspiro[2.3]hexan-5-yl)pyrrolidin-1-yl)-7,9-dihydrofuro[3,4-f]quinazolin-1-yl)amino)hexahydro-indolizin-5(1H)-one | 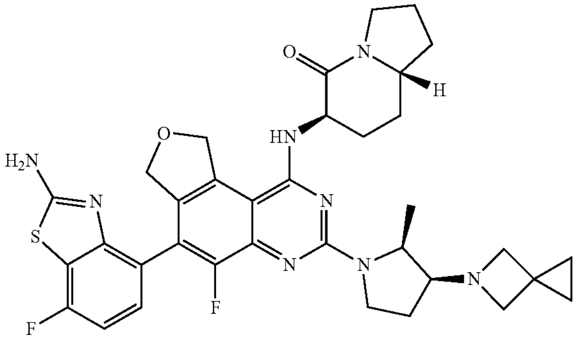 [SMILES: C[C@H]1[C@@H](N2CC3(CC3)C2)CCN1c1nc(N[C@@H]2CC[C@H]3CCCN3C2=O)c2c3c(c(-c4ccc(F)c5sc(N)nc45)c(F)c2n1)COC3] | 673 |
| 25B[64] | (6R,8aR)-6-((6-(2-Amino-7-fluorobenzo[d]thiazol-4-yl)-5-fluoro-3-((2S)-2-methyl-3-(5-azaspiro[2.3]hexan-5-yl)pyrrolidin-1-yl)-7,9-dihydrofuro[3,4-f]quinazolin-1-yl)amino)hexahydro-indolizin-5(1H)-one | 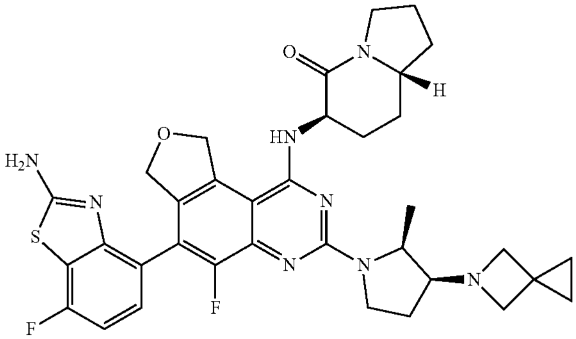 [SMILES: C[C@H]1[C@@H](N2CC3(CC3)C2)CCN1c1nc(N[C@@H]2CC[C@H]3CCCN3C2=O)c2c3c(c(-c4ccc(F)c5sc(N)nc45)c(F)c2n1)COC3] | 673 |
| 26B[65] | (6R,8aR)-6-((6-(2-Amino-7-fluorobenzo[d]thiazol-4-yl)-3-((6S)-1,6-dimethylhexahydropyrrolo[3,4-b]pyrrol-5(1H)-yl)-5-fluoro-7,9-dihydrofuro[3,4-f]quinazolin-1-yl)amino)hexahydroindolizin-5(1H)-one, Isomer 1 | 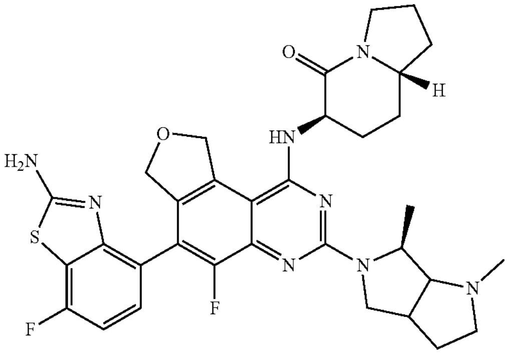 [SMILES: C[C@H]1C2C(CCN2C)CN1c1nc(N[C@@H]2CC[C@H]3CCCN3C2=O)c2c3c(c(-c4ccc(F)c5sc(N)nc45)c(F)c2n1)COC3] | 647 |
| 27B[65] | (6R,8aR)-6-((6-(2-Amino-7-fluorobenzo[d]thiazol-4-yl)-3-((6S)-1,6-dimethylhexahydropyrrolo[3,4-b]pyrrol-5(1H)-yl)-5-fluoro-7,9-dihydrofuro[3,4-f]quinazolin-1-yl)amino)hexahydroindolizin-5(1H)-one, Isomer 2 | 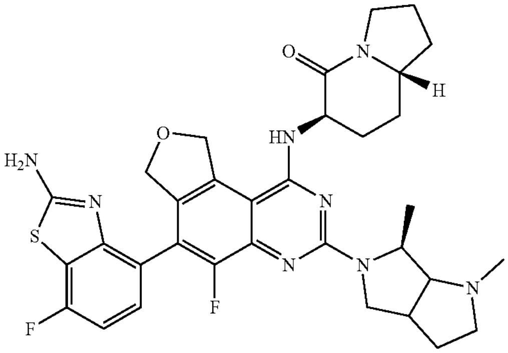 [SMILES: C[C@H]1C2C(CCN2C)CN1c1nc(N[C@@H]2CC[C@H]3CCCN3C2=O)c2c3c(c(-c4ccc(F)c5sc(N)nc45)c(F)c2n1)COC3] | 647 |

TABLE 25-continued

| Example | Chemical Name | Structure | MS (ES) m/z (M +1) |
|---|---|---|---|
| 28B[66] | 4-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,2-dimethyltetrahydropyridazin-3(2H)-one, Isomer 1 | 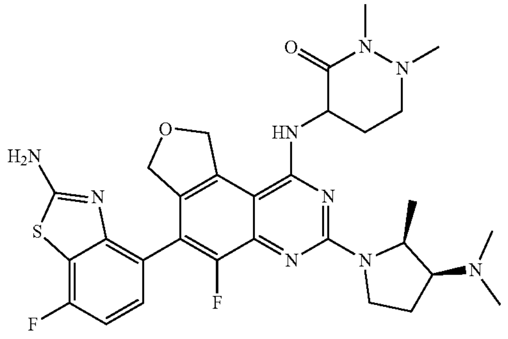 [SMILES: C[C@H]1[C@@H](N(C)C)CCN1c1nc(NC2CCN(C)N(C)C2=O)c2c3c(c(-c4ccc(F)c5sc(N)nc45)c(F)c2n1)COC3] | 624 |
| 29B[66] | 4-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f]quinazolin-1-yl)amino)-1,2-dimethyltetrahydro-pyridazin-3(2H)-one, Isomer 2 | 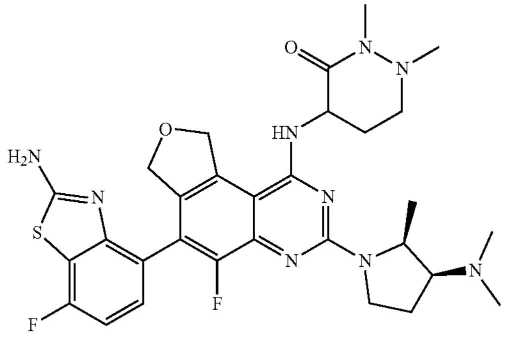 [SMILES: C[C@H]1[C@@H](N(C)C)CCN1c1nc(NC2CCN(C)N(C)C2=O)c2c3c(c(-c4ccc(F)c5sc(N)nc45)c(F)c2n1)COC3] | 624 |
| 30B | (6R,8aR)-6-((4-(2-Amino-7-fluorobenzo[d]thiazol-4-yl)-7-((2S,3S)-3-(dimethylamino)-2-methylpyrrolidin-1-yl)-5-fluoro-1,3-dihydrofuro[3,4-f]quinolin-9-yl)amino)hexahydroindolizin-5(1H)-one | 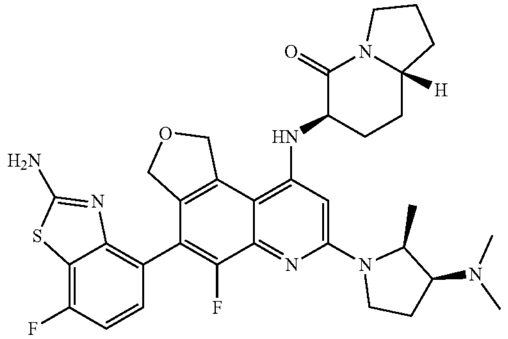 [SMILES: C[C@H]1[C@@H](N(C)C)CCN1c1cc(N[C@@H]2CC[C@H]3CCCN3C2=O)c2c3c(c(-c4ccc(F)c5sc(N)nc45)c(F)c2n1)COC3] | 634 |
| 31B | (6R,8aR)-6-((4-(2-Amino-7-fluorobenzo[d]thiazol-4-yl)-5-fluoro-7-((2'S,3'S)-2'-methyl-[1,3'-bipyrrolidin]-1'-yl)-1,3-dihydrofuro[3,4-f]quinolin-9-yl)amino)hexahydroindolizin-5(1H)-one | 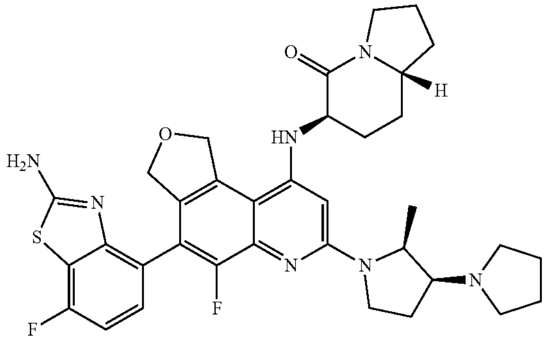 | 660 |

TABLE 25-continued

| Example | Chemical Name | Structure | MS (ES) m/z (M +1) |
|---|---|---|---|
| 32B[67] | (6R)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f] quinazolin-1-yl)amino)-6-(difluoromethyl)-1-methylpiperidin-2-one, Isomer 1 | 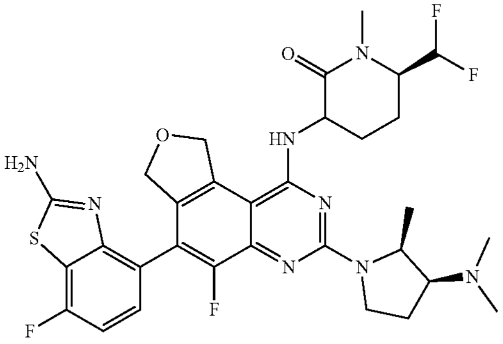 [SMILES: C[C@H]1[C@@H](N(C)C)CCN1c1nc(NC2CC[C@H](C(F)F)N(C)C2=O)c2c3c(c(-c4ccc(F)c5sc(N)nc45)c(F)c2n1)COC3] | 659 |
| 33B[67] | (6R)-3-((6-(2-Amino-7-fluorobenzo[d]thiazol-4-yl)-3-((2S,3S)-3-(dimethylamino)-2-methylpyrrolidin-1-yl)-5-fluoro-7,9-dihydrofuro[3,4-f] quinazolin-1-yl)amino)-6-(difluoromethyl)-1-methylpiperidin-2-one, Isomer 2 | 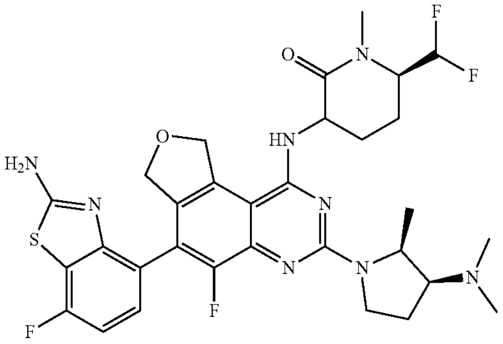 [SMILES: C[C@H]1[C@@H](N(C)C)CCN1c1nc(NC2CC[C@H](C(F)F)N(C)C2=O)c2c3c(c(-c4ccc(F)c5sc(N)nc45)c(F)c2n1)COC3] | 659 |
| 34B | (6R,8aR)-6-((6-(2-Amino-7-fluorobenzo[d]thiazol-4-yl)-3-((2S,3S)-3-(bis(methyl-d3)amino)-2-methylpyrrolidin-1-yl)-5-fluoro-7,9-dihydrofuro[3,4-f]quinazolin-1-yl)amino)hexahydro-indolizin-5(1H)-one | 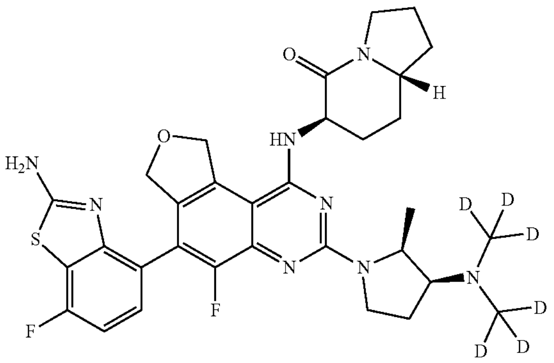 [SMILES: [2H]C([2H])([2H])N([C@H]1CCN(c2nc(N[C@@H]3CC[C@H]4CCCN4C3=O)c3c4c(c(-c5ccc(F)c6sc(N)nc56)c(F)c3n2)COC4)[C@H]1C)C([2H])([2H])[2H]] | 642 |
| 35B[68] | 7-((6-(2-Amino-7-fluorothiazolo[4,5-c]pyridin-4-yl)-5-chloro-3-((2S,3S)-3-(diethylamino)-2-methylpyrrolidin-1-yl)-7,9-dihydrofuro[3,4-f]quinazolin-1-yl)amino)-5-methyl-5-azaspiro[2.5]octan-6-one, Isomer 1 | 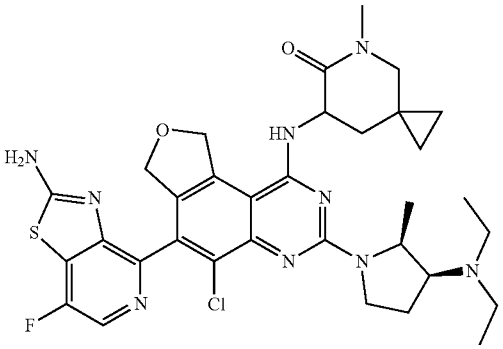 [SMILES: CCN(CC)[C@H]1CCN(c2nc(NC3CC4(CC4)CN(C)C3=O)c3c4c(c(-c5ncc(F)c6sc(N)nc56)c(Cl)c3n2)COC4)[C@H]1C] | 680 |

TABLE 25-continued

| Example | Chemical Name | Structure | MS (ES) m/z (M +1) |
|---|---|---|---|
| 36B[68] | 7-((6-(2-Amino-7-fluorothiazolo[4,5-c]pyridin-4-yl)-5-chloro-3-((2S,3S)-3-(diethylamino)-2-methylpyrrolidin-1-yl)-7,9-dihydrofuro[3,4-f]quinazolin-1-yl)amino)-5-methyl-5-azaspiro[2.5]octan-6-one, Isomer 2 | 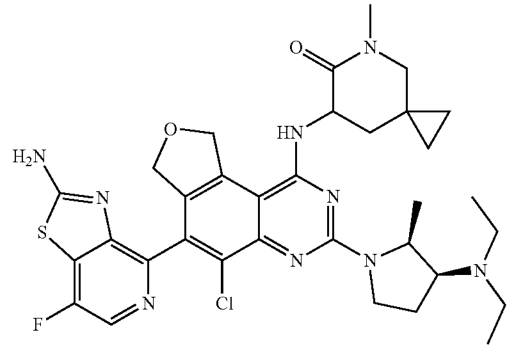 [SMILES: CCN(CC)[C@H]1CCN(c2nc(NC3CC4(CC4)CN(C)C3=O)c3c4c(c(-c5ncc(F)c6sc(N)nc56)c(Cl)c3n2)COC4)[C@H]1C] | 680 |
| 37B[32] | (8aR)-6-((6-(2-Amino-7-fluorothiazolo[4,5-c]pyridin-4-yl)-5-chloro-3-((2S,3S)-3-(6-fluoro-2-azaspiro[3.3]heptan-2-yl)-2-methylpyrrolidin-1-yl)-7,9-dihydrofuro[3,4-f]quinazolin-1-yl)amino)hexahydro-indolizin-5(1H)-one | 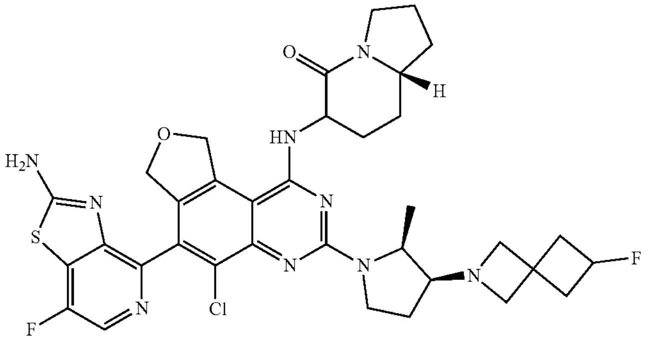 [SMILES: C[C@H]1[C@@H](N2CC3(CC(F)C3)C2)CCN1c1nc(NC2CC[C@H]3CCCN3C2=O)c2c3c(c(-c4ncc(F)c5sc(N)nc45)c(Cl)c2n1)COC3] | 722 |
| 38B[32] | (8aR)-6-((6-(2-Amino-7-fluorothiazolo[4,5-c]pyridin-4-yl)-5-chloro-3-((2S,3S)-2-methyl-3-(5-azaspiro[2.3]hexan-5-yl)pyrrolidin-1-yl)-7,9-dihydrofuro[3,4-f]quinazolin-1-yl)amino) hexahydroindolizin-5(1H)-one | 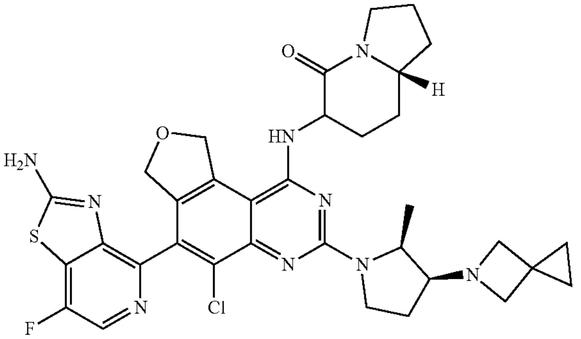 [SMILES: C[C@H]1[C@@H](N2CC3(CC3)C2)CCN1c1nc(NC2CC[C@H]3CCCN3C2=O)c2c3c(c(-c4ncc(F)c5sc(N)nc45)c(Cl)c2n1)COC3] | 690 |
| 39B[32] | (8aR)-6-((6-(2-Amino-7-fluorothiazolo[4,5-c]pyridin-4-yl)-5-chloro-3-((2S,3S)-3-((3-fluorocyclobutyl) (methyl)amino)-2-methylpyrrolidin-1-yl)-7,9-dihydrofuro[3,4-f]quinazolin-1-yl)amino)hexahydro-indolizin-5(1H)-one | 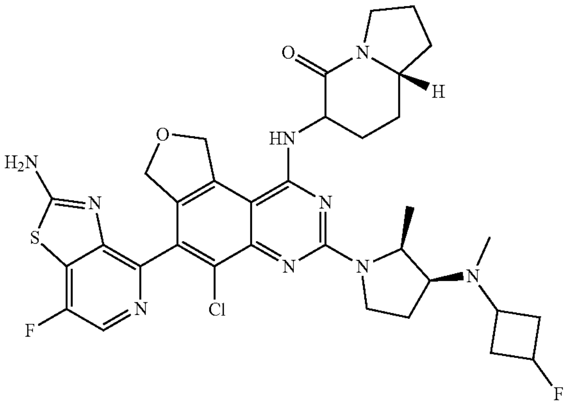 [SMILES: C[C@H]1[C@@H](N(C)C2CC(F)C2)CCN1c1nc(NC2CC[C@H]3CCCN3C2=O)c2c3c(c(-c4ncc(F)c5sc(N)nc45)c(Cl)c2n1)COC3] | 710 |

TABLE 25-continued

| Example | Chemical Name | Structure | MS (ES) m/z (M +1) |
|---|---|---|---|
| 40B[32] | (8aR)-6-((6-(2-Amino-7-fluorothiazolo[4,5-c]pyridin-4-yl)-5-chloro-3-((2S,3S)-3-(3-(fluoromethyl)azetidin-1-yl)-2-methylpyrrolidin-1-yl)-7,9-dihydrofuro[3,4-f]quinazolin-1-yl)amino)hexahydro-indolizin-5(1H)-one | 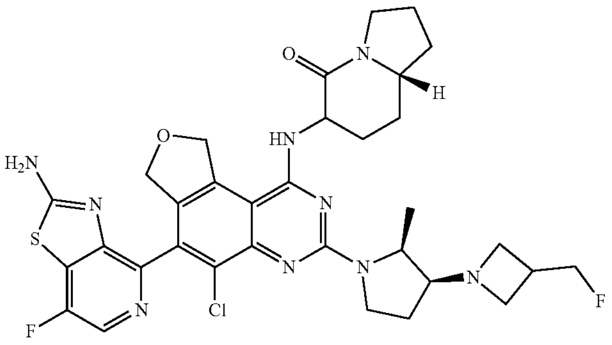 [SMILES: C[C@H]1[C@@H](N2CC(CF)C2)CCN1c1nc(NC2CC[C@H]3CCCN3C2=O)c2c3c(c(-c4ncc(F)c5sc(N)nc45)c(Cl)c2n1)COC3] | 696 |
| 41B[69] | 4-((6-(2-Amino-7-fluorothiazolo[4,5-c]pyridin-4-yl)-5-chloro-3-((2S,3S)-3-(dimethylamino)-2-methylpyrrolidin-1-yl)-7,9-dihydrofuro[3,4-f]quinazolin-1-yl)amino)-1,2-dimethyltetrahydro-pyridazin-3(2H)-one | 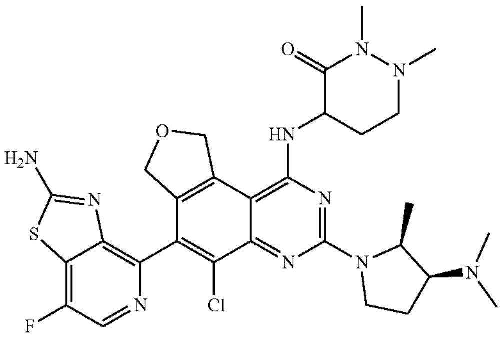 [SMILES: C[C@H]1[C@@H](N(C)C)CCN1c1nc(NC2CCN(C)N(C)C2=O)c2c3c(c(-c4ncc(F)c5sc(N)nc45)c(Cl)c2n1)COC3] | 641 |
| 42B[70] | 4-((6-(2-Amino-7-fluorothiazolo[4,5-c]pyridin-4-yl)-5-chloro-3-((2S,3S)-3-(ethyl(methyl)amino)-2-methylpyrrolidin-1-yl)-7,9-dihydrofuro[3,4-f]quinazolin-1-yl)amino)-1,2-dimethyltetrahydro-pyridazin-3(2H)-one | 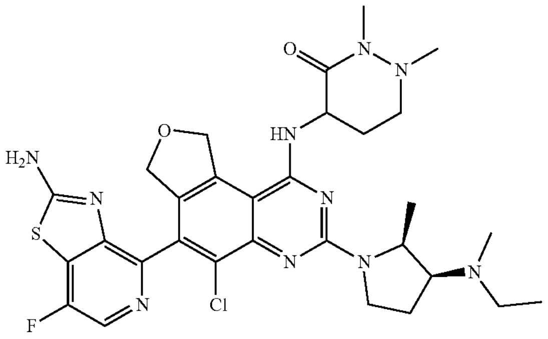 [SMILES: CCN(C)[C@H]1CCN(c2nc(NC3CCN(C)N(C)C3=O)c3c4c(c(-c5ncc(F)c6sc(N)nc56)c(Cl)c3n2)COC4)[C@H]1C] | 655 |
| 43B | (6R,8aR)-6-((4-(2-Amino-7-fluorothiazolo[4,5-c]pyridin-4-yl)-5-chloro-7-((2S,3S)-3-(dimethylamino)-2-methylpyrrolidin-1-yl)-1,3-dihydrofuro[3,4-f]quinolin-9-yl)amino)hexahydro-indolizin-5(1H)-one | 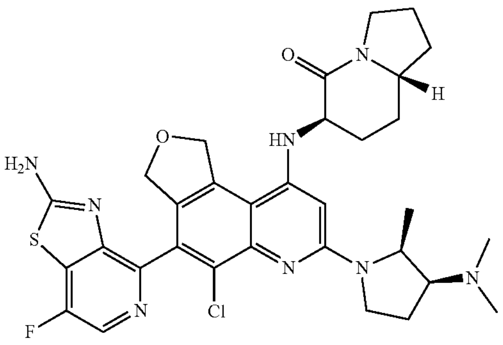 [SMILES: C[C@H]1[C@@H](N(C)C)CCN1c1cc(N[C@@H]2CC[C@H]3CCCN3C2=O)c2c3c(c(-c4ncc(F)c5sc(N)nc45)c(Cl)c2n1)COC3] | 651 |

TABLE 25-continued

| Example | Chemical Name | Structure | MS (ES) m/z (M +1) |
|---|---|---|---|
| 44B | (6R,8aR)-6-((6-(2-Amino-7-fluorothiazolo[4,5-c]pyridin-4-yl)-5-fluoro-3-((2'S,3'S)-2'-methyl-[1,3'-bipyrrolidin]-1'-yl)-7,9-dihydrofuro[3,4-f]quinazolin-1-yl)amino)hexahydro-indolizin-5(1H)-one | 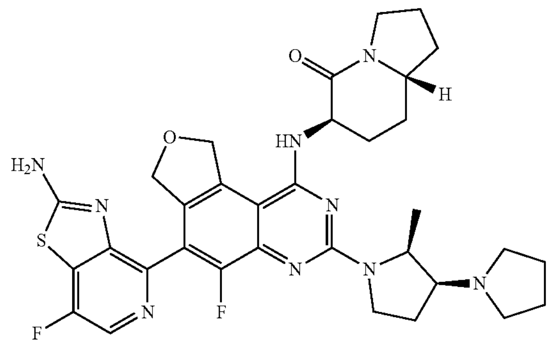 [SMILES: C[C@H]1[C@@H](N2CCCC2)CCN1c1nc(N[C@@H]2CC[C@H]3CCCN3C2=O)c2c3c(c(-c4ncc(F)c5sc(N)nc45)c(F)c2n1)COC3] | 662 |

[1]Clean atropisomer, chiral purification from Preparation 30

[2]Clean atropisomer, chiral purification from Preparation 34

[3]Clean enantiomer at the 6-position of the hexahydroindolizinone, chiral purification from Preparation 86

[4]Reverse Phase; C18, 51-100% acetonitrile in (10 mM ammonium acetate in 95:5 water:methanol). Enantiomer refers to a clean isomer at the 7-position of the azaspirononanone.

[5]Reverse Phase; C18, 56-100% acetonitrile in (10 mM ammonium acetate in 95:5 water:methanol). Enantiomer refers to a clean isomer at the 6-position of the azaspirooctane.

[6]Reverse Phase; C18, 51-100% (95:5 acetonitrile:water) in (95:5 10 mM aqueous ammonium bicarbonate pH 10:methanol). Enantiomer refers to a clean isomer at the 6-position of the azaspirooctanone. Mixed cis isomers on the pyrrolidine.

[7]Reverse Phase; C18, 43-100% acetonitrile in (10 mM ammonium acetate 95:5 water:methanol). Enantiomer refers to a clean isomer at the 7-position of the azaspirooctanone.

[8]Reverse Phase; C18, 47-100% acetonitrile in (10 mM ammonium acetate in 95:5 water:methanol). Diastereomer refers to a clean atropisomer and a clean isomer at the 6-position of the azaspirooctanone.

[9]Reverse Phase; C18, 39-100% acetonitrile in (10 mM ammonium acetate in 95:5 water:methanol), to give a mix of Diastereomers 1 and 2 and a mix of Diastereomers 3 and 4. Diastereomers 1 and 2 were further separated with Prep-Chiral-HPLC; Phenomenex Lux Cellulose-2, 30 ×150 mm, 10-70% ethanol in heptane, 42.5 mL/min. Diastereomers 3 and 4 were further separated with Prep-Chiral-HPLC; Phenomenex Lux i-Cellulose-5, 30 ×150 mm, 10-100% ethanol in heptane, 42.5 mL/min. Diastereomer refers to a clean atropisomer and a clean isomer at the 6-position of the azaspirooctanone.

[10]Reverse Phase; C18, 46-100% acetonitrile in (95:5 10 mM aqueous ammonium bicarbamate pH 10:methanol), to give a mix of Diastereomers 1 and 2 and a mix of Diastereomers 3 and 4. Diastereomers 1 and 2 were further separated with Prep-Chiral-HPLC; (S,S)-Whelk-O1, 30 ×150 mm, 25-100% (1:1 methanol:ethanol w/0.1% ispropylamine) in heptane, 45 mL/min. Diastereomers 3 and 4 were further separated with Prep-Chiral-HPLC; (S,S)-Whelk-O1, 30 ×150 mm, 20-100% (1:1 methanol:ethanol w/0.1% isopropylamine) in heptane, 45 mL/min. Diastereomer refers to a clean atropisomer and a clean isomer at the 7-position of the azaspirooctanone.

[11]Reverse Phase; C18, 10-70% acetonitrile in (95:5 10 mM aqueous ammonium bicarbonate pH 10:methanol). Enantiomer refers to a clean isomer at the 4-position of the azabicycloheptanone.

[12]Reverse Phase; C18, 35-100% acetonitrile in (95:5 10 mM aqueous ammonium bicarbonate pH 10:methanol). Enantiomer refers to a clean isomer at the 4-position of the azabicycloheptanone.

[13]Prep-Chiral-HPLC; (S,S)-Whelk-O1, 30 ×150 mm, 10-100% (1:1 methanol:ethanol w/0.1% isopropylamine) in heptane, 42.4 mL/min. Enantiomer refers to a clean isomer at the 2-position of the hexahydropyridozinopyridazinone.

[14]Reverse Phase; C18, 2-100% acetonitrile in (0.1% formic acid in water), followed by Prep-Chiral-HPLC; (S,S)-Whelk-O1, 30 ×150 mm, 10-80% (1:1 methanol:ethanol w/0.1% isopropylamine) in heptane, 42.5 mL/min. Enantiomer refers to a clean isomer at the 7-position of the azaspirononanone.

[15]Reverse Phase; C18, 53-100% acetonitrile in (10 mM ammonium acetate in 95:5 water:methanol). Diastereomer refers to a clean atropisomer and a clean isomer at the 7-position of the azaspirooctanone.

[16]Reverse Phase; C18, 55-100% acetonitrile in (10 mM ammonium acetate in 95:5 water:methanol). Diastereomer refers to a clean atropisomer and a clean isomer at the 6-position of the azaspirooctanone.

[17]Reverse Phase; C18, 46-100% acetonitrile in (10 mM ammonium acetate in 95:5 water:methanol), to give a mix of Diastereomers 1 and 2 and a mix of Diastereomers 3 and 4. Diastereomers 1 and 2 were further separated with Prep-Chiral-HPLC; (S,S)-Whelk-O1, 30 ×150 mm, 10-100% (ethanol w/0.1% isopropylamino) in heptane, 42.5 mL/min. Diastereomers 3 and 4 were further separated with Prep-Chiral-HPLC; (S,S)-Whelk-O1, 30 × 150 mm, 10-100% ethanol in heptane, 42.5 mL/min. Diastereomer refers to a clean atropisomer and a clean isomer at the 6-position of the azaspirooctanone.

[18]enriched toward (R) enantiomer

[19]Prep-Chiral-HPLC; Phenomenex Lux i-Cellulose-5, 30 ×150 mm, 15-100% (ethanol w/0.1% isopropylamine) in heptane, 42.5 mL/min. Enantiomer refers to a clean isomer at the 6-position of the tetrahydropyrazolopyridazinone.

[20]Prep-Chiral-HPLC; (S,S)-Whelk-O1, 30 ×150 mm, 10-100% ethanol in heptane, 42.5 mL/min. Enantiomer refers to a clean isomer at the 6-position of the azaspirooctanone.

[21]Prep-Chiral-HPLC; (S,S)-Whelk-O1, 30 ×150 mm, 25-85% (1:1 methanol-ethanol w/0.1% isopropylamine) in heptane, 45 mL/min. Enantiomer refers to a clean isomer at the 7-position of the azaspirooctanone.

[22]Prep-Chiral-HPLC; Phenomenex Lux i-Cellulose-5, 30 ×150 mm, 10-100% (1:1 methanol:ethanol w/0.1% isopropylamine) in heptane, 42.5 mL/min. Isomer refers to a clean isomer at the 7-position of the azaspirooctanone.

[23]Reverse Phase; C18, 10-70% acetonitrile in (95:5 10 mM aqueous ammonium bicarbonate pH 10:methanol). Isomer refers to a clean isomer at the 4-position of the azabicycloheptanone.

[24]Reverse Phase; C18, 35-100% acetonitrile in (95:5 10 mM aqueous ammonium bicarbonate pH 10:methanol). Isomer refers to a clean isomer at the 6-position of the tetrahydropyrazolopyridazinone.

[25]Reverse Phase; C18, 44-100% acetonitrile in (95:5 10 mM aqueous ammonium bicarbonate pH 10:methanol). Isomer refers to a clean isomer at the 6-position of the azaspirooctanone.

[26]Prep-Chiral-HPLC; (S,S)-Whelk-O1, 30 ×150 mm, 30-100% ethanol in heptane, 45 mL/min. Isomer refers to a clean isomer at the 6-position of the azaspiroheptanone.

[27]Prep-Chiral-HPLC; Phenomenex Lux Cellulose-4, 30 ×150 mm, 15-60% (1:1 methanol:ethanol) in heptane, 45 mL/min. Isomer refers to a clean isomer at the 2 position of the hexahydropyridazinopyridazinone.

[28]Clean isomer at the 6-position of the hexahydroindolizinone, chiral purification from Preparation 28A

[29]Clean isomer at the 6-position of the hexahydroindolizinone, chiral purification from Preparation 29A

[30]Reverse Phase; C18, 38-100% acetonitrile in (95:5 10 mM aqueous ammonium acetate pH 10:methanol). Isomer refers to a clean isomer at the 7-position of the azaspirononanone.

[31]Clean isomer at the 6-position of the hexahydroindolizinone, chiral purification from Preparation 13A

[32]Clean isomer at the 6-position of the hexahydroindolizinone, chiral purification from Preparation 14A

[33]Clean isomer at the 6-position of the azaspirooctanone, chiral purification from Preparation 112A

[34]Clean isomer at the 6-position of the azasprioctanone, chiral purification from Preparation 113A

[35]Chiral SFC; ChiralPak IJ, 30 ×250 mm, 20% (10 mM ammonium acetate in methanol) in $CO_2$, 85 mL/min, Isomer refers to a clean isomer at the 7-position of the azaspirooctanone.

[36]Prep-Chiral-HPLC; (S,S)-Whelk-O1, 30 ×150 mm, 10-100% (1:1 methanol:ethanol w/0.1% isopropylamine) in heptane, 45 mL/min. Isomer refers to a clean isomer at the 7-position of the azaspirooctanone.

[37]Clean isomer at the 3-position of the pyrrolidine, chiral purification from Preparation 73A

[38]Clean isomer at the 3-position of the pyrrolidine, chiral purification from Preparation 72A

[39]Chiral SFC; ChiralPak IH, 20 ×250 mm, 35% (isopropanol w/0.5% dimethylethylamine) in $CO_2$, 80 mL/min, Isomer refers to a clean isomer at the 7-position of the azaspirooctanone.

TABLE 25-continued

| Example | Chemical Name | Structure | MS (ES) m/z (M +1) |
|---|---|---|---|

[40]Clean isomer at the 7-position of the hexahydropyridoxazinone

[41]Prep-Chiral-HPLC; (S,S)-Whelk-O1, 30 ×150 mm, 20-100% (1:1 methanol:ethanol w/0.1% isopropylamine) in heptane, 45 mL/min. Isomer refers to a clean isomer at the 7-position of the azaspirononanone.

[42]Prep-Chiral-HPLC; Phenomenex Lux Celluslose-1, 30 ×150 mm, 20-65% ethanol in heptane, 45 mL/min. Isomer refers to a clean isomer at the 2-position of the hexahydropyridazinopyridazinone.

[43]Prep-Chiral-HPLC; Phenomenex Lux Cellulose-4, 30 ×150 mm, 25-100% ethanol in heptane, 45 mL/min. Isomer refers to a clean isomer at the 7-position of the azaspirononanone.

[44]Reverse Phase; C18, 31-100% acetonitrile in (95:5 10 mM aqueous ammonium bicarbonate pH 10:methanol). Isomer refers to a clean isomer at the 6-position of the hexahydroindolizinone.

[45]Prep-Chiral-HPLC; Phenomenex Lux i-Cellulose-5, 30 ×150 mm, 35-100% (1:1 methanol:ethanol w/0.1% isopropylamine) in heptane, 45 mL/min. Isomer refers to a clean atropisomer.

[46]Reverse Phase; C18, 25-100% acetonitrile in (95:5 10 mM aqueous ammonium acetate pH 10:methanol). Isomer refers to a clean atropisomer.

[47]Prep-Chiral-HPLC; Phenomenex Lux i-Cellulose-5, 30 ×150 mm, 15-100% ethanol in heptane, 42.5 mL/min. Isomer refers to a clean atropisomer.

[48]Prep-Chiral-HPLC; Phenomenex Lux i-Cellulose-5, 30 ×150 mm, 35-100% (1:1 methanol-ethanol) in heptane, 45 mL/min. Isomer refers to a clean atropisomer.

[49]Reverse Phase; C18, 39-100% acetonitrile in (95:5 10 mM aqueous ammonium bicarbonate pH 10:methanol). Isomer refers to a clean atropisomer.

[50]Prep-Chiral-HPLC; (S,S)-Whelk-O1, 30 ×150 mm, 10-100% (ethanol w/0.1% isopropylamine) in heptane, 42.5 mL/min. Diastereomer refers to a clean atropisomer and a clean isomer at the 6-position of the tetrahydropyrazolopyridazinone.

[51]Reverse Phase; C18, 44-100% acetonitrile in (10 mM ammonium acetate in 95:5 water:methanol). Isomer refers to a clean isomer at the 7-position of the azaspirononanone.

[52]Reverse Phase; C18, 26-100% acetonitrile in (10 mM ammonium acetate in 95:5 water:methanol). Isomer refers to a clean atropisomer.

[53]Reverse Phase; C18, 35-100% acetonitrile in (95:5 10 mM aqueous ammonium bicarbonate pH 10:methanol). Isomer refers to a clean isomer at the 7-position of the azaspirononanone.

[54]Reverse Phase; C18, 10-100% acetonitrile in (0.1% formic acid in water). Isomer refers to a clean isomer at the 6-position of the hexahydroindolizinone.

[55]Prep-Chiral-HPLC; (S,S)-Whelk-O1, 30 ×150 mm, 25-100% (1:1 methanol:ethanol) in heptane, 45 mL/min. Isomer refers to a clean atropisomer.

[56]Clean atropisomer, chiral purification from Preparation 6B

[57]Clean isomer at the 3-position of the azabicyclooctanone, chiral purification from Preparation 17B

[58]Clean atropisomer, chiral purification from Preparation 32

[59]Clean isomer at the 6-position of the hexahydroindolizinone, chiral purification from Preparation 18B

[60]Prep-Chiral-HPLC; Phenomenex Lux Cellulose-4, 30 ×150 mm, 20-100% (1:1 methanol:ethanol) in heptane, 45 mL/min. Isomer refers to a clean atropisomer.

[61]Prep-Chiral-HPLC; Phenomenex Lux i-Amylose-3, 30 ×150 mm, 30-100% (ethanol w/0.1% isopropylamine) in heptane, 45 mL/min. Isomer refers to a clean atropisomer.

[62]Prep-Chiral-HPLC; Phenomenex Lux i-Cellulose-5, 30 ×150 mm, 30-100% (1:1 methanol:ethanol w/0.1% isopropylamino) in heptane, 45 mL/min. Isomer refers to a clean atropisomer.

[63]Clean diastereomer on the pyrrolidine, chiral purification from Preparation 84B

[64]Clean diastereomer on the pyrrolidine, chiral purification from Preparation 85B

[65]Prep-Chiral-HPLC; Phenomenex Lux i-Amylose-3, 30 ×150 mm, 25-100% (ethanol w/0.1% isopropylamine) in heptane, 45 mL/min. Isomer refers to a clean cis stereocenter on the pyrrolopyrrol.

[66]Prep-Chiral-HPLC; Chiral Art Cellulose-SB, 30 ×250 mm, 50% ethanol in (hexanes w/0.5% 2M ammoniated methanol), 40 mL/min. Isomer refers to a clean isomer at the 4-position of the pyridazinone.

[67]Prep-Chiral-HPLC; (S,S)-Whelk-O1, 30 ×150 mm, 10-100% (ethanol w/0.1% isopropylamine) in heptane, 42.5 mL/min. Isomer refers to a clean isomer at the 3-position of the piperidinone.

[68]Chiral SFC; ChiralPak IC, 20 ×250 mm, 50% (ethanol w/0.5% dimethylethylamine) in $CO_2$, 80 mL/min, Isomer refers to a clean isomer at the 7-position of the azaspirooctanone.

[69]Clean isomer at the 4-position of the pyridazinone, chiral purification from Preparation 78B

[70]Clean isomer at the 4-position of the pyridazinone, chiral purification from Preparation 79B isopropylamine) in heptane, 42.5 mL/min. Isomer refers to a clean isomer at the 3-position of the piperidinone.

[68] Chiral SFC; ChiralPak IC, 20×250 mm, 50% (ethanol w/0.5% dimethylethylamine) in $CO_2$, 80 mL/min, Isomer refers to a clean isomer at the 7-position of the azaspirooctanone.

[69] Clean isomer at the 4-position of the pyridazinone, chiral purification from Preparation 78B

[70] Clean isomer at the 4-position of the pyridazinone, chiral purification from Preparation 79B The following compounds in Table 26 were prepared in similar manner as described in Preparation 28. Different coupling conditions, such as base, ligands, or palladium sources, may have been substituted. Various methods were used to purify the compounds, which would be apparent to one skilled in the art.

TABLE 26

| Example | Chemical Name | Structure | MS (ES) m/z (M + 1) |
|---|---|---|---|
| 110 [1,3] | (8aR)-6-((6-(2-Aminobenzo[d]oxazol-4-yl)-5-chloro-3-((2S,3S)-3-(dimethylamino)-2-methylpyrrolidin-1-yl)-7,9-dihydrofuro[3,4-f]quinazolin-1-yl)amino)hexahydro-indolizin-5(1H)-one | 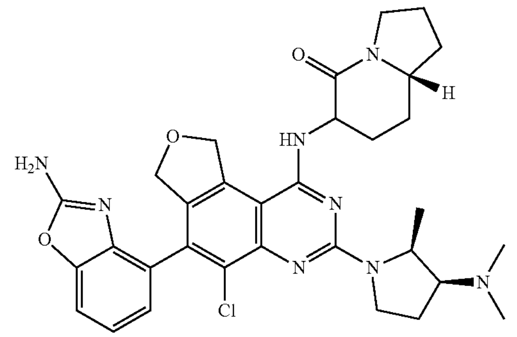 [SMILES: C[C@H]1[C@@H](N(C)C)CCN1c1nc(NC2CC[C@H]3CCCN3C2=O)c2c3c(c(-c4cccc5oc(N)nc45)c(Cl)c2n1)COC3] | 617 |

TABLE 26-continued

| Example | Chemical Name | Structure | MS (ES) m/z (M + 1) |
| --- | --- | --- | --- |
| 111 [2,3] | (8aR)-6-((6-(2-Aminobenzo[d]oxazol-4-yl)-5-chloro-3-((2S,3S)-3-(dimethylamino)-2-methylpyrrolidin-1-yl)-7,9-dihydrofuro[3,4-f]quinazolin-1-yl)amino)hexahydro-indolizin-5(1H)-one | 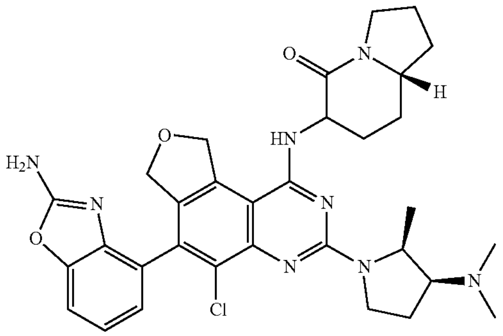 [SMILES: C[C@H]1[C@@H](N(C)C)CCN1c1nc(NC2CC[C@H]3CCCN3C2=O)c2c3c(c(-c4cccc5oc(N)nc45)c(Cl)c2n1)COC3] | 617 |
| 45B [2,3] | (8aR)-6-((6-(2-Aminobenzo[d]oxazol-4-yl)-5-chloro-3-((2'S,3'S)-2'-methyl-[1,3'-bipyrrolidin]-1'-yl)-7,9-dihydrofuro[3,4-f]quinazolin-1-yl)amino)hexahydro-indolizin-5(1H)-one | 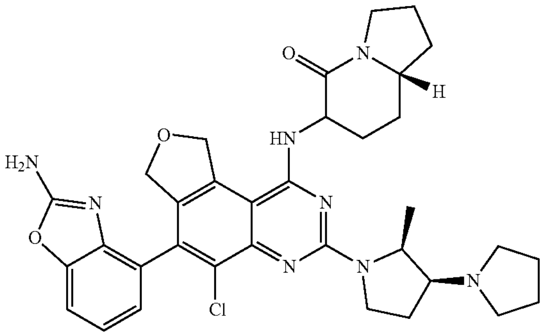 [SMILES: C[C@H]1[C@@H](N2CCCC2)CCN1c1nc(NC2CC[C@H]3CCCN3C2=O)c2c3c(c(-c4cccc5oc(N)nc45)c(Cl)c2n1)COC3] | 643 |
| 46B [3] | (6R,8aR)-6-((6-(2-Amino-7-fluorobenzo[d]oxazol-4-yl)-5-fluoro-3-((2'S,3'S)-2'-methyl-[1,3'-bipyrrolidin]-1'-yl)-7,9-dihydrofuro[3,4-f]quinazolin-1-yl)amino)hexahydro-indolizin-5(1H)-one | 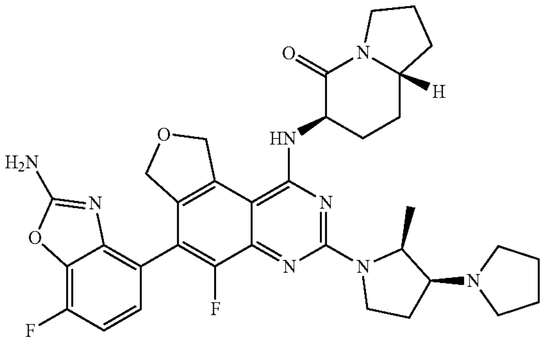 [SMILES: C[C@H]1[C@@H](N2CCCC2)CCN1c1nc(N[C@@H]2CC[C@H]3CCCN3C2=O)c2c3c(c(-c4ccc(F)c5oc(N)nc45)c(F)c2n1)COC3] | 645 |

[1] Clean isomer at the 6-position of the hexahydroindolizinone, chiral purification from Preparation 13A

[2] Clean isomer at the 6-position of the hexahydroindolizinone, chiral purification from Preparation 14A

[3] BOC deprotection on the aminobenzoxazole occurred during the reaction

The following compounds in Table 27 were prepared in similar manner as described in Preparation 102B. Various methods were used to purify the compounds, which would be apparent to one skilled in the art.

TABLE 27

| Example | Chemical Name | Structure | MS (ES) m/z (M + 1) |
|---|---|---|---|
| 47B [1] | 2-Amino-4-(5-chloro-1-(((6R,8aR)-5-oxooctahydroindolizin-6-yl)amino)-7,9-dihydrofuro[3,4-f]quinazolin-6-yl)-5-fluorobenzo[b]thiophene-3-carbonitrile | 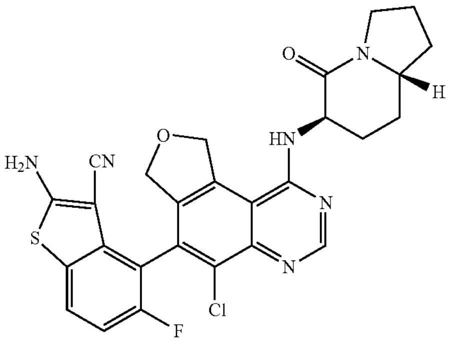 | 549 |

[1] Clean atropisomer, chiral purification from Preparation 34

The following compounds in Table 28 were prepared in similar manner as described in Preparation 96. Different bases may have been substituted. Various methods were used to purify the compounds, which would be apparent to one skilled in the art.

TABLE 28

| Example | Chemical Name | Structure | MS (ES) m/z (M + 1) |
|---|---|---|---|
| 48B [1,2] | 2-Amino-4-(5-chloro-1-(((6R,8aR)-5-oxooctahydroindolizin-6-yl)amino)-3-(1-oxa-6-azaspiro[3.4]octan-6-yl)-7,9-dihydrofuro[3,4-f]quinazolin-6-yl)-7-fluorobenzo[b]thiophene-3-carbonitrile, Isomer 1 | 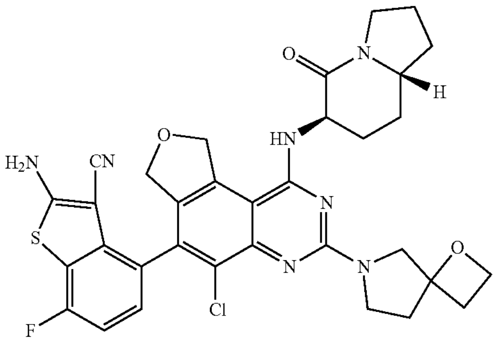 [SMILES: N#Cc1c(N)sc2c(F)ccc(-c3c4c(c5c(N[C@@H]6CC[C@H]7CCCN7C6=O)nc(N6CCC7(CCO7)C6)nc5c3Cl)COC4)c12] | 660 |
| 49B [1,2] | 2-Amino-4-(5-chloro-1-(((6R,8aR)-5-oxooctahydroindolizin-6-yl)amino)-3-(1-oxa-6-azaspiro[3.4]octan-6-yl)-7,9-dihydrofuro[3,4-f]quinazolin-6-yl)-7-fluorobenzo[b]thiophene-3-carbonitrile, Isomer 2 | 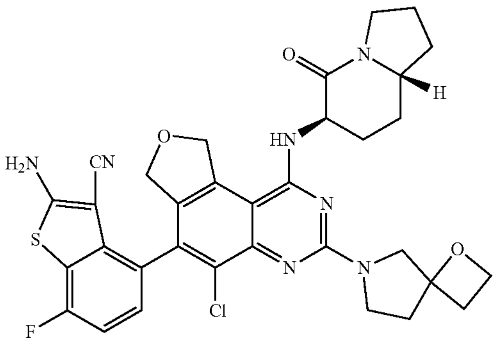 [SMILES: N#Cc1c(N)sc2c(F)ccc(-c3c4c(c5c(N[C@@H]6CC[C@H]7CCCN7C6=O)nc(N6CCC7(CCO7)C6)nc5c3Cl)COC4)c12] | 660 |

TABLE 28-continued

| Example | Chemical Name | Structure | MS (ES) m/z (M + 1) |
| --- | --- | --- | --- |
| 50B [1] | 2-Amino-4-(5-chloro-1-(((6R,8aR)-5-oxooctahydroindolizin-6-yl)amino)-3-(2-oxa-6-azaspiro[3.3]heptan-6-yl)-7,9-dihydrofuro[3,4-f]quinazolin-6-yl)-7-fluorobenzo[b]thiophene-3-carbonitrile | 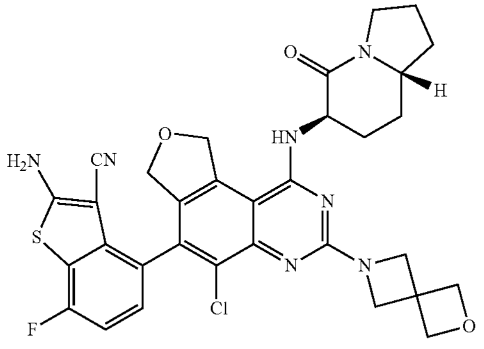 [SMILES: N#Cc1c(N)sc2c(F)ccc(-c3c4c(c5c(N[C@@H]6CC[C@H]7CCCN7C6=O)nc(N6CC7(COC7)C6)nc5c3Cl)COC4)c12] | 646 |
| 51B [1] | 2-Amino-4-(5-chloro-1-(((6R,8aR)-5-oxooctahydroindolizin-6-yl)amino)-3-(7-oxa-2-azaspiro[3.5]nonan-2-yl)-7,9-dihydrofuro[3,4-f]quinazolin-6-yl)-7-fluorobenzo[b]thiophene-3-carbonitrile | 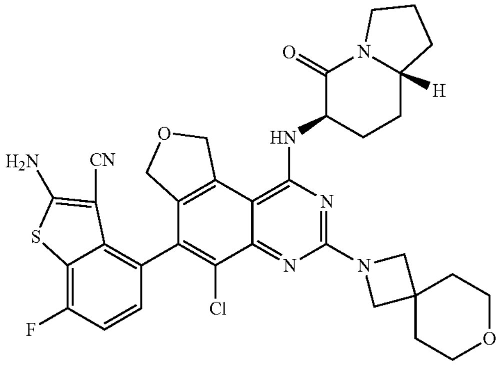 [SMILES: N#Cc1c(N)sc2c(F)ccc(-c3c4c(c5c(N[C@@H]6CC[C@H]7CCCN7C6=O)nc(N6CC7(CCOCC7)C6)nc5c3Cl)COC4)c12] | 674 |
| 52B [1] | 2-Amino-4-(5-chloro-1-(((6R,8aR)-5-oxooctahydroindolizin-6-yl)amino)-3-(5,8-dioxa-2-azaspiro[3.5]nonan-2-yl)-7,9-dihydrofuro[3,4-f]quinazolin-6-yl)-7-fluorobenzo[b]thiophene-3-carbonitrile | 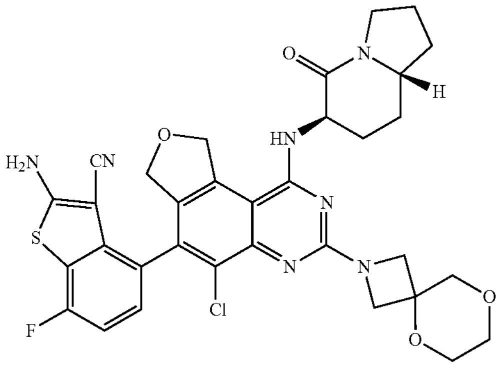 [SMILES: N#Cc1c(N)sc2c(F)ccc(-c3c4c(c5c(N[C@@H]6CC[C@H]7CCCN7C6=O)nc(N6CC7(COCCO7)C6)nc5c3Cl)COC4)c12] | 676 |
| 53B [1] | 2-Amino-4-(5-chloro-3-morpholino-1-(((6R,8aR)-5-oxooctahydroindolizin-6-yl)amino)-7,9-dihydrofuro[3,4-f]quinazolin-6-yl)-7-fluorobenzo[b]thiophene-3-carbonitrile | 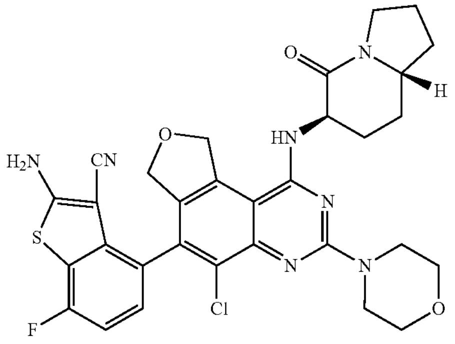 [SMILES: N#Cc1c(N)sc2c(F)ccc(-c3c4c(c5c(N[C@@H]6CC[C@H]7CCCN7C6=O)nc(N6CCOCC6)nc5c3Cl)COC4)c12] | 634 |

TABLE 28-continued

| Example | Chemical Name | Structure | MS (ES) m/z (M + 1) |
|---|---|---|---|
| 54B [1] | 4-(3-((((S)-1,4-Dioxan-2-yl)methyl)(methyl)amino)-5-chloro-1-(((6R,8aR)-5-oxooctahydroindolizin-6-yl)amino)-7,9-dihydrofuro[3,4-f]quinazolin-6-yl)-2-amino-7-fluorobenzo[b]thiophene-3-carbonitrile | 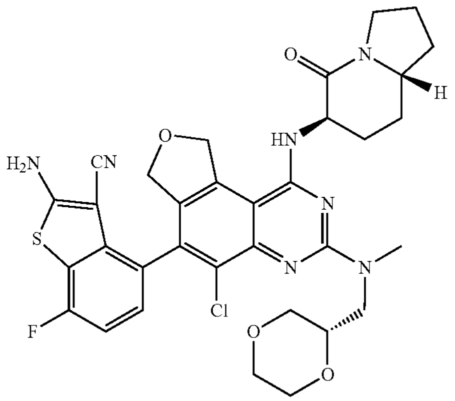 [SMILES: CN(C[C@H]1COCCO1)c1nc(N[C@@H]2CC[C@H]3CCCN3C2=O)c2c3c(c(-c4ccc(F)c5sc(N)c(C#N)c45)c(Cl)c2n1)COC3] | 678 |

[1] Clean atropisomer, chiral purification from Preparation 30

[2] Prep-Chiral-HPLC; (S,S)-Whelk-O1, 30 x 150 mm, 30-100% (1:1 methanol:ethanol w/0.1% isopropylamine) in heptane, 45 mL/min. Isomer refers to a clean isomer on the azaspirooctane.

Biological Assays

The following assays demonstrate that the exemplified compounds are inhibitors of KRAS G12V and inhibit growth of certain tumors in vitro and/or in vivo.

Cellular Phospho-ERK AlphaLISA® Assay for KRAS Inhibition

The purpose of these assays is to quantify the ability of test compounds to selectively inhibit KRAS signaling in cells with amplified KRAS and expressing activating KRAS G12 mutations (Table 1A). Cancer cell lines used in this study were selected based on the presence of homozygous activating KRAS G12 mutations, or amplification of the KRAS gene.

TABLE 1A

| Cell Line Information | | |
|---|---|---|
| Cell Line Name | RAS Mutation/Features | Assay Seeding Density (Cells/Well) |
| MKN45 | WT KRAS Amplification/ Human Gastric Cancer | 20,000 |
| SW620 | KRAS G12V/Human Colorectal Cancer | 20,000 |

The compounds' activity is determined by measuring changes in the phosphorylation levels of the downstream effector Extracellular Signal-regulated Kinase-1 and 2 (ERK1/2) in the compound treated cells. Phosphorylation levels of ERK-1/2 are measured using the AlphaLISA® SureFire® Ultra™ p-ERK 1/2 (Thr202/Tyr204) Assay Kit (#ALSU-PERK-A50K, PerkinElmer® Waltham, MA). The AlphaLISA® assay is a quantitative sandwich immunoassay that can be used to detect phosphorylation of target proteins from cellular lysates using bead-based Alpha technology. The assay kit contains two antibodies, one that binds the phospho-Thr202/Tyr204 epitope on ERK-1/2, and another one that recognizes a separate site on the protein. One of these antibodies is biotinylated and associated with streptavidin-coated Alpha Donor beads, the other antibody is conjugated to AlphaLISA® Acceptor beads. When ERK-1/2 is phosphorylated in cellular lysate, the Donor and Acceptor beads are brought into proximity with each other. When the Donor bead is excited by 600 nm wavelength light, a photosensitizer inside the bead converts ambient oxygen to an excited singlet state. When the Acceptor bead is within 200 nm of this reaction, the singlet oxygen reacts with the Acceptor leading to a chemiluminescent emission. The amount of light measured is proportional to the amount of phosphorylated ERK-1/2 in the lysate. The AlphaLISA® SureFire® Ultra™ p-ERK 1/2 (Thr202/Tyr204) Assay Kit contains AlphaLISA® antibody-conjugated Donor and Acceptor Beads, Lysis buffer concentrate, and a set of proprietary buffers (Activation Buffer, Reaction Buffer 1, Reaction Buffer 2, and Dilution Buffer).

To perform the assays, test compounds and controls are acoustically dispensed (Labcyte ECHO®, San Jose, CA) into a white 384-well assay plate (Proxiplate-384, PerkinElmer #6008280) in a 10-point 3-fold dilution series in 30 nL DMSO. Cells are then added to the assay plate in 8 μL per well assay medium (HBSS, Sigma #55021C, 10% FBS, GIBCO #10082-147) at a cell line specific density (Table 1A). The final compound concentrations range from 0.5 to 10,000 nM and the final DMSO concentration is 0.375% in each well. Maximum signal control wells contain 0.375% DMSO only (negative control), and minimum signal control wells contain 10,000 nM control compound (positive control). Cells in suspension are incubated with the test and reference compounds for 2 h at 37° C./5% $CO_2$. Following the 2 h incubation, cells are lysed by adding 2 μL of the AlphaLISA® Lysis buffer concentrate (5×) supplemented with protease/phosphatase inhibitor cocktail (Thermo Scientific #78442). The assay plate is covered with an opaque lid and shaken at 750 rpm on a multi-plate shaker (Heidolph, Schwabach, Germany) for 30 min at room temperature to induce cell lysis. During the lysis, the AlphaLISA® Acceptor beads are diluted 1:50 in a prepared buffer mixture (1:1 AlphaLISA® Reaction Buffers 1 and 2 with a 1:25 dilution of AlphaLISA® Activation Buffer). Following cell lysis, plates are centrifuged briefly, and 5 μL per well prepared Acceptor beads are added. The plate is then covered and incubated in the dark for 2 h at room temperature. During the Acceptor bead incubation, Donor beads are prepared by diluting the Alpha streptavidin Donor beads 1:50 in AlphaLISA® Dilution buffer. Following the Acceptor bead incubation, 5 μL per well of Donor bead mixture is added to the plates. Plates are then covered and allowed to incubate in the dark at room temperature for 2 h. After this incubation period, the AlphaLISA signal is read using a PHERAstar® FSX multimode plate reader (BMG Labtech, Ortenberg, Germany) equipped with an AlphaLISA® compatible optics cube.

Raw signal obtained from the AlphaLISA® assay is analyzed using Genedata Screener® 17.0.3. Within the program, data is normalized to 32 wells treated with inhibition control (max inhibition/positive control) and 32 wells treated with 0.375% DMSO only (minimum inhibition/negative control) to calculate the % Activity of the compound:

$$\% \text{ Activity} = 100x\left(1 - \frac{(\text{treated value} - \text{positive control})}{(\text{negative control} - \text{positive control})}\right) \quad \text{eq. 1}$$

% Activity values are fit to a four-parameter non-linear logistic equation using Genedata Screener® 17.0.3. to -determine $IC_{50}$ values:

$$y = \text{Bottom} + \frac{\text{Top} - \text{Bottom}}{1 + \left(\frac{10^{\text{Log}(IC_{50})}}{10^x}\right)^h} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

Compounds of Examples 1, 5, 7, 9, 11, 14, 17, 22, 25, 27, 30, 32, 34, 38, 42, 45-47, 49, 51, 53, 55-57, 60, 61, 63, 64, 66, 68-70, 73-75, 78, 80, 81, 84-86, 88, 90, 91, 93, 94, 96, 98, 100, 102, 105, 109, 111, 1B, 3B, 4B, 6B, 8B, 11B-15B, 17B, 18B, 20B, 22B-27B, 29B-31B, 33B, 34B, 36B-48B and 50B-54B were tested in the SW620 Cellular Phospho-ERK AlphaLISA® Assay and exhibited an ability to reduce levels of phosphorylated ERK-1/2 in cells expressing KRAS indicating inhibition of constitutive RAS activity in cells expressing KRAS G12V with a relative IC50 of <50 nM. Compounds of Examples 1, 2, 5, 7, 9, 11, 13-15, 17, 22, 25, 27, 30, 32-35, 37-39, 42, 43, 45-47, 49, 51-53, 55-57, 60, 61, 64, 66, 68-70, 73-82, 84-86, 88, 90, 91, 93, 94, 96, 98, 100-103, 105, 109, 111, 1B, 6B, 14B, 20B, 22B-26B, 31B, 33B, 34B, 36B-40B, 43B-46B, 48B and 50B-54B were tested in both assays above (SW620, and MKN 45 Cellular Phospho-ERK AlphaLISA® Assays) and showed a greater than 5-fold selective inhibition preference for KRAS G12V mutant over KRAS wild-type. Further, the compounds of Examples 1, 2, 5, 7, 9, 11, 14, 15, 17, 22, 25, 27, 32, 34, 35, 37-39, 42, 45, 47, 51, 53, 55, 69, 70, 75, 77, 78, 80-82, 84, 93, 94, 96, 105, 6B, 20B, 40B, 50B and 54B showed a greater than 10-fold selective inhibition preference for KRAS G12V mutant over KRAS wild-type.

This data shows that compounds of Formula I as described herein are inhibitors of KRAS human cancer cells expressing KRAS demonstrating the ability to inhibit KRAS G12V mutants with a selective inhibition preference for the KRAS G12V mutant over KRAS WT.

CellTiter-Glo® Luminescent Cell Viability Assay for Anti-Proliferative Activity

The purpose of these assays is to quantify the ability of test compounds to selectively inhibit proliferative activity in cells harboring KRAS wild-type (WT) and activating KRAS G12 mutations (Table 1B) grown as tumor spheroids. Cancer cell lines used in this study were selected based on the presence of homozygous activating KRAS G12 mutations, or the KRAS WT gene.

TABLE 1B

| Cell Line Information | | |
|---|---|---|
| Cell Line Name | RAS Mutation/Features | Assay Seeding Density (Cells/Well) |
| MKN45 | KRAS WT/Human Gastric Cancer | 1,000 |
| SW620 | KRAS G12V/Human Colorectal Cancer | 1,000 |

The compounds' anti-proliferative activity is determined by CellTiter-Glo 2.0 assay which quantifies changes in the cellular levels of ATP in compound treated cells. In the presence of $Mg^{2+}$, ATP and molecular oxygen, Ultra-Glo™ Recombinant Luciferase catalyzes the mono-oxygenation of beetle luciferin and generates light. The luminescence readout is directly proportional to metabolically active cells in culture.

To perform the assays, 75 nL of test compounds, controls, and DMSO are acoustically dispensed using an ECHO 655 Acoustic Liquid Handler (Beckman Life Sciences) into clear round bottom ultra-low attachment spheroid 384-well assay plate (Spheroid Microplates, Corning®# CLS 3830) in a 10-point 3-fold dilution series. The spheroid microplates aid the formation of spheroids in the center of well by inhibiting cellular attachment. A Multidrop Combi Reagent Dispenser (Thermo Fisher Scientific) is used to dispense 40 μL/well of cell suspension in microplates containing compounds. Cells (Table 1B) were seeded at a density of 25,000 live cells/mL or 1,000 cells/well in growth medium (RPMI Gibco #11875-093, 10% FBS Gibco #10082-147). The final compound concentrations range from 0.5 to 10,000 nM and the final DMSO concentration is 0.2% in each well. Maximum signal control wells contain 0.2% DMSO only (negative control), and minimum signal control wells contain 10,000 nM control compound (positive control). Plates were sealed with Breathe-Easy® sealing membranes (Diversified Biotech), transferred to a 37° C. incubator with 5% $CO_2$, and allowed to incubate for 4 days.

After 4-day incubation, CTG 2.0 reagent and assay plates were equilibrated at 25° C. for at least 30 minutes. A Multidrop Combi Reagent Dispenser (Thermo Fisher Scientific) was used to dispense 40 μL/well of CTG reagent in microplates. The assay plate was placed on a multi-plate shaker (Heidolph, Schwabach, Germany) at 750 RPM for 10 min at room temperature to induce cell lysis, followed by a 1-minute centrifugation at 1200 RPM. The luminescence was read using a PHERAstar FSX Multimode Plate reader (BMG LABTECH).

Raw luminescence data obtained by CTG assay were analyzed using Genedata Screener® 20.0.5. Within the program, data were normalized to the average signal from 14 wells treated with the positive control (10 mM LY3841814) and the average signal from 14 wells treated with the negative control (0.2% DMSO) to calculate the % Activity of the compound:

$$\% \text{ Activity} = 100x\left(1 - \frac{(\text{treated value} - \text{positive control})}{(\text{negative control} - \text{positive control})}\right) \quad \text{eq. 1}$$

% Activity values were fit to a four-parameter non-linear regression in Genedata Screener® 20.0.5. to determine IC50 values:

$$y = \text{Bottom} + \frac{\text{Top} - \text{Bottom}}{1 + \left(\frac{10^{\text{Log}(IC_{50})}}{10^{x}}\right)^{h}} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

Compounds of Examples 1, 5, 7, 9, 11, 14, 17, 22, 25, 27, 30, 32, 34, 35, 38, 42, 45-47, 49, 51, 53, 55-57, 60-62, 64, 66, 68-70, 73-75, 78, 81, 84-86, 88, 90, 91, 93, 94, 96, 98, 100, 102, 105, 109, 111, 1B, 3B, 4B, 6B, 8B, 11B-15B, 17B, 18B, 20B, 23B-27B, 29B-31B, 33B, 34B, 36B-38B and 40B-54B were tested in the SW620 4-day 3D proliferation assay and exhibited an ability to reduce ATP levels indicating inhibition of proliferative activity with a relative IC50 of <250 nM. Further, the compounds of Examples 1, 5, 7, 9, 11, 14, 17, 22, 25, 30, 32, 46, 47, 49, 57, 61, 66, 68, 73, 74, 81, 85, 86, 88, 90, 96, 98, 100, 102, 109, 1B, 3B, 4B, 8B, 11B, 13B-15B, 18B, 24B, 27B, 29B-31B, 33B, 34B, 41B-43B, 45B and 47B exhibited an ability to reduce ATP levels indicating inhibition of proliferative activity with a relative IC50 of <50 nM. Compounds of Examples 1, 5, 7, 9, 11, 14, 17, 22, 25, 27, 30, 32, 34, 35, 38, 42, 45, 46, 49, 51, 53, 55-57, 60-62, 68-70, 73-76, 78, 80, 81, 85, 86, 91, 93, 94, 96, 100, 102, 105, 109, 111, 1B, 3B, 4B, 6B, 8B, 9B, 11B, 13B-15B, 17B, 22B, 24B, 30B, 31B, 33B, 38B-51B, 53B and 54B were tested in both assays above (SW620 and MKN45 4-day 3D proliferation assays) and showed a greater than 5-fold selective inhibition preference for KRAS G12V mutant over KRAS wild-type.

These data show that compounds of Formula I as described herein are inhibitors of proliferative activity in KRAS tumor spheroids and inhibit KRAS G12V mutant with a selective inhibition preference over KRAS WT.

TABLE 1C

| Abbreviations | |
|---|---|
| KRAS | Kirsten Rat Sarcoma Virus |
| ERK | Extracellular Signal-Regulated Kinase |
| AlphaLISA | Alpha-Linked Immunosorbent Assay |
| DMSO | Dimethyl Sulfoxide |
| HBSS | Hank's Balanced Salt Solution |
| FBS | Fetal Bovine Serum |
| $CO_2$ | Carbon Dioxide |
| ATP | Adenosine triphosphate |
| CTG | CellTiter-Glo |
| RPMI | Roswell Park Memorial Institute |

What is claimed is:

1. A compound of the formula:

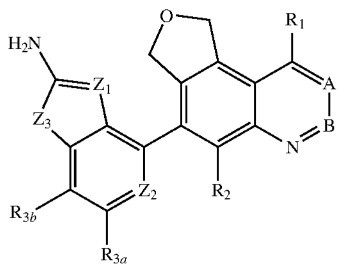

wherein:

A is —C(H)— or —N—;

B is —$C(R_4)$— or —N—;

$R_1$ is a group of the formula

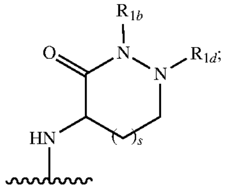

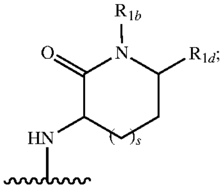

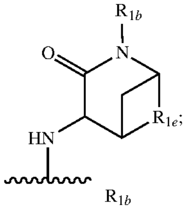

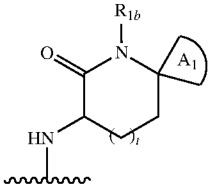

;

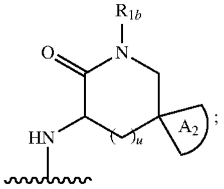

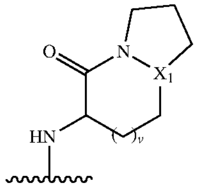

;

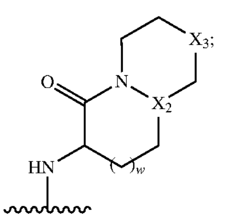

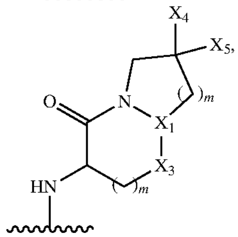

or

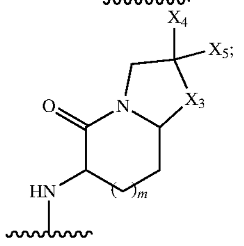

$R_{1b}$ is H or $C_{1-3}$ alkyl;

$R_{1d}$ is $C_{1-3}$ alkyl, $C_{1-3}$ haloalkyl or $C_{3-4}$ cycloalkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

$X_4$ and $X_5$ are each independently $C_{1-3}$ alkyl, halogen, or H;

m, m', s, t, u, v, and w are each 0 or 1;

$R_2$ is halogen or $C_{1-3}$ alkyl;

$Z_1$ is —C(CN)— or —N—;

$Z_2$ is —C($R_{3c}$)— or —N—;

$Z_3$ is —O— or —S—;

$R_{3a}$, $R_{3b}$, and $R_{3c}$ are each independently H, halogen, or $C_{1-3}$ alkyl;

$R_4$ is H, $C_{1-3}$ alkyl, $C_{1-3}$ alkoxy optionally substituted with 1, 2, 3, or 4 substituents independently selected from hydroxyl and methyl, or $R_4$ is a group of the formula (i)

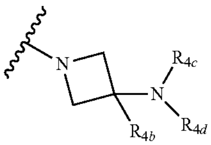

or

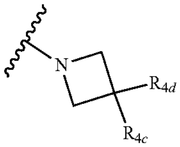

, wherein $R_{4b}$ is H or methyl;

and $R_{4c}$ and $R_{4d}$ are each independently $C_{1-3}$ alkyl, hydroxyl, or $C_{1-3}$ haloalkyl; or $R_{4c}$ and $R_{4d}$ together with the nitrogen or carbon atom to which they are attached form a 4-, 5-, or 6-membered heterocycle; or (ii)

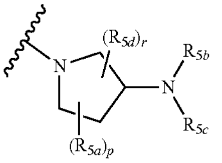

or

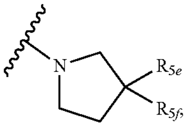

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5d}$ is $C_{1-3}$ alkyl;

$R_{5e}$ and $R_{5f}$ together with the carbon atom to which they are attached form a 4-, 5-, or 6-membered heterocycle;

$R_{5b}$ and $R_{5c}$ are each independently H, $C_{1-6}$ alkyl optionally substituted with one or more deuterium, $C_{3-5}$ cycloalkyl optionally substituted with halogen or $C_{1-3}$ haloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle or a 6-, 7-, or 8-membered spiro heterocycle, wherein each heterocycle or spiro heterocycle optionally contains a further heteroatom selected from N, O, and S, and wherein the heterocycle and the spiro heterocycle is each optionally substituted with one or more halogen, deuterium, $C_{1-3}$ alkyl, or $C_{1-3}$ haloalkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p and r are each 0, 1, or 2;

(iii)

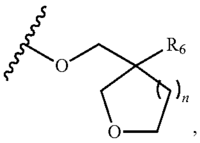

, wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, and $C_{1-3}$ dialkylamino; and n is 0 or 1; and (iv)

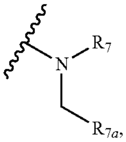

wherein $R_7$ is a $C_{1-3}$ alkyl; and $R_{7a}$ is a 4-, 5-, or 6-membered heterocycle optionally containing a further heteroatom selected from N, O, and S; or $R_7$ and $R_{7a}$ together with the atoms to which they are attached form a 4-, 5-, or 6-membered heterocyclic ring optionally containing a further heteroatom selected from N, O, and S;

or a pharmaceutically acceptable salt thereof.

2. The compound of claim 1, wherein the compound is of the formula:

Formula I'

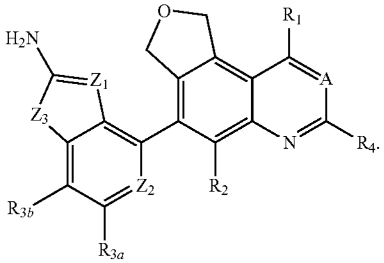

wherein:

$R_1$ is a group of the formula

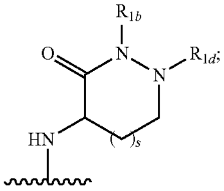

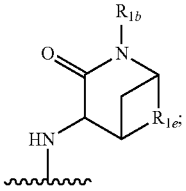

-continued

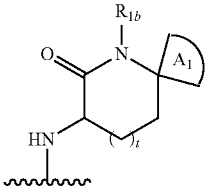 ; 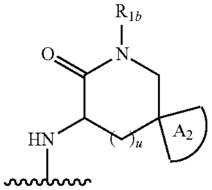 ;

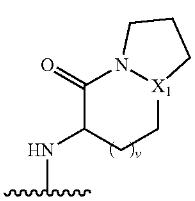 ; 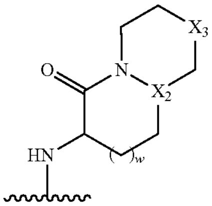 ; or

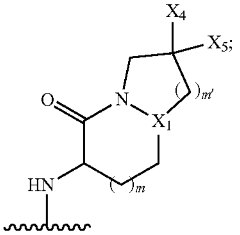

$R_{1b}$ is H or $C_{1-3}$ alkyl;

$R_{1d}$ is $C_{1-3}$ alkyl;

$R_{1e}$ is $C_{1-3}$ alkylene;

Ring $A_1$ and Ring $A_2$ are $C_{3-4}$ cycloalkyl or a 3- or 4-membered heterocycle containing a heteroatom selected from N, O, and S;

$X_1$ and $X_2$ are —CH— or —N—;

$X_3$ is —$CH_2$— or —O—;

$X_4$ and $X_5$ are each independently $C_{1-3}$ alkyl, halogen, or H;

m, m', s, t, u, v, and w are each 0 or 1;

$R_2$ is halogen;

$Z_1$ is —C(CN)— or —N—;

$Z_2$ is —C($R_{3c}$)— or —N—;

$Z_3$ is —O— or —S—;

$R_{3a}$, $R_{3b}$, and $R_{3c}$ are each independently H or halogen;

$R_4$ is a group of the formula (i)

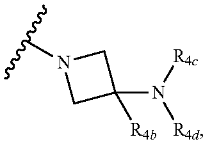

wherein $R_{4b}$ is H or methyl; and $R_{4c}$ and $R_{4d}$ are each independently $C_{1-3}$ alkyl; or (ii)

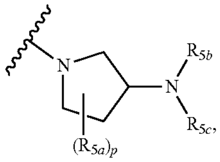

wherein $R_{5a}$ is halogen, hydroxy, $C_{1-3}$ alkyl, $C_{1-3}$ alkoxy, or $C_{1-3}$ alkoxy-$C_{1-3}$ alkyl;

$R_{5b}$ and $R_{5c}$ are each independently H, $C_{1-6}$ alkyl, $C_{3-5}$ cycloalkyl, or 3-, 4-, or 5-membered heterocycle containing a heteroatom selected from N, O, and S; or $R_{5b}$ and $R_{5c}$ together with the nitrogen atom to which they are attached form an optionally substituted 4-, 5-, or 6-membered heterocycle optionally containing a further heteroatom selected from N, O, and S, wherein the heterocycle is optionally substituted with a $C_{1-3}$ alkyl; or $R_{5a}$ and $R_{5b}$ together with the atoms to which they are attached form a 4-, 5-, or 6-membered heterocyclic fused ring optionally containing a further heteroatom selected from N, O, and S, $R_{5c}$ is $C_{1-3}$ alkyl, and the 4-, 5-, or 6-membered fused ring is optionally further substituted with a $C_{1-3}$ alkyl; and p is 0, 1, or 2;

(iii)

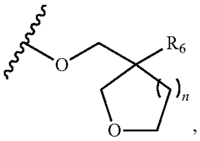 , wherein $R_6$ is selected from halogen, hydroxy, $C_{1-3}$ alkyl, $C_{1-3}$ haloalkyl, $C_{1-3}$ hydroxyalkyl, $C_{1-3}$ alkoxy, and $C_{1-3}$ dialkylamino; and n is0 or 1;

or a pharmaceutically acceptable salt thereof.

3. The compound according to claim 1, wherein A is —C(H)—, or a pharmaceutically acceptable salt thereof.

4. The compound according to claim 1, wherein A is —N—, or a pharmaceutically acceptable salt thereof.

5. The compound according to claim 1, wherein B is —C($R_4$)—, or a pharmaceutically acceptable salt thereof.

6. The compound according to claim 1, wherein B is —N—, or a pharmaceutically acceptable salt thereof.

7. The compound according to claim 1, wherein $R_1$ is a group of formula

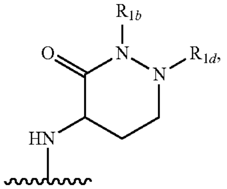 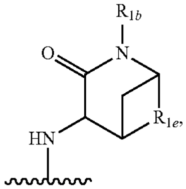

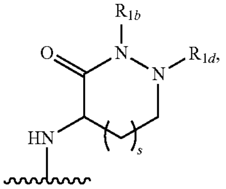 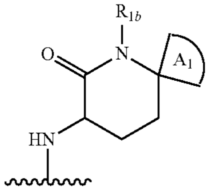 ,

-continued
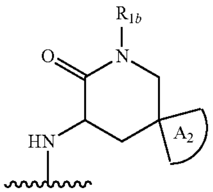
,
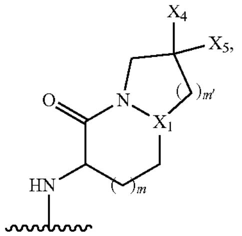
or
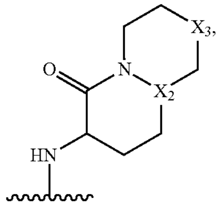
or a pharmaceutically acceptable salt thereof.
8. The compound according to claim 1, wherein $R_1$ is a group of the formula
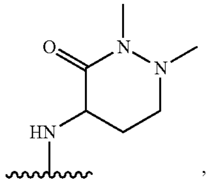
,
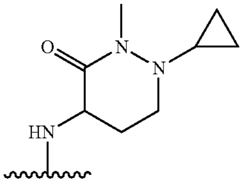
,
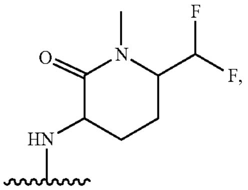
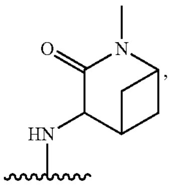
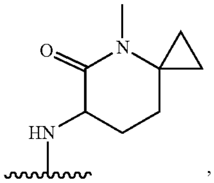
,
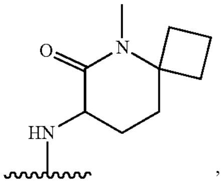
,
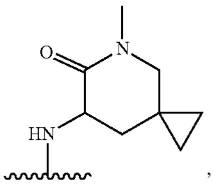
,
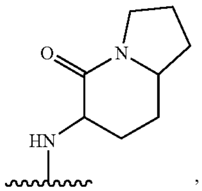
,
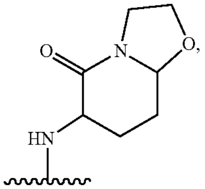
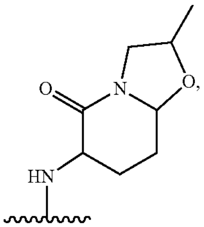
-continued
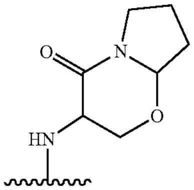
,
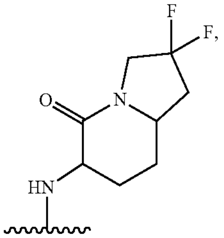
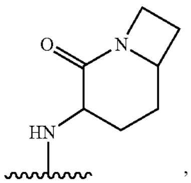
,
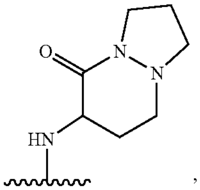
,
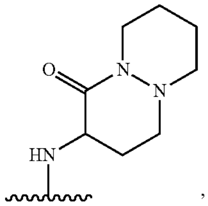
,
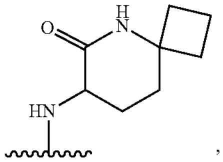
,
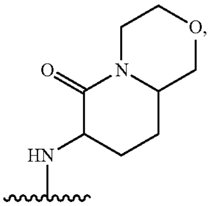
or
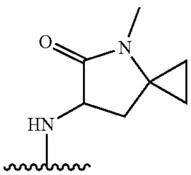
,
or a pharmaceutically acceptable salt thereof.
9. The compound according to claim 1, wherein $R_1$ is a group of the formula
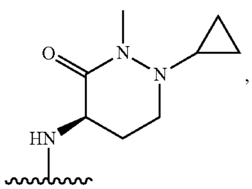
,
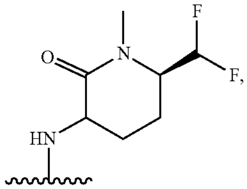
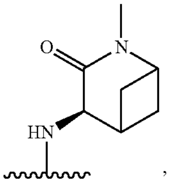
,
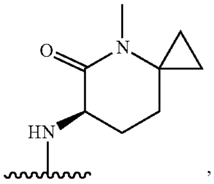
,
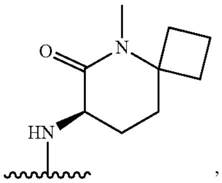
,
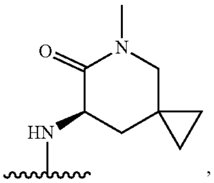
, -continued

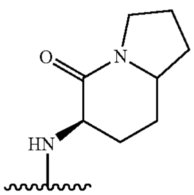
,
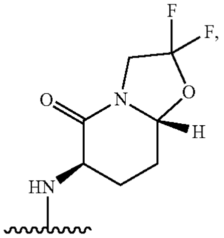
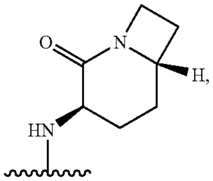
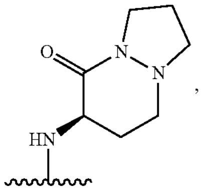
,
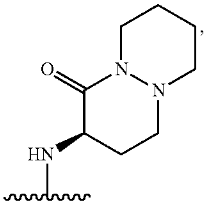
, or
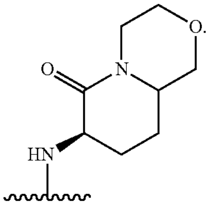

or a pharmaceutically acceptable salt thereof.

10. The compound according to claim 1, wherein $R_2$ is F, Cl, or methyl, or a pharmaceutically acceptable salt thereof.

11. The compound according to claim 1, wherein $R_2$ is F or Cl, or a pharmaceutically acceptable salt thereof.

12. The compound according to claim 1, wherein $Z_1$ is —C(CN)—, $Z_2$ is —C($CR_{3c}$), $Z_3$ is —S—, and $R_{3a}$ is H, or a pharmaceutically acceptable salt thereof.

13. The compound according to claim 1, wherein $Z_1$ is —C(CN)—, $Z_2$ is —N—, $Z_3$ is —S—, and $R_{3a}$ is H, or a pharmaceutically acceptble salt thereof.

14. The compound according to claim 1, wherein $Z_1$ is —N—, $Z_2$ is —C($R_{3c}$)—, $Z_3$ is —S—, and $R_{3a}$ is H, or a pharmaceutically acceptable salt thereof.

15. The compound according to claim 1, wherein $Z_1$ is —N—, $Z_2$ is —N—, $Z_3$ is —S—, and $R_{3a}$ is H, or a pharmaceutically acceptable salt thereof.

16. The compound according to claim 1, wherein $Z_1$ is —N—, $Z_2$ is —C($R_{3c}$)—, $Z_3$ is —O—, and $R_{3a}$ is H, or a pharmaceutically acceptable salt thereof.

17. The compound according to claim 1, wherein $R_4$ is H, $C_{1-3}$ alkyl, or $C_{1-3}$ alkoxy optionally substituted with 1, 2, 3, or 4 substituents independently selected from hydroxyl and methyl, or a pharmaceutically acceptable salt thereof.

18. The compound according to claim 1, wherein $R_4$ is a group of the formula

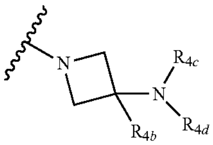
or
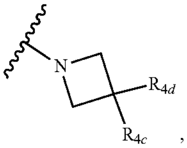
, or a pharmaceutically acceptable salt thereof.

19. The compound according to claim 1, wherein $R_4$ is a group of the formula

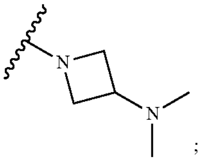
;
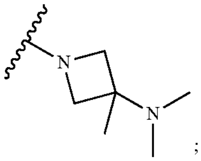
;
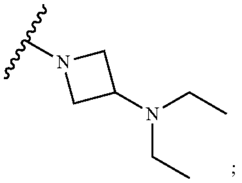
;
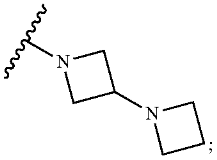
;
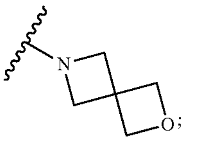
;
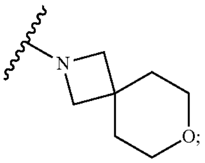
; or
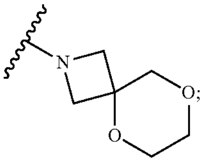
;

or a pharmaceutically acceptable salt thereof.

20. The compound according to claim 1, wherein $R_4$ is a group of the formula

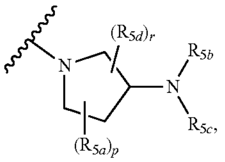

or a pharmaceutically acceptable salt thereof.

21. The compound according to claim 1, wherein $R_4$ is a group of the formula

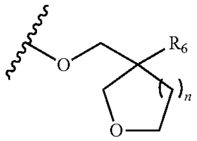
or
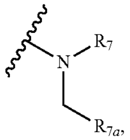

or a pharmaceutically acceptable salt thereof.

22. The compound according to claim 1, wherein $R_4$ is a group of the formula

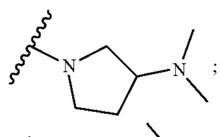
;
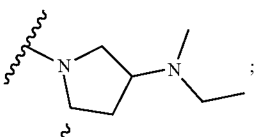
;
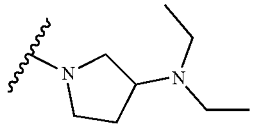
;
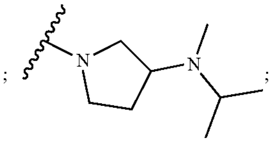
;

-continued
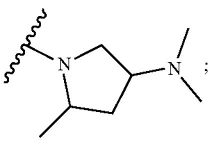 ;
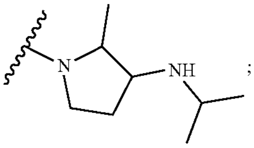 ;
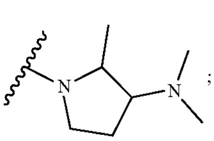 ;
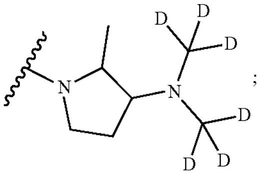 ;
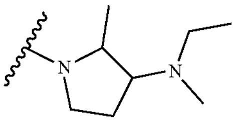 ;
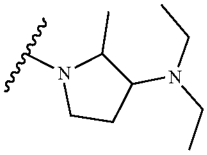 ;
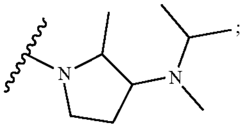 ;
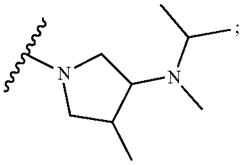 ;
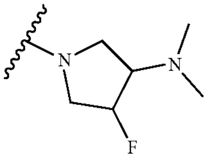 ;
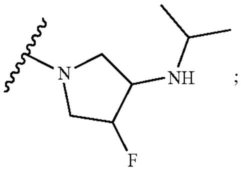 ;
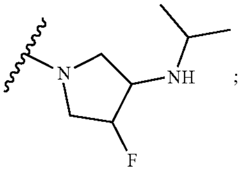 ;
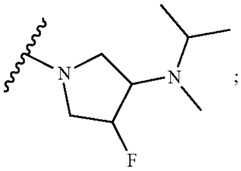 ;
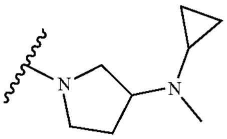 ;
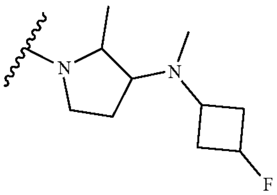 ;
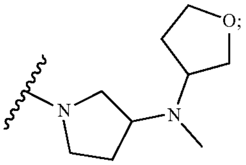
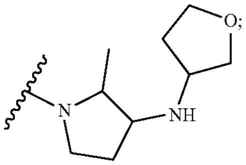
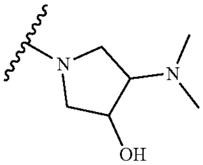 ;
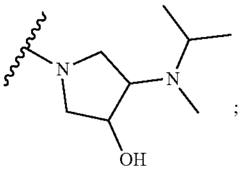 ;
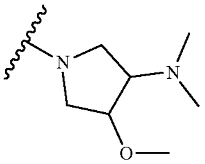 ;
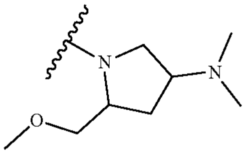 ;
-continued
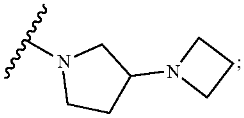
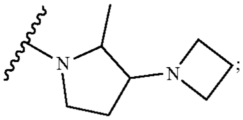
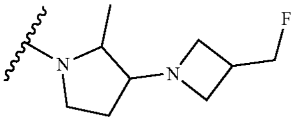 ;
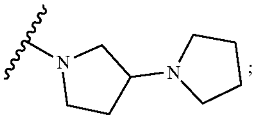 ;
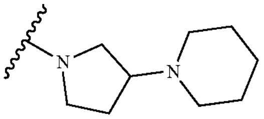
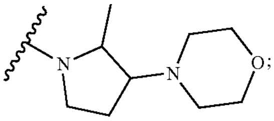
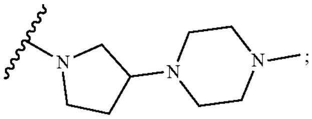
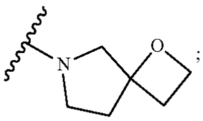 ;
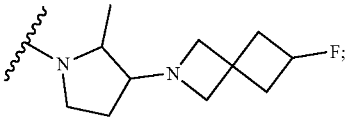
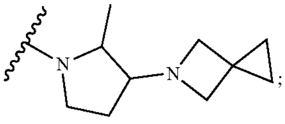
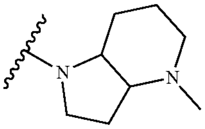 ;
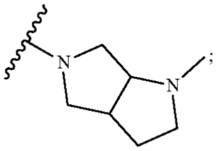
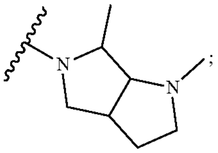
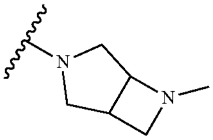
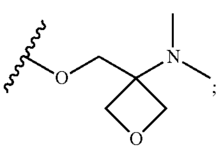 ;
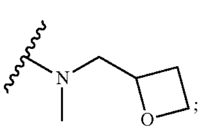
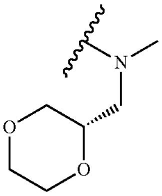 ; or
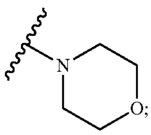 [SMILES: *N1CCOCC1]
or a pharmaceutically acceptable salt thereof.
23. The compound according to claim 1, wherein the compound is selected from

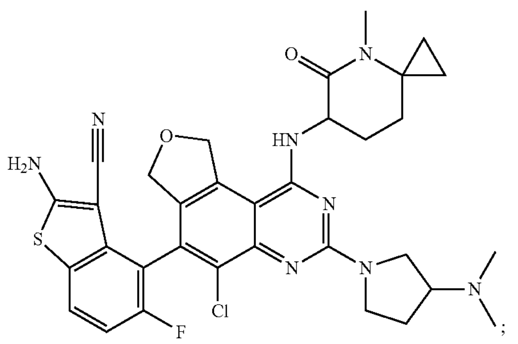
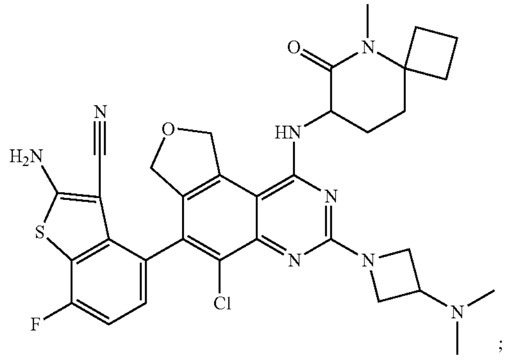
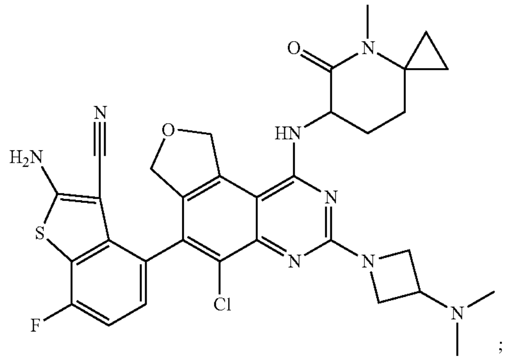
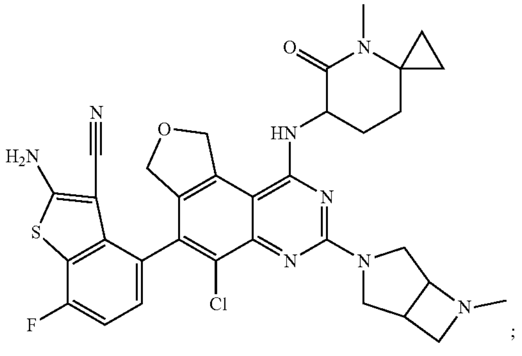
-continued
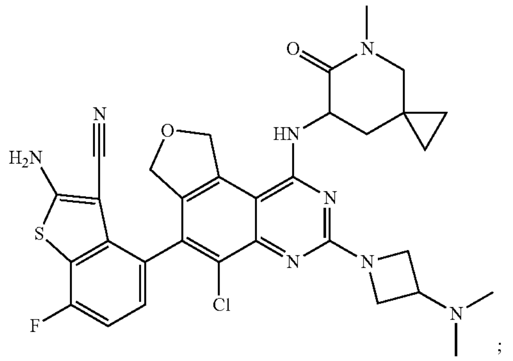
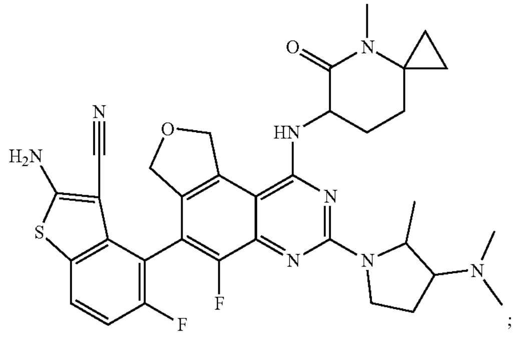
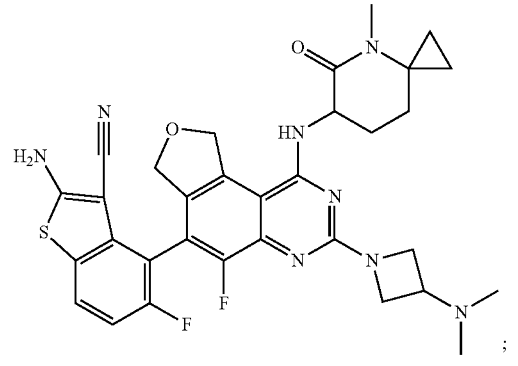
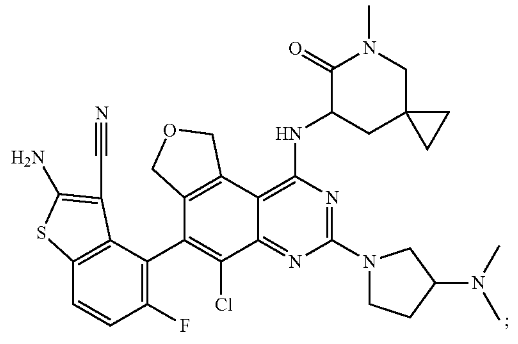

-continued
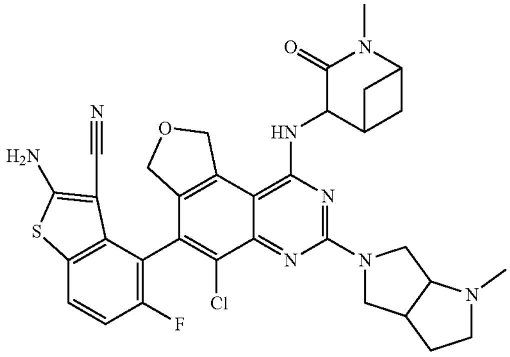
;
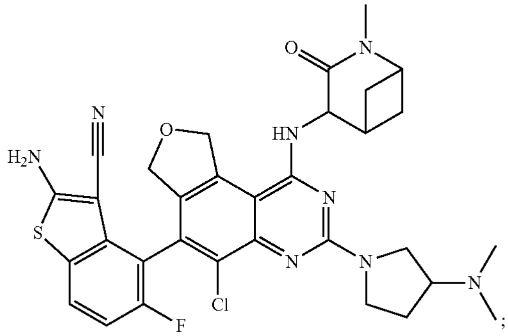
;
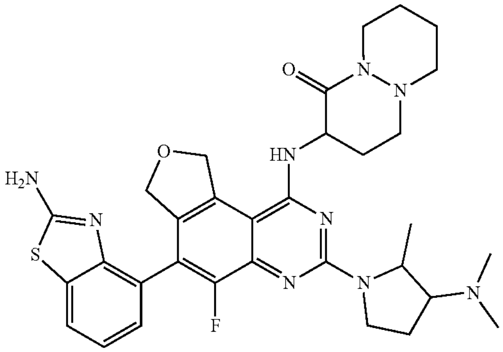
;
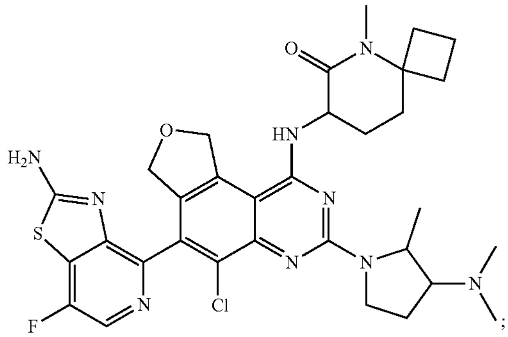
;
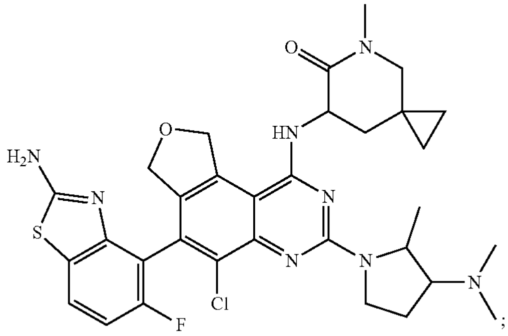
;
-continued
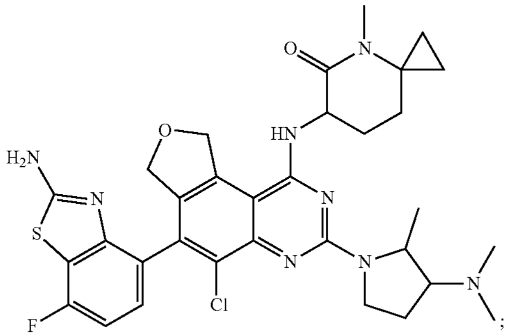
;
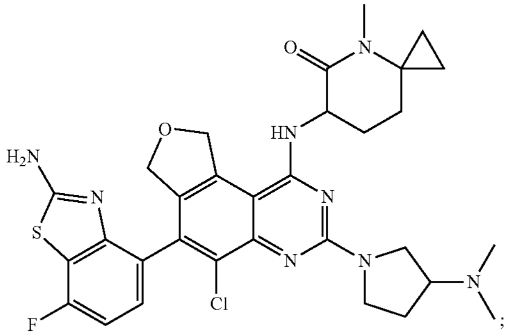
;
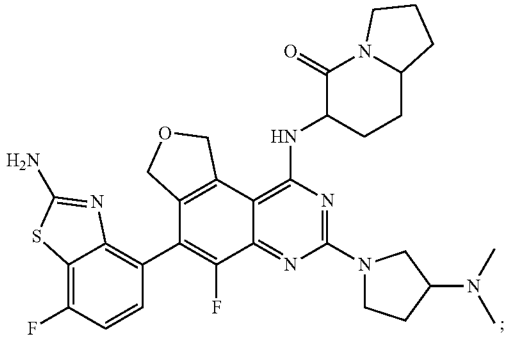
;
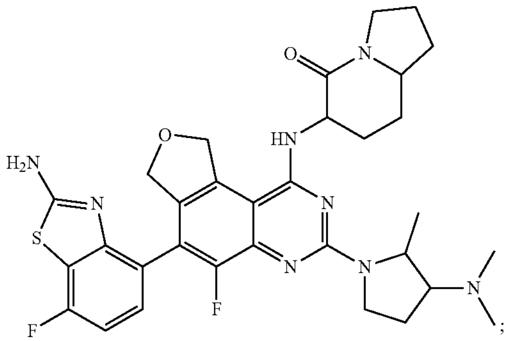
;
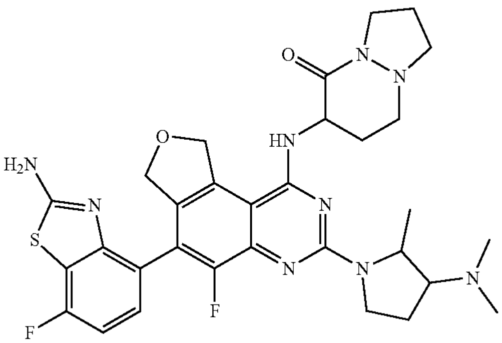
;

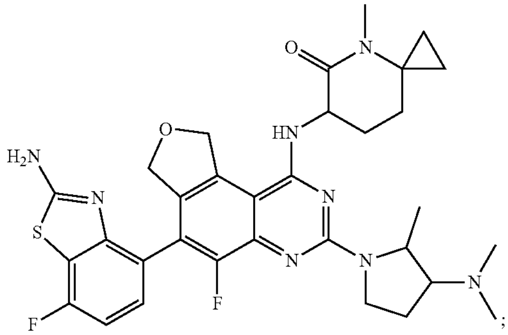
;
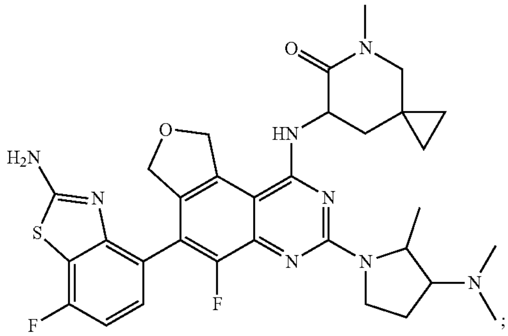
;
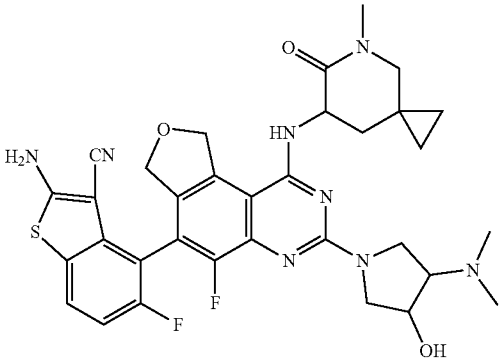
;
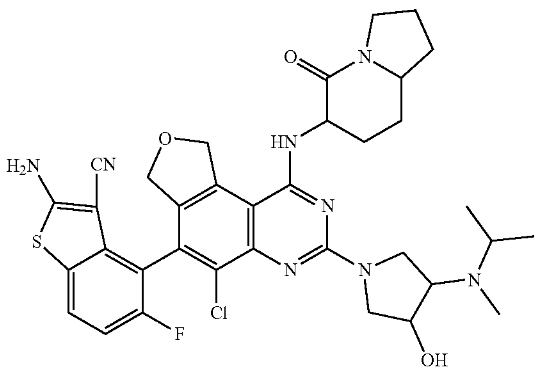
;
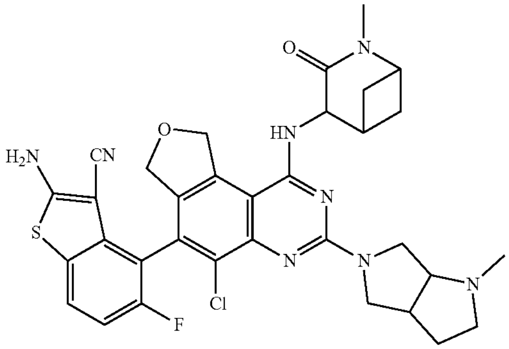
;
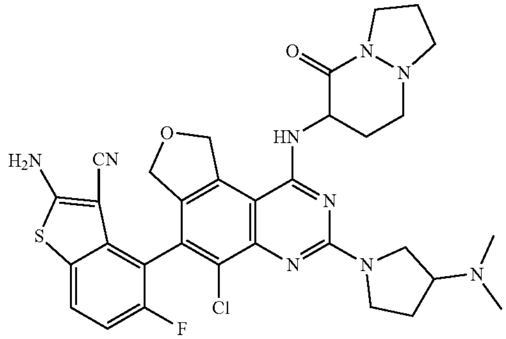
;
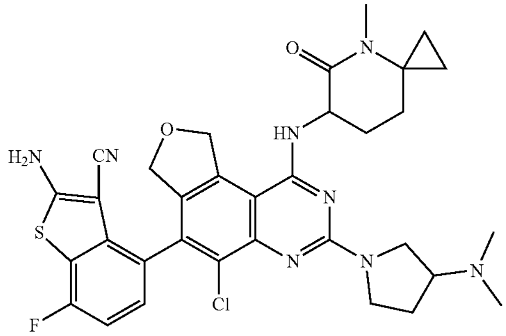
;
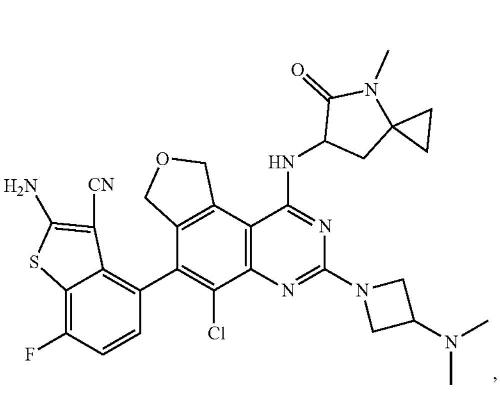
, -continued
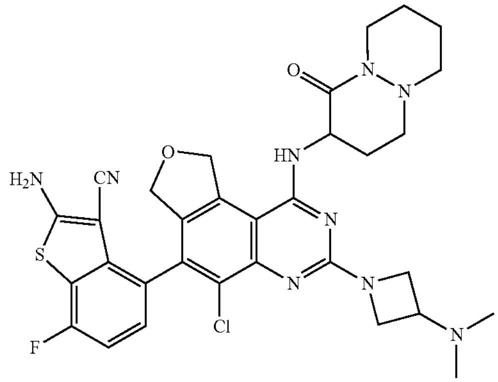
;
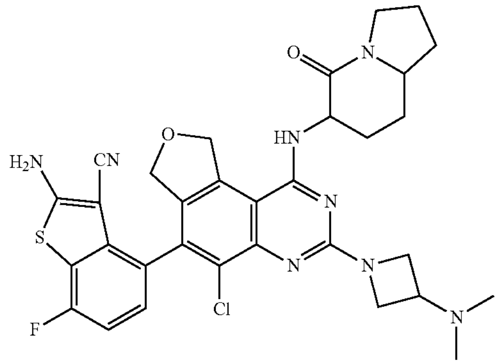
;
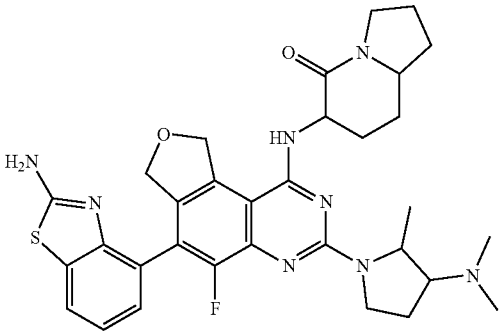
;
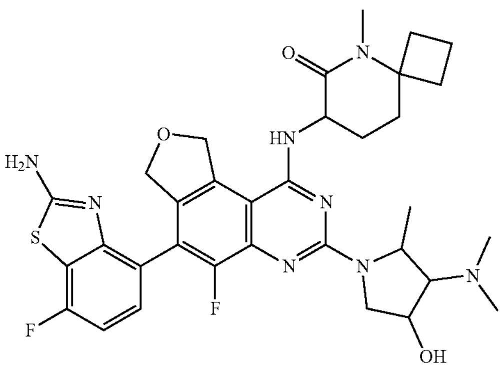
;
-continued
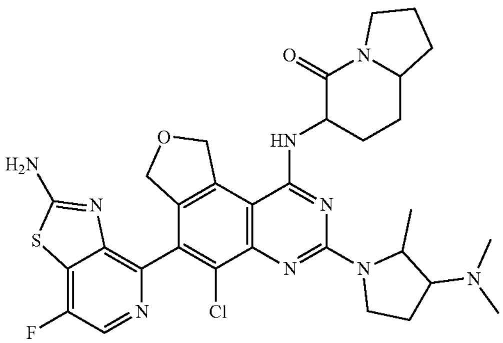
;
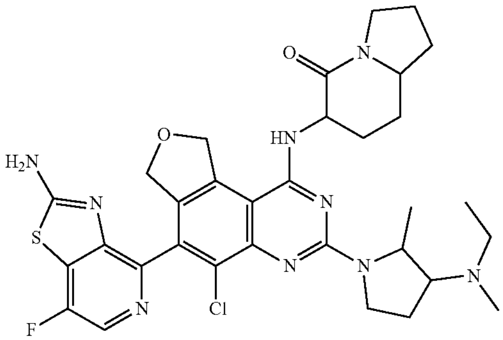
;
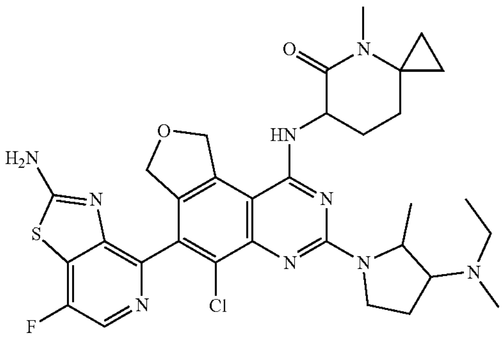
;
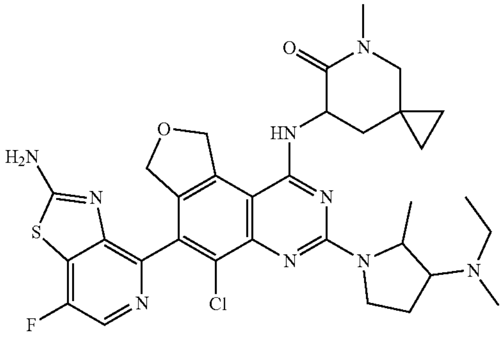
;
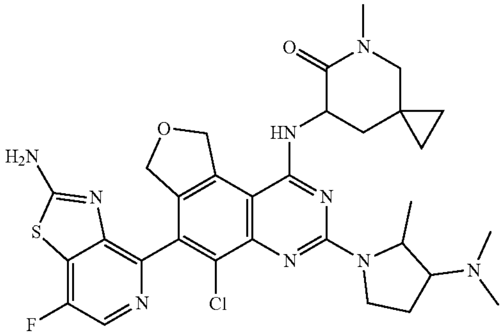
;

-continued
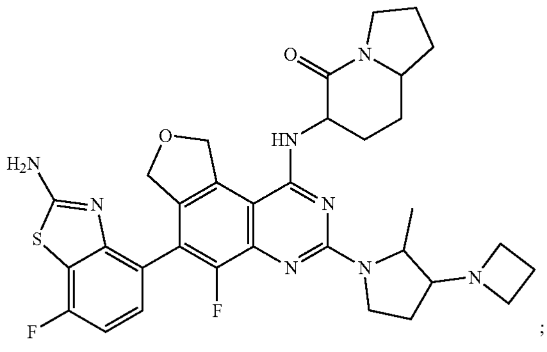
;
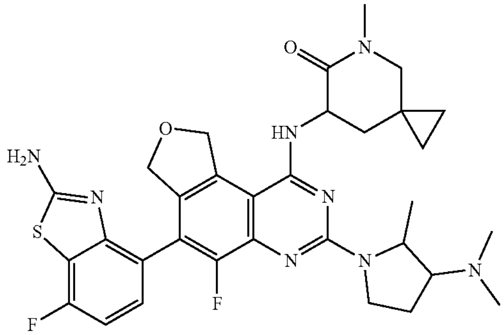
;
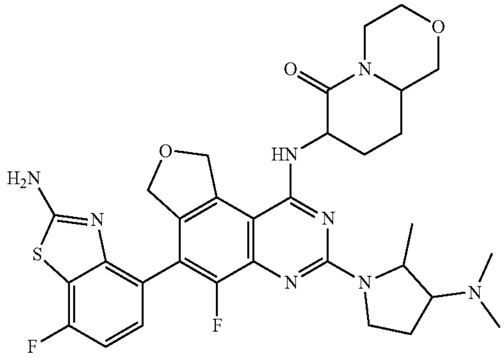
;
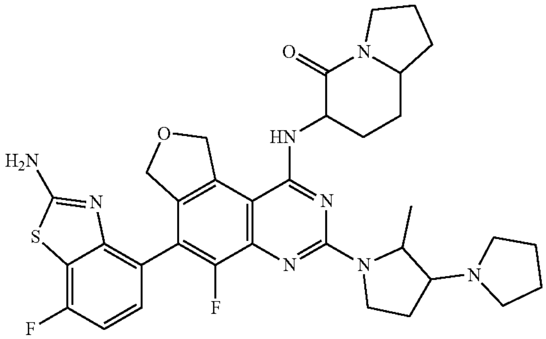
;
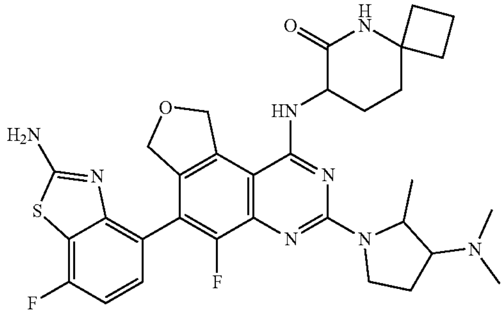
;
-continued
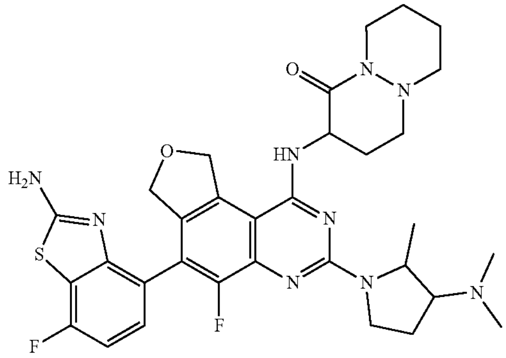
;
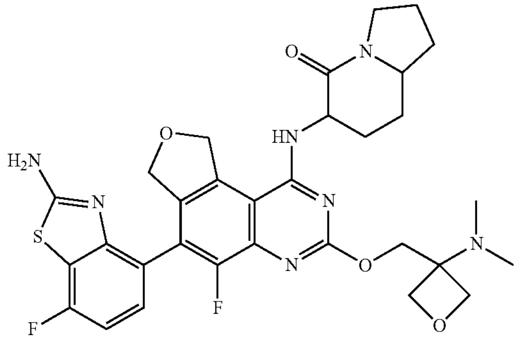
;
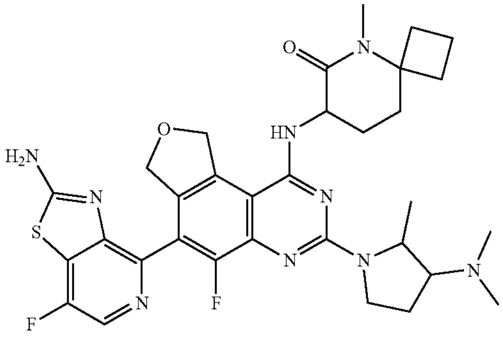
;
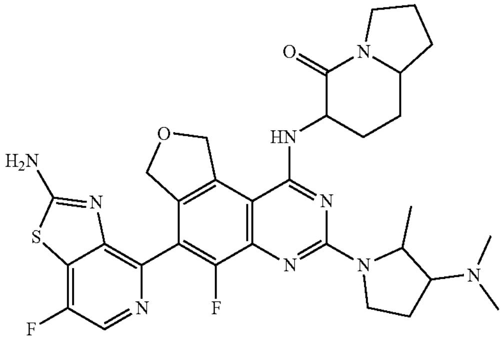
;
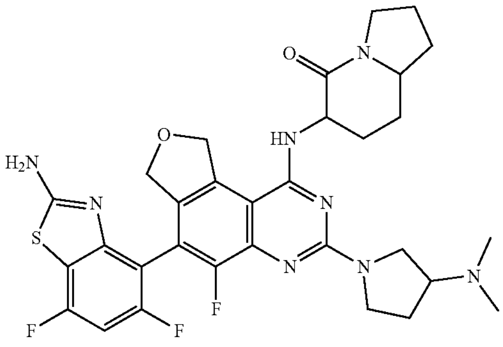
;

-continued
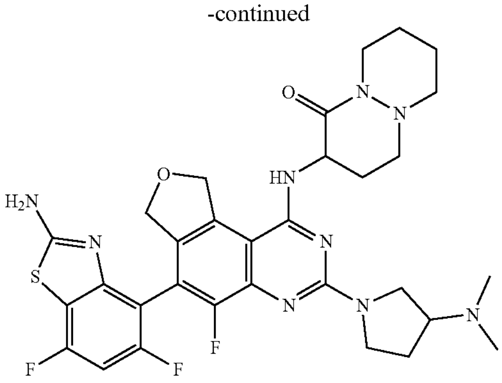
;
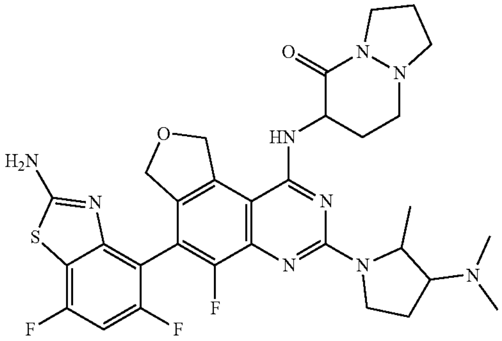
;
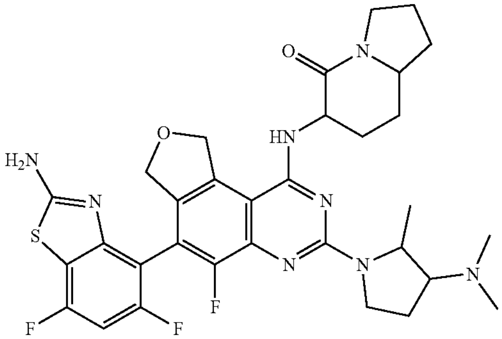
;
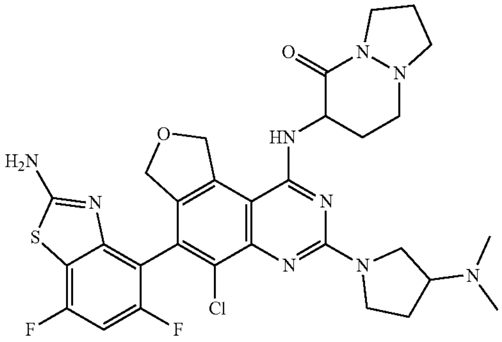
;
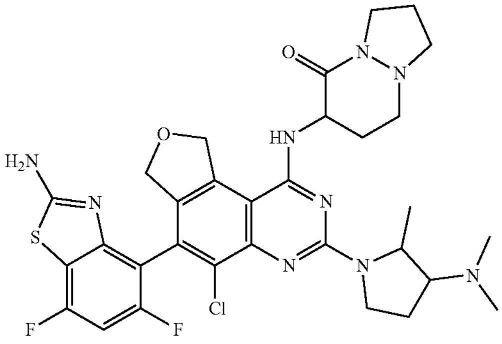
;
-continued
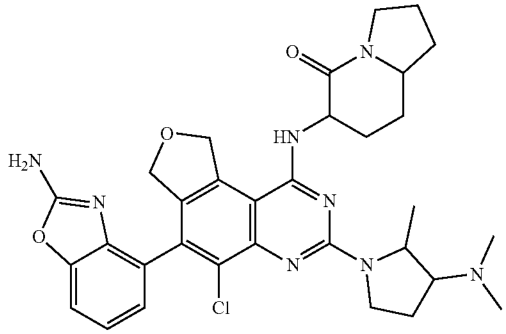
;
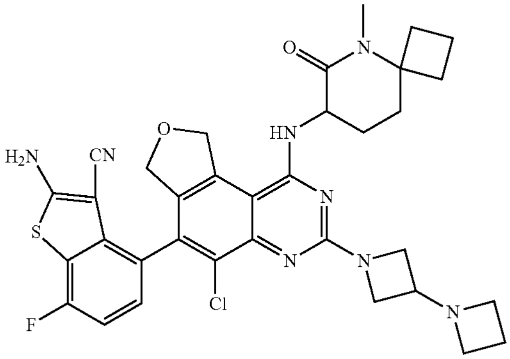
;
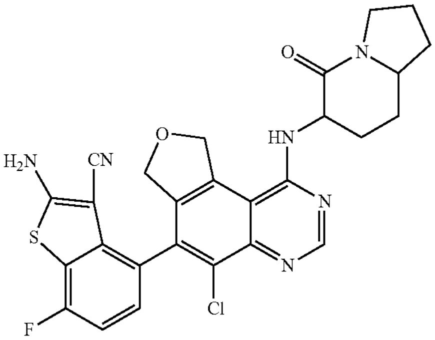
;
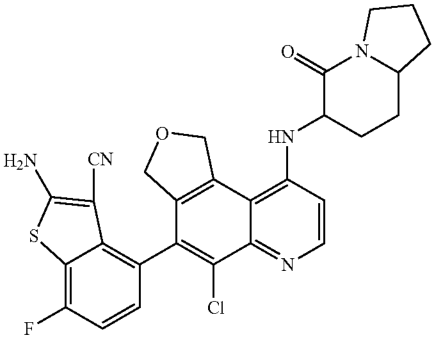
;
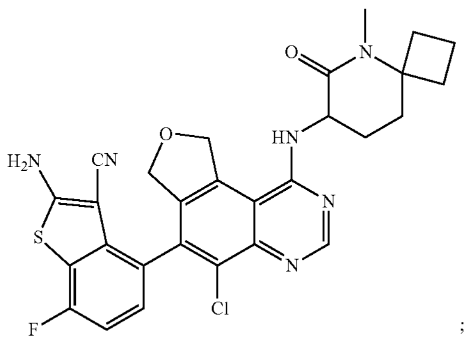
;

-continued
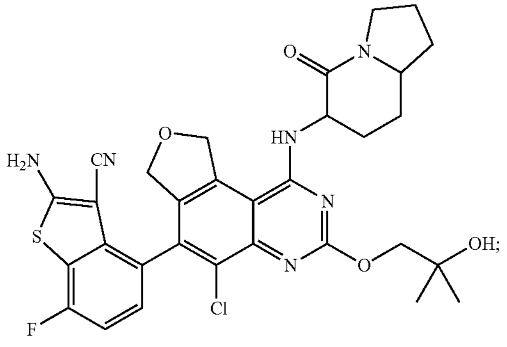
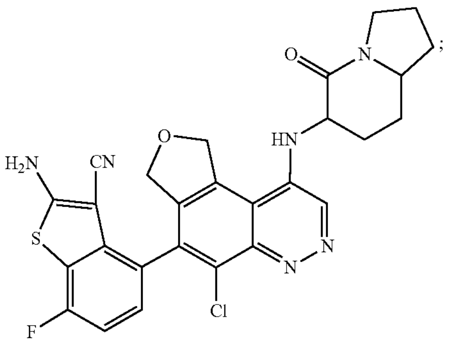
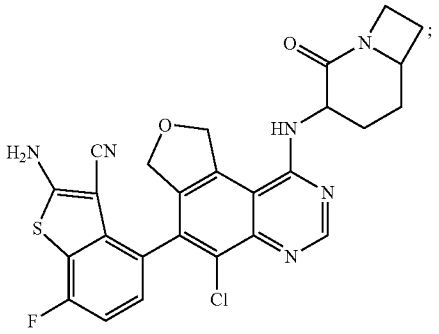
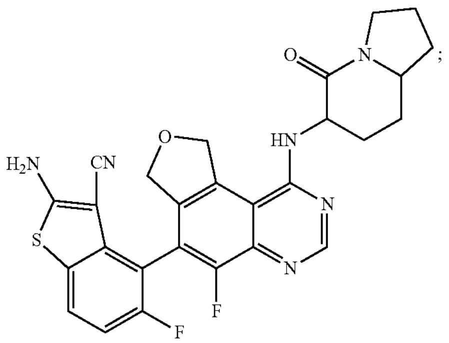
-continued
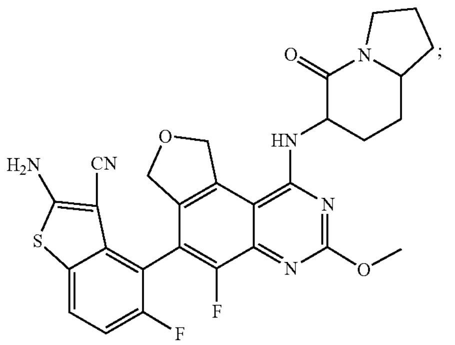
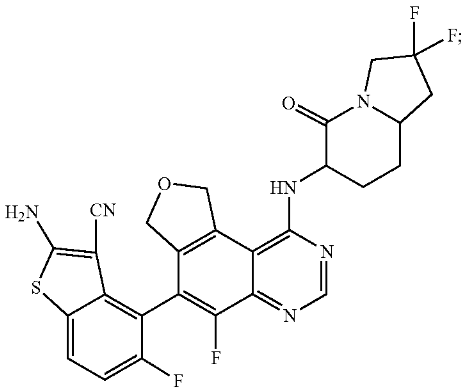
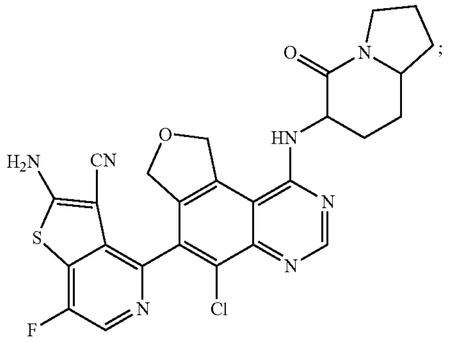
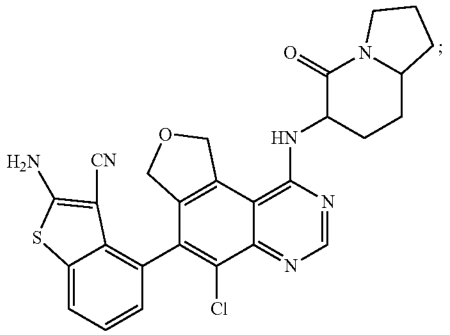

-continued
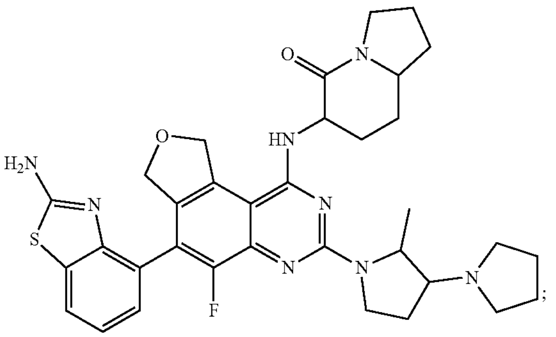
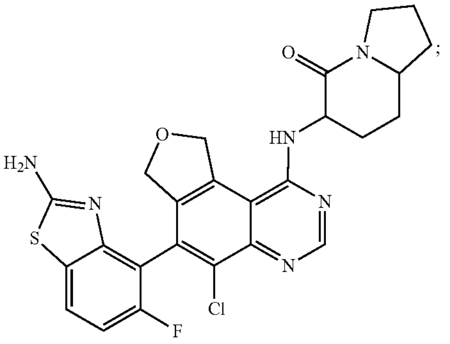
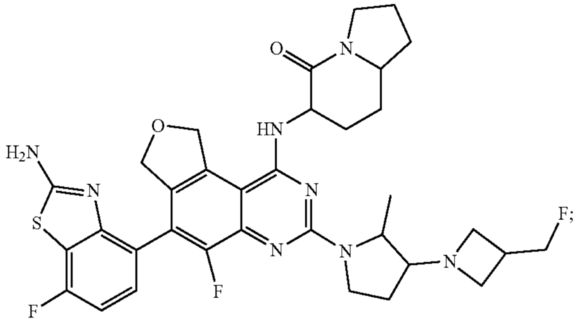
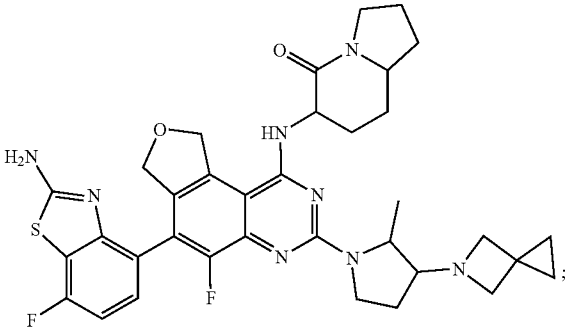
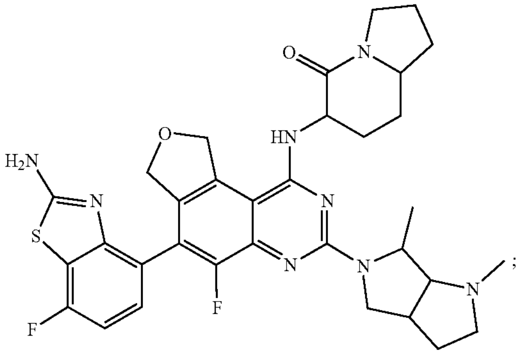
-continued
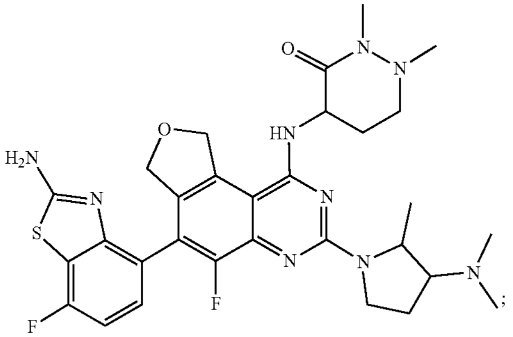
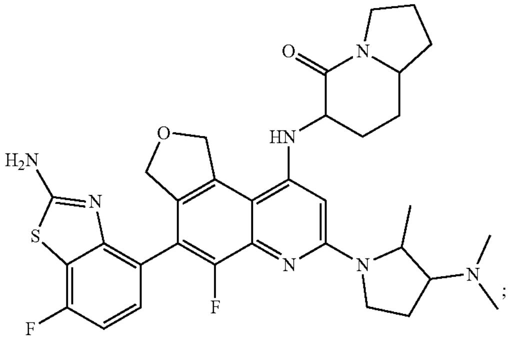
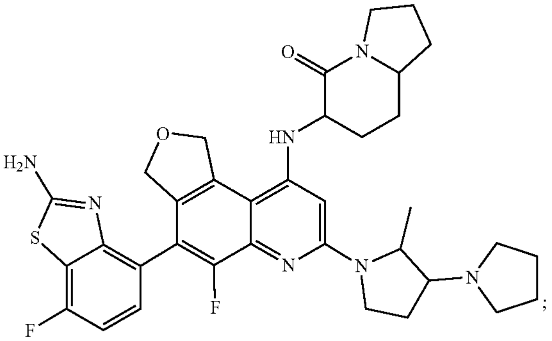
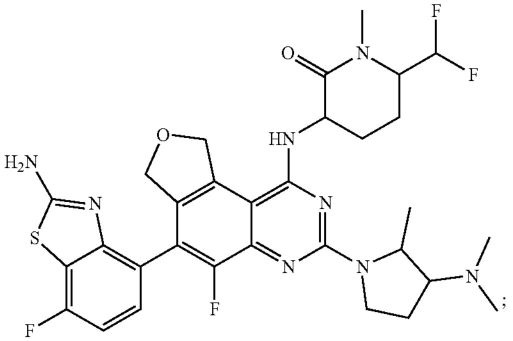
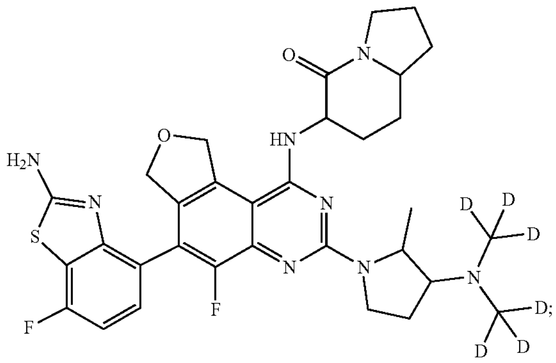

-continued
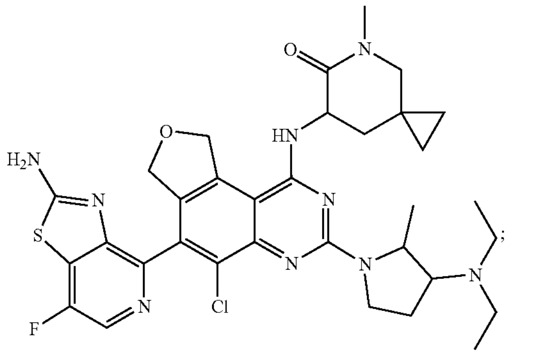
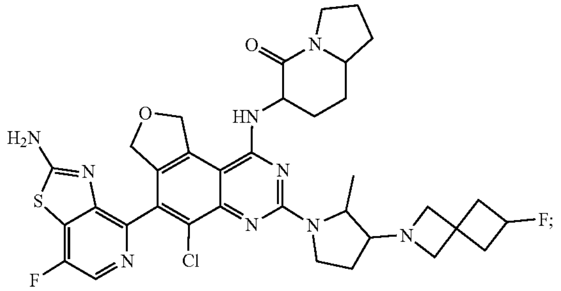
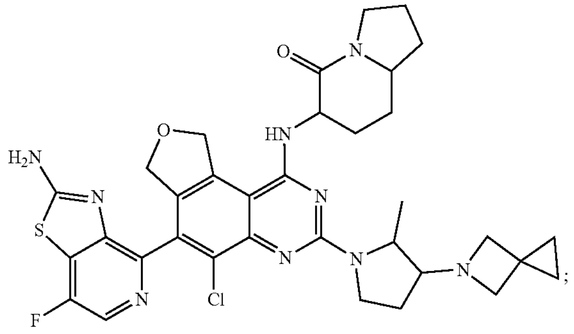
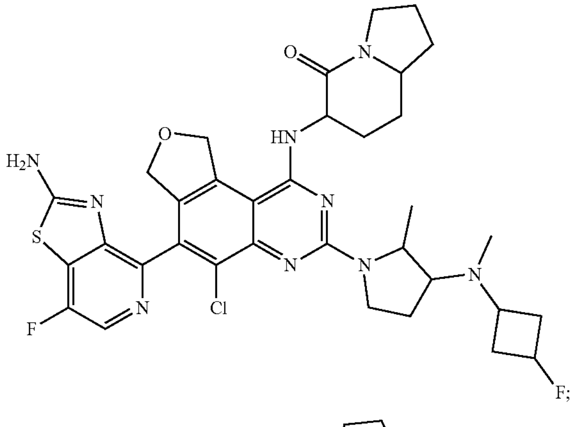
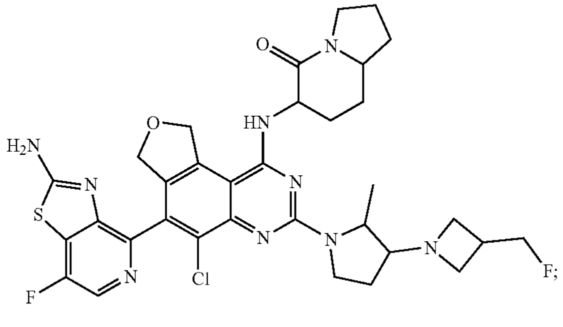
-continued
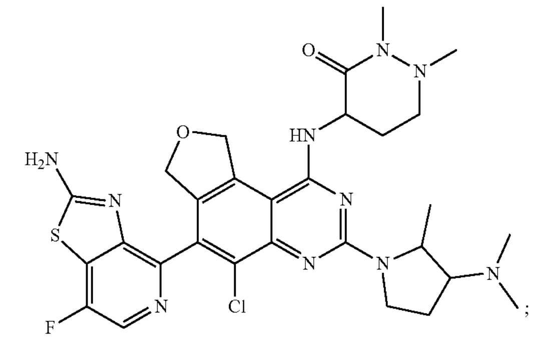
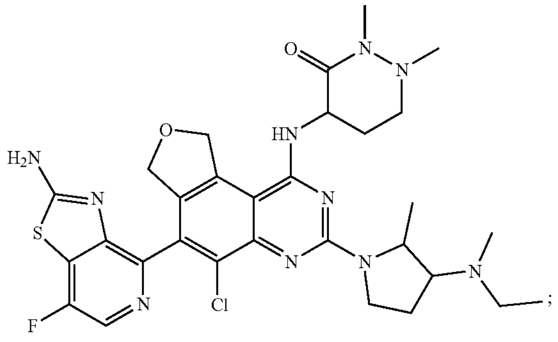
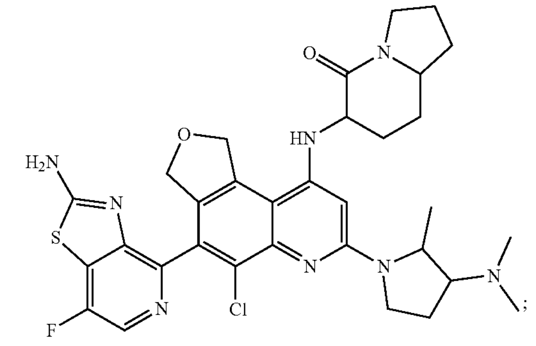
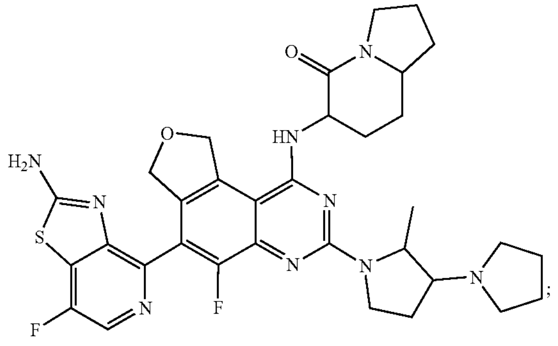
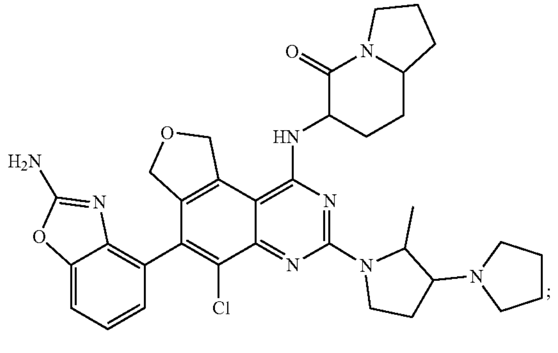

-continued
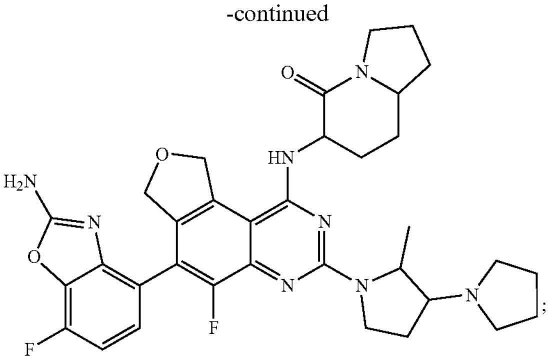
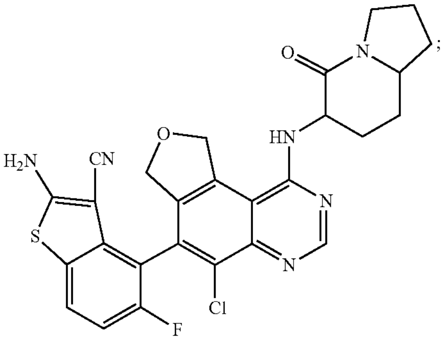
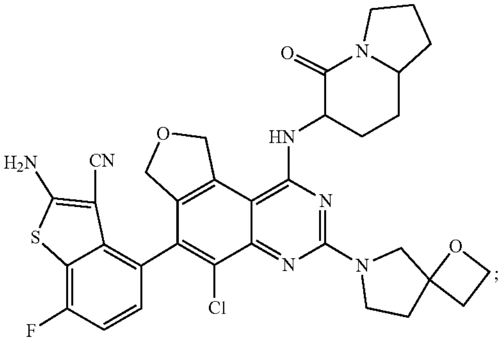
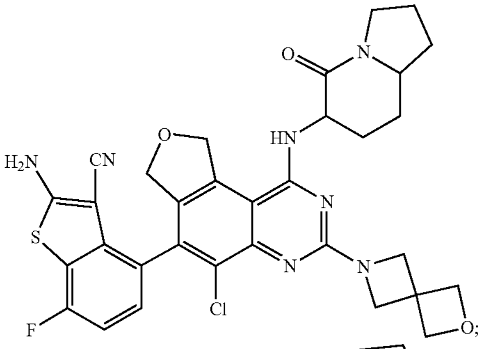
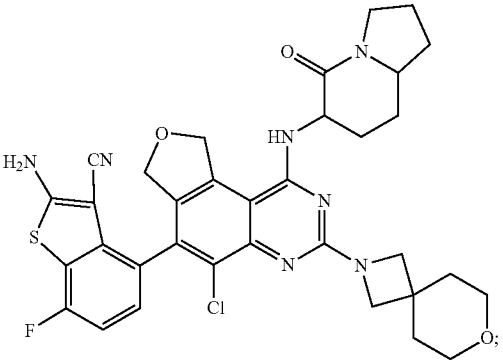
-continued
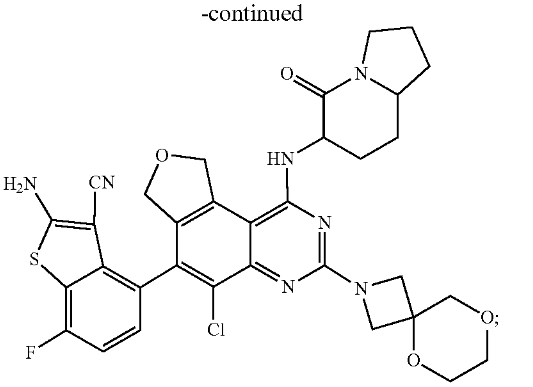
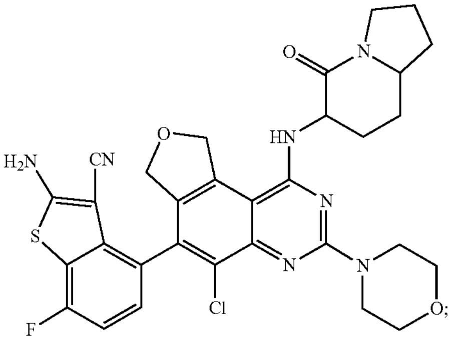
and
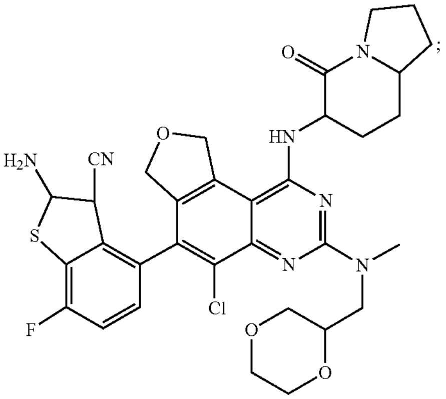
or a pharmaceutically acceptable salt thereof.
24. The compound according to claim 1, wherein the compound is selected from
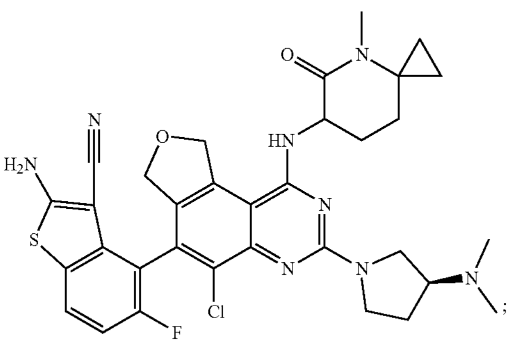

-continued
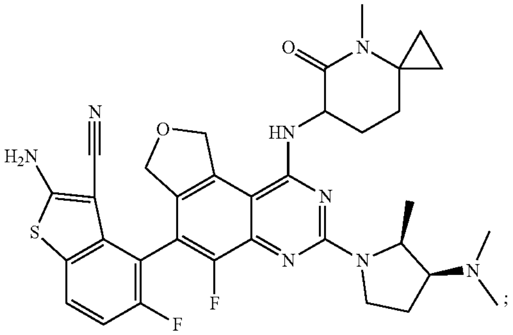
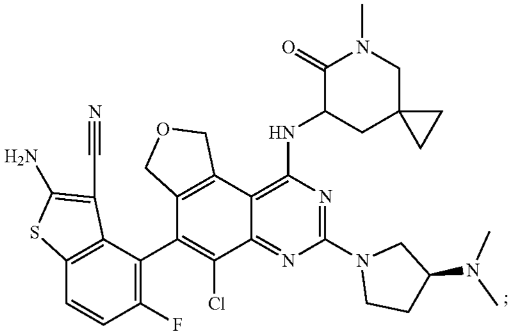
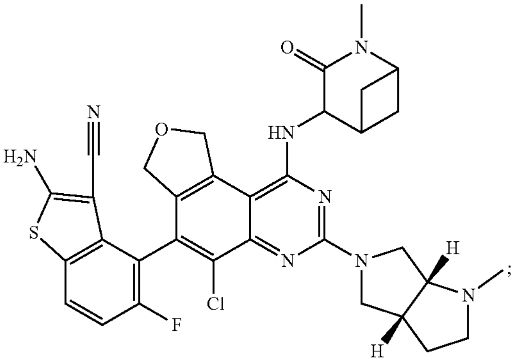
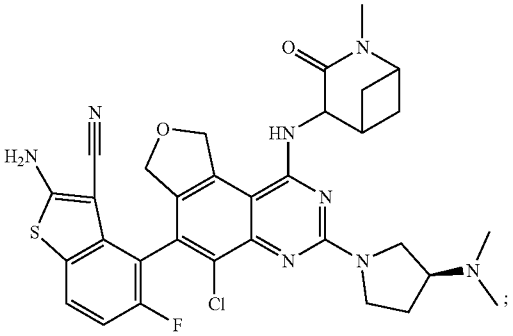
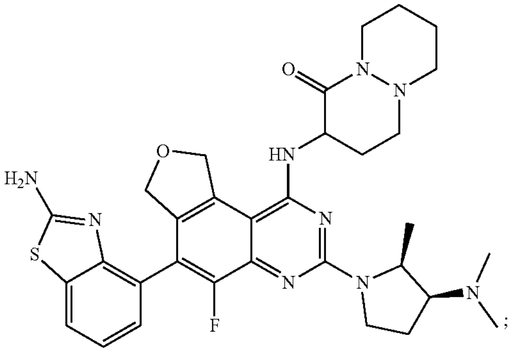
-continued
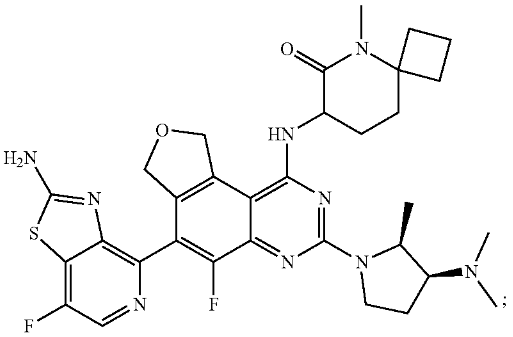
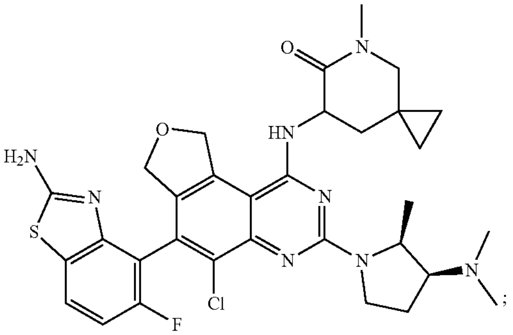
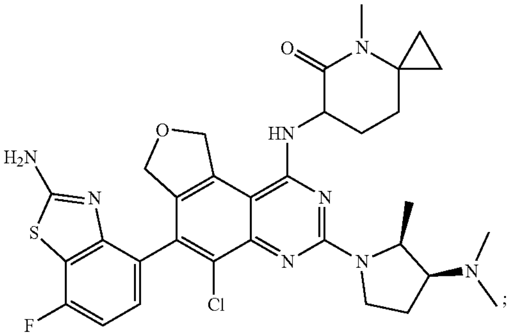
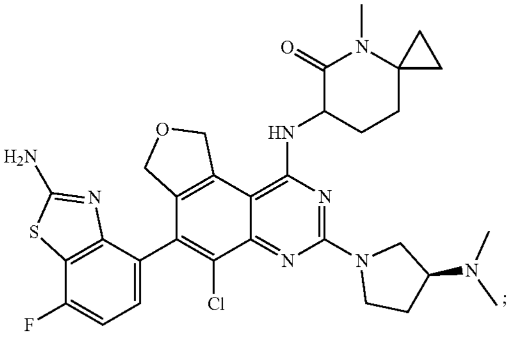
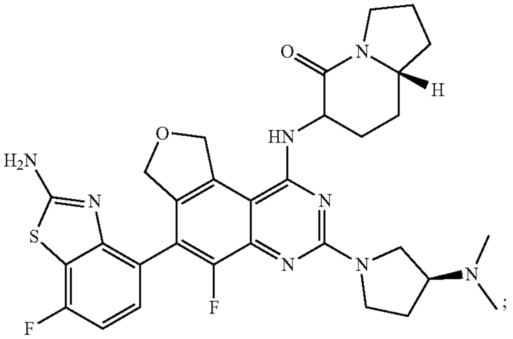

-continued
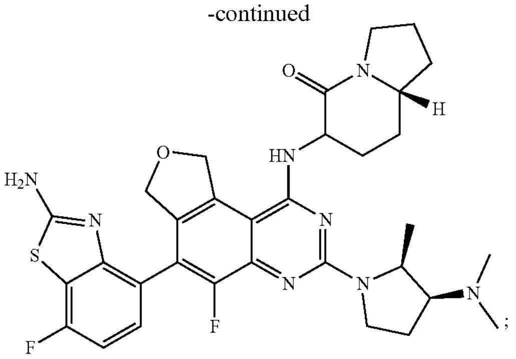
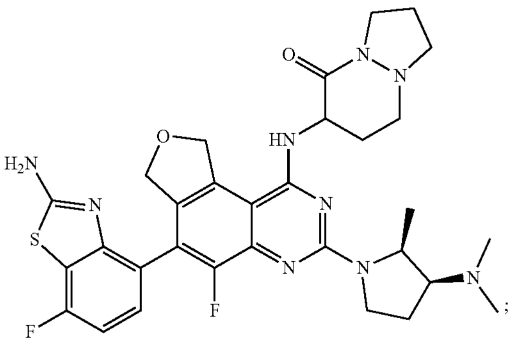
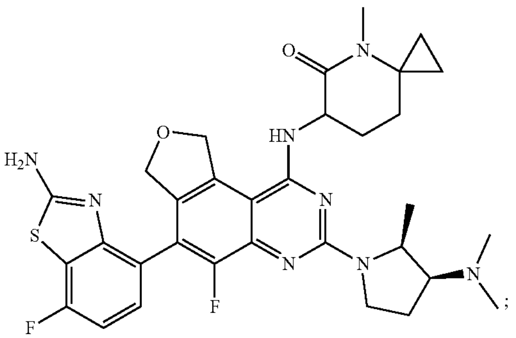
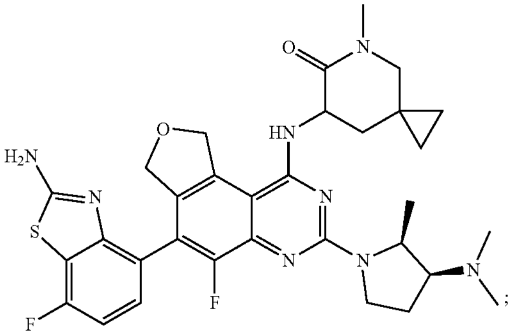
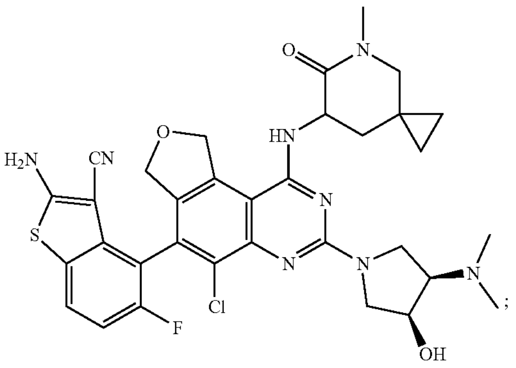
-continued
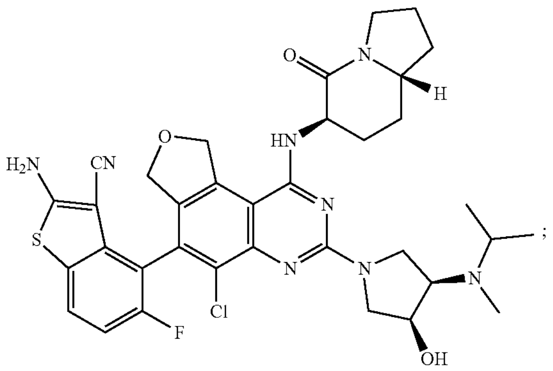
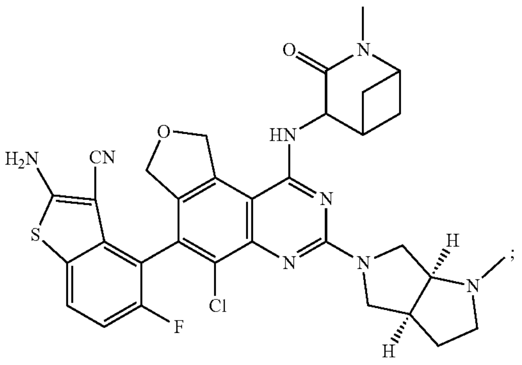
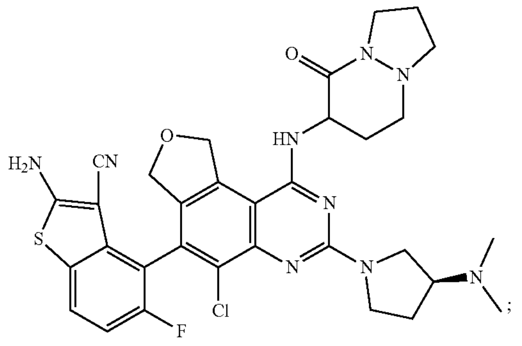
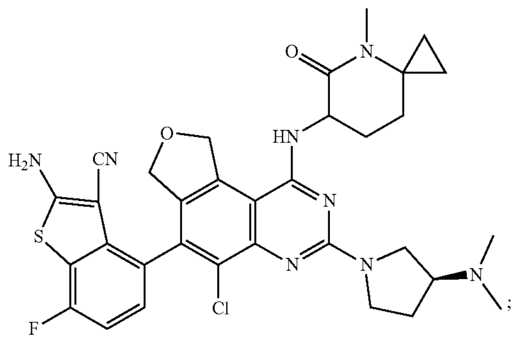

-continued
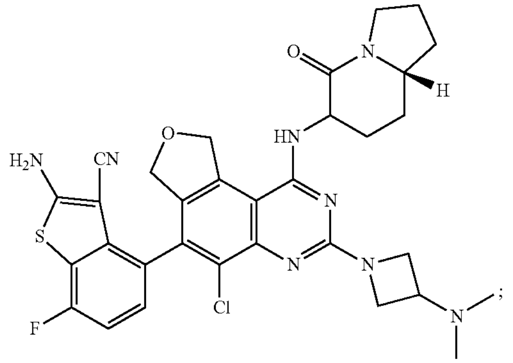
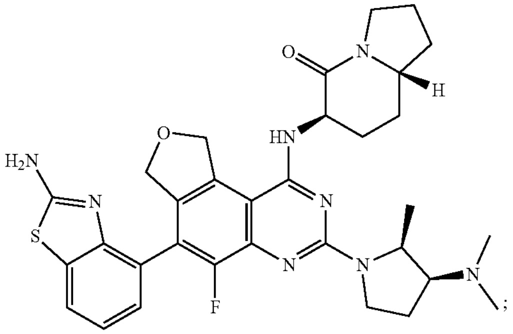
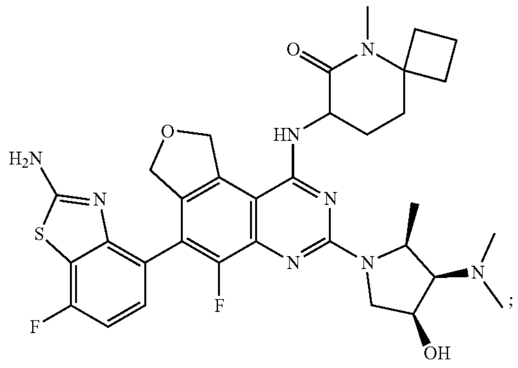
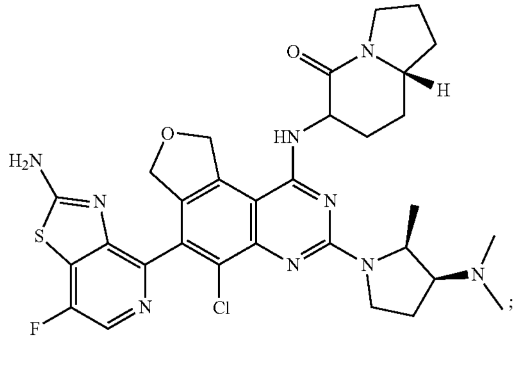
-continued
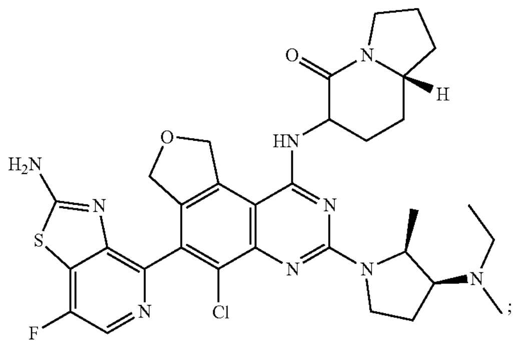
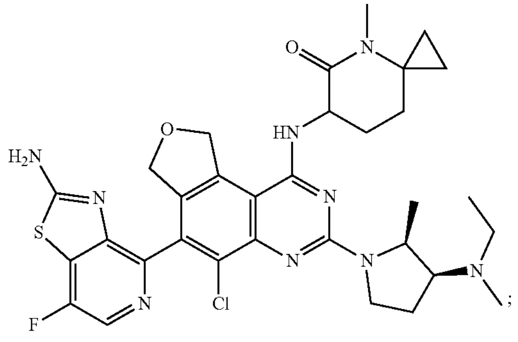
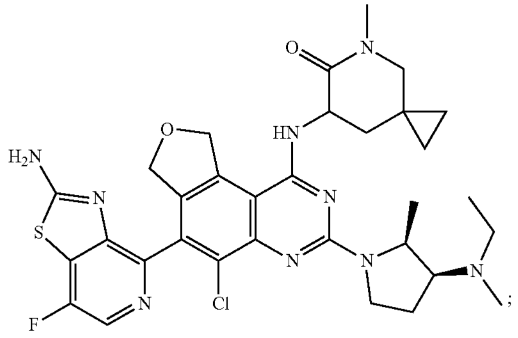
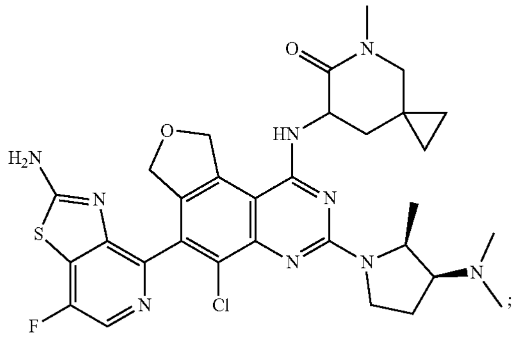
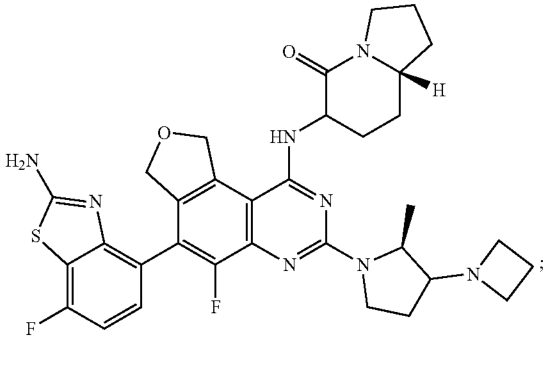

-continued
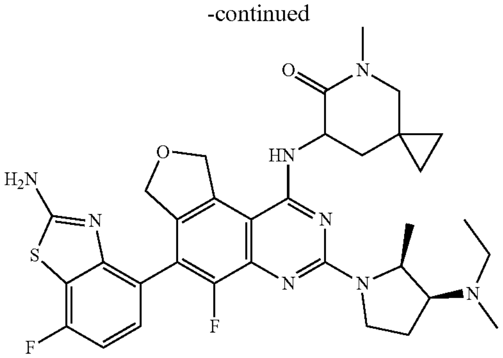
;
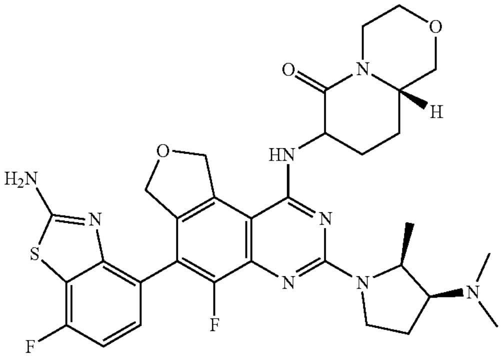
;
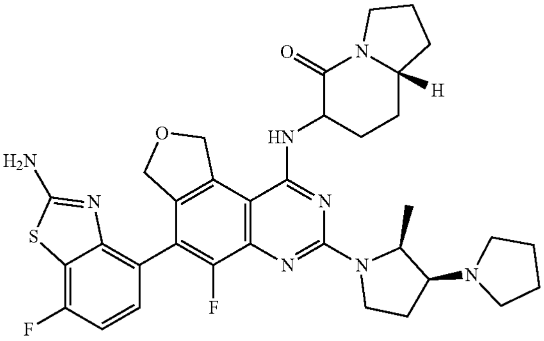
;
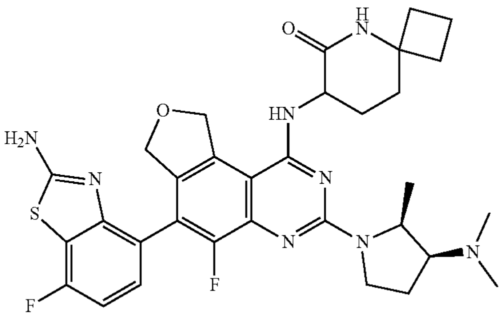
;
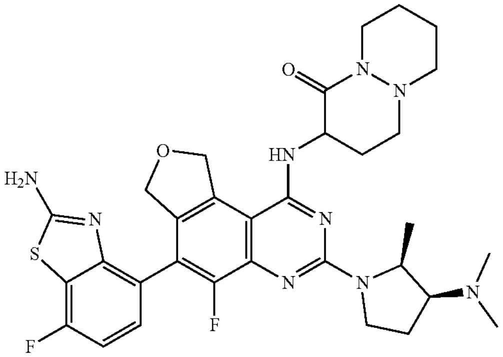
;
-continued
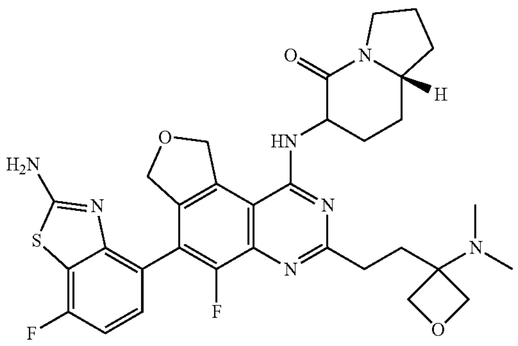
;
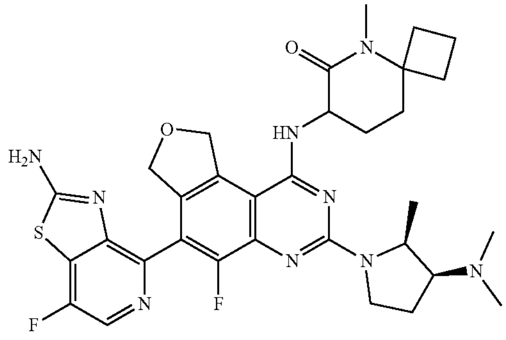
;
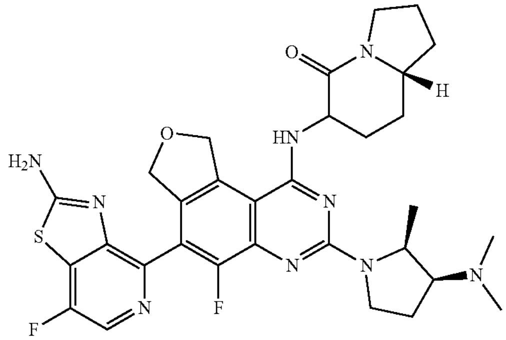
;
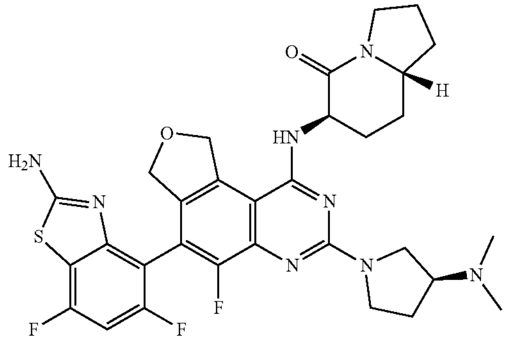
;
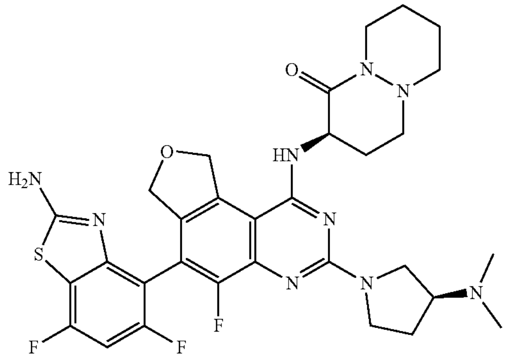
;

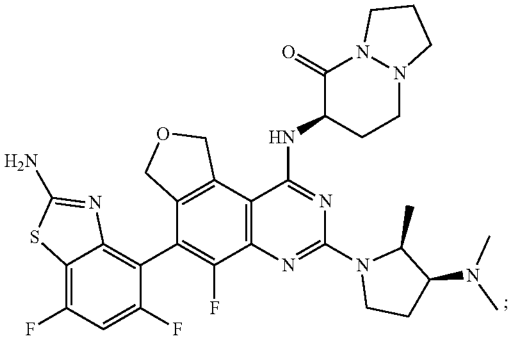
;
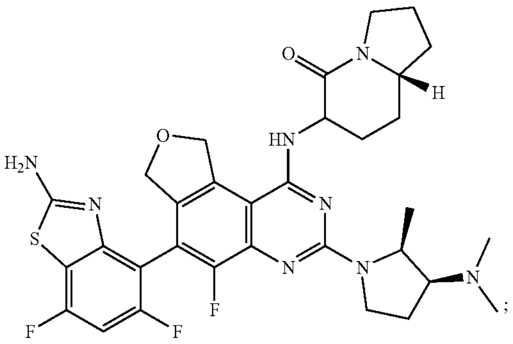
;
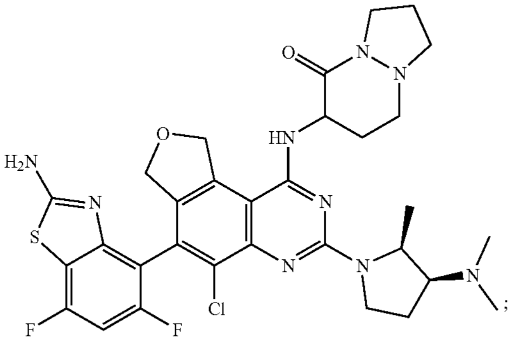
;
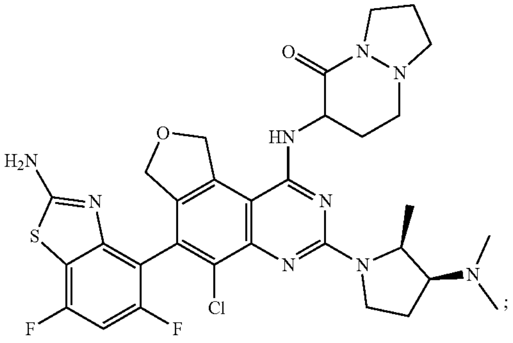
;
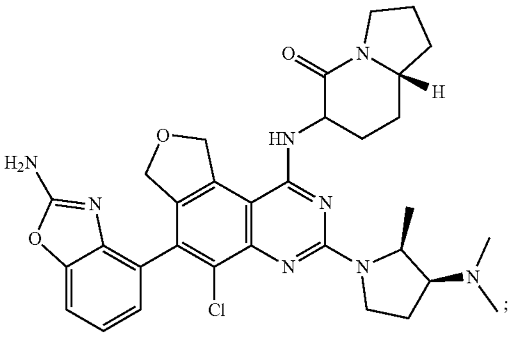
;
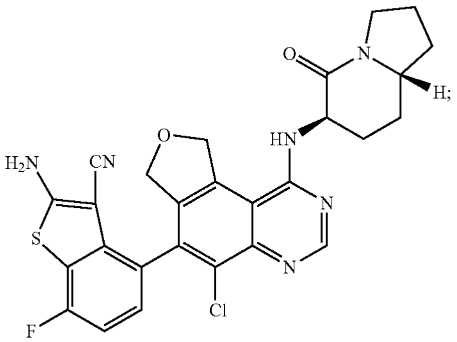
;
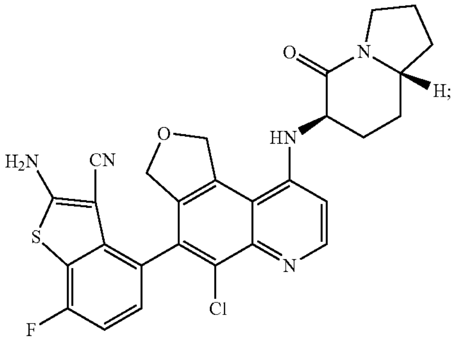
;
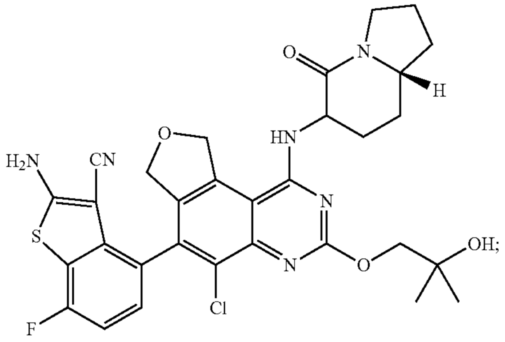
;
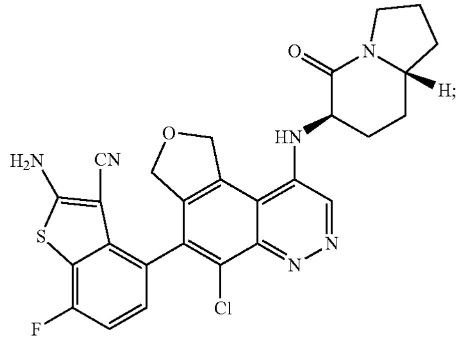
;
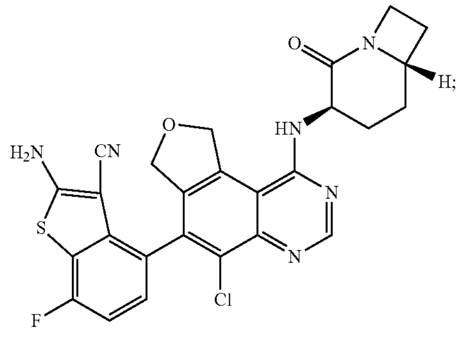
;

-continued
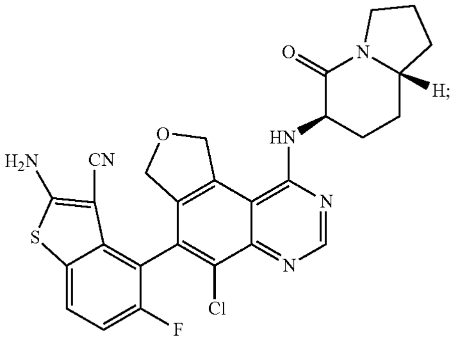
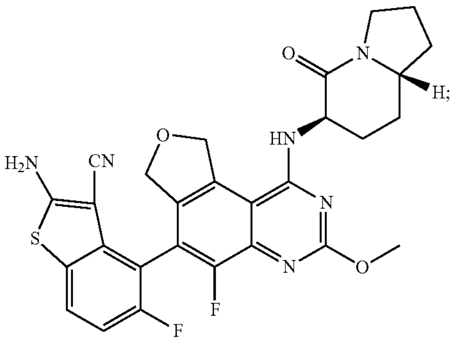
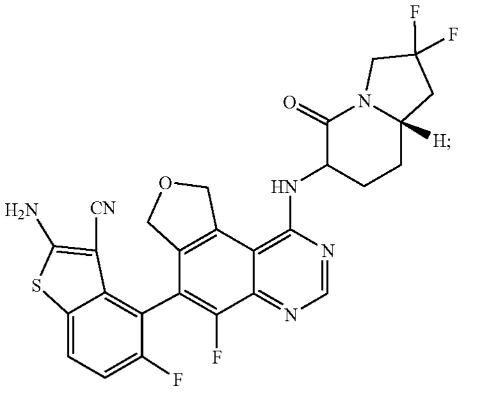
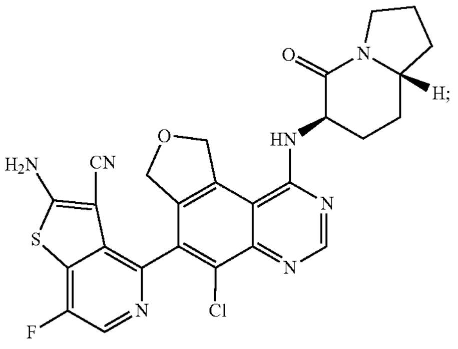
-continued
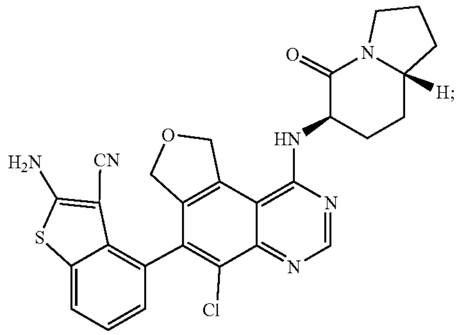
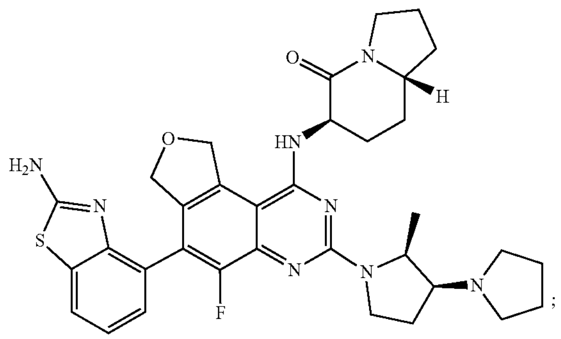
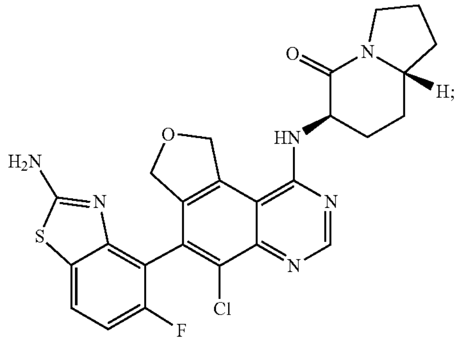
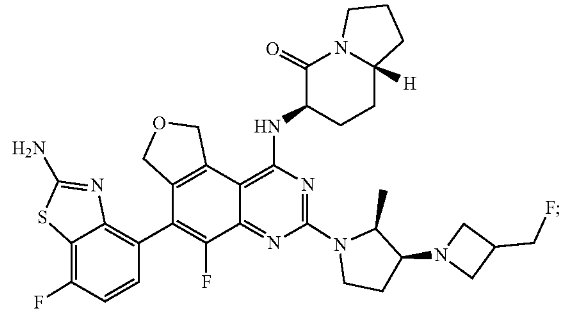
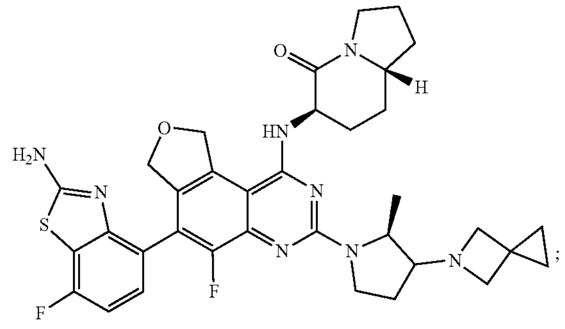

-continued
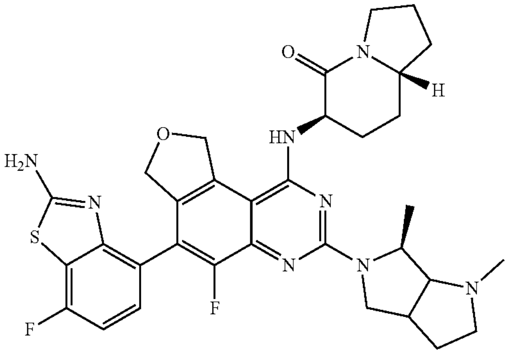
;
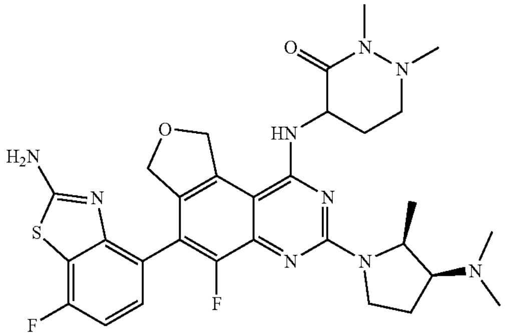
;
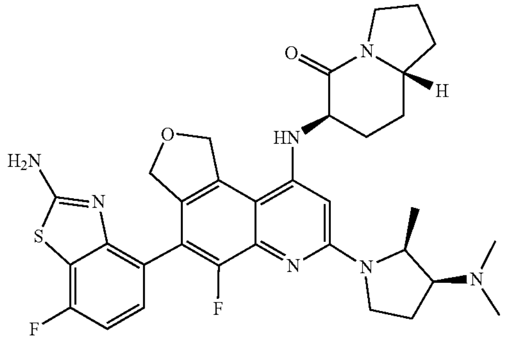
;
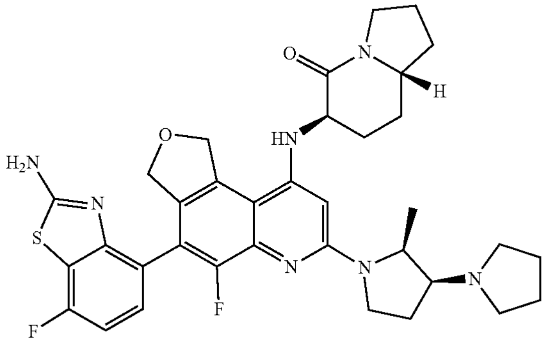
;
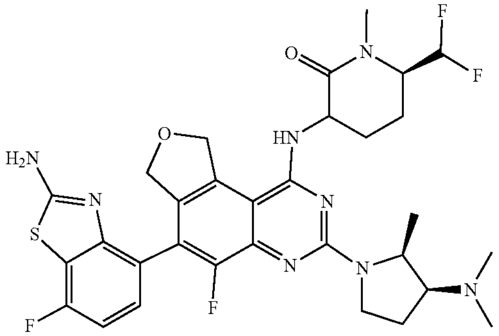
;
-continued
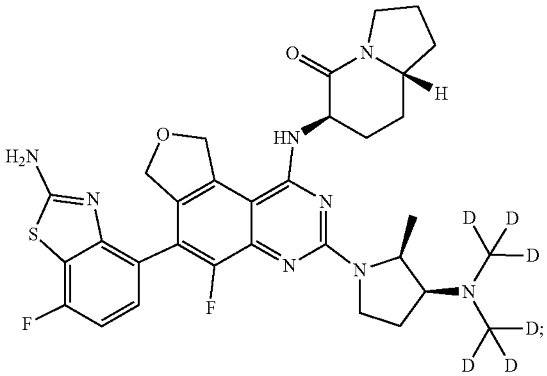
;
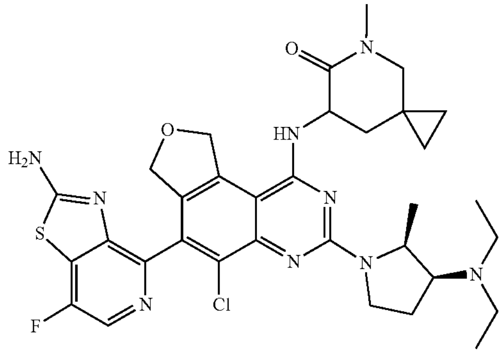
;
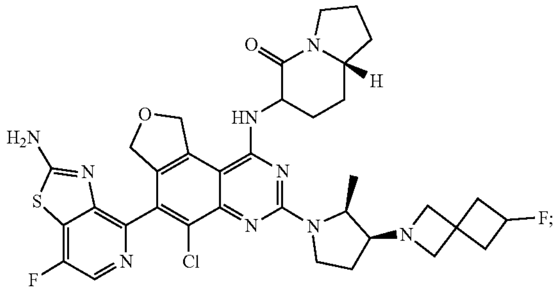
;
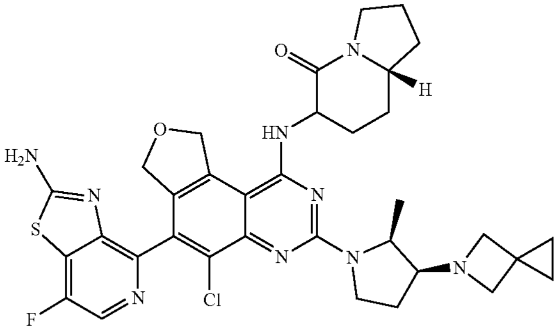
;

-continued
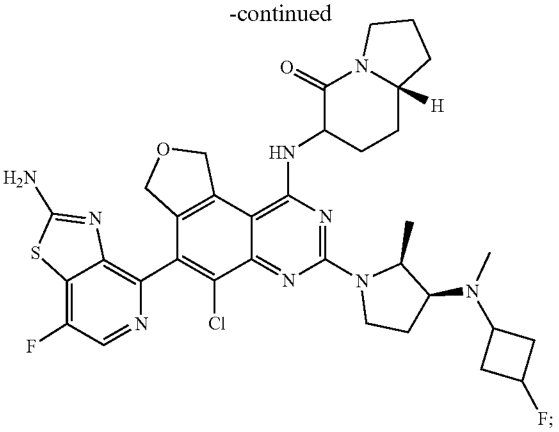
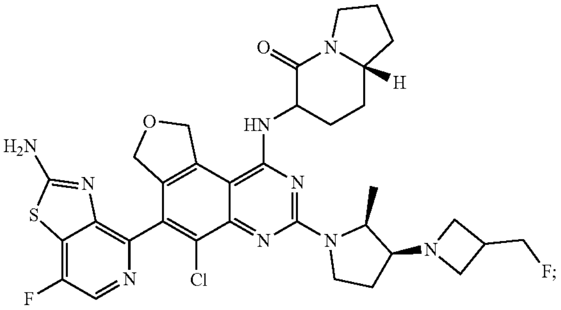
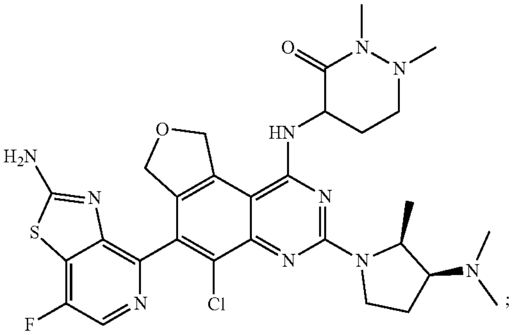
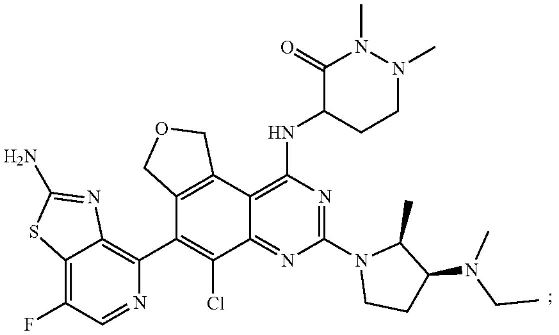
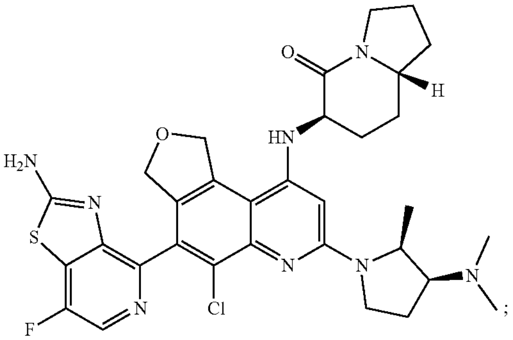
-continued
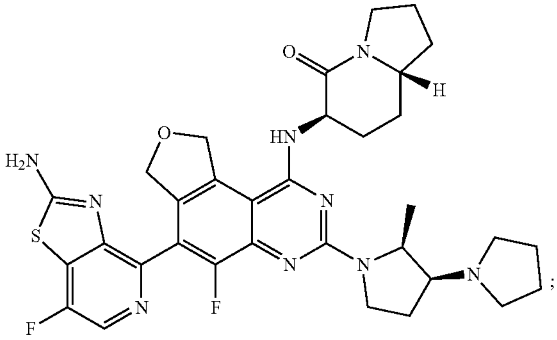
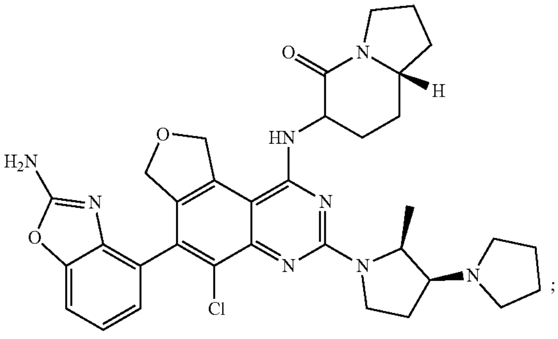
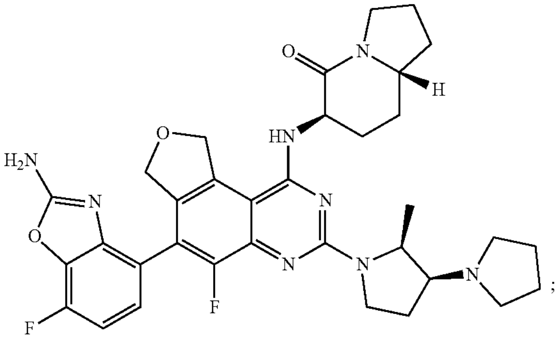
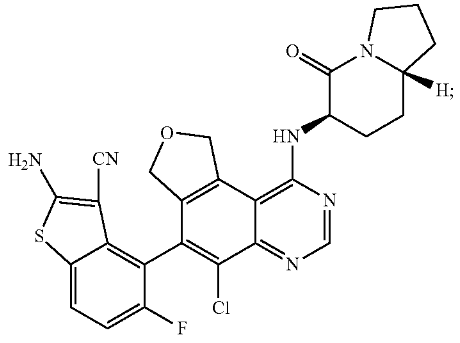
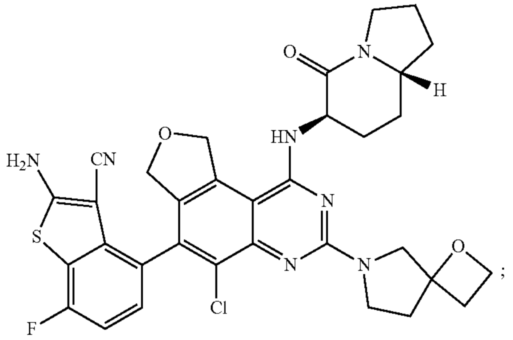

-continued

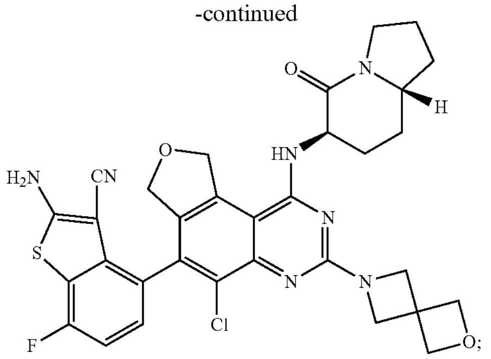

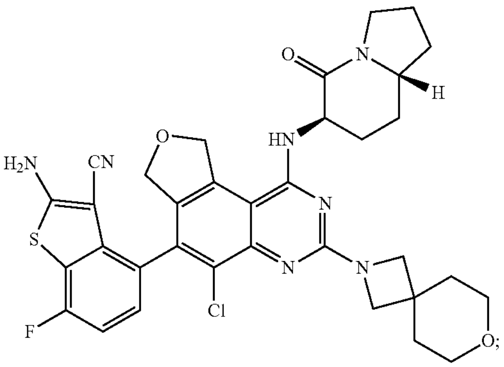

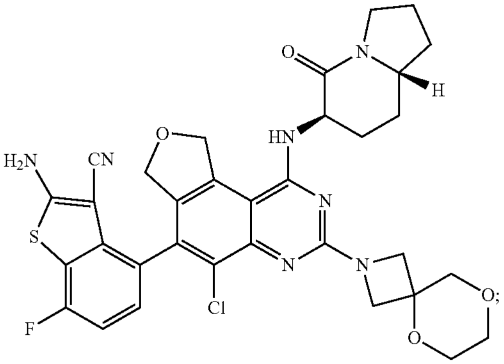

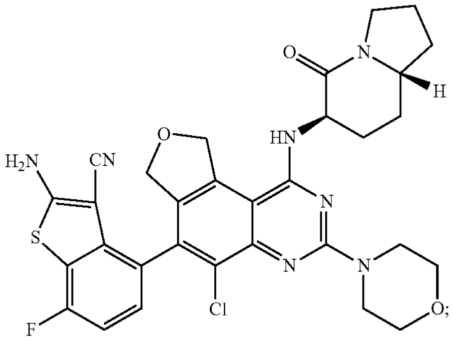

and

-continued

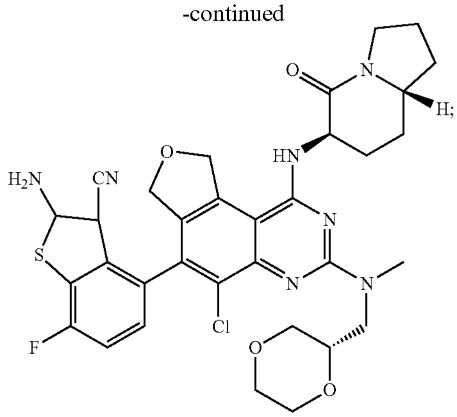

or a pharmaceutically acceptable salt thereof.

25. A pharmaceutical composition comprising a compound according to claim 1, or a pharmaceutically acceptable salt thereof, and a pharmaceutically acceptable carrier, diluent or excipient.

26. A method of treating a patient with cancer, comprising administering to a patient in need thereof, an effective amount of a pharmaceutical composition according to claim 25, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

27. A method of treating a patient with cancer, comprising administering to a patient in need thereof, an effective amount of a compound according to claim 1, or a pharmaceutically acceptable salt thereof, wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

28. The method according to claim 27, wherein the patient has a cancer that was determined to have one or more cells expressing the KRAS G12V mutant protein prior to administration of the compound or a pharmaceutically acceptable salt thereof.

29. A method of treating a patient with a cancer that has a KRAS G12V mutation comprising administering to a patient in need thereof an effective amount of a compound according to claim 1, or a pharmaceutically acceptable salt thereof, and wherein the cancer is selected from lung cancer, pancreatic cancer, cervical cancer, esophageal cancer, endometrial cancer, ovarian cancer, cholangiocarcinoma, colorectal cancer, stomach adenocarcinoma, invasive ductal carcinoma, uterine carcinosarcoma, germ cell tumors, bladder cancer, small bowel adenocarcinoma, appendix cancer, and peritoneum cancer.

30. The method according to claim 27, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

* * * * *